(12) United States Patent  (10) Patent No.: US 8,022,223 B2
Aicher et al.                (45) Date of Patent:     Sep. 20, 2011

(54) 2-AMINOPYRIDINE ANALOGS AS GLUCOKINASE ACTIVATORS

(75) Inventors: Thomas D. Aicher, Superior, CO (US); Steven Armen Boyd, Longmont, CO (US); Mark Joseph Chicarelli, Longmont, CO (US); Kevin Ronald Condroski, Broomfield, CO (US); Ronald Jay Hinklin, Longmont, CO (US); Ajay Singh, Longmont, CO (US)

(73) Assignee: Array Biopharma, Inc., Boulder, CO (US)

( * ) Notice: Subject to any disclaimer, the term of this patent is extended or adjusted under 35 U.S.C. 154(b) by 308 days.

(21) Appl. No.: 12/282,600

(22) PCT Filed: Mar. 23, 2007

(86) PCT No.: PCT/US2007/007444
§ 371 (c)(1),
(2), (4) Date: Oct. 28, 2008

(87) PCT Pub. No.: WO2007/117381
PCT Pub. Date: Oct. 18, 2007

(65) Prior Publication Data
US 2009/0156603 A1    Jun. 18, 2009

Related U.S. Application Data

(60) Provisional application No. 60/785,460, filed on Mar. 24, 2006.

(51) Int. Cl.
*C07D 417/00*    (2006.01)
*C07D 401/00*    (2006.01)

(52) U.S. Cl. .................................. 546/270.7; 546/256
(58) Field of Classification Search ............... 546/270.7, 546/256; 544/279
See application file for complete search history.

(56) References Cited

U.S. PATENT DOCUMENTS

| 2005/0192294 A1 | 9/2005 | Rudolph et al. |
| 2006/0258701 A1 | 11/2006 | Mitsuya et al. |
| 2008/0032996 A1 | 2/2008 | Mitsuya et al. |

FOREIGN PATENT DOCUMENTS

WO    2007/058482 A1    5/2007

*Primary Examiner* — Nizal Chandrakumar
(74) *Attorney, Agent, or Firm* — Banner & Witcoff, Ltd.

(57) ABSTRACT

Provided are compounds of formula I that are useful in the treatment and/or prevention of diseases mediated by deficient levels of glucokinase activity, such as diabetes meilitus. Also provided are methods of treating or preventing diseases and disorders characterized by underactivity of glucokinase or which can be treated by activating glucokinase.

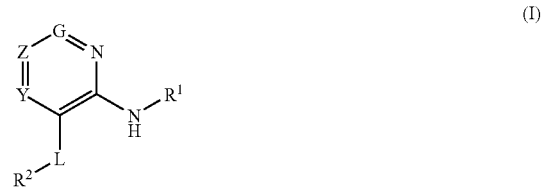

(I)

20 Claims, No Drawings

2-AMINOPYRIDINE ANALOGS AS GLUCOKINASE ACTIVATORS

PRIORITY OF INVENTION

This application claims priority to U.S. Provisional Application No. 60/785,460 that was filed on 24 Mar. 2006, which is hereby incorporated herein by reference in its entirety.

FIELD OF THE INVENTION

Provided are compounds that are useful in the treatment and/or prevention of diseases mediated by deficient levels of glucokinase activity, such as diabetes mellitus, and methods of preparing such compounds. Also provided are methods of treating diseases and disorders characterized by underactivation of glucokinase activity or which can be treated by activating glucokinase, comprising administering an effective amount of a compound of this invention.

BACKGROUND OF THE INVENTION

Diabetes mellitus comprises a group of syndromes characterized by an inability of the body to produce adequate insulin or to properly use insulin. Most diabetes patients can be classified clinically as having either insulin-dependent diabetes mellitus (IDDM) or non-insulin-dependent diabetes mellitus (NIDDM). Nearly all forms of diabetes mellitus result from either a decrease in the secretion and blood concentration of insulin or a decrease in the response of tissues to insulin (insulin resistance), often associated with an elevated level of hormones (e.g., glucagon) that act contrary to insulin. Such abnormalities give rise to changes in carbohydrate, lipid and protein metabolism. The syndrome's hallmark is hyperglycemia; other complications can include cardiovascular disease, retinopathy, neuropathy, nephropathy, skin disorders and gastroparesis.

Diabetes mellitus affects millions of persons worldwide, including over 18 million in the United States. It is estimated that IDDM (Type I diabetes), which results from the body's failure to produce insulin, accounts for 5-10% of the cases of diabetes diagnosed in the United States. The majority of diabetes patients in the United States are diagnosed with NIDDM (Type T diabetes), which results from insulin resistance combined with the inability of the pancreas to secrete sufficient insulin to overcome such resistance. Type II diabetes occurs in at least 5% of the United States population, and in 1996 alone NIDDM affected 16 million people (Roman, S. H.; Harris, M. I., *Endocrinology and Metabolism Clinics of North America*, 1997, 26.3, 443-474). Impaired glucose tolerance (IGT), a syndrome characterized by impaired glucose processing that presents symptoms similar to a mild form of Type II diabetes, is even more prevalent, affecting 35 to 40 million adults in the United States.

Diabetes is most frequently diagnosed either by the presentation of a fasting plasma glucose of greater than or equal to 126 mg/dL on two occasions, or by an oral glucose tolerance test (OGTT) with a 2 hour post load value of greater than 200 mg/dL plus classic symptoms such as polydipsia, polyphagia and/or polyuria (The Expert Committee on the Diagnosis and Classification of Diabetes Mellitus, *Diabetes Care,* 1998, 21, S5-19). In the case of IGT, a fasting plasma glucose of less than 126 mg/dL but a 2-hour post-oral glucose challenge lever greater than 140 mg/dL is observed.

A primary goal in the treatment of each of these conditions is the reduction and control of blood glucose levels. The reduction of hyperglycemia in insulin-dependent diabetes (IDDM) can attenuate the development of many of the attendant complications of IDDM (Diabetes Control and Complications Trial Research Group, *New England J. Med.,* 1993, 329, 977-986). For example, tight control of blood glucose levels through intensive insulin therapy can reduce the development of retinopathy, nephropathy and neuropathy by >50% each in IDDM patients. These findings, together with the similarity of the pathologies seen in IDDM and NIDDM, suggest that control of blood glucose levels would produce similar benefits in NIDDM patients (American Diabetes Association, *Diabetes Care,* 1998, 21, S88-90), as has been reported (Ohkubo, Y., et al., *Diabetes Res. Clin. Pract.* 1995, 28, 103-117).

Several methods to treat hyperglycemia have been attempted. Patients with Type I diabetes receive insulin. In patients with Type II diabetes, the pancreas secretes insulin, but in insufficient amounts to overcome the intrinsic insulin resistance of the disease. The administration of agents such as metformin (De Fronzo, R. A.; Goodman, A. M. *N. Engl. J. Med.,* 1995, 333, 541-549; Bailey, C. J. Biguanides and NIDDM, *Diabetes Care* 1992, 15, 773-784) and glitazone (PPAR agonist class of drugs; Willson, T. M., et al., *J. Med. Chem.* 1996, 39, 665-668) can at least partially ameliorate insulin resistance, but these agents do not promote insulin secretion. Treatment with certain sulfonylureas has been shown to promote insulin secretion by affecting an ion channel; however, the increase in insulin caused by this class of drugs is not glucose dependent or even glucose sensitive, and such treatment can actually raise the risk of overt hypoglycemia. DPP-IV inhibitors, such as Januvia, or GLP or a GLP mimetic (such as Exedin), promote cAMP secretion at the β-cell through an incretin mechanism, and administration of these agents promotes insulin release in a glucose dependent manner (Vahl, T. P., D'Alessio, D. A., *Expert Opinion on Invest. Drugs* 2004, 13, 177-188). However, even with these potential treatments, it is difficult to achieve tight control of blood glucose levels in NIDMM patients in accordance with the guidelines recommended by the American Diabetes Association. Accordingly, there is significant demand for novel therapeutic approaches that allow sufficient glycemic control.

Possible approaches to glycemic control include enhancing clearance of glucose from the blood and increasing the rate of glucose storage or utilization. Glucose enters most cells by a specific transport protein, where it is phosphorylated to form glucose-6-phosphate in a reaction catalyzed by a hexokinase. Inside the cell, glucose-6-phosphate has one of several fates: it can be broken down by the glycolytic pathway, converted into glycogen or it can be oxidized by the pentose phosphate pathway.

Glucokinase (GK) (ATP:D-hexose 6-phosphotransferase), one of the four types of mammalian hexokinases (hexokinase IV), plays an essential role in blood glucose homeostasis. Expression of glucokinase is largely localized in the liver and pancreatic β-cells, where several types of glucokinase are expressed: these types differ in the sequence of the 15 N-terminal amino acids due to differences in splicing, but their enzymatic properties are virtually identical. Glucokinase is also expressed in a population of neurons in the hypothalamus.

Unlike the enzymatic activities of the other three hexokinases (I, II, III), each of which becomes saturated at a glucose concentration of below 1 mM, glucokinase has a $K_m$ for glucose of 8 mM, which is close to the physiological glucose level (5 mM). Thus, at lower glucose levels, glucose is more rapidly utilized in brain, muscle and other peripheral tissues—through conversion by a hexokinase other than glucokinase—than in the liver. At elevated glucose levels, such as after a meal or overnutrition (the postprandial glucose level can exceed 10-15 mM), glucokinase-mediated glucose metabolism in the liver and pancreas is accelerated. Moreover, hexokinases I, II and III are inhibited by high concentrations of glucose-6-phosphate, lowering glucose utilization, whereas glucokinase continues to catalyze utilization of glucose even at high levels of glucose-6-phosphate.

In tissues where glucokinase is expressed, it plays an important role in glucose uptake and utilization: in the β-cell, the glucose-6-phosphate produced is a necessary signal for insulin release; in the hypothalamus glucose-6-phosphate acts as a satiety signal and might contribute to the secretion of enteroincretins; and in the liver, where glucose-6-phosphate production by the action of glucokinase acts as a mechanism for disposal of excessive glucose through storage as glycogen (Printz, R. L., et al., *Annu. Rev. Nutr.,* 1993, 13, 463-496). Glucokinase-catalyzed glucose phosphorylation is the rate-limiting reaction for glycolysis in hepatocytes and pancreatic β-cells. In the liver, glucokinase determines the rates of both glucose uptake and glycogen synthesis, and it is also thought to be essential for the regulation of various glucose-responsive genes (Girard, J., et al., *Annu. Rev. Nutr.,* 1997, 17, 325-352). In both liver and pancreatic β-cells, glucokinase is rate limiting for glucose utilization, and consequently is a major component of the regulation of insulin secretion from the β-cell and glycogen storage in the liver. The control of insulin secretion and the control of glycogen storage are deficient in diabetes (DeFronzo, R. A., *Diabetes,* 1988, 37, 667-687).

The theoretical importance of glucokinase in diabetes is supported by studies of genetic populations and genetic manipulation of animal models of NIDDM. Mutation of glucokinase to a less active form of the kinase is the cause of the Maturity Onset of Diabetes in the Young (MODY-2) (Froguel, P., et al., *New England J. Med.,* 1993, 328, 697-702; Bell, G. I., et al., *Annual Rev. of Physiol.,* 1996, 58, 171-186). Conversely, humans with a glucokinase activation mutation are less prone to hyperglycemia and have increased insulin secretion in response to a glucose challenge (Christesen, H. B., et al., *Diabetes,* 2002, 51, 1240-1246; Gloyn, A. L, et al., *Diabetes,* 2003, 52, 2433-2440; Glaser, B., et al., *New England J. Med.,* 1998, 338, 226-230). Also, NIDDM patients have been reported to have inappropriately low glucokinase activity. Furthermore, over expression of glucokinase in dietary or genetic animal models of diabetes either prevents, ameliorates, or reverses the progress of pathological symptoms in the disease (Caro, J. F., et al., *Hormone & Metabolic Res.,* 1995, 27, 19-22). For these reasons, compounds that activate glucokinase have been sought by the pharmaceutical industry.

Substituted benzyl carbamoyl, substituted heterobenzyl carbamoyl, substituted phenyl carbamoyl, and substituted heteroaryl carbamoyl compounds have been disclosed as glucokinase activators. See, for example, WO 03/000267, WO 03/015774, WO 04/045614, WO 04/046139, WO 05/04480, WO 05/054200, WO 05/054233, WO 05/044801, WO 05/056530, WO 03/080585, WO 04/076420, WO 04/081001, WO 04/063194, WO 04/050645, WO 03/055482, WO 04/002481, WO 05/066145, WO 04/072031, WO 04/072066, U.S. Pat. No. 6,610,846, WO 00/058293, WO 03/095438, WO 01/44216, WO 01/083465, WO 01/083478, WO 01/085706, WO 01/085707, WO 02/008209, WO 02/014312, WO 02/046173, WO 02/048106, WO 03/095438, WO 04/031179, and WO 04/052869. These compounds either lower the $K_m$ for glucose and/or increase the $V_{max}$ of glucokinase.

SUMMARY OF THE INVENTION

The present invention relates to novel compounds that are activators of glucokinase which are useful in the treatment of diseases and disorders that would benefit from activation of glucokinase.

More specifically, one aspect of this invention provides compounds of Formula I

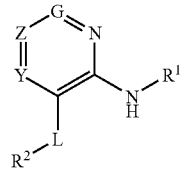

and solvates, metabolites, salts and pharmaceutically acceptable prodrugs thereof, wherein L, Y, Z, G, $R^1$ and $R^2$ are as defined below.

The invention also provides pharmaceutical compositions comprising a compound of Formula I, or a solvate, metabolite, and solvate, metabolite, salt or pharmaceutically acceptable prodrugs thereof, and a pharmaceutically acceptable carrier.

The inventive compounds may be used advantageously in combination with other known therapeutic agents. Accordingly, this invention also provides pharmaceutical compositions comprising a compound of Formula I or a solvate, metabolite, or pharmaceutically acceptable salt or prodrug thereof, in combination with a second therapeutic agent.

This invention also provides methods of preventing or treating a disease or disorder characterized by underactivation of glucokinase or which can be treated by activating glucokinase in a mammal, comprising administrating to said mammal one or more compounds of Formula I, or a metabolite, solvate, or pharmaceutically acceptable salt or prodrug thereof, in an amount effective to treat said disease or disorder. The compounds of the present invention can be used, for example, as prophylactics or therapeutic agents for treating diseases or disorders mediated by deficient levels of glucokinase activity, including, but not limited to, diabetes mellitus (type I and type II), impaired glucose tolerance, IFG (impaired fasting glucose) and IFG (impaired fasting glycemia), as well as other diseases and disorders characterized by underactivation of glucokinase or which can be treated by activation of glucokinase, such as those discussed below.

This invention also provides compounds of Formula I for use in therapy.

An additional aspect of the invention is the use of a compound of Formula I for the preparation of a medicament for use as a glucokinase activator.

This invention further provides kits for the treatment or prevention of a disease or disorder characterized by underactivation of glucokinase, said kit comprising a compound of Formula I, or a solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, 1-heptyl, 1-octyl, and the like.

In certain embodiments, the term "alkyl" refers to a saturated linear or branched-chain monovalent hydrocarbon radical of one to six carbon atoms, wherein the alkyl radical may be optionally substituted independently with one or more substituents described below.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

In certain embodiments, the term "alkylene" refers to a linear or branched saturated divalent hydrocarbon radical of one to four carbon atoms, wherein the alkylene radical may be optionally substituted independently with one or more substituents described herein.

The term "alkenyl" as used herein refers to a linear or branched-chain monovalent hydrocarbon radical of two to twelve carbon atoms with at least one site of unsaturation, i.e., a carbon-carbon sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), 1-buten-1-yl, 1-buten-2-yl, and the like.

In certain embodiments, the term "alkenyl" as used herein refers to a linear or branched-chain monovalent hydrocarbon radical of two to six carbon atoms with at least one site of unsaturation, wherein the alkenyl radical may be optionally substituted independently with one or more substituents described herein, and includes radicals having "cis" and "trans" orientations.

The term "alkenylene" as used herein refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkenylene" includes linear or branched divalent hydrocarbon radical of two to four carbons containing at least one double bond, wherein the alkenylene radical may be optionally substituted independently with one or more substituents described herein.

The term "alkynyl" as used herein refers to a linear or branched monovalent hydrocarbon radical of two to twelve carbon atoms with at least one site of unsaturation, i.e., a carbon-carbon sp triple bond, wherein the alkynyl radical may be optionally substituted independently with one or more substituents described herein. Examples include, but are not limited to, ethynyl (—C≡CH), propynyl (propargyl, —CH$_2$C≡CH) and the like.

In certain embodiments, the term "alkynyl" refers to a linear or branched monovalent hydrocarbon radical of two to six carbon atoms with at least one carbon-carbon sp triple bond.

The term "alkynylene" as used herein refers to a linear or branched divalent hydrocarbon radical of two to twelve carbons containing at least one triple bond, wherein the alkynylene radical may be optionally substituted independently with one or more substituents described herein. Examples include, but are not limited to, ethynylene, propynylene, and the like.

In certain embodiments, the term "alkynylene" refers to a linear or branched divalent hydrocarbon radical of two to four carbons containing at least one triple bond.

The terms "cycloalkyl," "carbocycle," "carbocyclyl" and "carbocyclic ring" are used interchangeably and refer to a saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated, partially unsaturated or aromatic cycloalkyl or heterocyclic ring. Examples of cycloalkyl groups include, but are not limited to, cyclopropyl, cyclobutyl, cyclopentyl, cyclopentenyl, cyclohexyl, cyclohexenyl, cycloheptyl, cycloheptenyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo [2.2.2]octane, and bicyclo[3.2.2]nonane. The cycloalkyl may be optionally substituted independently with one or more substituents described herein.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a saturated, partially unsaturated ring, or aromatic carbocyclic or heterocyclic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like. Aryl groups may be optionally substituted independently with one or more substituents described herein.

The terms "heterocycle", "heterocyclyl" and "heterocyclic ring" as used herein are used interchangeably and refer to a saturated or partially unsaturated carbocyclic radical of 3 to 12 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocyclyl" also includes radicals where heterocycle radicals are fused with a saturated, partially unsaturated, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are unsubstituted or, as specified, substituted in one or more substitutable positions with various groups described herein.

In certain embodiments, the term "heterocycle" includes bridged heterocycles.

The term "heteroaryl" as used herein refers to a monovalent aromatic radical of a 5-, 6-, or 7-membered ring, and includes fused ring systems (at least one of which is aromatic) of 5-12 atoms, containing at least one heteroatom independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently at one or more substitutable positions with one or more substituents described herein. Particular examples of heteroaryl groups include thiazolyl, thiadiazolyl, oxadiazolyl, oxazolyl, thiazolo[5,4-b]pyridinyl, thiazolo[5,4-b]pyrazinyl, and thiazolo[5,4-e][1,2,4]triazine.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" as used herein means fluoro, chloro, bromo or iodo.

The term "a" as used herein means one or more.

As used herein, the terms "compound of this invention," "compounds of the present invention" and "compounds of Formula I" include compounds of Formula I and tautomers, resolved enantiomers, resolved diastereomers, racemic mixtures, solvates, metabolites, salts and prodrugs thereof, including pharmaceutically acceptable salts and prodrugs.

In general, the various moieties or functional groups of the compounds of this invention may be optionally substituted by one or more substituents. Examples of substituents suitable for purposes of this invention include, but are not limited to, oxo, halogen, CN, nitro, trifluoromethyl, difluoromethyl, fluoromethyl, fluoromethoxy, difluoromethoxy, trifluoromethoxy, azido, $V_n$—NR"SO$_2$R', $V_n$—SO$_2$NR'R", $V_n$—C(=O)R', $V_n$—C(=O)OR', $V_n$—OC(=O)R', $V_n$—NR"C(=O)OR', $V_n$—NR"C(=O)R', $V_n$—C(=O)NR'R", $V_n$—NR'R", $V_n$—NR'"C(=O)N'R", $V_n$—OR', $V_n$—SR', $V_n$—S(O)R', $V_n$—S(O)$_2$R', alkyl, alkenyl, alkynyl, $V_n$-cycloalkyl; $V_n$-heterocyclyl, $V_n$-aryl, and $V_n$-heteroaryl, where R', R" and R'" are independently H, alkyl, alkenyl, alkynyl, cycloalkyl, heterocyclyl, aryl, or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

Glucokinase Activators

The present invention provides compounds, and pharmaceutical formulations thereof, that are useful in the treatment of diseases, conditions and/or disorders characterized by underactivation of glucokinase or which can be treated by activation of glucokinase.

One aspect of the invention provides compounds of Formula I

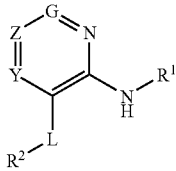

I and tautomers, resolved enantiomers, resolved diastereomers, racemic mixtures, solvates, metabolites, salts and pharmaceutically acceptable prodrugs thereof, wherein:

L is O, S, C(=O) or $CHR^{14}$;
Y is N or $CR^4$;
Z is N or $CR^3$, wherein at least one of G or Z is not N;
G is N or $CR^{11}$;
$R^1$ is a heteroaryl ring represented by the formula

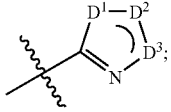

$D^1$ is S, O, or N;
$D^2$ is N or $CR^{12}$;
$D^3$ is S, O or $CR^{13}$;
$R^2$ is aryl, heteroaryl, saturated or partially unsaturated cycloalkyl, or saturated or partially unsaturated heterocyclyl, wherein said aryl, heteroaryl, cycloalkyl and heterocyclyl are monocyclic or bicyclic and are optionally substituted with one or more groups independently selected from $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl, heteroaryl, F, Cl, Br, I, $CF_3$, CN, $NO_2$, $OR^6$, $C(=O)R^6$, $C(=O)OR^6$, $OC(=O)R^6$, $O(CH_2)_nC(=O)OR^6$, $O(CH_2)_nC(=O)NR^6R^7$, $C(=O)NR^6R^7$, $NR^6R^7$, $NR^6C(=O)R^7$, $SR^6$, $S(O)R^6$, and $S(O)_2R^6$, and wherein said alkyl, alkenyl, alkynyl, cycloalkyl, heterocyclyl, aryl, and heteroaryl are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ $V_n$—Cycloalkyl, saturated and partially unsaturated $C_1$-$C_6$ $V_n$-heterocyclyl, $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—C(=O)$R^8$, $V_n$—C(=O)$OR^8$, $V_n$—OC(=O)$R^8$, $V_n$—C(=O)$NR^8R^9$, $V_n$—$NR^8R^9$, $V_n$—$NR^8C(=O)R^9$, $V_n$—$SR^8$, $V_n$—S(O)$R^8$, and $V_n$—S(O)$_2R^8$;

$R^3$ is H, $C_1$-$C_{12}$ alkyl, $C_2$-$C_{12}$ alkenyl, $C_2$-$C_{12}$ alkynyl, saturated or partially unsaturated $C_3$-$C_{12}$ cycloalkyl, saturated or partially unsaturated $C_1$-$C_{12}$ heterocyclyl, aryl, heteroaryl, F, Cl, Br, I, CN, $OR^6$, $C(=O)R^6$, $C(=O)OR^6$, $OC(=O)R^6$, $C(=O)NR^6R^7$, $OC(=O)NR^6R^7$, $OC(=S)$ $NR^6R^7$, $NR^6R^7$, $NR^6C(=O)R^7$, $SR^6$, $S(O)R^6$, $S(O)_2R^6$ or $S(O)_2NR^6R^7$, wherein said alkyl, alkenyl, alkynyl, cycloalkyl, heterocyclyl, aryl and heteroaryl are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—C(=O)$R^8$, $V_n$—C(=O)$OR^8$, $V_n$—OC(=O)$R^8$, $V_n$—C(=O)$NR^8R^9$, $V_n$—$NR^8R^9$, $V_n$—$NR^8C(=O)R^9$, $V_n$—$SR^8$, $V_n$—S(O)$R^8$, $V_n$—S(O)$_2R^8$ and $V_n$—S(O)$_2NR^8R^9$;

$R^4$ is H, methyl, ethyl, F, Cl, Br, I, $CF_3$, $CHF_2$ or $CH_2F$;

$R^6$ and $R^7$ are independently H, $C_1$-$C_{12}$ alkyl, $C_2$-$C_{12}$ alkenyl, $C_2$-$C_{12}$ alkynyl, saturated or partially unsaturated $C_3$-$C_{12}$ cycloalkyl, saturated or partially unsaturated $C_1$-$C_{12}$ heterocyclyl, $V_n$-aryl, or $V_n$-heteroaryl, wherein said alkyl, alkenyl, alkynyl, cycloalkyl, heterocyclyl, aryl and heteroaryl portions are optionally substituted with one or more groups independently selected from $CF_3$, oxo, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl [optionally substituted with C(O)O(1-6C alkyl), (1-6C)alkyl or (1-6C alkyl)OH], $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—C(=O)$R^8$, $V_n$—C(=O)$OR^8$, $V_n$—OC(=O)$R^8$; $V_n$—C(=O)$NR^8R^9$, $V_n$—$NR^8R^9$, $V_n$—$NR^8C(=O)R^9$, $V_n$—$SR^8$, $V_n$—S(O)$R^8$, $V_n$—S(O)$_2R^8$, $V_n$—S(O)$_2NR^8R^9$, and ($C_1$-$C_6$ alkyl)OH;

or $R^6$ and $R^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—Cl, $V_n$—Br, $V_n$—I, $V_n$—$OR^8$, $V_n$—C(=O)$OR^8$, $V_n$—C(=O)$NR^8R^9$, $V_n$—$NR^8R^9$, $V_n$—$NR^8C(=O)R^9$, $V_n$—$NR^8C(=O)NR^9R^{10}$, $C_1$-$C_6$ alkyl, $C_2$-$C_6$ alkenyl, and $C_2$-$C_6$ alkynyl;

$R^8$, $R^9$ and $R^{10}$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl or heteroaryl, wherein said alkyl, alkenyl, alkynyl, cycloalkyl, heterocyclyl, aryl and heteroaryl are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, $V_n$-heteroaryl, $V_n$—F, $V_n$—Cl, $V_n$—Br, $V_n$—I, $V_n$—$OR^a$, $V_n$—$NR^aR^b$, $V_n$—C(=O)$OR^a$, $V_n$—C(=O)$NR^aR^b$, and $V_n$—$NR^aC(=O)R^b$, or $R^8$ and $R^9$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $C_1$-$C_6$ alkyl, $C_2$-$C_6$ alkenyl, $C_2$-$C_6$ alkynyl, $V_n$—F, $V_n$—Cl, $V_n$—Br, $V_n$—I, $V_n$—$OR^a$, and $V_n$—CN, or $R^9$ and $R^{10}$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $C_1$-$C_6$ alkyl, $C_2$-$C_6$ alkenyl, $C_2$-$C_6$ alkynyl, $V_n$—F, $V_n$—Cl, $V_n$—Br, $V_n$—I, $V_n$—$OR^a$, and $V_n$—CN;

$R^{11}$ is H, methyl, ethyl, F, Cl, Br, I, $CF_3$, $CHF_2$, $CH_2F$, OH, O—($C_1$-$C_4$ alkyl), or $NH_2$;

$R^{12}$ and $R^{13}$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $CH_2$-heterocyclyl, aryl, heteroaryl, (1-3C alkyl)heteroaryl, $(CH_2)_n(CR^xR^y)C(O)NR^8R^9$, F, Cl, Br, I, $CF_3$, CN, $OR^6$, $C(=O)R^6$, $C(=O)OR^6$, $OC(=O)R^6$, $C(=O)NR^6R^7$, $NR^6R^7$, $NR^6C(=O)R^7$, $SR^6$, $S(O)R^6$, $S(O)_2R^6$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—$CF_3$, $V_n$—CN, $V_n$—$OR^8$, $V_n$—$C(=O)OR^8$, $V_n$—$OC(=O)R^8$, $V_n$—$C(=O)NR^8R^9$) $V_n$—$NR^8R^9$, $V_n$—$NR^8C(=O)R^9$, $C(O)(C_1$-$C_6$ alkyl), C(O)-heterocycle [optionally substituted with O—($C_1$-$C_6$ alkyl], $SR^a$, $SO_2R^f$, $SO_2NR^cR^e$, $C(O)(C_1$-$C_6$ alkyl)$NR^cR^d$, $C(O)(C_1$-$C_6$ alkyl)$OR^c$, $C(O)CH_2C(O)(C_1$-$C_6$ alkyl), $C(=O)CHR^gNHC(=O)(C_1$-$C_6$ alkyl), $C(=O)CH_2C(=O)(C_1$-$C_6$ alkyl), $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, and $V_n$-heteroaryl, wherein said heterocyclyl is optionally substituted with one or more oxo, or $R^{12}$ and $R^{13}$ together with the atoms to which they are attached form a saturated, partially unsaturated or aromatic carbocyclic or heterocyclic ring, wherein said carbocyclic and heterocyclic rings are optionally substituted with one or more groups independently selected from $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl, heteroaryl, oxo, F, Cl, Br, 0.1, $CF_3$, CN, $OR^6$, $C(=O)R^6$, $C(=O)OR^6$, $OC(=O)R^6$, $C(=O)NR^6R^7$, $NR^6R^7$, $NR^6C(=O)R^7$, $SR^6$, $S(O)R^6$, $S(O)_2R^6$ and $SO_2NR^6R^7$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—$CF_3$, $V_n$—CN, $V_n$—$OR^8$, $V_n$—$C(=O)OR^8$, $V_n$—$OC(=O)R^8$, $V_n$—$C(=O)NR^8R^9$, $V_n$—$NR^8R^9$, $V_n$—$NR^8C(=O)R^9$, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, and $V_n$-heteroaryl;

$R^{14}$ is H, methyl, ethyl or OH;

$R^a$ and $R^b$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocyclyl, $V_n$-aryl, and $V_n$-heteroaryl are optionally substituted with one or more OH;

each $R^c$, $R^e$ and $R^g$ is independently H or $C_1$-$C_6$ alkyl;

$R^d$ is H, $C_1$-$C_6$ alkyl or $C(O)O(C_1$-$C_6$ alkyl);

$R^f$ is $C_1$-$C_6$ alkyl or $(C_1$-$C_6$ alkyl)$NH_2$;

$R^x$ is H or $C_1$-$C_6$ alkyl;

$R^y$ is H, $C_1$-$C_6$ alkyl, or —O($C_1$-$C_6$ alkyl);

V is alkylene having from 1 to 12 carbons, or alkenylene or alkynylene each having from 2 to 12 carbons, wherein said alkylene, alkenylene, or alkynylene are optionally substituted with one or more groups independently selected from $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl, heteroaryl, F, Cl, Br, I, $CF_3$, cyano, $OR^8$, $C(=O)OR^8$, $OC(=O)R^8$, $C(=O)NR^8R^9$, $NR^8R^9$, $(C_1$-$C_6$ alkyl)$NR^cR^e$; and $NR^8C(=O)R^9$; and n is 0 or 1.

In certain embodiments, $R^6$ and $R^7$ are optionally substituted with one or more groups independently selected from OXO, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—$C(=O)R^8$, $V_n$—$C(=O)OR^8$, $V_n$—$OC(=O)R^8$, $V_n$—$C(=O)NR^8R^9$, $V_n$—$NR^8R^9$, $V_n$—$NR^8C(=O)R^9$, $V_n$—$SR^8$, $V_n$—$S(O)R^8$, $V_n$—$S(O)_2R^8$, and $V_n$—$S(O)_2WR^9$.

In certain embodiments, $R^{12}$ and $R^{13}$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl, heteroaryl, F, Cl, Br, I, $CF_3$, CN, $OR^6$, $C(=O)R^6$, $C(=O)OR^6$, $OC(=O)R^6$, $C(=O)NR^6R^7$, $NR^6R^7$, $NR^6C(=O)R^7$, $SR^6$, $S(O)R^6$ or $S(O)_2R^6$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—$CF_3$, $V_n$—CN, $V_n$—$OR^8$, $V_n$—$C(=O)OR^8$, $V_n$—$OC(=O)R^8$, $V_n$—$C(=O)NR^8R^9$, $V_n$—$NR^8R^9$, $V_n$—$NR^8C(=O)R^9$, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, and $V_n$-heteroaryl, wherein said heterocyclyl is optionally substituted with one or more oxo.

In certain embodiments of compounds of Formula I, G is $R^{11}$.

In certain embodiments of compounds of Formula I, $R^{11}$ is hydrogen.

In certain embodiments of compounds of Formula I, Y is N.

In other embodiments, Y is $CR^4$. In certain embodiments, $R^4$ is H.

In certain embodiments of compounds of Formula I, L is O.

In certain embodiments of compounds of Formula I, L is S.

In certain embodiments of compounds of Formula I, L is $CHR^{14}$. In certain embodiments, $R^{14}$ is H.

The compounds of Formula I include compounds having the Formula Ia:

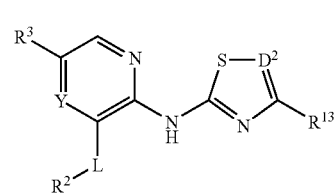

Ia and tautomers, resolved enantiomers, resolved diastereomers, racemic mixtures, solvates, metabolites, salts and pharmaceutically acceptable prodrugs thereof, wherein:

L is O, S, or $CH_2$;

Y is N or CH;

$D^2$ is N or $CR^{12}$;

$R^2$ is aryl, heteroaryl, saturated or partially unsaturated cycloalkyl, or saturated or partially unsaturated heterocyclyl, wherein said aryl, heteroaryl, cycloalkyl and heterocyclyl are monocyclic or bicyclic and are optionally substituted with one or more groups independently selected from $C_1$-$C_6$ alkyl, $(C_1$-$C_6$ alkyl)OH, $C_1$-$C_6$ heterocyclyl, F, Cl, Br, $CF_3$, CN, $NO_2$, $OR^6$, $C(=O)R^6$, $C(=O)OR^6$, $C(=O)NR^6R^7$, $S(O)_2R^6$, $C(O)CH_2NH_2$, and $C(O)CH_2NR^aR^b$;

R³ is H, C₁-C₁₂ alkyl, aryl, heteroaryl, F, Cl, Br, OR⁶, or SR⁶, wherein said alkyl, aryl and heteroaryl are optionally substituted with one or more groups independently selected from C₁-C₆ alkyl, C₂-C₆ alkenyl, saturated and partially unsaturated C₁-C₆ heterocyclyl, $V_n$—OR⁸, $V_n$—C(=O)OR⁸, and $V_n$—NR⁸R⁹;

R⁶ and R⁷ are independently H, C₁-C₁₂ alkyl, saturated or partially unsaturated C₃-C₁₂ cycloalkyl, saturated or partially unsaturated C₁-C₁₂ heterocyclyl, $V_n$-aryl, or $V_n$-heteroaryl, wherein said alkyl, cycloalkyl, heterocyclyl, aryl and heteroaryl portions are optionally substituted with one or more groups independently selected from C₁-C₆ alkyl, saturated and partially unsaturated C₁-C₆ heterocyclyl [optionally substituted with C(O)O(C₁-C₆ alkyl) or (C₁-C₆ alkyl)OH], aryl, heteroaryl, F, Cl, Br, I, CN, OR⁸, C(=O)R⁸, C(=O)OR⁸, C(=O)NR⁸R⁹, NR¹R⁹, NR⁸C(=O)R⁹ or (C₁-C₆ alkyl)OH, or R⁶ and R⁷ together with the atoms to which they are attached form a saturated or partially unsaturated heterocyclic ring, wherein said heterocyclic ring optionally comprises one or more additional ring heteroatoms independently selected from N, O or S;

R⁸, R⁹ and R¹⁰ are independently H, C₁-C₆ alkyl, or saturated and partially unsaturated C₁-C₆ heterocyclyl, wherein said alkyl and heterocyclyl are optionally substituted with one or more groups independently selected from C₁-C₆ alkyl, saturated and partially unsaturated C₁-C₆ heterocyclyl, OR$^a$, NR$^a$R$^b$, C(=O)OR$^a$ and C(=O)NR$^a$R$^b$, or R⁸ and R⁹ together with the atoms to which they are attached form a saturated or partially unsaturated heterocyclic ring;

or R⁹ and R¹⁰ together with the atoms to which they are attached form a saturated or partially unsaturated heterocyclic ring;

R¹² is H or C₁-C₆ alkyl;

R¹³ is H, C₁-C₆ alkyl, saturated and partially unsaturated C₃-C₆ cycloalkyl, saturated and partially unsaturated C₁-C₆ heterocyclyl, CH₂-heteroaryl, aryl, heteroaryl, (1-3C alkyl) heteroaryl, or (CH₂)$_n$(CR$^x$R$^y$)C(O)NR⁸R⁹, wherein said alkyl, alkenyl, alkynyl, cycloalkyl, CH₂-heterocyclyl, heterocyclyl, aryl, heteroaryl and (1-3C alkyl)heteroaryl are optionally substituted with one or more groups independently selected from oxo, F, Cl, CF₃, CN, OR⁸, C(=O)OR⁸, C(=O)NR⁸R⁹, NR⁸R⁹, C(O)(C₁-C₆ alkyl), C(O)-heterocycle [optionally substituted with O—(C₁-C₆ alkyl) or oxo], SR$^a$, SO₂R$^f$, SO₂NR$^c$R$^e$, C(O)(C₁-C₆ alkyl)NR$^c$R$^d$, C(O)(C₁-C₆ alkyl)OR$^c$, C(O)CH₂C(O)(C₁-C₆ alkyl), C(=O)CHR$^g$NHC(=O)(C₁-C₆ alkyl), C(O)CH₂C(=O)(C₁-C₆ alkyl), C₁-C₆ alkyl, 5-6 membered heterocycle (optionally substituted with oxo) and aryl, or R¹² and R¹³ together with the atoms to which they are attached form an heteroaryl ring;

R$^a$ and R$^b$ are independently H, C₁-C₆ alkyl, saturated or partially unsaturated C₁-C₆ heterocyclyl;

each R$^c$, R$^e$ and R$^g$ is independently H or C₁-C₆ alkyl;

R$^d$ is H, C₁-C₆ alkyl or C(O)O(C₁-C₆ alkyl);

R$^f$ is C₁-C₆ alkyl or (C₁-C₆ alkyl)NH₂;

V is alkylene having from 1 to 4 carbons, or alkenylene having from 2 to 4 carbons, wherein said alkylene and alkenylene are optionally substituted with C₁-C₆ alkyl, O(C₁-C₆ alkyl), or (C₁-C₆ alkyl)NR$^c$R$^e$; and n is 0 or 1.

Exemplary embodiments of R¹ include, but are not limited to, heteroaryl rings selected from

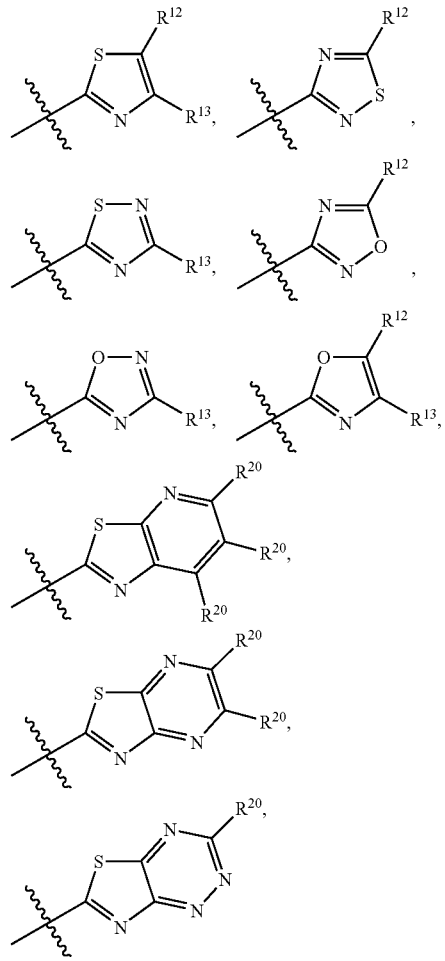

wherein R²⁰ is H, alkyl, alkenyl, alkynyl, saturated or partially unsaturated cycloalkyl, saturated or partially unsaturated heterocyclyl, aryl, heteroaryl, F, Cl, Br, I, CF₃, CN, OR⁶, C(=O)R⁶, C(=O)OR⁶, OC(=O)R⁶, C(=O)NR⁶R⁷, NR⁶R⁷, NR⁶C(=O)R⁷, SR⁶, S(O)R⁶, S(O)₂R⁶ or SO₂NR⁶R⁷, wherein said alkyl, alkenyl, alkynyl, cycloalkyl, heterocyclyl, aryl and heteroaryl are optionally substituted with one or more groups independently selected from $V_n$—F, $V_n$—Cl, $V_n$—Br, $V_n$—I, $V_n$—CF₃, $V_n$—CN, $V_n$—OR⁸, $V_n$—C(=O)OR⁸, $V_n$—OC(=O)R⁸, $V_n$—C(=O)NR⁸R⁹, $V_n$—NR⁸R⁹, $V_n$—NR⁸C(=O)R⁹, alkyl, alkenyl, alkynyl, saturated and partially unsaturated $V_n$-cycloalkyl, saturated and partially unsaturated $V_n$-heterocyclyl, $V_n$-aryl, and $V_n$-heteroaryl, and each R²⁰ is independent of the other.

In certain embodiments, R¹ is

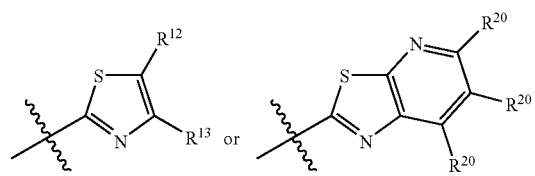

wherein R¹² and R¹³ are as defined herein.

In particular embodiments, R²⁰ is H.

In other embodiments, $R^1$ is

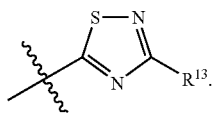

In certain embodiments, $R^{12}$ and $R^{13}$ are independently selected from H, alkyl, or cycloalkyl, wherein said alkyl and cycloalkyl are optionally substituted. For example, in certain embodiments $R^{12}$ and $R^{13}$ are independently selected from H, methyl, ethyl, isopropyl, butyl, isobutyl, cyclopropyl, $CH_2CH_2COOMe$, $CH_2COOH$, and $CH_2CH_2COOH$.

In certain embodiments, $R^{12}$ is H or $C_1$-$C_6$ alkyl.

In certain embodiments, $R^{12}$ is H.

In other embodiments, $R^{13}$ is selected from H, $C_1$-$C_6$ alkyl, cycloalkyl, heterocyclyl, $CH_2$-heterocyclyl, aryl, heteroaryl, (1-3C alkyl)heteroaryl, or $(CH_2)_m(CR^xR^y)C(O)NR^8R^9$, wherein said alkyl, cycloalkyl, heterocyclyl, $CH_2$-heterocyclyl, aryl, heteroaryl, and (1-3C alkyl)heteroaryl are optionally substituted with one or more groups independently selected from oxo, F, Cl, $CF_3$, CN, $OR^8$, $C(=O)OR^8$, $C(=O)NR^8R^9$, $NR^8R^9$, $C(O)(C_1$-$C_6$ alkyl), C(O)-heterocycle [optionally substituted with O—($C_1$-$C_6$ alkyl], $SR^a$, $SO_2R^f$, $SO_2NR^cR^e$, $C(O)(C_1$-$C_6$ alkyl)$NR^cR^d$, $C(O)(C_1$-$C_6$ alkyl)$OR^c$, $C(O)CH_2C(O)(C_1$-$C_6$ alkyl), $C(=O)CHR^gNHC(=O)(C_1$-$C_6$ alkyl), $C(=O)CH_2C(=O)(C_1$-$C_6$ alkyl), $C_1$-$C_6$ alkyl, $C_1$-$C_6$heterocyclyl (optionally substituted with oxo), and aryl.

For example, in certain embodiments $R^{13}$ is selected from H, $C_1$-$C_6$ alkyl, chloro($C_1$-$C_6$ alkyl), $CF_3$, (3-6C)cycloalkyl, ($C_1$-$C_6$ alkyl)CN, ($C_1$-$C_6$ alkyl)$CO_2R^8$, ($C_1$-$C_6$ alkyl)$SR^a$, ($C_1$-$C_6$ alkyl)$SO_2R^f$, ($C_1$-$C_6$ alkyl)aryl, ($C_1$-$C_6$ alkyl)$OR^8$, ($C_1$-$C_6$ alkyl)$NR^8R^9$, $(CH_2)_n(CR^xR^y)C(O)NR^8R^9$, $(CH_2)_n(CR^xR^y)C(O)NH—N=CHNR^8R^9$, ($C_1$-$C_6$ alkyl)C(O)-heterocyclyl, aryl, heteroaryl, ($C_1$-$C_6$ alkyl)$hetAr^1$, $CH_2(CR^xR^y)C(O)OR^8$, $CH_2(CR^xR^y)C(O)$heterocyclyl [optionally substituted with one or two groups selected from O—($C_1$-$C_6$ alkyl) and oxo], $CH_2CH(CO_2H)$—$CH_2CH_2NHR^a$, $hetCyc^1$ and $CH_2hetCyc^2$, wherein:

$R^x$ and $R^y$ are independently H, methyl or OMe, n is 0 or 1, $hetCyc^1$ is a heterocyclic ring optionally substituted with one or more groups independently selected from $C_1$-$C_6$ alkyl, $C(O)(C_1$-$C_6$ alkyl), ($C_1$-$C_6$ alkyl)OH, $C(O)O(C_1$-$C_6$ alkyl), $C(O)(C_1$-$C_6$ alkyl)$NR^cR^d$, $C(O)(C_1$-$C_6$ alkyl)$OR^c$, $C(O)CH_2C(O)(C_1$-$C_6$ alkyl), $C(O)NR^aR^b$, $SO_2NR^cR^e$, $SO_2R^f$, $C(=O)CHR^gNHC(=O)(C_1$-$C_6$ alkyl), and $C(=O)CH_2OC(=O)(C_1$-$C_6$ alkyl).

$hetCyc^2$ is a heterocyclic ring optionally substituted with one or more groups independently selected from $C_1$-$C_6$ alkyl, $C(O)(C_1$-$C_6$ alkyl), $C(O)O(C_1$-$C_6$ alkyl), and oxo, and $hetAr^1$ is a heteroaryl ring optionally substituted with $C_1$-$C_6$ alky, OH or $CF_3$, and $R^a$, $R^b$, $R^c$, $R^d$, $R^e$ and $R^f$ are as defined herein.

Examples of $R^{13}$ when represented by $C_1$-$C_6$ alkyl include methyl, ethyl, isopropyl, isobutyl, and butyl.

Examples $R^{13}$ when represented by chloro($C_1$-$C_6$ alkyl) include alkyl groups wherein any one of the hydrogens is replaced with a chloro group. A particular example is $CH_2Cl$.

Examples of $R^{13}$ when represented by (3-6C)cycloalkyl include cyclobutyl and cyclohexyl.

Examples of $R^{13}$ when represented by ($C_1$-$C_6$ alkyl)CN include alkyl groups wherein any one of the hydrogens is replaced with a nitrile group. A particular example is $CH_2CN$.

Examples of $R^{13}$ when represented by ($C_1$-$C_6$ alkyl)$CO_2R^8$ include alkyl groups wherein any one of the hydrogens is replaced with a $CO_2R^8$ group. In certain embodiments, $R^8$ is H or $C_1$-$C_6$ alkyl. Particular values of $R^{13}$ include $CH_2CH_2CO_2H$, $CH_2CH_2CO_2Me$, $CH_2CO_2H$, $C(CH_3)_2CO_2H$, $CH_2C(CH_3)_2CO_2H$, and $C(CH_3)_2CH_2CO_2H$.

Examples of $R^{13}$ when represented by ($C_1$-$C_6$ alkyl)$SR^a$ include alkyl groups wherein any one of the hydrogens is replaced with a $SR^a$ group. In certain embodiments, $R^a$ is $C_1$-$C_6$ alkyl, aryl or heteroaryl. Examples of heteroaryl groups include 5-membered rings having 1-3 atoms independently selected from N and O (provide the ring does not contain an O—O bond). In certain embodiments, the heteroaryl is substituted with $C_1$-$C_6$ alkyl. Particular values of $R^{12}$ and $R^{13}$ when represented by ($C_1$-$C_6$ alkyl)$SR^a$ include $CH_2CH_2SMe$, $CH_2SPh$ and $CH_2$—S-(2-methyl-1,3,4-oxadiazol-5-yl).

Examples of $R^{13}$ when represented by ($C_1$-$C_6$ alkyl)$SO_2R^f$ include alkyl groups wherein any one of the hydrogens is replaced with a $SO_2R^f$ group. In certain embodiments, $R^f$ is ($C_1$-$C_6$ alkyl). Particular values of $R^{12}$ and $R^{13}$ include $CH_2CH_2SO_2Me$.

Examples of $R^{13}$ when represented by ($C_1$-$C_6$ alkyl)aryl include $CH_2Ph$ and $CH_2CH_2Ph$.

Examples of $R^{13}$ when represented by ($C_1$-$C_6$ alkyl)$OR^9$ include alkyl groups wherein any one of the hydrogens is replaced with a $OR^8$ group. In certain embodiments, $R^8$ is aryl or heteroaryl. Examples of heteroaryl groups include 5-membered rings having 1-3 atoms independently selected from N and O (provide the ring does not contain an O—O bond). In certain embodiments, the heteroaryl ring is substituted with one or more groups independently selected from $C_1$-$C_6$ alkyl and $CF_3$. Particular values of $R^{13}$ when represented by ($C_1$-$C_6$ alkyl)$OR^8$ include $CH_2OPh$ and $CH_2O$-(1-methyl-3-(trifluoromethyl)-1H-pyrazol-5-yl).

Examples of $R^{13}$ when represented by ($C_1$-$C_6$ alkyl)$NR^8R^9$ include alkyl groups wherein any one of the hydrogens is replaced with a $NR^8R^9$ group. In certain embodiments, $R^8$ is H or methyl and $R^9$ is aryl or heteroaryl. Examples of heteroaryl groups include 5-membered rings having 1-3 atoms independently selected from N and O (provide the ring does not contain an O—O bond). In certain embodiments, the heteroaryl ring is substituted with $C_1$-$C_6$ alkyl. Particular values of $R^{12}$ and $R^{13}$ when represented by ($C_1$-$C_6$ alkyl)$NR^8R^9$ include $CH_2NHPh$ and $CH_2NH$(2-methyl-1,3,4-oxadiazol-5-yl).

In certain embodiments, $R^{13}$ are an alkyl group that is substituted with two or three groups independently selected from $C_1$-$C_6$ alkyl, $O(C_1$-$C_6$ alkyl) and $NR^8R^9$. In one embodiment, $R^{12}$ and $R^{13}$ can be represented by the formula $(CH_2)_n(CR^xR^y)C(O)NR^8R^9$ wherein $R^x$ and $R^y$ are independently H, Me or OMe and n is 0 or 1.

Examples of $R^{13}$ when represented by $(CH_2)_n(CR^xR^y)C(O)NR^8R^9$ include groups wherein $R^8$ and $R^9$ are independently H or ($C_1$-$C_6$ alkyl), and $R^x$ and $R^y$ are H. Particular values include $CH_2CH_2C(O)NHMe$, $CH_2CH_2C(O)NMe_2$, $CH_2C(O)NHMe$, and $CH_2C(O)NMe_2$.

Additional examples of $R^{13}$ when represented by $(CH_2)_n(CR^xR^y)C(O)NR^8R^9$ include groups wherein $R^8$ is H or Me, $R^9$ is ($C_1$-$C_6$ alkyl)OH or ($C_1$-$C_6$ alkyl)O($C_1$-$C_6$ alkyl), $R^x$ is H or Me, and $R^y$ is H, Me, or OMe. Particular values include $CH_2CH_2C(O)NHCH_2CH_2OMe$, $CH_2CH_2C(O)NHCH_2CH_2OH$, $CH_2C(O)NHCH_2CH_2OMe$, $CH_2C(O)NHCH_2CH_2OH$, $CH_2C(CH_3)_2C(O)NHCH_2CH_2OH$, $CH_2C(CH_3)(OMe)C(O)NHCH_2CH_2OH$, and $CH_2C(CH_3)(OMe)C(O)NHCH_2CH_2OMe$.

Additional examples of $R^{13}$ when represented by $(CH_2)_n(CR^xR^y)C(O)NR^8R^9$ include groups wherein $R^x$ and $R^y$ are H, $R^8$ is H or Me, and $R^9$ is $(C_1-C_6$ alkyl$)NR^aR^b$. In certain embodiments, $R^a$ and $R^b$ are independently H or $C_1-C_6$ alkyl. Particular values include $CH_2CH_2C(O)NHCH_2CH_2NMe_2$ and $CH_2C(O)NHCH_2CH_2NMe_2$.

Examples of $^{13}$ when represented by $(CH_2)_n(CR^xR^y)C(O)NH-N=CHNR^aR^b$ include groups wherein $R^a$ and $R^b$ are independently H or $C_1-C_6$ alkyl. Particular values include $CH_2C(CH_3)(OMe)C(O)NH-N=CHNMe_2$.

Examples of $R^{13}$ when represented by $(C_1-C_6$ alkyl$)C(O)$heterocyclyl include alkyl groups wherein any one of the hydrogens is replaced with a $C(O)$heterocyclyl moiety. In certain embodiments, the heterocyclyl is a 5-6 membered ring having at least one nitrogen atom, for example a pyrrolidinyl ring. Particular values include $CH_2CH_2C(O)$(pyrrolidin-1-yl) and $CH_2C(O)$(pyrrolidin-1-yl).

An example of $R^{13}$ when represented by aryl is a phenyl group.

Examples of $R^{13}$ when represented by heteroaryl include 5-6 membered heteroaryl rings having one or two atoms independently selected from N and S. Particular values include pyridyl and thienyl.

Examples of $R^{13}$ when represented by $(C_1-C_6$ alkyl$)$hetAr$^1$ include alkyl groups wherein any one of the hydrogens is replaced with a hetAr$^1$ group. In certain embodiments, hetAr$^1$ is a 5-6 membered heteroaryl ring having 2-4 atoms independently selected from N and O (provided the ring does not have an O—O bond). Examples include oxazolyl, oxadiazolyl and tetrazolyl rings. In certain embodiments, hetAr$^1$ is substituted with $C_1-C_6$ alkyl or OH. Particular values of $R^{13}$ when represented by $(C_1-C_6$ alkyl$)$hetAr$^1$ include the structures:

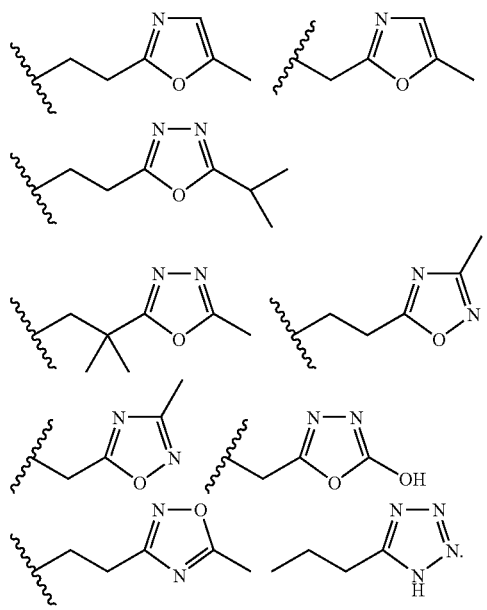

Examples of $R^{13}$ when represented by $CH_2(CR^xR^y)C(O)OR^8$ include groups wherein $R^8$ is H or $C_1-C_6$ alkyl. Particular values include $CH_2C(CH_2)(OMe)CO_2Me$ and $CH_2C(CH_2)(OMe)CO_2H$.

Examples of $R^{13}$ when represented by $CH_2(CR^xR^y)C(O)$heterocyclyl include groups wherein the heterocyclyl is a 5-membered heterocyclyl having at least one nitrogen, for example pyrrolidinyl. In certain embodiments the heterocyclyl is substituted with O—$(C_1-C_6$ alkyl$)$. Particular values include $CH_2C(CH_2)(OMe)C(O)$(pyrrolidin-1-yl) and $CH_2C(CH_2)(OMe)C(O)$-(3-methoxypyrrolidin-1-yl).

Examples of $R^{13}$ when represented by $CH_2CH(CO_2H)-CH_2CH_2NHR^8$ include groups wherein $R^8$ is H or $C_1-C_6$ alkyl. Particular values include $CH_2CH(CO_2H)-CH_2CH_2NH_2$ and $CH_2CH(CO_2H)-CH_2CH_2NHCO_2$-(t-butyl).

Examples of $R^{13}$ when represented by hetCyc$^1$ include groups wherein hetCyc$^1$ is a 5-6 membered ring having an atom selected from N and O.

An exemplary embodiment of hetCyc$^1$ is tetrahydrofuranyl.

Further exemplary embodiments of hetCyc$^1$ include piperidinyl and pyrrolidinyl rings.

In certain embodiments, hetCyc$^1$ is C-linked, that is, hetCyc$^1$ is linked to $R^1$ through a carbon atom of the hetCyc$^1$ ring.

In certain embodiments, hetCyc$^1$ is a piperidinyl or pyrrolidinyl ring substituted by one or two groups independently selected from $C_1-C_6$ alkyl, $C(O)(C_1-C_6$ alkyl$)$, $(C_1-C_6$ alkyl$)$OH, $C(O)O(C_1-C_6$ alkyl$)$, $C(O)(C_1-C_6$ alkyl$)NR^cR^d$, $C(O)(C_1-C_6$ alkyl$)OR^e$, $C(O)CH_2C(O)(C_1-C_6$ alkyl$)$, $C(O)NR^aR^b$, $SO_2NR^cR^e$, and $SO_2R^f$.

For example, in certain embodiments, hetCyc$^1$ is a piperidinyl or pyrrolidinyl ring optionally substituted with one or two groups independently selected from methyl, $C(O)(C_1-C_6$ alkyl$)$, $(C_1-C_6$ alkyl$)$OH, $C(O)O(C_1-C_6$ alkyl$)$, $C(O)(C_1-C_6$ alkyl$)$NH$(C_1-C_6$ alkyl$)$, $C(O)(C_1-C_6$ alkyl$)$NH$(C_1-C_6$ alkyl$)$, $C(O)(C_1-C_6$ alkyl$)$NHCO$_2(C_1-C_6$ alkyl$)$, $C(O)(C_1-C_6$ alkyl$)$OH, $C(O)CH_2C(O)(C_1-C_6$ alkyl$)$, $C(O)NH_2$, $C(O)NH(C_1-C_6$ alkyl$)$, $C(O)N(C_1-C_6$ alkyl$)_2$, $SO_2NH_2$, $SO_2NMe_2$, $SO_2Me$, $SO_2(C_2-C_6$ alkyl$)NH_2$, $C(=O)CHR^gNHC(=O)(C_1-C_6$ alkyl$)$, and $C(=O)CH_2C(=O)(C_1-C_6$ alkyl$)$.

In certain embodiments, the substituent is on the N atom of hetCyc$^1$.

Particular values for $R^{13}$ when represented by hetCyc$^1$ include the structures:

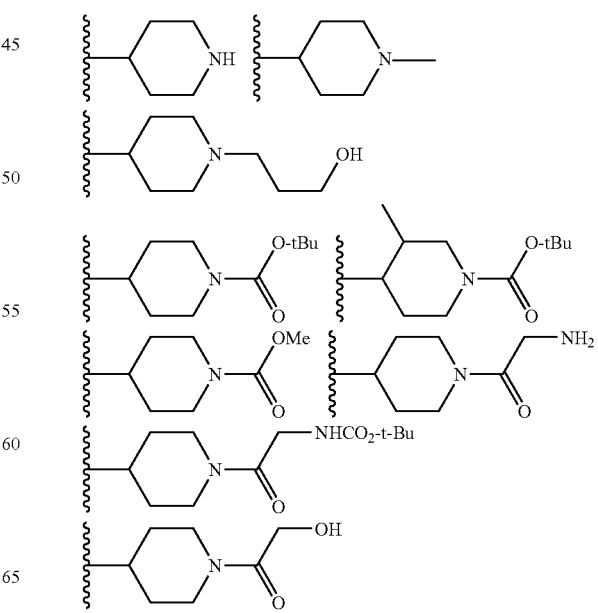

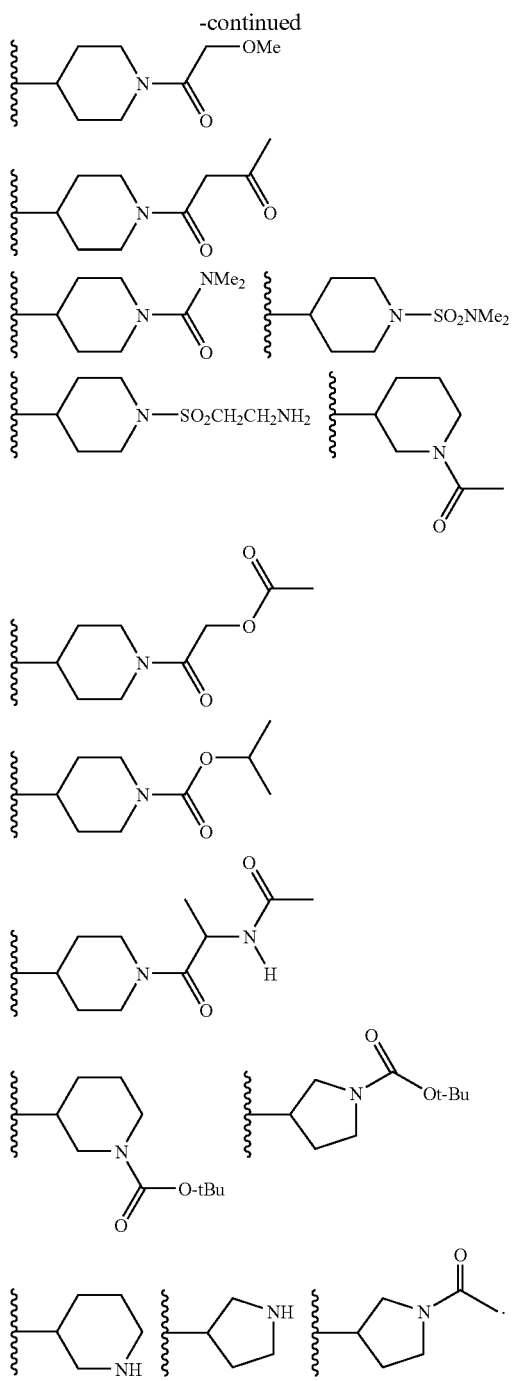

In particular embodiment of Formula I, hetCyc¹ has the formula

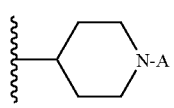

wherein A is C(=O)(C₁-C₆ alkyl), C(=O)NH₂, C(=O)NMe₁, CO₂Me, or SO₂NH₂, wherein any one of the carbons atoms of hetCyc¹ is optionally substituted with methyl. Particular values of hetCyc¹ include the formulas:

Examples of $R^{13}$ when represented by $CH_2hetCyc^2$ include groups wherein $hetCyc^2$ is a 5-6 membered ring having one or two nitrogen atoms. Examples include piperidinyl, pyrrolidinyl and piperazinyl groups. In certain embodiments, $hetCyc^2$ is substituted with one or more groups independently selected from $C_1$-$C_6$ alkyl, $C(O)(C_1$-$C_6$ alkyl), $C(O)O(C_1$-$C_6$ alkyl), and oxo. Particular values for $R^{13}$ when represented by $CH_2hetCyc^2$ include the structures:

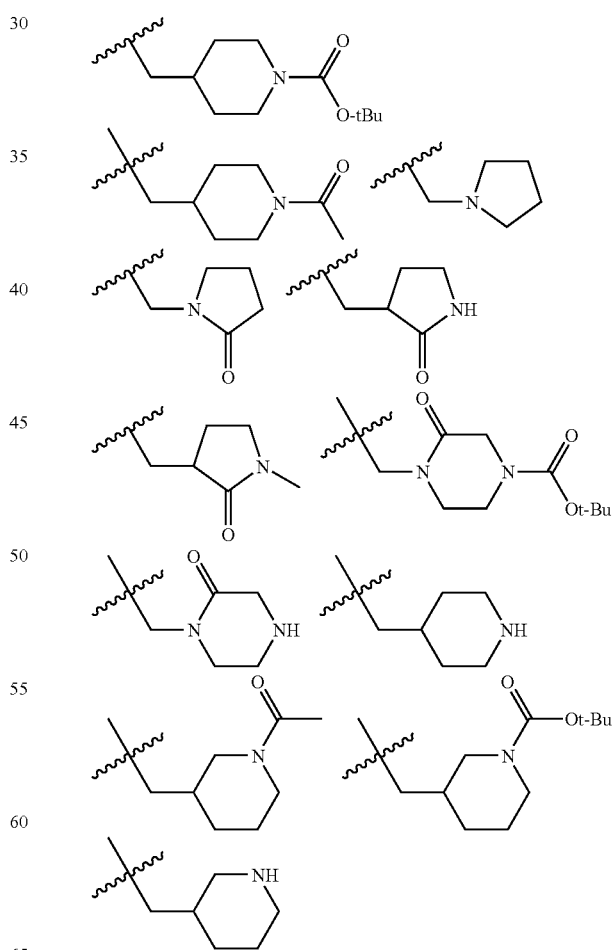

In certain embodiments, $R^{12}$ is H.

In certain embodiments of Formula I, $R^2$ includes, but are not limited to, an aryl, or a saturated or partially unsaturated cycloalkyl ring selected from phenyl, 1-naphthyl, 2-naphthyl, 1-tetrahydronaphthalenyl, 2-tetrahydronaphthalenyl, 3-tetrahydronaphthalenyl, 4-tetrahydronaphthalenyl, 5-tetrahydronaphthalenyl, 6-tetrahydronaphthalenyl, 7-tetrahydronaphthalenyl, 8-tetrahydronaphthalenyl, cyclohexyl, cyclopentyl, cyclohexenyl, and substituted forms thereof.

In certain embodiments, $R^2$ is selected from

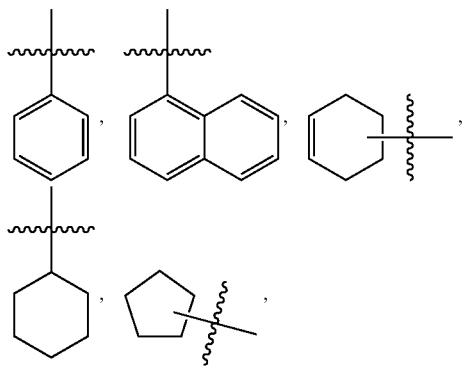

wherein $R^2$ is optionally substituted with one or more $R^{20a}$ groups, wherein $R^{20a}$ is selected from alkyl, alkenyl, alkynyl, saturated or partially unsaturated cycloalkyl, saturated or partially unsaturated heterocyclyl, aryl, heteroaryl, F, Cl, Br, I, $CF_3$, CN, $OR^6$, $C(=O)R^6$, $C(=O)OR^6$, $OC(=O)R^6$, $C(=O)NR^6R^7$, $NR^6R^7$, $NR^6C(=O)R^7$, $SR^6$, $S(O)R^6$, $S(O)_2R^6$ and $SO_2NR^6R^7$.

For example, in certain embodiments, $R^2$ is phenyl optionally substituted with one or more groups independently selected from F, Cl, Br, I, CN, alkyl, $NO_2$, $SO_2R^6$, $OR^6$, $C(=O)OR^6$, and $NR^6C(=O)R^7$, wherein said alkyl is optionally substituted with $V_n$—$NR^8R^9$, $V_n$—$C(=O)OR^8$, or $V_n$—$OC(=O)R^8$.

In other embodiments, $R^2$ is phenyl optionally substituted with one or more groups independently selected from F, Cl, Br, CN, $CF_3$, $C_1$-$C_6$ alkyl, $NO_2$, —$SO_2(C_1$-$C_6$ alkyl), OH, —O($C_1$-$C_6$ alkyl), —$CO_2H$, —$CO_2(C_1$-$C_6$ alkyl), —C(O)heterocyclyl [optionally substituted with $C_1$-$C_6$ alkyl], heterocyclyl and —C(O)$NR^8R^9$. In certain embodiments, $R^8$ is H or $C_1$-$C_6$ alkyl and $R^9$ is H or $C_1$-$C_6$ alkyl optionally substituted with $NH_2$, $NH(C_1$-$C_6$ alkyl) or $N(C_1$-$C_6$ alkyl). Examples of the heterocycle group for the C(O)heterocyclyl substituent of $R^2$ include 5-6 membered heterocyclic rings having one or two atoms selected from N and O (for example morpholinyl).

In particular embodiments of Formula I, $R^2$ is phenyl optionally substituted with one or two groups independently selected from F, Cl, Br, CN, $CF_3$, $NO_2$, $SO_2Me$, OMe, OH, $CO_2H$, $CO_2Me$, $CO_2Et$, $C(O)NHCH_2CH_2NMe_2$, $C(O)NH_2$, C(O)(4-methylpiperazinyl), and morpholinyl.

Exemplary embodiments of $R^2$ include, but are not limited to, the structures:

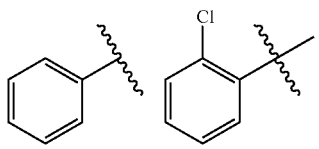

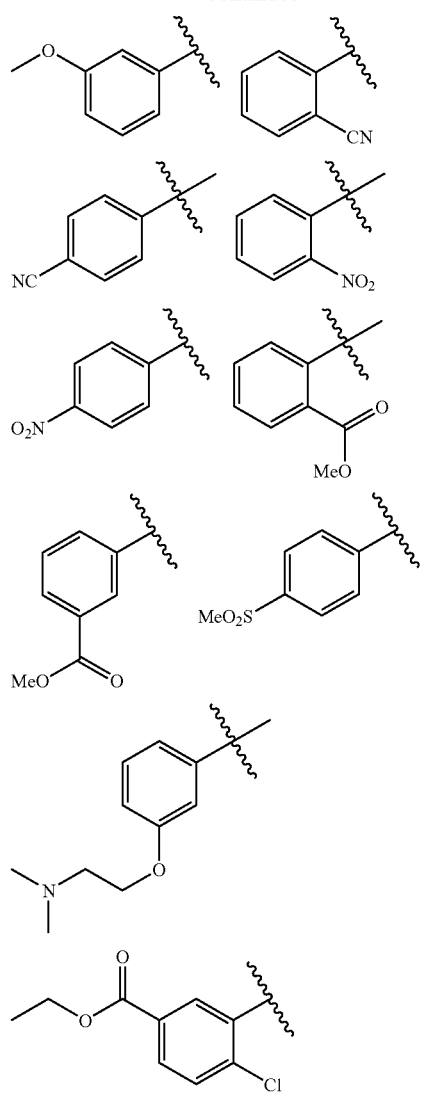

Further exemplary embodiments of $R_2$ include the structures:

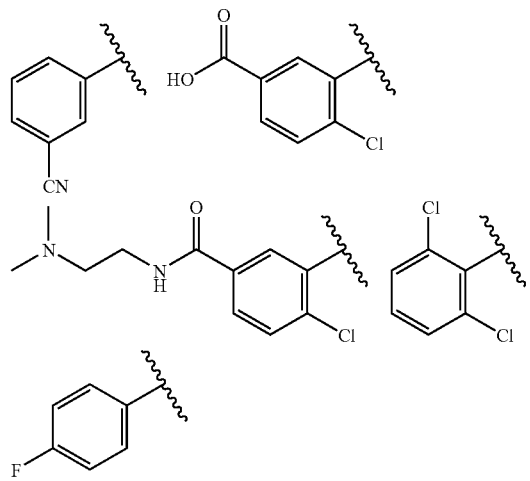

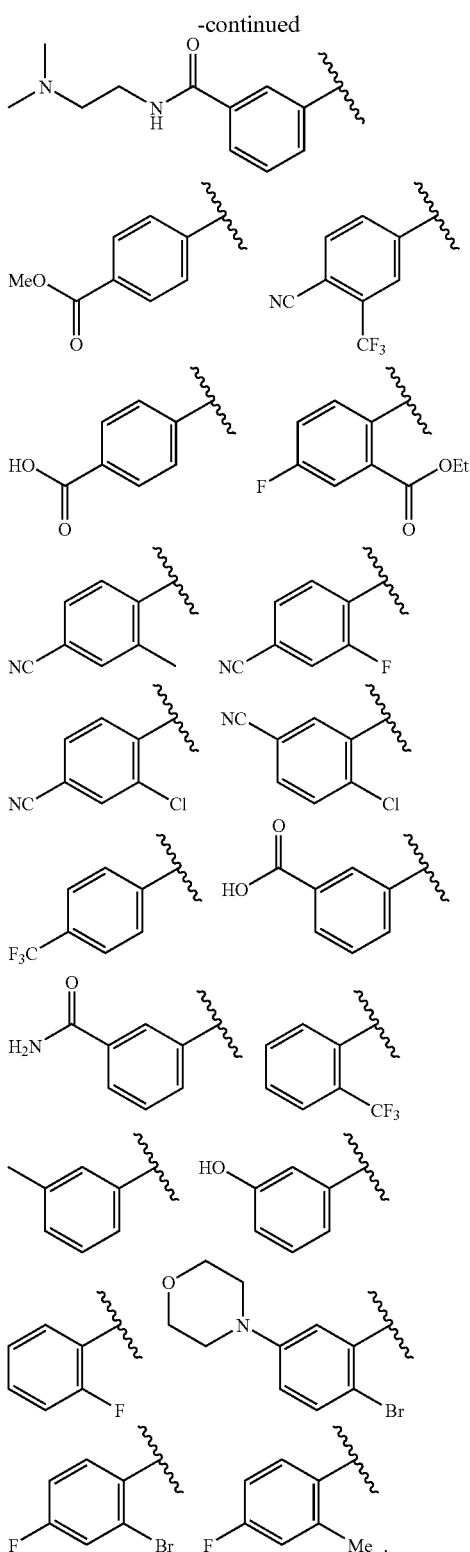

olyl, 5-benzo[d]thiazolyl, 6-benzo[d]thiazolyl, 7-benzo[d]thiazolyl, 2-1H-benzo[d]imidazolyl, 1H-benzo[d]imidazole-4-yl, 1H-benzo[d]imidazole-5-yl, 1H-benzo[d]imidazole-6-yl, 1H-benzo[d]imidazole-7-yl, 2-thiophenyl, 3-thiophenyl, 5-tetrahydroquinolinyl, 6-tetrahydroquinolinyl, 7-tetrahydroquinolinyl, 8-tetrahydroquinolinyl, 5-tetrahydroisoquinolinyl, 6-tetrahydroisoquinolinyl, 7-tetrahydroisoquinolinyl, 8-tetrahydroisoquinolinyl, 1-pyrazolyl, 2-pyrazolyl, 3-pyrazolyl, 4-pyrazolyl, 5-pyrazolyl, 1-piperidinyl, 2-piperidinyl, 3-piperidinyl, 4-piperidinyl, 2-pyrrolinyl, 3-pyrrolinyl, 4-pyrrolinyl, 5-pyrrolinyl, 2-piperidinyl, 3-piperidinyl, 4-piperidinyl, 5-piperidinyl, 6-piperidinyl, 2-pyrrolidinyl, 3-pyrrolidinyl, 4-pyrrolidinyl, 5-pyrrolidinyl, and substituted forms thereof.

In other embodiments, $R^2$ is a 5-6 membered heteroaryl ring having 1-2 nitrogen atoms. Examples of heteroaryl rings include 2-pyridyl, 3-pyridyl, 4-pyridyl, 2-pyrimidyl, 2-imidazolyl, and 4-imidazolyl. In certain embodiments, $R^2$ is a heteroaryl ring optionally substituted with one or two groups independently selected from $C_1$-$C_6$ alkyl, $CO_2(C_1$-$C_6$ alkyl), $C(O)NH(C_1$-$C_6$ alkyl), $C(O)NH(C_1$-$C_6$ alkylN(di-$C_1$-$C_6$ alkyl), or ($C_1$-$C_6$ alkyl)OH.

In other embodiments, $R^2$ is a 9-10 membered bicyclic heteroaryl ring having a having 1 to 2 ring atoms independently selected from N and S.

In other embodiments, $R^2$ is a 5 membered heterocyclic ring having at least one nitrogen atom, for example a pyrrolidinyl ring. In certain embodiments, the heterocyclic ring is substituted with $CO_2$—($C_1$-$C_6$ alkyl), $C(O)NH(C_1$-$C_6$ alkyl), $C(O)CH_2N(C_1$-$C_6$ alkyl)$_2$, $C(O)(C_1$-$C_6$ alkyl)$CO_2H$, or $SO_2$— (heteroaryl), wherein said heteroaryl of the $SO_2$-heteraryol group is a 5-membered ring having 1-2 nitrogen atoms and optionally substituted with $C_1$-$C_6$ alkyl.

For example, in certain embodiments $R^2$ is selected from the structures:

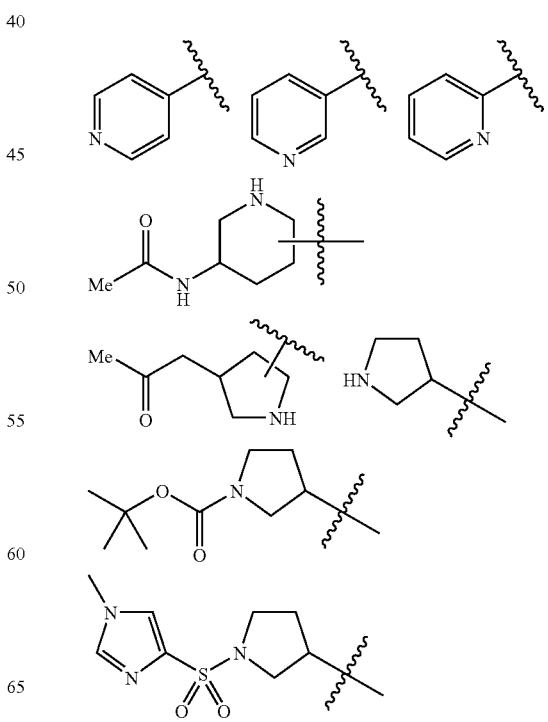

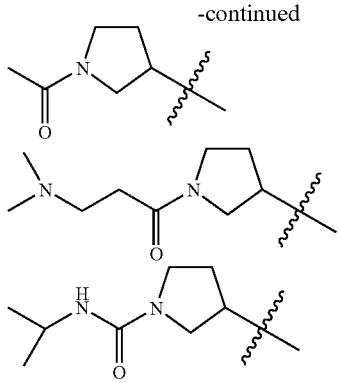

and substituted forms thereof.

Further exemplary embodiments of $R^2$ when represented by a heteroaryl ring include the structures:

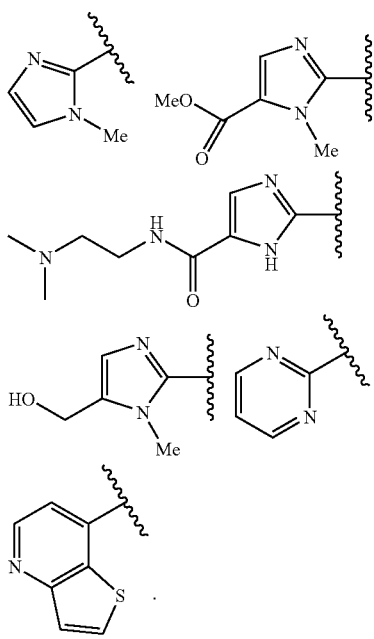

In certain embodiments of Formula I, Z is N.

In other embodiments of Formula I, Z is $CR^3$.

In certain embodiment, $R^3$ is selected from halogen, $C(=O)R^6$, $SR^6$, $OR^6$, heteroaryl, alkyl, or alkenyl, wherein said heteroaryl, alkyl and alkenyl are optionally substituted.

In other embodiments, $R^3$ is H, Br, Cl, $SR^6$, $OR^6$, aryl, heteroaryl, or $C_1$-$C_6$ alkyl wherein said aryl is optionally substituted with Cl and said alkyl is optionally substituted with $C(O)OR^8$, $NR^8R^9$, or $OR^8$.

In certain embodiments, $R^3$ includes Br, Cl and $C(=O)H$.

In certain embodiments, $R^3$ is H.

In certain embodiments, $R^3$ is Br.

In certain embodiments, $R^3$ is $SR^6$.

For example, in certain embodiments, $R^3$ is $SR^6$ wherein $R^6$ is $V_n$-aryl, $V_n$-heteroaryl, $V_n$-heterocyclyl, $V_n$-cycloalkyl or alkyl, wherein said aryl, heteroaryl, heterocyclyl, cycloalkyl and alkyl portions are optionally substituted. Exemplary embodiments include, but are not limited to, the structures:

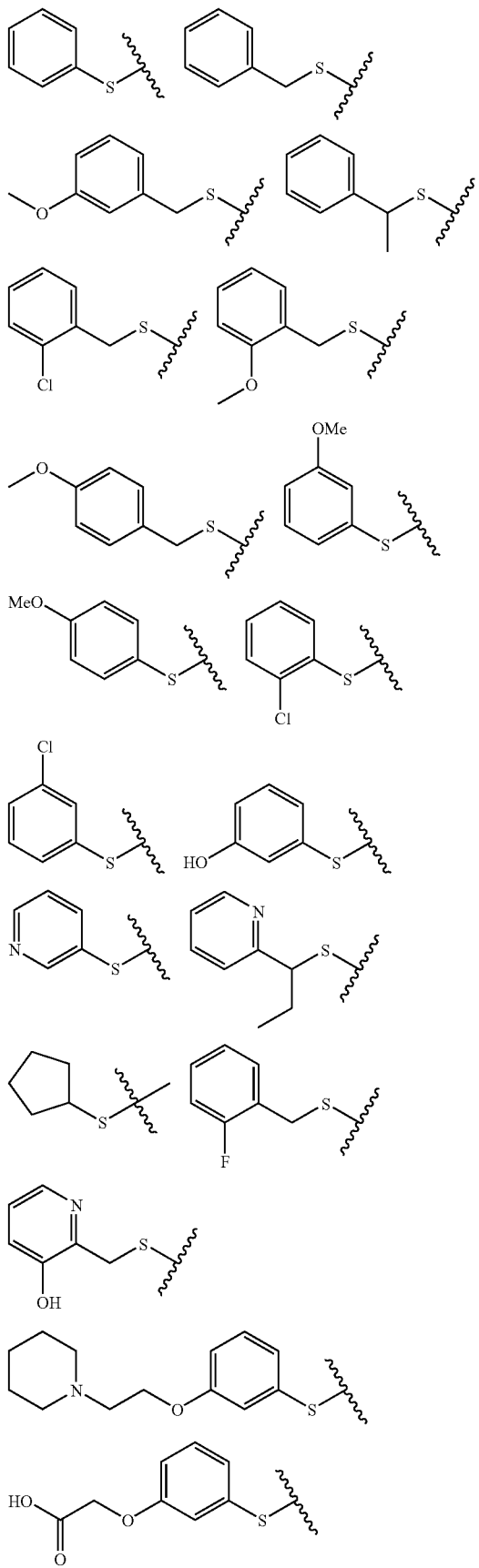

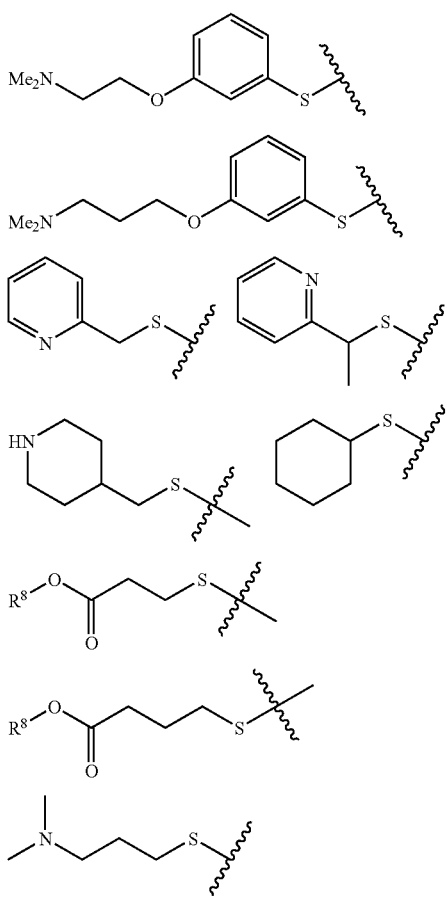

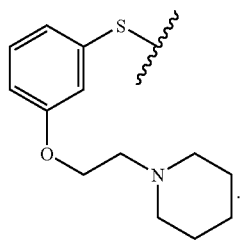

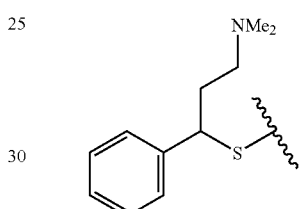

and substituted forms thereof.

In other embodiments, $R^3$ is $SR^6$ wherein $R^6$ is $V_n$-aryl, n is 0, and aryl is phenyl optionally substituted with one or two groups independently selected from Cl, OH, CN, $CF_3$, $CO_2H$, —O($C_1$-$C_6$ alkyl), —O($C_1$-$C_6$ alkyl)$CO_2H$, —O($C_1$-$C_6$ alkyl)$NR^aR^b$, or —O($C_1$-$C_6$ alkyl)heterocycle wherein heterocycle is a 5-6 membered ring having a nitrogen atom. In certain embodiments, $R^a$ and $R^b$ are independently H or $C_1$-$C_6$ alkyl.

Particular values of $R^3$ when represented by S—($V_n$-aryl) include —S-phenyl, —S-(2-chlorophenyl), —S-(3-chlorophenyl), —S-(4-methoxyphenyl), —S-(3-hydroxyphenyl), —S-(4-cyanophenyl), S-(4-carboxyphenyl), —S-(2-chloro-5-methoxyphenyl), —S-(3-methoxyphenyl), —S-(2,5-dimethoxyphenyl), —S-(2,5-dichlorophenyl), —S-(2,5-dimethylphenyl), —S-(2-hydroxyphenyl), —S-(2-trifluoromethyl-4-cyanophenyl), —S-(3-trifluoromethyl-4-cyanophenyl), —S-(4-cyanophenyl),

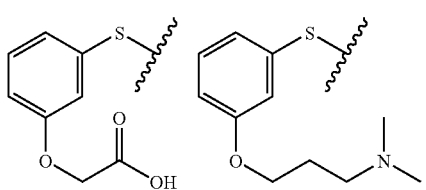

In other embodiments, $R^3$ is $SR^6$ wherein $R^6$ is $V_n$-aryl, n is 1, V is alkyl optionally substituted with $CH_2CH_2NR^aR^b$, and aryl is phenyl optionally substituted with F, Cl, or O($C_1$-$C_6$ alkyl). In certain embodiments $R^a$ and $R^b$ are independently H or alkyl.

Particular values of $R^3$ when represented by S—($V_n$-aryl) further include S—$CH_2$—Ph, S—$CH_2$-(3-methoxyphenyl), S—$CH_2$-(4-methoxyphenyl), S—$CH_2$-(3-chlorophenyl), S—$CH_2$-(2-fluorophenyl), and

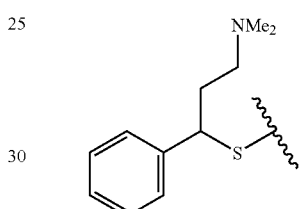

In other embodiments, $R^3$ is $SR^6$ wherein $R^6$ is $V_n$-heteroaryl, n is 1 and V is $C_1$-$C_6$ alkyl. In certain embodiments, V is substituted with $C_1$-$C_6$ alkyl. Examples of heteroaryl groups include 5-6 membered rings having 1-2 atoms independently selected from N, S and O (provided the ring does not contain an O—O bond). Particular examples of heteroaryl groups include pyridyl, thiazolyl, thiadiazolyl, oxadiazolyl, and oxazolyl rings. In certain embodiments, the heteroaryl ring is substituted with one or two groups independently selected from Cl, OH, —O($C_1$-$C_6$ alkyl), $C_1$-$C_6$ alkyl, (3-6C) cycloalkyl and —NHC(O)($C_1$-$C_6$ alkyl). Particular values for $R^3$ when represented by S—$V_n$-heteroaryl include

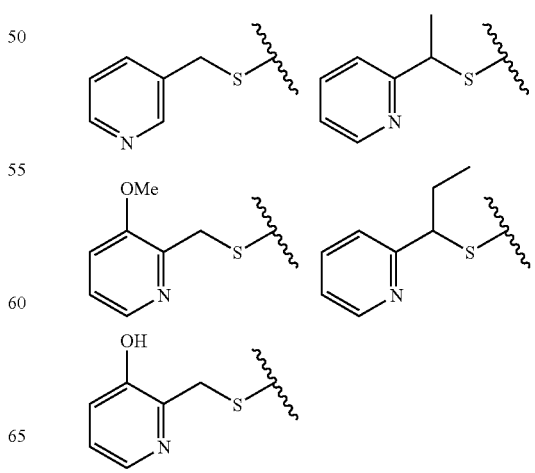

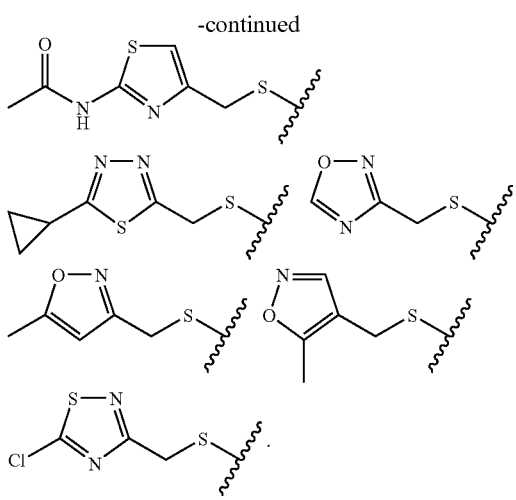

In other embodiments, $R^3$ is $SR^6$ wherein $R^6$ is $V_n$-heteroaryl, n is 1, V is $C_1$-$C_6$ alkyl, and heteroaryl is a 10-membered bicyclic heteroaryl having at least one nitrogen, such as quinolinyl. A particular value of $R^3$ when represented by S—$V_n$-heteroaryl is:

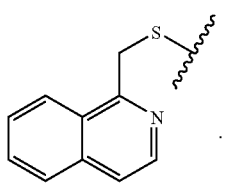

In certain embodiments, $R^3$ is —$SR^6$ wherein $R^1$ is $V_n$-heteroaryl, n is 0, and the heteroaryl group is a 5-6 membered ring having 1-4 atoms independently selected from N and S. Examples include pyridyl, pyrimidyl, thiazolyl, tetrazolyl, and triazolyl rings. In certain embodiments, the heteroaryl ring is substituted with one or two groups independently selected from Cl, CN, $C_1$-$C_6$ alkyl, —O($C_1$-$C_6$ alkyl), —($C_1$-$C_6$ alkyl)$NR^aR^b$, —($C_1$-$C_6$ alkyl)CN, C(=O)O($C_1$-$C_6$ alkyl), and $CF_3$. In certain embodiments, $R^a$ and $R^b$ are independently H or, $C_1$-$C_6$ alkyl.

Particular values for $R^3$ when represented by —S-heteroaryl include —S-(2-pyridyl), —S-(3-pyridyl), —S-(4-pyridyl), —S-(2-pyrimidyl), —S-(6-methylpyrid-2-yl), —S-(2-chloropyrid-4-yl), —S-(2-chloropyrimind-4-yl), —S-(4,6-dimethylpyrimid-2-yl), —S-(4-methoxypyrimid-2-yl), —S-(2-methoxymethylpyrimid-4-yl), —S-(4-methylthiazol-2-yl), —S-(1-(2-dimethylaminoethyl)-1H-tetrazol-5-yl), —S-(4-methyl-4H-1,2,4-triazol-3-yl), —S-(5-cyanomethyl-4H-1,2,4-triazol-3-yl), —S-(5-cyanopyrid-2-yl), —S-(2-cyano-3-methoxypyrid-5-yl), —S-(2-trifluoromethylpyrid-5-yl), and —S-(2-ethoxycarbonylpyrid-6-yl).

In certain embodiments, $R^3$ is represented by —S—$CHR^{6a}R^{6b}$. In certain embodiments, $R^{6b}$ is pyridyl or pyrimidyl and $R^{6a}$ is piperidyl or a group having the formula,

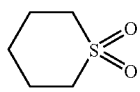

wherein $R^{6a}$ is optionally substituted with $C_1$-$C_6$ alkyl, C(O)O($C_1$-$C_6$ alkyl), or $C_1$-$C_6$ alkyl)OH. Particular values for $R^3$ when represented by S—$CHR^{6a}R^{6b}$ include:

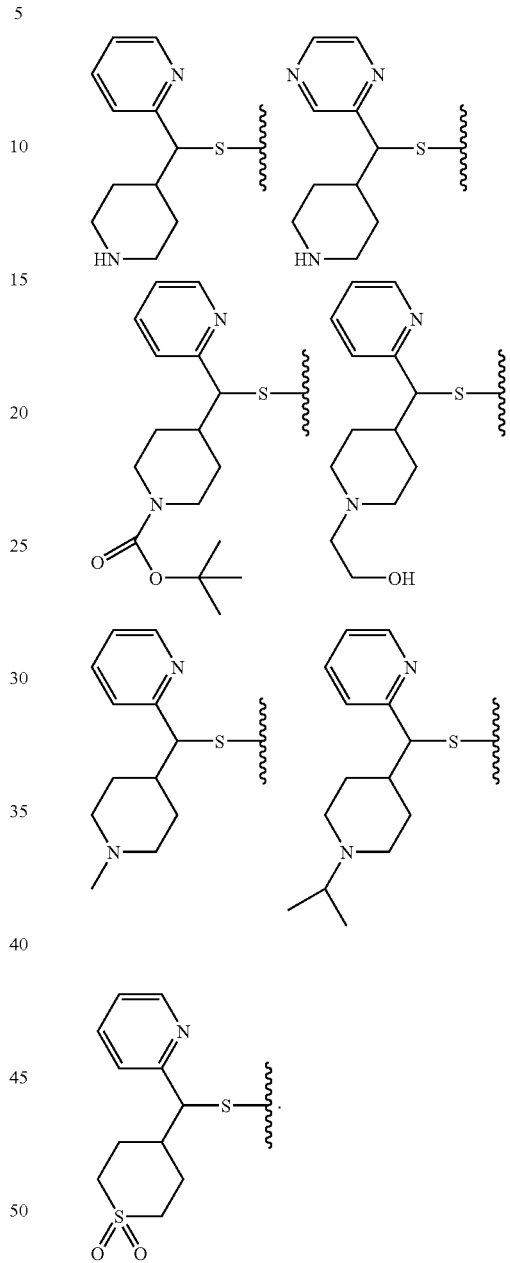

In other embodiments, $R^3$ is represented by S—$CHR^{6a}R^{6b}$ wherein $R^{6a}$ is a piperidyl ring optionally substituted with $C_1$-$C_6$ alkyl, and $R^{6b}$ is C(O)O($C_1$-$C_6$ alkyl), ($C_1$-$C_6$ alkyl) OH, C(O)NH($C_1$-$C_6$ alkyl) or C(O)NH-heterocycle. Examples of heterocycle groups include 5-6 membered rings having at least one nitrogen atom (e.g., pyrrolidinyl or piperidinyl), a 10-membered partially unsaturated bicyclic ring having at least one nitrogen atom (e.g., tetrahydroquinolinyl), and a 7-membered bridged heterocyclic ring having at least one nitrogen atom (e.g., 7-azabicyclo[2.2.1]heptyl). In certain embodiments the heterocyclic ring is substituted with $C_1$-$C_6$ alkyl. Particular values for $R^3$ when represented by S—$CHR^{6a}R^{6b}$ further include:

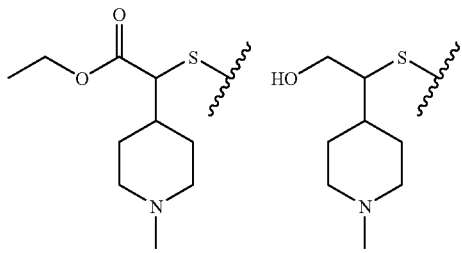
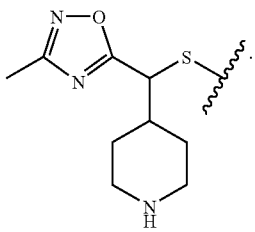
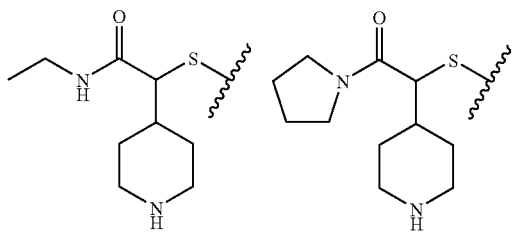
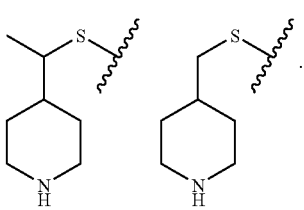
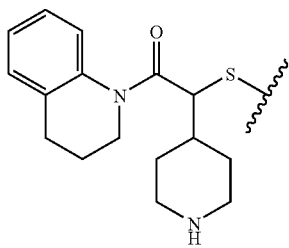
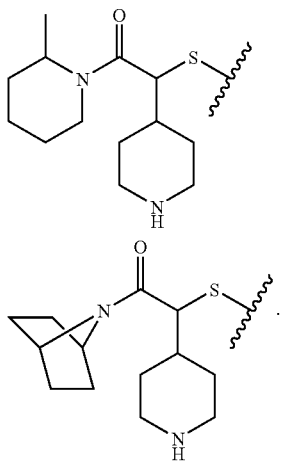

In other embodiments, $R^3$ is represented by S—$CHR^{6a}R^{6b}$ wherein $R^{6a}$ is piperidyl optionally substituted with ($C_1$-$C_6$ alkyl)OH, and $R^{6b}$ is heteroaryl. Examples of heteroaryl groups include 5 membered rings having 1-3 atoms selected from N and O (provided the ring does not contain an O—O bond), for example oxadiazolyl. In certain embodiments, the heteroaryl ring is substituted with $C_1$-$C_6$ alkyl. A particular value of $R^3$ when represented by S—$CHR^{6a}R^{6b}$ further includes:

In other embodiments, $R^3$ is represented by S—$CHR^{62}R^{6b}$ wherein $R^{6a}$ is piperidyl and $R^{6b}$ is H or $C_1$-$C_6$ alkyl. Particular examples include:

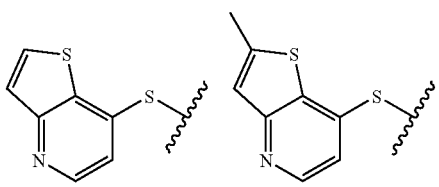

In certain embodiments, $R^3$ is $SR^6$ wherein $R^6$ is $V_n$-heteroaryl, n is 0, and the heteroaryl group is a 9-10 membered bicyclic heteroaromatic ring having 2-3 atoms independently selected from N, S and O (provided the ring does not contain O—O bonds). Examples include 5-6-membered heteroaryl rings fused to 5-6 membered heteroaryl, heterocyclyl, or cycloalkyl rings. Particular examples include thienopyridyl, thienopyrimidyl, isoxazolopyridyl, cyclopentapyridyl, pyrazolopyrimidyl, furopyridyl, tetrahydropyridopyrimidyl, and triazolopyridyl rings. In certain embodiments, the heteroaryl ring is substituted with one or two groups independently selected from I, Br, $C_1$-$C_6$ alkyl and $CO_2H$.

Particular values of $R^3$ when represented by S-heteroaryl include:

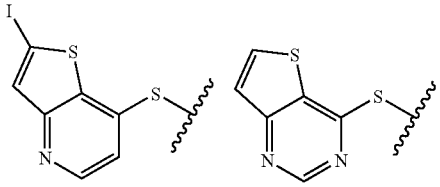
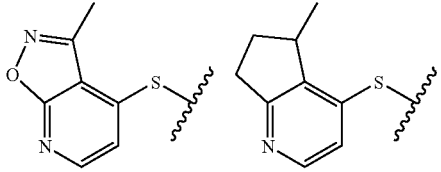

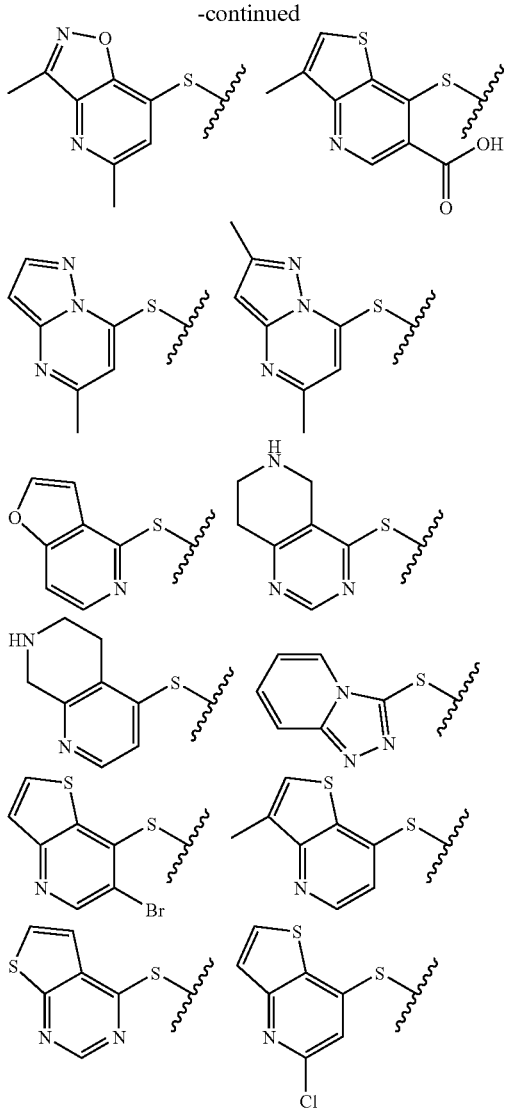

In certain embodiments, $R^3$ is $SR^6$ wherein $R^6$ is cycloalkyl. A particular value of $R^3$ is S-cyclohexyl.

In certain embodiments, $R^3$ is $SR^6$ wherein $R^6$ is heterocycle. Examples of heterocycles include 6 membered rings having at least one nitrogen atom (e.g., piperidinyl). In certain embodiments, the heterocycle is substituted with oxo. A particular value of $R^3$ is

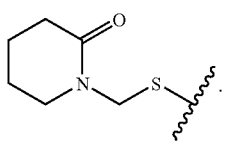

In certain embodiments, $R^3$ is $SR^6$ wherein $R^6$ is $(C_1-C_6$ alkyl)$C(O)OR^s$. Examples include alkyl groups wherein any one of the hydrogens is replaced with a $C(O)OR^8$ moiety. In certain embodiments, $R^8$ is $C_1-C_6$ alkyl. A particular value of $R^3$ is $S—CH_2CH_2C(O)OCH_3$.

In certain embodiments, $R^3$ is $SR^6$ wherein $R^6$ is $CH_2C(O)$-heterocycle, $CH_2C(O)—NR^8(C_1-C_6$ alkyl)$NR^aR^b$, $CH_2C(O)—NR^8(C_1-C_6$ alkyl)heterocycle, or $(C_1-C_6$ alkyl)$NR^8R^9$.

In certain embodiments, each $R^8$, $R^9$, $R^a$ and $R^b$ is independently selected from H and $(C_1-C_6$ alkyl). Examples of heterocycle groups include 5-6 membered rings having 1-2 nitrogen atoms, wherein the ring is optionally substituted with $(C_1-C_6$ alkyl). Particular values for $R^3$ include

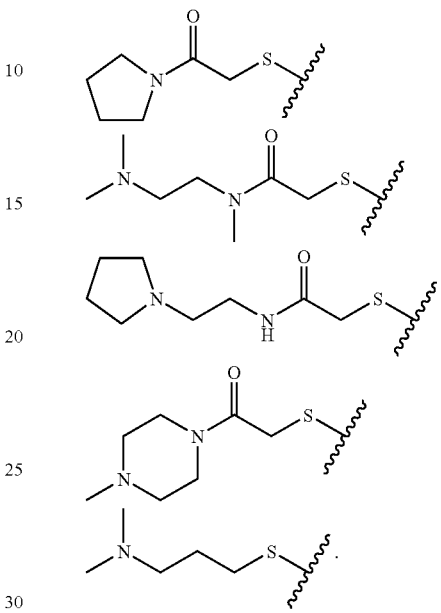

In certain embodiments, $R^3$ is $OR^6$ wherein $R^6$ is H, alkyl, $V_n$-aryl, or $V_n$-heteroaryl, wherein said alkyl, $V_n$-aryl, and $V_n$-heteroaryl are optionally substituted.

In other embodiments, $R^3$ is $OR^6$ wherein $R^6$ is H, $C_1-C_6$ alkyl, $(C_1-C_6$ alkyl)aryl, $(C_1-C_6$ alkyl)heterocycle, $(C_1-C_6$ alkyl)$NR^8R^9$, or phenyl optionally substituted with Br. In certain embodiments, $R^8$ and $R^9$ are independently H or $(C_1-C_6$ alkyl). Examples of heterocycles include 5-6 membered rings having at least one nitrogen atom, for example piperidyl.

Exemplary embodiments of $OR^6$ include, but are not limited to, OH, OMe,

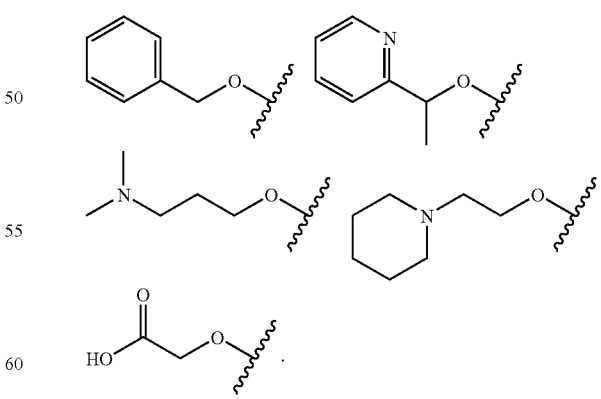

Further exemplary embodiments of $R^3$ when represented by $OR^6$ include phenoxy and 3-bromophenoxy.

In certain embodiments $R^3$ is optionally substituted aryl or heteroaryl.

Examples of $R^3$ when represented by an aryl group include phenyl optionally substituted with a halogen, for example chloro. A particular example is 2-chlorophenyl.

Examples of $R^3$ when represented by a heteroaryl group include 6 membered rings having at least one nitrogen atom. Exemplary embodiments include, but are not limited to, the structures:

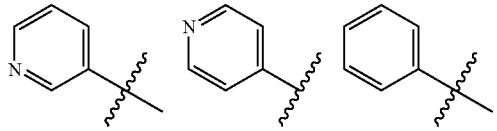

and substituted forms thereof.

In certain embodiments $R^3$ is optionally substituted alkyl or alkenyl.

In certain embodiments, $R^3$ is $C_1$-$C_6$ alkyl, $(C_1$-$C_1$ alkyl)heterocycle, $(C_1$-$C_1$ alkyl)heteroaryl, $(C_1$-$C_1$ alkyl)OH, $(C_1$-$C_1$ alkyl)$CO_2R^8$, $(C_1$-$C_1$ alkyl)$CO_2(C_1$-$C_1$ alkyl), $(C_1$-$C_1$ alkyl)$NR^8R^9$, or $(C_2$-$C_6$ alkenyl)$CO_2R^8$, wherein $R^8$ and $R^9$ are independently H or $C_1$-$C_6$ alkyl. Examples of heterocyclic rings include 5-6 membered rings having one or two atoms independently selected from N and O. Examples of heteroaryl rings include 5-6 membered rings having at least one nitrogen atom.

Exemplary embodiments of $R^3$ include, but are not limited to, the structures:

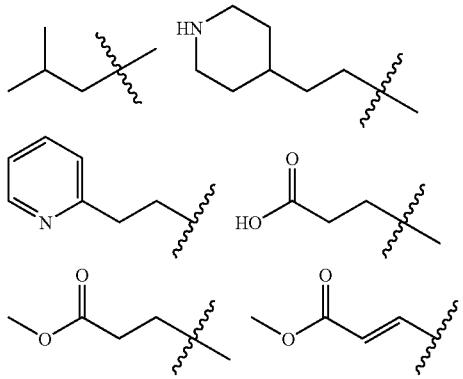

and substituted forms thereof.

Additional examples of $R^3$ include $CH_2OH$, $CH_2$—(tetrahydro-2H-pyran-4-yl), 4-dimethylaminobuten-1-yl, and 4-dimethylaminobutyl.

The compounds of Formula I include compounds having the Formula Ib

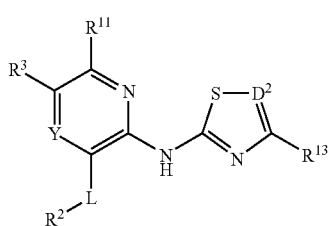

and salts thereof, wherein:

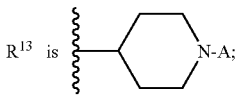

$R^{13}$ is

A is $C(\!=\!O)(C_1$-$C_6$ alkyl), $C(\!=\!O)NH_2$, $C(\!=\!O)NMe_2$, $SO_2Me$, or $SO_2NH_2$;
L is O or S;
Y is CH;
$D^2$ is N or $CR^{12}$;
$R^2$ is aryl or heteroaryl, wherein said aryl and heteroaryl are optionally substituted with one or more groups independently selected from $C_1$-$C_6$ alkyl, F, Cl, Br, $CF_3$, CN, $OR^6$, $C(\!=\!O)R^6$, $C(\!=\!O)OR^6$, $C(\!=\!O)NR^6R^7$, $S(O)_2R^6$, and $C(O)CH_2NH_2$;
$R^3$ is $SR^6$ or $OR^6$;
$R^6$ is $V_n$-aryl or $V_n$-heteroaryl, wherein said aryl and heteroaryl portions are optionally substituted with one or more groups independently selected from $C_1$-$C_6$ alkyl, saturated and partially unsaturated $C_1$-$C_6$ heterocyclyl [optionally substituted with $C(O)O(C_1$-$C_6$ alkyl) or $(C_1$-$C_6$ alkyl)OH], aryl, heteroaryl, F, Cl, Br, I, CN, $OR^8$, $C(\!=\!O)R^8$, $C(\!=\!O)OR^8$, $C(\!=\!O)NR^8R^9$, $NR^8R^9$, $NR^8C(\!=\!O)R^9$ or $(C_1$-$C_6$ alkyl)OH;
$R^7$ is H or $C_1$-$C_{12}$ alkyl;
$R^{11}$ is H;
$R^{12}$ is H or $C_1$-$C_6$ alkyl;
V is alkylene having from 1 to 4 carbons, wherein said alkylene is optionally substituted with $C_1$-$C_6$ alkyl, $O(C_1$-$C_6$ alkyl), or $(C_1$-$C_6$ alkyl)$NR^cR^e$;
each $R^c$ and $R^e$ is independently H or $C_1$-$C_6$ alkyl; and
n is 0 or 1.

The compounds of Formula I include compounds having the Formula Ic

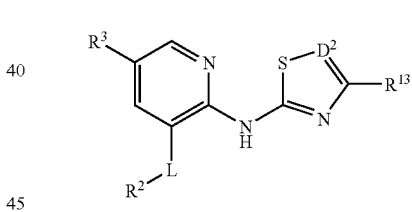

and salts thereof, wherein:

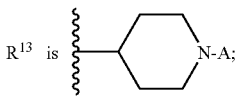

$R^{13}$ is

A is $C(\!=\!O)(C_1$-$C_6$ alkyl), $C(\!=\!O)NH_2$, $C(C\!=\!O)NH(C_1$-$C_6$ alkyl), $C(\!=\!O)N(C_1$-$C_6$ alkyl)$_2$, $C(\!=\!O)CH(C_1$-$C_6$ alkyl)$N(C_1$-$C_6$ alkyl)$_2$, $SO_2(C_1$-$C_6$ alkyl), $SO_2NH_2$, $SO_2NH(C_1$-$C_6$ alkyl), $S(C_1$-$C_6$ alkyl)$_2$ or $C(O)CH(CH_3)OH$;
L is O;
$D^2$ is N or CH;
$R^2$ is aryl optionally substituted with one or more groups independently selected from $C_1$-$C_6$ alkyl, F, Br, and $CF_3$;
$R^3$ is $SR^6$;
$R^6$ is aryl, hetAr$^a$ or hetAr$^b$, wherein $R^6$ is optionally substituted with one or more groups independently selected from $C_1$-$C_6$ alkyl, Br, Cl, $CF_3$, CN, $OR^8$, and $C(\!=\!O)OR^8$;
$R^8$ is $C_1$-$C_6$ alkyl;

hetAr$^a$ is a 5-6 membered heteroaryl ring having 1-4 nitrogen atoms; and hetAr$^b$ is a 9-10 membered bicyclic heteroaromatic ring having 2-6 atoms independently selected from N, S and O (provided the ring does not contain an O—O bond).

In one embodiment, A is selected from C(=O)(C$_1$-C$_6$ alkyl), C(=O)NH$_2$, C(=O)NMe$_2$, C(O)CH$_2$NMe$_2$, SO$_2$Me, SO$_2$NH$_2$, and C(O)CH(CH$_3$)OH.

In certain embodiments of Formula Ic, A is C(=O)(C$_1$-C$_6$ alkyl).

In certain embodiments of Formula Ic, A is C(=O)NH$_2$.

In certain embodiments of Formula Ic, A is C(=O)NMe$_2$.

In certain embodiments of Formula Ic, A is C(=O)CH$_2$NMe$_2$.

In certain embodiments of Formula Ic, A is SO$_2$Me.

In certain embodiments of Formula Ic, A is SO$_2$NH$_2$.

In certain embodiments of Formula Ic, A is C(O)CH(CH$_3$)OH.

In certain embodiments, R$^2$ is aryl optionally substituted with one or more groups independently selected from C$_1$-C$_6$ alkyl, Br, Cl, CF$_3$, CN, OR$^8$, and C(=O)OR$^8$. In certain embodiments, R$^2$ is phenyl. Particular values for R$^2$ include phenyl optionally substituted with one or two groups independently selected from F, Br and CF$_3$.

Exemplary embodiments of R$^2$ for Formula Ic include, but are not limited to, the structures:

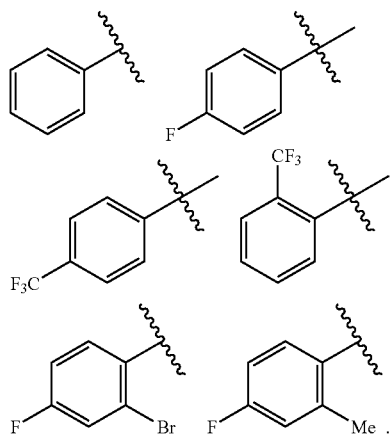

In certain embodiments of Formula Ic, R$^3$ is SR$^6$ wherein R$^6$ is aryl. In particular embodiment, the aryl group is phenyl. In certain embodiments, the aryl group is substituted with one or two groups independently selected from CN, CF$_3$, and —O(C$_1$-C$_6$ alkyl). Particular values of R$^3$ when represented by S-aryl include the structures:

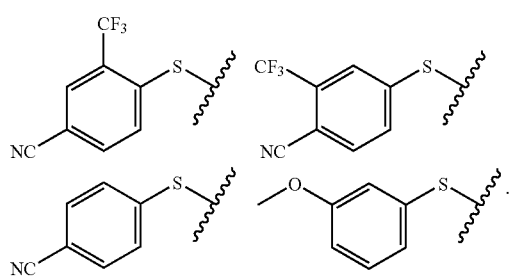

In certain embodiments of Formula Ic, R$^3$ is SR$^6$ wherein R$^6$ is hetAr$^a$, and hetAr$^a$ is a 5-6 membered heteroaryl ring having 1-4 nitrogen atoms. In particular examples, hetAr$^a$ is a 5-6 membered ring having 1-2 nitrogen atoms. Examples include pyridyl and pyrimidyl rings. In certain embodiments, hetAr$^a$ is substituted with one or two groups independently selected from Cl, CN, —O(C$_1$-C$_6$ alkyl), C(=O)O(C$_1$-C$_6$ alkyl), and CF$_3$. Particular values for R$^3$ for Formula Ic when represented by S-hetAr$^a$ include the structure:

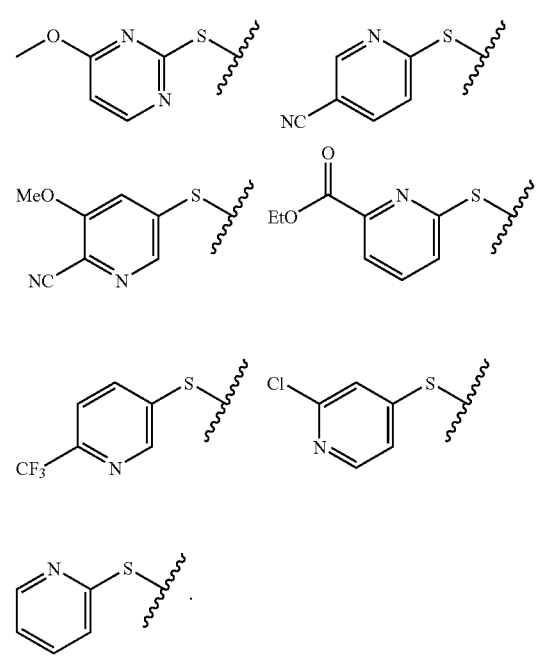

In certain embodiments of Formula I, R$^3$ is SR$^6$ wherein R$^6$ is hetAr$^b$ and hetAr$^b$ is a 9-10 membered bicyclic heteroaromatic ring having 2-6 heteroatoms independently selected from N, S and O (provided the ring does not contain an O—O bond). In particular embodiments, hetAr$^b$ is a 9-10 membered bicyclic heteroaromatic ring having 2-3 heteroatoms independently selected from N, S and O. Examples include 5-6-membered heteroaryl rings fused to 5-6 membered heteroaryl rings. Particular examples include thienopyridyl, thienopyrimidyl, isoxazolopyridyl, pyrazolopyrimidyl and rings. In certain embodiments, hetAr$^b$ is substituted with one or two groups independently selected from Br, Cl and C$_1$-C$_6$ alkyl. Particular values of R$^3$ for Formula Ic when represented by S-hetAr$^b$ include the structures:

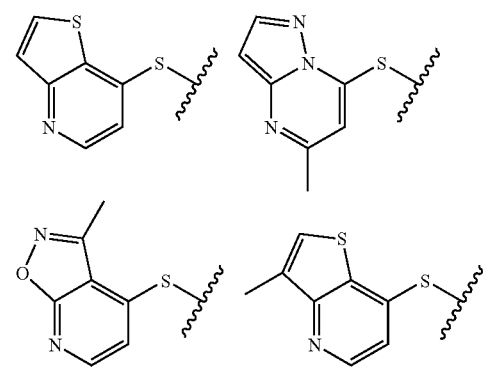

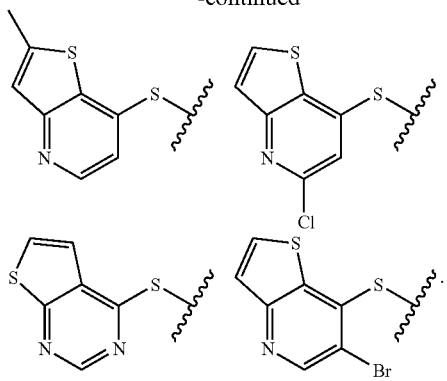

The compound of Formula I also include compound of Formula Id:

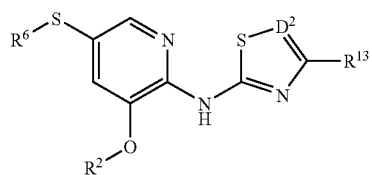

and salts thereof, wherein:

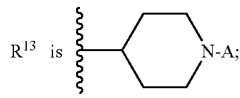

A is C(=O)(C$_1$-C$_6$ alkyl), C(=O)NH$_2$, C(=O)NMe$_2$, C(=O)CH$_2$NMe$_2$, SO$_2$Me, or SO$_2$NH$_2$;

D$^2$ is N or CH;

R$^2$ is phenyl optionally substituted with F; and

R$^3$ is selected from

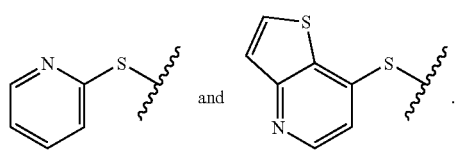

Exemplary embodiments of compounds of Formula I include, but are not limited to, compounds of the general formulas

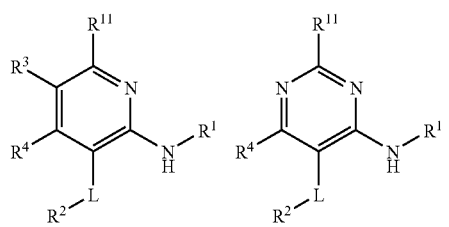

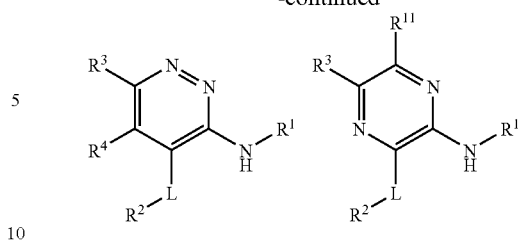

and substituted forms thereof, wherein L, R$^1$, R$^2$, R$^3$, R$^4$ and R$^{11}$ are as defined herein.

Additional exemplary embodiment of compounds of Formula I include, but are not limited to, compounds of the general formulas

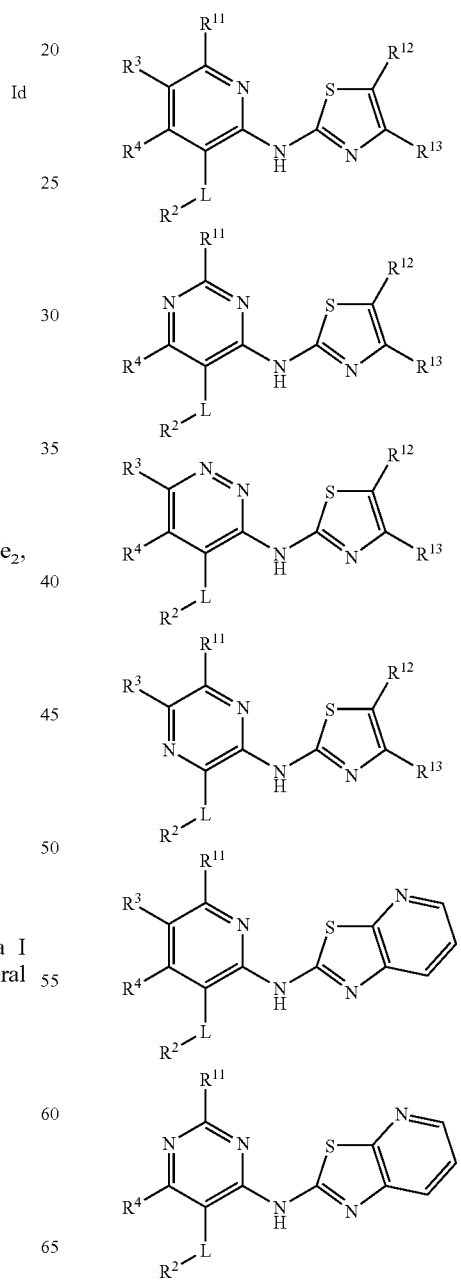

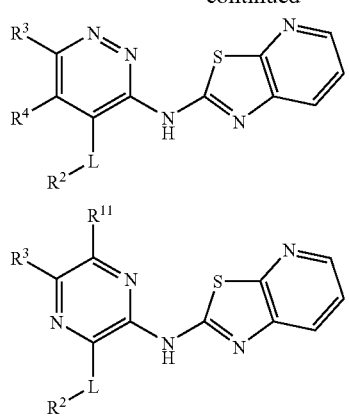

and substituted forms thereof, wherein L, $R^2$, $R^3$, $R^4$, $R^{11}$, $R^{12}$ and $R^{13}$ are as defined herein.

Additional exemplary embodiment of compounds of Formula I include, but are not limited to, compounds of the general formulas

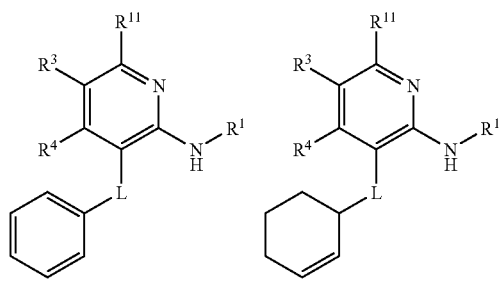

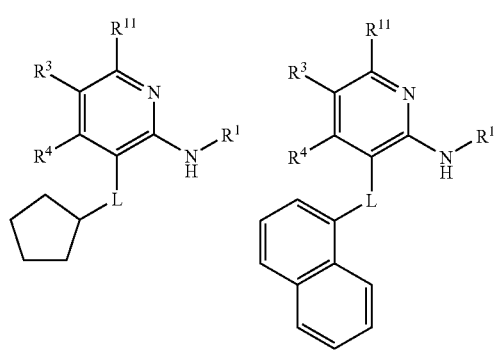

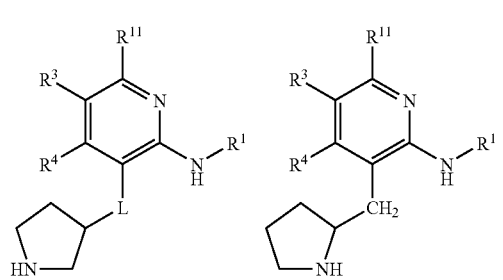

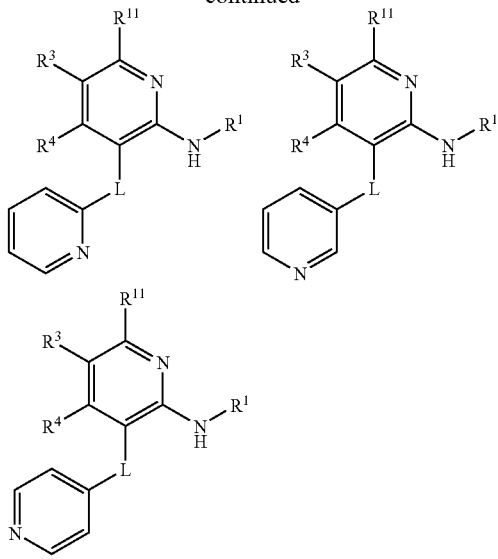

and substituted forms thereof, wherein L, $R^1$, $R^3$, $R^4$, and $R^{11}$ are as defined herein.

Additional exemplary embodiment of compounds of Formula I include, but are not limited to, compounds of the general formulas

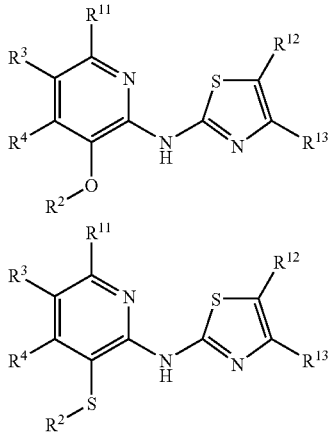

and substituted forms thereof, wherein $R^1$, $R^3$, $R^4$, and $R^{11}$ are as defined herein.

Additional exemplary embodiment of compounds of Formula I include, but are not limited to, compounds of the general formulas

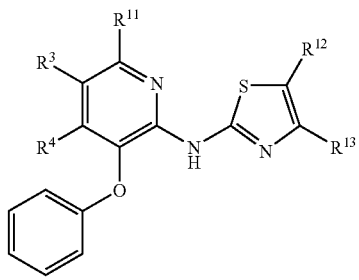

-continued

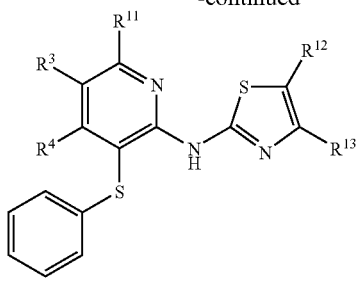

and substituted forms thereof, wherein $R^1$, $R^3$, $R^4$, $R^{11}$, $R^{12}$ and $R^{13}$ are as defined herein. In certain embodiments, the phenyl ring is optionally substituted with one or more $R^{20a}$ groups independently selected from F, Cl, Br, I, CN, $C_1$-$C_{12}$ alkyl, $NO_2$, $SO_2R^6$, $OR^6$, C(=O)$OR^6$, and $NR^6$C(=O)$R^7$, wherein said alkyl is optionally substituted. In certain embodiments, the phenyl group is optionally substituted with one or more groups independently selected from Cl, OMe, CN, $NO_2$, C(=O)OMe, C(=O)OEt, $SO_2$Me, and $OCH_2CH_2NMe_2$. In certain embodiments, $R^{12}$ is H and $R^{13}$ is selected from $C_1$-$C_6$ alkyl, $C_3$-$C_6$ cycloalkyl, and $(CH_2)_{1-2}CO_2R^6$. In certain embodiments, $R^{13}$ is methyl, ethyl, propyl, isopropyl, n-butyl, isobutyl, cyclopropyl, $CH_2CH_2COOMe$, $CH_2COOEt$, $CH_2COOH$, or $CH_2CR_2COOH$.

Additional exemplary embodiment of compounds of Formula I include, but are not limited to, compounds of the general formulas

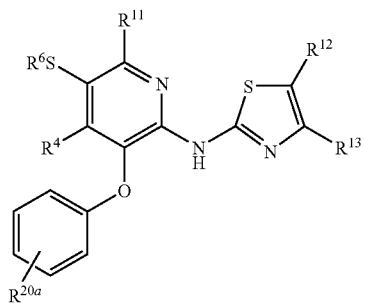

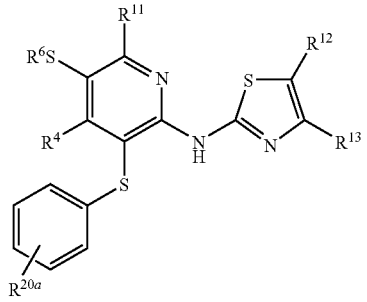

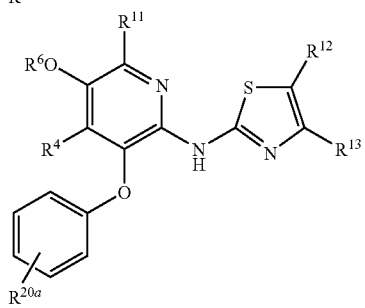

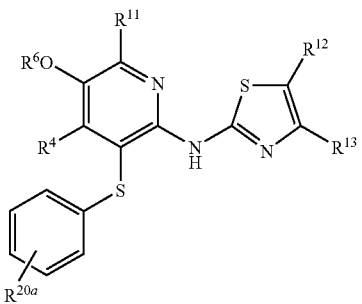

wherein $R^4$, $R^6$, $R^{11}$, $R^{12}$, $R^{13}$, and $R^{20a}$ are as defined herein.

Additional exemplary embodiment of compounds of Formula I include, but are not limited to, compounds of the general formulas

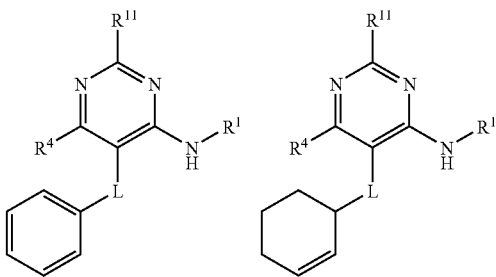

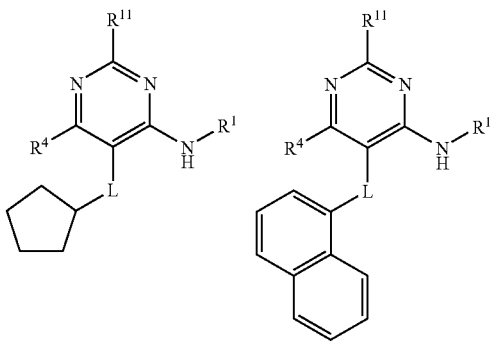

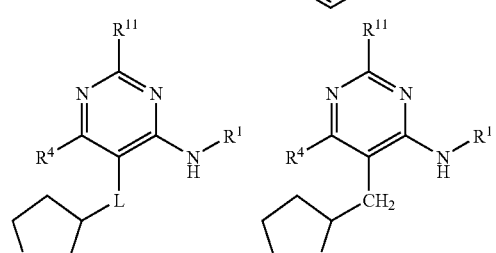

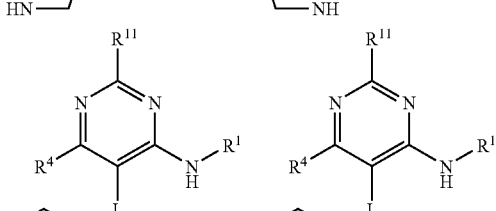

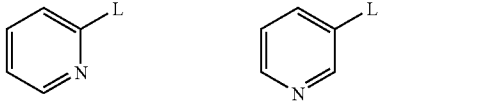

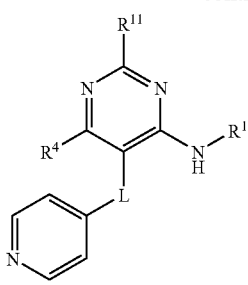

and substituted forms thereof, wherein L, $R^1$, $R^4$, and $R^{11}$ are as defined herein.

Additional exemplary embodiment of compounds of Formula I include, but are not limited to, compounds of the general formulas

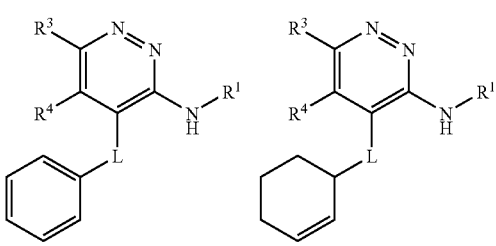

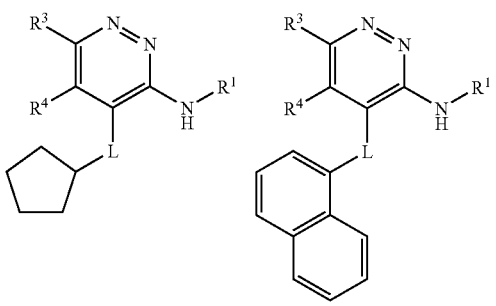

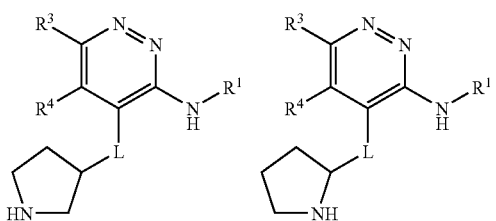

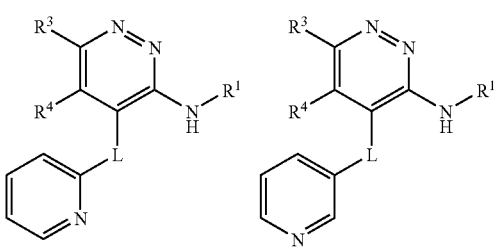

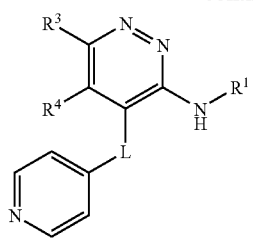

and substituted forms thereof, wherein L, $R^1$, $R^3$, and $R^4$ are as defined herein.

Additional exemplary embodiment of compounds of Formula I include, but are not limited to, compounds of the general formulas

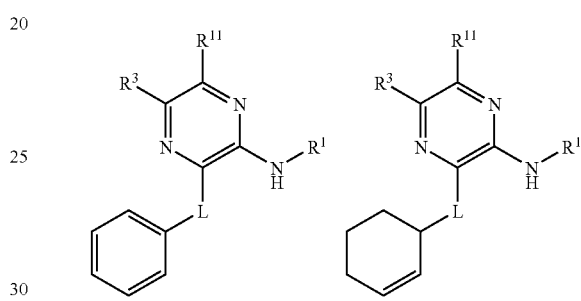

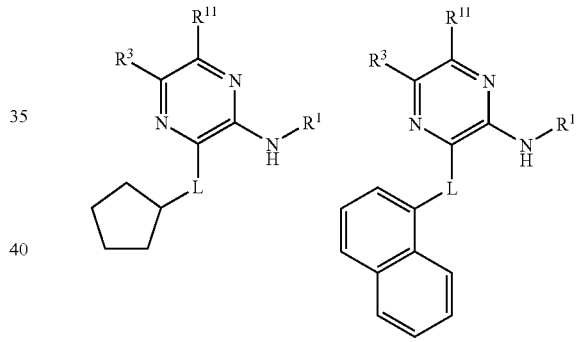

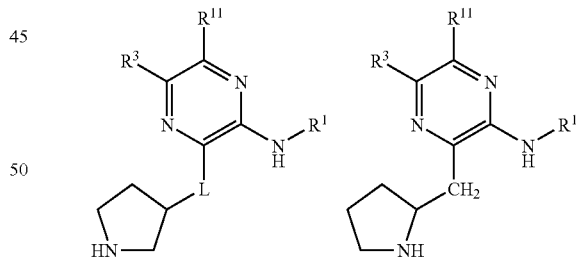

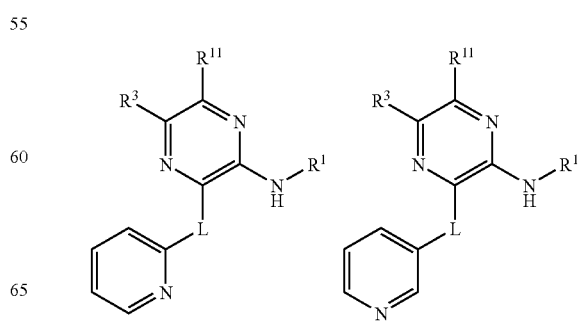

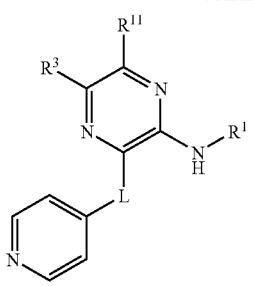

and substituted forms thereof, wherein L, R¹, R³, and R¹¹ are as defined herein.

Additional exemplary embodiment of compounds of Formula I include, but are not limited to, compounds of the general formulas

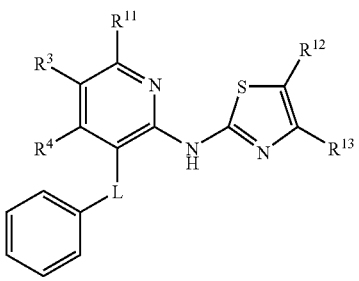

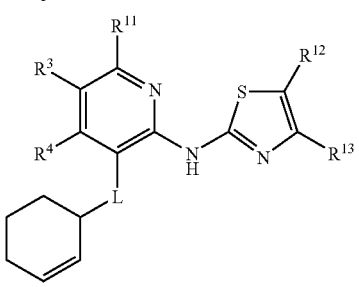

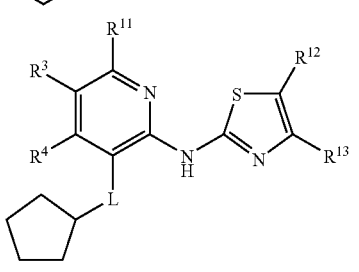

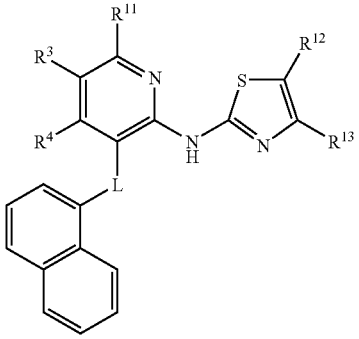

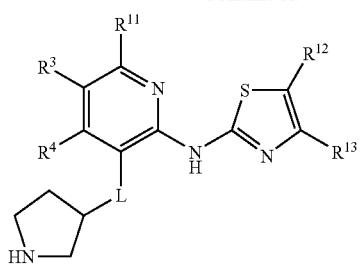

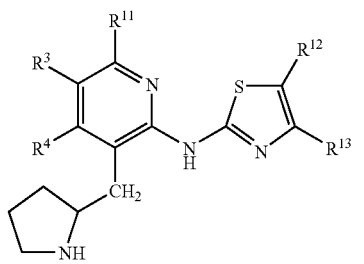

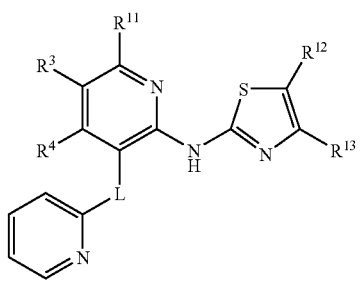

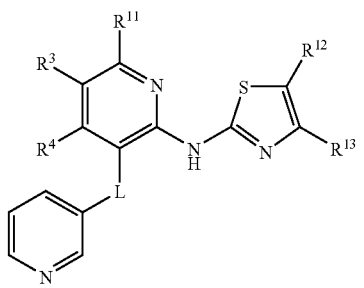

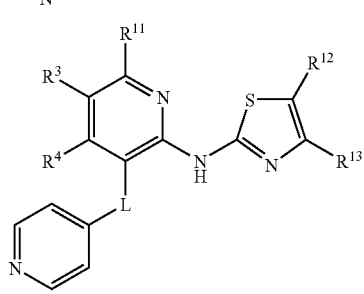

and substituted forms thereof, wherein L, R³, R⁴, R¹¹, R¹² and R¹³ are as defined herein.

Additional exemplary embodiment of compounds of Formula I include, but are not limited to, compounds of the general formulas

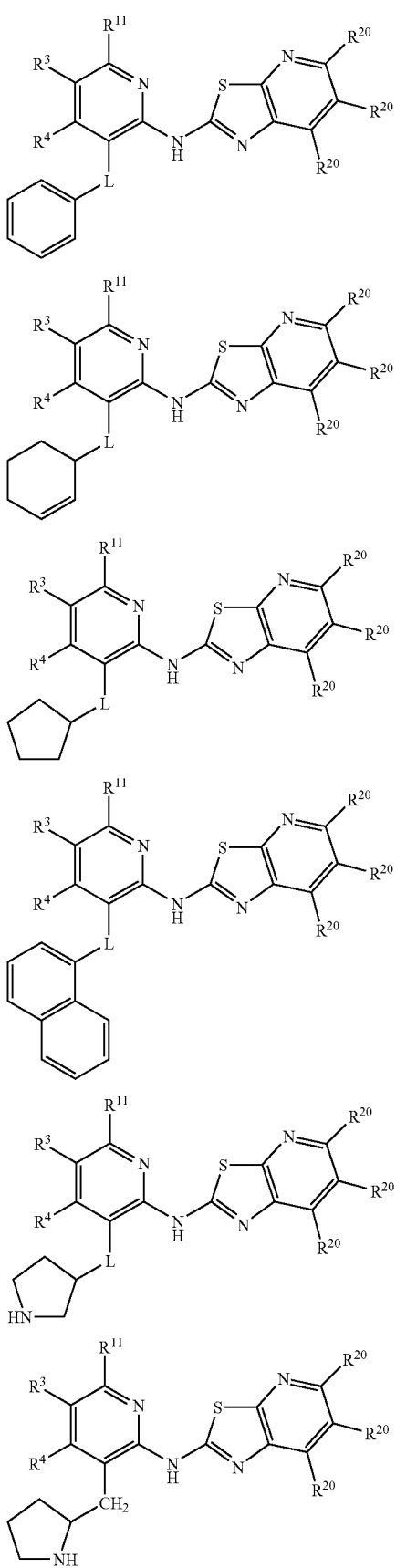
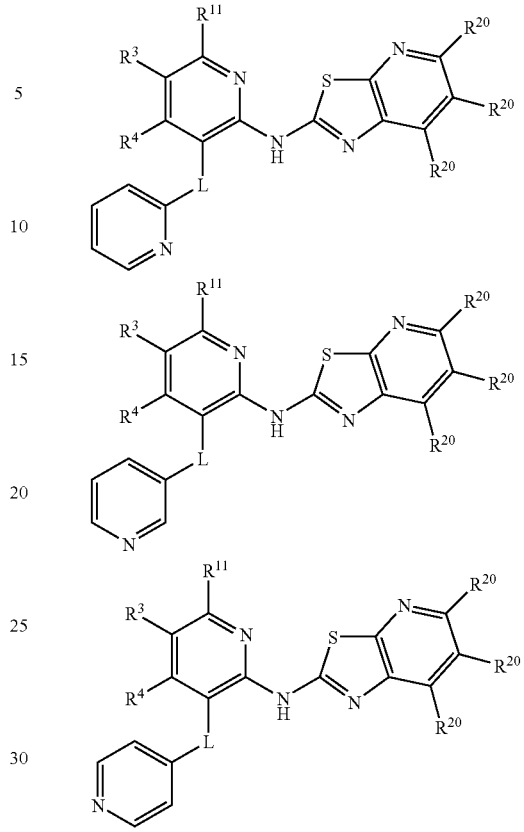

and substituted forms thereof, wherein L, $R^3$, $R^4$, $R^{11}$ and $R^{20}$ are as defined herein, and each $R^{20}$ is independent of the other.

The compounds of this invention may possess one or more asymmetric centers; such compounds can therefore be produced as individual (R)—or (S)-stereoisomers or as mixtures thereof. Unless indicated otherwise, the description or naming of a particular compound in the specification and claims is intended to include both individual enantiomers and diastereomers, and mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible by a low energy barrier. For example, proton tautomers (also known as prototropic tautomers) include interconversions by migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formula I, the invention also includes solvates, pharmaceutically acceptable prodrugs, and salts of such compounds.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" can also be used to refer to a complex wherein the solvent molecule is water.

A "prodrug" is a compound that may be converted under physiological conditions or by solvolysis to the specified compound or to a salt of such compound. Prodrugs include compounds wherein an amino acid residue, or a polypeptide chain of two or more amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.*, 1996, 39, 10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, —C(OH)C(O)OY whereinY is H, $(C_1-C_6)$alkyl or benzyl, —$C(OY_0)Y_1$ wherein $Y_0$ is $(C_1-C_4)$alkyl and $Y_1$ is $(C_1-C_6)$alkyl, carboxy$(C_1-C_6)$ alkyl, amino$(C_1-C_4)$alkyl or mono-N— or di-N,N—$(C_1-C_6)$ alkylaminoalkyl, or —$C(Y_2)Y_3$ whereinY$_2$ is 1 or methyl and $Y_3$ is mono-N— or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8: 1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

A compound of the invention may possess a sufficiently acidic group, a sufficiently basic group, or both functional groups, and accordingly react with any of a number of inorganic or organic bases or acids to form a salt. Examples of salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

In certain embodiments, the salt of a compound of Formula I is a pharmaceutically acceptable salt. The phrase "pharmaceutically acceptable" indicates that the substance or composition is compatible chemically and/or toxicologically with the other ingredients comprising a formulation, and/or the mammal being treated therewith. A "pharmaceutically acceptable salt," unless otherwise indicated, includes salts that retain the biological effectiveness of the corresponding free acid or base of the specified compound and are not biologically or otherwise undesirable.

The present invention also embraces isotopically-labeled compounds of the present invention which are identical to those recited herein, but for the fact that one or more atoms are replaced by an atom having an atomic mass or mass number different from the atomic mass or mass number usually found in nature.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result, for example, from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Synthesis of Gluocokinase Activators

Compounds of this invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds of Formula I or salts thereof.

For illustrative purposes, Schemes A-U show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

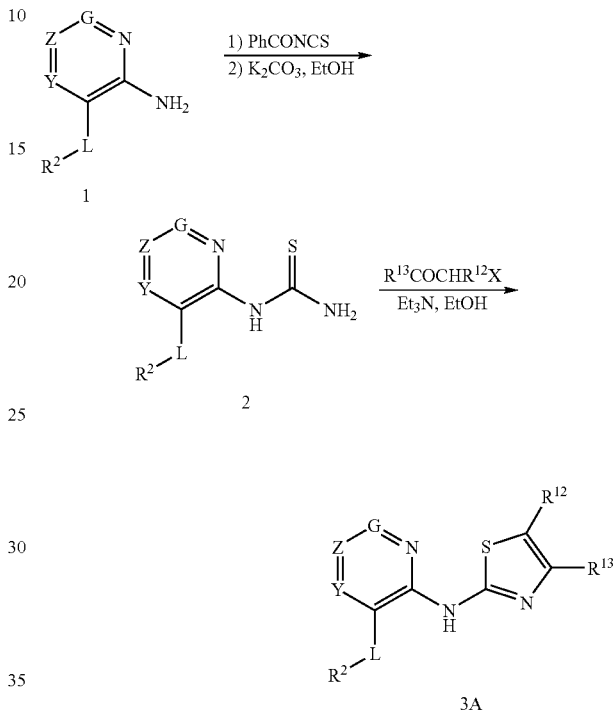

Scheme A shows a method of preparing compounds (3A) of Formula I wherein $R^1$ is thiazolyl and L=O or S. To prepare compound (3A), a 2-aminoheterocycle (1) is reacted with benzoylisothiocyanate to afford a benzoylthiourea intermediate, which is hydrolyzed to the thiourea (2) with a base such as, but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one step. Treatment of the thiourea (2) with an α-haloketone $R^{13}COCHR^{12}X$, wherein X=OTs, Cl, Br, I, or $NR^3$ (wherein R=$C_1$-$C_6$ alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCHR^{12}X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of β-keto esters followed by decarboxylation.

Scheme B

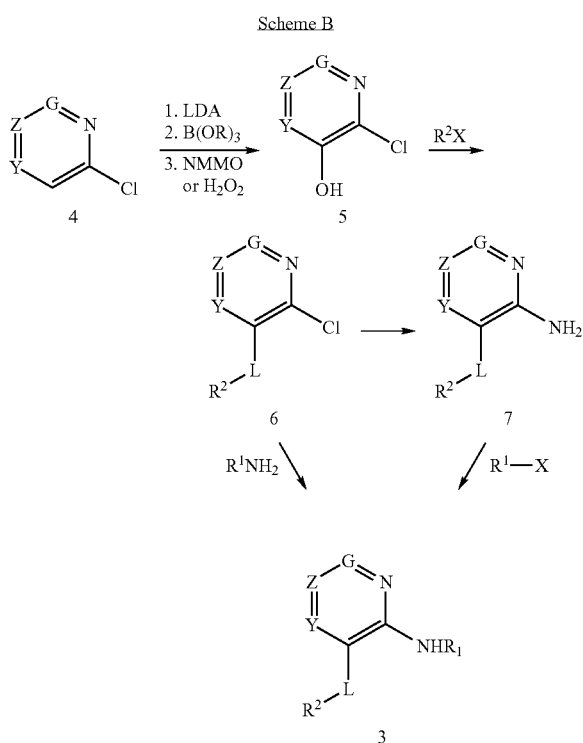

cesium carbonate or sodium hydride and in a suitable solvent such as, but not limited to, DMF to afford compound (6) wherein L is O. Examples of $R^2X$ that may be utilized include substituted 2- and 4-nitrohalobenzenes, substituted 2- and 4-cyanohalobenzenes, 2-chloro-1-fluorobenzene, halogenated pyridines, halogenated pyrimidines, and other halogenated heterocycles. Compound (6) can be converted to compound (7) by the method of Hartwig et al. (for an example of this transformation by analogy see: *Organic Letters* (2001) 2729-2732), or by treatment with a Pd catalyst and benzophenone imine, or by heating in the presence of ammonia (or $NH_2PG$ where PG is a protecting group).

Compounds of the formulas (6) and (7) wherein L is S can be prepared according to methods described in Schemes I, J, K, M, N, O, and P. Compounds of the formulas (6) and (7) wherein L is $CH_2$ can be prepared according to methods described below in Schemes I, K, M, N, O, and P. Compounds of formulas (6) and (7) subsequently can be used in Schemes A-H.

Compound (7) can be converted to compound (3) of Formula I upon reaction with an aryl or heteroaryl halide $R^1X$ in the presence of a base catalyst or metal (e.g., copper or palladium) catalyst. Alternatively, compound (6) can be converted directly to a compound (3) of Formula I upon treatment with $R^1NH_2$ by base catalysis or by copper or palladium catalysis; i.e., the Buchwald reaction.

Scheme C

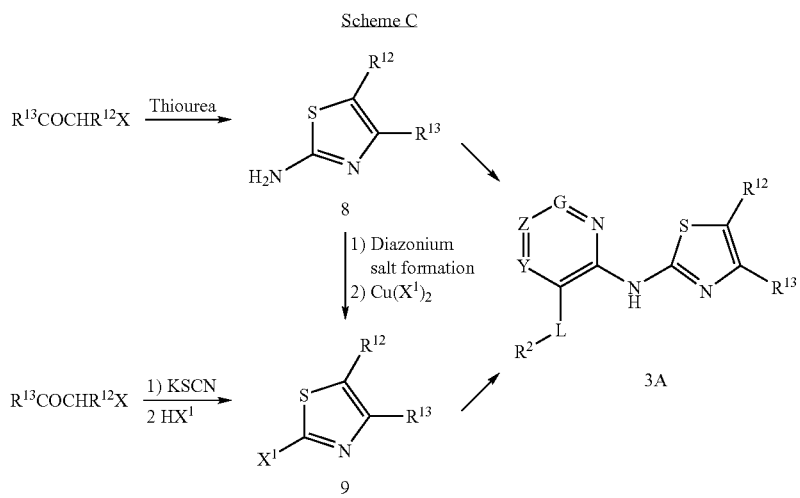

Scheme B shows an alternative method of preparing a compound of Formula I. According to Scheme B, hydroxylated heteroaryl halide (5) (if not commercially available) can be prepared from heteroaryl halide (4) by: 1) ortho metalation with LDA or another suitable base; 2) conversion of the anion to the boronate by reaction with $B(OR)_3$; and 3) oxidation of the boronate with a suitable oxidant such as N-methylmorpholine oxide or hydrogen peroxide. The ortho metalated species can also be quenched with $(TMSO)_2$ to obtain the hydroxylated material (5) directly upon acidic workup. The hydroxylated heteroaromatic compound (5) can be alkylated with $R^2X$ in the presence of a base such as, but not limited to, Scheme C shows a method of preparing 2-aminothiazole and 2-bromothiazole intermediates (8) and (9), respectively, which are suitable for use in preparing compounds of Formula I as shown in Scheme B. According to Scheme C, α-haloketone $R^{13}COCHR^{12}X$ can be treated with thiourea in the presence of a suitable base such as potassium carbonate or triethylamine in an appropriate solvent such as DMF or ethanol to afford aminothiazole (8). The aminothiazole (8) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (9). Alternatively, using the Hantzsch synthetic method, the α-haloketone R¹³COCHR¹²X can be treated first with KSCN, then with HX wherein X is Cl or Br, to provide the 2-halothiazole (9). The 2-halothiazole compounds (8) and (9) can be converted into compound (3A) by the methods shown in Scheme B.

3-bromo-1,2,4-thiadiazole (12) (EP 0307142). The chloro derivative of compound (12) could also be synthesized through the use of CuCl₂. Alternatively, palladium-mediated coupling of the commercially available 3-bromo-5-chloro-1, 2,4-thiadiazole (13) with a zinc reagent affords 3-bromo-1,2,

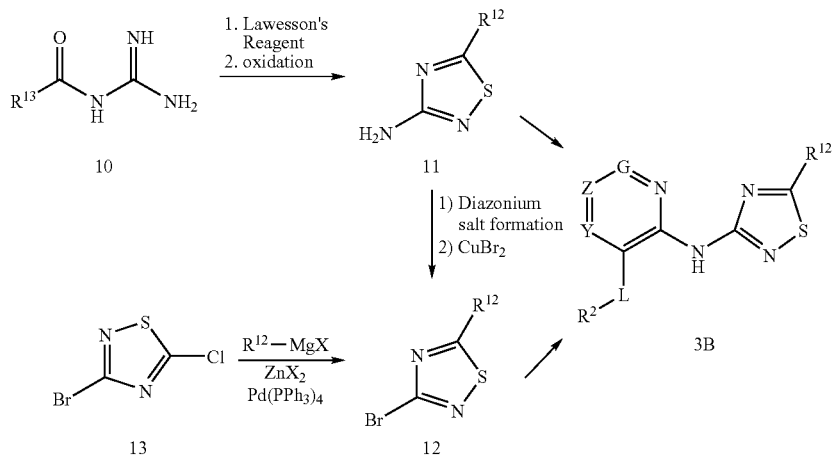

Scheme D

Scheme D shows a method of preparing 3-aminothiadiazole and 3-bromothiadiazole intermediates (11) and (12), respectively, which are suitable for use in preparing compounds of Formula I as shown in Scheme B. According to Scheme D, acylguanidine (10) (*Can. J. Chem.*, (1961) 39, 1017-29) can be treated with Lawesson's reagent or similar reagent in an appropriate solvent such as toluene to afford the corresponding thioamide (EP 0307142). Oxidation of the thioamide to form 3-amino-1,2,4 thiadiazole (11) can be accomplished with bromine, iodine, hydrogen peroxide or nitric acid. Cyclization of compound (10) may also be achieved by treatment with hydroxylamine-O-sulphonic acid in an alcohol solvent such as methanol or ethanol in the presence of pyridine (EP 0307142). Formation of the diazonium salt of compound (11), followed by treatment of the in situ diazonium salt with CuBr₂, affords the corresponding 3-bromo-1,2,4-thiadiazole (12) (WO 2003/037894). Intermediate thiadiazoles (11) and (12) can be converted into compound (3B) of Formula I by the methods shown in Scheme B.

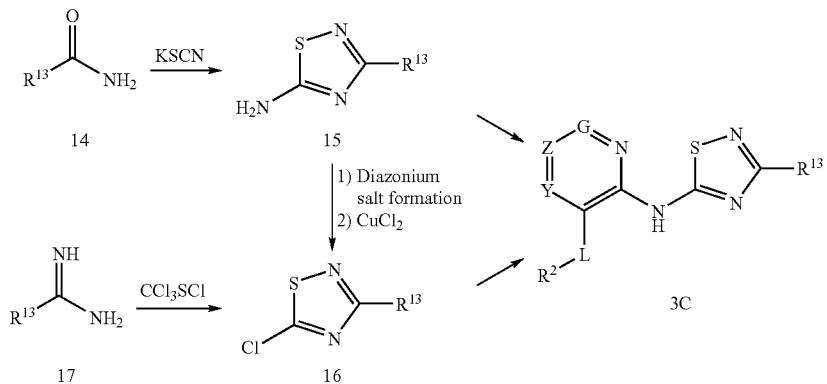

Scheme E

Scheme E shows a method of preparing 5-amino-1,2,4-thiadiazole and 5-chloro-1,2,4-thiadiazole intermediates (15) and (16), respectively, which are suitable for use in preparing compounds of Formula I as shown in Scheme B. According to Scheme E, primary amide (14) can be converted into 5-amino-1,2,4 thiadiazole (15) by heating with KSCN in an appropriate solvent such as methanol or ethanol (*Achv. Heterocycl. Chem.*, (1982) 32, 285). Formation of the diazonium salt of compound (15), followed by treatment of the in situ diazonium salt with CuCl₂ affords the corresponding 5-chloro-1,2,4-thiadiazole (16). The corresponding bromo derivative can also be synthesized through the use of CuBr₂. Alternatively, reaction of amidine (17) with perchloromethyl mercaptan affords 5-chloro-1,2,4-thiadiazole (16) (*Bioorg.*

Med. Chem., (2003) 11, 5529-5537). Intermediates (15) and (16) can be converted into compound (3C) of Formula I by the methods shown in Scheme B.

Scheme G shows a method of preparing 5-amino-1,2,4-oxadiazole and 5-chloro-1,2,4-oxadiazole intermediates (23) and (24), respectively, which are suitable for use in preparing

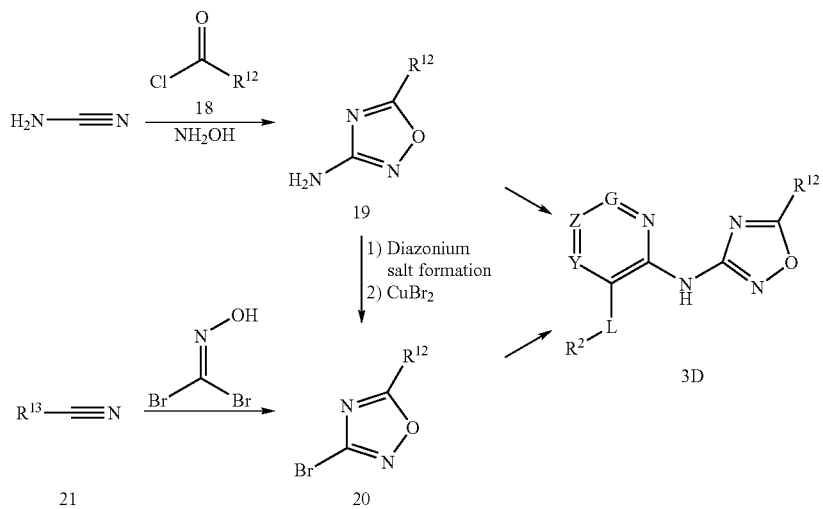

Scheme F shows a method of preparing 3-amino-1,2,4-oxadiazole and 3-bromo-1,2,4-oxadiazole intermediates (19) and (20), respectively, which are suitable for use in preparing compounds of Formula I as shown in Scheme B. According to Scheme F, cyanamide can be reacted with an appropriate acylchloride (18) or the corresponding anhydride, and subsequently reacted with hydroxylamine to afford 3-amino-1,2,4-oxadiazole (19) (*Heterocycles*, (2002) 57, 811-823). Formation of the diazonium salt of (19), followed by treatment of the in situ diazonium salt with CuBr$_2$ affords the corresponding 3-bromo-1,2,4-oxadiazole (20). The chloro derivative could also be synthesized through the use of CuCl$_2$ Alternatively, alkyl nitrile (21) can be reacted with dibromoformaldoxime (neat) in the presence of an appropriate base such as sodium bicarbonate to afford 3-bromo-1,2,4-oxadiazole (20) (*J. Heterocyclic Chem.*, (1989) 26, 23-24). The oxadiazole intermediates (19) and (20) can be converted into compound (3D) of Formula I by the methods shown in Scheme B.

compounds of Formula I as shown in Scheme B. According to Scheme G, imidate hydrochloride salt (22) (made by the Pinner reaction) can be reacted with cyanamide in a suitable solvent such as methanol or ethanol to afford an intermediate N-cyanoimidate. Cyclization can be achieved by reacting the N-cyanoimidate with hydroxylamine hydrochloride in an appropriate solvent such as methanol or ethanol in the presence of an appropriate base such as triethylamine, Hunig's base, pyridine or sodium acetate to afford 5-amino-1,2,4-oxadiazole (23) (*J. Org. Chem.*, (1963) 28, 1861-21). Formation of the diazonium salt of compound (23), followed by treatment of the in situ diazonium salt with CuCl$_2$ affords the corresponding 5-chloro-1,2,4-oxadiazole (24). The bromo derivative could also be synthesized through the use of CuBr$_2$. Alternatively, alkyl nitrile (21) can be converted into 5-chloro-1,2,4-oxadiazole (24) (WO 95/005368) by reaction with hydroxylamine hydrochloride in an appropriate solvent such as methanol or ethanol, in the presence of an appropriate

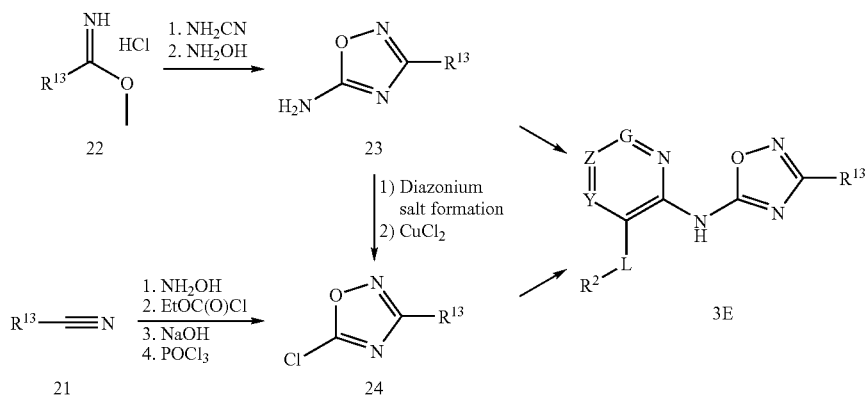

base such as triethylamine, Hunig's base, pyridine or sodium acetate, followed by cyclization to a 1,2,4-oxadiazolone with a bisacylating agent such as ethyl chloroformate, carbonyldiimidazole or phosgene. In certain embodiments, the cyclization requires the use of a base such as NaOH, NaH or triethylamine to allow for the formation of the 1,2,4-oxadiazolone. Reaction of the 1,2,4-oxadiazolone with a dehydrating agent such as $POCl_3$, $POBr_3$ or $PCl_5$ affords the 5-halo-1,2,4-oxadiazole (24). The oxadiazole intermediates (23) and (24) can be converted into a compound (3E) of Formula I by the methods shown in Scheme B.

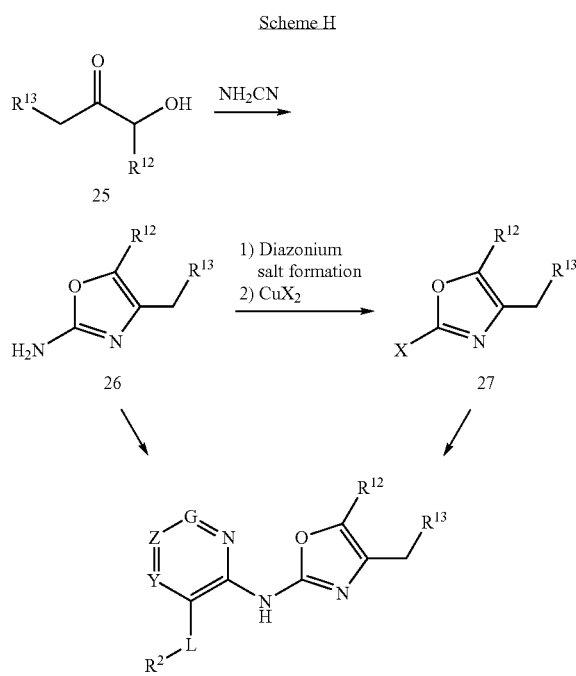

Scheme H shows a method of preparing 2-aminooxazole and 2-halo-oxazole intermediates (26) and (27), respectively, which are suitable for use in preparing compounds of Formula I as shown in Scheme B. According to Scheme H, α-hydroxyketone (25) is reacted with cyanamide to afford 2-aminooxazole (26) (Aust. J. Chem. (1985), 38, 447-458). Formation of the diazonium salt of compound (26), followed by treatment of the in situ diazonium salt with $CuX_2$ (where X=Cl or Br) affords the corresponding 5-halo-1,2,4-thiadiazole (27). Intermediates (26) and (27) can be converted into compound (3F) of Formula I by the method of Scheme B.

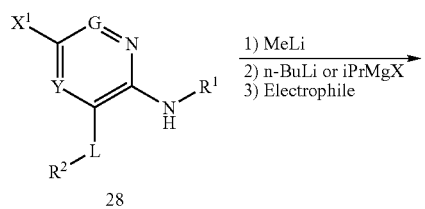

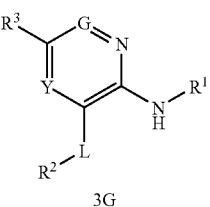

Scheme I shows a method of preparing compound (3G) of Formula I wherein Z is $CR^3$. According to Scheme I, the halo-substituted heterocycle (28) (prepared by the method of Scheme A or B) wherein $X^1$=Cl, Br or I, is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with an electrophile to provide compound (3G). Suitable electrophiles include, but are not limited to: 1) aldehydes, 2) nitriles, 3) N-methoxy-N-methylamides (Weinreb amides), 4) dialkylsulphides, 5) hexachloroethane, 6) trialkyl boronates, 7) sulphonyl chlorides, 8) sulfamyl chlorides, 9) isocyanates, 10) carbon dioxide, (11) alkyl halides, (12) trifluoroiodomethane (13) Mander's reagent, and (14) chloroformates. Exemplary compounds of the present invention which can be prepared according to the method of Scheme I include compounds (3G) wherein $R^3$ is alkyl, phenylalkyl, cycloalkyl, hydroxylalkyl (from $R^3Si(CH_2)_nI$), Cl, SH, SR', SOR', $SO_2R'$, OR', I, $SCH_2R'$, $OCH_2R'$, $CO_2H$, CH(OH)—R', and C(=O)R', wherein R' is alkyl, alkenyl, alkynyl, cycloalkyl, or aryl.

Alternatively, the halo-substituted heterocycle (28) can be converted to compound (3G) wherein $R^3$ is alkyl, aryl, heteroaryl, alkenyl or alkynyl, by a metal (e.g., Cu or Pd) mediated coupling reaction such as, but not limited to, the Negishi reaction, the Suzuki reaction, the Sonogashira reaction, or the Stille reaction.

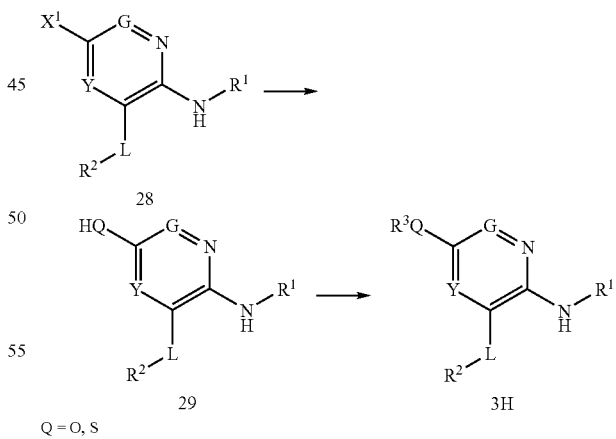

Scheme J shows a method of preparing compounds (3H) of Formula I, wherein Z=C—$SR^3$ or C—$OR^3$, and Q=O or S, from a halo substituted heterocycle (28). According to Scheme J, the halo-substituted heterocycle (28), prepared by the method of Scheme A or B, can be converted to a thiol or alcohol (29) by one of several procedures. According to one method, the halo-substituted heterocycle (28) is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with either elemental sulfur or bis(trimethylsilyl) peroxide to form the corresponding mercapto- or hydroxyl-substituted compound (29). Alternatively, the anion can be quenched with trimethyl borate and oxidized with either hydrogen peroxide (*J. Med. Chem.* (2004) 3089-3104) or N-methyl morpholine oxide (*Syn. Lett.* (1995) 931-932) to afford the phenol (29). As a third synthetic route, the halide (28) can be converted under Pd-mediated conditions to thiol or phenol (29) utilizing potassium triisopropylsilanethiolate (*Tetrahedron Letters* (1994) 3225-3226) or sodium tert-butyldimethylsiloxide (*J. Org. Chem.*, (2002) 5553-5566). The thiol or phenol (29) can be alkylated with a variety of electrophiles using standard reaction conditions to provide the corresponding ether (3H) of Formula I. Suitable electrophiles include, but are not limited to, alkyl halides, benzylic halides, heteraroyl-CH₂X, cycloalkyl halides, Michael acceptors, and activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine, 4-halopyrimidine, aryl halides and heteroaryl halides.

Alternatively, halide (28) can be converted to an alkyl sulfide using Pd-mediated conditions with appropriately functionalized sulfides. Examples of such sulfides include, but are not limited to, esters of 3-mercaptopropanoic acid, 3-mercaptopropanenitrile or 2-(trimethylsilyl)ethanethiol. Sulfides of this type can be deprotected to the thiol and alkylated with a variety of electrophiles under standard conditions (*Chemical & Pharmaceutical Bulletin* (1990), 38(10), 2667-75).

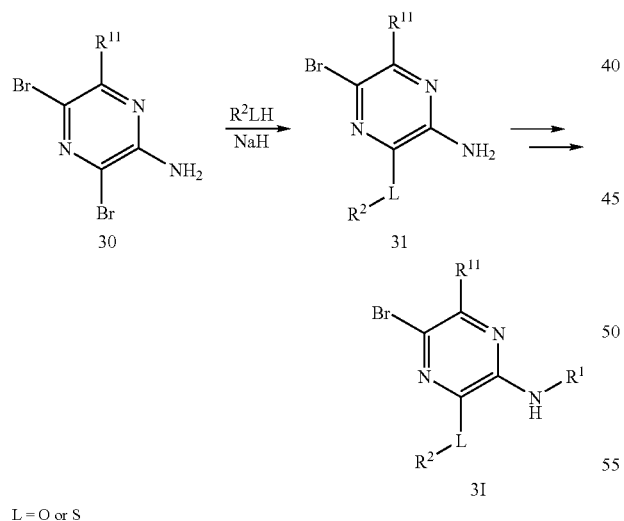

Scheme K

L = O or S

Scheme K shows a method of adding a linker L, wherein L is O or S, to a core heterocycle to provide a compound (31) of Formula I wherein G=CR$^{11}$, Z=C—Br, and Y=N. According to Scheme K, 2-amino-3,5-dibromopyrazine (30) is reacted with R$^2$LH, wherein L is O or S, in the presence of a suitable base such as K$_2$CO$_3$ or NaH in a suitable solvent such as DMF or ethanol to afford compound (31) regioselectively. Compound (31) can be converted to compound (3I) of Formula I by the method of Scheme A or B. Compound (3I) can be converted into additional 5-substituted compounds of Formula I by the methods shown in Scheme I or J.

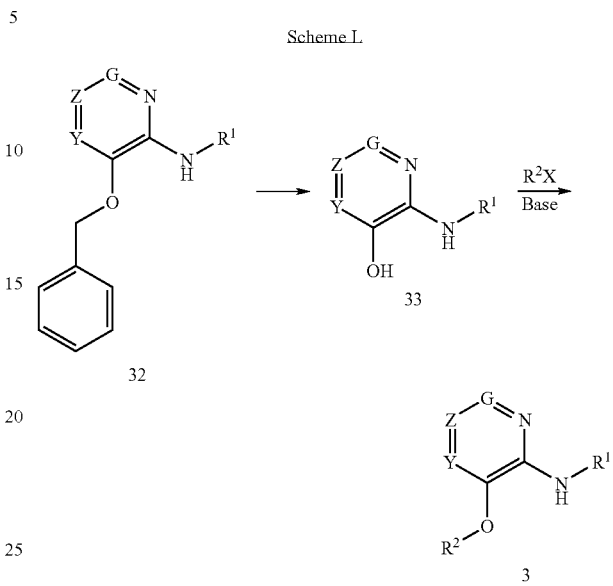

Scheme L

Scheme L shows an alternate method of adding the linker OR$^2$ to a core heterocycle to provide a compound (3) of Formula I wherein L is O. According to Scheme L, a benzyl ether (32), prepared by the method of Scheme A or B, can be converted to the hydroxyl substituted heterocycle (33), for example by hydrolysis with a strong acid (e.g., 6N HCl) or by hydrogenation (e.g., H$_2$ or ammonium formate in the presence of a metal catalyst). Alkylation of the hydroxylated heterocycle (33) with R$^2$X, wherein X=F, Cl, Br, I, or NR$^3$, in the presence of a base such as, but not limited to, cesium carbonate, in a suitable solvent such as, but not limited to, DMF, or by copper or palladium catalysis (i.e., the Ullman reaction) affords compound (3) of Formula I.

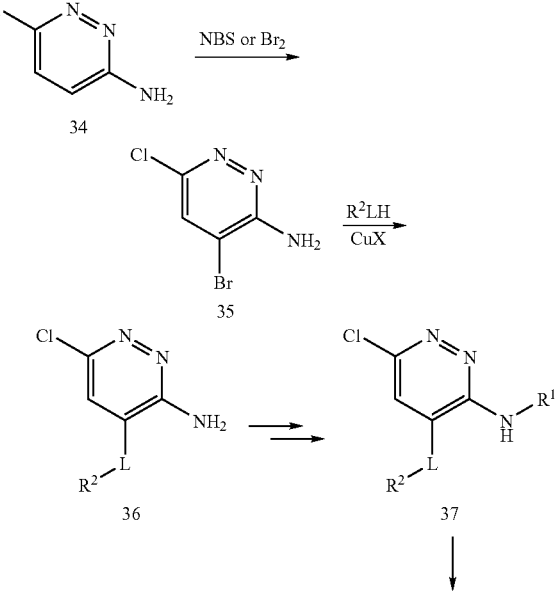

Scheme M

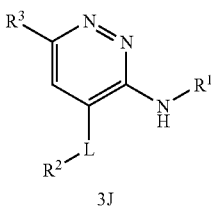

Scheme M shows a method of preparing a compound (3J) of Formula I wherein G=N, Z=CR³, Y=CH, and L=O or S. According to Scheme M, 6-chloropyridazin-3-amine (34) is regioselectively brominated with a suitable brominating agent such as bromine, NBS, etc., to provide compound (35). Reaction of compound (35) with R²LH (wherein L is O or S) in the presence of a suitable base such cesium carbonate or sodium hydride either with or without a metal catalyst (e.g., CuI) in DMSO or DMF regioselectively affords compound (36). Compound (36) can be converted to the chlorinated compound (37) of Formula I by the method of Scheme A or B. Compound (37) can be converted into a 5-substituted compound (3J) of Formula I by the method of Scheme I or J.

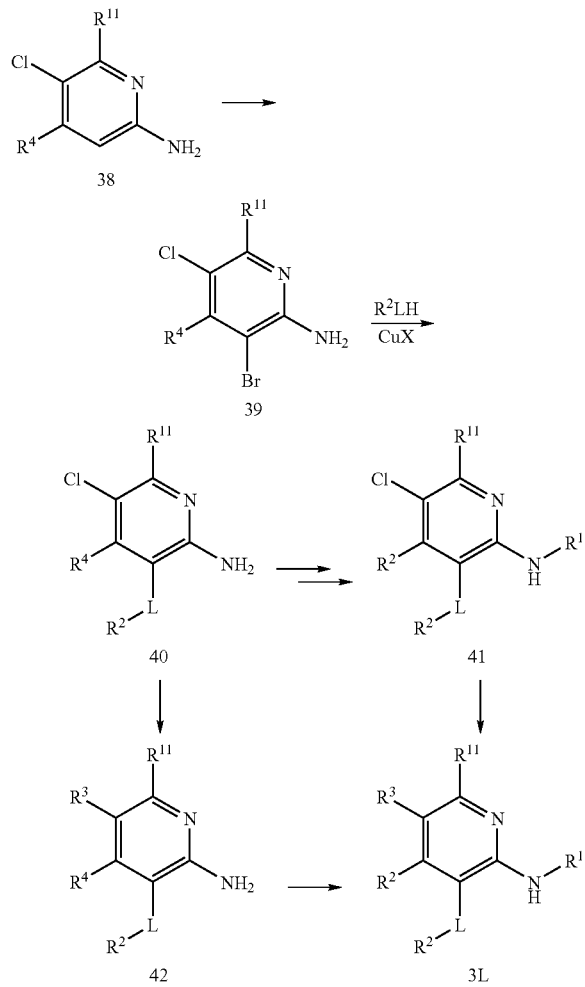

Scheme N shows a method of preparing a compound (3L) of Formula I wherein G=CR¹¹, Z=CR³, Y=CR⁴, and L is O or S. According to Scheme N, the 2-aminopyridine (38) is regioselectively brominated with a suitable brominating agent such as NBS or bromine to provide compound (39). The brominated compound can be converted to compound (40) upon reaction with R²LH (wherein L is O or S) in the presence of a suitable base such as cesium carbonate, sodium hydride or triethylamine in the presence of a metal catalyst (i.e.; CuI or Pd₂dba₃) in a suitable solvent such as DMSO or DMF. The chlorinated product (40) can be converted to compound (41) by the method of Scheme A or B. Compound (41) can be converted to a 5-substituted compound (3L) of Formula I by the method of Scheme I or J. Alternatively, the chlorinated 2-aminopyridine (40) can be converted to a 5-substituted compound (42) by the method of Scheme I or J, and then the heterocyclyl group R¹ can be added to compound (42) by the method of Scheme A or B to provide compound (3L).

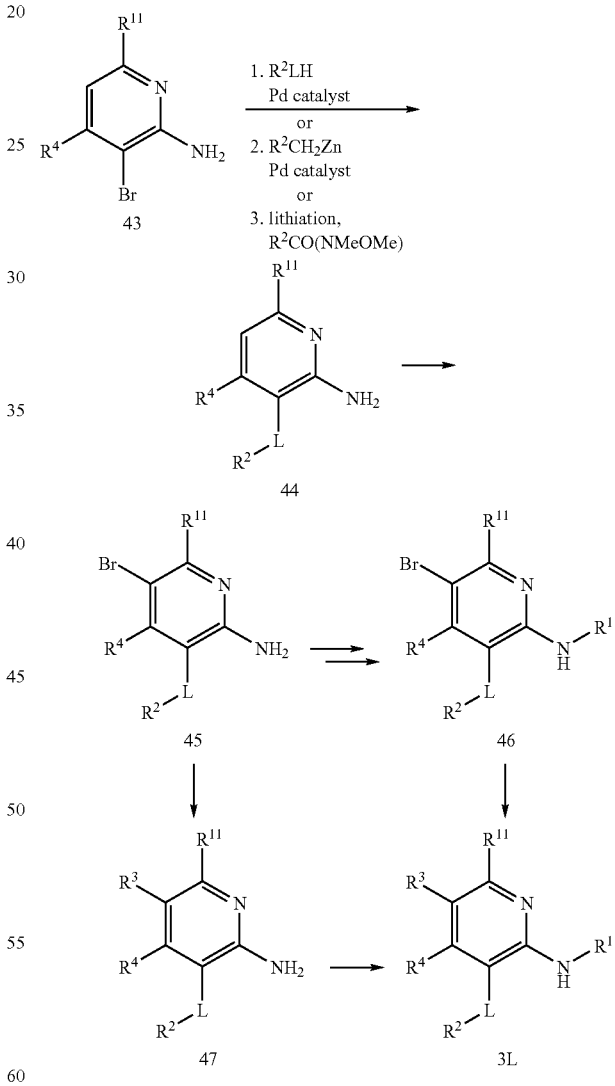

Scheme O shows a method of preparing a compound (3L) of Formula I wherein G=CR¹¹, Z=CR³, Y=CR⁴, and L is O or S. According to Scheme O, reaction of compound (43) with R²LH (wherein L is O or S) in the presence of a suitable base such cesium carbonate or sodium hydride either with or without a metal catalyst (i.e.; Pd₂dba₃ or CuI) in DMSO or DMF affords compound (44) wherein L is O or S. Alternatively, reaction of compound (43) with $R^2CH_2Zn$ under similar conditions affords compound (44) wherein L is $CH_2$. To prepare compound (44) wherein L is C=O, compound (43) can be treated to lithiation conditions as described in Scheme 1, followed by treatment with $R^2CO(NMeOMe)$.

The 2-aminopyridine (44) is then regioselectively brominated with a suitable brominating agent such as NBS or bromine to provide compound (45). The brominated product (45) can be converted to compound (46) by the method of Scheme A or B. Compound (46) can be converted to 5-substituted compounds (3L) of Formula I by the method of Scheme I or J. Alternatively, the brominated 2-aminopyridine (45) can be converted to a 5-substituted compound (47) by the method of Scheme I or J, and then the heterocyclyl group $R^1$ can be added to compound (47) by the method of Scheme A or B to provide compound (3L).

lectively brominated with a suitable brominating agent such as NBS or bromine to provide compound (50). The brominated product (50) can be converted to compound (51) by the method of Scheme A or B. Compound (51) can be converted to 5-substituted compounds (3L) of Formula I by Buchwald ether or thioether formation (with $R^2OH$ when L=O or $R^2SH$ when L=S), Negishi reactions (with $R^2CH_2Zn$ when L=$CH_2$), or by lithiation chemistry as described in Scheme I (when L is C=O) to provide compound (3L). Alternatively, the brominated 2-aminopyridine (50) can first be converted to compound (52) by the Buchwald, Negishi, or lithiation chemistry, and compound (52) can be converted to compound (3L) by the method of Scheme A or B.

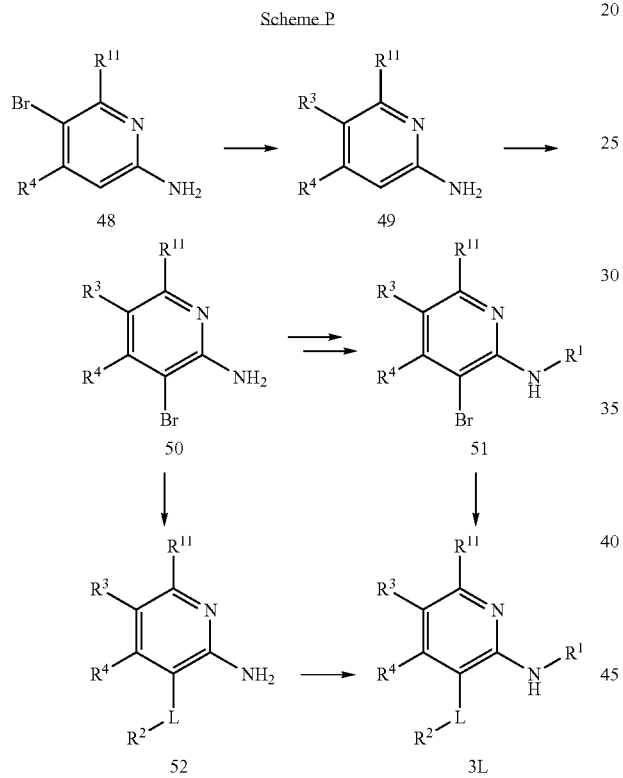

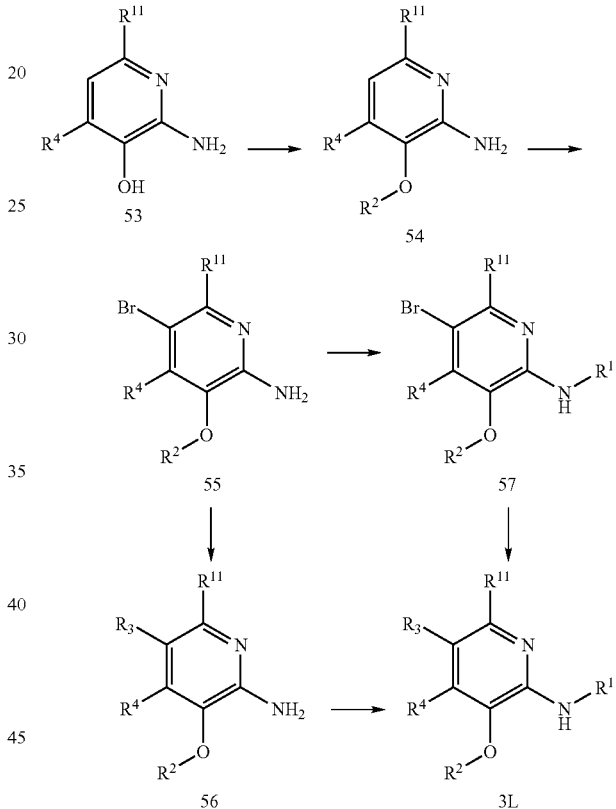

Scheme P shows an alternative method of preparing a compound (3L) of Formula I wherein G=$CR^{11}$, Z=$CR^3$, Y=$CR^4$, and L is O, S or $CH_2$. According to Scheme P, reaction of compound (48) (which if not commercially available can be made from commercial aminopyridines by regioselective bromination) in the presence of a suitable base such cesium carbonate or sodium hydride and with or without a metal catalyst (e.g., $Pd_2dba_3$ or CuI) in DMSO or DMF affords compound (49) by a method such as: ipso replacement (with $R^6OH$ or $R^6SH$ to provide compound (49) wherein $R^3$ is $OR^6$ or $SR^6$, respectively); Buchwald ether or thioether formation (with $R^6OH$ or $R^6SH$ to provide compound (49) wherein $R^3$ is $OR^6$ or $SR^6$, respectively); a Negishi reaction (with $R^3Zn$); an aryl or alkyl Suzuki reaction (with $R^3B(OH)_2$); a Heck reaction, etc., according to procedures well known in the literature and further exemplified in the Examples below. The 2-aminopyridine (49) is then regiose- Scheme Q shows a method of preparing a compound (3L) of Formula I wherein G=$CR^{11}$, Z=$CR^3$, Y=$CR^4$ and L is O. Treatment of compound (53) with $R^2X$ in the presence of a suitable base such as cesium carbonate or sodium hydride, with or without a metal catalyst, affords compound 54. Examples of $R^2X$ that can be utilized include substituted 2- and 4-nitrohalobenzenes, substituted 2- and 4-cyanohalobenzenes, 2-chloro-1-fluorobenzene, halogenated pyridines, halogenated pyrimidines, and other halogenated heterocycles. When $R^2X$ contains two halogens, the halogen ortho or para to an electron withdrawing group is selectively displaced in preference to the meta substituted halogen, and the leaving group potential using sodium hydride as a base is F>Cl>Br>I. In this way, a bromine-containing compound suitable for further functionalization can be made. For example using a brominated version of 2-chloro-1-fluorobenzene with 3-hydroxy-2-amino pyridine affords a brominated version of compound (54). The bromine can be converted to a variety of functional groups at this stage to form other analogs of compound (54) using palladium mediated or anion chemistry. Subsequently, compound (54) can be regioselectively brominated to afford compound (55). This compound can be converted to compound (56) by the methods described in Schemes I or J. Compound (56) is then converted to compound (3L) by the procedures found in Schemes A or B. Alternatively, compound (55) can be converted to compound (57) by the procedures found in Schemes A or B, and then converted to compound (3L) by the procedures found in Schemes I or J.

Scheme R

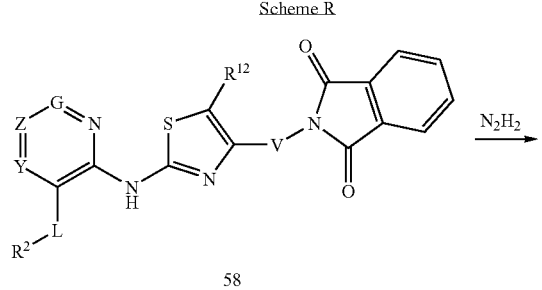

58

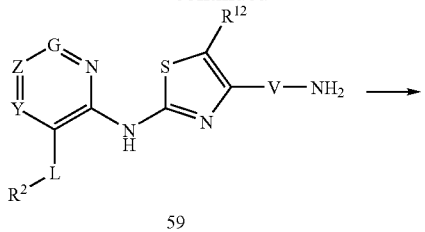

59

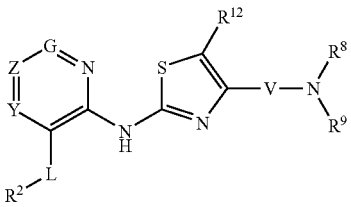

60

Scheme R shows a method of preparing compounds of Formula I wherein $R^1$ is a substituted thiazolyl. According to Scheme R, phthalimide-containing compound (58) wherein V is alkylene optionally substituted by one or more alkyl groups (which can be prepared by the method of Scheme A or B), can be converted to amine (59) by treatment with hydrazine. Amine (59) can be elaborated to the amide, carbamate, urea, thiourea, monoalkylamine, dialkylamine, amidine, or guanidine (60) by routine methods in the literature.

Scheme S

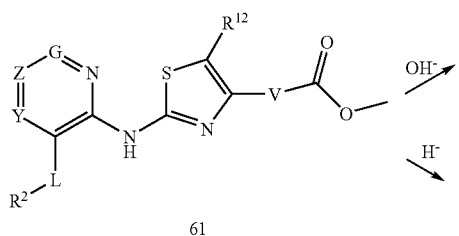

61

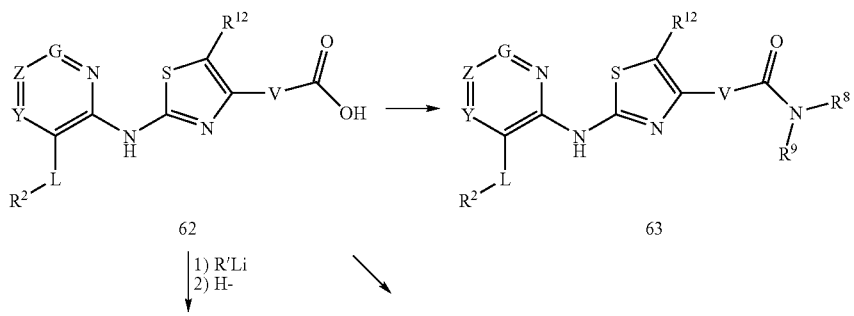

62   63

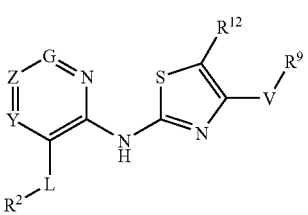

64   65

Scheme S shows an alternative method of preparing compounds of Formula I wherein $R^1$ is a substituted thiazolyl. According to Scheme S, the ester-containing compound (61), wherein V is alkylene optionally substituted by one or more alkyl groups (which can be prepared by the method of Scheme A or B), can be converted to carboxylic acid (62) by reduction or hydrolysis with a hydride or hydroxide, respectively. Compound (62) can be converted to alcohol (64) upon treatment with a lithium reagent R'Li. Alternatively, the carboxylic acid (62) can be converted to a primary, secondary or tertiary amide (63) using a variety of amide coupling methods known to those skilled in the art. Compound (62) can also be converted to compound (65), wherein $R^9$ is a heterocyclyl group such as, but not limited to, tetrazolyl, imidazolyl, triazolyl, or thiazoyl, by coupling methods known to those skilled in the art.

Scheme T describes the preparation of intermediates (68), (72) and (75) and substituted forms thereof suitable for use in preparing compounds of Formula (3A) wherein $R^{12}$ and $R^{13}$ form a fused heterocyclic ring. To prepare intermediate (68), 2-halo-3-aminopyridine (66) is reacted with a thiocyanate (for example, sodium or potassium thiocyanate) in acidic media (for example, acetic acid) to provide thiazolopyridine (67). Compound (67) is converted to the corresponding 2-halo compound (68) by standard methods (for example, by diazotization of the amine with $NaNO_2$ and $HX_3$, followed by reaction with $Cu(X^3)_2$).

To prepare intermediate (72), the 2-amino-3-halopyridazine (69) is reacted with a protected isothiocyanate to provide protected 2-aminothiazolopyridazine (70), which is deprotected under standard hydrolytic conditions to provide 2-aminothiazolopyridazine (71) (Koren, B., et al., *Heterocycles* 1987, 26(3), 689-697). The aminoheterocyclic compound (71) is converted to the corresponding 2-halo compound (72), for example, as described above.

To prepare intermediate (75), compound (73) is converted to the 2-aminothiazolotriazine (74), for example, using the method of Jacobsen, et al., (*Aust. J. Chem.* 1987, 40(3), 491-499). The aminoheterocyclic compound (74) is then converted to the corresponding 2-halo compound (75), for example, as described above.

It will be appreciated that the aminoheterocycles (68), (72) and (75) can be further functionalized if desired, for example by halogenation of the 6-membered ring (for example with NBS or bromine). Such halogenated derivatives may be further modified using well known methods.

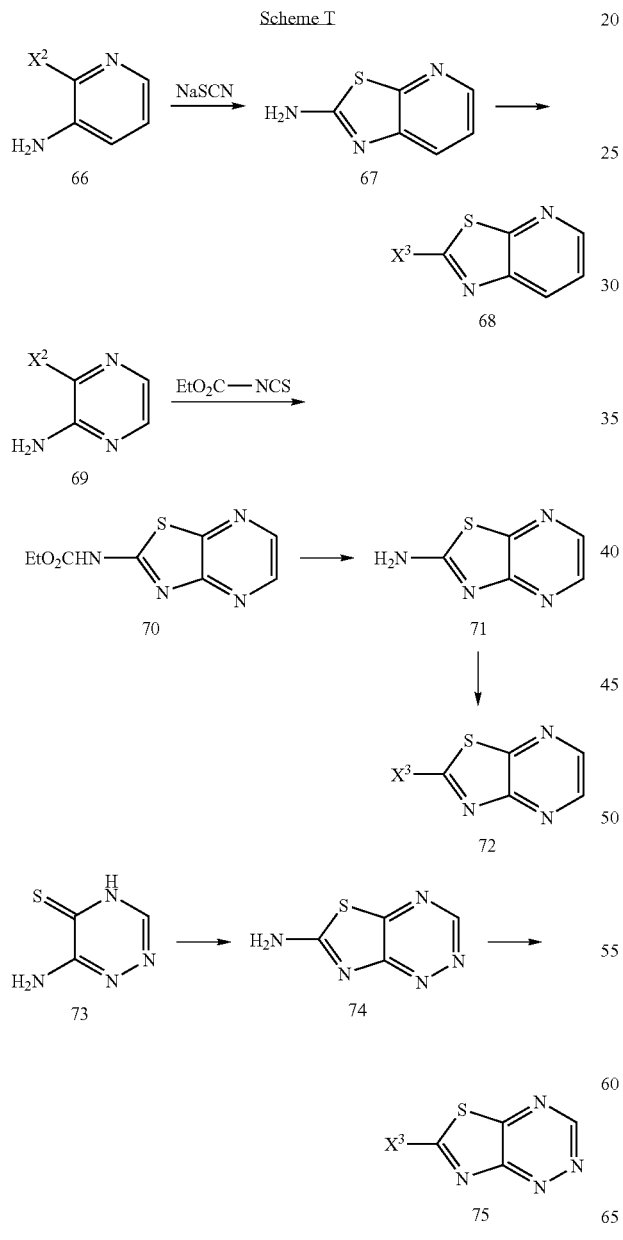

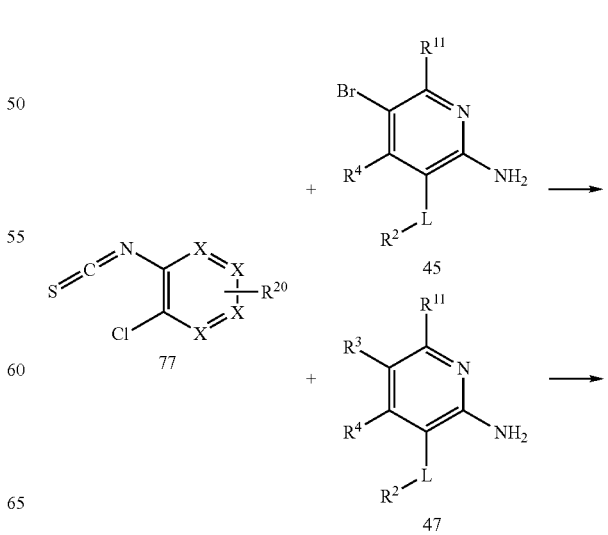

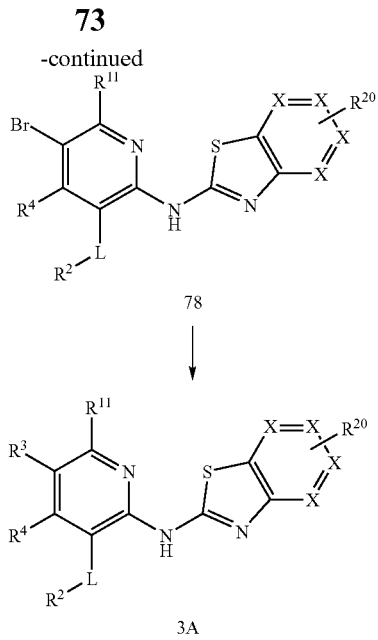

Scheme U shows an alternative method of preparing compounds of Formula (3A) wherein $R^{12}$ and $R^{13}$ form a fused heterocyclic ring. Substituted 2-halo-aminoheterocycles (76), wherein at least one X=N, but no more than two consecutive X are N, is reacted with thiophosgene to provide the isothiocyanate (77). Refluxing the isothiocyanate (77) with the 5-brominated aminopyridine (45) in a suitable solvent such as ethanol or THF affords the heterocycle (78), which can be converted to compounds of Formula (3A) by the methods described in Scheme P. Alternatively, the aminopyridine (47), prepared as in Scheme P, is refluxed with the isocyanate (77) to afford compounds of structure (3A).

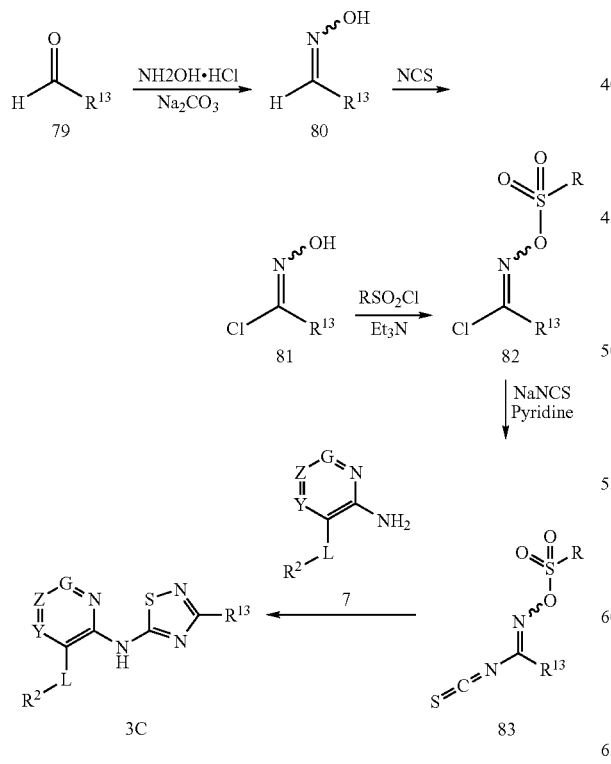

Scheme V shows an alternative method for producing compounds of the formula 3C wherein $D^2$ is N. Formation of oxime (80) from aldehyde (79) allows for the chlorination with N-chlorosuccinimide in a suitable solvent, such as DMF, to produce compound (81). Compound (81) is sulfonylated with a sulfonyl chloride having the formula R'SO$_2$Cl wherein R' is, $C_1$-$C_6$ alkyl (for example, methyl) or aryl optionally substituted with $C_1$-$C_6$ alkyl (for example, tolyl) in the presence of a base, such as but not limited to triethylamine, to afford compound (82) (See, for example, Gibbons, L. U.S. Pat. No. 3,983,246). Reaction of compound (82) with a thiocyanate salt, such as NaNCS, in a suitable solvent, such as acetonitrile, and in the presence of a base, such as but not limited to pyridine, affords the activated intermediate (83) (see, for example, Takeuchi, K., JP 2001081084). Intermediate (83) can be reacted in situ with an appropriate amino heterocycle (7) to afford compounds of the structure (3C) of Formula I.

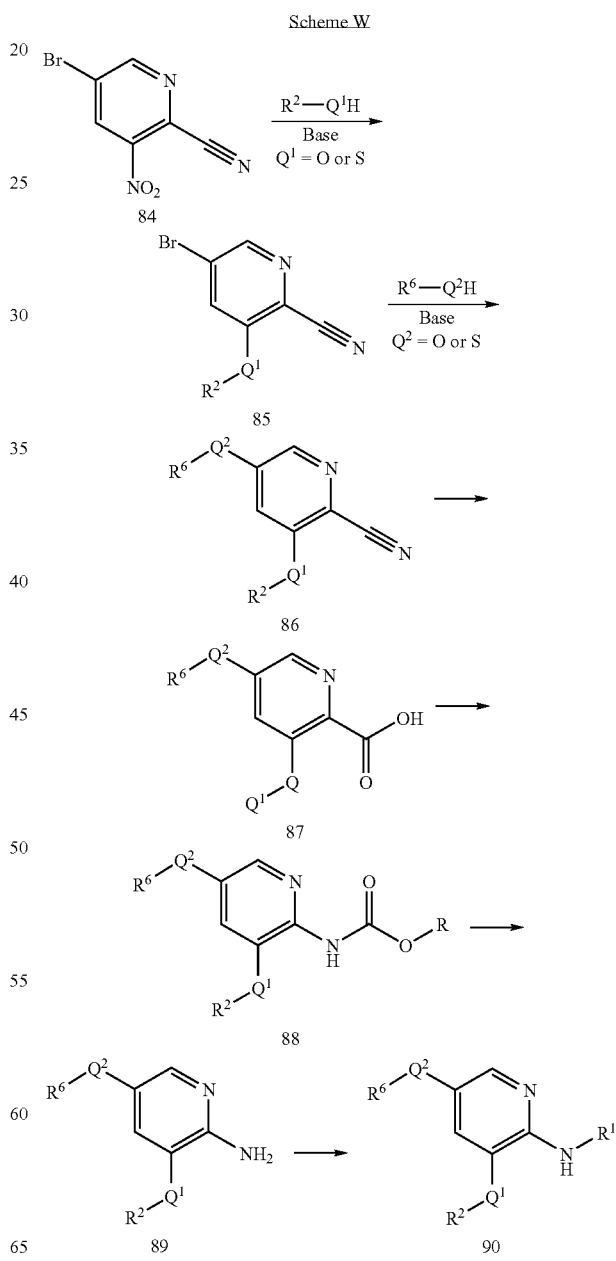

Scheme W shows an alternative method for the construction of compounds of Formula I where G and Y are CH, Z is C—SR$^6$ or C—OR$^6$, and L is O or S. Starting from the commercially available 2-cyanopyridine (84), selective nucleophilic displacement can be achieved with compounds of the formula R$^2$Q$^1$H, where Q$^1$ is O or S, and an appropriate base, such as sodium hydride, in a suitable solvent, such as DMF to provide compound (85). Addition of a second nucleophile having the formula R$^6$Q$^2$H, wherein Q$^2$ is O or S, under similar conditions, affords the functionalized 2-cyanopyridine (86). Hydrolysis of the nitrile can occur under many conditions, with NaOH in aqueous ethanol being preferred, to afford the picolinate (87). Curtius rearrangement in the presence of an appropriate alcohol affords the carbamate (88). The carbamate can be removed using various conditions, depending on the alcohol used in the previous step, to provide the 2-aminopyridine (89). Using procedures outlined in Schemes A, B or T, compounds (90) of the Formula I can be synthesized from compound (89).

Accordingly, another embodiment of the invention provides a method for preparing a compound of Formula I or a salt thereof, comprising:

(a) reacting a corresponding compound of the formula

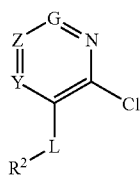

with a compound of the formula R$^1$NH$_2$ in the presence of a base catalyst or metal catalyst; or (b) reacting a corresponding compound of the formula

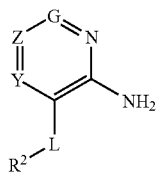

with a compound of the formula R$^1$—X, wherein X is Cl or Br, in the presence of a base catalyst or metal catalyst; or (c) for a compound of Formula I wherein R$^1$ is

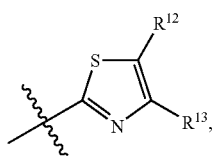

reacting a corresponding compound of the formula

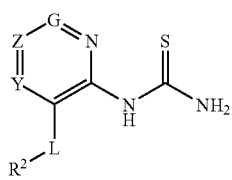

with a compound of the formula R$^{13}$COCHR$^{12}$X, wherein X is a leaving group such as OTs, Cl, Br, I, or NR$^3$ and R is C$_1$-C$_6$ alkyl, in the presence of a base; or (d) for a compound of Formula I wherein R$^1$ is

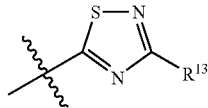

reacting a corresponding compound of the formula

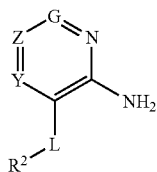

with a compound having the formula

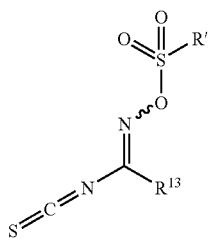

where R' is C$_1$-C$_6$ alkyl or aryl optionally substituted with C$_1$-C$_6$ alkyl, in the presence of a base; or (e) for a compound of Formula I wherein Z is SR$^6$, reacting a corresponding compound having the formula

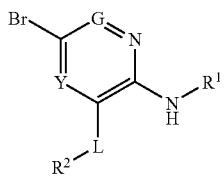

with a compound having the formula R$^6$SSR$^6$ in the presence of a suitable base, for example, an alkyl lithium such as methyl lithium, butyl lithium, or a mixture thereof; or (e) for a compound of Formula I wherein Z is SR$^6$, reacting a corresponding compound having the formula

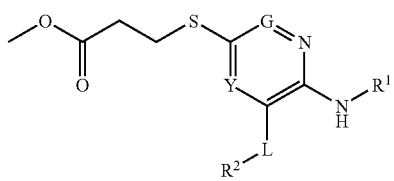

with a compound having the formula $R^6X$ wherein X is a leaving group or atom such as a halogen (e.g., F, Cl or Br) or a sulfonate (e.g., OMs or OTs) in the presence of a suitable base, for example an alkali metal alkoxide such as potassium t-butoxide; or (f) for a compound of Formula I wherein $R^1$ is

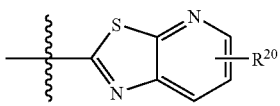

reacting a corresponding compound having the formula

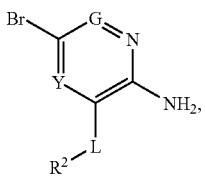

with a compound having the formula

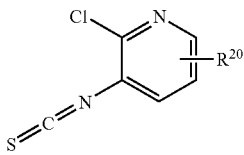

in a suitable solvent, for example DMF, at elevated temperatures, for example 80-110° C.; or g) for a compound of Formula I wherein Z is $CR^3$, reacting a corresponding compound having the formula

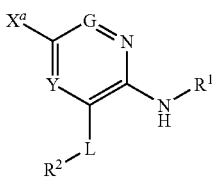

wherein $X^a$ is a leaving group or atom (e.g., a halogen such as Br, Cl or I,) with a compound having the formula $R^3$—$X^b$ wherein $X^b$ is a leaving group or atom, in the presence of a suitable base (e.g., an alkyl lithium such as methyl lithium, butyl lithium, or a combination thereof); or h) for a compound of Formula I wherein Z is C—$SR^6$ and $R^6$ is alkyl, $CH_2$-aryl, heteroaryl, or aryl and wherein said $R^6$ groups are optionally substituted, reacting a corresponding compound having the formula

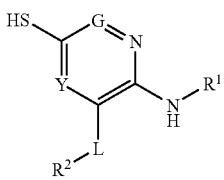

with a compound having the formula $R^6$—$X^c$ wherein $X^c$ is a leaving group or atom (e.g., a halogen such as Cl or Br) in the presence of a suitable base; or i) for a compound of Formula I wherein L is O, reacting a corresponding compound having the formula

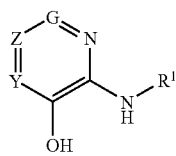

with a compound having the formula $R^2$—$X^d$, wherein $X^d$ is a leaving group or atom (e.g., a halogen such as Cl or Br; or a triflate or tosylate group), in the presence of a base (e.g., an alkali metal carbonate such as $CsCO_3$) or in the presence of a copper or palladium catalyst; or j) for a compound of Formula I wherein L is O or S, reacting a corresponding compound having the formula

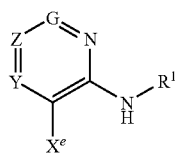

wherein $X^e$ is a leaving group or atom (e.g., Br, I or OTf) with a compound having the formula $R^2LH$ wherein L is O or S, respectively; in the presence of a palladium catalyst (e.g., $Pd(OAc)_2$ and a ligand) and a suitable base (e.g., $K_2CO_3$, NaH, NaOt-Bu) and a suitable solvent (e.g., toluene) at temperatures ranging from ambient temperature to 100° C.; or k) for a compound of Formula I wherein L is $CH_2$, reacting a corresponding compound having the formula

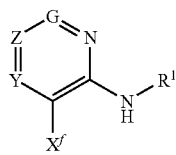

wherein $X^f$ is a leaving group or atom (e.g., Cl, Br, I, OTf or acetyloxy) in the presence of an organozinc compound having the formula $R^2$—Zn—$X^g$ wherein $X^g$ is a halide (e.g., Cl, Br, or I) and a nickel or palladium catalyst; and removing any protecting group or groups and, if desired, forming a salt.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH—Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art.

Methods of Treatment with Compounds of Formula I

The compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Accordingly, another aspect of the invention provides methods of treating or preventing diseases or conditions described herein by administering to a mammal, such as a human, a therapeutically effective amount of a compound of Formula I.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "mammal" refers to a warm-blooded animal that has or is at risk of developing a disease described herein and includes, but is not limited to, guinea pigs, dogs, cats, rats, mice, hamsters, and primates, including humans.

In certain embodiments, the methods of this invention are useful for treating diabetes mellitus. Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

In certain embodiments, the methods of this invention are useful for treating the syndrome of impaired glucose tolerance (IGT). IGT is diagnosed by the presentation of a fasting plasma glucose level of less than 126 mg/dL and a 2-hour post-oral glucose challenge lever greater than 140 mg/dL.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), myocardiac infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

This invention also provides the use of a compound of Formula I in the treatment of diseases or disorders mediated by deficient levels of glucokinase activity or which can be treated by activating glucokinase.

An additional aspect of the invention is the use of a compound of Formula I in the preparation of a medicament for the treatment or prevention of diseases or disorders mediated by deficient levels of glucokinase activity or which can be treated by activating glucokinase.

Combination Therapy

The compounds of the present invention can be used in combination with one or more additional drugs such as described below. The dose of the second drug can be appropriately selected based on a clinically employed dose. The proportion of the compound of the present invention and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of the present invention.

The second compound of the pharmaceutical combination formulation or dosing regimen preferably has complementary activities to the compound of this invention such that they do not adversely affect each other. Such drugs are suitably present in combination in amounts that are effective for the purpose intended. Accordingly, another aspect of the present invention provides a composition comprising a compound of this invention in combination with a second drug, such as described herein.

A compound of this invention and the additional pharmaceutically active agent(s) may be administered together in a unitary pharmaceutical composition or separately and, when administered separately this may occur simultaneously or sequentially in any order. Such sequential administration may be close in time or remote in time. The amounts of the compound of this invention and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The compounds of the present invention can be used, for example, in combination with additional drug(s) such as a therapeutic agent for diabetes mellitus, and/or a therapeutic agent for diabetic complications, as defined above. Examples of known therapeutic agents for diabetes mellitus which can be used in combination with a compound of this invention include insulin preparations (e.g., animal insulin preparations extracted from the bovine or swine pancreas; human insulin preparations synthesized by a genetic engineering technique using *Escherichia coli* or a yeast), a fragment of insulin or derivatives thereof (e.g., INS-1), agents for improving insulin resistance (e.g., pioglitazone hydrochloride, troglitazone, rosiglitazone or its maleate, GI-262570, JTT-501, MCC-555, YM-440, KRP-297, CS-011, FK-614), alpha-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or its calcium salt hydrate, GLP-1], dipeptidylpeptidase IV inhibitors (e.g., NVP-DPP-278, PT-100), beta-3 agonists (e.g., CL-316243, SR-58611-A, UL-TG-307, SB-226552, AJ-9677, BMS-196085, AZ-40140, etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), and the like.

Examples of known therapeutic agents for diabetic complications include aldose reductase inhibitors (e.g., tolrestat, epalrestat, zenarestat, zopolrestat, minalrestat, fidarestat (SNK-860), CT-112), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g., thioctic acid), and cerebral vasodilators (e.g., tiapuride, mexiletine).

The compounds of the present invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include, but are not limited to, statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The compounds of the present invention can also be used, for example, in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include, but are not limited to, angiotensin converting enzyme inhibitors (e.g., captopril, enalapril, delapril), angiotensin II antagonists (e.g., candesartan cilexetil, losartan, eprosartan, valsantan, termisartan, irbesartan, tasosartan), calcium antagonists (e.g., manidipine, nifedipine, nicardipine, amlodipine, efonidipine), and clonidine.

The compounds of the present invention can be used in combination with antiobesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centers. The satiety center may be activated by the increases in plasma glucose and/or insulin that follow a meal. Examples of antiobesity agents include, but are not limited to, antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-316243, SR-58611-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-15849).

Routes of Administration

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with, for example, the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of this invention in association with a pharmaceutically acceptable diluent or carrier.

In another embodiment of the invention, an article of manufacture, or "kit", containing materials useful for the treatment of the disorders described above is provided. In one embodiment, the kit comprises a container comprising a compound of this invention. Suitable containers include, for example, bottles, vials, syringes, blister pack, etc. The container may be formed from a variety of materials such as glass or plastic. The container may hold a compound of this invention or a formulation thereof which is effective for treating the condition and may have a sterile access port (for example, the container may be an intravenous solution bag or a vial having a stopper pierceable by a hypodermic injection needle).

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other glucokinase activators of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

The compounds of this invention also include the compounds of Examples 1-478 described below, with the exception of the examples labeled as "reference examples". Compounds labeled "Reference Examples" were found to be weakly active in the in vitro assays described below, and are provided to illustrate representative methodology in preparing compounds of Formula I.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents by syringe. Glassware was oven dried and/or heat dried.

Column chromatography was done on a Biotage system (Manufacturer: Dyax Corporation) having a silica gel column or on a silica SepPak cartridge (Waters). $^1$H NMR spectra were recorded on a Varian instrument operating at 400 MHz. $^1$H NMR spectra were obtained as $CDCl_3$ or $d_6$-DMSO solutions (reported in ppm), using (7.25 ppm) or tetramethylsilane (0.00 ppm) as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2-(2-(4-Methylthiazol-2-ylamino)pyridin-3-yloxy)benzonitrile

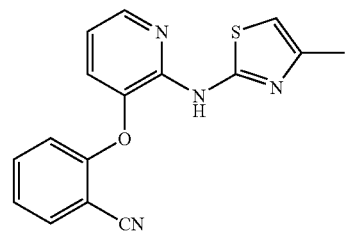

Step A: 2-(2-chloropyridin-3-yloxy)benzonitrile: A 50 mL round bottom flask was charged with 2-chloropyridin-3-ol (2.5 g, 19 mmol), 2-fluorobenzonitrile (2.6 g, 21 mmol) and potassium carbonate (6.7 g, 48 mmol) in DMF (10 mL) and heated at 90° C. for 1.5 days. Water was added water, and the reaction mixture was extracted with ethyl acetate, dried over magnesium sulfate, filtered and concentrated. The residue was purified by silica gel column chromatography using 10-20% ethyl acetate in hexanes as eluent to afford the title compound as an off white solid (2.1 g, 47% yield).

Step B: 2-(2-(4-methylthiazol-2-ylamino)pyridin-3-yloxy)benzonitrile: A 50 mL round bottom flask was charged with 2-(2-chloropyridin-3-yloxy)benzonitrile (0.667 g, 2.89 mmol), 4-methylthiazol-2-amine (0.300 g, 2.63 mmol), potassium phosphate (0.614 g, 2.89 mmol) and toluene (7 mL). The reaction mixture was degassed with nitrogen. Tris (dibenzylideneacetone)-dipalladium (0) (0.0602 g, 0.0657 mmol) and 4,5-bis(diphenylphosphino)-9,9-dimethyl-9H-xanthene (0.0418 g, 0.0723 mmol) were added, and the reaction mixture was degassed with nitrogen. The reaction mixture was warmed to 90° C. and degassed water (2 mL) was added. The reaction mixture was stirred at 90° C. overnight. Water was added and the reaction mixture was extracted with ethyl acetate. The organic layer was dried over magnesium sulfate, filtered and concentrated. The residue was purified by silica gel column chromatography using 10-40% ethyl acetate in hexanes as eluent to afford the title compound as a yellow solid (0.385 g, 46.6% yield). $^1$H NMR (CDCl$_3$) δ 8.19 (dd, 1H), 7.68 (dd, 1H), 7.49 (m, 1H), 7.19 (dd, 1H), 7.15 (dd, 1H), 6.85 (m, 2H), 6.39 (m, 1H), 2.29 (d, 3H); Mass spectrum (esi) m/z=309 (100).

Example 2

4-(2-(4-Methylthiazol-2-ylamino)pyridin-3-yloxy)benzonitrile

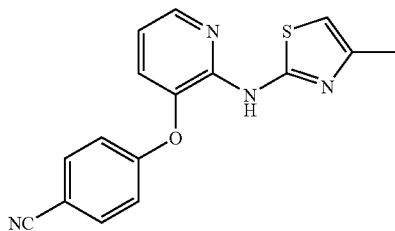

Prepared according to the method of Example 1, starting with 4-(2-chloropyridin-3-yloxy)benzonitrile. $^1$H NMR (CDCl$_3$) δ 8.19 (dd, 1H), 7.62 (m, 1H), 7.59 (m, 1H), 7.21 (dd, 1H), 7.02 (m, 1H), 7.00 (m, 1H), 6.87 (dd, 1H), 6.39 (m, 1H), 2.28 (d, 3H); Mass spectrum (esi) m/z=309 (100).

Example 3

2-(2-(3-Methyl-1,2,4-thiadiazol-5-ylamino)pyridin-3-yloxy)benzonitrile

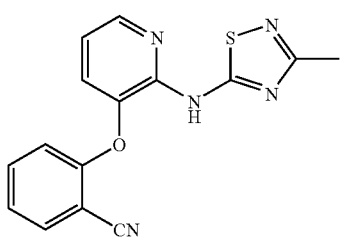

Prepared according to the method of Example 1, Step B, starting with 2-(2-chloropyridin-3-yloxy)benzonitrile. $^1$H NMR (CDCl$_3$) δ 9.14 (bs, 1H), 8.28 (dd, 1H), 7.73 (dd, 1H), 7.56 (m, 1H), 7.24-7.29 (m, 2H), 7.00 (dd, 1H), 6.94 (d, 1H) 2.52 (s, 3H); Mass spectrum (esi) m/z=310 (100).

Example 4

Representative Example

N-(4-methylthiazol-2-yl)-3-(2-nitrophenoxy)pyridin-2-amine

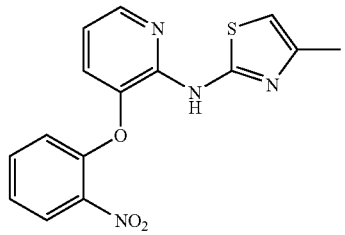

Prepared according to the method of Example 1, Step B, starting with 4-methylthiazol-2-amine. $^1$H NMR (CDCl$_3$) δ 10.12 (bs, 1H), 8.13 (m, 1H), 7.84 (dd, 1H), 7.71 (dt, 1H), 7.59 (m, 2H), 7.41 (dd, 1H), 7.11 (dd, 1H), 6.23 (m, 1H), 2.28 (d, 3H); Mass spectrum (esi) m/z=329 (100).

Example 5

N-(4-Methylthiazol-2-yl)-3-(4-nitrophenoxy)pyridin-2-amine

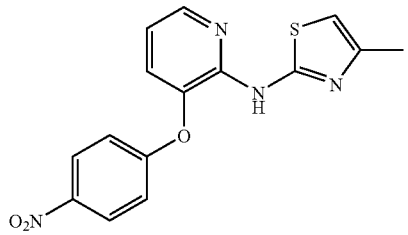

Prepared according to the method of Example 1, Step B, starting with 4-methylthiazol-2-amine. $^1$H NMR (CDCl$_3$) δ 9.30 (bs, 1H), 8.24 (m, 1H), 8.22 (m, 1H), 8.00 (dd, 1H), 7.44 (dd, 1H), 7.33 (m, 1H), 7.30 (m, 1H), 7.21 (dd, 1H), 6.53 (m, 1H), 2.36 (d, 3H); Mass spectrum (esi) m/z=329 (100).

Example 6

3-(4-(Methylsulfonyl)phenoxy)-N-(4-methylthiazol-2-yl)pyridin-2-amine hydrochloride

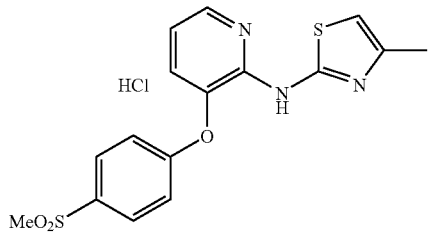

Prepared according to the method of Example 1, starting with 2-chloro-3-(4-(methylsulfonyl)phenoxy)pyridine. $^1$H NMR (CDCl$_3$) δ 8.28 (dd, 1H), 7.94 (m, 1H), 7.92 (m, 1H), 7.63 (dd, 1H), 7.23 (m, 1H), 7.21 (m, 1H), 7.13 (dd, 1H), 6.74 (bs, 1H), 3.20 (s, 3H), 2.26 (d, 3H); Mass spectrum (esi) m/z=362 (100).

Example 7

5-Chloro-N-(4-methylthiazol-2-yl)-3-phenoxypyridin-2-amine

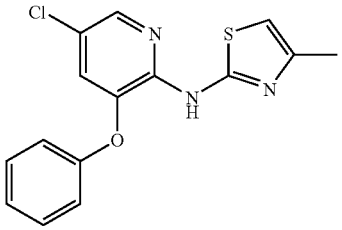

Step A: 3-bromo-5-chloropyridin-2-amine: A 250 mL round-bottomed flask was charged with 5-chloropyridin-2-amine (80 g, 622.3 mmol) and CHCl$_3$ (100 mL). Added bromine (31.98 mL, 622.3 mmol) and stirred at room temperature for 30 minutes. The reaction mixture was poured into saturated bicarbonate and NaHSO$_3$ and extracted with CH$_2$Cl$_2$. The organic layer was dried with sodium sulfate, filtered and concentrated to afford the title compound (113.8 g, 88.1% yield) as a tan solid. $^1$H NMR (d$_6$-DMSO) δ 7.97 (d, 1H), 7.90 (d, 1H), 6.44 (bs, 2H).

Step B: 5-chloro-3-phenoxypyridin-2-amine: 3-Bromo-5-chloropyridin-2-amine (50.0 g, 241 mmol), phenol (45.4 g, 482 mmol), copper(I)oxide (1.72 g, 12.1 mmol), (E)-2-hydroxybenzaldehyde oxime (6.61 g, 48.2 mmol), Cs$_2$CO$_3$ (157 g, 482 mmol), and 3A powdered molecular (72.3 g) sieves were placed in DMF (300 mL) and heated at 110° C. for 3 days. Reaction was cooled, then filtered through celite. Reaction was then partitioned between water and ether. An emulsion was formed and was filtered through a plug of celite. Water was extracted with ether then dried, filtered, and concentrated. Crude material was purified on a first silica gel chromatography (5-10% EtOAc in hexanes), and then on a second column to provide the title compound (8.00 g, 15.0% yield). $^1$H NMR (CDCl$_3$) δ 7.80 (d, 1H), 7.39 (t, 2H), 7.19 (t, 1H), 7.03 (d, 2H), 6.94 (d, 1H), 4.76 (bs, 2H); Mass spectrum (apci) m/z=221 (100).

Step C: 1-benzoyl-3-(5-chloro-3-phenoxypyridin-2-yl) thiourea: 5-chloro-3-phenoxypyridin-2-amine (8.493 g, 38.490 mmol) and benzoyl isothiocyanate (6.9096 g, 42.339 mmol) were placed in THF (200 mL) and stirred at room temperature for 2 hours. THF was removed. A suspension was made by adding Hexanes:EtOAc (9:1). The suspension was filtered and the solid was washed with hexanes then dried to afford the title compound (13.752 g, 93.1% yield) as a yellow solid. $^1$H NMR (d$_6$-DMSO) δ 12.35 (s, 1H), 11.84 (s, 1H), 8.34 (d, 1H), 7.95 (d, 2H), 7.66 (t, 1H), 7.53 (t, 2H), 7.44 (m, 3H), 7.24 (t, 1H), 7.18 (m, 2H); Mass spectrum (apci) m/z=383.1 (M+H).

Step D: 1-(5-chloro-3-phenoxypyridin-2-yl)thiourea: A 250 mL round-bottomed flask was charged with 1-benzoyl-3-(5-chloro-3-phenoxypyridin-2-yl)thiourea (13.752 g, 35.826 mmol) and THF (100 mL). 3M NaOH (119.42 mL, 358.26 mmol) was added and the reaction mixture was heated to 90° C. for 18 hours. The reaction mixture was cooled to room temperature and concentrated. The resulting solids were filtered, washed with water, and dried to provide the title compound (9.49 g, 94.689% yield) as a yellow solid. $^1$H NMR (d$_6$-DMSO) δ 9.97 (s, 1H), 9.25 (s, 1H), 8.87 (s, 1H), 8.11 (d, 1H), 7.49 (t, 2H), 7.31 (d, 1H), 7.28 (m, 2H), 7.23 (d, 2H); Mass spectrum (apci) m/z=279.9 (M+H).

Step E: 5-chloro-N-(4-methylthiazol-2-yl)-3-phenoxypyridin-2-amine: A mixture of 1-chloropropan-2-one (3.827 g, 41.36 mmol), 1-(5-chloro-3-phenoxypyridin-2-yl)thiourea (8.265 g, 29.54 mmol), triethylamine (7.001 mL, 50.23 mmol), and ethanol (30 mL) was refluxed for 3 hours. The ethanol was removed to about one third original volume, and then the reaction mixture was cooled in an ice bath and filtered. The solids were washed with cold ethanol and dried to afford the title compound (8.35 g, 88.96% yield) as a light yellow powder. $^1$H NMR (d$_6$-DMSO) δ 10.94 (bs, 1H), 8.15 (d, 1H), 7.43 (t, 2H), 7.32 (d, 1H), 7.20 (t, 1H), 7.19 (d, 2H), 6.60 (s, 1H), 2.23 (s, 3H); Mass spectrum (apci) m/z=318.2 (M+H).

Example 8

N-(4-methylthiazol-2-yl)-3-phenoxy-5-(phenylthio)pyridin-2-amine hydrochloride

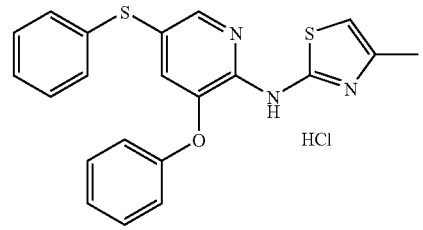

5-Chloro-N-(4-methylthiazol-2-yl)-3-phenoxypyridin-2-amine (0.150 g, 0.472 mmol) was placed in THF (30 mL) and cooled to −78° C. MeLi (0.369 mL, 0.590 mmol) was slowly added and the reaction mixture was stirred for 10 minutes. Butyllithium (0.236 mL, 0.590 mmol) was added and the reaction mixture was stirred for 30 minutes. 1,2-Diphenyldisulfane (0.103 g, 0.472 mmol) was added and the reaction mixture was warmed to room temperature, then stirred for 15 minutes. The reaction mixture was quenched with ammonium chloride and extracted with CH$_2$Cl$_2$. The organic layer was dried, filtered, and concentrated. The residue was purified by silica gel chromatography (10-20% EtOAc in hexanes), and then by reverse phase chromatography to give the title compound (0.0572 g, 28.3% yield) after salt formation. $^1$H NMR (d$_6$-DMSO) δ 10.94 (bs, 1H), 8.15 (d, 1H), 7.43 (t, 2H), 7.32 (d, 1H), 7.20 (t, 1H), 7.19 (d, 2H), 6.60 (s, 1H), 2.23 (s, 3H); Mass spectrum (apci) m/z=392.2 (M+H—HCl).

Example 9

N-(4-methylthiazol-2-yl)-3-phenoxy-5-phenylpyridin-2-amine hydrochloride

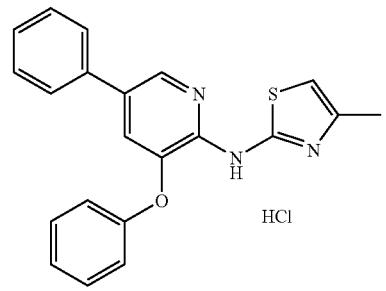

5-Chloro-N-(4-methylthiazol-2-yl)-3-phenoxypyridin-2-amine (0.150 g, 0.472 mmol), phenylboronic acid (0.0691 g, 0.566 mmol), Pd(PPh$_3$)$_4$ (0.0545 g, 0.0472 mmol), in DME (10 mL), and 2M Na$_2$CO$_3$ (5 mL) were placed in a round bottom flask, heated to 80° C. and stirred overnight. An extra equivalent of Pd(PPh$_3$)$_4$ (0.0545 g, 0.0472 mmol), and phenylboronic acid (0.0691 g, 0.566 mmol) were added and the reaction mixture was heated for 2 weeks. The reaction mixture was cooled to room temperature and partitioned between CH$_2$Cl$_2$ and water. The organic layer was dried, filtered, and concentrated. The residue was purified by silica gel chromatography and then by reverse phase chromatography to give the title compound (0.0134 g, 7.17% yield) after salt formation. $^1$H NMR (d$_6$-DMSO) δ 8.53 (d, 1H), 7.65 (m, 3H), 7.45 (m, 4H), 7.37 (m, 1H), 7.21 (t, 1H), 7.16 (d, 2H), 6.78 (s, 1H), 2.29 (s, 3H); Mass spectrum (apci) m/z=360.3 (M+H—HCl).

Example 10

5-Bromo-N-(4-methylthiazol-2-yl)-3-phenoxypyridin-2-amine

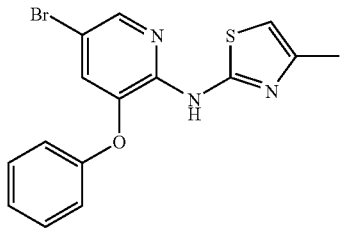

Step A: 3-phenoxypyridin-2-amine: Prepared according to the method of Example 7 Step A, starting with bromopyridin-2-amine, phenol, and (E)-2-hydroxybenzaldehyde oxime (20.61 g, 150.3 mmol).

Step B: 5-bromo-3-phenoxypyridin-2-amine: 3-Phenoxypyridin-2-amine (20.50 g, 110.1 mmol) was placed in acetic acid (50 mL) and cooled to 0° C. Bromine (d 3.12) (7.049 mL, 137.6 mmol) was slowly added and the reaction mixture was stirred for 1 hour. The reaction mixture was poured onto saturated sodium bisulfite and ice and allowed to sit overnight. Solids were removed by filtration and washed with water to give pure 5-bromo-3-phenoxypyridin-2-amine. The filtrate was then extracted with CH$_2$Cl$_2$ several times, combined, and washed with water. Organic layer was dried, filtered, and concentrated. The residue was purified by silica gel (5-20% EtOAc in hexanes) to give additional 5-bromo-3-phenoxypyridin-2-amine (total yield: 22.69 g, 77.74% yield).

Step C: 1-benzoyl-3-(5-bromo-3-phenoxypyridin-2-yl) thiourea: Prepared according to the method of Example 7 Step C.

Step D: 1-(5-bromo-3-phenoxypyridin-2-yl)thiourea: Prepared according to the method of Example 7 Step D.

Step E 5-bromo-N-(4-methylthiazol-2-yl)-3-phenoxypyridin-2-amine: Prepared according to the method of Example 7 Step E, using 1-chloropropan-2-one. $^1$H NMR (d$_6$-DMSO) δ 10.90 (bs, 1H), 8.21 (d, 1H), 7.43 (t, 2H), 7.39 (d, 1H), 7.20 (t, 1H), 7.09 (d, 2H), 6.61 (s, 1H), 2.23 (s, 3H); Mass spectrum (apci) m/z=364.1 (M+H).

Example 11

N-(4-methylthiazol-2-yl)-3-phenoxy-5-(pyridin-3-yl) pyridin-2-amine dihydrochloride

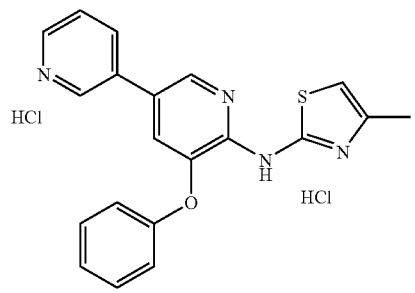

5-Bromo-N-(4-methylthiazol-2-yl)-3-phenoxypyridin-2-amine (0.070 g, 0.1932 mmol), pyridin-3-ylboronic acid (0.02850 g, 0.2319 mmol), Pd(PPh$_3$)$_4$ (0.02233 g, 0.01932 mmol), DME (10 mL), and 2M sodium bicarbonate (2 mL) were combined, heated to 80° C. and stirred overnight. The reaction mixture was cooled and partitioned between CH$_2$Cl$_2$ and water. The organic layer was dried, filtered, and concentrated. The residue was purified by silica gel chromatography (30-40% EtOAc in hexane) to give N-(4-methylthiazol-2-yl)-3-phenoxy-5-(pyridin-3-yl)pyridin-2-amine. N-(4-methylthiazol-2-yl)-3-phenoxy-5-(pyridin-3-yl)pyridin-2-amine was dissolved in CH$_2$Cl$_2$ and 2M HCl in ether was added to give N-(4-methylthiazol-2-yl)-3-phenoxy-5-(pyridin-3-yl) pyridin-2-amine dihydrochloride (0.050 g, 59.71% yield). $^1$H NMR (d$_6$-DMSO) δ 9.19 (d, 1H), 8.78 (dd, 1H), 8.70 (m, 2H), 7.93 (m, 2H), 7.42 (t, 2H), 7.18 (t, 1H), 7.12 (d, 2H), 6.74 (s, 1H), 2.28 (s, 3H); Mass spectrum (apci) m/z=361.2 (M+H-2HCl).

Example 12

N-(4-methylthiazol-2-yl)-3-phenoxy-5-(pyridin-4-yl) pyridin-2-amine dihydrochloride

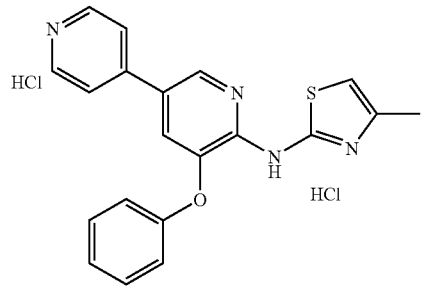

Prepared according to the method of Example 1-1, using 5-bromo-N-(4-methylthiazol-2-yl)-3-phenoxypyridin-2-amine and pyridin-4-ylboronic acid. $^1$H NMR (d$_6$-DMSO) δ 8.96 (d, 1H), 8.86 (d, 2H), 8.05 (d, 1H), 7.42 (t, 2H), 7.17 (t, 1H), 7.17 (t, 1H), 7.10 (d, 2H), 6.73 (s, 1H), 2.26 (s, 3H); Mass spectrum (apci) m/z=361.3 (M+H-2HCl).

Example 13

Methyl 3-(6-(4-methylthiazol-2-ylamino)-5-phenoxypyridin-3-ylthio)propanoate

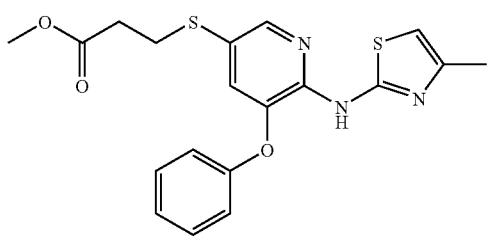

A 25 mL round-bottomed flask was charged with 5-bromo-N-(4-methylthiazol-2-yl)-3-phenoxypyridin-2-amine (350 mg, 0.966 mmol), Pd$_2$dba$_3$ (22.1 mg, 0.024 mmol), 4,5-bis(diphenylphosphino)-9,9-dimethyl-9H-xanthene (27.9 mg, 0.048 mmol), N-ethyl-N-isopropylpropan-2-amine (0.33 mL, 1.9 mmol), methyl 3-mercaptopropanoate (0.12 mL, 1.1 mmol), and dioxane (10 mL). The reaction mixture was heated to 100° C. under nitrogen for 2 hours. The reaction mixture was cooled to room temperature, filtered and concentrated. The residue was purified by silica gel chromatography (40% EtOAc in hexanes) to afford the title compound (328 mg, 84.5% yield) as a pale yellow solid. HCl salt made for characterization. $^1$H NMR (d$_6$-DMSO) δ 8.18 (d, 1H), 7.45 (m, 2H), 7.36 (d, 1H), 7.22 (t, 1H), 7.13 (d, 2H), 6.79 (s, 1H), 3.55 (s, 3H), 3.07 (t, 2H), 2.57 (t, 2H), 2.29 (s, 3H); Mass spectrum (esi) m/z=402.2 (100)(M+H—HCl).

Example 14

N-(cyclohexylthio)-3-phenoxypyridin-2-yl)-4-methylthiazol-2-amine hydrochloride

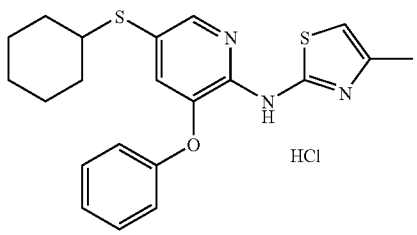

Prepared according to the method of Example 13, using 5-bromo-N-(4-methylthiazol-2-yl)-3-phenoxypyridin-2-amine and cyclohexanethiol. $^1$H NMR (d$_6$-DMSO) δ 8.17 (d, 1H), 7.45 (m, 2H), 7.30 (d, 1H), 7.22 (t, 1H), 7.13 (m, 2H), 6.80 (s, 1H), 3.08 (m, 1H), 2.29 (s, 3H), 1.82 (m, 2H), 1.66 (m, 2H), 1.52 (m, 1H), 1.23 (m, 5H); Mass spectrum (esi) m/z=398.2 (100)(M+H—HCl).

Example 15

N-(5-(benzylthio)-3-phenoxypyridin-2-yl)-4-methylthiazol-2-amine hydrochloride

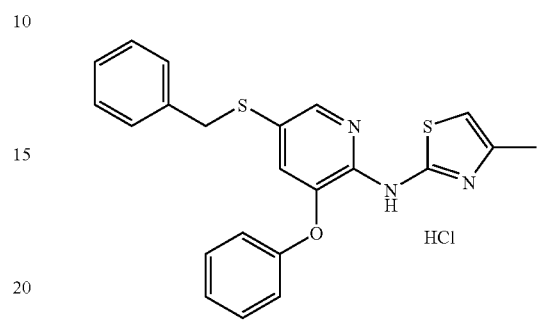

Prepared according to the method of Example 13, using 5-bromo-N-(4-methylthiazol-2-yl)-3-phenoxypyridin-2-amine and phenylmethanethiol. $^1$H NMR (d$_6$-DMSO) δ 8.08 (d, 1H), 7.42 (m, 2H), 7.28-7.15 (m, 7H), 6.98 (m, 2H), 6.74 (s, 1H), 4.12 (s, 2H), 2.27 (s, 3H); Mass spectrum (esi) m/z=406.2 (100) (M+H—HCl).

Example 16

4-Methyl-N-(3-phenoxy-5-(pyridin-2-ylmethylthio)pyridin-2-yl)thiazol-2-amine dihydrochloride

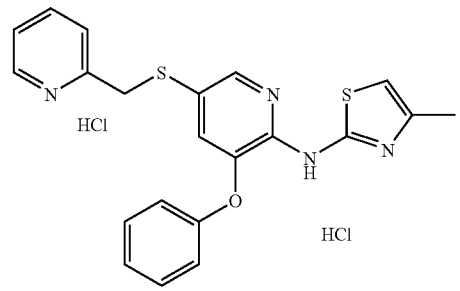

A 20 mL vial was charged with methyl 3-(6-(4-methylthiazol-2-ylamino)-5-phenoxypyridin-3-ylthio)propanoate (135.8 mg, 0.338 mmol) and THF (0.5 mL). 1M KOtBu in THF (1.184 mL, 1.184 mmol) was added and the reaction mixture was stirred at room temperature for 30 seconds. 2-(Bromomethyl)pyridine hydrobromide (85.55 mg, 0.3382 mmol) was added and the reaction mixture was stirred at room temperature for 30 minutes. Saturated aqueous ammonium chloride was added and the reaction mixture was extracted with EtOAc. The concentrated residue was purified on silica gel to afford N-(4-methylthiazol-2-yl)-3-phenoxy-5-(pyridin-2-ylmethylthio)pyridin-2-amine dihydrochloride (98.2 mg, 60.5% yield) as a pale yellow solid after HCl salt formation. $^1$H NMR (d$_6$-DMSO) δ 8.66 (dd, 1H), 8.22 (td, 1H), 8.12 (d, 1H), 7.70 (t, 1H), 7.62 (d, 1H), 7.45 (m, 2H), 7.23 (t, 1H), 7.16 (d, 1H), 7.06 (m, 2H), 6.82 (m, 1H), 4.42 (s, 2H), 2.29 (s, 3H); Mass spectrum (esi) m/z=407.2 (100) (M+H-2HCl).

Example 17

4-Methyl-N-(3-phenoxy-5-(piperidin-4-ylmethylthio)pyridin-2-yl)thiazol-2-amine dihydrochloride

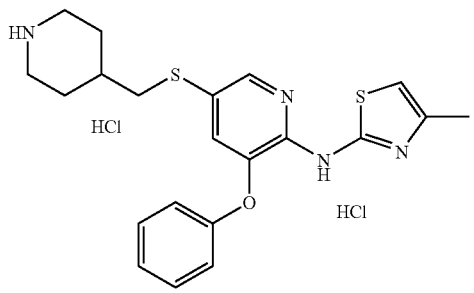

Prepared according to the method of Example 16, using methyl 3-(6-(4-methylthiazol-2-ylamino)-5-phenoxypyridin-3-ylthio)propanoate. $^1$H NMR (d$_6$-DMSO) δ 8.83 (m, 1H), 8.52 (m, 1H), 8.18 (dd, 1H), 7.43 (m, 2H), 7.36 (dd, 1H), 7.20 (td, 1H), 7.10 (m, 2H), 6.72 (s, 1H), 3.57 (d, 1H), 3.21 (m, 2H), 2.86 (m, 2H), 2.79 (m, 2H), 2.26 (s, 3H), 1.87 (m, 2H), 1.67 (m, 1H), 1.35 (m, 2H); Mass spectrum (esi) m/z=413.1 (100)(M+H-2HCl).

Example 18

N-(5-Chloro-3-phenoxypyridin-2-yl)-4-ethylthiazol-2-amine

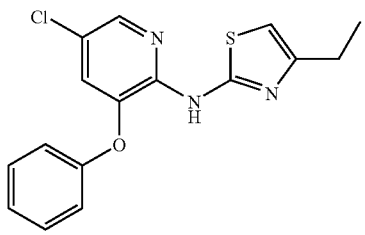

Prepared according to the method of Example 7, using 1-bromobutan-2-one. Mass spectrum (esi) m/z=332 (100), 334 (38).

Example 19

N-(5-chloro-3-phenoxypyridin-2-yl)-4,5-dimethylthiazol-2-amine

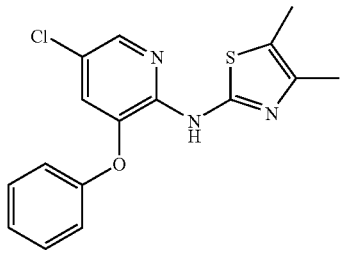

Prepared according to the method of Example 7, using 3-chlorobutan-2-one. $^1$H NMR (d$_6$-DMSO) δ 10.78 (bs, 1H), 8.11 (s, 1H), 7.42 (t, 2H), 7.29 (s, 1H), 7.19 (t, 1H), 7.09 (d, 2H), 2.22 (s, 3H), 2.12 (s, 3H); Mass spectrum (esi) m/z 332 (100), 334 (38).

Example 20

N-(5-Chloro-3-phenoxypyridin-2-yl)-4-isobutylthiazol-2-amine

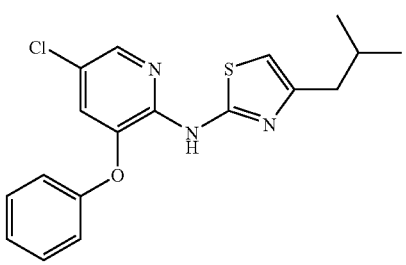

Prepared according to the method of Example 7, using 1-chloro-4-methylpentan-2-one. $^1$H NMR (d$_6$-DMSO) δ 10.89 (bs, 1H), 8.15 (s, 1H), 7.43 (t, 2H), 7.31 (s, 1H), 7.20 (t, 1H), 7.11 (d, 2H), 6.61 (s, 1H), 2.42 (d, 2H), 1.98 (m, 1H), 0.88 (d, 6H); Mass spectrum (esi) m/z=360 (100), 362 (37).

Example 21

4-Butyl-N-(5-chloro-3-phenoxypyridin-2-yl)thiazol-2-amine

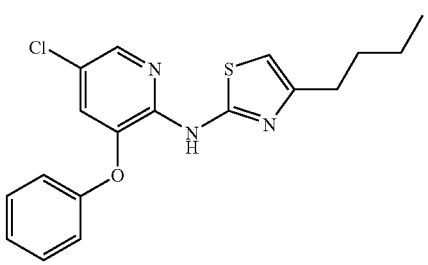

Prepared according to the method of Example 7, using 1-chlorohexan-2-one. $^1$H NMR (d$_6$-DMSO) δ 10.89 (bs, 1H), 8.15 (s, 1H), 7.42 (t, 2H), 7.32 (s, 1H), 7.21 (t, 1H), 7.10 (d, 2H), 6.61 (s, 1H), 2.56 (t, 2H), 1.59 (m, 2H), 1.31 (m, 2H), 0.87 (t, 3H); Mass spectrum (esi) m/z=360 (100), 362 (37).

Example 22

N-(5-chloro-3-phenoxypyridin-2-yl)-4-cyclopropylthiazol-2-amine

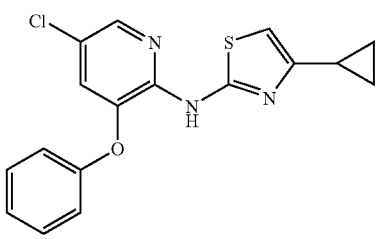

Prepared according to the method of Example 7, using 2-bromo-1-cyclopropylethanone. ¹H NMR (d₆-DMSO) δ 10.82 (bs, 1H), 8.15 (s, 1H), 7.43 (t, 2H), 7.31 (s, 1H), 7.21 (t, 1H), 7.10 (d, 2H), 6.64 (s, 1H), 1.94 (m, 1H), 0.72-0.85 (m, 4H); Mass spectrum (esi) m/z 344 (100), 346 (37).

Example 23

5-(2-Methoxybenzylthio)-N-(4-methylthiazol-2-yl)-3-phenoxypyridin-2-amine hydrochloride

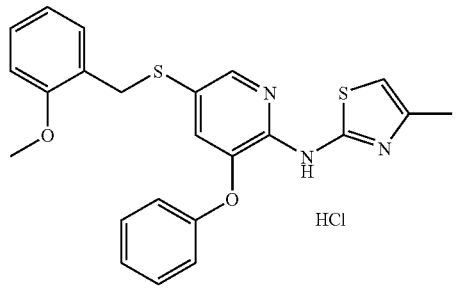

Prepared according to the method of Example 16 with 1-(chloromethyl)-2-methoxybenzene. ¹H NMR (d₆-DMSO) δ 8.05 (d, 1H), 7.43 (t, 2H), 7.21 (q, 2H), 7.11 (d, 1H), 7.01 (m, 3H), 6.93 (d, 1H), 6.80 (t, 1H), 6.69 (s, 1H), 4.01 (s, 2H), 3.68 (s, 3H), 2.26 (s, 3H); Mass spectrum (apci) m/z=436.2 (M+H—HCl).

Example 24

5-(4-Methoxybenzylthio-N-(4-methylthiazol-2-yl)-3-phenoxypyridin-2-amine hydrochloride

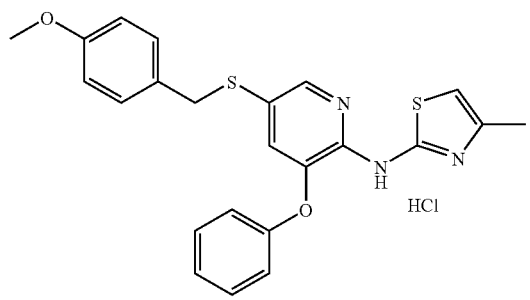

Prepared according to the method of Example 16 with 1-(chloromethyl)-4-methoxybenzene. ¹H NMR (d₆-DMSO) δ 8.09 (d, 1H), 7.42 (t, 2H), 7.21 (t, 1H), 7.14 (d, 1H), 7.10 (d, 2H), 7.00 (d, 2H), 6.81 (d, 2H), 6.75 (s, 1H), 4.06 (s, 2H), 3.71 (s, 3H), 2.27 (s, 3H); Mass spectrum (apci) m/z=436.2 (M+H—HCl).

Example 25

5-(2-Chlorobenzylthio)-N-(4-methylthiazol-2-yl)-3-phenoxypyridin-2-amine hydrochloride F Prepared according to the method of Example 16, with 1-(bromomethyl)-2-chlorobenzene (0.0512 g, 0.249 mmol) were reacted to provide 5-(2-chlorobenzylthio)-N-(4-methylthiazol-2-yl)-3-phenoxypyridin-2-amine hydrochloride (0.073 g, 61.5%) after HCl salt formation. ¹H NMR (d₆-DMSO) δ 8.09 (d, 1H), 7.42 (m, 3H), 7.27 (dt, 1H), 7.18 (m, 3H), 7.08 (d, 1H), 7.00 (d, 2H), 6.71 (s, 1H), 4.15 (s, 2H), 2.26 (s, 3H); Mass spectrum (apci) m/z=440.1 (M+H—HCl).

Example 26

Representative Example

N-(4-Methylthiazol-2-yl)-3-phenoxy-5-(1-phenylethylthio)pyridin-2-amine hydrochloride

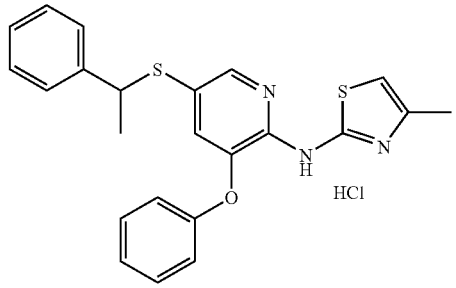

Prepared according to the method of Example 16 with 1-(1-bromoethyl)benzene (0.0461 g, 0.249 mmol) were reacted to provide N-(4-methylthiazol-2-yl)-3-phenoxy-5-(1-phenylethylthio)pyridin-2-amine hydrochloride (0.058 g, 51.1%). ¹H NMR (d₆-DMSO) δ 8.05 (d, 1H), 7.42 (t, 2H), 7.22 (m, 6H), 7.03 (d, 1H), 6.94 (d, 2H), 6.73 (s, 1H), 4.43 (q, 1H), 2.26 (s, 3H), 1.51 (d, 3H); Mass spectrum (apci) m/z=420.1 (M+H—HCl).

Example 27

N-(4-methylthiazol-2-yl)-3-(phenylthio)pyridin-2-amine hydrochloride

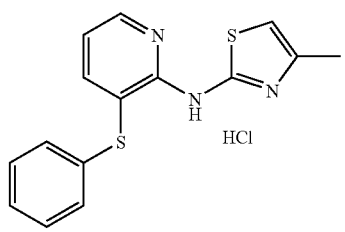

Prepared according to the method of Example 13 with 3-bromo-N-(4-methylthiazol-2-yl)pyridin-2-amine and benzenethiol. $^1$H NMR (d$_6$-DMSO) δ 8.42 (m, 1H), 7.90 (m, 1H), 7.41-7.25 (m, 5H), 7.12 (m, 1H), 6.74 (m, 1H), 2.25 (s, 3H); Mass spectrum (esi) m/z=300.2 (100)(M+H—HCl).

Example 28

3-(2-Chlorophenylthio)-N-(4-methylthiazol-2-yl)pyridin-2-amine hydrochloride

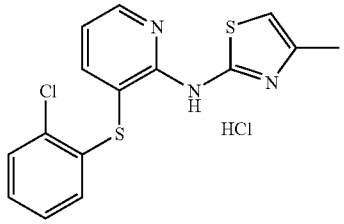

Prepared according to the method of Example 13, with 3-bromo-N-(4-methylthiazol-2-yl)pyridin-2-amine and 2-chlorobenzenethiol. $^1$H NMR (d$_6$-DMSO) δ 8.45 (m, 1H), 7.80 (bs, 1H), 7.57 (m, 1H), 7.27 (m, 2H), 7.07 (m, 1H), 6.84 (m, 1H), 6.62 (m, 1H), 2.21 (s, 3H); Mass spectrum (esi) m/z=334.2 (100)(M+H—HCl).

Example 29

3-(3-Methoxyphenylthio)-N-(4-methylthiazol-2-yl)pyridin-2-amine hydrochloride

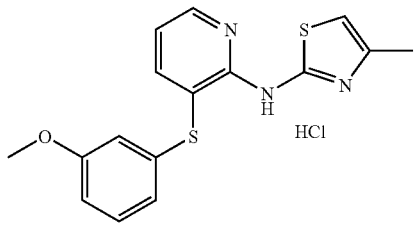

Prepared according to the method of Example 13, with 3-bromo-N-(4-methylthiazol-2-yl)pyridin-2-amine and 3-methoxybenzenethiol. $^1$H NMR (d$_6$-DMSO) δ 8.43 (d, 1H), 7.92 (bs, 1H), 7.27 (m, 1H), 7.12 (m, 1H), 6.86 (m, 2H), 6.80 (d, 1H), 6.72 (s, 1H), 3.72 (s, 3H), 2.25 (s, 3H).

Example 30

Methyl 2-(2-(4-methylthiazol-2-ylamino)pyridin-3-ylthio)benzoate hydrochloride

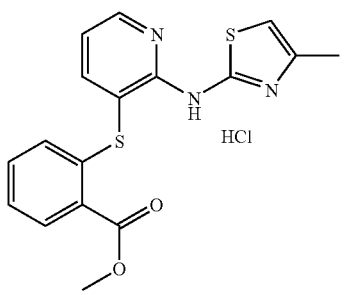

Prepared according to the method of Example 13, with 3-bromo-N-(4-methylthiazol-2-yl)pyridin-2-amine and methyl 2-mercaptobenzoate. $^1$H NMR (d$_6$-DMSO) δ 8.54 (d, 1H), 8.07 (s, 1H), 8.01 (dd, 1H), 7.41 (m, 1H), 7.28 (m, 1H), 7.19 (m, 1H), 6.73 (m, 1H), 6.61 (d, 1H), 3.92 (s, 3H), 2.21 (s, 3H).

Example 31

3-(Cyclopentylthio)-N-(4-methylthiazol-2-yl)pyridin-2-amine hydrochloride

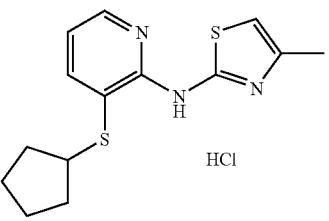

Prepared according to the method of Example 13, with 3-bromo-N-(4-methylthiazol-2-yl)pyridin-2-amine and cyclopentanethiol. $^1$H NMR (d$_6$-DMSO) δ 8.39 (d, 1H), 8.05 (d, 1H), 7.18 (dd, 1H), 6.89 (s, 1H), 3.64 (m, 1H), 2.33 (s, 3H), 1.95 (m, 2H), 1.75 (m, 2H), 1.53 (m, 4H); Mass spectrum (esi) m/z=292.1 (100)(M+H–HCl).

Example 32

N-(4-methylthiazol-2-yl)-3-phenoxypyridin-2-amine hydrochloride

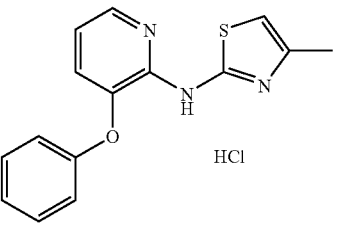

Prepared according to the method of Example 8, using 5-bromo-N-(4-methylthiazol-2-yl)-3-phenoxypyridin-2-amine. 1H NMR (d$_6$-DMSO) δ 8.20 (d, 1H), 7.46 (t, 2H), 7.39 (d, 1H), 7.24 (t, 1H), 7.15 (m, 3H), 6.89 (s, 1H), 2.33 (s, 3H); Mass spectrum (apci) m/z=284.2 (M+H–HCl).

Example 33

N-(4-methylthiazol-2-yl)-3-phenoxy-5-(1-(pyridin-2-yl)ethylthio)pyridin-2-amine dihydrochloride

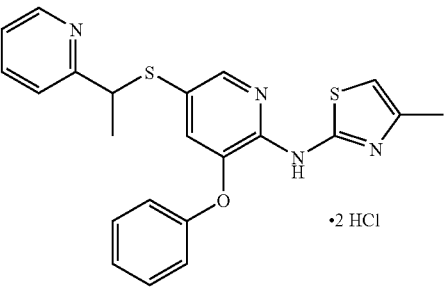

Step A: Preparation of 2-(1-bromoethyl)pyridine: 2-Ethylpyridine (20.0 g, 186.65 mmol) was placed in carbon tetrachloride (830 mL) and benzoyl peroxide (4.5211 g, 18.665 mmol) and 1-bromopyrrolidine-2,5-dione (33.221 g, 186.65 mmol) were added. The reaction mixture was heated to reflux for 18 hours, then cooled to room temperature and filtered. The filtrate was concentrated and the residue was purified over a plug of silica to give 2-(1-bromoethyl)pyridine (17.312 g, 49.9%). $^1$H NMR (CDCl$_3$) δ 8.58 (d, 1H), 7.69 (td, 1H), 7.76 (d, 1H), 7.20 (dd, 1H), 5.24 (q, 1H), 2.08 (d, 3H)

Step B: Preparation of N-(4-methylthiazol-2-yl)-3-phenoxy-5-(1-(pyridin-2-yl)ethylthio)pyridin-2-amine dihydrochloride: Following the procedure in Example 16, methyl 3-(6-(4-methylthiazol-2-ylamino)-5-phenoxypyridin-3-ylthio)propanoate (0.325 g, 0.809 mmol), 1M potassium 2-methylpropan-2-olate (2.83 mL, 2.83 mmol), and 2-(1-bromoethyl)pyridine (0.151 g, 0.809 mmol) were reacted to provide N-(4-methylthiazol-2-yl)-3-phenoxy-5-(1-(pyridin-2-yl)ethylthio)pyridin-2-amine hydrochloride (0.114 g, 30.8%) after reverse phase purification and HCl salt formation. $^1$H NMR (d$_6$-DMSO) δ 8.58 (d, 1H), 8.09 (m, 1H), 8.04 (d, 1H), 7.58 (d, 2H), 7.45 (t, 2H), 7.23 (t, 1H), 7.02 (d, 2H), 6.95 (d, 1H), 6.79 (s, 1H), 4.67 (q, 1H), 2.28 (s, 3H), 1.62 (d, 3H); Mass spectrum (esi) m/z=421.1 (M+H-2HCl).

Example 34

5-(3-Methoxybenzylthio)-N-(4-methylthiazol-2-yl)-3-phenoxypyridin-2-amine hydrochloride

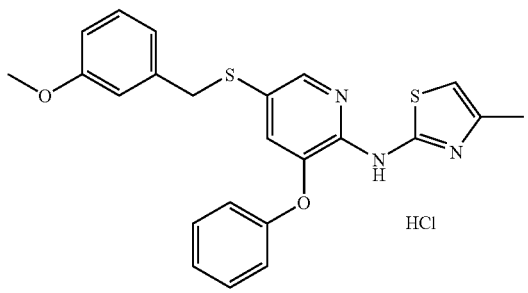

Prepared according to the method of Example 16, using methyl 3-(6-(4-methylthiazol-2-ylamino)-5-phenoxypyridin-3-ylthio)propanoate and 1-(chloromethyl)-3-methoxybenzene. $^1$H NMR (d$_6$-DMSO) δ 8.09 (d, 1H), 7.42 (t, 2H), 7.18 (m, 3H), 6.98 (d, 2H), 6.76 (m, 4H), 4.09 (s, 2E), 3.68 (s, 3H), 2.26 (s, 3H); Mass spectrum (esi) m/z=436.2 (M+H-1HCl).

Example 35

3-(Cyclohex-2-enyloxy)-N-(4-methylthiazol-2-yl)pyridin-2-amine

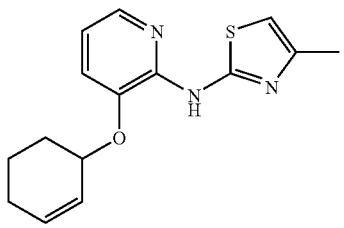

2-(4-Methylthiazol-72-ylamino)pyridin-3-ol (0.250 g, 1.21 mmol) and Cs$_2$CO$_3$ (1.18 g, 3.62 mmol) were added to DMF (3 mL). 3-Bromocyclohex-1-ene (0.216 g, 1.21 mmol) was added, and the reaction mixture was stirred for 3 hours. Water was added and the reaction mixture was extracted with ether. The organic layer was dried, filtered, and concentrated. The residue was purified by silica gel chromatography provide 3-(cyclohex-2-enyloxy)-N-(4-methylthiazol-2-yl)pyridin-2-amine (0.130 g, 37.5%). $^1$H NMR (d$_6$-DMSO) δ 9.53 (s, 1H), 7.85 (dd, 1H), 7.41 (d, 1H), 6.90 (dd, 1H), 6.58 (s, 1H), 6.00 (m, 1H), 6.88 (m, 1H), 6.88 (m, 1H), 4.99 (m, 1H), 2.24 (s, 3H), 2.05 (m, 2H), 1.87 (m, 3H), 1.62 (m, 1H); Mass spectrum (apci) m/z=288.0 (M+M).

Example 36

Representative Example 3-(Cyclohexyloxy)-N-(4-methylthiazol-2-yl)pyridin-2-amine hydrochloride

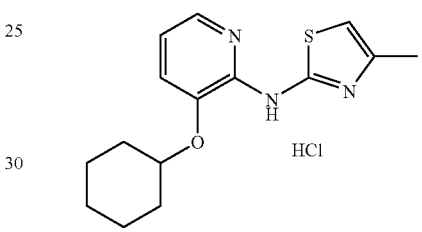

3-(Cyclohex-2-enyloxy)-N-(4-methylthiazol-2-yl)pyridin-2-amine (0.115 g, 0.400 mmol) and 4-methylbenzenesulfonohydrazide (1.12 g, 6.00 mmol) were placed in dimethoxyethane (5, mL). NaOAc (0.492 g, 6.00 mmol) was dissolved in water (2 mL) and added to the above solution and refluxed. Additional 4-methylbenzenesulfonohydrazide (1.12 g, 6.00 mmol) was added and the reaction mixture was refluxed overnight. An aqueous work up was done and the crude material was purified by silica gel chromatography to provide 3-(cyclohexyloxy)-N-(4-methylthiazol-2-yl)pyridin-2-amine (0.064 g, 55.3%) after HCl salt formation. $^1$H NMR (d$_6$-DMSO) δ 7.79 (d, 1H), 7.57 (d, 1H), 7.09 (m, 1H), 6.83 (s, 1H), 4.54 (m, 1H), 2.32 (s, 3H), 1.97 (m, 2H), 1.79, (m, 2H), 1.57 (m, 3H), 1.36 (m, 3H); Mass spectrum (apci) m/z=291.1 (M+H—HCl).

Example 37

3-(Cyclopentyloxy)-N-(4-methylthiazol-2-yl)pyridin-2-amine hydrochloride

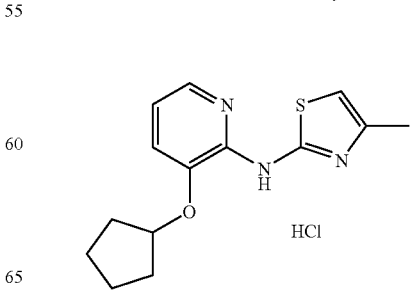

Prepared according to the method of Example 35 with iodocyclopentane. $^1$H NMR (d$_6$-DMSO) δ 7.92 (d, 1H), 7.46 (d, 1H), 7.08 (dd, 1H), 6.80 (s, 1H), 5.49 (m, 1H), 2.32 (s, 3H), 1.88 (m, 6H), 1.60 (m, 2H); Mass spectrum (apci) m/z=276.1 (M+H—HCl).

Example 38

5-(3-(Dimethylamino)propylthio)-N-(4-methylthiazol-2-yl)-3-phenoxypyridin-2-amine dihydrochloride

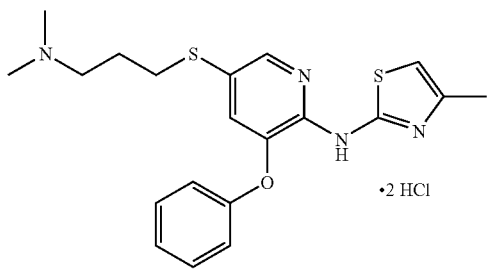

Prepared according to Example 16 from methyl 3-(6-(4-methylthiazol-2-ylamino)-5-phenoxypyridin-3-ylthio)propanoate and potassium 2-methylpropan-2-olate, with the exception that the reaction mixture was heated to 50° C. for 30 minutes. $^1$H NMR (d$_6$-DMSO) δ 9.90 (s, 1H), 8.21 (d, 1H), 7.43 (t, 2H), 7.39 (d, 1H), 7.18 (t, 1H), 7.08 (d, 2H), 6.67 (s, 1H), 3.10 (m, 2H), 2.92 (t, 2H), 2.72 (d, 6H), 2.24 (s, 3H), 1.85 (m, 2H); Mass spectrum (apci) m/z=401.2 (M+H-2HCl).

Example 39

Representative Example

Ethyl 3-(5-bromo-2-(4-methylthiazol-2-ylamino)pyridin-3-yloxy)-4-chlorobenzoate

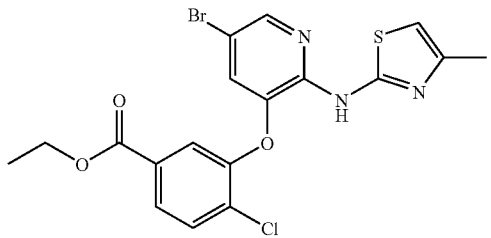

Step A: Preparation of 3-(5-bromo-2-chlorophenoxy)pyridin-2-amine: 4-2-aminopyridin-3-ol (7.56 g, 68.6 mmol) was added to a mixture of sodium hydride (1.72 g, 71.9 mmol) in DMF (20 mL) and stirred for 10 minutes. 4-Bromo-1-chloro-2-fluorobenzene (13.69 g, 65.4 mmol) was added and the reaction mixture was stirred at 100° C. for 38 hours. The reaction mixture was cooled to room temperature and partition between 1N NaOH and ether. The organic layer was dried over sodium sulfate, filtered, and concentrated. The residue was triturated with hexanes to give 3-(5-bromo-2-chlorophenoxy)pyridin-2-amine (11.30 g, 57.7%) as a yellow solid.

Step B: Preparation of ethyl 3-(2-aminopyridin-3-yloxy)-4-chlorobenzoate: 3-(5-Bromo-2-chlorophenoxy)pyridin-2-amine (11.30 g, 37.72 mmol), triethylamine (3.817 g, 37.72 mmol), Pd(OAc)$_2$ (0.8469 g, 3.772 mmol), and triphenylphosphine (0.9894 g, 3.772 mmol) were added to ethanol (100 mL) in a bomb. The bomb was pressurized with 100 psi CO and heated to 100° C. for 4 hours. The reaction mixture was cooled to room temperature and filtered. Dichloromethane was added and solids were filtered off. The filtrate was washed with water. The organic layer was dried over sodium sulfate, filtered, and concentrated. The residue was purified by silica gel chromatography to give ethyl 3-(2-aminopyridin-3-yloxy)-4-chlorobenzoate (7.555 g, 68.42%).

Step C: Preparation of ethyl 3-(2-amino-5-bromopyridin-3-yloxy)-4-chlorobenzoate: Prepared according to the method of Example 10, Step B.

Step D: Preparation of ethyl 3-(2-(3-benzoylthioureido)-5-bromopyridin-3-yloxy)-4-chlorobenzoate: Ethyl 3-(2-amino-5-bromopyridin-3-yloxy)-4-chlorobenzoate (9.645 g, 25.95 mmol) and benzoyl isothiocyanate (4.659 g, 28.55 mmol) were placed in THF (250 mL) and the reaction mixture was stirred at room temperature for 18 hours, then heated at 55° C. for two days. THF was removed and the residue was purified by silica gel chromatography (5-25% EtOAc in hexane) to provide ethyl 3-(2-(3-benzoylthioureido)-5-bromopyridin-3-yloxy)-4-chlorobenzoate (7.08 g, 51.0%) as a yellow solid.

Step E: Preparation of ethyl 3-(5-bromo-2-thioureidopyridin-3-yloxy)-4-chlorobenzoate: Ethyl 3-(2-(3-benzoylthioureido)-5-bromopyridin-3-yloxy)-4-chlorobenzoate (8.05 g, 15.1 mmol) and K$_2$CO$_3$ (10.4 g, 75.3 mmol) were placed in ethanol (150 mL) and heated to reflux for 2 days and then cooled. The reaction mixture was filtered and the filtrate was concentrated, triturated with water, and dried. The remaining solid was dissolved in CH$_2$Cl$_2$ and purified by silica gel chromatography to give ethyl 3-(5-bromo-2-thioureidopyridin-3-yloxy)-4-chlorobenzoate (1.70 g, 26.2% yield).

Step F: Ethyl 3-(5-bromo-2-(4-methylthiazol-2-ylamino)pyridin-3-yloxy)-4-chlorobenzoate: 1-chloropropan-2-one (0.469 g, 5.07 mmol), ethyl 3-(5-bromo-2-thioureidopyridin-3-yloxy)-4-chlorobenzoate (1.680 g, 3.39 mmol), triethylamine (0.671 g, 6.63 mmol), and ethanol (70 mL) were reacted according to the method of Example 10, Step E, to provide the title compound (1.40 g, 77% yield). $^1$H NMR (d$_6$-DMSO) δ 8.26 (d, 1H), 7.78 (m, 2H), 7.50 (s, 1H), 7.46 (d, 1H), 6.59 (s, 1H), 4.29 (q, 2H), 2.23 (s, 3H), 1.28 (t, 3H); Mass spectrum (apci) m/z=470.1 (M+H).

Example 40

N-(5-Bromo-3-(phenylthio)pyridin-2-yl)-4-methylthiazol-2-amine

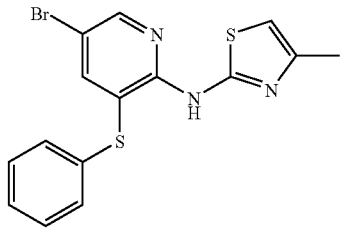

Step A: Preparation of 3-(phenylthio)pyridin-2-amine: A mixture of 3-bromopyridin-2-amine (167 mg, 0.966 mmol), Pd$_2$dba$_3$ (22.1 mg, 0.024 mmol), 4,5-bis(diphenylphosphino)-9,9-dimethyl-9H-xanthene (27.9 mg, 0.048 mmol), N-ethyl-N-isopropylpropan-2-amine (0.33 mL, 1.9 mmol), thiophenol (121 mg, 1.1 mmol), and dioxane (10 mL) was heated at 100° C. under nitrogen for 2 hours. The reaction mixture was cooled to room temperature, filtered and concentrated. The reaction mixture was purified by MPLC to afford 3-(phenylthio)pyridin-2-amine.

Step B: Preparation of 5-bromo-3-(phenylthio)pyridin-2-amine: Prepared according to the method of Example 10, Step B.

Steps C-E: N-(5-bromo-3-(phenylthio)pyridin-2-yl)-4-methylthiazol-2-amine: Prepared according to the method of Example 7 Steps C-E. $^1$H NMR (CDCl$_3$) δ 9.01 (s, 1H), 8.42 (m, 1H), 7.92 (m, 1H), 7.32-7.15 (m, 5H), 6.44 (m, 1H0, 2.32 (m, 3H). Mass spectrum (apci) m/z=379.8 (M+H).

Example 41

Representative Example

Preparation of 6-(4-methylthiazol-2-ylamino)-5-phenoxypyridin-3-ol

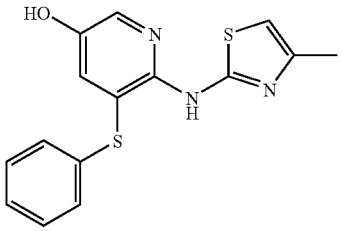

N-(5-Bromo-3-phenoxypyridin-2-yl)-4-methylthiazol-2-amine (2.66 mmol) is dissolved in THF (30 mL) and cooled to −78° C. MeLi (2.07 mL, 3.32 mmol) is slowly added and the reaction mixture is stirred for 10 minutes. n-Butyllithium (1.33 mL, 3.32 mmol) is added and the reaction mixture is stirred for 15 minutes. Triisopropylborate (0.613 mL, 2.66 mmol) is added and the reaction mixture is stirred for 30 minutes. The reaction mixture is warmed to 0° C., and methanol (5 mL), 10% aqueous NaOH (5.1 mL, 12.8 mmol), and 30% aqueous H$_2$O$_2$ (1.27 mL, 13.3 mmol) are added. The reaction mixture is stirred at 0° C. for 1 hour, then purified by silica gel chromatography (10-20% EtOAc in hexanes) to afford 6-(4-methylthiazol-2-ylamino)-5-phenoxypyridin-3-ol.

Example 42

Preparation of 5-(2-chlorophenylthio)-6-(4-methylthiazol-2-ylamino)pyridin-3-ol

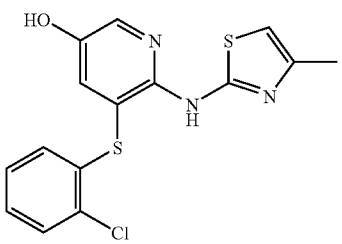

A degassed mixture of N-(5-bromo-3-(2-chlorophenylthio)pyridin-2-yl)-4-methylthiazol-2-amine (1.10 g, 2.66 mmol), 4,4,4',4',5,5,5',5'-octamethyl-2,2'-bi(1,3,2-dioxaborolane) (1.35 g, 5.32 mmol), Pd(OAc)$_2$ (60 mg, 0.27 mmol), tricyclopentylphosphine (93 mg, 0.40 mmol) and cesium fluoride (3.64 g, 23.9 mmol) in acetonitrile is heated at 90° C. for 5 hours. The reaction mixture is cooled and partitioned between ether and water. The crude product is dissolved in THF. N-morpholine N-oxide (1.40 g, 12.0 mmol) is added and the reaction mixture is heated at reflux for 12 hours. The reaction mixture is cooled and partitioned between ether and water. The organic layer is washed with water and brine, dried and concentrated. The residue is purified by silica gel chromatography, eluting with 10-20% EtOAc in hexanes to afford the title compound.

Example 43

Preparation of N-(5-methoxy-3-phenoxypyridin-2-yl)-4-methylthiazol-2-amine

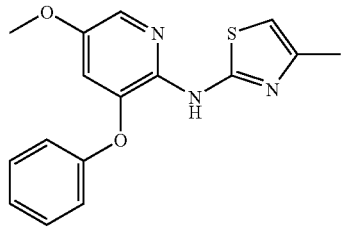

Iodomethane (0.0362 g, 0.255 mmol) is added to a mixture of 6-(4-methylthiazol-2-ylamino)-5-phenoxypyridin-3-ol (0.255 mmol) and potassium carbonate (0.0794 g, 0.574 mmol) in DMF (3 mL) and stirred overnight at room temperature. The reaction mixture is partitioned between water and ether. The organic layer is washed with water, dried, and concentrated. The residue is purified by silica gel chromatography, eluting with 15-20% EtOAc in hexanes, to afford the title compound.

Example 44

Preparation of methyl 3-(6-(4-methylthiazol-2-ylamino)-5-phenoxypyridin-3-yl)propanoate

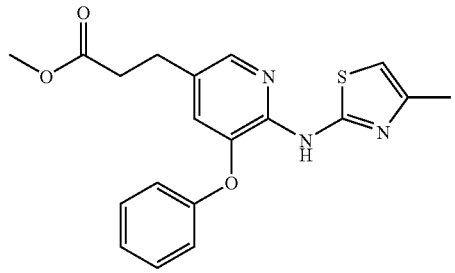

Step A: N-(5-bromo-3-phenoxypyridin-2-yl)-4-methylthiazol-2-amine (724 mg, 2.00 mmol) was dissolved in THF (20 mL) and cooled to −78° C. MeLi (1.30 mL, 2.20 mmol) is added slowly, and stirred for 10 minutes. n-Butyllithium (0.88 mL, 2.20 mmol) was added and the reaction mixture was stirred for 15 minutes. DMF (0.31 mL, 4.00 mmol) was added, and the reaction mixture was stirred for 30 minutes. The reaction mixture was warmed to room temperature and AcOH (2 mL) is added. The reaction mixture was stirred at room temperature for 1 hour, poured into saturated aqueous sodium bicarbonate and extracted with ethyl acetate. The combined organic layers were dried over sodium sulfate, filtered and concentrated. The residue was purified by silica gel (10-20% EtOAc in hexanes) to afford 6-(4-methylthiazol-2-ylamino)-5-phenoxynicotinaldehyd.

Step B: Step B: To a mixture of mL6-(4-methylthiazol-2-ylamino)-5-phenoxynicotinaldehyde (311 mg, 1.00 mmol) and THF (10 mL) was added methyl(triphenylphosphoranylidene)acetate (500 mg, 1.5 mmol) and the reaction mixture was stirred at room temperature. After 4 hours, additional methyl(triphenylphosphoranylidene)acetate (500 mg, 1.5 mmol) was added and the reaction mixture was stirred overnight. Filtered, concentrated the filtrate, and purified by silica gel chromatography (1:1 EtOAc in hexanes) to afford (E)-methyl 3-(6-(4-methylthiazol-2-ylamino)-5-phenoxypyridin-3-yl)acrylate.

Step C: A mixture of mL (E)-methyl 3-(6-(4-methylthiazol-2-ylamino)-5-phenoxypyridin-3-yl)acrylate (500 mg, 1.36 mmol), 4-methylbenzenesulfonohydrazide (1.27 g, 6.8 mmol), and toluene (15 mL) was heated at reflux for 12 hours, cooled to room temperature and concentrated. The residue was purified by silica gel (20 to 30% EtOAc in hexanes) to afford the title compound.

Example 45

Preparation of 3-(6-(4-methylthiazol-2-ylamino)-5-phenoxypyridin-3-yl)propanoic acid hydrochloride

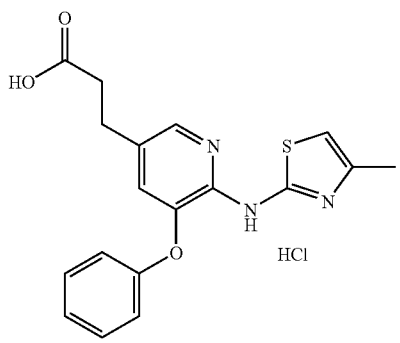

A mixture of mLmethyl 3-(6-(4-methylthiazol-2-ylamino)-5-phenoxypyridin-3-yl)propanoate (1.50 mmol) and ethanol (30 mL) and 1M NaOH (10 mL) was stirred and heated at 60° C. for 3 hours. Concentrated and water and 6N HCl (2 mL) were added. Filtered and dried to yield the title compound.

Example 46

3-Benzyl-N-(4-methylthiazol-2-yl)pyridin-2-amine hydrochloride

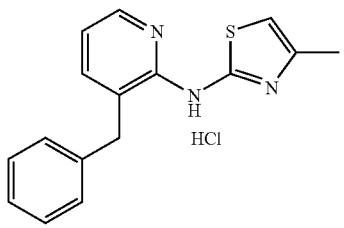

A mixture of mL3-bromo-N-(4-methylthiazol-2-yl)pyridin-2-amine (70 mg, 0.26 mmol), $Cs_2CO_3$ (250 mg, 0.78 mmol), $PdCl_2(dppf)$ (21.2 mg, 0.026 mmol), and DM (2 mL) and water (0.5 mL) was purged with nitrogen and 9-benzyl-9-bora-bicyclo[3.3.1]nonane (1.5 mL, 0.78 mmol) was added and heated to 60° C. overnight. Additional 9-benzyl-9-bora-bicyclo[3.3.1]nonane (1.5 mL, 0.78 mmol) was added and heated again overnight. Poured into water and extracted with ether. The organic layer was dried with sodium sulfate, filtered and concentrated. The residue was purified on silica gel (10% EtOAc in hexanes) to afford the title compound (41.7 mg, 50.6% yield) as a white solid after HCl salt formation. $^1$H NMR ($d_6$-DMSO) δ 8.30 (d, 1H), 7.62 (d, 1H), 7.35-7.10 (m, 6H), 6.82 (s, 1H), 4.21 (s, 2H), 2.32 (s, 3H); Mass spectrum (esi) m/z=282.2 (100)(M+H—HCl).

Example 47

Preparation of N-(5-bromo-3-(2-chlorophenylthio)pyridin-2-yl)-4-methylthiazol-2-amine

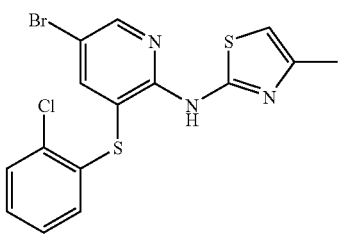

Prepared according to the method of Example 40. $^1$H NMR ($CDCl_3$) δ 8.95 (bs, 1H), 8.49 (d, 1h), 7.95 (d, 1h), 7.41 (dd, 1H), 7.19-7.08 (m, 2H), 6.69 (dd, 1H), 6.45 (s, 1H), 2.32 (s, 3H); Mass spectrum (esi) m/z=414.1 (M+H).

Example 48

N-(3-(2-chlorophenylthio)-5-(phenylthio)pyridin-2-yl)-4-methylthiazol-2-amine hydrochloride

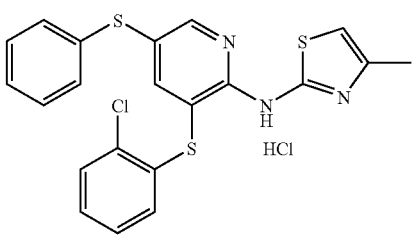

Prepared according to the method of Example 13 from N-(5-bromo-3-(2-chlorophenylthio)pyridin-2-yl)-4-methylthiazol-2-amine (prepared according to Example 47) and benzenethiol. $^1$H NMR ($d_6$-DMSO) δ 8.36 (bs, 1H), 7.57 (dd, 1H), 7.40-7.15 (m, 10H), 6.54 (s, 1H), 2.20 (s, 3H); Mass spectrum (esi) m/z=442.2 (M+H−HCl).

Example 49

Methyl 3-(5-(2-chlorophenylthio)-6-(4-methylthiazol-2-ylamino)pyridin-3-ylthio)propanoate

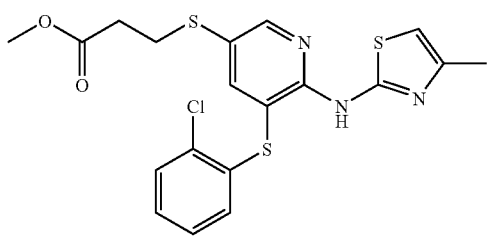

Prepared according to the method of Example 13 from N-(5-bromo-3-(2-chlorophenylthio)pyridin-2-yl)-4-methylthiazol-2-amine (prepared according to Example 47) and methyl 3-mercaptopropanoate. $^1$H NMR (CDCl$_3$) δ 9.01 (bs, 1H), 8.52 (d, 1H), 7.95 (d, 1H), 7.40 (dd, 1H), 7.16-7.06 (m, 2H), 6.66 (dd, 1H), 6.46 (s, 1H), 3.68 (s, 3H), 3.07 (t, 2H), 2.61 (t, 2H), 2.32 (s, 3H); Mass spectrum (esi) m/z=452.1 (M+H).

Example 50

N-(3-(2-chlorophenylthio)-5-(1-(pyridin-2-yl)ethylthio)pyridin-2-yl)-4-methylthiazol-2-amine dihydrochloride

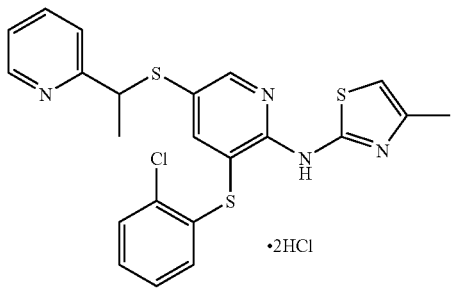

Prepared according to the method of Example 16 from methyl 3-(5-(2-chlorophenylthio)-6-(4-methylthiazol-2-ylamino)pyridin-3-ylthio)propanoate (prepared according to Example 49), and 2-(1-bromoethyl)pyridine. $^1$H NMR (d$_6$-DMSO) δ 8.54 (d, 1H), 8.19 (bs, 1H), 7.97 (m, 1H), 7.61 (dd, 1H), 7.50 (m, 2H), 7.37 (m, 2H), 7.04 (bs, 2H), 6.52 (s, 1H), 4.56 (q, 1H), 2.18 (s, 3H), 1.59 (d, 3H); Mass spectrum (esi) m/z=471.2 (M+H-2HCl).

Example 51

N-(3-(2-chlorophenylthio)-5-(piperidin-4-ylmethylthio)pyridin-2-yl)-4-methylthiazol-2-amine dihydrochloride

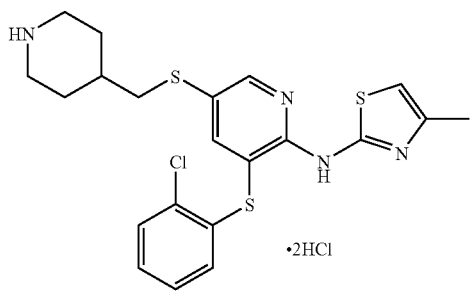

Prepared according to the method of Example 16 using methyl 3-(5-(2-chlorophenylthio)-6-(4-methylthiazol-2-ylamino)pyridin-3-ylthio)propanoate and tert-butyl 4-(bromomethyl)piperidine-1-carboxylate. $^1$H NMR (d$_6$-DMSO) δ 12.15 (bs, 1H), 10.05 (bs, 1H), 8.64 (m, 1H), 8.32 (m, 2H), 7.63 (m, 1H), 7.36 (m, 2H), 6.52 (s, 1H), 3.22 (m, 2H), 2.79 (m, 4H), 2.17 (s, 3H), 1.86 (m, 2H), 1.61 (m, 1H), 1.36 (m, 2H); Mass spectrum (esi) m/z=463.0 (M+H-2HCl).

Example 52

N-(3-(2-chlorophenylthio)-5-(3-(dimethylamino)propylthio)pyridin-2-yl)-4-methylthiazol-2-amine dihydrochloride

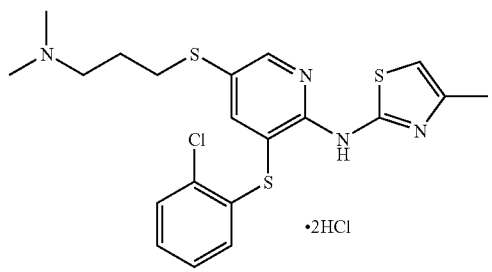

Prepared according to the method of Example 16 using methyl 3-(5-(2-chlorophenylthio)-6-(4-methylthiazol-2-ylamino)pyridin-3-ylthio)propanoate and 3-chloro-N,N-dimethylpropan-1-amine hydrochloride. $^1$H NMR (d$_6$-DMSO) δ 10.12 (bs, 1H), 8.41 (s, 1H), 7.61 (d, 1H), 7.33 (m, 2H), 7.07 (m, 1H), 6.52 (s, 1H), 3.09 (m, 2H), 2.90 (m, 2H), 2.70 (d, 6H), 2.18 (s, 3H), 1.84 (m, 2H); Mass spectrum (esi) m/z 451.0 (M+H-2HCl).

Example 53

N-(5-(2-chlorophenylthio)-3-phenoxypyridin-2-yl)-4-methylthiazol-2-amine hydrochloride

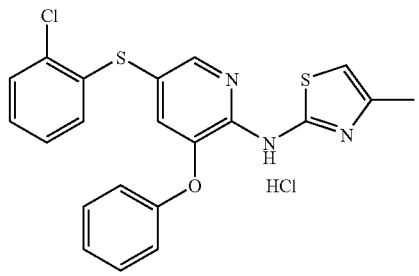

Prepared according to the method of Example 13, using 5-bromo-N-(4-methylthiazol-2-yl)-3-phenoxypyridin-2-amine and 2-chlorobenzenethiol. $^1$H NMR (d$_6$-DMSO) δ 8.26 (d, 1H), 7.49 (dd, 1H), 7.42 (t, 2H), 7.29 (d, 1H), 7.27-7.12 (m, 4H), 6.96 (dd, 1H), 6.80 (s, 1H), 2.30 (s, 3H); Mass spectrum (esi) m/z=426.4 (M+H—HCl).

Example 54

N-(5-(3-chlorophenylthio)-3-phenoxypyridin-2-yl)-4-methylthiazol-2-amine hydrochloride

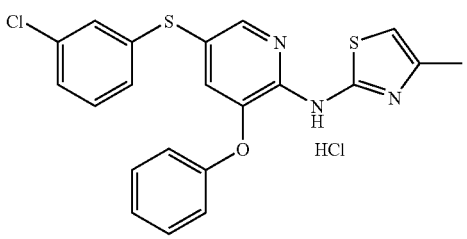

Prepared according to the method of Example 13, using 3-chlorobenzenethiol. $^1$H NMR (d$_6$-DMSO) δ 8.27 (d, 1H), 7.42 (t, 2h), 7.35-7.10 (m, 8H), 6.81 (s, 1H), 2.30 (s, 3H); Mass spectrum (esi) m/z=426.3 (M+H—HCl).

Example 55

N-(5-(2-methoxyphenylthio)-3-phenoxypyridin-2-yl)-4-methylthiazol-2-amine hydrochloride

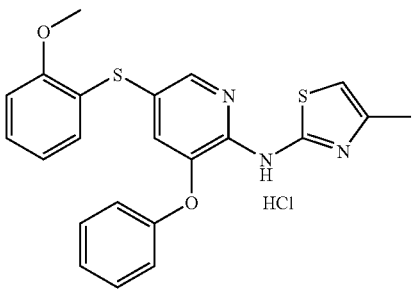

Prepared according to the method of Example 13, using 2-methoxybenzenethiol. $^1$H NMR (d$_6$-DMSO) δ 8.14 (d, 1H), 7.42 (t, 2H), 7.27-7.18 (m, 2H), 7.13 (m, 2H), 7.02 (d, 1H), 6.98 (d, 1H), 6.89 (t, 1H), 6.80 (s, 1H), 3.77 (s, 3H), 2.30 (s, 3H); Mass spectrum (esi) m/z=422.2 (M+H—HCl).

Example 56

N-(5-(3-methoxyphenylthio)-3-phenoxypyridin-2-yl)-4-methylthiazol-2-amine hydrochloride

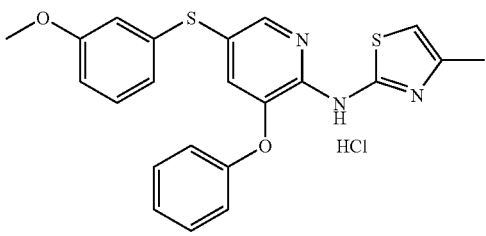

Prepared according to the method of Example 13, using 3-methoxybenzenethiol. $^1$H NMR (d$_6$-DMSO) δ 8.22 (s, 1H), 7.42 (m, 2H), 7.27-7.18 (m, 3h), 7.14 (m, 2H), 6.86-6.77 (m, 4H), 3.71 (s, 3H), 2.31 (s, 3H); Mass spectrum (esi) m/z=422.2 (M+H–HCl).

Example 57

3-(6-(4-methylthiazol-2-ylamino)-5-phenoxypyridin-3-ylthio)phenol

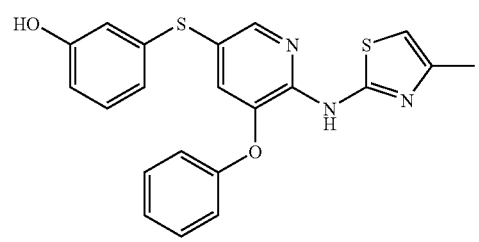

A mixture of N-(5-(3-methoxyphenylthio)-3-phenoxypyridin-2-yl)-4-methylthiazol-2-amine (prepared according to Example 56; 1.1 g, 2.6 mmol) and CH$_2$Cl$_2$ (20 mL) was cooled to 0° C. and tribromoborane (1M in CH$_2$Cl$_2$, 7.83 mL, 7.83 mmol) was added and stirred at 0° C. for 1 hour. The reaction was slowly poured into saturated aqueous sodium bicarbonate and extracted with 10% methanol in CH$_2$Cl$_2$. The organic layer was dried with sodium sulfate, filtered and concentrated. The residue was purified on silica gel (50 to 80% EtOAc in hexanes) to afford 3-(6-(4-methylthiazol-2-ylamino)-5-phenoxypyridin-3-ylthio)phenol (692 mg, 65.1% yield) as a white solid. $^1$H NMR (d$_6$-DMSO) δ 8.18 (dd, 1H), 7.37 (m, 2H), 7.31 (d, 1H), 7.19 (m, 1H), 7.16 (dd, 1H), 7.11-7.02 (m, 3H), 6.69-6.61 (m, 3H), 6.45 (m, 1H), 2.33 (s, 3H); Mass spectrum (esi) m/z=408.2 (M+H).

Example 58

2-(3-(6-(4-methylthiazol-2-ylamino)-5-phenoxypyridin-3-ylthio)phenoxy)acetic acid hydrochloride

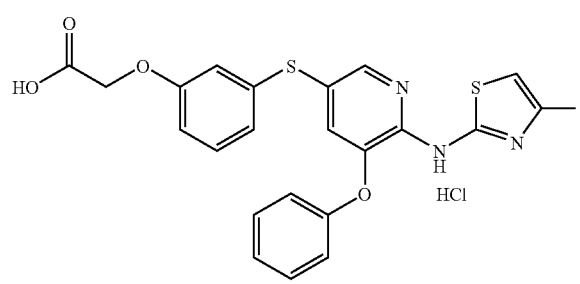

A mixture of 3-(6-(4-methylthiazol-2-ylamino)-5-phenoxypyridin-3-ylthio)phenol (prepared according to Example 57; 200 mg, 0.491 mg), potassium carbonate (203 mg, 1.47 mmol), tert-butyl 2-bromoacetate (0.0725 mL, 0.491 mmol), and DMF (4 mL) was stirred at room temperature for 30 minutes. Water (15 mL) was added and the reaction mixture was extracted with ether. The organic layer was dried with sodium sulfate, filtered and concentrated. The residue was purified on silica gel (10 to 15% EtOAc in hexanes) to afford the tert-butyl ester of the desired material. The material was dissolved in CH$_2$Cl$_2$ (3 mL) and 4N HCl in dioxane added (4 mL) and stirred at room temperature overnight and concentrated. The residue was dissolved in a small amount of CH₂Cl₂ and added to vigorously stirred ether. The resultant precipitate was filtered to afford 2-(3-(6-(4-methylthiazol-2-ylamino)-5-phenoxypyridin-3-ylthio)phenoxy)acetic acid hydrochloride (21.1 mg, 8.56% yield) as a white solid. ¹H NMR (d₆-DMSO) δ 9.70 (bs, 1H), 8.17 (d, 1H), 7.36 (t, 2H), 7.19 (d, 1H), 7.15 (m, 2H), 6.99 (d, 2H), 6.71 (m, 2H), 6.65 (m, 3H), 4.86 (s, 2H), 2.15 (s, 3H); Mass spectrum (esi) m/z=466.1 (M+H—HCl).

Example 59

4-methyl-N-(3-phenoxy-5-(3-(2-(piperidin-1-yl)ethoxy)phenylthio)pyridin-2-yl)thiazol-2-amine

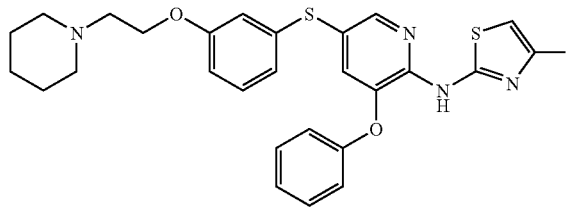

A mixture of 3-(6-(4-methylthiazol-2-ylamino)-5-phenoxypyridin-3-ylthio)phenol (prepared according to Example 57; 70.0 mg, 0.172 mmol), potassium carbonate (71.2 mg, 0.515 mmol), 1-(2-chloroethyl)piperidine hydrochloride (31.6 mg, 0.172 mmol), and DMF (2 mL) was stirred at room temperature for 30 minutes and heated to 50° C. overnight. The reaction was cooled to room temperature and water (15 mL) was added and extracted with ether. A white precipitate formed in the ether layer and was filtered to afford N-(4-methylthiazol-2-yl)-3-phenoxy-5-(3-(2-(piperidin-1-yl)ethoxy)phenylthio)pyridin-2-amine (34.2 mg, 38.4% yield) as a white solid. ¹H NMR (d₆-DMSO) δ 9.56 (s, 1H), 8.29 (dd, 1H), 7.50 (dd, 1H), 7.28 (m, 2H), 7.11 (t, 1H), 7.00 (t, 1H), 6.82 (m, 2H), 6.65 (m, 1H), 6.58 (m, 1H), 6.54 (m, 1H), 6.35 (m, 1H), 3.79 (t, 2H), 2.23 (s, 3H), 2.17 (m, 4H), 2.12 (t, 2H), 1.38 (m, 4H), 1.31 (m, 2H); Mass spectrum (esi) m/z=519.1 (M+H).

Example 60

N-(5-(3-(3-(dimethylamino)propoxy)phenylthio)-3-phenoxypyridin-2-yl)-4-methylthiazol-2-amine

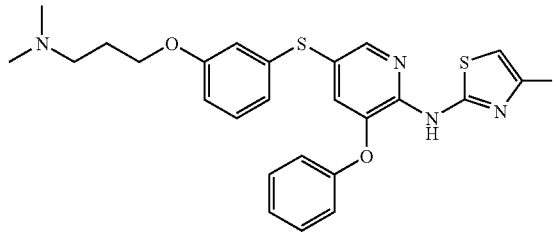

Prepared according to the method of Example 60 using 3-(6-(4-methylthiazol-2-ylamino)-5-phenoxypyridin-3-ylthio)phenol and 3-chloro-N,N-dimethylpropan-1-amine hydrochloride. ¹H NMR (d₆-DMSO)δ 9.55 (s, 1H), 8.28 (dd, 1H), 7.49 (dd, 1H), 7.29 (m, 2H), 7.11 (t, 1H), 7.00 (t, 1H), 6.85 (m, 2H), 6.65 (m, 1H), 6.58 (m, 1H), 6.54 (m, 1H), 6.38 (m, 1H), 3.70 (m, 2H), 2.21 (s, 3H), 2.04 (s, 6H) 1.96 (t, 2H), 1.44 (m, 2H); Mass spectrum (esi) m/z=493.1 (M+H).

Example 61

Representative Example tert-butyl 3-(5-bromo-2-(4-methylthiazol-2-ylamino)pyridin-3-yloxy)pyrrolidine-1-carboxylate

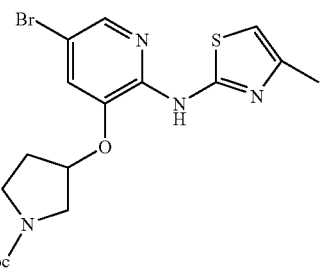

A mixture of 5-bromo-2-(4-methylthiazol-2-ylamino)pyridin-3-ol hydrochloride (1.0 g, 3.10 mmol), tert-butyl 3-bromopyrrolidine-1-carboxylate (WO 2003/062224) (1.01 g, 4.03 mmol), K₂CO₃ (1.29 g, 9.30 mmol), and DMF (20 mL) were reacted at 50° C. over the weekend. The reaction was cooled to room temperature, poured into water (250 mL) and extracted with EtOAc:ether (1:1). The organic layer was dried with sodium sulfate, filtered and concentrated. The residue was purified on silica gel (40% EtOAc in hexanes) to afford tert-butyl 3-(5-bromo-2-(4-methylthiazol-2-ylamino)pyridin-3-yloxy)pyrrolidine-1-carboxylate (584 mg, 41.4% yield) as a tan solid. ¹H NMR (CDCl₃) δ 8.42 (bs, 1H), 8.02 (s, 1h), 7.10 (d, 1H), 6.42 (s, 1H), 4.95 (m, 1H), 3.75-3.44 (m, 4H), 2.35 (d, 3H), 2.21 (m, 2H), 1.50 (s, 9H); Mass spectrum (apci) m/z=456.9 (M+H).

Example 62

Representative Example

N-(5-bromo-3-(pyrrolidin-3-yloxy)pyridin-2-yl)-4-methylthiazol-2-amine dihydrochloride

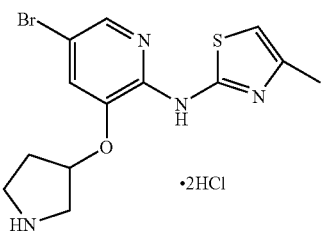

A mixture of tert-butyl 3-(5-bromo-2-(4-methylthiazol-2-ylamino)pyridin-3-yloxy)pyrrolidine-1-carboxylate (prepared according to Example 61; 550 mg, 1.21 mmol) and CH₂Cl₂ (10 mL) and MeOH (2 mL) was stirred at room temperature. 4N HCl in dioxane (5 mL) was added and the reaction mixture was stirred at room temperature for 30 minutes. The reaction was concentrated and dissolved in small amount of CH$_2$Cl$_2$/methanol and added to vigorously stirred ether and filtered to afford N-(5-bromo-3-(pyrrolidin-3-yloxy)pyridin-2-yl)-4-methylthiazol-2-amine dihydrochloride (478 mg, 92.4% yield) as a white solid. $^1$H NMR (d$_6$-DMSO) δ 11.18 (bs, 1H), 9.80 (bs, 1H), 9.27 (bs, 1H), 8.09 (d, 1H), 7.83 (d, 1H), 6.80 (s, 1H), 5.42 (m, 1H), 3.62-3.30 (m, 4H), 2.31 (s, 3H), 2.22 (m, 2H); Mass spectrum (apci) m/z 357.0 (M+H-2HCl).

Example 63

1-(3-(5-bromo-2-(4-methylthiazol-2-ylamino)pyridin-3-yloxy)pyrrolidin-1-yl)ethanone hydrochloride

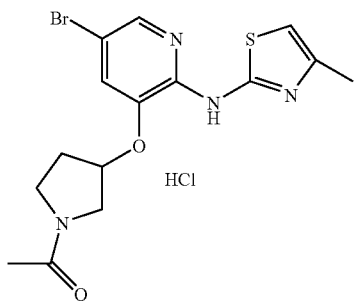

A mixture of N-(5-bromo-3-(pyrrolidin-3-yloxy)pyridin-2-yl)-4-methylthiazol-2-amine dihydrochloride (prepared according to Example 62; 70 mg, 0.16 mmol), triethylamine (0.11 mL, 0.82 mmol), and THF (2 mL) was stirred at room temperature. Acetyl chloride (0.009 mL, 0.16 mmol) was added and stirred at room temperature for 30 minutes. Water (15 mL) was added and extracted with EtOAc. The organic layer was dried with sodium sulfate, filtered and concentrated. The residue was purified on silica gel (10% methanol in EtOAc) to afford 1-(3-(5-bromo-2-(4-methylthiazol-2-ylamino)pyridin-3-yloxy)pyrrolidin-1-yl)ethanone hydrochloride (16 mg, 22.56% yield) as a white solid after HCl salt formation. $^1$H NMR (d$_6$-DMSO) δ 11.60 (bs, 1H), 8.11 (m, 1H), 7.82 (m, 1H), 6.90 (m, 1H), 5.28 (m, 1H), 3.81 (m, 1H), 3.59 (m, 3H), 2.33 (s, 3H), 2.25 (m, 2H), 1.97 (m, 3H); Mass spectrum (apci) m/z=399.1 (M+H—HCl).

Example 64

1-(3-(5-bromo-2-(4-methylthiazol-2-ylamino)pyridin-3-yloxy)pyrrolidin-1-yl)-2-(dimethylamino)ethanone dihydrochloride

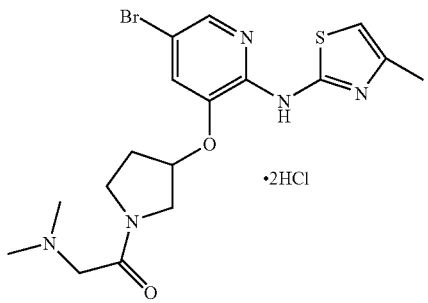

Prepared according to the method of Example 63, using 2-(dimethylamino)acetyl chloride hydrochloride. $^1$H NMR (d$_6$-DMSO) δ 11.13 (bs, 1H), 9.75 (bs, 1H), 8.07 (d, 1H), 7.75 (m, 1H), 6.78 (s, 1H), 5.33 (m, 1H), 4.25 (m, 2H), 4.10 (m, 1H), 3.71 (m, 4H), 2.83 (m, 6H), 2.29 (m, 5H); Mass spectrum (apci) m/z=440.1 (M+H-2HCl).

Example 65

3-(5-bromo-2-(4-methylthiazol-2-ylamino)pyridin-3-yloxy)-N-isopropylpyrrolidine-1-carboxamide

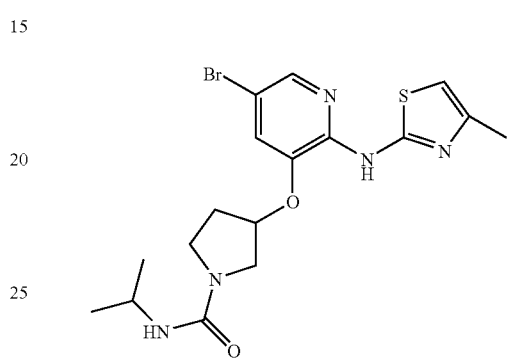

Prepared according to the method of Example 63 using 2-isocyanatopropane. $^1$H NMR (d$_6$-DMSO) δ 10.49 (bs, 1H), 7.97 (m, 1H), 7.52 (m, 1H), 6.61 (m, 1H), 5.82 (d, 1H), 5.17 (m, 1H), 3.75 (m, 1H), 3.56 (m, 2H), 3.45 (m, 2H), 2.28-2.20 (m, 4H), 2.12 (m, 1H), 1.05 (m, 6H); Mass spectrum (apci) m/z=440.1 (M+H).

Example 66

N-(5-bromo-3-(1-(1-methyl-1H-imidazol-4-ylsulfonyl)pyrrolidin-3-yloxy)pyridin-2-yl)-4-methylthiazol-2-amine

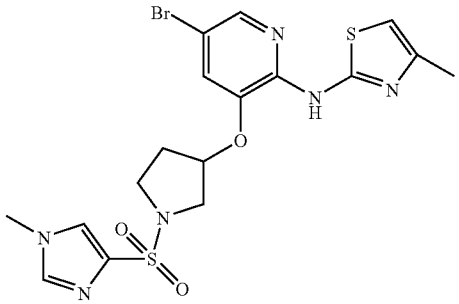

Prepared according to the method of Example 63 using 1-methyl-1H-imidazole-4-sulfonyl chloride. $^1$H NMR (d$_6$-DMSO) δ 10:05 (bs, 1H), 7.96 (d, 1H), 7.79 (s, 1H), 7.49 (m, 2H), 6.65 (s, 1H), 5.07 (m, 1H), 3.63 (m, 2H), 3.55-3.40 (m, 5H), 2.28 (s, 3H), 2.19 (m, 1H), 2.02 (m, 1H); Mass spectrum (apci) m/z=501.1 (M+H).

Example 67

5-(2-fluorobenzylthio)-N-(4-methylthiazol-2-yl)-3-phenoxypyridin-2-amine hydrochloride

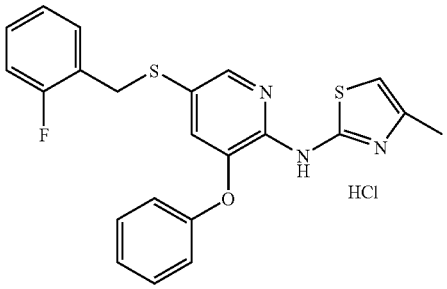

Prepared according to the method of Example 16 using 1-(chloromethyl)-2-fluorobenzene. $^1$H NMR (d$_6$-DMSO) δ 8.06 (d, 1H), 7.42 (t, 2H), 7.28 (m, 1H), 7.15 (m, 4H), 7.09 (m, 1H), 6.97 (d, 2H), 6.69 (s, 1H), 4.09 (s, 2H), 2.25 (s, 3H); Mass spectrum (esi) m/z=424.2 (100) (M+H—HCl).

Example 68

N-(4-methylthiazol-2-yl)-3-phenoxy-5-(1-(pyridin-2-yl)propylthio)pyridin-2-amine dihydrochloride

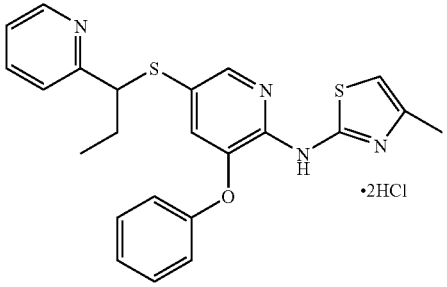

Step A: Preparation of 2-(1-bromopropyl)pyridine: Prepared according to the method of Example 33, Step A from 2-propylpyridine.

Step B: Preparation of N-(4-methylthiazol-2-yl)-3-phenoxy-5-(1-(pyridin-2-yl)propylthio)pyridin-2-amine dihydrochloride: Prepared according to the method of Example 16.

$^1$H NMR (d$_6$-DMSO) δ 8.47 (s, 1H), 7.98 (d, 1H), 7.80 (m, 1H), 7.43 (t, 2H), 7.33 (m, 2H), 7.20 (t, 1H), 6.95 (d, 2H), 6.92 (d, 1H), 6.65 (s, 1H), 4.26 (t, 1H), 2.24 (s, 3H), 1.95 (m, 2H), 0.85 (t, 3H). Mass spectrum (esi) m/z=435.1 (100) (M+H-2HCl).

Example 69

2-((6-(4-methylthiazol-2-ylamino)-5-phenoxypyridin-3-ylthio)methylpyridin-3-ol dihydrochloride

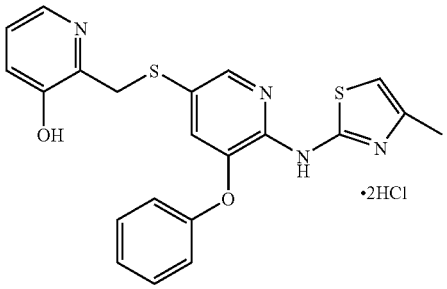

Prepared according to the method of Example 16 with 2-(bromomethyl)pyridin-3-ol hydrobromide. $^1$H NMR (d$_6$-DMSO) δ 8.16 (d, 1H), 8.11 (d, 1H), 7.82 (m, 1H), 7.64 (m, 1H), 7.45 (t, 2H), 7.22 (t, 1H), 7.08 (m, 3H), 6.76 (s, 1H), 4.26 (s, 2H), 2.28 (s, 3H); Mass spectrum (esi) m/z=423.1 (100) (M+H-2HCl).

Example 70

3-(2-(3-phenoxy-5-(1-(pyridin-2-yl)ethylthio)pyridin-2-ylamino)thiazol-4-yl)propanoic acid dihydrochloride

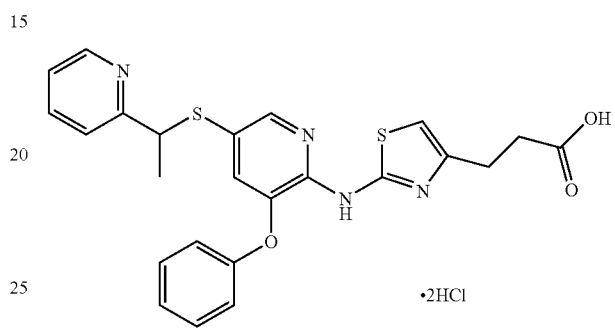

Step A: Preparation of methyl 5-bromo-4-oxopentanoate: A solution of bromine (27.71 g, 173.4 mmol) in methanol (40 mL) was added dropwise to a solution of ethyl 4-oxopentanoate (25.0 g, 173.4 mmol) in methanol (200 mL) at room temperature over a period of 30 minute, and the reaction mixture was stirred overnight. The reaction mixture was concentrated, and the residue was partitioned between 3:1 ether: ethyl acetate and water, washed with saturated sodium bicarbonate, water, brine, dried, and concentrated to afford 17 g of a crude clear oil. The oil was purified by MPLC (Biotage) eluting with 8:1 hexane ethyl acetate to afford methyl 5-bromo-4-oxopentanoate (10.65 g, 29.38% yield) as a clear oil. $^1$H NMR (CDCl$_3$) δ 3.96 (s, 2H), 3.69 (s, 3H), 2.96 (t, 2H), 2.66 (t, 2H).

Step B: Preparation of methyl 3-(2-(5-bromo-3-phenoxypyridin-2-ylamino)thiazol-4-yl)propanoate: Prepared according to the method of Example 7, Step E, using 1-(5-bromo-3-phenoxypyridin-2-yl)thiourea. $^1$H NMR (d$_6$-DMSO) δ 10.95 (s, 1H), 8.22 (d, 1H), 7.43 (t, 2H), 7.39 (s, 1H), 7.21 (t, 1H), 7.10 (d, 2H), 6.68 (s, 1H), 3.59 (s, 3H), 2.84 (t, 2H), 2.68 (t, 2H); Mass spectrum (esi) m/z=435.1 (100) (M+H).

Step C: Preparation of methyl 3-(2-(5-(3-methoxy-3-oxopropylthio)-3-phenoxypyridin-2-ylamino)thiazol-4-yl)propanoate: Prepared according to the method of Example 13. $^1$H NMR (d$_6$-DMSO) δ 10.87 (s, 1H), 8.13 (d, 1H), 7.42 (t, 2H), 7.32 (d, 1H), 7.17 (t, 1H), 7.08 (d, 2H), 6.67 (s, 1H), 3.59 (s, 3H), 3.55 (s, 3H), 3.03 (t, 2H), 2.84 (t, 2H), 2.68 (t, 2H), 2.56 (t, 2H); Mass spectrum (esi) m/z=474.1 (100) (M+H).

Step D: Preparation of 3-(2-(3-phenoxy-5-(1-(pyridin-2-yl)ethylthio)pyridin-2-ylamino)thiazol-4-yl)propanoic acid dihydrochloride: Prepared according to Example 16. The product was further purified by reverse phase to give 106 mg of the t-Butyl ester. This was dissolved in CH$_2$Cl$_2$, and 4M HCl in dioxane was added and the mixture was stirred at room temperature for 5 hours. The mixture was concentrated to give impure product. The product was dissolved in 1N NaOH and extracted with ether. The aqueous layer was acidified with 1M HCl and concentrated. The residue was dissolved in 10%

MeOH in CH₂Cl₂, filtered, and concentrated. The residue was dissolved in 1N NaOH and extract with 10% EtOAc in Ether. The aqueous layer was acidified with 1M HCl and concentrated. The residue was dissolved in 10% MeOH in CH₂Cl₂, filtered and concentrated without the aid of heat to give 3-(2-(3-phenoxy-5-(1-(pyridin-2-yl)ethylthio)pyridin-2-ylamino)thiazol-4-yl)propanoic acid dihydrochloride (0.027 g, 5.80% yield). ¹H NMR (d₆-DMSO) δ 8.41 (s, 1H), 7.99 (s, 1H), 7.65 (t, 1H), 7.40 (t, 2H), 7.20 (m, 3H), 6.92 (m, 3H), 6.50 (s, 1H), 4.42 (m, 1H), 2.70 (m, 2H), 2.29 (m, 2H), 1.54 (d, 3H); Mass spectrum (esi) m/z 479.1 (100) (M+H-2HCl).

Example 71

4-chloro-3-(2-(4-methylthiazol-2-ylamino)-5-(phenylthio)pyridin-3-yloxy benzoic acid hydrochloride

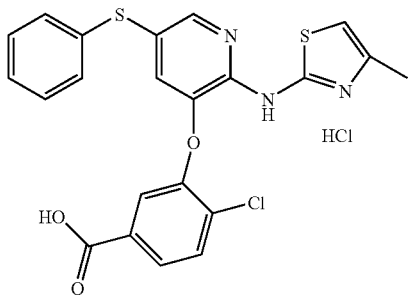

Step A: Preparation of ethyl 4-chloro-3-(2-(4-methylthiazol-2-ylamino)-5-(phenylthio)pyridin-3-yloxy)benzoate: Prepared according to the method of Example 13, using Ethyl 3-(5-bromo-2-(4-methylthiazol-2-ylamino)pyridin-3-yloxy)-4-chlorobenzoate and benzenethiol.

Step B: Preparation of 4-chloro-3-(2-(4-methylthiazol-2-ylamino)-5-(phenylthio)pyridin-3-yloxy)benzoic acid hydrochloride: Prepared according to the method of Example 45. ¹H NMR (d₆-DMSO) δ 8.26 (d, 1H), 7.71 (s, 2H), 7.41 (m, 1H), 7.30 (m, 3H), 7.19 (m, 3H), 6.62 (s, 1H), 2.23 (s, 3H); Mass spectrum (esi) m/z=470.2 (100) (M+H—HCl).

Example 72

4-chloro-N-(2-(dimethylaminoethyl)-3-(2-(4-methylthiazol-2-ylamino)-5-(phenylthio)pyridin-3-yloxy)benzamide dihydrochloride

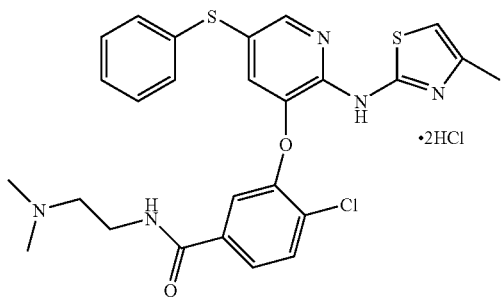

4-Chloro-3-(2-(4-methylthiazol-2-ylamino)-5-(phenylthio)pyridin-3-yloxy)benzoic acid (prepared according to Example 71; 0.131 g, 0.279 mmol) and TEA (0.117 mL, 0.836 mmol) were placed in a flask and cooled to 0° C. Ethyl carbonochloridate (0.0303 g, 0.279 mmol) was added, and the reaction mixture was stirred at 0° C. for 30 minutes. N1,N1-dimethylethane-1,2-diamine (0.0306 mL, 0.279 mmol) was added, and the reaction mixture was stirred at room temperature for 1 hour. Water was added and the reaction mixture was extracted with CH₂Cl₂. The organic layer was concentrated and the residue was purified first by silica gel chromatography and then by reverse phase chromatography to provide the desired product as the free base. The free base was dissolved in CH₂Cl₂ and HCl in ether was added to give 4-chloro-N-(2-(dimethylamino)ethyl)-3-(2-(4-methylthiazol-2-ylamino)-5-(phenylthio)pyridin-3-yloxy)benzamide dihydrochloride (0.069 g, 40.4% yield). ¹H NMR (d₆-DMSO) δ 9.83 (bs, 1H), 8.90 (m, 1H), 8.24 (m, 1H), 7.75 (m, 2H), 7.58 (s, 1H), 7.30 (m, 2H), 7.19 (m, 4H), 6.67 (s, 1H), 3-59 (m, 2H), 3.23 (m, 2H), 2.80 (d, 6H), 2.25 (s, 3H); Mass spectrum (esi) m/z=540.1 (100) (M+H-2HCl).

Example 73

4-chloro-3-(2-(4-methylthiazol-2-ylamino)-5-(1-(pyridin-2-yl)ethylthio)pyridin-3-yloxy)benzoic acid sodium salt

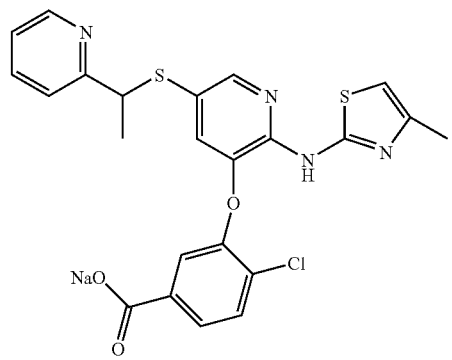

Step A: Preparation of ethyl 4-chloro-3-(5-(3-methoxy-3-oxopropylthio)-2-(4-methylthiazol-2-ylamino)pyridin-3-yloxy)benzoate: Prepared according to the method of Example 13 from ethyl 3-(5-bromo-2-(4-methylthiazol-2-ylamino)pyridin-3-yloxy)-4-chlorobenzoate. ¹H NMR (d₆-DMSO) δ 11.12 (bs, 1H), 8.18 (d, 1H), 7.77 (s, 2H), 7.44 (s, 1H), 7.35 (d, 1H), 6.61 (s, 1H), 4.47 (q, 2H), 3.54 (s, 3H), 3.04 (t, 2H), 2.54 (t, 2H), 2.23 (s, 3H), 1.26 (t, 3H); Mass spectrum (esi) m/z=508.2 (100) (M+H).

Step B: Preparation of 4-chloro-3-(2-(4-methylthiazol-2-ylamino)-5-(1-(pyridin-2-yl)ethylthio)pyridin-3-yloxy)benzoic acid sodium salt: Prepared according to the method of Example 16 using 2-(1-bromoethyl)pyridine. ¹H NMR (d₆-DMSO) δ 8.49 (m, 1H), 8.04 (d, 1H), 7.89 (m, 1H), 7.78 (m, 2H), 7.40 (m, 3H), 6.98 (d, 1H), 6.68 (s, 1H), 4.60 (m, 1H), 2.25 (s, 3H), 1.58 (d, 3H); Mass spectrum (esi) m/z=499.1 (100) (M+H—Na).

Example 74

4-chloro-N-(2-(dimethylamino)ethyl)-3-(2-(4-methylthiazol-2-ylamino)-5-(1-(pyridin-2-yl)ethylthio)pyridin-3-yloxy)benzamide trihydrochloride

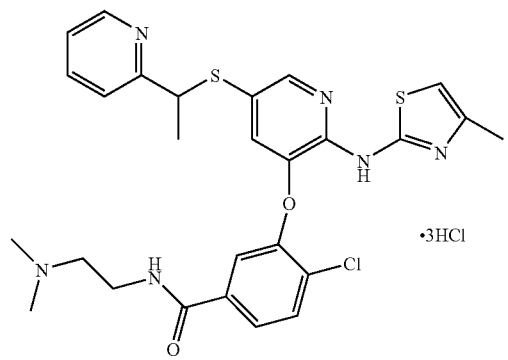

4-chloro-3-(2-(4-methylthiazol-2-ylamino)-5-(1-(pyridin-2-yl)ethylthio)pyridin-3-yloxy)benzoic acid (prepared according to Example 73; 0.131 g, 0.263 mmol), TEA (d. 0.726) (0.0732 mL, 0.525 mmol), ethyl carbonochloridate (0.057 g, 0.525 mmol), and N1,N1-dimethylethane-1,2-diamine (0.0231 g, 0.263 mmol) were reacted according the method of Example 72. 1N NaOH was added and the reaction mixture was stirred for 3 hours. The reaction mixture was extracted with $CH_2Cl_2$. The combined extracts were concentrated and purified by silica gel chromatography (4% MeOH in $CH_2Cl_2$, using 2% 7N ammonia in MeOH) and then purified by reverse phase chromatography to give the compound as the free base. The free base was dissolved in $CH_2Cl_2$ and HCl in ether was added. The mixture was concentrated to give 4-chloro-N-(2-(dimethylamino)ethyl)-3-(2-(4-methylthiazol-2-ylamino)-5-(1-(pyridin-2-yl)ethylthio)pyridin-3-yloxy)benzamide trihydrochloride (0.025 g, 14.8% yield). $^1$H NMR ($d_6$-DMSO) δ 9.73 (s, 1H), 8.91 (m, 1H), 8.42 (m, 1H), 8.01 (d, 1H), 7.78 (m, 3H), 7.51 (s, 1H), 7.29 (m, 2H), 6.83 (s, 1H), 6.66 (m, 1H), 4.48 (q, 1H), 3.60 (m, 2H), 3.24 (m, 2H), 2.81 (d, 6H), 2.24 (s, 3H), 1.54 (d, 3H); Mass spectrum (esi) m/z=569.2 (100) (M+H-3HCl).

Following the procedure of Example 13, the following compounds were also prepared.

| Example | Structure | Name | Data |
|---|---|---|---|
| 75 | 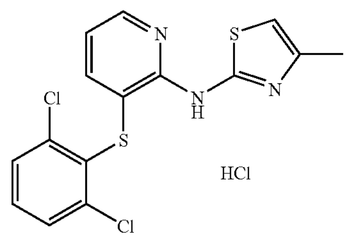 | N-(3-(2,6-dichlorophenylthio)-pyridin-2-yl)-4-methylthiazol-2-amine hydrochloride | $^1$H NMR (CDCl$_3$) δ 12.32 (bs, 1 H), 8.25 (dd, 1 H), 7.42 (d, 2 H), 7.38 (dd, 1 H), 7.28 (dd, 1 H), 6.98 (dd, 1 H), 6.47 (s, 1 H), 2.48 (s, 3 H). Mass spectrum (apci) m/z = 368.2 (M + H − HCl). |
| 76 | 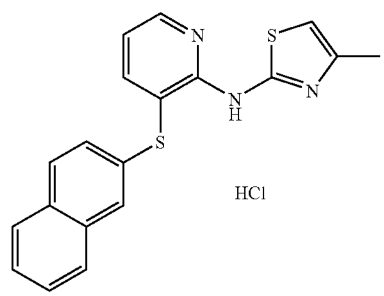 | 4-methyl-N-(3-(naphthalen-2-ylthio)pyridin-2-yl)thiazol-2-amine hydrochloride | $^1$H NMR (DMSO-d$_6$) δ 8.43 (d, 1 H), 7.94-7.82 (m, 5 H), 7.52 (m, 2 H), 7.39 (dd, 1 H), 7.12 (m, 1 H), 6.71 (s, 1 H), 2.24 (s, 3 H). Mass spectrum (apci) m/z = 350.2 (M + H − HCl). |
| 77 | 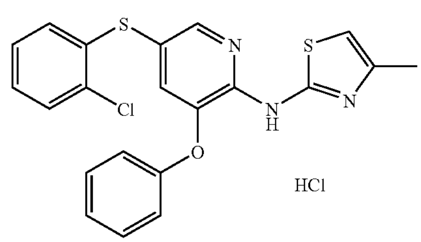 | N-(5-(2-chlorophenylthio)-3-phenoxypyridin-2-yl)-4-methylthiazol-2-amine hydrochloride | $^1$H NMR (DMSO-d$_6$) δ 8.26 (d, 1 H), 7.49 (dd, 1 H), 7.42 (t, 2 H), 7.29 (d, 1 H), 7.25 (td, 2 H), 7.19 (t, 1 H), 7.15 (d, 2 H), 6.96 (dd, 1 H), 6.80 (s, 1 H), 2.30 (s, 3 H). Mass spectrum (apci) m/z = 426.4 (M + H − HCl). |
| 78 | 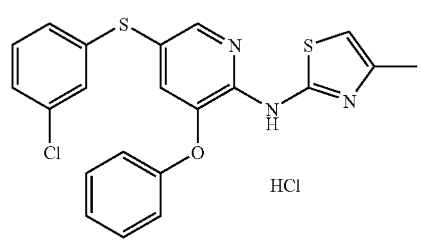 | N-(5-(3-chlorophenylthio)-3-phenoxypyridin-2-yl)-4-methylthiazol-2-amine hydrochloride | $^1$H NMR (DMSO-d$_6$) δ 8.27 (d, 1 H), 7.42 (t, 2 H), 7.35-7.11 (m, 8 H), 6.81 (s, 1 H), 2.30 (s, 3 H). Mass spectrum (apci) m/z = 426.3 (M + H − HCl). |

| Example | Structure | Name | Data |
|---|---|---|---|
| 79 | 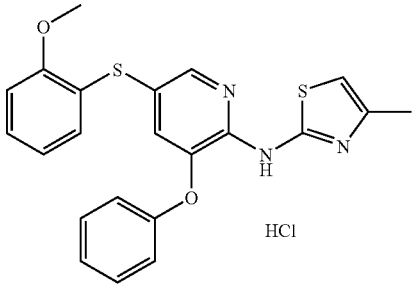 | N-(5-(2-methoxyphenylthio)-3-phenoxypyridin-2-yl)-4-methylthiazol-2-amine hydrochloride | $^1$H NMR (DMSO-d$_6$) δ 8.14 (d, 1 H), 7.43 (t, 2 H), 7.23 (m, 2 H), 7.13 (m, 3 H), 7.02 (d, 1 H), 6.98 (d, 1 H), 6.89 (t, 1 H), 6.80 (s, 1 H), 3.77 (s, 3 H), 2.30 (s, 3 H). Mass spectrum (apci) m/z = 422.2 (M + H − HCl). |
| 80 | 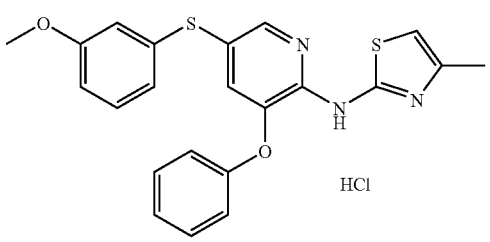 | N-(5-(3-methoxyphenylthio)-3-phenoxypyridin-2-yl)-4-methylthiazol-2-amine hydrochloride | $^1$H NMR (DMSO-d$_6$) δ 8.22 (d, 1 H), 7.42 (m, 2 H), 7.27-7.19 (m, 3 H), 7.14 (m, 2 H), 6.85 (s, 1 H), 6.84-6.77 (m, 3 H), 3.71 (s, 3 H), 2.31 (s, 3 H). Mass spectrum (apci) m/z = 422.2 (M + H − HCl). |
| 81 | 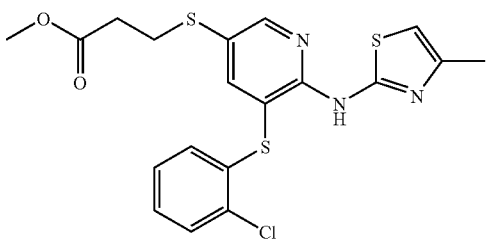 | methyl 3-(5-(2-chlorophenylthio)-6-(4-methylthiazol-2-ylamino)pyridin-3-ylthio)propanoate | $^1$H NMR (CDCl$_3$) δ 9.01 (s, 1 H), 8.52 (d, 1 H), 7.95 (d, 1 H), 7.40 (dd, 1 H), 7.11 (m, 2 H), 6.66 (dd, 1 H), 6.46 (s, 1 H), 3.68 (s, 3 H), 3.07 (t, 2 H), 2.61 (t, 2 H), 2.32 (s, 3 H) Mass spectrum (apci) m/z = 452.1 (M + H). |
| 82 | 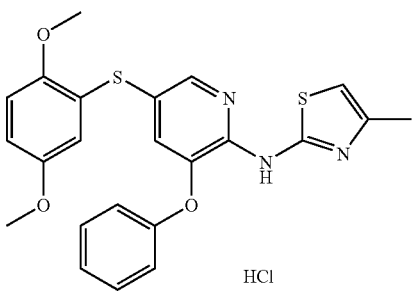 | N-(5-(2,5-dimethoxyphenylthio)-3-phenoxypyridin-2-yl)-4-methylthiazol-2-amine hydrochloride | $^1$H NMR (DMSO-d$_6$) δ 8.16 (d, 1 H), 7.42 (m, 2 H), 7.20 (m, 2 H), 7.11 (m, 2 H), 6.95 (d, 1 H), 6.79 (dd, 1 H), 6.75 (s, 1 H), 6.44 (d, 1 H), 3.72 (s, 3 H), 3.61 (s, 3 H), 2.28 (s, 3 H). Mass spectrum (apci) m/z = 452.2 (M + H − HCl). |
| 83 | 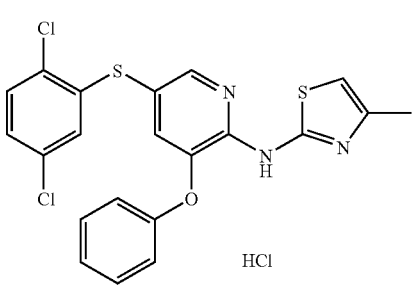 | N-(5-(2,5-dichlorophenylthio)-3-phenoxypyridin-2-yl)-4-methylthiazol-2-amine hydrochloride | $^1$H NMR (DMSO-d$_6$) δ 8.31 (d, 1 H), 7.52 (d, 1 H), 7.40 (m, 3 H), 7.28 (dd, 1 H), 7.17 (d, 1 H), 7.11 (d, 2 H), 6.84 (d, 1 H), 6.71 (s, 1 H), 2.27 (s, 3 H). Mass spectrum (apci) m/z = 460.2 (M + H − HCl). |

| Example | Structure | Name | Data |
|---|---|---|---|
| 84 | 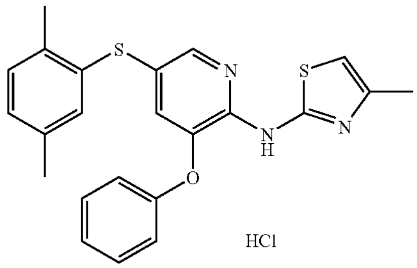 | N-(5-(2,5-dimethylphenylthio)-3-phenoxypyridin-2-yl)-4-methylthiazol-2-amine hydrochloride | $^1$H NMR (DMSO-d$_6$) δ 8.08 (d, 1 H), 7.40 (t, 2 H), 7.21-7.06 (m, 5 H), 6.99 (d, 1 H), 6.92 (s, 1 H), 6.75 (s, 1 H), 2.28 (s, 3 H), 2.25 (s, 3 H), 2.19 (s, 3 H). Mass spectrum (apci) m/z = 420.3 (M + H − HCl). |
| 85 | 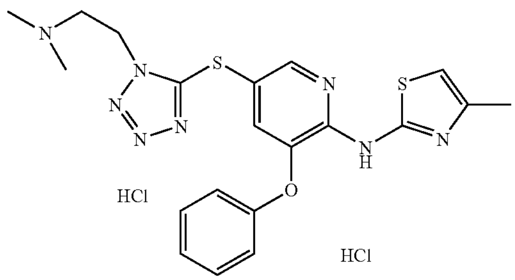 | N-(5-(1-(2-(dimethylamino)ethyl)-1H-tetrazol-5-ylthio)-3-phenoxypyridin-2-yl)-4-methylthiazol-2-amine dihydrochloride | $^1$H NMR (DMSO-d$_6$) δ 10.62 (bs, 1 H), 8.42 (d, 1 H), 7.57 (d, 1 H), 7.43 (t, 2 H), 7.20 (t, 1 H), 7.11 (d, 2 H), 6.74 (s, 1 H), 4.85 (t, 2 H), 3.65 (m, 2 H), 2.84 (s, 6 H), 2.26 (s, 3 H). Mass spectrum (apci) m/z = 455.0 (M + H − 2HCl). |
| 86 | 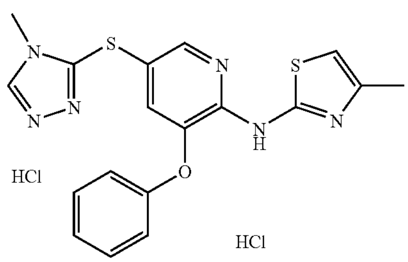 | 4-methyl-N-(5-(4-methyl-4H-1,2,4-triazol-3-ylthio)-3-phenoxypyridin-2-yl)thiazol-2-amine dihydrochloride | $^1$H NMR (DMSO-d$_6$) δ 8.72 (s, 1 H), 8.21 (dd, 1 H), 7.42 (t, 2 H), 7.30 (dd, 1 H), 7.21 (t, 1 H), 7.08 (d, 2 H), 6.71 (s, 1 H), 3.62 (s, 3 H), 2.25 (s, 3 H). Mass spectrum (apci) m/z = 397.1 (M + H − 2HCl). |
| 87 | 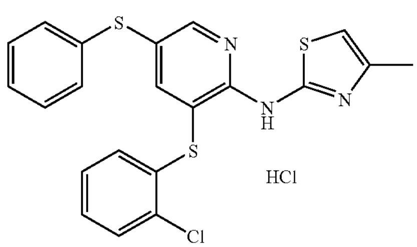 | 3-(2-chlorophenylthio)-N-(4-methylthiazol-2-yl)-5-(phenylthio)pyridin-2-amine hydrochloride | $^1$H NMR (DMSO-d$_6$) δ 8.35 (s, 1 H), 7.57 (dd, 1 H), 7.40-7.15 (m, 9 H), 6.54 (s, 1 H), 2.20 (s, 3 H). Mass spectrum (apci) m/z = 442.2 (M + H − HCl). |
| 88 | 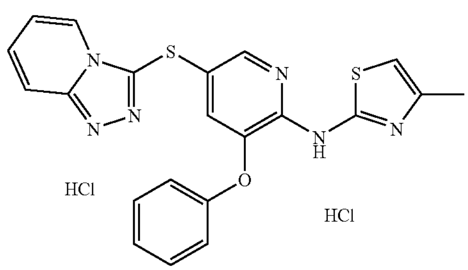 | N-(5-([1,2,4]triazolo[4,3-a]pyridin-3-ylthio)-3-phenoxypyridin-2-yl)-4-methylthiazol-2-amine dihydrochloride | $^1$H NMR (DMSO-d$_6$) δ 11.00 (bs, 1 H), 8.59 (m, 1 H), 8.27 (m, 1 H), 7.87 (m, 1 H), 7.50 (m, 1 H), 7.37 (m, 2 H), 7.24 (m, 1 H), 7.17 (m, 1 H), 7.12 (m, 1 H), 6.98 (d, 2 H), 6.62 (s, 1 H), 2.21 (s, 3 H). Mass spectrum (apci) m/z = 433.1 (M + H − 2HCl). |
| 89 | 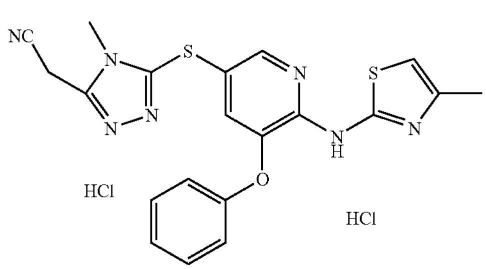 | 2-(4-methyl-5-(6-(4-methylthiazol-2-ylamino)-5-phenoxypyridin-3-ylthio)-4H-1,2,4-triazol-3-yl)acetonitrile dihydrochloride | $^1$H NMR (DMSO-d$_6$) δ 8.21 (t, 1 H), 7.43 (m, 2 H), 7.32 (t, 1 H), 7.21 (t, 1 h), 7.08 (d, 2 H), 6.72 (s, 1 H), 4.37 (d, 2 H), 3.55 (d, 3 H), 2.26 (s, 3 H). Mass spectrum (apci) m/z = 436.2 (M + H − 2HCl). |

| Example | Structure | Name | Data |
|---|---|---|---|
| 90 | 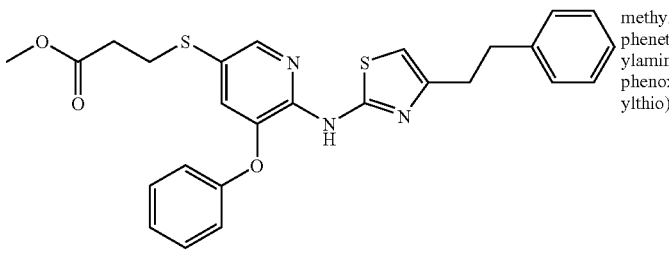 | methyl 3-(6-(4-phenethylthiazol-2-ylamino)-5-phenoxypyridin-3-ylthio)propanoate | $^1$H NMR (CDCl$_3$) δ 8.76 (bs, 1 H), 8.16 (d, 1 H), 7.42 (m, 2 H), 7.30-7.16 (m, 6 H), 7.14 (d, 1 H), 7.06 (m, 2 H), 6.42 (s, 1 H), 3.65 (s, 3 H), 3.05-2.90 (m, 6 H), 2.26 (t, 2 H). Mass spectrum (apci) m/z = 492.3 (M + H). |
| 91 | 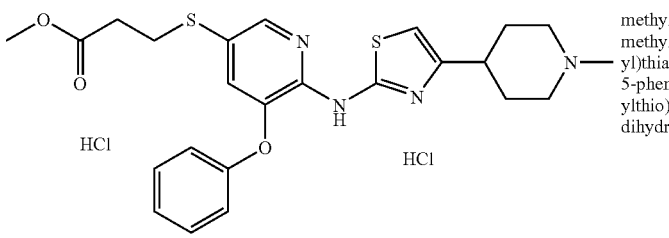 | methyl 3-(6-(4-(1-methylpiperidin-4-yl)thiazol-2-ylamino)-5-phenoxypyridin-3-ylthio)propanoate dihydrochloride | $^1$H NMR (DMSO-d$_6$) δ 10.92 (bs, 1 H), 10.03 (bs, 1 H), 8.15 (d, 1 H), 7.43 (m, 2 H), 7.33 (d, 1 H), 7.20 (m, 1 H), 7.09 (m, 2 H), 6.76 (s, 1 H), 3.55 (s, 3 H), 3.47 (m, 2 H), 3.04 (m, 4 H), 2.81 (m, 1 H), 2.75 (d, 3 H), 2.56 (t, 2 H), 2.15 (m, 2 H), 1.85 (m, 2 H). Mass spectrum (apci) m/z = 485.3 (M + H − 2HCl). |
| 92 | 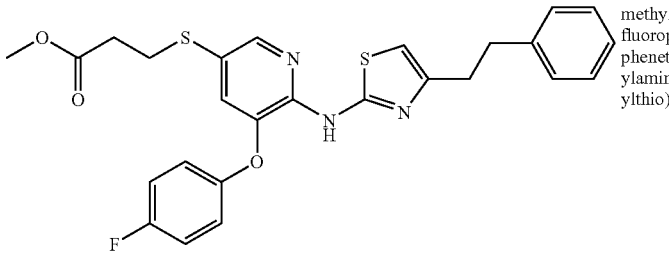 | methyl 3-(5-(4-fluorophenoxy)-6-(4-phenethylthiazol-2-ylamino)pyridin-3-ylthio)propanoate | $^1$H NMR (CDCl$_3$) δ 8.76 (bs, 1 H), 8.15 (d, 1 H), 7.28 (m, 2 H), 7.20 (m, 3 H), 7.15-7.02 (m, 6 H), 6.43 (s, 1 H), 3.65 (s, 3 H), 3.05-2.92 (m, 6 H), 2.56 (t, 2 H). Mass spectrum (apci) m/z = 510.3 (M + H). |
| 93 | 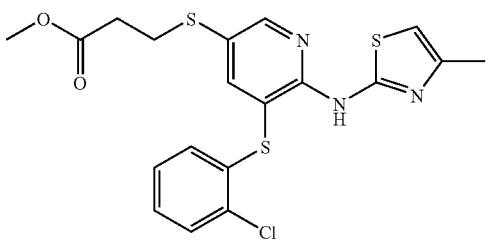 | methyl 3-(5-(2-chlorophenylthio)-6-(4-methylthiazol-2-ylamino)pyridin-3-ylthio)propanoate | $^1$H NMR (CDCl$_3$) δ 9.01 (s, 1 H), 8.52 (d, 1 H), 7.95 (d, 1 H), 7.40 (dd, 1 H), 7.11 (m, 2 H), 6.66 (dd, 1 H), 6.46 (s, 1 H), 3.68 (s, 3 H), 3.08 (t 2 H), 2.60 (t, 2 H), 2.32 (s, 3 H). Mass spectrum (apci) m/z = 459.1 (M + H). |
| 94 | 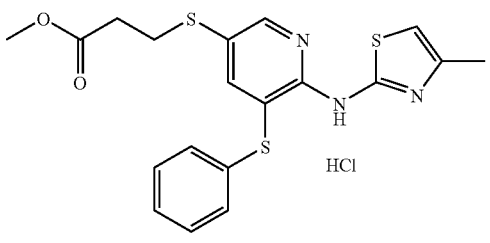 | methyl 3-(6-(4-methylthiazol-2-ylamino)-5-(phenylthio)pyridin-3-ylthio)propanoate hydrochloride | $^1$H NMR (d$_6$-DMSO) δ 8.33 (s, 1 H), 7.64 (bs, 1 H), 7.46-7.33 (m, 5 H), 6.64 (s, 1 H), 3.56 (s, 3 H), 3.04 (t, 2 H), 2.54 (t, 2 H), 2.23 (s, 3 H). Mass spectrum (apci) m/z = 417.7 (M + H − HCl). |

| Example | Structure | Name | Data |
|---|---|---|---|
| 95 | 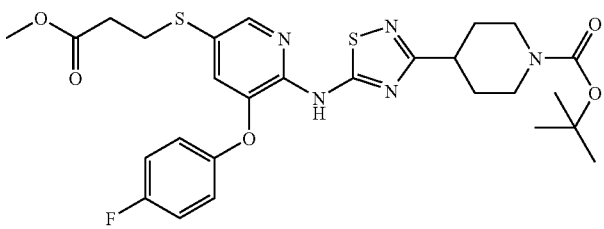 | tert-butyl 4-(5-(3-(4-fluorophenoxy)-5-(3-methoxy-3-oxopropylthio)pyridin-2-ylamino)-1,2,4-thiadiazol-3-yl)piperidine-1-carboxylate | $^1$H NMR (CDCl$_3$) δ 9.02 (s, 1 H), 8.20 (m, 1 h), 7.13 (m, 3 H), 7.07 (m, 2 H), 4.15 (m, 2 H), 3.65 (s, 3 H), 3.03 (t, 2 H), 2.98 (m, 1 H), 2.90 (m, 2 H), 2.57 (t, 2 H), 2.04 (m, 2 H), 1.81 (m, 2 H), 1.46 (s, 9 H). Mass spectrum (apci) m/z = 490.3 (M + H − Boc). |
| 96 | 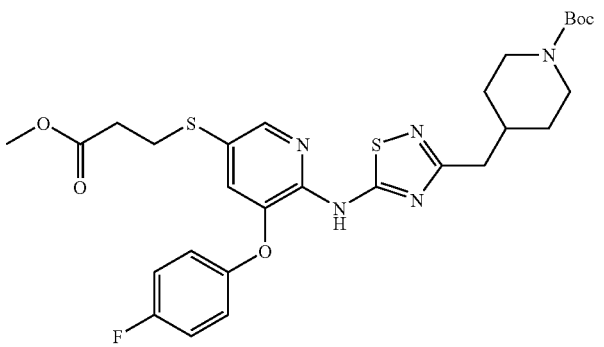 | tert-butyl 4-((5-(3-(4-fluorophenoxy)-5-(3-methoxy-3-oxopropylthio)pyridin-2-ylamino)-1,2,4-thiadiazol-3-yl)methyl)piperidine-1-carboxylate | $^1$H NMR (CDCl$_3$) δ 9.01 (s, 1 H), 8.20 (d, 1 H), 7.13 (m, 3 H), 7.07 (m, 2 H), 4.08 (m, 2 H), 3.66 (s, 3 H), 3.03 (t, 2 H), 2.78 (d, 2 H), 2.71 (m, 2 H), 2.57 (t, 2 H), 2.05 (m, 1 H), 1.68 (m, 2 H), 1.45 (s, 9 H), 1.24 (m, 2 H). Mass spectrum (apci) m/z = 504.3 (M + H − Boc). |

Following the procedure of Example 16, the following compounds were also prepared:

| Example | Structure | Name | Data |
|---|---|---|---|
| 97 | 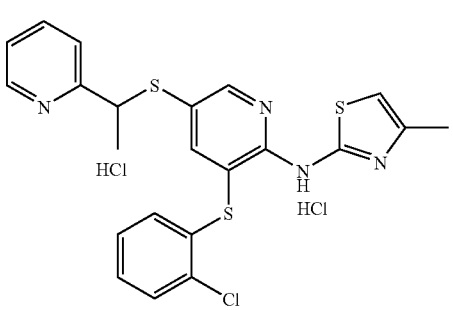 | N-(3-(2-chlorophenylthio)-5-(1-(pyridin-2-yl)ethylthio)pyridin-2-yl)-4-methylthiazol-2-amine dihydrochloride | $^1$H NMR (DMSO-d$_6$) δ 8.54 (d, 1 H), 8.19 (s, 1 H), 7.98 (t, 1 H), 7.61 (dd, 1 H), 7.51 (d, 1 H), 7.47 (d, 1 H), 7.37 (m, 2 H), 7.04 (bs, 2 H), 6.52 (s, 1 H), 4.56 (q, 1 H), 2.18 (s, 3 H), 1.58 (d, 3 H). Mass spectrum (apci) m/z = 471.2 (M + H − 2HCl). |
| 98 | 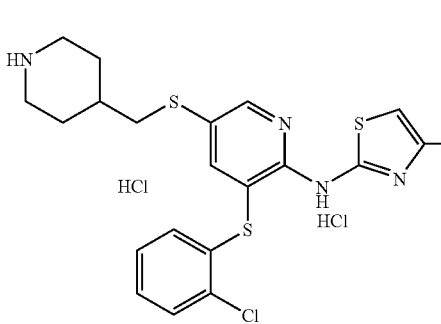 | N-(3-(2-chlorophenylthio)-5-(piperidin-4-ylmethylthio)pyridin-2-yl)-4-methylthiazol-2-amine dihydrochloride | $^1$H NMR (DMSO-d$_6$) δ 12.20 (bs, 1 H), 10.05 (bs, 1 H), 8.65 (d, 1 H), 8.34 (m, 2 H), 7.64 (d, 1 H), 7.38 (m, 2 H), 3.22 (d, 2 H), 2.79 (q, 4 H), 2.17 (s, 3 H), 1.86 (d, 2 H), 1.61 (m, 1 H), 1.30 (m, 2 H). Mass spectrum (apci) m/z = 463.0 (M + H − 2HCl). |

| Example | Structure | Name | Data |
|---|---|---|---|
| 99 | 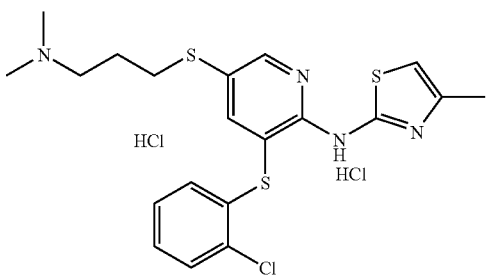 | N-(3-(2-chlorophenylthio)-5-(3-(dimethylamino)propylthio)pyridin-2-yl)-4-methylthiazol-2-amine dihydrochloride | $^1$H NMR (DMSO-$d_6$) δ 10.13 (bs, 1 H), 8.42 (s, 1 H), 7.61 (d, 1 H), 7.34 (m, 2 H), 7.09 (m, 1 H), 6.52 (s, 1 H), 3.09 (m, 2 H), 2.91 (t, 2 H), 2.70 (d, 6 H), 2.19 (s, 3 H), 1.84 (m, 2 H). Mass spectrum (apci) m/z = 451.1 (M + H − 2HCl). |
| 100 | 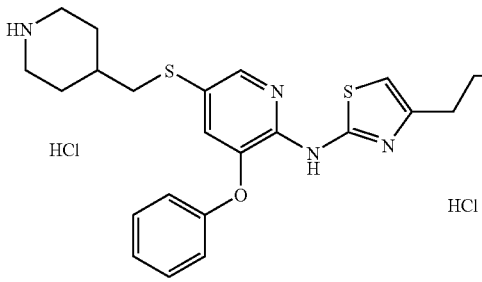 | 4-phenethyl-N-(3-phenoxy-5-(piperidin-4-ylmethylthio)pyridin-2-yl)thiazol-2-amine dihydrochloride | $^1$H NMR (DMSO-$d_6$) δ 11.20 (bs, 1 H), 8.81 (m, 1 H), 8.50 (m, 1 H), 8.18 (d, 1 H), 7.44 (m, 2 H), 7.36 (d, 1 H), 7.30-7.15 (m, 6 H), 7.10 (d, 2 H), 6.71 (s, 1 H), 3.22 (m, 2 H), 2.98-2.73 (m, 8 H), 1.88 (m, 2 H), 1.67 (m, 1 H), 1.34 (m, 2 H). Mass spectrum (apci) m/z = 503.2 (M + H − 2HCl). |

Example 101

3-(6-(4-methylthiazol-2-ylamino)-5-phenoxypyridin-3-ylthio)phenol

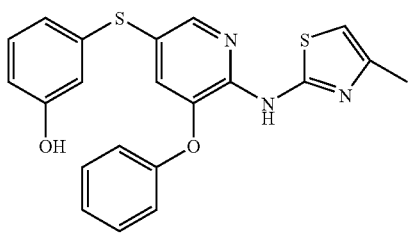

Prepared according to the method of Example 57. $^1$H NMR (CDCl$_3$) δ 8.18 (dd, 1H), 7.38 (m, 2H), 7.31 (d, 1H), 7.19 (tq, 1H), 7.16 (dd, 1H), 7.10-7.03 (m, 3H), 6.69-6.61 (m, 3H), 6.45 (t, 1H), 2.33 (s, 3H). Mass Spectrum (apci): 408.2 (M+H).

Example 102

4-methyl-N-(3-phenoxy-5-(3-(2-(piperidin-1-yl)ethoxy)phenylthio)pyridin-2-yl)thiazol-2-amine

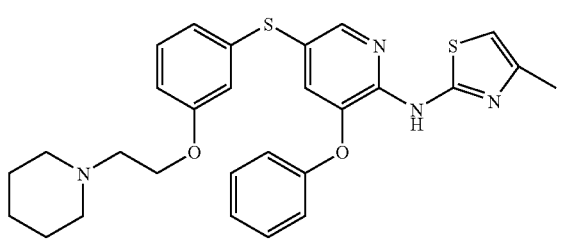

Prepared according to the method of Example 59. $^1$H NMR (d$_6$-DMSO) δ 9.56 (s, 1H), 8.29 (dd, 1H), 7.50 (dd, 1H), 7.28 (m, 2H), 7.12 (t, 1H), 7.00 (t, 1H), 6.83 (m, 2H), 6.65 (m, 1H), 6.58 (m, 1H), 6.54 (m, 1H), 6.35 (s, 1H), 3.79 (t, 2H), 2.24 (s, 3H), 2.18 (m, 4H), 2.12 (t, 2H), 1.38 (m, 4H), 1.31: (m, 2H). MS (apci): 519.1 (M+H).

Example 103

2-(3-(6-(4-methylthiazol-2-ylamino)-5-phenoxypyridin-3-ylthio)phenoxy)acetic acid hydrochloride

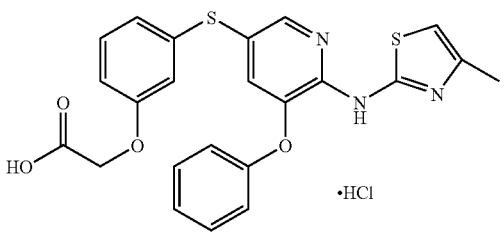

Prepared according to the method of Example 58. $^1$H NMR (d$_6$-DMSO) δ 9.70 (bs, 1H), 8.17 (d, 1H), 7.36 (t, 2H), 7.19 (d, 1H), 7.15 (m, 2H), 6.99 (d, 2H), 6.71 (d, 1H), 6.66 (d, 1H), 6.63 (d, 2H), 4.86 (s, 2H), 2.15 (s, 3H). Mass Spectrum (apci): 466.1 (M+H—HCl).

Example 104

N-(5-(3-(3-(dimethylamino)propoxy)phenylthio)-3-phenoxy)pyridin-2-yl)-4-methylthiazol-2-amine

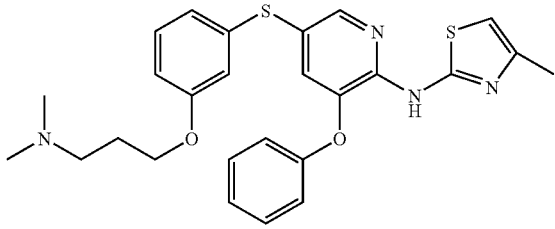

Prepared according to the method of Example 60. $^1$H NMR (d$_6$-DMSO) δ 9.55 (s, 1H), 8.28 (d, 1H), 7.49 (d, 1H), 7.29 (t, 2H), 7.11 (t, 1H), 7.00 (t, 1H), 6.85 (d, 2H), 6.65 (d, 1H), 6.58 (dd, 1H), 6.54 (m, 1H), 6.38 (s, 1H), 3.70 (m, 2H), 2.21 (s, 3H), 2.04 (s, 6H), 1.96 (t, 2H), 1.44 (m, 2H). Mass Spectrum (apci): 493.1 (M+H).

Example 105

1-(3-(5-bromo-2-(4-methylthiazol-2-ylamino)pyridin-3-yloxy)pyrrolidin-1-yl)ethanone hydrochloride

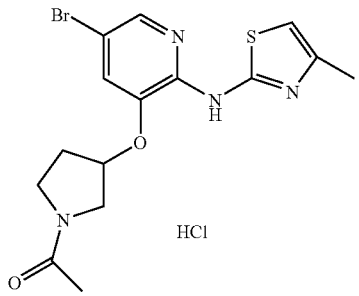

Prepared according to the method of Example 63. $^1$H NMR (d$_6$-DMSO) δ 11.55 (bs, 1H), 8.11 (d, 1H), 7.81 (d, 1H), 6.90 (d, 1H), 5.28 (m, 1H), 4.00-3.52 (m, 4H), 2.33 (s, 3H), 2.31-2.09 (m, 2H), 1.98 (d, 3H). Mass spectrum (apci) m/z=399.1 (M+H—HCl).

Following the procedure of Example 105, Step H, the following compounds were also prepared.

| Example | Structure | Name | Data |
|---|---|---|---|
| 106 | ![structure] | 1-(3-(5-bromo-2-(4-methylthiazol-2-ylamino)pyridin-3-yloxy)pyrrolidin-1-yl)-2-(dimethylamino)ethanone dihydrochloride | $^1$H NMR (d$_6$-DMSO) δ 11.12 (bs, 1 H), 9.75 (bs, 1 H), 8.08 (d, 1 H), 7.75 (d, 1 H), 6.78 (s, 1 H), 5.32 (dt, 1 H), 4.31-4.06 (m, 2 H), 3.85-3.56 (m, 4 H), 2.83 (m, 6 H), 2.40-2.10 (m, 5 H). Mass spectrum (apci) m/z = 440.1 (M + H − 2HCl). |
| 107 | ![structure] | 4-(3-(5-bromo-2-(4-methylthiazol-2-ylamino)pyridin-3-yloxy)pyrrolidin-1-yl)-4-oxobutanoic acid | $^1$H NMR (d$_6$-DMSO) δ 12.20 (bs, 1 H), 11.65 (bs, 1 H), 7.97 (m, 1 H), 7.58 (m, 1 H), 6.62 (m, 1 H), 5.20 (dt, 1 H), 3.92-3.42 (m, 4 H), 2.60-2.40 (m, 4 H), 2.32-2.05 (m, 5 H). Mass spectrum (apci) m/z = 457.1 (M + H). |

-continued

| Example | Structure | Name | Data |
|---|---|---|---|
| 108 | 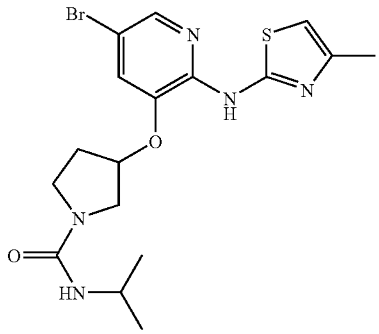 | 3-(5-bromo-2-(4-methylthiazol-2-ylamino)pyridin-3-yloxy)-N-isopropylpyrrolidine-1-carboxamide | $^1$H NMR (d$_6$-DMSO) δ 10.48 (bs, 1 H), 7.96 (m, 1 H), 7.52 (m, 1 H), 6.61 (m, 1 H), 5.82 (d, 1 H), 5.17 (m, 1 H), 3.75 (m, 1 H), 3.61-3.42 (m, 4 H), 2.28-2.05 (m, 5 H), 1.05 (d, 6 H). Mass spectrum (apci) m/z = 440.1 (M + H). |
| 109 | 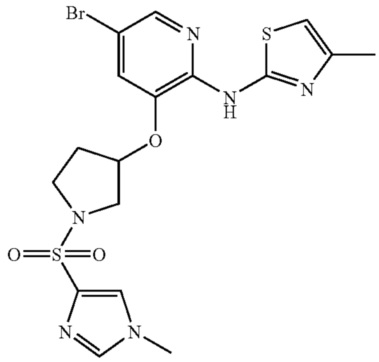 | N-(5-bromo-3-(1-(1-methyl-1H-imidazol-4-ylsulfonyl)pyrrolidin-3-yloxy)pyridin-2-yl)-4-methylthiazol-2-amine | $^1$H NMR (d$_6$-DMSO) δ 10.06 (bs, 1 H), 7.96 (d, 1 H), 7.79 (s, 1 H), 7.49 (m, 2 H), 6.65 (s, 1 H), 5.07 (m, 1 H), 3.69-3.39 (m, 7 H), 2.28 (s, 3 H), 2.20 (m, 1 H), 2.03 (m, 1 H). Mass spectrum (apci) m/z = 501.1 (M + H). |

Example 110

N-(5-bromo-3-(2-chlorophenylthio)pyridin-2-yl)-4-methylthiazol-2-amine

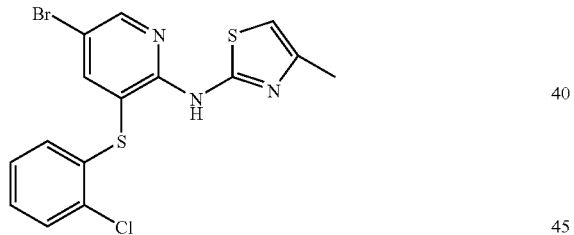

Prepared according to the method of Example 40. $^1$H NMR (CDCl$_3$) δ 8.96 (bs, 1H), 8.49 (d, 1H), 7.95 (d, 1H), 7.41 (dd, 1H), 7.13 (m, 2H), 6.69 (dd, 1 h), 6.46 (s, 1H), 2.32 (s, 3H). Mass spectrum (apci) m/z=414.1 (M+H).

The following compounds were prepared according to the method of Example 7.

| Example | Structure | Name | Data |
|---|---|---|---|
| 111 | 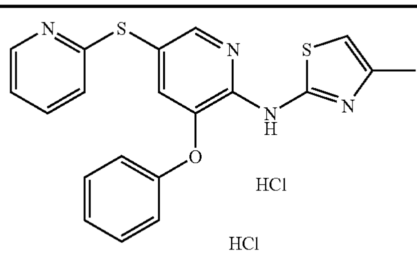 | 4-methyl-N-(3-phenoxy-5-(pyridin-2-ylthio)pyridin-2-yl)thiazol-2-amine dihydrochloride | $^1$H NMR (d$_6$-DMSO) δ 8.39 (ddd, 1 H), 8.35 (dd, 1 H), 7.70 (tdd, 1 H), 7.45 (m, 3 H), 7.20 (m, 5 H), 6.92 (s, 1 H), 2.34 (s, 3 H). Mass spectrum (apci) m/z = 393.2 (M + H − 2HCl). |

| Example | Structure | Name | Data |
|---|---|---|---|
| 112 | 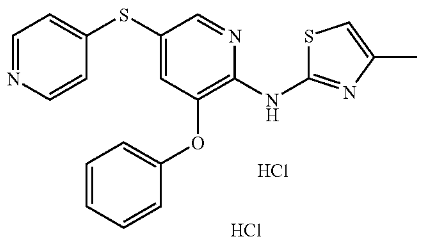 | 4-methyl-N-(3-phenoxy-5-(pyridin-4-ylthio)pyridin-2-yl)thiazol-2-amine dihydrochloride | $^1$H NMR (d$_6$-DMSO) δ 8.59 (d, 2 H), 8.40 (m, 1 H), 7.68 (m, 1 H), 7.66 (d, 1 H), 7.51 (m, 1 H), 7.43 (m, 2 H), 7.19 (m, 3 H), 6.79 (s, 1 H), 2.29 (s, 3 H). Mass spectrum (apci) m/z = 393.2 (M + H − 2HCl). |
| 113 | 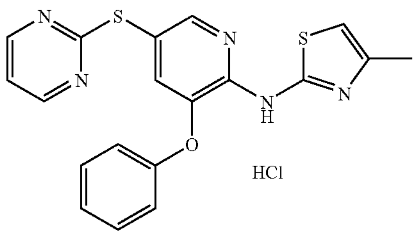 | 4-methyl-N-(3-phenoxy-5-(pyrimidin-2-ylthio)pyridin-2-yl)thiazol-2-amine hydrochloride | $^1$H NMR (d$_6$-DMSO) δ 8.61 (m, 2 H), 8.30 (d, 1 H), 7.48 (d, 1 H), 7.43 (m, 2 H), 7.25 (t, 1 H), 7.17 (m, 3 H), 6.75 (s, 1 H), 2.28 (s, 3 H). Mass spectrum (apci) m/z = 394.2 (M + H − HCl). |
| 114 | 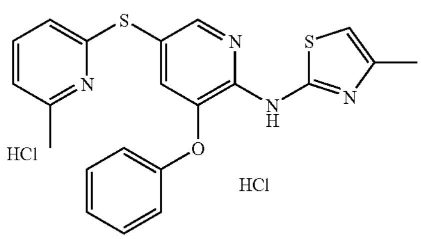 | 4-methyl-N-(5-(6-methylpyridin-2-ylthio)-3-phenoxypyridin-2-yl)thiazol-2-amine dihydrochloride | $^1$H NMR (d$_6$-DMSO) δ 8.31 (d, 1 h), 7.58 (t, 1 H), 7.43 (m, 3 H), 7.20 (m, 3 H), 7.04 (d, 1 H), 6.89 (d, 1 H), 6.82 (s, 1 H), 2.37 (s, 3 H), 2.30 (s, 3 H). Mass spectrum (apci) m/z = 407.2 (M + H − 2HCl). |
| 115 | 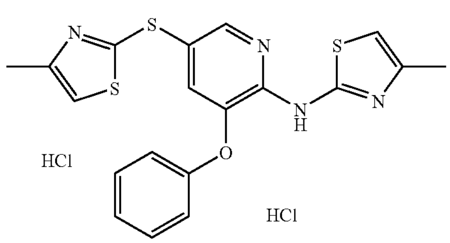 | 4-methyl-N-(5-(4-methylthiazol-2-ylthio)-3-phenoxypyridin-2-yl)thiazol-2-amine dihydrochloride | $^1$H NMR (d$_6$-DMSO) δ 8.38 (d, 1 H), 7.49 (d, 1 H), 7.43 (m, 2 H), 7.22 (d, 1 H), 7.19 (d, 1 H), 7.12 (m, 2 H), 6.77 (s, 1 H), 2.28 (s, 3 H). Mass spectrum (apci) m/z = 413.1 (M + H − 2HCl). |
| 116 | 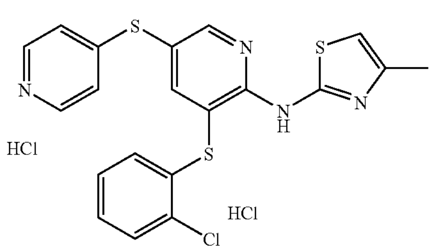 | N-(3-(2-chlorophenylthio)-5-(pyridin-4-ylthio)pyridin-2-yl)-4-methylthiazol-2-amine dihydrochloride | $^1$H NMR (d$_6$-DMSO) δ 8.58 (m, 2 H), 8.46 (s, 1 H), 7.60 (m, 3 H), 7.40 (m, 3 H), 7.22 (bs, 1 H), 6.53 (s, 1 H), 2.21 (s, 3 H). Mass spectrum (apci) m/z = 443.2 (M + H − 2HCl). |
| 117 | 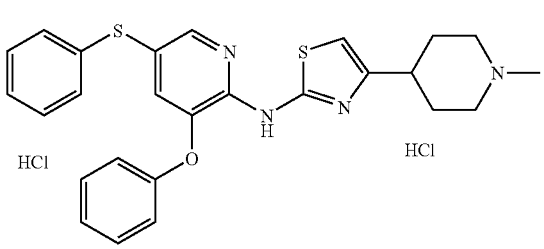 | 4-(1-methylpiperidin-4-yl)-N-(3-phenoxy-5-(phenylthio)pyridin-2-yl)thiazol-2-amine dihydrochloride | $^1$H NMR (d$_6$-DMSO) δ 11.05 (bs, 1 H), 10.00 (bs, 1 H), 8.20 (d, 1 H), 7.40 (m, 2 H), 7.32 (m, 2 H), 7.25-7.15 (m, 5 H), 7.08 (m, 2 H), 6.78 (s, 1 H), 3.45 (m, 2 H), 3.06 (m, 2 H), 2.82 (m, 1 H), 2.75 (d, 3 H), 2.15 (m, 2 H), 1.85 (m, 2 H). Mass spectrum (apci) m/z = 475.3 (M + H − 2HCl). |

| Example | Name | Data |
|---|---|---|
| 118 | N-(3,5-bis(phenylthio)-pyridin-2-yl)-4-methylthiazol-2-amine hydrochloride | ¹H NMR (d₆-DMSO) δ 8.33 (s, 1 H), 7.44-7.16 (m, 11 H), 6.63 (s, 1 H), 2.24 (s, 3 H). Mass spectrum (apci) m/z = 407.7 (M + H − HCl). |
| 119 | 4-methyl-N-(3-(phenylthio)-5-(pyridin-2-ylthio)pyridin-2-yl)thiazol-2-amine hydrochloride | ¹H NMR (d₆-DMSO) δ 8.43 (s, 1 H), 8.36 (m, 1 H), 7.68 (m, 1 H), 7.61 (bs, 1 H), 7.48-7.32 (m, 5 H), 7.16 (m, 1 H), 7.07 (d, 1 H), 6.66 (s, 1 H), 2.25 (s, 3 H). Mass spectrum (apci) m/z = 408.7 (M + H − HCl). |
| 120 | 3-methyl-N-(3-(phenylthio)-5-(pyridin-2-ylthio)pyridin-2-yl)-1,2,4-oxadiazol-5-amine dihydrochloride | ¹H NMR (d₆-DMSO) δ 8.36 (ddd, 1 H), 8.30 (bs, 1 H), 7.68 (m, 1 H), 7.50-7.37 (m, 6 H), 7.17 (m, 2 H), 2.25 (s, 3 H). Mass spectrum (apci) m/z = 394.1 (M + H − 2HCl). |
| 121 | 3-methyl-N-(3-phenoxy-5-(pyridin-2-ylthio)pyridin-2-yl)-1,2,4-thiadiazol-5-amine dihydrochloride | ¹H NMR (d₆-DMSO) δ 12.30 (bs, 1 H), 8.37 (m, 2 H), 7.67 (m, 1 H), 7.43 (m, 3 H), 7.15 (m, 5 H), 2.43 (s, 3 H). Mass spectrum (apci) m/z = 394.2 (M + H − 2HCl). |
| 122 | N-(5-(4-methoxyphenylthio)-3-phenoxypyridin-2-yl)-3-methyl-1,2,4-thiadiazol-5-amine hydrochloride | ¹H NMR (d₆-DMSO) δ 12.10 (bs, 1 H), 8.10 (m, 1 H), 7.38 (m, 4 H), 7.18 (m, 1 H), 7.14 (m, 1 H), 7.05 (m, 2 H), 6.94 (m, 2 H), 3.74 (s, 3 H), 2.40 (s, 3 H). Mass spectrum (apci) m/z = 423.2 (M + H − HCl). |
| 123 | N-(3-(4-fluorophenoxy)-5-(pyridin-2-ylthio)pyridin-2-yl)-3-isobutyl-1,2,4-thiadiazol-5-amine | ¹H NMR (CDCl₃) δ 9.13 (bs, 1 H), 8.36 (m, 1 H), 8.33 (m, 1 H), 7.50 (m, 1 H), 7.28 (m, 1 H), 7.09 (m, 4 H), 7.02 (m, 2 H), 2.73 (d, 2 H), 2.23 (m, 1 H), 0.98 (d, 6 H). Mass spectrum (apci) m/z = 454.2 (M + H). |

Example 124

(6-(4-Methylthiazol-2-ylamino)-5-phenoxypyridin-3-yl)methanol

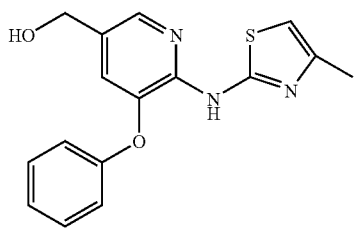

To a mixture of mL 6-(4-methylthiazol-2-ylamino)-5-phenoxynicotinaldehyde (Example 44, Step A; 150 mg, 0.48 mmol) and EtOH (5 mL) was added sodium borohydride (27.3 mg, 0.72 mmol) and stirred at ambient temperature for 30 minutes. Poured into saturated aqueous $NH_4Cl$ and extracted with $CH_2Cl_2$. The organic layer was dried with sodium sulfate, filtered and concentrated. The residue was purified on silica gel (1:1 EtOAc:hexanes) to afford the title compound (132 mg, 87.4% yield) as a white solid. $^1$H NMR ($CDCl_3$) δ 8.66 (bs, 1H), 8.06 (d, 1H), 7.38 (m, 2H), 7.19 (m, 1H), 7.12 (d, 1H), 7.03 (m, 2H), 6.42 (q, 1H), 4.58 (s, 2H), 2.33 (d, 3H), 1.77 (bs, 1H).

Example 125

N-(5-(4-(dimethylamino)but-1-enyl)-3-phenoxypyridin-2-yl)-4-methylthiazol-2-amine dihydrochloride

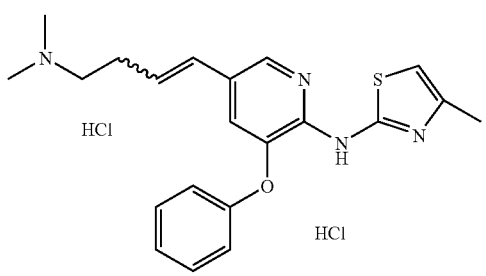

A mixture of mL [3-(dimethylamino)propyl]-triphenylphosphonium bromide (413 mg, 0.964 mmol) and THF (5 mL) was cooled to 0° C. Butyllithium (0.385 mL , 0.964 mmol) was added and stirred at 0° C. for 20 minutes. 6-(4-Methylthiazol-2-ylamino)-5-phenoxynicotinaldehyde (100 mg, 0.321 mmol) was added and stirred at ambient temperature for 20 minutes. The reaction was poured into aqueous $NH_4Cl$ and extracted with EtOAc. The organic layer was dried with sodium sulfate, filtered and concentrated. The residue was purified on silica gel (0 to 20% methanol in EtOAc) to afford both isomers of desired material as white solids after HCl salt formation. Cis-isomer: $^1$H NMR ($CDCl_3$) δ 12.82 (bs, 1H), 12.55 (bs, 1H), 8.06 (s, 1H), 7.42 (m, 2H), 7.21 (m, 3H), 7.04 (m, 1H), 6.47 (s, 1H), 6.39 (d, 1H), 5.67 (m, 1H), 3.05 (m, 2H), 2.84 (m, 2H), 2.74 (d, 6H), 2.46 (s, 3H). Mass spectrum (apci) m/z=381.2 (M+H-2HCl). Trans-isomer: $^1$H NMR ($CDCl_3$) δ 12.73 (bs, 1H), 12.50 (bs, 1H), 8.04 (d, 1H), 7.41 (m, 2H), 7.21 (m, 4H), 6.43 (m, 2H), 6.02 (m, 1H), 3.09 (m, 2H), 2.81 (m, 8H), 2.45 (s, 3H). Mass spectrum (apci) m/z=-381.2 (M+H-2HCl).

Example 126

5-(4-(dimethylamino)butyl)-N-(4-methylthiazol-2-yl)-3-phenoxypyridin-2-amine dihydrochloride

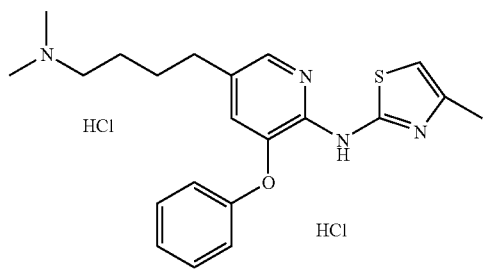

Prepared according to the method of Example 44, Step C from 5-(4-(dimethylamino)but-1-enyl)-N-(4-methylthiazol-2-yl)-3-phenoxypyridin-2-amine. $^1$H NMR ($CDCl_3$) δ 12.59 (bs, 1H), 12.25 (bs, 1H), 7.94 (s, 1H), 7.40 (m, 2H), 7.21 (t, 1H), 7.15 (m, 2H), 7.03 (s, 1H), 6.42 (s, 1H), 2.96 (m, 2H), 2-76 (d, 6H), 2.61 (t, 2H), 2.44 (s, 3H), 1.90 (m, 2H), 1.63 (m, 2H). Mass spectrum (apci) m/z=383.2 (M+H-2HCl).

Example 127

5-(2-chloropyridin-4-ylthio)-N-(4-methylthiazol-2-yl)-3-phenoxypyridin-2-amine dihydrochloride

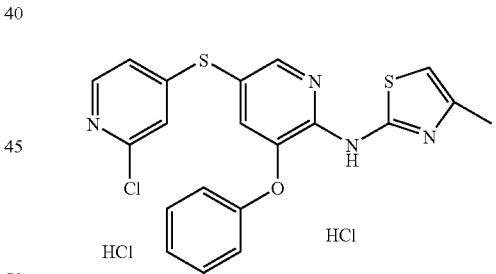

A mixture of methyl 3-(6-(4-methylthiazol-2-ylamino)-5-phenoxypyridin-3-ylthio)propanoate (72 mg, 0.18 mmol), 2-chloro-4-nitropyridine (85.3 mg, 0.54 mmol) and DMSO (2.0 mL) and purged with nitrogen for 5 minutes. Potassium 2-methylpropan-2-olate (60.4 mg, 0.54 mmol) was added and stirred for 30 minutes. The reaction was poured into aqueous $NH_4Cl$ and extracted with EtOAc (1×20 mL). The organic phase was washed with water, dried with sodium sulfate, filtered and concentrated. The residue was purified on silica gel (25% EtOAc in hexanes) to afford the title compound (37.1 mg, 41.4% yield) as a white solid after HCl salt formation. $^1$H NMR ($CDCl_3$) δ 12.89 (bs, 1H), 8.24 (m, 2H), 8.17 (d, 1H), 7.43 (t, 2H), 7.31 (d, 1H), 7.28-7.18 (m, 3H), 6.88 (s, 1H), 6.84 (m, 1H), 6.53 (s, 1H), 3.93 (s, 1H), 2.50 (s, 3H). Mass spectrum (apci) m/z=427.2 (M+H-2HCl).

The following compounds were prepared according to the method of Example 127.

| Example | Structure | Name | Data |
|---|---|---|---|
| 128 | 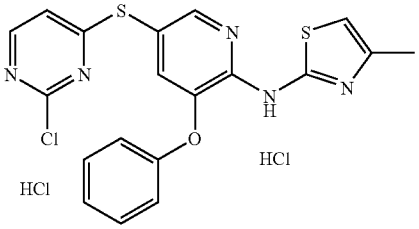 | N-(5-(2-chloropyrimidin-4-ylthio)-3-phenoxypyridin-2-yl)-4-methylthiazol-2-amine dihydrochloride | ¹H NMR (CDCl₃) δ 8.29 (d, 1 H), 8.24 (d, 1 H), 7.42 (m, 3 H), 7.26 (m, 3 H), 6.94 (d, 1 H), 6.52 (d, 1 H), 2.48 (d, 3 H). Mass spectrum (apci) m/z = 428.2 (M + H − 2HCl). |
| 129 | 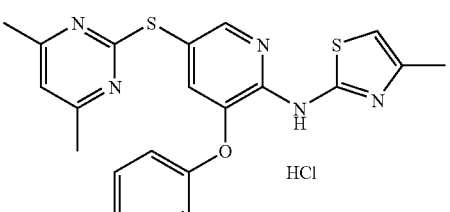 | 5-(4,6-dimethylpyrimidin-2-ylthio)-N-(4-methylthiazol-2-yl)-3-phenoxypyridin-2-amine dihydrochloride | ¹H NMR (CDCl₃) δ 12.63 (bs, 1 H), 8.25 (m, 1 H), 7.57 (m, 1 H), 7.35 (t, 2 H), 7.25 (m, 3 H), 7.18 (m, 1 H), 6.73 (s, 1 H), 6.46 (s, 1 H), 2.47 (s, 3 H), 2.34 (s, 6 H). Mass spectrum (apci) m/z = 422.2 (M + H − 2HCl). |
| 130 | 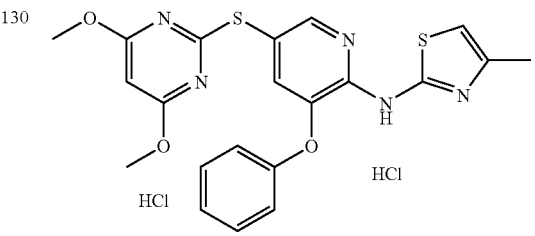 | N-(5-(4,6-dimethoxypyrimidin-2-ylthio)-3-phenoxypyridin-2-yl)-4-methylthiazol-2-amine dihydrochloride | ¹H NMR (d₆-DMSO) δ 8.30 (d, 1 H), 7.52 (d, 1 H), 7.42 (m, 2 H), 7.19 (t, 1 H), 7.11 (d, 1 H), 6.75 (s, 1 H), 5.97 (s, 1 H), 3.70 (s, 6 H), 2.28 (s, 3 H). Mass spectrum (esi) m/z = 454.2 (M + H − 2HCl). |
| 131 | 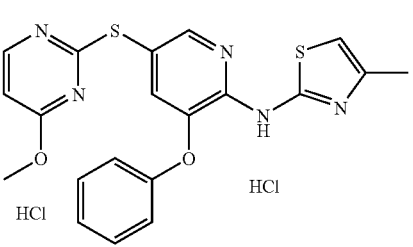 | 5-(4-methoxypyrimidin-2-ylthio)-N-(4-methylthiazol-2-yl)-3-phenoxypyridin-2-amine dihydrochloride | ¹H NMR (d₆-DMSO) δ 8.30 (m, 2 H), 7.50 (m, 1 H), 7.43 (m, 2 H), 7.19 (m, 1 H), 7.13 (d, 2 H), 6.75 (s, 1 H), 6.67 (dd, 1 H), 3.73 (s, 3 H), 2.28 (s, 3 H). Mass spectrum (esi) m/z = 424.2 (M + H − 2HCl). |
| 132 | 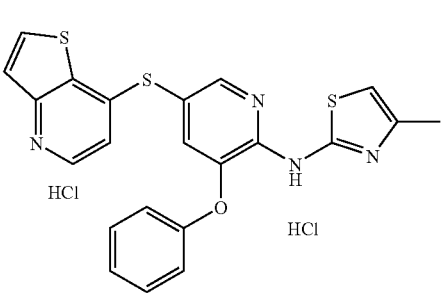 | N-(4-methylthiazol-2-yl)-3-phenoxy-5-(thieno[3,2-b]pyridin-7-ylthio)pyridin-2-amine dihydrochloride | ¹H NMR (d₆-DMSO) δ 8.58 (d, 1 H), 8.42 (d, 1 H), 8.34 (d, 1 H), 7.68 (d, 1 H), 7.47 (d, 1 H), 7.40 (m, 2 H), 7.19-7.07 (m, 4 H), 6.73 (s, 1 H), 2.27 (s, 3 H). Mass spectrum (apci) m/z = 449.2 (M + H − 2HCl). |

| Example | Structure | Name | Data |
|---|---|---|---|
| 133 | 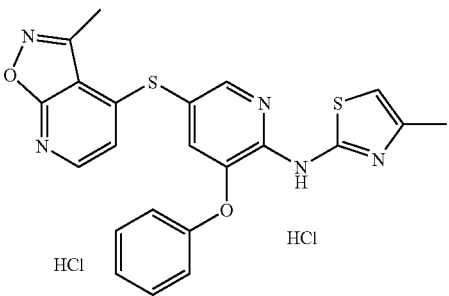 | 4-methyl-N-(5-(3-methylisoxazolo[5,4-b]pyridin-4-ylthio)-3-phenoxypyridin-2-yl)thiazol-2-amine dihydrochloride | $^1$H NMR (d$_6$-DMSO) δ 8.38 (m, 1 H), 8.33 (dd, 1 H), 7.42 (m, 3 H), 7.17 (m, 3 H), 6.74 (m, 2 H), 2.69 (s, 3 H), 2.28 (s, 3 H). Mass spectrum (apci) m/z = 448.2 (M + H − 2HCl). |
| 134 | 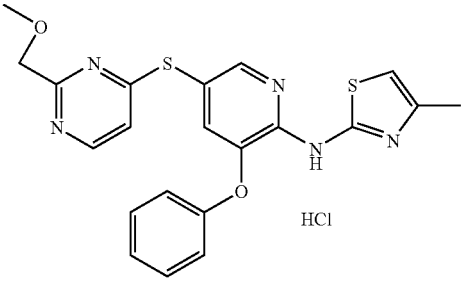 | N-(5-(2-(methoxymethyl)-pyrimidin-4-ylthio)-3-phenoxypyridin-2-yl)-4-methylthiazol-2-amine dihydrochloride | $^1$H NMR (d$_6$-DMSO) δ 8.48 (d, 1 H), 8.35 (dd, 1 H), 7.49 (dd, 1 H), 7.43 (m, 2 H), 7.18 (m, 3 H), 7.08 (d, 1 H), 6.80 (s, 1 H), 4.44 (s, 2 H), 3.30 (s, 3 H), 2.30 (s, 3 H). Mass spectrum (apci) m/z = 438.2 (M + H − 2HCl). |
| 135 | 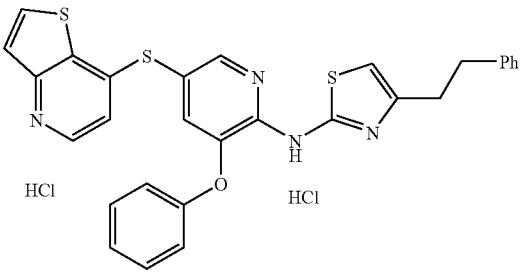 | 4-phenethyl-N-(3-phenoxy-5-(thieno[3,2-b]pyridin-7-ylthio)pyridin-2-yl)thiazol-2-amine dihydrochloride | $^1$H NMR (d$_6$-DMSO) δ 8.54 (d, 1 H), 8.40 (d, 1 H), 8.25 (d, 1 H), 7.63 (d, 1 H), 7.45 (d, 1 H), 7.39 (m, 2 H), 7.31-7.10 (m, 8 H), 7.01 (d, 1 H), 6.72 (s, 1 H), 3.00-2.85 (m, 4 H). Mass spectrum (apci) m/z = 539.3 (M + H − 2HCl). |
| 136 | 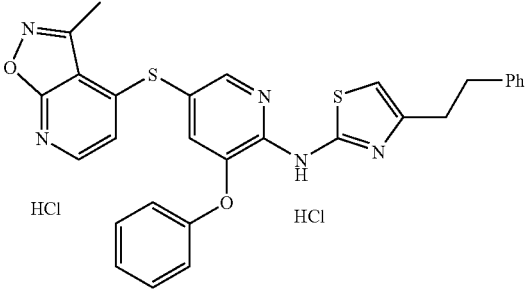 | N-(5-(3-methylisoxazolo[5,4-b]pyridin-4-ylthio)-3-phenoxypyridin-2-yl)-4-phenethylthiazol-2-amine dihydrochloride | $^1$H NMR (d$_6$-DMSO) δ 8.38 (d, 1 H), 8.33 (d, 1 H), 7.42 (m, 3 H), 7.31-7.15 (m, 8 H), 6.74 (m, 2 H), 3.00-2.86 (m, 4 H), 2.69 (s, 3 H). Mass spectrum (apci) m/z = 538.3 (M + H − 2HCl). |
| 137 | 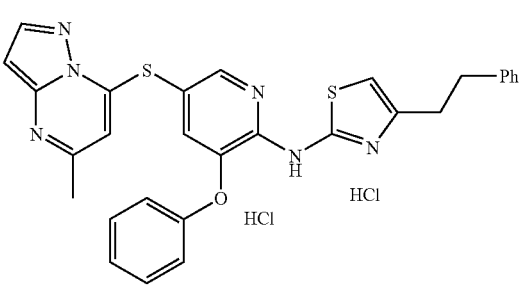 | N-(5-(5-methylpyrazolo[1,5-a]pyrimidin-7-ylthio)-3-phenoxypyridin-2-yl)-4-phenethylthiazol-2-amine dihydrochloride | $^1$H NMR (d$_6$-DMSO) δ 8.43 (d, 1 H), 8.20 (d, 1 H), 7.56 (d, 1 H), 7.42 (m, 2 h), 7.31-7.14 (m, 8 H), 6.75 (s, 1 H), 6.57 (d, 1 H), 6.31 (s, 1 H), 3.00-2.87 (m, 4 H), 2.42 (s, 3 H). Mass spectrum (apci) m/z = 537.3 (M + H − 2HCl). |

-continued

| Example | Structure | Name | Data |
|---|---|---|---|
| 138 | 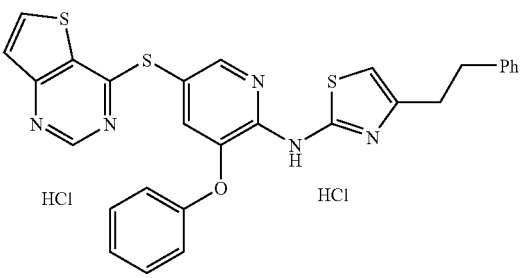 | 4-phenethyl-N-(3-phenoxy-5-(thieno[3,2-d]pyrimidin-4-ylthio)pyridin-2-yl)thiazol-2-amine dihydrochloride | $^1$H NMR (d$_6$-DMSO) δ 8.90 (s, 1 H), 8.43 (m, 2 H), 7.63 (d, 1 H), 7.60 (d, 1 H), 7.43 (m, 2 H), 7.32-7.14 (m, 8 H), 6.80 (s, 1 H), 3.01-2.90 (m, 4 H). Mass spectrum (apci) m/z = 540.3 (M + H − 2HCl). |
| 139 | 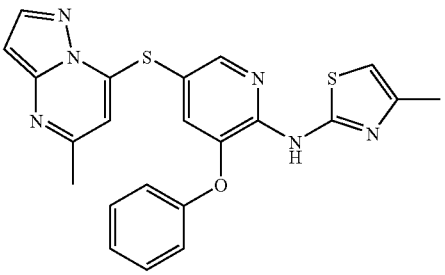 | 4-methyl-N-(5-(5-methylpyrazolo[1,5-a]pyrimidin-7-ylthio)-3-phenoxypyridin-2-yl)thiazol-2-amine | $^1$H NMR (d$_6$-DMSO) δ 11.28 (bs, 1 H), 8.42 (d, 1 H), 8.20 (d, 1 H), 7.53 (d, 1 H), 7.40 (m, 2 H), 7.22-7.10 (m, 3 H), 6.69 (s, 1 H), 6.57 (d, 1 H), 6.30 (s, 1 H), 2.42 (s, 3 H), 2.26 (s, 3 H). Mass spectrum (apci) m/z = 447.2 (M + H). |
| 140 | 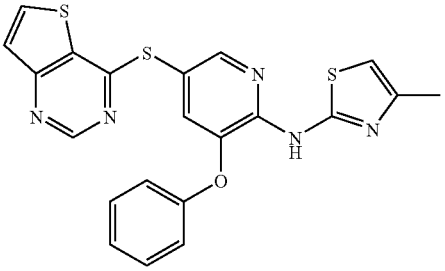 | 4-methyl-N-(3-phenoxy-5-(thieno[3,2-d]pyrimidin-4-ylthio)pyridin-2-yl)thiazol-2-amine | $^1$H NMR (d$_6$-DMSO) δ 11.18 (bs, 1 H), 8.89 (s, 1 H), 8.42 (d, 1 H), 8.39 (d, 1 H), 7.62 (d, 1 H), 7.55 (d, 1 H), 7.40 (m, 2 H), 7.18-7.10 (m, 3 H), 6.67 (s, 1 H), 2.26 (s, 3 H). Mass spectrum (apci) m/z = 450.2 (M + H). |
| 141 | 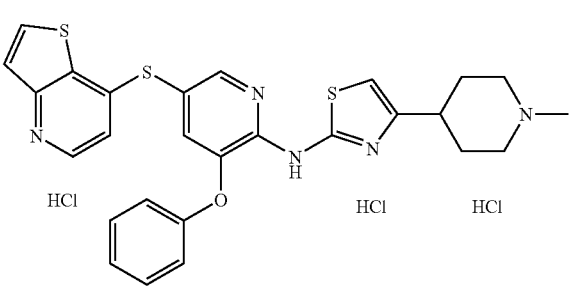 | 4-(1-methylpiperidin-4-yl)-N-(3-phenoxy-5-(thieno[3,2-b]pyridin-7-ylthio)pyridin-2-yl)thiazol-2-amine trihydrochloride | $^1$H NMR (d$_6$-DMSO) δ 10.63 (bs, 1 H), 8.62 (m, 1 H), 8.43 (m, 2 H), 7.74 (d, 1 H), 7.51 (t, 1 H), 7.41 (m, 2 H), 7.16 (m, 4 H), 6.85 (s, 1 H), 3.46 (m, 2 H), 3.05 (m, 2 H), 2.85 (m, 1 H), 2.73 (d, 3 H), 2.15 (m, 2 H), 1.94 (m, 2 H). Mass spectrum (apci) m/z = 532.3 (M + H − 3HCl. |
| 142 | 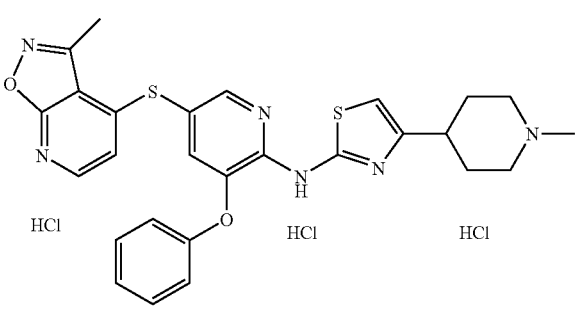 | N-(5-(3-methylisoxazolo[5,4-b]pyridin-4-ylthio)-3-phenoxypyridin-2-yl)-4-(1-methylpiperidin-4-yl)thiazol-2-amine trihydrochloride | $^1$H NMR (d$_6$-DMSO) δ 11.35 (bs, 1 H), 10.34 (bs, 1 H), 8.38 (d, 1 H), 8.33 (d, 1 H), 7.42 (m, 3 H), 7.18 (m, 3 H), 6.84 (s, 1 H), 6.73 (d, 1 H), 3.47 (m, 2 H), 3.05 (m, 2 H), 2.85 (m, 1 H), 2.74 (d, 3 H), 2.69 (s, 3 H), 2.16 (m, 2 H), 1.90 (m, 2 H). Mass spectrum (apci) m/z = 531.3 (M + H − 3HCl). |

-continued

| Example | Structure | Name | Data |
|---|---|---|---|
| 143 | 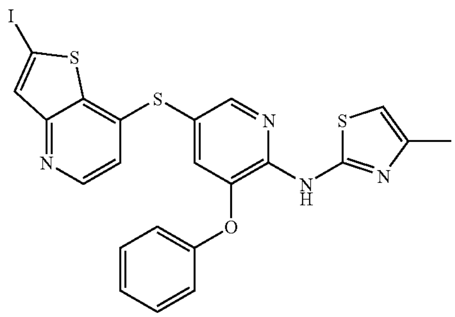 | N-(5-(2-iodothieno[3,2-b]pyridin-7-ylthio)-3-phenoxypyridin-2-yl)-4-methylthiazol-2-amine | $^1$H NMR (CDCl$_3$) δ 8.86 (bs, 1 H), 8.37 (m, 1 H), 8.29 (m, 1 H), 7.75 (s, 1 H), 7.39 (m, 3 H), 7.20 (m, 1 H), 7.16 (m, 1 H), 7.05 (m, 2 H), 6.70 (d, 1 H), 6.50 (m, 1 H), 2.36 (s, 3 H). Mass spectrum (apci) m/z = 575.1 (M + H). |
| 144 | 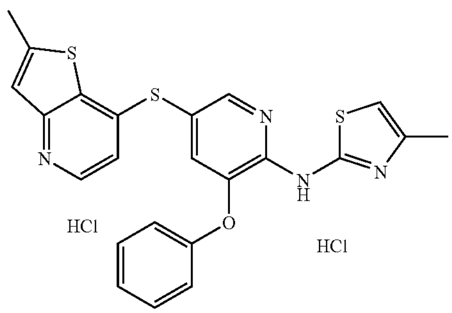 | 4-methyl-N-(5-(2-methylthieno[3,2-b]pyridin-7-ylthio)-3-phenoxypyridin-2-yl)thiazol-2-amine dihydrochloride | $^1$H NMR (d$_6$-DMSO) δ 8.87 (dd, 1 H), 8.45 (dd, 1 H), 7.54 (m, 2 H), 7.41 (m, 2 H), 7.17 (m, 4 H), 6.78 (s, 1 H), 2.74 (s, 3 H), 2.29 (s, 3 H). Mass spectrum (apci) m/z = 463.2 (M + H − 2HCl). |
| 145 | 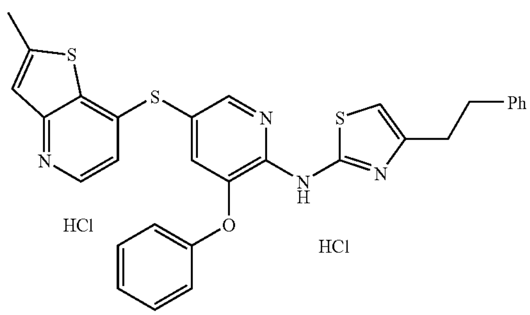 | N-(5-(2-methylthieno[3,2-b]pyridin-7-ylthio)-3-phenoxypyridin-2-yl)-4-phenethylthiazol-2-amine dihydrochloride | $^1$H NMR (d$_6$-DMSO) δ 8.56 (d, 1 H), 8.43 (d, 1 H), 7.52 (m, 2 H), 7.41 (m, 2 H), 7.31-7.11 (m, 9 H), 6.76 (s, 1 H), 3.00-2.87 (m, 4 H), 2.73 (s, 3 H). Mass spectrum (apci) m/z = 553.3 (M + H − 2HCl). |
| 146 | 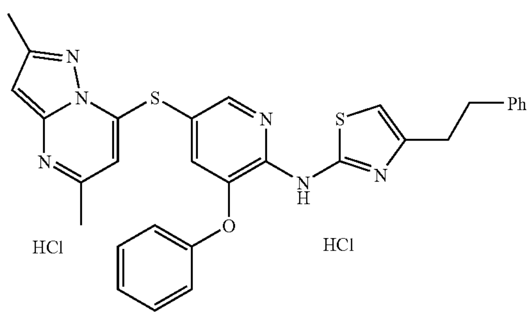 | N-(5-(2,5-dimethylpyrazolo[1,5-a]pyrimidin-7-ylthio)-3-phenoxypyridin-2-yl)-4-phenethylthiazol-2-amine dihydrochloride | $^1$H NMR (d$_6$-DMSO) δ 8.42 (dd, 1 H), 7.54 (dd, 1 H), 7.42 (m, 2 H), 7.31-7.15 (m, 8 H), 6.76 (s, 1 H), 6.37 (s, 1 H), 6.21 (s, 1 H), 3.00-2.87 (m, 4 H), 2.42 (s, 3 H), 2.38 (s, 3 H). Mass spectrum (apci) m/z = 551.3 (M + H − 2HCl). |
| 147 | 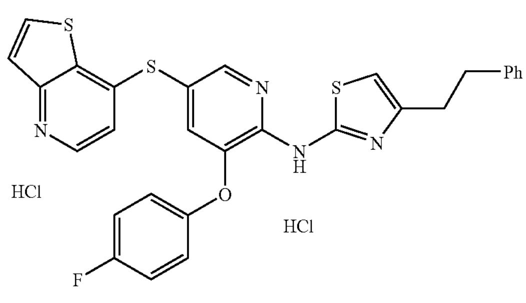 | N-(3-(4-fluorophenoxy)-5-(thieno[3,2-b]pyridin-7-ylthio)pyridin-2-yl)-4-phenethylthiazol-2-amine dihydrochloride | $^1$H NMR (d$_6$-DMSO) δ 8.62 (d, 1 H), 8.42 (m, 2 H), 7.73 (d, 1 H), 7.51 (d, 1 H), 7.31-7.13 (m, 10 H), 6.77 (s, 1 H), 3.01-2.88 (m, 4 H). Mass spectrum (apci) m/z = 557.3 (M + H − 2HCl). |

| Example | Structure | Name | Data |
|---|---|---|---|
| 148 | 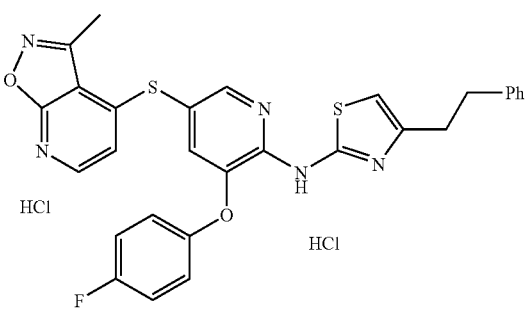 | N-(3-(4-fluorophenoxy)-5-(3-methylisoxazolo[5,4-b]pyridin-4-ylthio)pyridin-2-yl)-4-phenethylthiazol-2-amine dihydrochloride | $^1$H NMR (d$_6$-DMSO) δ 8.38 (d, 1 H), 8.32 (d, 1 H), 7.45 (d, 1 H), 7.31-7.16 (m, 9 H), 6.80 (s, 1 H), 6.74 (d, 1 H), 3.02-2.90 (m, 4 H), 2.69 (s, 3 H). Mass spectrum (apci) m/z = 556.3 (M + H − 2HCl). |
| 149 | 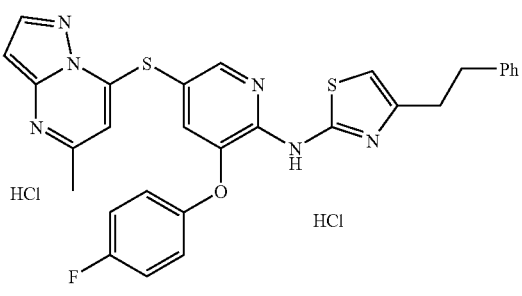 | N-(3-(4-fluorophenoxy)-5-(5-methylpyrazolo[1,5-a]pyrimidin-7-ylthio)pyridin-2-yl)-4-phenethylthiazol-2-amine dihydrochloride | $^1$H NMR (d$_6$-DMSO) δ 8.42 (m, 1 H), 8.20 (d, 1 H), 7.54 (d, 1 H), 7.31-7.16 (m, 9 H), 6.75 (s, 1 H), 6.57 (d, 1 H), 6.30 (s, 1 H), 3.01-2.88 (m, 4 H), 2.42 (s, 3 H). Mass spectrum (apci) m/z = 555.2 (M + H − 2HCl). |
| 150 | 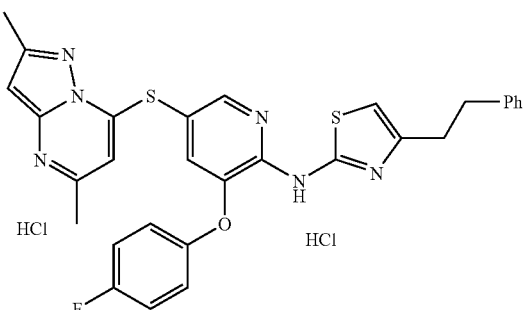 | N-(5-(2,5-dimethylpyrazolo[1,5-a]pyrimidin-7-ylthio)-3-(4-fluorophenoxy)-pyridin-2-yl)-4-phenethylthiazol-2-amine dihydrochloride | $^1$H NMR (d$_6$-DMSO) δ 8.40 (m, 1 H), 7.52 (m, 1 H), 7.31-7.16 (m, 9 H), 6.75 (s, 1 H), 6.37 (s, 1 H), 6.20 (m, 1 H), 3.01-2.88 (m, 4 H), 2.42 (s, 3 H), 2.38 (s, 3 H). Mass spectrum (apci) m/z = 569.2 (M + H − 2HCl). |
| 151 | 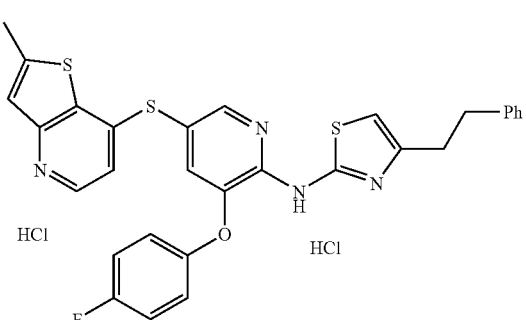 | N-(3-(4-fluorophenoxy)-5-(2-methylthieno[3,2-b]pyridin-7-ylthio)pyridin-2-yl)-4-phenethylthiazol-2-amine dihydrochloride | $^1$H NMR (d$_6$-DMSO) δ 8.55 (m, 1 H), 8.41 (m, 1 H), 7.50 (m, 2 H), 7.31-7.16 (m, 9 H), 7.10 (d, 1 H), 6.75 (s, 1 H), 3.01-2.88 (m, 4 H), 2.73 (s, 3 H). Mass spectrum (apci) m/z = 571.3 (M + H − 2HCl). |
| 152 | 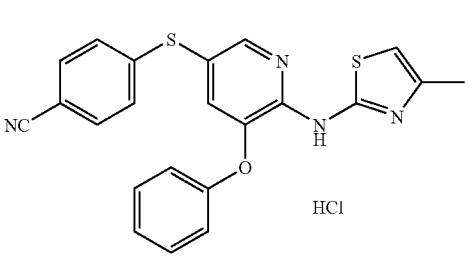 | 4-(6-(4-methylthiazol-2-ylamino)-5-phenoxypyridin-3-ylthio)benzonitrile hydrochloride | $^1$H NMR (d$_6$-DMSO) δ 8.30 (m, 1 H), 7.71 (d, 2 h), 7.41 (t, 2 H), 7.33 (m, 1 H), 7.26 (d, 2 H), 7.18 (t, 1 H), 7.12 (d, 2 H), 6.72 (s, 1 H), 2.27 (s, 3 H). Mass spectrum (apci) m/z = 417.0 (M + H − HCl). |

| Example | Structure | Name | Data |
|---|---|---|---|
| 153 | 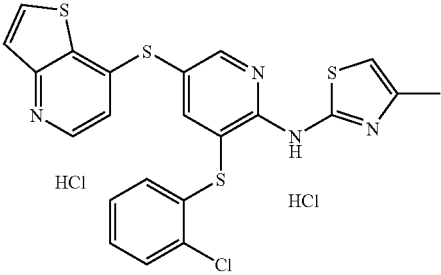 | N-(3-(2-chlorophenylthio)-5-(thieno[3,2-b]pyridin-7-ylthio)pyridin-2-yl)-4-methylthiazol-2-amine dihydrochloride | $^1$H NMR (d$_6$-DMSO) δ 8.66 (dd, 1 H), 8.54 (d, 1 H), 8.49 (d. 1 H), 7.78 (dd, 1 h), 7.58 (m, 1 H), 7.43-7.31 (m, 4 H), 7.12 (d, 1 H), 6.56 (s, 1 H), 2.22 (s, 3 H). Mass spectrum (esi) m/z = 498.8 (M + H − 2HCl). |
| 154 | 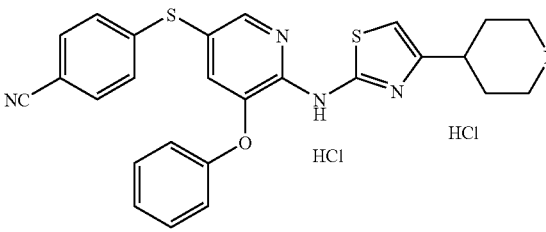 | 4-(5-phenoxy-6-(4-(piperidin-4-yl)thiazol-2-ylamino)pyridin-3-ylthio)benzonitrile dihydrochloride | $^1$H NMR (d$_6$-DMSO) δ 11.30 (bs, 1 H), 9.01 (m, 1 H), 8.85 (m, 1 H), 8.30 (m, 1 H), 7.72 (m, 2 H), 7.45-7.10 (m., 8 H), 6.82 (s, 1 H), 3.57 (m, 1 H), 3.31 (m, 2 H), 2.96 (m, 3 H), 2.12 (m, 2 H), 1.82 (m, 2 H). Mass spectrum (apci) m/z = 485.6 (M + H − 2HCl). |
| 155 | 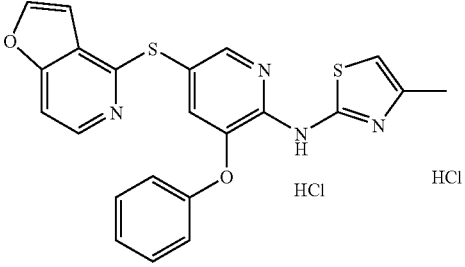 | N-(5-(furo[3,2-c]pyridin-4-ylthio)-3-phenoxypyridin-2-yl)-4-methylthiazol-2-amine dihydrochloride | $^1$H NMR (d$_6$-DMSO) δ 8.28 (m, 1 H), 8.19 (m, 1 H), 8.09 (m, 1 H), 7.48 (m, 1 H), 7.41 (m, 1 H), 7.37 (m, 2 H), 7.11 (m, 3 H), 6.89 (m, 1 H), 6.74 (s, 1 H), 2.24 (s, 3 H). Mass spectrum (apci) m/z = 433.2 (M + H − 2HCl). |
| 156 | 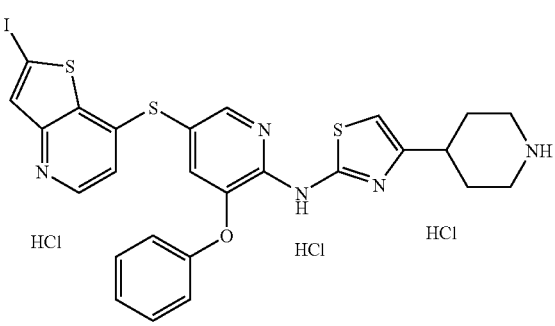 | N-(5-(2-iodothieno[3,2-b]pyridin-7-ylthio)-3-phenoxypyridin-2-yl)-4-(piperidin-4-yl)thiazol-2-amine trihydrochloride | $^1$H NMR (d$_6$-DMSO) δ 11.25 (bs, 1 H), 8.80 (m, 1 H), 8.58 (m, 1 H), 8.44 (m, 1 H), 8.38 (m, 1 H), 7.40 (m, 3 H), 7.12 (m, 4 H), 6.95 (m, 1 H), 6.81 (s, 1 H0, 3.32 (m, 2 H), 2.96 (m, 3 H), 2.12 (m, 2 H), 1.78 (m, 2 H). Mass spectrum (apci) m/z 644.3 (M + H − 3HCl). |
| 157 | 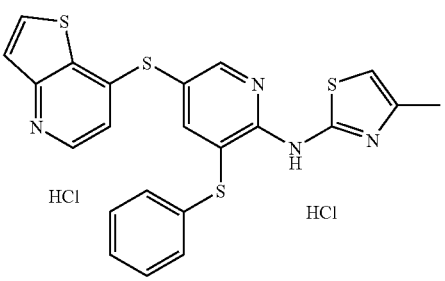 | 4-methyl-N-(3-(phenylthio)-5-(thieno[3,2-b]pyridin-7-ylthio)pyridin-2-yl)thiazol-2-amine dihydrochloride | $^1$H NMR (d$_6$-DMSO) δ 8.56 (d, 1 H), 8.43 (s, 1 H), 8.32 (d, 1 H), 7.67 (d, 1 H), 7.47 (m, 2 H), 7.39 (m, 3 H), 7.26 (bs, 1 H), 6.96 (d, 1 H), 6.52 (s, 1 H), 2.22 (s, 3 H). Mass spectrum (apci) m/z = 464.7 (M + H − 2HCl). |

| Example | Structure | Name | Data |
|---|---|---|---|
| 158 | 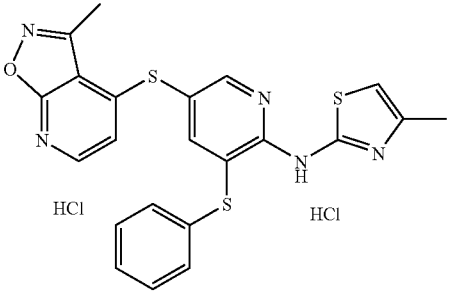 | 4-methyl-N-(5-(3-methylisoxazolo[5,4-b]pyridin-4-ylthio)-3-(phenylthio)pyridin-2-yl)thiazol-2-amine dihydrochloride | $^1$H NMR (d$_6$-DMSO) δ 8.40 (bs, 1 H), 8.32 (d, 1 H), 7.51 (m, 2 H), 7.40 (m, 3 H), 7.25 (bs, 1 H), 6.61 (d, 1 H), 6.52 (s, 1 H), 2.67 (s, 3 H), 2.22 (s, 3 H). Mass spectrum (apci) m/z = 463.6 (M + H − 2HCl). |
| 159 | 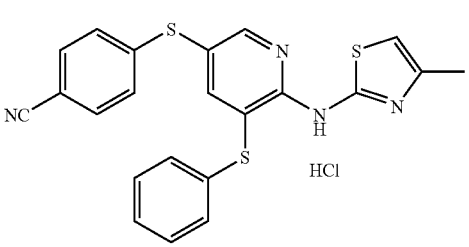 | 4-(6-(4-methylthiazol-2-ylamino)-5-(phenylthio)pyridin-3-ylthio)benzonitrile hydrochloride | $^1$H NMR (d$_6$-DMSO) δ 8.36 (s, 1 H), 7.71 (m, 2 H), 7.48-7.35 (m, 5 H), 7.19 (m, 2 H), 6.55 (s, 1 H), 2.22 (s, 3 H). Mass spectrum (apci) m/z = 431.9 (M + H − HCl). |
| 160 | 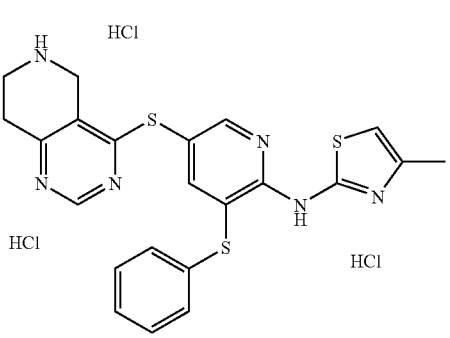 | 4-methyl-N-(3-(phenylthio)-5-(5,6,7,8-tetrahydropyrido[4,3-d]pyrimidin-4-ylthio)pyridin-2-yl)thiazol-2-amine trihydrochloride | $^1$H NMR (d$_6$-DMSO) δ 9.67 (bs, 2 H), 8.71 (s, 1 H), 8.29 (s, 1 H), 7.50-7.35 (m, 6 H), 6.53 (s, 1 H), 4.18 (m, 2 H), 3.47 (m, 2 H), 3.04 (t, 2 H), 2.21 (s, 3 H). Mass spectrum (apci) m/z = 464.7 (M + H − 3HCl). |
| 161 | 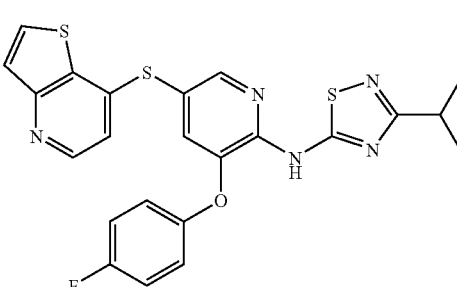 | tert-butyl 4-(5-(3-(4-fluorophenoxy)-5-(thieno[3,2-b]pyridin-7-ylthio)pyridin-2-ylamino)-1,2,4-thiadiazol-3-yl)piperidine-1-carboxylate | $^1$H NMR (CDCl$_3$) δ 9.16 (s, 1 H), 8.49 (d, 1 H), 8.37 (d, 1 H), 7.74 (d, 1 H), 7.56 (d, 1 H), 7.17 (d, 1 H), 7.08 (m, 4 H), 6.76 (d, 1 H), 4.16 (m, 2 H), 3.00 (m, 1 H), 2.91 (m, 2 H), 2.05 (m, 2 H), 1.82 (m, 2 H), 1.47 (s, 9 H). Mass spectrum (apci) m/z = 537.2 (M + H − Boc). |

Example 162

N-(4-cyclopropylthiazol-2-yl)-3-phenoxy-5-(pyridin-4-ylthio)pyridin-2-amine dihydrochloride

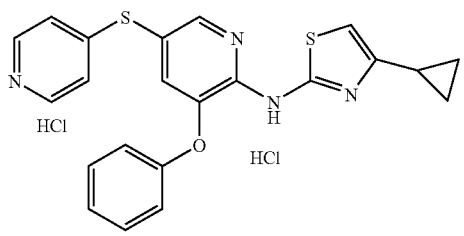

Step A: Preparation of 4-(2-(pyridin-4-yl)disulfanyl)pyridine: A mixture of 5-bromo-3-phenoxypyridin-2-amine (2.1 g, 7.9 mmol) THF (80 mL) was purged with nitrogen and cooled to −78° C. Methyllithium (5.9 mL, 9.5 mmol) was added and stirred for 5 minutes. Butyllithium (3.8 mL, 9.5 mmol) was added and stirred for 10 minutes at −78° C. 4-(2-(Pyridin-4-yl)disulfanyl)pyridine (4.4 g, 20 mmol) was added and warmed to ambient temperature. The reaction was poured into saturated aqueous NH₄Cl and extracted with EtOAc. The organic layer was dried, filtered and concentrated. The residue was dissolved in methanol and NaBH₄ (excess) added. The reaction was poured into saturated aqueous NH₄Cl and extracted with EtOAc (2×75 mL). The organic layer was dried with sodium sulfate, filtered and concentrated. The residue was purified on silica gel (50% EtOAc in hexanes to 5% methanol in EtOAc) to afford the title compound (4.4 g, 20 mmol).

Steps B-D: Preparation of N-(4-cyclopropylthiazol-2-yl)-3-phenoxy-5-(pyridin-4-ylthio)pyridin-2-amine dihydrochloride: Prepared according to the method of Example 7, Steps C-E. ¹H NMR (d-DMSO) δ 8.52 (m, 2H), 8.34 (d, 1H), 7.52 (m, 2H), 7.42 (m, 3H), 7.17 (m, 3H), 6.72 (s, 1H), 1.97 (m, 1H), 0.84 (m, 2H), 0.78 (m, 2H). Mass spectrum (apci) m/z=419.3 (M+H-2HCl).

The following compounds were prepared according to the method of Example 7, Step E.

| Example | Structure | Name | Data |
|---|---|---|---|
| 163 | 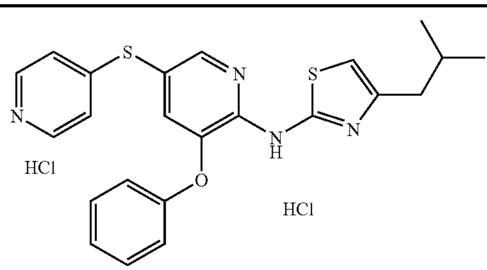 | 4-isobutyl-N-(3-phenoxy-5-(pyridin-4-ylthio)pyridin-2-yl)thiazol-2-amine dihydrochloride | ¹H NMR (d₆-DMSO) δ 8.57 (m, 2 H), 8.38 (dd, 1 H), 7.63 (m, 2 H), 7.47 (dd, 1 H), 7.42 (m, 2 H), 7.17 (m, 3 H), 6.74 (s, 1 H), 2.47 (d, 2 H), 2.00 (m, 1 H), 0.89 (d, 6 H). Mass spectrum (apci) m/z = 435.3 M + H − 2HCl). |
| 164 | 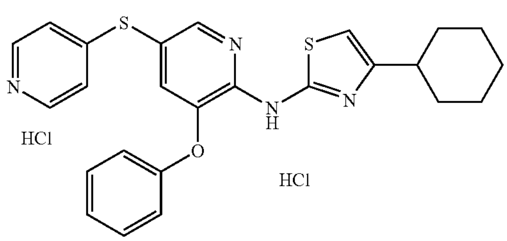 | 4-cyclohexyl-N-(3-phenoxy-5-(pyridin-4-ylthio)pyridin-2-yl)thiazol-2-amine dihydrochloride | ¹H NMR (d₆-DMSO) δ 8.57 (m, 2 H), 8.38 (d, 1 H), 7.63 (m, 2 H), 7.48 (d, 1 H), 7.42 (m, 2 H), 7.17 (m, 3 H), 6.72 (s, 1 H), 2.59 (m, 1 H), 1.97 (m, 2 H), 1.80-1.65 (m, 3 H), 1.46-1.14 (m, 5 H). Mass spectrum (apci) m/z = 461.3 (M + H − 2HCl). |
| 165 | 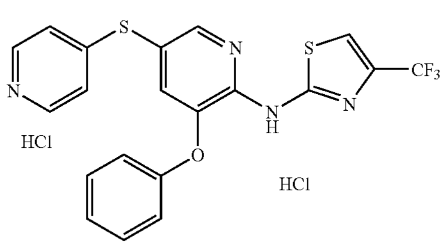 | N-(3-phenoxy-5-(pyridin-4-ylthio)pyridin-2-yl)-4-(trifluoromethyl)thiazol-2-amine dihydrochloride | ¹H NMR (d₆-DMSO) δ 12.08 (s, 1 H), 8.57 (m, 2 H), 8.44 (dd, 1 H), 7.92 (s, 1 H), 7.62 (m, 2 H), 7.56 (dd, 1 H), 7.43 (m, 2 H), 7.19 (m, 3 H). Mass spectrum (apci) m/z = 447.3 (M + H − 2HCl). |
| 166 | 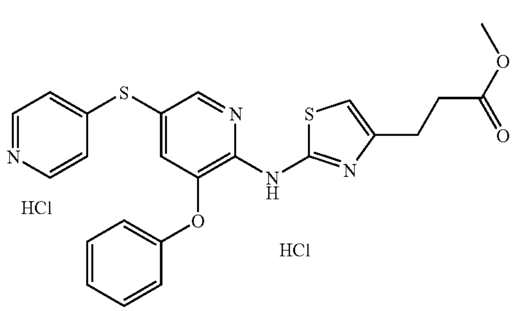 | methyl 3-(2-(3-phenoxy-5-(pyridin-4-ylthio)pyridin-2-ylamino)thiazol-4-yl)propanoate dihydrochloride | ¹H NMR (d₆-DMSO) δ 8.56 (m, 2 H), 8.37 (d, 1 H), 7.62 (m, 2 H), 7.46 (d, 1 H), 7.42 (m, 2 H), 7.17 (m, 3 H), 6.77 (s, 1 H), 3.59 (s, 3 H), 2.87 (t, 2 H), 2.70 (t, 2 H). Mass spectrum (apci) m/z = 465.2 (M + H − 2HCl). |

| Example | Name | Data |
|---|---|---|
| 167 | N-(3-phenoxy-5-(pyridin-4-ylthio)pyridin-2-yl)-4-(pyridin-2-yl)thiazol-2-amine trihydrochloride | $^1$H NMR (d$_6$-DMSO) δ 11.70 (bs, 1 H), 8.70 (m, 1 H), 8.59 (m, 2 H), 8.44 (d, 1 H), 8.25 (m, 3 H), 7.68 (m, 2 H), 7.62 (m, 1 H), 7.53 (d, 1 H), 7.44 (m, 2 H), 7.22 (m, 3 H). Mass spectrum (apci) m/z = 456.3 (M + H − 3HCl). |
| 168 | N-(3-phenoxy-5-(pyridin-4-ylthio)pyridin-2-yl)-4-phenylthiazol-2-amine dihydrochloride | $^1$H NMR (d$_6$-DMSO) δ 11.55 (bs, 1 H), 8.57 (d, 2 H), 8.41 (dd, 1 H), 7.95 (d, 2 H), 7.65 (d, 2 H), 7.62 (s, 1 H), 7.48 (d, 1 H), 7.43 (m, 4 H), 7.32 (t, 1 H), 7.21 (m, 3 H). Mass spectrum (apci) m/z = 455.3 (M + H − 2HCl). |
| 169 | N-(3-phenoxy-5-(pyridin-4-ylthio)pyridin-2-yl)-4-(thiophen-3-yl)thiazol-2-amine dihydrochloride | $^1$H NMR (d$_6$-DMSO) δ 11.55 (bs, 1 H), 8.58 (d, 2 H), 8.40 (d, 1 H), 7.81 (m, 1 H), 7.67 (d, 2 H), 7.59 (m, 2 H), 7.50 (d, 1 H), 7.43 (m, 3 H), 7.20 (m, 3 H). Mass spectrum (apci) m/z = 461.2 (M + H − 2HCl). |
| 170 | 4-phenethyl-N-(3-phenoxy-5-(pyridin-4-ylthio)pyridin-2-yl)thiazol-2-amine dihydrochloride | $^1$H NMR (d$_6$-DMSO) δ 8.58 (m, 2 H), 8.38 (dd, 1 H), 7.65 (m, 2 H), 7.48 (dd, 1 H), 7.42 (m, 2 H), 7.31-7.14 (m, 8 H), 6.74 (s, 1 H), 2.96 (m, 2 H), 2.90 (m, 2 H). Mass spectrum (apci) m/z = 483.3 (M + H − 2HCl). |
| 171 | 4-ethyl-N-(3-phenoxy-5-(pyridin-4-ylthio)pyridin-2-yl)thiazol-2-amine dihydrochloride | $^1$H NMR (d$_6$-DMSO) δ 8.58 (m, 2 H), 8.38 (d, 1 H), 7.65 (m, 2 H), 7.48 (d, 1 H), 7.42 (m, 2 H), 7.17 (m, 3 H), 6.74 (s, 1 H), 2.63 (q, 2 H), 1.21 (t, 3 H). Mass spectrum (apci) m/z = 407.3 (M + H − 2HCl). |
| 172 | N-(3-phenoxy-5-(pyridin-4-ylthio)pyridin-2-yl)thiazol-2-amine dihydrochloride | $^1$H NMR (d$_6$-DMSO) δ 8.54 (m, 2 H), 8.38 (m, 1 H), 7.55 (m, 2 H), 7.49 (dd, 1 H), 7.43 (m, 3 H), 7.18 (m, 4 H). Mass spectrum (apci) m/z = 379.2 (M + H − 2HCl). |

| Example | Structure | Name | Data |
|---------|-----------|------|------|
| 173 | 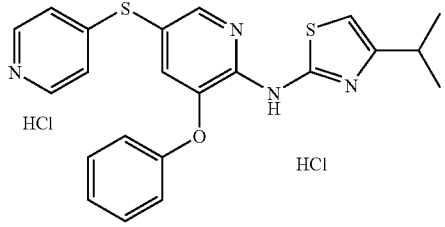 | 4-isopropyl-N-(3-phenoxy-5-(pyridin-4-ylthio)pyridin-2-yl)thiazol-2-amine dihydrochloride | $^1$H NMR (d$_6$-DMSO) δ 8.58 (m, 2 H), 8.38 (m, 1 H), 7.63 (m, 2 H), 7.47 (m, 1 H), 7.42 (m, 2 H), 7.18 (m, 3 H), 6.72 (s, 1 H), 2.92 (m, 1 H), 1.24 (d, 6 H). Mass spectrum (apci) m/z = 421.3 (M + H − 2HCl). |

Example 174

N-(5-bromo-3-phenoxypyridin-2-yl)-4-(piperidin-4-yl)thiazol-2-amine dihydrochloride

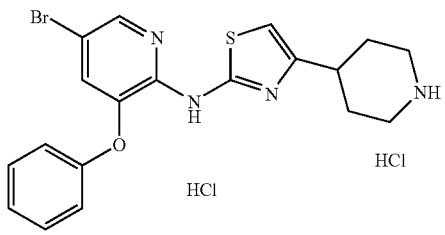

Step A: Following the procedure in Example 7, step E using 1-(5-bromo-3-phenoxypyridin-2-yl)thiourea and tert-butyl 4-(2-bromoacetyl)piperidine-1-carboxylate provided tert-butyl 4-(2-(5-bromo-3-phenoxypyridin-2-ylamino)thiazol-4-yl)piperidine-1-carboxylate.

Step B: tert-Butyl 4-(2-(5-bromo-3-phenoxypyridin-2-ylamino)thiazol-4-yl)piperidine-1-carboxylate was dissolved in 1:1 CH$_2$Cl$_2$:methanol and 4N HCl in dioxane was added and stirred at room temperature for 1 hour. The solvents were removed to afford the title compound. $^1$H NMR (d$_6$-DMSO) δ 10.98 (bs, 1H), 8.90 (bs, 1H), 8.70 (bs, 1H), 8.23 (d, 1H), 7.45 (m, 2H), 7.40 (d, 1H), 7.22 (m, 1H), 7.12 (m, 2H), 6.76 (s, 1H), 3.31 (m, 2H), 2.98 (m, 2H), 2.89 (m, 1H), 2.10 (m, 2H), 1.79 (m, 2H). Mass spectrum (apci) m/z=431.2, 433.2 (M+H-2HCl).

Example 175

N-(5-bromo-3-phenoxypyridin-2-yl)-4-(1-methylpiperidin-4-yl)thiazol-2-amine dihydrochloride

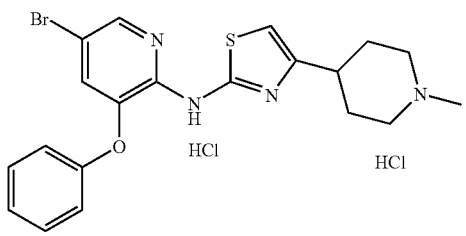

To a mixture of 5-bromo-3-phenoxy-N-(4-(piperidin-4-yl)thiazol-2-yl)pyridin-2-amine dihydrochloride (80 mg, 0.16 mmol), paraformaldehyde (7.15 mg, 0.24 mmol), and ClCH$_2$CH$_2$Cl (2 mL) was added NaBH(OAc)$_3$ (134 mg, 0.64 mmol) and the reaction was stirred at ambient temperature for 2 days. Poured into saturated aqueous NaHCO$_3$ and extracted with EtOAc. The organic layer was dried with sodium sulfate, filtered and concentrated. The residue was purified on silica gel (10% methanol in EtOAc with 0.2% NH$_3$) to afford the title compound (51.2 mg, 62.3% yield) as a white solid after HCl salt formation. $^1$H NMR (d$_6$-DMSO) δ 11.00 (bs, 1H), 10.22 (bs, 1H), 8.23 (s, 1H), 7.48-7.38 (m, 3H), 7.22 (t, 1H), 7.12 (m, 2H), 6.77 (s, 1H), 3.46 (m, 2H), 3.05 (m, 2H), 2.82 (m, 1H), 2.74 (d, 3H), 2.14 (m, 2H), 1.88 (m, 2H). Mass spectrum (apci) m/z=445.3 (4+H-2HCl).

Example 176

2-(4-(2-(5-bromo-3-phenoxypyridin-2-ylamino)thiazol-4-yl)piperidin-1-yl)ethanol dihydrochloride

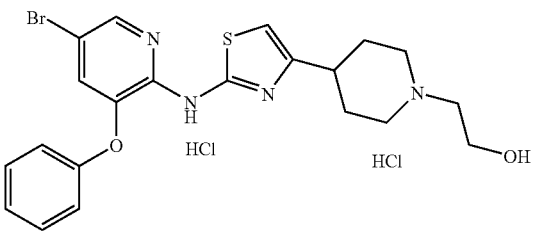

Prepared according to the method of Example 175. $^1$H NMR (d$_6$-DMSO) δ 11.00 (bs, 1H), 9.94 (bs, 1H), 8.23 (d, 1H), 7.48-7.38 (m, 3H), 7.23 (m, 1H), 7.12 (m, 2H), 6.76 (s, 1H), 3.79 (m, 2H), 3.74 (m, 1H), 3.58 (m, 2H), 3.23-3.02 (m, 4H), 2.85 (m, 1H), 2.16 (m, 2H), 1.93 (m, 2H). Mass spectrum (apci) m/z=475.3 (+H-2HCl).

Example 177

1-(4-(2-(5-bromo-3-phenoxypyridin-2-ylamino)thiazol-4-yl)piperidin-1-yl)ethanone hydrochloride

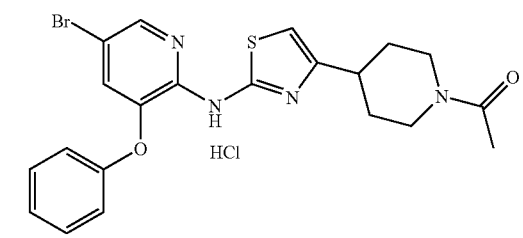

To mL 5-bromo-3-phenoxy-N-(4-(piperidin-4-yl)thiazol-2-yl)pyridin-2-amine dihydrochloride (80 mg, 0.159 mmol), triethylamine (0.088 mL, 0.64 mmol) and THF (2 mL) was added acetic anhydride (0.015 mL, 0.16 mmol) and stirred at ambient temperature for 30 minutes. Poured into saturated aqueous NaHCO₃ and extract with EtOAc (2×20 mL). The organic layer was dried with sodium sulfate, filtered and concentrated. The residue was purified on silica gel (5% methanol in EtOAc) to afford the title compound (47.6 mg, 58.8% yield) as a white solid after HCl salt formation. ¹H NMR (d₆-DMSO) δ 11.00 (bs, 1H), 8.23 (d, 1H), 7.44 (m, 2H), 7.40 (d, 1H), 7.21 (t, 1H), 7.11 (d, 2H), 6.70 (s, 1H), 4.41 (d, 1H), 3.12 (m, 1H), 2.83 (tt, 1H), 2.62 (td, 1H), 2.50 (m, 1H), 2.00 (s, 3H), 1.93 (m, 2H), 1.55 (qd, 1H), 1.42 (qd, 1H). Mass spectrum (apci) m/z=475.2 (M+H—HCl).

Example 178

N-(5-Bromo-3-phenoxypyridin-2-yl)-4-phenethylthiazol-2-amine

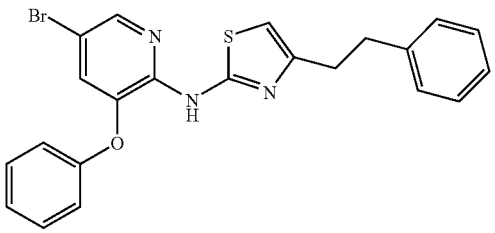

Prepared according to the method of Example 7 Step E from 1-(5-bromo-3-phenoxypyridin-2-yl)thiourea and 1-bromo-4-phenylbutan-2-one. ¹H NMR (d₆-DMSO) δ 8.26 (m, 1H), 7.45 (m, 3H), 7.31-7.11 (m, 8H), 6.74 (s, 1H), 2.92 (m, 4H). Mass spectrum (apci) m/z 452.3 (M+H).

Example 179

N-(5-Bromo-3-(4-fluorophenoxy)pyridin-2-yl)-4-phenethylthiazol-2-amine

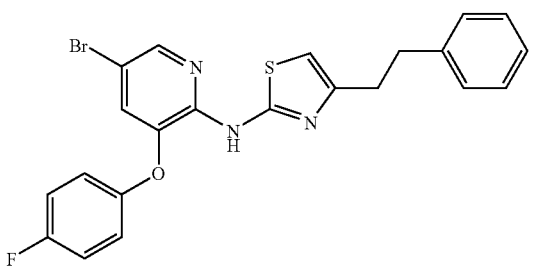

Step A: 5-bromo-3-(4-fluorophenoxy)picolinonitrile: To a solution of 4-fluorophenol (0.49 g, 4.4 mmol) in DMF (10 mL) cooled to 0° C. was added 60% sodium hydride (0.19 g, 4.8 mmol) was added and the reaction was warmed to ambient temperature. 5-Bromo-3-nitropicolinonitrile (1.0 g, 4.4 mmol, solution in 5 mL DMF) and stirred for 3 hours. Poured into water, filtered, washed with water, and dried to yield the title compound (1.0 g, 78%).

Step B: 5-bromo-3-(4-fluorophenoxy)-picolinamide To 5-bromo-3-(4-fluorophenoxy)picolinonitrile (48.5 g, 165 mmol) was added concentrated sulfuric acid (200 mL) and stirred overnight at ambient temperature, then added portionwise to water (1000 mL) cooled in an ice bath at a rate such that the solution temperature did not exceed above 35° C. The aqueous layer was extracted with ethyl acetate. The combined organics were washed with water, brine, dried, and concentrated to 200 mL, filtered and dried to yield the title compound (49 g, 95%).

Step C: 5-bromo-3-(4-fluorophenoxy)pyridin-2-amine: To a solution of 2M sodium hydroxide (300 mL) at 0° C. was added bromine (6.94 mL, 135 mmol). The reaction was stirred at 0° C. for 15 minutes, followed by addition of 5-bromo-3-(4-fluorophenoxy)picolinamide (35 g, 113 mmol) in dioxanes (600 mL). Stirred at room temperature for 1 hour, then heated at 80° C. for 2 hours. The reaction was acidified with 1N HCl (800 mL) until no off gas was produced. The aqueous layer was basified using 1N NaOH. The aqueous layer was extracted with ethyl acetate. The organic layer was washed with water, brine, dried and concentrated. The residue was purified by chromatography using 15% ethyl acetate/CH₂Cl₂ as eluent to yield the title compound (27.3 g, 86%).

Step D: Following the procedure in Example 7, Step C, 5-bromo-3-(4-fluorophenoxy)pyridin-2-amine (800 mg, 2.83 mmol) and benzoyl isothiocyanate (0.457 mL, 3.39 mmol) afforded 1-benzoyl-3-(5-bromo-3-(4-fluorophenoxy)pyridin-2-yl)thiourea (1150 mg, 91.2% yield).

Step E: Following the procedure in Example 7, Step D, 1-benzoyl-3-(5-bromo-3-(4-fluorophenoxy)pyridin-2-yl) thiourea (1150 mg, 2.58 mmol) and 3M sodium hydroxide (1.7 mL, 5.1 mmol) provided 1-(5-bromo-3-(4-fluorophenoxy)pyridin-2-yl)thiourea (743 mg, 84.3% yield) as a white solid.

Step F: Following the procedure in Example 7 Step E, 1-(5-bromo-3-(4-fluorophenoxy)pyridin-2-yl)thiourea (740 mg, 2.163 mmol), 1-bromo-4-phenylbutan-2-one (687.6 mg, 3.028 mmol) and triethylamine (0.5014 mL, 3.676 mmol) afforded 5-bromo-3-(4-fluorophenoxy)-N-(4-phenethylthiazol-2-yl)pyridin-2-amine (1040 mg, 102.2% yield) as a white solid after drying. ¹H NMR (CDCl₃) δ 8.71 (bs, 1H), 8.13 (d, 1H), 7.28 (m, 2H), 7.20 (m, 3H), 7.13 (m, 2H), 7.06 (m, 3H), 6.43 (s, 1H), 3.05-2.92 (m, 4H). Mass spectrum (apci) m/z=470.2, 472.2 (M+H).

Example 180

N-(5-Bromo-3-(phenylthio)pyridin-2-yl)-4-methylthiazol-2-amine

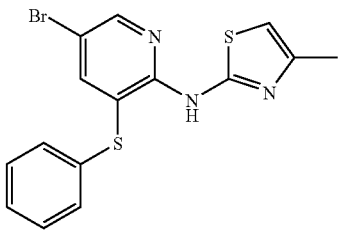

Step A: Preparation of 2-nitro-3-(phenylthio)pyridine: 3-chloro-2-nitropyridine (30.6 g, 193 mmol) was dissolved in DMSO (200 mL). Benzenethiol (20.7 mL, 203 mmol) was added followed by cesium carbonate (69.3 g, 212 mmol) and stirred at ambient temperature for 1.5 hours. The solution was diluted with water (750 mL) and the solids filtered. The crude material was recrystallized from EtOAc (400 mL) and with adding hexanes (1L) to give an A-crop of 23.5 g. The filtrate was concentrated and recrystallized from EtOAc/hexanes to give 7.87 g. The solids were dried on high vacuum to provide the title compound (31.38 g, 69.8% yield).

Step B: Preparation of 5-bromo-3-(phenylthio)pyridin-2-amine: mL2-Nitro-3-(phenylthio)pyridine (16.3 g, 70.2 mmol) and AcOH (250 mL) were cooled in a water bath. Zinc (22.9 g, 351 mmol) was slowly added and stirred for 5 minutes. Filtered through celite and the cake washed with $CH_2Cl_2$. The $CH_2Cl_2$ was removed and to the solution was added bromine (3.6 mL, 70.2 mmol). After 10 minutes, the HOAc was removed and partitioned between EtOAc and saturated aqueous sodium bicarbonate. The organic layer was dried with sodium sulfate, filtered and concentrated. The residue was purified on silica gel (1.5 L $SiO_2$ and 30% EtOAc in hexanes) to afford the title compound (18.2 g, 92.21% yield).

Step C: Preparation of 1-benzoyl-3-(5-bromo-3-(phenylthio)pyridin-2-yl)thiourea: mL5-Bromo-3-(phenylthio)pyridin-2-amine (17 g, 60.5 mmol), benzoyl isothiocyanate (9.79 mL, 72.6 mmol), and THF (300 mL) was stirred at 40° C. overnight. Concentrated to half of the original volume and 9:1 hexanes:EtOAc (500 mL) was added. Filtered to afford the title compound (25.7 g, 95.7% yield).

Step D: Preparation of 1-(5-bromo-3-(phenylthio)pyridin-2-yl)thiourea: To 1-Benzoyl-3-(5-bromo-3-(phenylthio)pyridin-2-yl)thiourea (25.7 g, 57.8 mmol) and MeOH (250 mL) was added sodium hydroxide (38.6 mL, 116 mmol) and stirred at ambient temperature for 8 hours. Diluted with water (250 mL) and filtered and washed with water. The precipitate was dried in vacuum oven to afford the title compound (19.0 g, 96.5% yield).

Step E: Preparation of 5-bromo-N-(4-methylthiazol-2-yl)-3-(phenylthio)pyridin-2-amine: mL1-(5-Bromo-3-(phenylthio)pyridin-2-yl)thiourea (5.0 g, 14.69 mmol), triethylamine (6.0 mL, 44 mmol), 1-chloropropan-2-one (2.3 mL, 29.4 mmol), and EtOH (100 mL) were heated to 70° C. for 6 hours. The ethanol was reduced to ~½ volume and water (150 mL) added and the precipitate was filtered to afford the title compound (5.6 g, 100% yield) as a tan solid after drying. $^1$H NMR ($CDCl_3$) δ 9.01 (s, 1H), 8.42 (m, 1H), 7.92 (m, 1H), 7.32-7.15 (m, 5H), 6.44 (m, 1H0, 2.32 (m, 3H). Mass spectrum (apci) m/z=379.8 (M+H).

Example 181

N-(5-bromo-3-(phenylthio)pyridin-2-yl)thiazolo[5,4-b]pyridin-2-amine hydrochloride

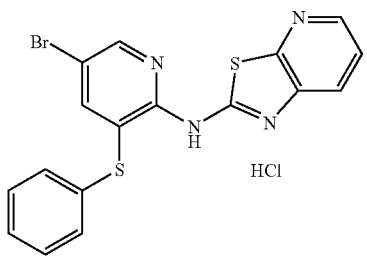

mL5-Bromo-3-(phenylthio)pyridin-2-amine (1.0 g, 3.6 mmol), 2-chloro-3-isothiocyanatopyridine (0.61 g, 3.6 mmol), DMF (2 mL) were heated to 90° C. for 8 hours. Cooled to ambient temperature and the solids were diluted with mLCH$_2$Cl$_2$ (2 mL) and filtered and washed with small amount of $CH_2Cl_2$ to afford the title compound (0.98 g, 61% yield). $^1$H NMR (d$_6$-DMSO) δ 8.50 (d, 1H), 8.39 (dd, 1H), 7.98 (s, 1H), 7.92 (dd, 1 h), 7.38-7.25 (m, 6H). Mass spectrum (apci) m/z=414.8 (M+H).

Example 182

N-(5-Bromo-3-(phenylthio)pyridin-2-yl)-3-methyl-1,2,4-oxadiazol-5-amine

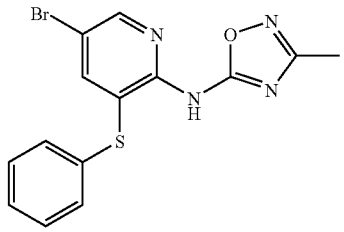

Step A: Preparation of methyl N'-5-bromo-3-(phenylthio)pyridin-2-yl-N-(1-(dimethylamino)ethylidene)carbamimidothioate: 1-(5-Bromo-3-(phenylthio)pyridin-2-yl)thiourea (100 mg, 0.29 mmol) and 1,1-dimethoxy-N,N-dimethylethanamine (0.096 mL, 0.59 mmol) were heated to 70° C. for 1 hour. The reaction was cooled to ambient temperature to afford 120 mg of the title compound as a crude mixture.

Step B: Preparation of 5-bromo-N-(3-methyl-1,2,4-oxadiazol-5-yl)-3-(phenylthio)pyridin-2-amine: To N'-5Bromo-3-(phenylthio)pyridin-2-yl-N-(1-(dimethylamino)ethylidene)carbamimidothioate (120 mg, 0.283 mmol), sodium acetate (69.8 mg, 0.850 mmol), and THF (2 mL) was added hydroxylamine hydrochloride (59.1 mg, 0.850 mmol) followed by 0.1 mL water. Stirred at 50° C. for 3 hours and poured into saturated aqueous $NaHCO_3$ and extracted with EtOAc. The organic layer was dried with sodium sulfate, filtered and concentrated. The residue was purified on silica gel (1:1 EtOAc in hexanes) to afford the title compound (89 mg, 86.5% yield). $^1$H NMR ($CDCl_3$) δ 8.54 (m, 1H), 8.49 (bs, 1H), 7.96 (m, 1H), 7.64-7.49 (m, 1H), 7.31 (m, 3H), 7.21 (m, 2H), 2.35 (s, 3H). Mass spectrum (apci) m/z=362.4, 364.2 (M+H).

Example 183

N-(5-bromo-3-phenoxypyridin-2-yl)-3-(tetrahydrofuran-2-yl)-1,2,4-thiadiazol-5-amine

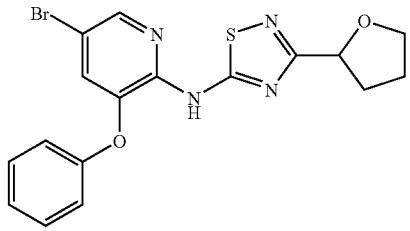

Step A: Preparation of tetrahydrofuran-2-carbaldehyde oxime: Tetrahydrofuran-2-carbaldehyde (100 g, 500 mmol, 50 wt % in water) was dissolved in methanol:water (1:1, 1500 mL) and cooled in an ice bath. Sodium carbonate (26.5 g, 250 mmol) and hydroxylamine hydrochloride (41.6 g, 600 mmol)

were added and the reaction was stirred overnight at ambient temperature. The reaction was concentrated to half volume and extracted with EtOAc (2×800 mL). The organic layer was dried over magnesium sulfate, filtered and concentrated to afford the title compound (44.3 g, 80%).

Step B: Preparation of tetrahydrofuran-2-carbonyl chloride oxime: A 250 mL round-bottomed flask was charged with tetrahydrofuran-2-carbaldehyde oxime (2.0 g, 17 mmol) and DMF (100 mL). 1-chloropyrrolidine-2,5-dione (2.3 g, 17 mmol) was added and stirred at ambient temperature overnight. The reaction was poured into 1:1 brine:water (800 mL) and extracted with EtOAc (500 mL). The organic layer was washed twice with water, dried over sodium sulfate, filtered and concentrated to afford the title compound (2.6 g, 100%).

Step C: Preparation of N-(methylsulfonyloxy)tetrahydrofuran-2-carbimidoyl chloride: A 500 mL round-bottomed flask was charged with tetrahydrofuran-2-carbonyl chloride oxime (2.6 g, 17.4 mmol), methanesulfonyl chloride (1.4 mL, 17.4 mmol), and Et$_2$O (200 mL). Triethylamine (2.4 mL, 17.4 mmol) was added dropwise over 1 minute and stirred at ambient temperature for 10 minutes. The solids were filtered and the filtrate was concentrated. The residue was purified on silica gel (100% CH$_2$Cl$_2$) to afford the title compound (2.1 g, 53.07% yield).

Step D: Preparation of 5-bromo-3-phenoxy-N-(3-(tetrahydrofuran-2-yl)-1,2,4-thiadiazol-5-yl)pyridin-2-amine: A 20 mL vial was charged with N-(methylsulfonyloxy)tetrahydrofuran-2-carbimidoyl chloride (129 mg, 0.57 mmol), pyridine (0.137 mL, 1.7 mmol), NaSCN (45.9 mg, 0.57 mmol) and CH$_3$CN (4 mL). The reaction was heated to 40° C. for 40 minutes. 5-bromo-3-phenoxypyridin-2-amine (100 mg, 0.38 mmol) was added and the reaction was heated to 50° C. overnight. The reaction was poured into saturated aqueous NaHCO$_3$ and extracted with EtOAc. The organic layer was dried with sodium sulfate, filtered and concentrated. The residue was purified on silica gel (30% EtOAc in hexanes) to afford the title compound (121 mg, 76.5% yield) as a tan solid. $^1$H NMR (d$_6$-DMSO) δ 12.22 (s, 1H), 8.32 (d, 1H), 7.47 (d, 1H), 7.39 (m, 2H), 7.17 (m, 1H), 7.07 (m, 2H), 3.98 (t, 1H), 3.83-3.68 (m, 3H), 3.53 (m, 1H), 2.19 (q, 2H). Mass spectrum (apci) m/z=419.1 (M+H).

By the procedures in Example 183, the following compounds were also prepared.

| Example | Structure | Name | Data |
|---|---|---|---|
| 184 | 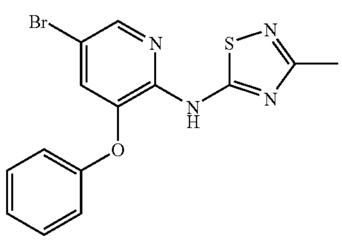 | N-(5-bromo-3-phenoxypyridin-2-yl)-3-methyl-1,2,4-thiadiazol-5-amine | $^1$H NMR (CDCl$_3$) δ 9.10 (s, 1 H), 8.20 (m, 1 H), 7.45 (m, 2 H), 7.28 (m, 1 H), 7.19 (d, 1 H), 7.08 (m, 2 H), 2.53 (s, 3 H). Mass spectrum (apci) m/z = 363.1, 365.0 (M + H). |
| 185 | 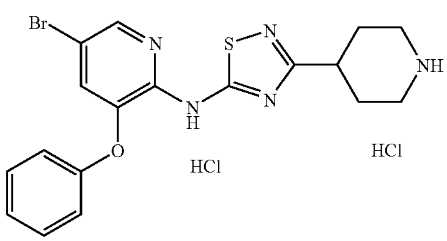 | N-(5-bromo-3-phenoxypyridin-2-yl)-3-(piperidin-4-yl)-1,2,4-thiadiazol-5-amine dihydrochloride | $^1$H NMR (d$_6$-DMSO) δ 12.20 (s, 1 H), 8.66 (bs, 1 H), 8.47 (bs, 1 H), 8.31 (d, 1 H), 7.46 (d, 1 H), 7.40 (m, 2 H), 7.18 (t, 1 H), 7.08 (d, 2 H), 3.51 (s, 2 H), 3.15-2.90 (m, 3 H), 2.10 (m, 2 H), 1.88 (m, 2 H). Mass spectrum (apci) m/z = 432.2 (M + H − 2HCl). |
| 186 | 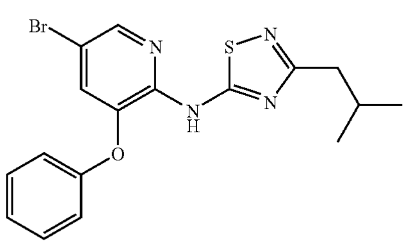 | N-(5-bromo-3-phenoxypyridin-2-yl)-3-isobutyl-1,2,4-thiadiazol-5-amine | $^1$H NMR (CDCl$_3$) δ 9.02 (s, 1 H0, 8.21 (d, 1 H), 7.45 (m, 2 H), 7.28 (m, 1 H), 7.19 (d, 1 H), 7.08 (m, 2 H), 2.71 (d, 2 H), 2.22 (m, 1 H), 0.98 (d, 6 H). Mass spectrum (apci) m/z = 405.1 (M + H). |
| 187 | 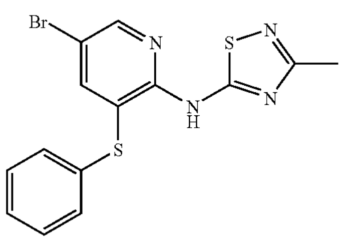 | N-(5-bromo-3-(phenylthio)pyridin-2-yl)-3-methyl-1,2,4-thiadiazol-5-amine | $^1$H NMR (CDCl$_3$) δ 9.30 (bs, 1 H), 8.50 (d, 1 H), 7.98 (d, 1 H), 7.30 (m, 3 H), 7.20 (m, 2 H), 2.51 (s, 3 H). Mass spectrum (apci) m/z = 379.1, 381.0 (M + H). |

-continued

| Example | Structure | Name | Data |
|---|---|---|---|
| 188 | (structure) | N-(5-bromo-3-(phenylthio)pyridin-2-yl)-3-isopropyl-1,2,4-thiadiazol-5-amine hydrochloride | $^1$H NMR (CDCl$_3$) δ 9.30 (bs, 1 H), 8.51 (m, 1 H), 7.96 (m, 1 H), 7.30 (m, 3 H), 7.20 (m, 2 H), 3.14 (m, 1 H), 1.35 (d, 6 H). Mass spectrum (apci) m/z = 407.1 (M + H − HCl). |
| 189 | (structure) | N-(5-bromo-3-(4-fluorophenoxy)-pyridin-2-yl)-3-methyl-1,2,4-thiadiazol-5-amine | $^1$H NMR (CDCl$_3$) δ 9.04 (bs, 1 H), 8.20 (d, 1 H), 7.14 (m, 3 H), 7.07 (m, 2 H), 2.54 (s, 3 H). Mass spectrum (apci) m/z = 381.1, 383.1 (M + H). |
| 190 | (structure) | N-(5-bromo-3-(4-fluorophenoxy)-pyridin-2-yl)-3-isobutyl-1,2,4-thiadiazol-5-amine | $^1$H NMR (CDCl$_3$) δ 9.05 (bs, 1 H), 8.21 (d, 1 H), 7.14 (m, 3 H), 7.07 (m, 2 H), 2.72 (d, 2 H), 2.22 (m, 1 H), 0.98 (d, 6 H). Mass spectrum (apci) m/z = 423.1, 425.2 (M + H). |
| 191 | (structure) | tert-butyl 4-(5-(5-bromo-3-(4-fluorophenoxy)-pyridin-2-ylamino)-1,2,4-thiadiazol-3-yl)piperidine-1-carboxylate | $^1$H NMR (CDCl$_3$) δ 9.01 (bs, 1 H), 8.20 (d, 1 H), 7.15 (m, 3 H), 7.07 (m, 2 H), 4.14 (m, 2 H), 2.93 (m, 3 h), 2.04 (m, 2 H), 1.81 (m, 2 H), 1.46 (s, 9 H). Mass spectrum (apci) m/z = 450.2 (M + H − Boc). |
| 192 | (structure) | tert-butyl 4-((5-(5-bromo-3-(4-fluorophenoxy)-pyridin-2-ylamino)-1,2,4-thiadiazol-3-yl)methyl)piperidine-1-carboxylate | $^1$H NMR (CDCl$_3$) δ 9.01 (bs, 1 H), 8.21 (m, 1 H), 7.15 (m, 3 H), 7.08 (m, 2 H), 4.09 (m, 2 H), 2.78 (d, 2 H), 2.71 (m, 2 H), 2.04 (m, 1 H), 1.69 (m, 2 H), 1.45 (s, 9 H), 1.24 (m, 2 H). Mass spectrum (apci) m/z = 464.2 (M + H − Boc). |

Example 193

4-methyl-N-(3-(phenylthio)-5-((tetrahydro-2H-pyran-4-ylmethyl)pyridin-2-yl)thiazol-2-amine hydrochloride

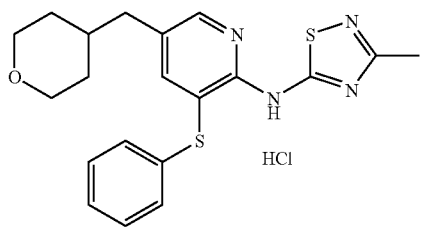

Step A: Preparation of (6-(4-methylthiazol-2-ylamino)-5-(phenylthio)Pyridin-3-yl)(tetrahydro-2H-pyran-4-yl)methanol hydrochloride: A 10 mL round-bottomed flask was charged with 5-bromo-N-(4-methylthiazol-2-yl)-3-(phenylthio)pyridin-2-amine (250 mg, 0.661 mmol), THF (6 mL) and cooled to −78° C. and methyllithium (0.496 mL, 0.793 mmol) was added. The reaction was stirred for 5 minutes and butyllithium (0.317 mL, 0.793 mmol) was added. The reaction was stirred for 10 minutes and tetrahydro-2H-pyran-4-carbaldehyde (151 mg, 1.32 mmol) was added. The reaction was warmed to ambient temperature and poured into saturated aqueous NH$_4$Cl and extracted with EtOAc (2×20 mL). The organic layer was dried with sodium sulfate, filtered and concentrated. The residue was purified on silica gel (50% EtOAc in hexanes) to afford the title compound (217 mg, 73.0% yield) after HCl salt formation.

Step B: Preparation of N-(4-methylthiazol-2-yl)-3-(phenylthio)-5-((tetrahydropyran-4-ylidene)methyl)pyridin-2-amine hydrochloride: A 10 mL round-bottomed flask was charged with (6-(4-methylthiazol-2-ylamino)-5-(phenylthio)pyridin-3-yl)(tetrahydro-2H-pyran-4-yl)methanol hydrochloride (125 mg, 0.278 mmol), 4-methylbenzenesulfonic acid hydrate (5.28 mg, 0.0278 mmol), Toluene (5 mL) and heated to reflux in dean stark trap for 24 7 hours. The reaction was cooled to ambient temperature and partitioned between saturated aqueous sodium bicarbonate and CH$_2$Cl$_2$. The organic layer was dried with sodium sulfate, filtered and concentrated. The residue was purified on silica gel (25% EtOAc in hexanes) to afford the title compound (42 mg, 35.0% yield) as after HCl salt formation. $^1$H NMR (CDCl$_3$) δ 12.24 (bs, 1H), 8.18 (m, 1H), 7.71 (m, 1H), 7.54 (m, 2H), 7.30 (m, 3H), 6.40 (s, 1H), 6.20 (s, 1H), 3.78 (t, 2H), 3.65 (t, 2H), 2.45 (s, 3H), 2.42 (m, 4H). Mass spectrum (apci) m/z=396.2 (M+H—HCl).

Step C: Preparation of N-(4-methylthiazol-2-yl)-3-(phenylthio)-5-((tetrahydro-2H-pyran-4-yl)methyl)pyridin-2-amine hydrochloride: Prepared according to the method of Example 44, Step C. $^1$H NMR (d$_6$-DMSO) δ 8.26 (s, 1H), 7.85 (s, 1H), 7.35-7.19 (m, 5H), 6.82 (s, 1H), 3.74 (m, 2H), 3.15 (t, 2H), 2.49 (d, 2H), 2.24 (s, 3H), 1.67 (m, 1H), 1.38 (m, 2H), 1.12 (m, 2H). Mass spectrum (apci) m/z=398.3 (M+H—HCl).

Example 194

N-(5-(2-chloro-5-methoxyphenylthio)-3-phenoxypyridin-2-yl)-4-methylthiazol-2-amine hydrochloride

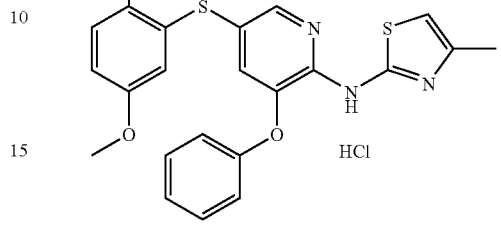

Step A: Preparation of 1,2-bis(2-chloro-5-methoxyphenyl)disulfane: To a solution of 2-bromo-1-chloro-4-methoxybenzene (4.42 g, 19.9 mmol) in THF stirring at −10° C. under nitrogen was added isopropylmagnesium chloride (9.9 mL, 19.9 mmol, 2M in THF). The reaction was allowed to warm to ambient temperature stirred for 4 hours. The reaction was cooled to −40° C. and zinc(II) chloride (19.9 mL, 19.9 mmol, 1M in ether) was added and the solution stirred for 30 minutes. The reaction was cooled to −78° C. and sulfurothioyl dichloride (0.80 mL, 9.9 mmol) was added. After stirring for 15 minutes at −78° C., saturated NH$_4$Cl was added and the mixture was warmed to ambient temperature and extracted multiple times with EtOAc. The combined organic layers were dried with sodium sulfate, filtered, and concentrated to give a residue which was purified by silica chromatography (10% EtOAc in hexanes) to afford the title compound (1.52 g, 21.9% yield).

Step B: Preparation of 5-(2-chloro-5-methoxyphenylthio)-N-(4-methylthiazol-2-yl)-3-phenoxypyridin-2-amine hydrochloride: Prepared according to the method of Example 8, using 1,2-bis(2-chloro-5-methoxyphenyl)disulfane to afford the title compound (0.960 g, 56.5% yield) after HCl salt formation. $^1$H NMR (d$_6$-DMSO) δ 8.26 (m, 1H), 7.40 (m, 3H), 7.32 (m, H), 7.18 (t, 1H), 7.11 (d, 2H), 6.81 (dd, 1H), 6.73 (s, 1H), 6.41 (d, 1H), 3.64 (s, 3H), 2.27 (s, 3H). Mass spectrum (apci) m/z=456.3 (M+H—HCl).

Example 195

(R)-4-methyl-N-(5-(5-methyl-6,7-dihydro-5H-cyclopenta[d]pyrimidin-4-ylthio)-3-phenoxypyridin-2-yl)thiazol-2-amine dihydrochloride

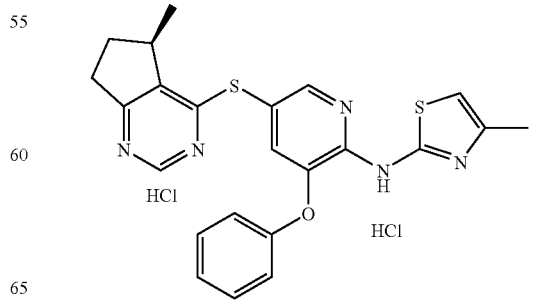

Step A: Preparation of (2R)-ethyl 2-methyl-5-(propan-2-ylidene)cyclopentanecarboxylate: To a 3 L round bottom flask was added (r)-Pulegone (300 g, 1.97 mol), anhydrous NaHCO$_3$ (82 g, 0.99 mol) and Ether (1.5 L). The mixture was cooled to −5° C. ice-salt bath under N$_2$. Then bromine (101 mL, 1.97 mol) was added dropwise over 45 minutes. The mixture was filtered and carefully added dropwise (addition is exothermic in nature) to NaOEt (20 wt %, 4.3 mol) cooled at 0° C. The reaction was allowed to stir with warming to ambient temperature overnight. Then 1L of 5% HCl and 300 mL of ether was added. The aqueous phase was extracted with ether and the combined organic layers washed with brine, dried with MgSO$_4^-$ and concentrated. The resulting brown oil diluted with EtOH was added to a warm solution of semicarbazide HCl (150 g, 1.3 mol), NaOAc (150 g, 1.8 mol) and H$_2$O (2 L) to give a brownish solution. The mixture was then refluxed for 3 hours and stirred at ambient temperature overnight. The mixture was treated with 1 L of water and 500 mL of ether. The aqueous phase was extracted with ether. The combined organic layers were dried with MgSO$_4$ and concentrated to give a brown oil. The oil was subject to vacuum distillation, and the title compound (247 g, 64% yield) was collected at 73-76° C.

Step B: Preparation of (2R)-ethyl 2-methyl-5-oxocyclopentanecarboxylate: The (2R)-ethyl 2-methyl-5-(propan-2-ylidene)cyclopentanecarboxylate (139 g, 662 mmol) in EtOAc (900 mL) was cooled to −78° C. using a dry ice-isopropanol bath. This mixture was subjected to ozonolysis until the reaction turn purple in color. Ozone generation ceased and the reaction removed from the dry-ice bath. Oxygen was bubbled through the reaction until the reaction turned yellow. The reaction was concentrated and the resulting residue dissolved in 60 mL of glacial acetic acid. The solution was cooled to 0° C. and Zn dust was added portionwise over 30 minutes. The reaction was then allowed to stir for 1 hour, then filtered through celite to remove the zinc. The acetic acid was neutralized to pH 7 with aqueous NaOH and NaHCO$_3$ and extracted with ether. The organics were dried with brine, MgSO$_4$ and concentrated to give the desired material as a brownish liquid. The material was passed through a silica plug (eluting 8:1, hex/EtOAc) to remove polar impurities to afford the title compound (82 g, 73% yield).

Step C: Preparation of (R)-ethyl 2-amino-5-methylcyclopent-1-enecarboxylate: To a solution of (R)-ethyl 2-methyl-5-oxocyclopentanecarboxylate (106 g, 622 mmol) in 1.2 L MeOH was added ammonium acetate (240 g, 3.1 mol). The reaction was stirred for 20 hours and concentrated to remove MeOH. The resulting residue was dissolved in CH$_2$Cl$_2$, washed with H$_2$O, brine, dried (Na$_2$SO$_4$), filtered and concentrated to give the title compound (102 g, 97% yield) as an orange oil.

Step D: Preparation of (R)-5-methyl-6,7-dihydro-5H-cyclopenta[d]pyrimidin-4-ol: A 2 L 3-neck round bottom flask equipped with a condenser, internal temperature probe, was charged with (R)-ethyl 2-amino-5-methylcyclopent-1-enecarboxylate (185 g, 1093 mmol) and ammonium formate (103.4 g, 1640 mmol) in formamide (400 mL) and toluene (200 mL). The reaction was heated to an internal temperature of 150° C. and stirred for 36 hours. The reaction was cooled and transferred to a 2 L single next flask and excess formamide was removed by high vacuum distillation. The resulting oil was dissolved in CH$_2$Cl$_2$ and washed with brine. The combined aqueous layers were extracted with CH$_2$Cl$_2$. The combined organic layers were dried over sodium sulfate, filtered and concentrated to give the crude product as a brown semi solid which was taken into the next step without any further purification.

Step E: Preparation of (R)-4-chloro-5-methyl-6,7-dihydro-5H-cyclopenta[d]pyrimidine: The solution of (R)-5-methyl-6,7-dihydro-5H-cyclopenta[d]pyrimidin-4-ol (2.08 g, 13.9 mmol) in POCl$_3$ (10 ml) was refluxed for 2 hours. After cooling, the excess POCl$_3$ was evaporated and the residue was dissolved in CH$_2$Cl$_2$ (50 ml) and was neutralized with saturated NaHCO$_3$. The aqueous phase was extracted with CH$_2$Cl$_2$. The organic phase was dried and concentrated. The residue purified on silica gel (20% EtOAc in hexanes) to afford the title compound (1.0 g, 44% yield).

Step F: Preparation of (R)-5-(5-methyl-6,7-dihydro-5H-cyclopenta[d]pyrimidin-4-ylthio)-N-(4-methylthiazol-2-yl)-3-phenoxypyridin-2-amine dihydrochloride: Prepared according to the method of Example 127 using (R)-4-chloro-5-methyl-6,7-dihydro-5H-cyclopenta[d]pyrimidine to afford the title compound (51.6 mg, 49.8% yield) after HCl salt formation. $^1$H NMR (d$_6$-DMSO) δ 8.63 (m, 1H), 8.26 (m, 1H), 7.42 (m, 3H), 7.16 (m, 3H), 6.75 (s, 1H), 3.29 (m, 1H), 3.03 (m, 1H), 2.80 (m, 1H), 2.28 (m, 4H), 1.72 (m, 1H), 1.27 (d, 3H). Mass spectrum (apci) m/z=448.3 (M+H-2HCl).

Example 196

3-(2-(3-phenoxy-5-(pyridin-4-ylthio)pyridin-2-ylamino)thiazol-4-yl)propanoic acid dihydrochloride

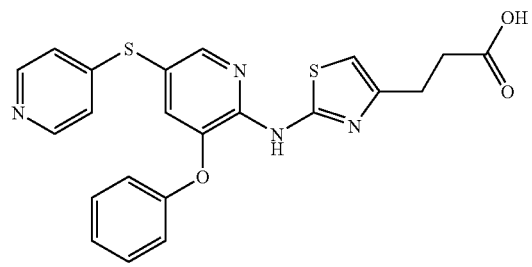

Prepared according to the method of Example 45 from Methyl 3-(2-(3-phenoxy-5-(pyridin-4-ylthio)pyridin-2-ylamino)thiazol-4-yl)propanoate. $^1$H NMR (d$_6$-DMSO) δ 8.58 (m, 2H), 8.38 (m, 1H), 7.64 (m, 2H), 7.48 (m, 1H), 7.43 (m, 2H), 7.18 (m, 3H), 6.78 (m, 1H), 2.86 (m, 2H), 2.71 (m, 1H), 2.62 (m, 1H). Mass spectrum (apci) m/z=451.2 (M+H-2HCl).

Example 197

N-(5-(3,5-dimethylisoxazolo[4,5-b]pyridin-7-ylthio)-3-phenoxypyridin-2-yl)-4-methylthiazol-2-amine dihydrochloride

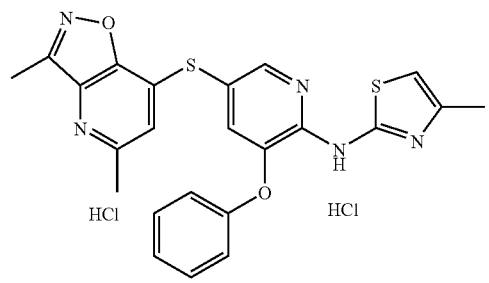

Step A: Preparation of 3,5-dimethylisoxazolo[4,5-b]pyridine 4-oxide: 3,5-dimethyl-4-nitroisoxazole (2.50 g, 17.6 mmol) in 25 mL EtOH was dissolved. Piperidine (0.174 mL, 1.76 mmol) was added followed by propionaldehyde (1.52 mL, 21.1 mmol). The solution was heated at 90° C. overnight. The solution was concentrated and chromatographed using EtOAc to obtain the title compound (0.650 g, 22.5% yield).

Step B: Preparation of 7-chloro-3,5-dimethylisoxazolo[4,5-b]pyridine: 3,5-dimethylisoxazolo[4,5-b]pyridine 4-oxide (0.650 g, 3.96 mmol) in chloroform (5 mL), was added POCl$_3$ (1.45 mL, 15.8 mmol) and the mixture was heated at 80° C. for 2 hours. The solution was cooled and poured onto ice water. The solution was neutralized with saturated NaHCO$_3$ and the solution was then extracted with EtOAc, dried, and concentrated. The solid was triturated with ether and filtered twice to obtain two crops of the title compound (0.417 g, 57.7% yield).

Step C: Preparation of 5-(3,5-dimethylisoxazolo[4,5-b]pyridin-7-ylthio)-N-(4-methylthiazol-2-yl)-3-phenoxypyridin-2-amine dihydrochloride: Prepared according to the method of Example 127. $^1$H NMR (d$_6$-DMSO) δ 8.39 (dd, 1H), 7.48 (dd, 1H), 7.39 (m, 3H), 7.15 (m, 3H), 7.06 (d, 1H), 6.74 (s, 1H), 2.54 (m, 3H), 2.52 (m, 3H), 2.28 (s, 3H). Mass spectrum (apci) m/z=461.9 (N+H-2HCl).

Example 198

1-(4-(2-(3-phenoxy-5-(thieno[3,2-b]pyridin-7-ylthio)pyridin-2-ylamino)thiazol-4-yl)piperidin-1-yl)ethanone dihydrochloride

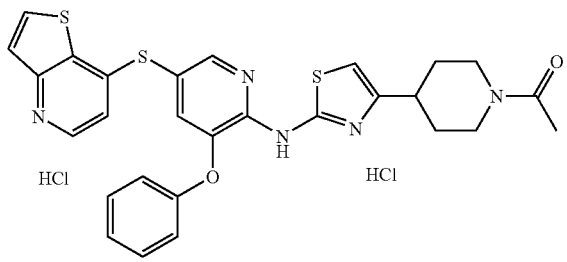

Step A: A 100 mL round-bottomed flask was charged with tert-butyl 4-(2-(5-bromo-3-phenoxypyridin-2-ylamino)thiazol-4-yl)piperidine-1-carboxylate (1.6 g, 3.0 mmol), N-ethyl-N-isopropylpropan-2-amine (1.0 mL, 6.0 mmol), Xantphos (0.087 g, 0.15 mmol), and Dioxane (25 mL). Nitrogen was bubbled through the solution for 10 minutes. Methyl 3-mercaptopropanoate (0.40 mL, 3.6 mmol) and Pd$_2$dba$_3$ (0.068 g, 0.075 mmol) were added and the reaction was plunged into a 95° C. oil bath for 6 hours. The reaction was cooled to room temperature and the solids filtered through celite and concentrated. The residue was purified on silica (30% EtOAc in hexanes) to afford tert-butyl 4-(2-(5-(3-methoxy-3-oxopropylthio)-3-phenoxypyridin-2-ylamino)thiazol-4-yl)piperidine-1-carboxylate (1.4 g, 81.48% yield) as a white foam.

Step B: A 25 mL round-bottomed flask was charged with tert-butyl 4-(2-(5-(3-methoxy-3-oxopropylthio)-3-phenoxypyridin-2-ylamino)thiazol-4-yl)piperidine-1-carboxylate (500 mg, 0.876 nmol), 7-chlorothieno[3,2-b]pyridine (178 mg, 1.05 mmol), and DMSO (8 mL). Nitrogen was bubbled through the solution for 10 minutes. Potassium 2-methylpropan-2-olate (295 mg, 2.63 mmol) was added and stirred at room temperature for 30 minutes. The reaction was poured into saturated aqueous NH$_4$Cl and extracted with EtOAc (2×20 mL). The organic layer was dried with sodium sulfate, filtered and concentrated. The residue was purified on silica (50% EtOAc in hexanes) to afford tert-butyl 4-(2-(3-phenoxy-5-(thieno[3,2-b]pyridin-7-ylthio)pyridin-2-ylamino)thiazol-4-yl)piperidine-1-carboxylate.

Step C: tert-Butyl 4-(2-(3-phenoxy-5-(thieno[3,2-b]pyridin-7-ylthio)pyridin-2-ylamino)thiazol-4-yl)piperidine-1-carboxylate was dissolved in 1:1 CH$_2$Cl$_2$:methanol and 4N HCl in dioxane added and stirred for 1 hour at room temperature. The reaction was concentrated and the residue was partitioned between CH$_2$Cl$_2$ and saturated aqueous sodium bicarbonate. The organic layer was dried over sodium sulfate, filtered and concentrated to afford 3-phenoxy-N-(4-(piperidin-4-yl)thiazol-2-yl)-5-(thieno[3,2-b]pyridin-7-ylthio)pyridin-2-amine (238 mg, 52.5% yield over 2 steps) as a white solid Step D: A 20 mL vial was charged with 3-phenoxy-N-(4-(piperidin-4-yl)thiazol-2-yl)-5-(thieno[3,2-b]pyridin-7-ylthio)pyridin-2-amine (80 mg, 0.15 mmol), triethylamine (0.043 mL, 0.31 mmol), and THF (2 mL). Acetyl chloride (0.011 mL, 0.15 mmol) was added and stirred at ambient temperature for 10 minutes. The reaction was poured into saturated aqueous NaHCO$_3$ and extracted with EtOAc. The organic layer was dried with sodium sulfate, filtered and concentrated. The residue was purified on silica gel (5 to 10% methanol in EtOAc) to afford the title compound (35.1 mg, 35.9% yield) as a yellow solid after HCl salt formation. $^1$H NMR (d$_6$-DMSO) δ 8.65 (d, 1H), 8.48 (d, 1H), 8.46 (d, 1H), 7.77 (d, 1H), 7.54 (d, 1H), 7.41 (m, 2H), 7.18 (m, 4H), 6.82 (s, 1H), 4.43 (m, 1H), 3.88 (m, 1H), 3.14 (m, 1H), 2.89 (m, 1H), 2.64 (m, 1H), 2.01 (s, 3H), 1.96 (m, 2H), 1.58 (m, 1H), 1.45 (m, 1H). Mass spectrum (apci) m/z=560.4 (M+H-2HCl).

The following compounds were also prepared according to the procedure of Example 198, Step D.

| Example | Structure | Name | Data |
|---|---|---|---|
| 199 | 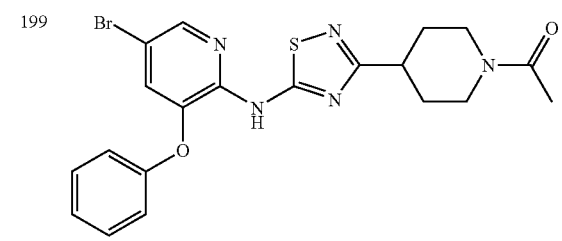 | 1-(4-(5-(5-bromo-3-phenoxypyridin-2-ylamino)-1,2,4-thiadiazol-3-yl)piperidin-1-yl)ethanone | $^1$H NMR (CDCl$_3$) δ 9.01 (s, 1 H), 8.21 (d, 1 H), 7.46 (m, 2 H), 7.30 (m, 1 h), 7.19 (d, 1 H), 7.09 (m, 2 H), 4.57 (m, 1 H), 3.89 (m, 1 h), 3.22 (m, 1 H), 3.07 (m, 1 H), 2.83 (m, 1 H), 2.11 (m, 5 H), 1.95-1.75 (m, 2 H). Mass spectrum (apci) m/z = 476.2 (M + H). |

-continued

| Example | Structure | Name | Data |
|---|---|---|---|
| 200 | 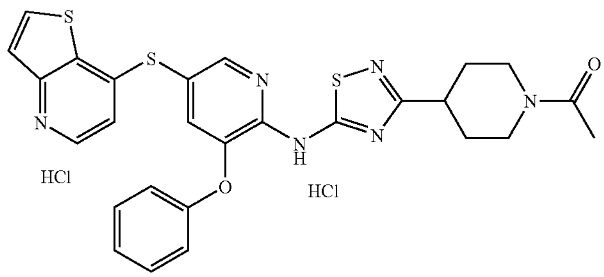 | 1-(4-(5-(3-phenoxy-5-(thieno[3,2-b]pyridin-7-ylthio)pyridin-2-ylamino)-1,2,4-thiadiazol-3-yl)piperidin-1-yl)ethanone dihydrochloride | ¹H NMR (d₆-DMSO) δ 12.48 (bs, 1 H), 8.56 (d, 1 H), 8.53 (d, 1 H), 8.28 (d, 1 H), 7.65 (d, 1 H), 7.57 (d, 1 H), 7.40 (m, 2 H), 7.18 (m, 1 H), 7.14 (m, 2 H), 7.07 (d, 1 H), 4.32 (m, 1 H), 3.20 (m, 1 H), 3.07 (m, 1 H), 2.77 (m, 1 H), 2.01 (m, 5 H), 1.73 (m, 1 H), 1.59 (m, 1 H). Mass spectrum (apci) m/z = 561.3 (M + H − 2HCl). |
| 201 | 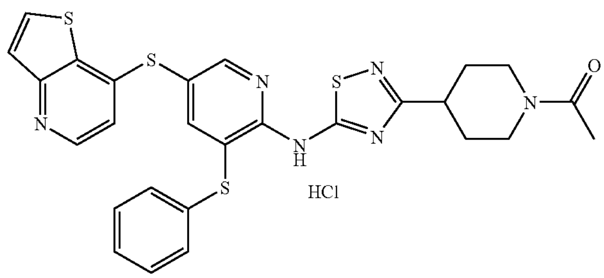 | 1-(4-(5-(3-(phenylthio)-5-(thieno[3,2-b]pyridin-7-ylthio)pyridin-2-ylamino)-1,2,4-thiadiazol-3-yl)piperidin-1-yl)ethanone hydrochloride | ¹H NMR (d₆-DMSO) δ 8.72 (s, 1 H), 8.61 (d, 1 H), 8.38 (d, 1 H), 7.86 (bs, 1 H), 7.71 (d, 1 H), 7.36 (m, 4 H), 7.31 (m, 1 H), 7.09 (d, 1 H), 4.33 (m, 1 H), 3.85 (m, 1 H), 3.18 (m, 1 H), 3.05 (m, 1 H), 2.74 (m, 1 H) 2.01 (m, 5 H), 1.73 (m, 1 H), 1.58 (m, 1 H). Mass spectrum (apci) m/z = 577.3 (M + H − HCl). |
| 202 | 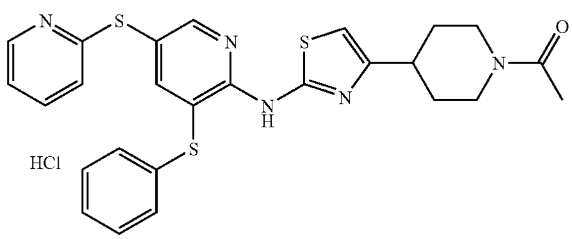 | 1-(4-(2-(3-(phenylthio)-5-(pyridin-2-ylthio)pyridin-2-ylamino)thiazol-4-yl)piperidin-1-yl)ethanone hydrochloride | ¹H NMR (d₆-DMSO) δ 8.46 (m, 1 H), 8.36 (m, 1 H), 7.68 (t, 2 H), 7.39 (m, 6 H), 7.17 (m, 1 H), 7.09 (d, 1 H), 6.73 (s, 1 H), 4.44 (m, 1 H), 3.89 (m, 1 H), 3.12 (m, 1 H), 2.87 (m, 1 H), 2.62 (m, 1 H), 2.01 (m, 5 H), 1.58 (m, 1 H), 1.43 (m, 1 H). Mass spectrum (apci) m/z = 520.3 (M + H − HCl). |
| 203 | 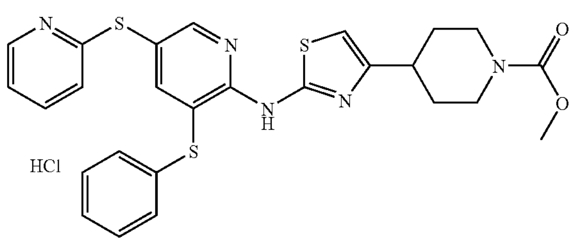 | methyl 4-(2-(3-(phenylthio)-5-(pyridin-2-ylthio)pyridin-2-ylamino)thiazol-4-yl)piperidine-1-carboxylate hydrochloride | ¹H NMR (d₆-DMSO) δ 8.43 (s, 1 H), 8.36 (m, 1 H), 7.66 (m, 2 H), 7.39 (m, 5 H), 7.15 (m, 1 H), 7.06 (m, 1 H), 6.68 (s, 1 H), 4.04 (m, 2 H), 3.60 (s, 3 H), 2.95-2.75 (m, 3 H), 1.93 (m, 2 H), 1.50 (m, 2 H). Mass spectrum (apci) m/z = 536.2 (M + H − HCl). |
| 204 | 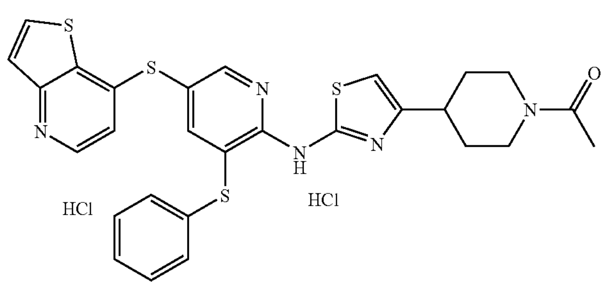 | 1-(4-(2-(3-(phenylthio)-5-(thieno[3,2-b]pyridin-7-ylthio)pyridin-2-ylamino)thiazol-4-yl)piperidin-1-yl)ethanone dihydrochloride | ¹H NMR (d₆-DMSO) δ 8.57 (d, 1 H), 8.49 (bs, 1 H), 8.32 (d, 1 H), 7.66 (d, 1 H), 7.39 (m, 6 H), 6.98 (d, 1 H), 6.61 (s, 1 H), 4.45 (m, 1 H), 3.88 (m, 1 H), 3.11 (m, 1 H), 2.82 (m, 1 H), 2.60 (m, 1 H), 2.02 (s, 3 H), 1.95 (m, 2 H), 1.57 (m, 1 H), 1.43 (m, 1 H). Mass spectrum (apci) m/z = 576.3 (M + H − 2HCl). |
| 205 | 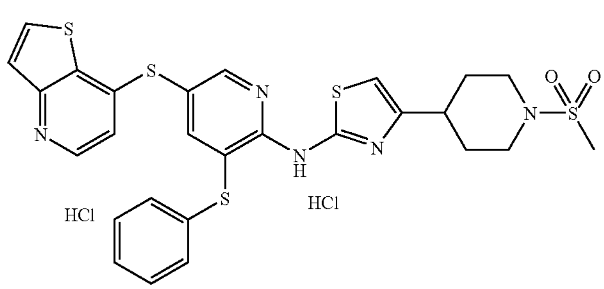 | 4-(1-(methylsulfonyl)piperidin-4-yl)-N-(3-(phenylthio)-5-(thieno[3,2-b]pyridin-7-ylthio)pyridin-2-yl)thiazol-2-amine dihydrochloride | ¹H NMR (d₆-DMSO) δ 8.59 (dd, 1 H), 8.51 (s, 1 H), 8.36 (dd, 1 H), 7.69 (dd, 1 H), 7.40 (m, 6 h), 7.02 (d, 1 H), 6.67 (s, 1 H), 3.64 (m, 2 H), 2.89 (s, 3 H), 2.81 (m, 2 H), 2.70 (m, 1 H), 2.07 (m, 2 H), 1.65 (m, 2 H). Mass spectrum (apci) m/z = 612.2 (M + H − 2HCl). |

| Example | Structure | Name | Data |
|---|---|---|---|
| 206 | 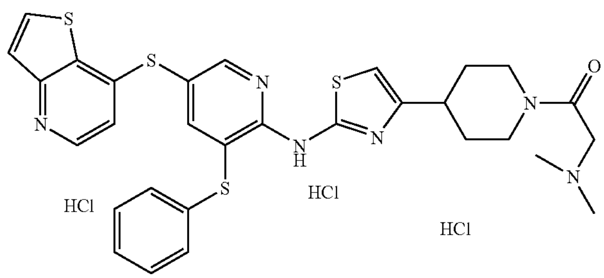 | 2-(dimethylamino)-1-(4-(2-(3-(phenylthio)-5-(thieno[3,2-b]pyridin-7-ylthio)pyridin-2-ylamino)thiazol-4-yl)piperidin-1-yl)ethanone trihydrochloride | $^1$H NMR (d$_6$-DMSO) δ 9.61 (s, 1 H), 8.59 (d, 1 H), 8.52 (s, 1 H), 8.35 (d, 1 H), 7.70 (d, 1 H), 7.39 (m, 6 H), 7.01 (d, 1 H), 6.65 (s, 1 H), 4.44 (m, 1 H), 4.31 (m, 2 H), 3.68 (m, 1 H), 3.16 (m, 1 H), 2.90 (m, 2 H), 2.82 (m, 6 H), 2.03 (m, 2 H), 1.62 (m, 1 H), 1.50 (m, 1 H). Mass spectrum (apci) m/z = 619.2 (M + H − 3HCl). |
| 207 | 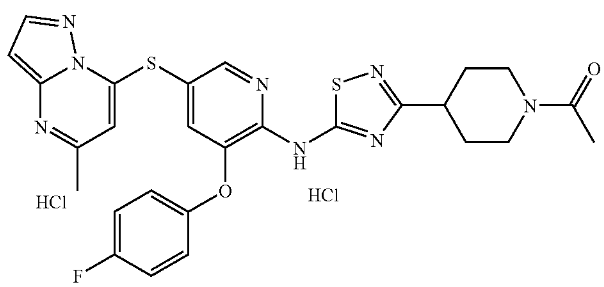 | 1-(4-(5-(3-(4-fluorophenoxy)-5-(5-methylpyrazolo[1,5-a]pyrimidin-7-ylthio)pyridin-2-ylamino)-1,2,4-thiadiazol-3-yl)piperidin-1-yl)ethanone dihydrochloride | $^1$H NMR (d$_6$-DMSO) δ 12.51 (s, 1 H), 8.53 (d, 1 H), 8.20 (d, 1 H), 7.65 (d, 1 H), 7.26 (m, 4 H), 6.58 (d, 1 H), 6.31 (s, 1 H), 4.33 (m, 1 H), 3.85 (m, 1 H), 3.20 (m, 1 H), 3.08 (m, 1 H), 2.78 (m, 1 H), 2.41 (s, 3 H), 2.02 (m, 5 H), 1.74 (m, 1 H), 1.60 (m, 1 H). Mass spectrum (apci) m/z = 577.2 (M + H − 2HCl). |
| 208 | 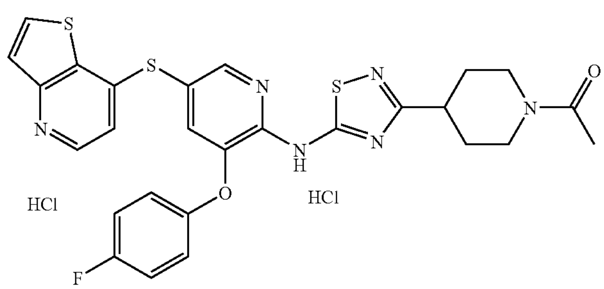 | 1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone dihydrochloride | $^1$H NMR (d$_6$-DMSO) δ 12.49 (bs, 1 H), 8.57 (d, 1 H), 8.52 (d, 1 H), 8.32 (d, 1 H), 7.67 (d, 1 H), 7.58 (d, 1 H), 7.21 (m, 4 H), 7.08 (d, 1 H), 4.32 (m, 1 H), 3.85 (m, 1 H), 3.20 (m, 1 H), 3.07 (m, 1 H), 2.77 (m, 1 H), 2.01 (m, 5 H), 1.74 (m, 1 H), 1.59 (m, 1 H). Mass spectrum (apci) m/z = 579.2 (M + H − 2HCl). |
| 209 | 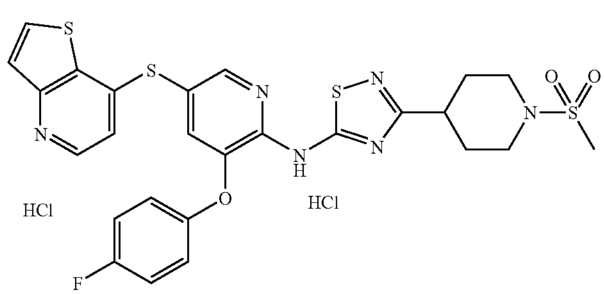 | N-(3-(4-fluorophenoxy)-5-(thieno[3,2-b]pyridin-7-ylthio)pyridin-2-yl)-3-(1-(methylsulfonyl)-piperidin-4-yl)-1,2,4-thiadiazol-5-amine dihydrochloride | $^1$H NMR (d$_6$-DMSO) δ 12.53 (bs, 1 H), 8.61 (d, 1 H), 8.54 (d, 1 H), 8.39 (d, 1 H), 7.72 (d, 1 H), 7.61 (d, 1 H), 7.23 (m, 4 H), 7.14 (d, 1 H), 3.60 (m, 2 H), 2.92 (m, 2 H), 2.88 (s, 3 H), 2.14 (m, 2 H), 1.82 (m, 2 H). Mass spectrum (apci) m/z = 615.2 (M + H − 2HCl). |
| 210 | 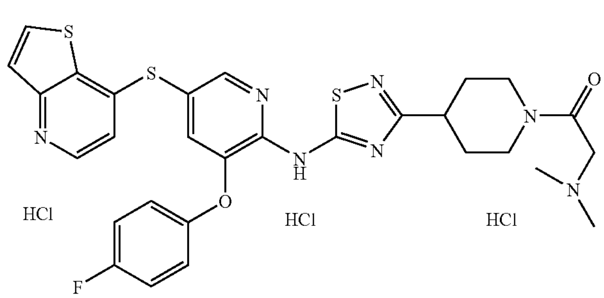 | 2-(dimethylamino)-1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone trihydrochloride | $^1$H NMR (d$_6$-DMSO) δ 12.49 (bs, 1 H), 9.61 (bs, 1 H), 8.58 (d, 1 H), 8.52 (d, 1 H), 8.33 (d, 1 H), 7.69 (d, 1 H), 7.59 (d, 1 H), 7.23 (m, 4 H), 7.08 (d, 1 H), 4.32 (m, 2 H), 3.65 (m, 1 H), 3.19 (m, 2 H), 2.96 (m, 1 H), 2.82 (m, 7H), 2.09 (m, 2 H), 1.82 (m, 1 H), 1.65 (m, 1 H). Mass spectrum (apci) m/z = 622.2 (M + H − 3HCl). |

Example 211

3-(phenylthio)-N-(3-(piperidin-4-yl)-1,2,4-thiadiazol-5-yl)-5-(thieno[3,2-b]pyridin-7-ylthio)pyridin-2-amine dihydrochloride

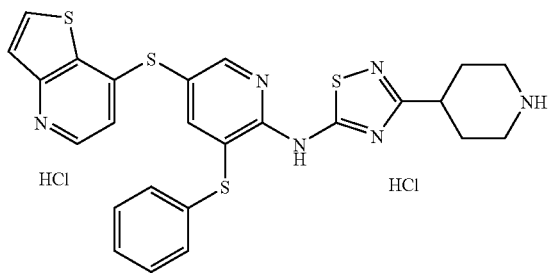

Step A: Preparation of tert-butyl 4-(2-(5-(3-methoxy-3-oxopropylthio)-3-(phenylthio)pyridin-2-ylamino)thiazol-4-yl)piperidine-1-carboxylate: Prepared according to the method of Example 13 from tert-butyl 4-(2-(5-bromo-3-(phenylthio)pyridin-2-ylamino)thiazol-4-yl)piperidine-1-carboxylate.

Step B: Preparation of tert-butyl 4-(5-(3-(phenylthio)-5-(thieno[3,2-b]pyridin-7-ylthio)pyridin-2-ylamino)-1,2,4-thiadiazol-3-yl)piperidine-1-carboxylate Prepared according to the method of Example 127.

Step C: Preparation of 3-(phenylthio)-N-(3-(piperidin-4-yl)-1,2,4-thiadiazol-5-yl)-5-(thieno[3,2-b]pyridin-7-ylthio)pyridin-2-amine dihydrochloride: Tert-butyl 4-(5-(3-(phenylthio)-5-(thieno[3,2-b]pyridin-7-ylthio)pyridin-2-ylamino)-1,2,4-thiadiazol-3-yl)piperidine-1-carboxylate was dissolved in 1:1 $CH_2Cl_2$:methanol (4 mL) and 4N HCl in dioxane added (2 mL) and stirred at ambient temperature for 1 hour. The solvent was removed and placed on high vacuum to afford the title compound (100 mg, 89.6% yield) as a yellow solid. $^1$H NMR ($d_6$-DMSO) δ 8.70 (m, 2H), 8.20 (m, 3H), 7.95 (m, 1H), 7.40 (m, 5H), 3.80-3.05 (m, 9H). Mass spectrum (apci) m/z=535.2 (M+H-3HCl).

Using the procedure in Example 211, steps A and B or steps A-C, the following compounds were prepared.

| Example | Structure | Name | Data |
|---|---|---|---|
| 212 | 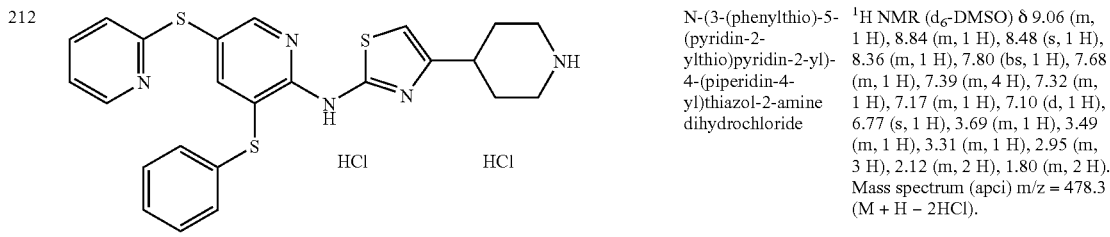 | N-(3-(phenylthio)-5-(pyridin-2-ylthio)pyridin-2-yl)-4-(piperidin-4-yl)thiazol-2-amine dihydrochloride | $^1$H NMR ($d_6$-DMSO) δ 9.06 (m, 1 H), 8.84 (m, 1 H), 8.48 (s, 1 H), 8.36 (m, 1 H), 7.80 (bs, 1 H), 7.68 (m, 1 H), 7.39 (m, 4 H), 7.32 (m, 1 H), 7.17 (m, 1 H), 7.10 (d, 1 H), 6.77 (s, 1 H), 3.69 (m, 1 H), 3.49 (m, 1 H), 3.31 (m, 1 H), 2.95 (m, 3 H), 2.12 (m, 2 H), 1.80 (m, 2 H). Mass spectrum (apci) m/z = 478.3 (M + H − 2HCl). |
| 213 | 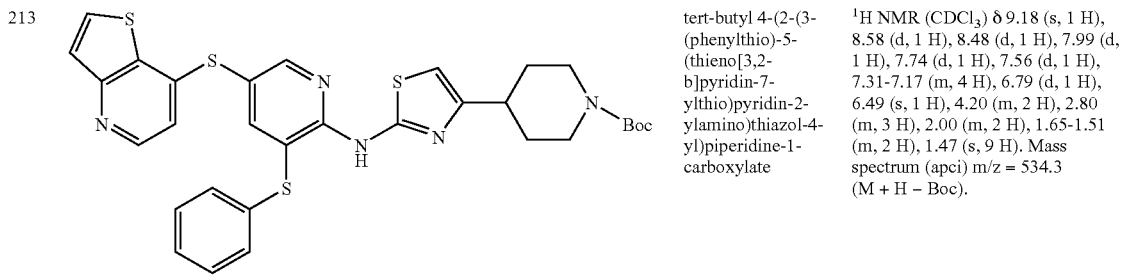 | tert-butyl 4-(2-(3-(phenylthio)-5-(thieno[3,2-b]pyridin-7-ylthio)pyridin-2-ylamino)thiazol-4-yl)piperidine-1-carboxylate | $^1$H NMR (CDCl$_3$) δ 9.18 (s, 1 H), 8.58 (d, 1 H), 8.48 (d, 1 H), 7.99 (d, 1 H), 7.74 (d, 1 H), 7.56 (d, 1 H), 7.31-7.17 (m, 4 H), 6.79 (d, 1 H), 6.49 (s, 1 H), 4.20 (m, 2 H), 2.80 (m, 3 H), 2.00 (m, 2 H), 1.65-1.51 (m, 2 H), 1.47 (s, 9 H). Mass spectrum (apci) m/z = 534.3 (M + H − Boc). |
| 214 | 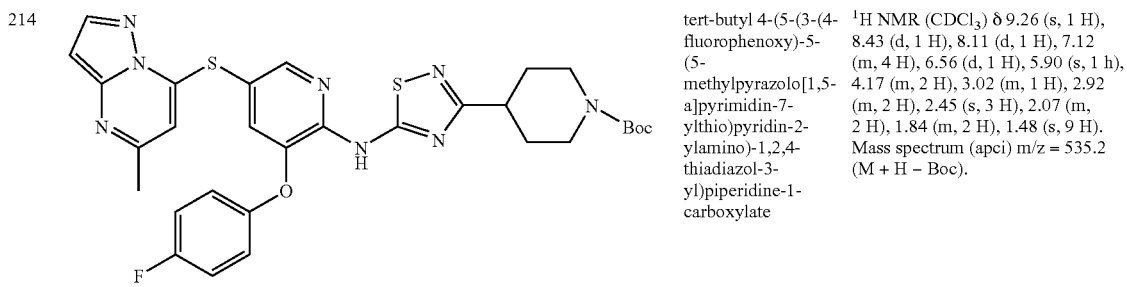 | tert-butyl 4-(5-(3-(4-fluorophenoxy)-5-(5-methylpyrazolo[1,5-a]pyrimidin-7-ylthio)pyridin-2-ylamino)-1,2,4-thiadiazol-3-yl)piperidine-1-carboxylate | $^1$H NMR (CDCl$_3$) δ 9.26 (s, 1 H), 8.43 (d, 1 H), 8.11 (d, 1 H), 7.12 (m, 4 H), 6.56 (d, 1 H), 5.90 (s, 1 h), 4.17 (m, 2 H), 3.02 (m, 1 H), 2.92 (m, 2 H), 2.45 (s, 3 H), 2.07 (m, 2 H), 1.84 (m, 2 H), 1.48 (s, 9 H). Mass spectrum (apci) m/z = 535.2 (M + H − Boc). |

Example 215

Sodium 4-(6-(4-methylthiazol-2-ylamino)-5-phenoxypyridin-3-ylthio)benzoate

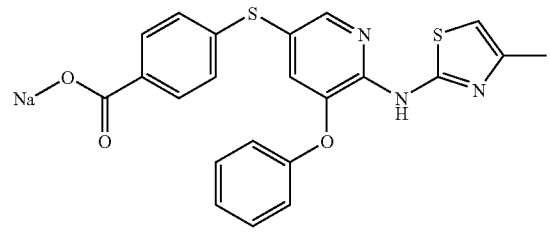

Step A: Preparation of methyl 4-(6-(4-methylthiazol-2-ylamino)-5-phenoxypyridin-3-ylthio)benzoate: Prepared according to the method of Example 127 from methyl 3-(6-(4-methylthiazol-2-ylamino)-5-phenoxypyridin-3-ylthio) propanoate.

Step B: Preparation of 4-(6-(4-methylthiazol-2-ylamino)-5-phenoxypyridin-3-ylthio)benzoic acid: Prepared according to the method of Example 45 to afford the title compound (10.3 mg, 38.0% yield) as a white solid. $^1$H NMR (d$_6$-DMSO) δ 8.26 (m, 1H), 7.82 (m, 2H), 7.39 (m, 2H), 7.28 (m, 1H), 7.18 (m, 3H), 7.10 (m, 2H), 6.65 (s, 1H), 2.25 (s, 3H). Mass spectrum (apci) m/z=436.3 (M+H—Na).

Using the procedure in Example 215, the following compounds were prepared.

Example 218

N-(5-(6,7-dihydro-5H-pyrrolo[3,4-b]pyridin-4-ylthio)-3-phenoxypyridin-2-yl)-4-methylthiazol-2-amine trihydrochloride

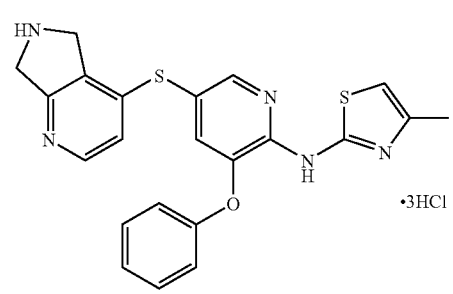

Step A: Preparation of ethyl 5H-pyrrolo[3,4-b]pyridine-6(7H)-carboxylate N-oxide: mCPBA (7.3 g, 30 mmol) was added into a solution of ethyl 5H-pyrrolo[3,4-b]pyridine-6(7H)-carboxylate (5 g, 26 mmol) in CH$_2$Cl$_2$ (200 mL) and stirred for 2 hours. The reaction was poured into water and extracted with CH$_2$Cl$_2$. The organic layer was washed with aqueous sodium bisulfate, NaHCO$_3$ and brine, dried with Na$_2$SO$_4$, filtered and concentrated to afford the title compound (4 g, 74% yield) as a white solid.

Step B: Preparation of ethyl 4-chloro-5H-pyrrolo[3,4-b]pyridine-6(7H)-carboxylate: POCl$_3$ (20 mL, 218 mmol) was

| Example | Structure | Name | Data |
|---|---|---|---|
| 216 | 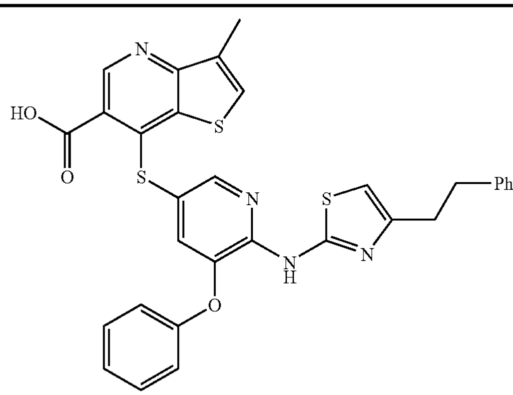 | 3-methyl-7-(6-(4-phenethylthiazol-2-ylamino)-5-phenoxypyridin-3-ylthio)thieno[3,2-b]pyridine-6-carboxylic acid | $^1$H NMR (d$_6$-DMSO) δ 11.20 (bs, 1 H), 8.94 (s, 1 H), 8.34 (m, 1 H), 7.77 (s, 1 H), 7.33-7.14 (m, 9 H), 7.08 (t, 1 H), 6.95 (d, 1 H), 6.68 (s, 1 H), 2.98-2.83 (m, 4 H), 2.36 (s, 3 H), Mass spectrum (apci) m/z = 597.2 (M + H). |
| 217 | | 3-methyl-7-(6-(4-methylthiazol-2-ylamino)-5-phenoxypyridin-3-ylthio)thieno[3,2-b]pyridine-6-carboxylic acid | $^1$H NMR (d$_6$-DMSO) δ 8.98 (s, 1H), 8.36 (d, 1 H), 7.87 (s, 1 H), 7.40-7.05 (m, 4 H), 6.95 (m, 2 H), 6.65 (bs, 1 H), 2.38 (s, 3 H), 2.24 (s, 3 H). Mass spectrum (apci) m/z = 507.1 (M + H). | added into ethyl 5H-pyrrolo[3,4-b]pyridine-6(7H)-carboxylate N-oxide (1 g, 4.80 mmol) and heated to 35° C. for 12 hours and 50° C. for another 5 hours. The solvent was evaporated and poured into water. The material was extracted with $CH_2Cl_2$, washed with $NaHCO_3$ and brine, dried with $Na_2SO_4$, filtered and concentrated. The residue was purified on silica gel to afford the title compound (0.5 g, 45.9% yield).

Step C: Preparation of 5-(6,7-dihydro-5H-pyrrolo[3,4-b]pyridin-4-ylthio)-N-(4-methylthiazol-2-yl)-3-phenoxypyridin-2-amine trihydrochloride: A 10 mL round-bottomed flask was charged with methyl 3-(6-(4-methylthiazol-2-ylamino)-5-phenoxypyridin-3-ylthio)propanoate (65 mg, 0.16 mmol), ethyl 4-chloro-5H-pyrrolo[3,4-b]pyridine-6(7H)-carboxylate (55 mg, 0.24 mmol), and DMSO (2 mL). The reaction was bubbled through with nitrogen and potassium 2-methylpropan-2-olate (54 mg, 0.49 mmol) was added and stirred at ambient temperature for 30 minutes. The reaction was poured into saturated aqueous $NH_4Cl$ and extracted with EtOAc. The organic layer was dried with sodium sulfate, filtered and concentrated. The residue was purified on silica gel (50% EtOAc in hexanes) to afford a residue that was dissolved in methanol, KOH (xs) and water (0.5 mL) added and heated to 60° C. over the weekend. The reaction was poured into saturated aqueous $NH_4Cl$ and extracted with EtOAc. The organic layer was dried with sodium sulfate, filtered and concentrated. The residue was purified on silica gel (100% EtOAc to 20% methanol in $CH_2Cl_2$ with 0.2% ammonia) to afford the title compound (29 mg, 33% yield) as a yellow solid after HCl salt formation. $^1H$ NMR ($d_6$-DMSO) δ 10.12 (bs, 2H), 8.34 (d, 1H), 8.31 (d, 1H), 7.42 (m, 2H), 7.36 (d, 1H), 7.17 (m, 3H), 6.84 (d, 1H), 6.76 (s, 1H), 4.47 (m, 4H), 2.28 (s, 3H). Mass spectrum (apci) m/z=434.2 (M+H-3HCl).

Example 219

N-(4-methylthiazol-2-yl)-3-phenoxy-5-(5,6,7,8-tetrahydropyrido[4,3-d]pyrimidin-4-ylthio)pyridin-2-amine trihydrochloride

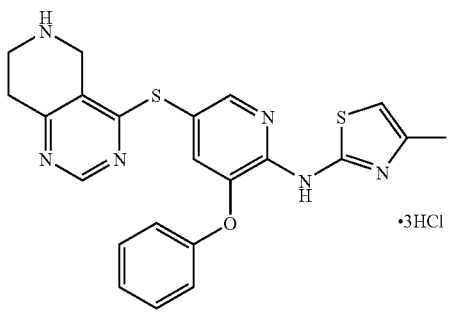

Step A: Preparation of tert-butyl 4-chloro-7,8-dihydropyrido[4,3-d]pyrimidine-6(5H)-carboxylate: A mixture of $PPh_3$ (81.4 g, 310 mmol) and N-chlorosuccinimide (41.4 g, 310 mmol) in dioxane (850 mL) was stirred at ambient temperature for 30 minutes. To this suspension was added tert-butyl 4-hydroxy-7,8-dihydropyrido[4,3-d]pyrimidine-6(5H)-carboxylate and the mixture stirred at 50° C. for 18 hours. The mixture was subsequently treated with triethylamine (25 mL, 183 mmol) and the resulting brown solution concentrated. The black oil was dry packed onto silica gel and purified by chromatography eluting with 15-20% EtOAc/Hexanes to give the title compound as a yellow gum.

Step B: Preparation of afford N-(4-methylthiazol-2-yl)-3-phenoxy-5-(5,6,7,8-tetrahydropyrido[4,3-d]pyrimidin-4-ylthio)pyridin-2-amine trihydrochloride: Prepared according to the method of Example 218, Step B. $^1H$ NMR ($d_6$-DMSO) δ 9.56 (bs, 2H), 8.75 (s, 1H), 8.24 (d, 1H), 7.43 (m, 2H), 7.34 (m, 1H), 7.15 (m, 3H), 6.70 (s, 1H), 4.21 (m, 2H), 3.04 (m, 2H), 2.26 (s, 3H). Mass spectrum (apci) m/z=449.2 (M+H-3HCl).

Example 220

1-(4-((5-(3-(4-fluorophenoxy)-5-(thieno[3,2-b]pyridin-7-ylthio pyridin-2-ylamino)-1,2,4-thiadiazol-3-yl)methyl)piperidin-1-yl)ethanone dihydrochloride

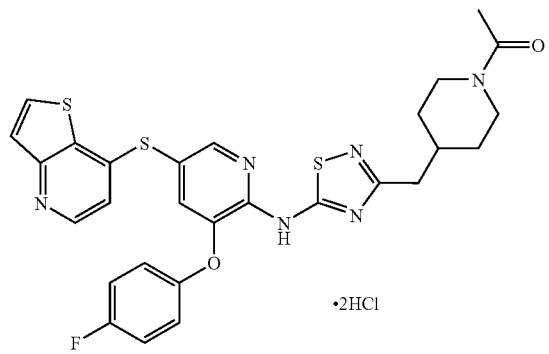

Step A: Preparation of tert-butyl 4-((5-(3-(4-fluorophenoxy)-5-(thieno[3,2-b]pyridin-7-ylthio)pyridin-2-ylamino)-1,2,4-thiadiazol-3-yl)methyl)piperidine-1-carboxylate: Prepared according to the method of Example 127.

Step B: Preparation of 3-(4-fluorophenoxy)-N-(3-(piperidin-4-ylmethyl)-1,2,4-thiadiazol-5-yl)-5-(thieno[3,2-b]pyridin-7-ylthio)pyridin-2-amine trihydrochloride: Prepared according to the method of Example 196, step C.

Step C: Preparation of 1-(4-((5-(3-(4-fluorophenoxy)-5-(thieno[3,2-b]pyridin-7-ylthio)pyridin-2-ylamino)-1,2,4-thiadiazol-3-yl)methyl)piperidin-1-yl)ethanone dihydrochloride: Prepared according to the method of Example 198. $^1H$ NMR ($d_6$-DMSO) δ 12.47 (bs, 1H), 8.57 (d, 1H), 8-51 (d, 1H), 8.33 (d, 1H), 7.68 (d, 1H), 7.57 (Z, 1H), 7.23 (m, 4H), 7.08 (d, 1 h), 4.34 (m, 1H), 3.78 (m, 1H), 2.98 (t, 1H), 2.72 (d, 2H), 2.09 (m, 1H), 1.97 (s, 3H), 1.65 (m, 2H), 1.18 (m, 1H), 1.05 (m, 1H). Mass spectrum (apci) m/z=593.2 (M+H-2HCl).

The following compounds were prepared according to the method of Example 220.

| Example | Structure | Name | Data |
|---|---|---|---|
| 221 | 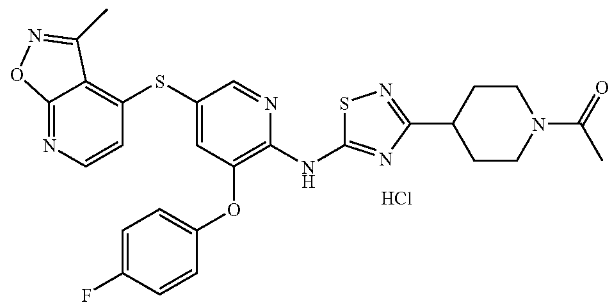 | 1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone hydrochloride | $^1$H NMR (d$_6$-DMSO) δ 12.48 (bs, 1 H), 8.49 (d, 1 H), 8.32 (d, 1 H), 7.54 (m, 1 H), 7.25 (m, 4 H), 6.75 (d, 1 H), 4.32 (m, 1 H), 3.85 (m, 1 H), 3.20 (m, 1 H), 3.07 (m, 1 H), 2.77 (m, 1 H), 2.69 (s, 3 H), 2.02 (m, 5 H), 1.74 (m, 1 H), 1.60 (m, 1 H). Mass spectrum (esi) m/z = 578.1 (M + H − HCl). |
| 222 | 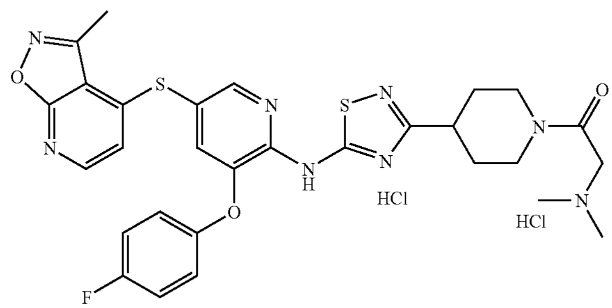 | 2-(dimethylamino)-1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone dihydrochloride | $^1$H NMR (d$_6$-DMSO) δ 12.48 (bs, 1 H), 9.54 (bs, 1 H), 8.49 (d, 1 H), 8.32 (d, 1 H), 7.55 (d, 1 H), 7.25 (m, 4 H), 6.74 (d, 1 H), 4.32 (m, 3 H), 3.65 (m, 1 H), 3.20 (m, 2 H), 2.96 (m, 1 H), 2.82 (d, 6 H), 2.70 (s, 3 H), 2.09 (m, 2 H), 1.82 (m, 1 H), 1.65 (m, 1 H). Mass spectrum (esi) m/z = 621.1 (M + H − 2HCl) |

Example 223 tert-Butyl 4-(5-(3-phenoxy-5-(thieno[3,2-b]pyridin-7-ylthio)pyridin-2-ylamino)-1,2,4-thiadiazol-3-yl)piperidine-1-carboxylate

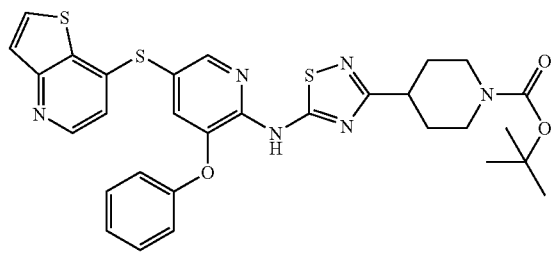

Step A: Preparation of tert-butyl 4-(5-(5-bromo-3-phenoxypyridin-2-ylamino)-1,2,4-thiadiazol-3-yl)piperidine-1-carboxylate: Prepared according to the method of Example 183 step D.

Step B: Preparation of tert-butyl 4-(5-(5-(3-methoxy-3-oxopropylthio)-3-phenoxypyridin-2-ylamino)-1,2,4-thiadiazol-3-yl)piperidine-1-carboxylate: Prepared according to the method of Example 13.

Step C: Preparation of tert-butyl 4-(5-(3-phenoxy-5-(thieno[3,2-b]pyridin-7-ylthio)pyridin-2-ylamino)-1,2,4-thiadiazol-3-yl)piperidine-1-carboxylate: Prepared according to the method of Example 127. $^1$H NMR (CDCl$_3$) δ 9.18 (s, 1H), 8.48 (d, 1H), 8.37 (d, 1H), 7.79 (d, 1H), 7.55 (d, 1H), 7.40 (m, 2H), 7.24 (m, 2H), 7.06 (m, 2H), 6.77 (d, 1H), 4.16 (m, 2H), 3.00 (m, 1H), 2.91 (m, 2H), 2.05 (m, 2H), 1.83 (m, 2H), 1.47 (s, 9H). Mass spectrum (esi) m/z=519.2 (M+H-Boc).

Example 224

N-(5-((3-methoxypyridin-2-ylmethylthio)-3-phenoxypyridin-2-yl)-4-methylthiazol-2-amine hydrochloride

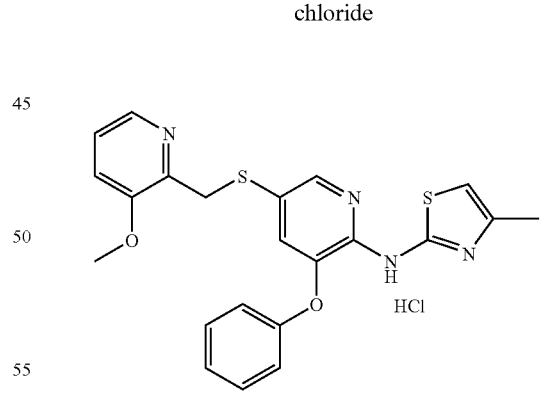

Placed 2-((6-(4-methylthiazol-2-ylamino)-5-phenoxypyridin-3-ylthio)methyl)pyridine-3-ol (prepared in Example 69) (0.180 g, 0.426 mmol) in DMF (5 mL) and cooled to 0° C. Sodium hydride (0.0307 g, 1.28 m-mol) was added and stirred for 10 minutes then MeI (0.0605 g, 0.426 mmol) was added stirred at ambient temperature for 30 minutes. Added water and extracted with CH$_2$Cl$_2$. The organic layer was concentrated and purified by silica gel. The product was still impure. Mixture was purified by medium pressure reverse phase followed by two high pressure reverse phase purifications. Combined all clean fractions then dissolved in $CH_2Cl_2$ and added HCl in ether, then concentrated to give the title compound (0.0085 g, 4.22% yield). $^1$H NMR ($d_6$-DMSO) δ 8.14 (m, 1H), 8.10 (d, 1H), 7.65 (m, 1H), 7.55 (m, 1H), 7.34-7.27 (m, 3H), 7.03 (m, 1H), 6.85 (d, 2H), 6.36 (s, 1H), 4.24 (s, 2H), 3.17 (s, 3H), 2.18 (s, 3H).

Example 225

4-methyl-N-(3-phenoxy-5-(piperidin-4-yl)pyridin-2-ylmethylthio)pyridin-2-yl)thiazol-2-amine tris(2,2,2-trifluoroacetate)

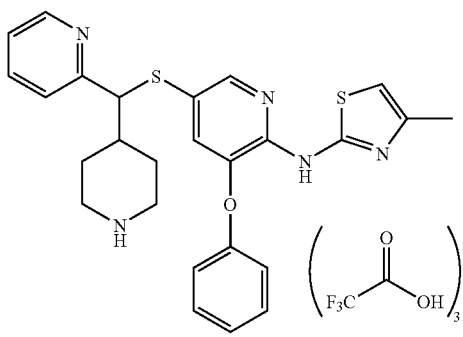

Step A: Preparation of give tert-butyl 4-(hydroxy(pyridin-2-yl)methyl)piperidine-1-carboxylate: Placed 2-bromopyridine (0.833 g, 5.27 mmol) in THF (25 mL) and cooled to −78° C. Butyllithium (2.11 mL, 5.27 mmol) was slowly added and stirred for 5 minutes. Dissolved tert-butyl 4-formylpiperidine-1-carboxylate (0.500 g, 2.34 mmol) in THF (3 mL) and added slowly to the above solution then stirred at −78° C. for 30 minutes. Added ammonium chloride and extracted with $CH_2Cl_2$. Concentrated and purified by silica gel to give the title compound (0.229 g, 33.4% yield)

Step B: Preparation of tert-butyl 4-((methylsulfonyloxy)(pyridin-2-yl)methyl)piperidine-1-carboxylate: Placed 2-bromopyridine (0.833 g, 5.27 mmol) in THF (25 mL) and cooled to −78° C. Slowly added butyl lithium (2.11 mL, 5.27 mmol) and stirred for 5 min. Dissolved tert-butyl 4-formylpiperidine-1-carboxylate (0.500 g, 2.34 mmol) in THF (3 mL) and added slowly to the above solution and stirred at −78° C. for 30 min. Added ammonium chloride and extracted with $CH_2Cl_2$. Concentrated and purified by silica gel to give the title compound (0.229 g, 33.4% yield)

Step C: Preparation of gave tert-butyl 4-((6-(4-methylthiazol-2-ylamino)-5-phenoxypyridin-3-ylthio)(pyridin-2-yl)methyl)piperidine-1-carboxylate: Prepared according to the method of Example 16.

Step D: Preparation of 4-methyl-N-(3-phenoxy-5-(piperidin-4-yl(pyridin-2-yl)methylthio)pyridin-2-yl)thiazol-2-amine tris(2,2,2-trifluoroacetate): Placed $Me_2S$ (0.0072 g, 0.12 mmol) in Trifluoroacetic acid (10 mL) followed by tert-butyl 4-((6-(4-methylthiazol-2-ylamino)-5-phenoxypyridin-3-ylthio)(pyridin-2-yl)methyl)piperidine-1-carboxylate (0.068 g, 0.12 mmol) stirred at ambient temperature for 30 minutes, then concentrated to give the title compound (0.086 g, 90% yield). $^1$H NMR ($d_6$-DMSO) δ 8.52 (bs, 1H), 8.42 (m, 1), 8.17 (bs, 1H), 8.00 (d, 1H), 7.70 (dt, 1H), 7.41 (t, 2H), 7.25-7.16 (m, 3H), 6.92 (d, 2H), 6.90 (s, 1H), 6.63 (s, 1H), 4.22 (d, 1H), 3.32 (d, 1H), 3.17 (d, 1H), 2.9872.74 (m, 2H), 2.30 (m, 2H), 2.23 (s, 3H), 1.45 (m, 2H), 1.30 (m, 1H).

The following compounds were also made according to the procedure of Example 225.

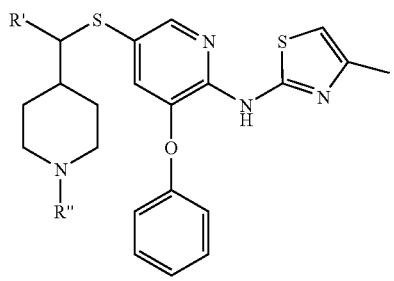

| Example | R | R" | Name | NMR |
|---|---|---|---|---|
| 226 | pyrazinyl-methyl | H | 4-methyl-N-(3-phenoxy-5-(piperidin-4-yl(pyrazin-2-yl)methylthio)pyridin-2-yl)thiazol-2-amine bis(2,2,2-trifluoroacetate) | $^1$H NMR ($d_6$-DMSO) δ 8.53-8.43 (m, 3 H), 8.16 (m, 1 H), 7.98 (s, 1 H), 7.42 (t, 2 H), 7.19 (t, 1 H), 6.92 (d, 2 H), 6.63 (s, 1 H), 4.34 (d, 1 H), 3.33 (d, 1 H), 3.17 (d, 1 H), 2.97-2.75 (m, 2 H), 2.33 (m, 2 H), 2.23 (s, 3 H), 1.47 (m, 2 H), 1.28 (m, 1 H) |
| 227 | pyrimidinyl-methyl | H | 4-methyl-N-(3-phenoxy-5-(piperidin-4-yl(pyrimidin-2-yl)methylthio)pyridin-2-yl)thiazol-2-amine bis(2,2,2-trifluoroacetate) | $^1$H NMR ($d_6$-DMSO) δ 8.67 (d, 2 H), 8.50 (m, 1 H), 8.16 (m, 1 H), 7.98 (d, 1 H), 7.43 (t, 2 H), 7.33 (t, 1 H), 7.20 (t, 1 H), 6.97 (d, 2 H), 6.90 (d, 1 H), 6.63 (s, 1 H), 4.15 (d, 1 H), 3.34 (d, 1 H), 3.16 (d, 1 H), 2.98-2.75 (m, 2 H), 2.35 (m, 2 H), 2.23 (s, 3 H), 1.60-1.23 (m, 3 H) |

-continued

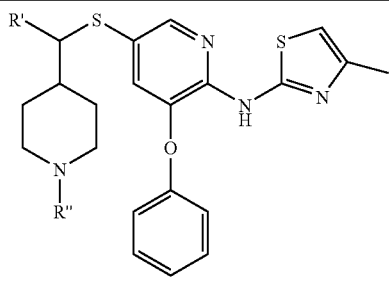

| Example | R | R" | Name | NMR |
|---|---|---|---|---|
| 228 | 3-chloro-2-methylpyridin-2-yl | BOC | tert-butyl 4-((3-chloropyridin-2-yl)(6-(4-methylthiazol-2-ylamino)-5-phenoxypyridin-3-ylthio)methyl)piperidine-1-carboxylate | $^1$H NMR ($d_6$-DMSO) δ 10.85 (bs, 1 H), 8.42 (m, 1 H), 7.89 (m, 1 H), 7.81 (d, 1 H), 7.43 (t, 2 H), 7.23 (m, 2 H), 6.97 (d, 2 H), 6.78 (m, 1 H), 6.61 (s, 1 H), 4.40 (d, 1 H), 4.01 (m, 1 H), 3.80 (m, 1 H), 2.70 (m, 1 H), 2.23 (m, 5 H), 1.32 (s, 9 H), 1.27-1.11 (m, 3 H), 0.94 (m, 1 H) |
| 229 | 3-chloro-2-methylpyridin-2-yl | H | N-(5-((3-chloropyridin-2-yl)(piperidin-4-yl)methylthio)-3-phenoxypyridin-2-yl)-4-methylthiazol-2-amine bis(2,2,2-trifluoroacetate) | $^1$H NMR ($d_6$-DMSO) δ 8.55 (d, 1 H), 8.41 (dd, 1 H), 8.15 (m, 1 H), 7.95 (d, 1 H), 7.85 (dd, 1 H), 7.44 (t, 2 H), 7.23 (dd, 1 H), 7.21 (t, 1 H), 6.97 (d, 2 H), 6.76 (d, 1 H), 6.64 (s, 1 H), 4.39 (d, 1 H), 3.35 (d, 1 H), 3.14 (d, 1 H), 2.93 (m, 1 H), 2.80 (m, 1 H), 2.40 (m, 2 H), 2.24 (s, 3 H), 1.51 (m, 1 H), 1.37 (m, 1 H), 1.25 (m, 1 H) |

Example 230

N-(2-(dimethylaminoethyl)-3-(2-(4-isobutylthiazol-2-ylamino)-5-(pyrimidin-2-ylthio)pyridin-3-yloxy)benzamide dihydrochloride

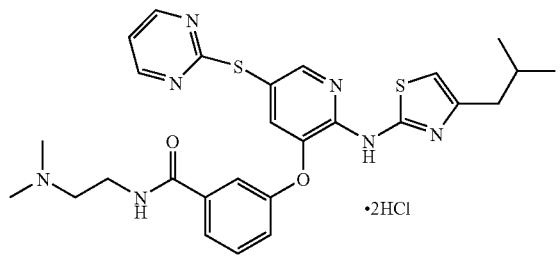

Step A: Preparation of ethyl 3-(2-aminopyridin-3-yloxy)benzoate hydrochloride: Placed ethyl 3-(2-aminopyridin-3-yloxy)-4-chlorobenzoate (prepared according to Example 39, Step B; 8.96 g, 30.6 mmol) and Pd(OH)$_2$/C (0.86 g, 6.2 mmol) in EtOH (200 mL) and placed under balloon hydrogen pressure for 18 hours. The reaction mixture was transferred to a Parr bottle and the pressure was increased to 30 psi for several hours, and then the hydrogen pressure was increased to 50 psi for 2 more days. The reaction mixture was filtered though a plug of celite and concentrated to give the title compound e (8.3 g, 92.04% yield).

Step B: Preparation of ethyl 3-(2-amino-5-bromopyridin-3-yloxy)benzoate: Prepared according to the method of Example 10, Step B.

Step C: Preparation of ethyl 3-(5-bromo-2-(3-(4-chlorobenzoyl)thioureido)pyridine-3-yloxy)benzoate: Prepared according to the method of Example 39, Step D.

Step D: Preparation of ethyl 3-(5-bromo-2-thioureidopyridin-3-yloxy)benzoate: Prepared according to the method of Example 39, Step E.

Step E: Preparation of 3-(5-bromo-2-(4-isobutylthiazol-2-ylamino)pyridine-3-yloxy)benzoate: Prepared according to the method of Example 39, Step F.

Step F: Preparation of ethyl 3-(2-(4-isobutylthiazol-2-ylamino)-5-(3-methoxy-3-oxopropylthio)pyridine-3-yloxy)benzoate: Prepared according to the method of Example 13.

Step G: Preparation of ethyl 3-(2-(4-isobutylthiazol-2-ylamino)-5-(pyrimidin-2-ylthio)pyridine-3-yloxy)benzoate: Prepared according to the method of Example 127.

Step H: Preparation of 3-(2-(4-isobutylthiazol-2-ylamino)-5-(pyrimidin-2-ylthio)pyridine-3-yloxy)benzoic acid: Prepared according to the method of Example 70, Step B.

Step I: Preparation of N-(2-(dimethylamino)ethyl)-3-(2-(4-isobutylthiazol-2-ylamino)-5-(pyrimidin-2-ylthio)-pyridine-3-yloxy)benzamide dihydrochloride: Prepared according to the method of Example 7.

Example 231

2-(4-((6-(4-methylthiazol-2-ylamino)-5-phenoxypyridin-3-ylthio)(pyridin-2-yl)methyl)piperidin-1-yl)ethanol trihydrochloride

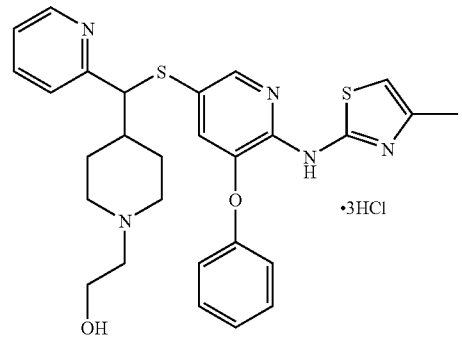

Prepared according to the method of Example 175 from N-(4-methylthiazol-2-yl)-3-phenoxy-5-(piperidin-4-yl(pyridin-2-yl)methylthio)pyridin-2-amine and 2-hydroxyacetaldehyde. $^1$H NMR (d$_6$-DMSO), δ 9.95 (bs, 1H), 8.50 (d, 1H), 8.04 (s, 1H), 7.88 (m, 1H), 7.48-7.36 (m, 4H), 7.22 (t, 1H), 6.97 (m, 3H), 6.76 (s, 1H), 4.32 (d, 1H), 3.73 (m, 2H), 3.57 (d, 1H), 3.40 (d, 1H), 3.07 (m, 2H), 3.01-2.80 (m, 2H), 2.40-2.21 (m, 6H), 1.71 (m, 1H), 1.57 (m, 1H), 1.42 (d, 1H).

The following compounds were made according to the method of Example 175.

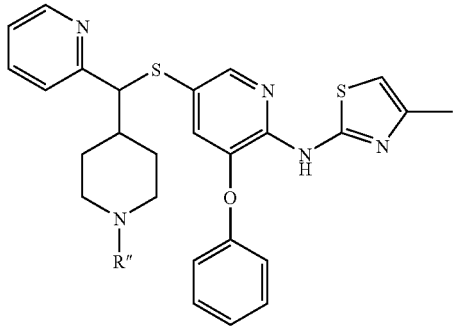

| Example | R" | Name | Data |
|---|---|---|---|
| 232 | Me | 4-methyl-N-(5-((1-methylpiperidin-4-yl)(pyridin-2-yl)methylthio)-3-phenoxypyridin-2-yl)thiazol-2-amine trihydrochloride | $^1$H NMR (d$_6$-DMSO) δ 10.15 (bs, 1H), 8.47 (d, 1H), 8.02 (d, 1H), 7.80 (t, 1H), 7.44 (t, 2H), 7.33 (m, 2H), 7.21 (t, 1H), 6.96 (m, 3H), 6.72 (s, 1H), 4.26 (d, 1H), 3.44 (m, 1H), 3.27 (m, 1H), 2.98-2.76 (m, 2H), 2.67 (d, 3H), 2.38 (d, 1H), 2.2 (s, 3H), 1.63 (m, 1H), 1.45 (m, 2H) |
| 233 | iPr | N-(5-((1-isopropylpiperidin-4-yl)(pyridine-2-yl)methylthio)-3-phenoxypyridin-2-yl)-4-methylthiazol-2-amine trihydrochloride | $^1$H NMR (d$_6$-DMSO) δ 9.72 (bs, 1H), 8.46 (d, 1H), 8.02 (d, 1H), 7.79 (t, 1H), 7.43 (t, 2H), 7.32 (m, 2H), 7.21 (t, 1H), 6.94 (m, 3H), 6.70 (s, 1H), 4.25 (d, 1H), 3.39 (m, 1H), 3.23 (m, 1H), 3.39 (m, 1H), 3.23 (m, 1H), 3.00-2.80 (m, 2H), 2.35 (m, 2H), 2.25 (s, 3H), 1.71 (m, 6H) |

Example 234

1-((6-(4-methylthiazol-2-ylamino)-5-phenoxypyridin-3-ylthio)methyl)pyrrolidin-2-one

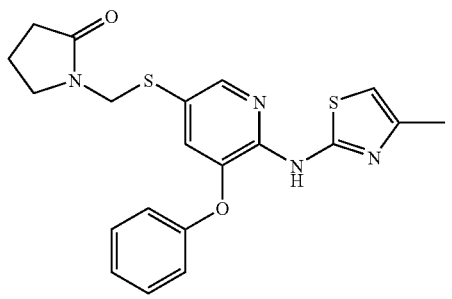

Step A: Preparation of 1-(chloromethyl)pyrrolidin-2-one: Placed pyrrolidin-2-one (2.00 g, 23.5 mmol), and paraformaldehyde (1.06 g, 35.3 mmol) in chlorotrimethylsilane (60 mL) and heated to reflux for 2 hours and then concentrated to give the title compound (2.97 g, 94.6% yield).

Step B: Preparation of 1-((6-(4-methylthiazol-2-ylamino)-5-phenoxypyridin-3-ylthio)methyl)pyrrolidin-2-one: Prepared according to the method of Example 16. $^1$H NMR (d$_6$-DMSO) δ 10.83 (bs, 1H), 8.16 (d, 1H), 7.41 (t, 2H), 7.34 (d, 1H), 7.17 (t, 1H), 7.07 (d, 2H), 6.62 (s, 1H), 4.59 (s, 2H), 3.40 (t, 2H), 2.23 (s, 3H), 2.08 (t, 2H), 1.84 (m, 2H).

Example 235

Ethyl 2-(1-methylpiperidin-4-yl)-2-(6-(4-methylthiazol-2-ylamino)-5-phenoxypyridin-3-ylthio)acetate dihydrochloride

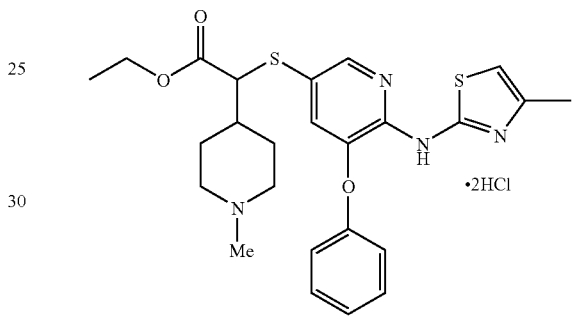

Step A: Preparation of tert-butyl 4-(2,2,2-trichloro-1-hydroxyethyl)piperidine-1-carboxylate: Placed 2,2,2-trichloroacetic acid (5.746 g, 35.17 mmol) in DMF (5 mL) and added slowly sodium 2,2,2-trichloroacetate (6.519 g, 35.17 mmol). The reaction was stirred for 10 minutes and tert-butyl 4-formylpiperidine-1-carboxylate (5.00 g, 23.44 mmol) was added. The reaction was stirred for 40 minutes then quenched with saturated sodium bicarbonate and filtered. The solids were washed with water and dried. The product was triturated with water and filtered to give the title compound (5.734 g, 73.53% yield).

Step B: Preparation of tert-butyl 4-(2-ethoxy-1-(6-(4-methylthiazol-2-ylamino)-5-phenoxypyridin-3-ylthio)-2-oxoethyl)piperidine-1-carboxylate: Placed methyl 3-(6-(4-methylthiazol-2-ylamino)-5-phenoxypyridin-3-ylthio) propanoate (2.20 g, 5.48 mmol), tert-butyl 4-(2,2,2-trichloro-1-hydroxyethyl)piperidine-1-carboxylate (1.86 g, 5.59 mmol), and sodium ethanolate (3.55 g, 10.9 mmol) in ethanol (75 mL) and stirred at ambient temperature for 4 hours. The reaction was quenched with sat NH$_4$Cl and extracted with CH$_2$Cl$_2$. The organic phase was concentrated and purified by silica gel (10-25% EtOAc in hex) to give the title compound (2.63 g, 75.5% yield).

Step C: Preparation of ethyl 2-(6-(4-methylthiazol-2-ylamino)-5-phenoxypyridin-3-ylthio)-2-(piperidin-4-yl)acetate: Prepared according to the method of Example 225, Step D.

Step D: Preparation of ethyl 2-(1-methylpiperidin-4-yl)-2-(6-(4-methylthiazol-2-ylamino)-5-phenoxypyridin-3-ylthio)acetate dihydrochloride: Prepared according to the method of Example 230. $^1$H NMR (d$_6$-DMSO) δ 9.84 (bs, 1H), 8.18 (d, 1H), 7.44 (t, 2H), 7.30 (d, 1H), 7.21 (t, 1H), 7.09 (d, 2H), 6.63 (s, 1H), 3.98 (q, 2H), 3.81 (m, 1H), 3.62 (d, 1H), 3.37 (m, 2H), 2.90 (m, 2H), 2.69 (d, 3H), 2.25 (s, 3H), 1.85-1.70 (m, 2H), 1.56 (m, 2H), 1.05 (t, 3H).

Example 236

2-(1-methylpiperidin-4-yl)-2-(6-(4-methylthiazol-2-ylamino)-5-phenoxypyridin-3-ylthio)ethanol

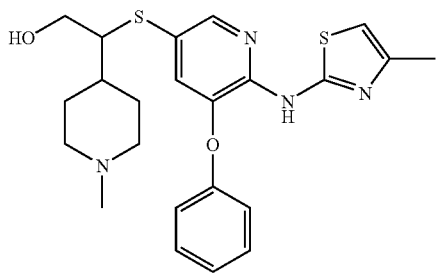

Placed ethyl 2-(1-methylpiperidin-4-yl)-2-(6-(4-methylthiazol-2-ylamino)-5-phenoxypyridin-3-ylthio)acetate (prepared in Example 235; 0.405 g, 0.812 mmol) in THF (8 mL) and cooled to 0° C. added LiAlH$_4$ (2.44 mL, 2.44 mmol) and warmed to ambient temperature for 30 minutes. Saturated NH$_4$Cl was slowly added and extracted with CH$_2$Cl$_2$. The organic layer was dried, filtered, and concentrated to give the title compound (0.315 g, 84.9% yield). $^1$H NMR (d$_6$-DMSO) δ 10.92 (bs, 1H), 8.16 (d, 1H), 7.41 (t, 2H), 7.33 (d, 1H), 7.17 (t, 1H), 7.05 (d, 2H), 6.60 (s, 1H), 4.82 (t, 1H), 3.49 (m, 2H), 2.87 (m, 1H), 2.80 (m, 2H), 2.23 (s, 3H), 2.15 (s, 3H), 1.86-1.53 (m, 6H), 1.29 (m, 1H).

Example 237

N-ethyl-2-(6-(4-methylthiazol-2-ylamino)-5-phenoxypyridin-3-ylthio)-2-(piperidin-4-yl)acetamide bis(2,2,2-trifluoroacetate)

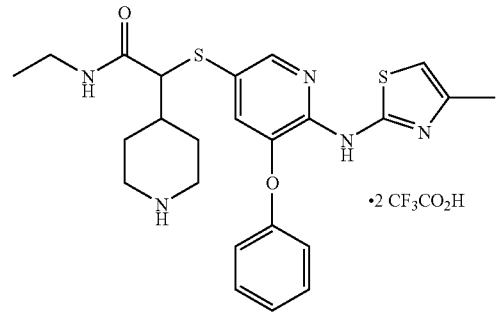

Step A: Preparation of 2-(1-(tert-butoxycarbonyl)piperidin-4-yl)-2-(6-(4-methylthiazol-2-ylamino)-5-phenoxypyridin-3-ylthio)acetic acid: Prepared according to the method of Example 70, Step B, using tert-butyl 4-(2-ethoxy-1-(6-(4-methylthiazol-2-ylamino)-5-phenoxypyridin-3-ylthio)-2-oxoethyl)piperidine-1-carboxylate (1.51 g, 2.59 mmol) and 4N NaOH (15 mL); (1.42 g, 98.6% yield).

Step B: Preparation of tert-butyl 4-(2-(ethylamino)-1-(6-(4-methylthiazol-2-ylamino)-5-phenoxypyridin-3-ylthio)-2-oxoethyl)piperidine-1-carboxylate: Prepared according to the method of Example 71, using ethyl carbonochloridate (0.0292 g, 0.269 mmol), and ethanamine; (0.034 g, 21.6% yield).

Step C: Preparation of N-ethyl-2-(6-(4-methylthiazol-2-ylamino)-5-phenoxypyridin-3-ylthio)-2-(piperidin-4-yl)acetamide bis(2,2,2-trifluoroacetate): Prepared according to the method of Example 225, Step D, to provide the title compound (0.040 g, 96% yield). $^1$H NMR (d$_6$-DMSO) δ 8.53 (m, 1H), 8.20 (m, 1H), 8.17 (d, 1H), 8.02 (t, 1H), 7.42 (t, 2H), 7.29 (d, 1H), 7.17 (t, 1H), 7.07 (d, 1H), 6.65 (s, 1H), 3.33 (d, 1H), 3.25 (t, 2H), 2.97 (m, 2H), 2.84 (m, 2H), 2.24 (s, 3H), 2.15 (d, 1H), 1.90 (m, 1H), 1.69 (d, 1H), 1.36 (m, 2H), 0.88 (t, 3H).

The following compounds were prepared according to the method of Example 237, Steps B and C.

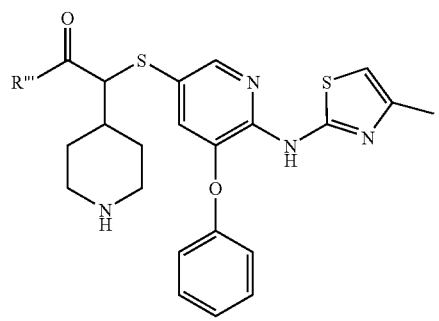

| Example | R''' | Name | NMR Data |
|---|---|---|---|
| 238 | (pyrrolidine) | 2-(6-(4-methylthiazol-2-ylamino)-5-phenoxypyridin-3-ylthio)-2-(piperidin-4-yl)-1-(pyrrolidin-1-yl)ethanone bis(2,2,2-trifluoroacetate) | $^1$H NMR (d$_6$-DMSO) δ 8.51 (m, 1 H), 8.14 (m, 2 H), 7.43 (t, 2 H), 7.20 (t, 1 H), 7.15 (d, 1 H), 7.10 (d, 2 H), 6.65 (s, 1 H), 3.65 (d, 1 H), 3.40 (m, 2 H), 3.31 (m, 1 H), 3.20 (m, 2 H), 3.04 (m, 1 H), 2.84 (m, 2 H), 2.31 (m, 1 H), 2.24 (s, 3 H), 1.95-1.78 (m, 2 H), 1.46-1.25 (m, 2 H) |

-continued

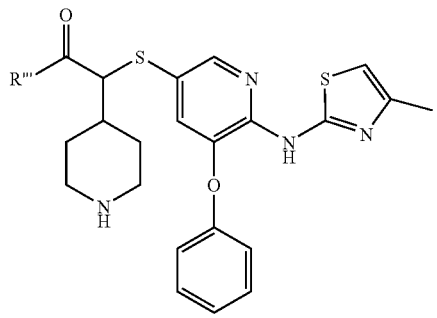

| Example | R''' | Name | NMR Data |
|---|---|---|---|
| 239 | (indolinyl group) | 1-(indolin-1-yl)-2-(6-(4-methylthiazol-2-ylamino)-5-phenoxypyridin-2-ylthio)-2-(piperidin-4-yl)ethanone bis(2,2,2-trifluoroacetate) | $^1$H NMR (CDCl$_3$) δ 9.45 (bs, 1 H), 9.15 (bs, 1 H), 8.13 (d, 1 H), 8.04 (d, 1 H), 7.30-7.03 (m, 9 H), 6.46 (s, 1 H), 4.19 (m, 1 H), 4.04 (m, 1 H), 3.53 (m, 1 H), 3.37 (d, 2 H), 3.19 (m, 2 H), 2.84 (m, 2 H), 2.63 (d, 1 H), 2.43 (s, 3 H), 2.02 (m, 2 H), 1.70 (m, 1 H), 1.55 (m, 1 H) |
| 240 | (7-azabicyclo[2.2.1]heptanyl group) | 1-(7-azabicyclo[2.2.1]heptan-7-yl)-2-(6-(4-methylthiazol-2-ylamino)-5-phenoxypyridin-3-ylthio)-2-(piperidin-4-yl)ethanone bis(2,2,2-trifluoroacetate) | $^1$H NMR (CDCl$_3$) δ 9.45 (bs, 1 H), 9.09 (bs, 1 H), 8.16 (s, 1 H), 7.41 (t, 2 H), 7.34 (s, 1 H), 7.18 (m, 3 H), 6.46 (s, 1 H), 4.56 (m, 1 H), 4.03 (m, 1 H), 3.50 (m, 1 H), 3.35 (m, 1 H), 3.28 (d, 1 H), 2.82 (m, 2 H), 2.52 (m, 1 H), 2.43 (s, 3 H), 1.95 (m, 2 H), 1.68 (m, 2 H), 1.55-1.35 (m, 6 H), 1.26 (m, 2 H) |
| 241 | (2-methylpiperidinyl group) | 1-(2-methylpiperidin-1-yl)-2-(6-(4-methylthiazol-2-ylamino)-5-phenoxypyridin-3-ylthio)-2-(piperidine-4-yl)ethanone bis(2,2,2-trifluoroacetate) *mixture of diastereomers | $^1$H NMR (CDCl$_3$) δ 8.14 (d, 1 H), 7.39 (t, 2 H), 7.30 (s, 1 H), 7.16 (m, 3 H), 6.47 (s, 1 H), 4.76 (bs, 0.5 H), 4.35 (m, 0.5 H), 4.12 (bs, 0.5 H), 3.65-3.25 (m, 3 H), 3.10 (m, 0.5 H), 2.85 (m, 2 H), 2.60 (m, 1 H), 2.43 (s, 3 H), 2.10-1.85 (m, 2 H), 1.71-1.35 (m, 6 H), 1.27-0.92 (m, 6 H) |

Example 242

2-(4-((6-(4-phenethylthiazol-2-ylamino)-5-phenoxypyridin-3-ylthio)(pyridin-2-yl)methylpiperidin-1-yl)ethanol

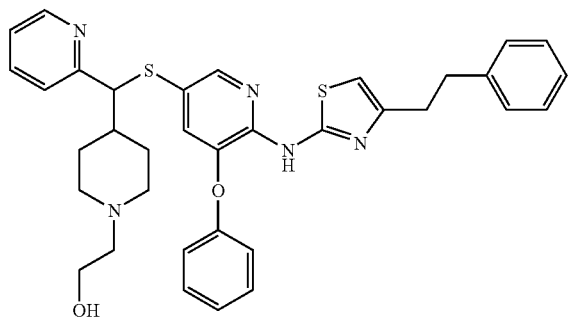

Step A: Preparation of tert-butyl 4-((6-(4-phenethylthiazol-2-ylamino)-5-phenoxypyridin-3-ylthio)(pyridin-2-yl)methyl)piperidine-1-carboxylate: Prepared according to the method of Example 16 from methyl 3-(6-(4-phenethylthiazol-2-ylamino)-5-phenoxypyridin-3-ylthio)propanoate, potassium 2-methylpropan-2-olate, and tert-butyl 4-((methylsulfonyloxy)(pyridin-2-yl)methyl)piperidine-1-carboxylate.

Step B: Preparation of N-(4-phenethylthiazol-2-yl)-3-phenoxy-5-(piperidin-4-yl(pyridin-2-yl)methylthio)pyridin-2-amine: Prepared according to the method of Example 225, Step C.

Step C: Preparation of 2-(4-((6-(4-phenethylthiazol-2-ylamino)-5-phenoxypyridin-3-ylthio)(pyridin-2-yl)methyl)piperidin-1-yl)ethanol: Prepared according to the method of Example 230. $^1$H NMR (d$_6$-DMSO) δ 10.95 (bs, 1H), 9.61 (bs, 1H), 8.41 (d, 1H), 8.79 (d, 1H), 7.67 (dt, 1H), 7.42 (t, 2H), 7.30-7.14 (m, 8H), 6.92 (m, 3H), 6.64 (s, 1H), 5.25 (s, 1H), 4.15 (s, 1H), 3.71 (m, 2H), 3.51 (m, 2H), 3.10-2.80 (m, 8H), 2.29 (m, 2H), 1.66 (m, 1H), 1.46 (m, 1H).

Example 243

2-(4-((3-methyl-1,2,4-oxadiazol-5-yl)(6-(4-methylthiazol-2-ylamino)-5-phenoxypyridin-3-ylthio)methyl)piperidin-1-yl)ethanol dihydrochloride

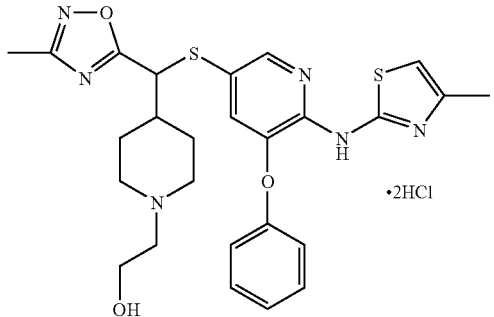

Step A: Preparation of tert-butyl 4-((3-methyl-1,2,4-oxadiazol-5-yl)(6-(4-methylthiazol-2-ylamino)-5-phenoxypyridin-3-ylthio)methyl piperidine-1-carboxylate: Placed 2-(1-(tert-butoxycarbonyl)piperidin-4-yl)-2-(6-(4-methylthiazol-2-ylamino)-5-phenoxypyridin-3-ylthio)acetic acid (0.250 g, 0.449 mmol), N-ethyl-N-isopropylpropan-2-amine (0.0638 g, 0.494 mmol) in DMF (10 mL) and added N-((dimethylamino)fluoromethylene)-N-methylmethanaminium hexafluorophosphate (V) (0.119 g, 0.449 mmol) and stirred for 30 minutes. Added N-hydroxyacetamidine (0.0366 g, 0.494 mmol) and heated to 110° C. for 4 days. The reaction was diluted with EtOAc and washed with water, dried, filtered and concentrated. The residue was purified by reverse phase chromatography to provide the title compound (0.122 g, 35.6%) Product was contaminated with ~15% acid. Crude material was used in Step B.

Step B: Preparation of 5-((3-methyl-1,2,4-oxadiazol-5-yl)(piperidin-4-yl)methylthio)-N-(4-methylthiazol-2-yl)-3-phenoxypyridin-2-amine: Prepared according to the method of Example 225, Step D.

Step C: Preparation of provide 2-(4-((3-methyl-1,24-oxadiazol-5-yl)(6-(4-methylthiazol-2-ylamino)-5-phenoxypyridin-3-ylthio)methyl)piperidin-1-yl)ethanol dihydrochloride: Prepared according to the method of Example 230. $^1$H NMR (CDCl$_3$) δ 11.96 (bs, 1H), 8.02 (s, 1H), 7.44 (t, 2H), 7.25 (t, 1H), 7.09 (d, 2H), 6.98 (s, 1H), 6.48 (s, 1H), 4.64 (s, 1H), 4.03 (m, 3H), 3.82 (d, 1H), 3.62 (d, 1H), 3.13 (s, 2H), 2.75 (m, 2H), 2.60 (d, 1H), 2.40 (s, 3H), 2.29 (s, 3H), 2.21 (m, 2H), 1.67 (m, 2H).

Example 244

4-methyl-N-(3-phenoxy-5-(1-(pyridin-2-yl)ethylthio)pyridin-2-yl)thiazol-2-amine hydrochloride

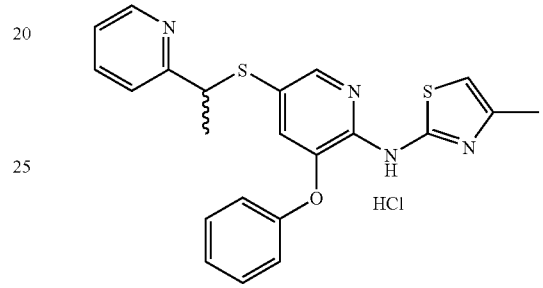

4-Methyl-N-(3-phenoxy-5-(1-(pyridin-2-yl)ethylthio)pyridin-2-yl)thiazol-2-amine hydrochloride prepared in Example 33 was purified by chiral chromatography to give two enantiomers. Enantiomer 1, $^1$H NMR (CDCl$_3$) δ 8.58 (d, 1H), 8.09 (m, 1H), 8.04 (d, 1H), 7.58 (d, 2H), 7.45 (t, 2H), 7.23 (t, 1H), 7.02 (d, 2H), 6.95 (d, 1H), 6.97 (s, 1H), 4.67 (q, 1H), 2.28 (s, 3H), 1.62 (d, 1H). Enantiomer 2, $^1$H NMR (CDCl$_3$) δ 8.58 (d, 1H), 8.09 (m, 1H), 8.04 (d, 1H), 7.58 (d, 2H), 7.45 (t, 2H), 7.23 (t, 1H), 7.02 (d, 2H), 6.95 (d, 1H), 6.97 (s, 1H), 4.67 (q, 1H), 2.28 (s, 3H), 1.62 (d, 1H).

Following the method of Example 16 the following compounds were made:

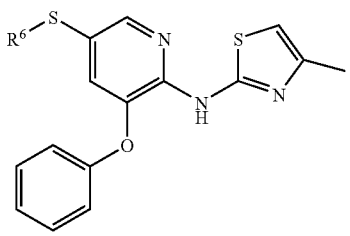

| Example | R$^6$ | Name | NMR Data |
|---|---|---|---|
| 245 | (phenyl-CH(CH$_3$)-CH$_2$CH$_2$-N(CH$_3$)$_2$) | N-(5-(3-(dimethylamino)-1-phenylpropylthio)-3-phenoxypyridin-2-yl)-4-methylthiazol-2-amine dihydrochloride | $^1$H NMR (d$_6$-DMSO) δ 10.41 (bs, 1 H), 8.04 (d, 1 H), 7.42 (t, 2 H), 7.29-7.17 (m, 6 H), 6.96 (d, 1 H), 6.93 (d, 2 H), 6.72 (s, 1 H), 4.33 (t, 1 H), 2.56 (m, 1 H), 2.88 (m, 1 H), 2.71 (d, 6 H), 2.28 (m, 2 H), 2.25 (s, 3 H). Mass spectrum (esi) m/z = 457.2 (M + H − 2HCl) |

-continued

| Example | R⁶ | Name | NMR Data |
|---|---|---|---|
| 246 | 5-cyclopropyl-1,3,4-thiadiazol-2-yl-methyl | 5-((5-cyclopropyl-1,3,4-thiadiazol-2-yl)methylthio)-N-(4-methylthiazol-2-yl)-3-phenoxypyridin-2-amine hydrochloride | $^1$H NMR (d$_6$-DMSO) δ 8.16 (d, 1 H), 7.74 (t, 2 H), 7.31 (d, 1 H), 7.21 (t, 1 H), 7.04 (d, 2 H), 6.75 (s, 1 H), 4.54 (s, 2 H), 2.45 (m, 1 H), 2.27 (s, 3 H), 1.18 (m, 2 H), 0.94 (m, 2 H); Mass spectrum (esi) m/z = 453.4 (M + H − HCl) |
| 247 | 1,2,4-oxadiazol-3-yl-methyl | 5-((1,2,4-oxadiazol-3-yl)methylthio)-N-(4-methylthiazol-2-yl)-3-phenoxypyridin-2-amine hydrochloride | $^1$H NMR (d$_6$-DMSO) δ 9.52 (s, 1 H), 8.16 (d, 1 H), 7.45 (t, 2 H), 7.32 (d, 1 H), 7.22 (t, 1 H), 7.07 (d, 2 H), 6.76 (s, 1 H), 4.29 (s, 2 H), 2.27 (s, 3 H); Mass spectrum (esi) m/z = 397.6 (M + H − HCl) |
| 248 | 5-methylisoxazol-3-yl-methyl | 5-((5-methylisoxazol-3-yl)methylthio)-N-(4-methylthiazol-2-yl)-3-phenoxypyridin-2-amine hydrochloride | $^1$H NMR (d$_6$-DMSO) δ 8.15 (d, 1 H), 7.74 (t, 2 H), 7.25 (d, 1 H), 7.22 (t, 1 H), 7.06 (d, 2 H), 6.75 (s, 1 H), 6.13 (s, 1 H), 4.09 (s, 2 H), 2.32 (s, 3 H), 2.27 (s, 3 H); Mass spectrum (esi) m/z = 410.6 (M + H − HCl) |
| 249 | 3,5-dimethylisoxazol-4-yl-methyl | 5-((3,5-dimethylisoxazol-4-yl)methylthio)-N-(4-methylthiazol-2-yl)-3-phenoxypyridin-2-amine hydrochloride | $^1$H NMR (d$_6$-DMSO) δ 8.08 (d, 1 H), 7.43 (t, 2 H), 7.24 (d, 1 H), 7.22 (t, 1 H), 7.03 (d, 2 H), 6.76 (s, 1 H), 3.91 (s, 2 H), 2.27 (s, 3 H), 2.12 (s, 3 H), 2.02 (s, 3 H); Mass spectrum (esi) m/z = 424.6 (M + H HCl) |
| 250 | 5-chloro-1,2,4-thiadiazol-3-yl-methyl | 5-((5-chloro-1,2,4-thiadiazol-3-yl)methylthio)-N-(4-methylthiazol-2-yl)-3-phenoxypyridin-2-amine hydrochloride | $^1$H NMR (d$_6$-DMSO) δ 8.50 (d, 1 H), 7.66 (d, 1 H), 7.43 (t, 2 H), 7.18 (t, 1 H), 7.12 (d, 2 H), 6.73 (s, 1 H), 4.85 (s, 2 H), 2.27 (s, 3 H); Mass spectrum (esi) m/z = 447.6 (M + H − HCl) |
| 251 | isoquinolin-1-ylmethyl | N-(5-(isoquinolin-1-ylmethylthio)-3-phenoxypyridin-2-yl)-4-methylthiazol-2-amine dihydrochloride, | $^1$H NMR (d$_6$-DMSO) δ 8.47 (d, 1 H), 8.41 (d, 1 H), 8.20 (m, 2 H), 8.03 (m, 2 H), 7.84 (t, 1 H), 7.41 (t, 2 H), 7.19 (t, 1 H), 6.92 (d, 2 H), 6.89 (s, 1 H), 6.74 (s, 1 H), 4.93 (s, 2 H), 2.27 (s, 3 H). |
| 252 | 2-acetamidothiazol-4-yl-methyl | N-(4-((6-(4-methylthiazol-2-ylamino)-5-phenoxypyridin-3-ylthio)methyl)thiazol-2-yl)acetamide hydrochloride | $^1$H NMR (d$_6$-DMSO) δ 12.11 (s, 1 H), 8.10 (d, 1 H), 7.39 (t, 2 H), 7.20 (t, 1 H), 7.04 (d, 1 H), 7.01 (d, 2 H), 6.72 (m, 2 H), 4.06 (s, 2 H), 2.26 (s, 3 H), 2.12 (s, 3 H). |

Following the procedure in Example 16 and using methyl 3-(6-(4-methylthiazol-2-ylamino)-5-(phenylthio)pyridin-3-ylthio)propanoate hydrochloride (Example 90) the following compounds were made:

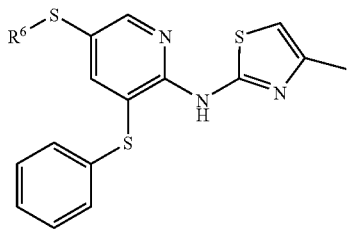

| Example | R⁶ | Name | NMR Data |
|---|---|---|---|
| 253 | 5-cyclopropyl-1,3,4-thiadiazol-2-yl)methyl | N-(5-((5-cyclopropyl-1,3,4-thiadiazol-2-yl)methylthio)-3-(phenylthio)pyridin-2-yl)-4-methylthiazol-2-amine | ¹H NMR (d₆-DMSO) δ 8.29 (bs, 1 H), 7.44-7.31 (m, 6 H), 6.57 (s, 1 H), 4.49 (s, 2 H), 2.46 (m, 1 H), 2.21 (s, 3 H), 1.18 (m, 2 H), 0.95 (m, 2 H) |
| 254 | (5-methylisoxazol-3-yl)methyl | 4-methyl-N-(5-((5-methylisoxazol-3-yl)methylthio)-3-(phenylthio)pyridin-2-yl)thiazol-2-amine | ¹H NMR (d₆-DMSO) δ 8.30 (s, 1 H), 7.73-7.31 (m, 6 H), 6.63 (s, 1 H), 6.12 (s, 1 H), 4.09 (s, 2 H), 2.33 (s, 3 H), 2.23 (s, 3 H) |
| 255 | (3,5-dimethylisoxazol-4-yl)methyl | N-(5-((3,5-dimethylisoxazol-4-yl)methylthio)-3-(phenylthio)pyridin-2-yl)-4-methylthiazol-2-amine | ¹H NMR (d₆-DMSO) δ 8.24 (s, 1 H), 7.44-7.30 (m, 6 H), 6.63 (s, 1 H), 3.87 (s, 2 H), 2.23 (s, 3 H), 2.09 (s, 3 H), 1.96 (s, 3 H) |

Example 256

2-(6-(4-methylthiazol-2-ylamino)-5-phenoxypyridin-3-ylthio)-1-(pyrrolidin-1-yl)ethanone hydrochloride

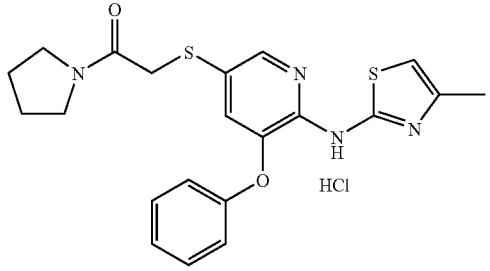

Step A: Preparation of 2-chloro-1-(pyrrolidin-1-yl)ethanone: A solution of mL2-chloroacetyl chloride (1.409 mL, 17.71 mmol) and THF (50 mL) was cooled to 0° C. and pyrrolidine (1.259 g, 17.71 mmol) was slowly added and stirred at ambient temperature for 3 hours. Partitioned between CH₂Cl₂ and water, and the organic layer was separated, dried, filtered, and concentrated to give the title compound (1.73 g, 66.19% yield) as a clear oil.

Step B: Preparation of 2-(6-(4-methylthiazol-2-ylamino)-5-phenoxypyridin-3-ylthio)-1-(pyrrolidin-1-yl)ethanone hydrochloride: Prepared according to the method of Example 16. ¹H NMR (d₆-DMSO) δ 8.21 (d, 1H), 7.45 (t, 2H), 7.39 (d, 1H), 7.23 (t, 1H), 7.13 (d, 2H), 6.83 (s, 1H), 3.83 (s, 2H), 3.41 (t, 2H), 2.30 (s, 3H), 1.82 (m, 2H), 1.73 (m, 2H).

Following the method of Example 32, Step A, and Example 16, the following compounds were made:

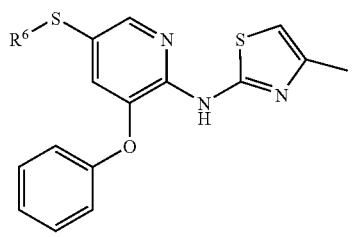

| Example | R⁶ | Name | NMR Data |
|---|---|---|---|
| 257 | 2-(dimethylamino)ethyl-N-methylamide | N-(2-(dimethylamino)ethyl)-N-methyl-2-(6-(4-methylthiazol-2-ylamino)-5-phenoxypyridin-3-ylthio)acetamide dihydrochloride | ¹H NMR (d₆-DMSO) δ 9.77 (bs, 1 H), 8.19 (d, 1 H), 7.42 (m, 3 H), 7.19 (d, 2 H), 6.69 (s, 1 H), 3.93 (s, 2 H), 3.59 (t, 2 H), 3.17 (q, 2 H), 3.00 (s, 3 H), 2.76 (d, 6 H), 2.25 (s, 3 H). |

| Example | R⁶ | Name | NMR Data |
|---|---|---|---|
| 258 | (4-methylpiperazinyl carbonyl methyl) | 1-(4-methylpiperazin-1-yl)-2-(6-(4-methylthiazol-2-ylamino)-5-phenoxypyridin-3-ylthio)ethanone dihydrochloride | $^1$H NMR (d$_6$-DMSO) δ 9.86 (bs, 1 H), 8.21 (d, 1 H), 7.42 (m, 3 H), 7.16 (t, 1 H), 7.06 (d, 2 H), 6.64 (s, 1 H), 4.35 (m, 1 H), 4.10 (m, 1 H), 3.93 (d, 2 H), 3.43 (m, 2 H), 3.31 (m, 1 H), 3.04 (m, 1 H), 2.87 (m, 2 H), 2.81 (s, 3 H), 2.24 (s, 3 H) |
| 259 | (2-(pyrrolidin-1-yl)ethyl)aminocarbonyl methyl | 2-(6-(4-methylthiazol-2-ylamino)-5-phenoxypyridin-3-ylthio)-N-(2-(pyrrolidin-1-yl)ethyl)acetamide dihydrochloride | $^1$H NMR (d$_6$-DMSO) δ 9.84 (bs, 1 H), 8.34 (t, 1 H), 8.18 (d, 1 H), 7.43 (t, 2 H), 7.38 (d, 1 H), 7.19 (t, 1 H), 7.07 (d, 2 H), 6.64 (s, 1 H), 3.55 (s, 2 H), 3.52 (m, 2 H), 3.34 (q, 2 H), 3.13 (q, 2 H), 2.94 (m, 2 H), 2.23 (s, 3 H), 1.96 (m, 2 H), 1.82 (m, 2 H) |

Example 260

{5-[(1,1-Dioxo-hexahydro-1λ⁶-thiopyran-4-yl)-pyridin-2-yl-methylsulfanyl]-3-phenoxy-pyridin-2-yl}-(4-methyl-thiazol-2-yl)-amine dihydrochloride

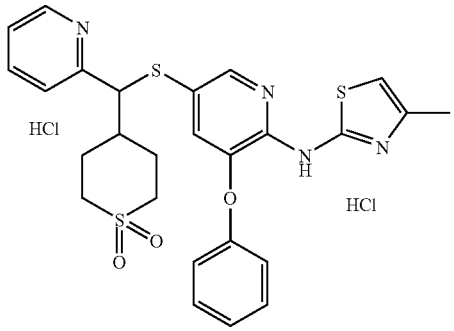

Step A: Preparation of pyridin-2-yl(tetrahydro-2H-thiopyran-4-yl)methanol: Prepared according to the method of Example 225, Step A, from 2-bromopyridine and tetrahydro-2H-thiopyran-4-carbaldehyde.

Step B: Preparation of (1,1-Dioxo-hexahydro-1λ⁶-thiopyran-4-yl)-pyridin-2-yl-methanol: Placed pyridin-2-yl(tetrahydro-2H-thiopyran-4-yl)methanol (1.560 g, 7.453 mmol) in glacial acetic acid (2 mL). Sodium perborate tetrahydrate (2.293 g, 14.91 mmol) was added and stirred for 18 hours. The reaction was partitioned between saturated sodium bisulfite and CH$_2$Cl$_2$. The solids were filtered off, washed with water and dried to afford the title compound (1.233 g, 68.56% yield)

Step C: Preparation of methanesulfonic acid (1,1-dioxo-hexahydro-1λ⁶-thiopyran-4-yl)-pyridin-2-yl-methyl ester: Prepared according to the method of Example 225, Step B.

Step D: Preparation of {5-[(1,1-Dioxo-hexahydro-1λ⁶-thiopyran-4-yl)-pyridin-2-yl-methylsulfanyl]-3-phenoxy-pyridin-2-yl}-(4-methyl-thiazol-2-yl)-amine dihydrochloride: Prepared according to the method of Example 16 using methyl 3-(6-(4-methylthiazol-2-ylamino)-5-phenoxypyridin-3-ylthio)propanoate. $^1$H NMR (d$_6$-DMSO) δ 8.47 (d, 1H), 8.02 (d, 1H), 7.76 (t, 1H), 7.43 (t, 2H), 7.29 (t, 2H), 7.20 (t, 1H), 7.01 (d, 1H), 6.95 (d, 2H), 6.70 (s, 1H), 4.45 (d, 1H), 3.21-2.95 (m, 5H), 2.36 (m, 1H), 2.25 (s, 3H), 1.85 (m, 1H), 1.74 (m, 1H), 1.61 (m, 1H).

Example 261

N-(5-bromo-3-phenoxypyridin-2-yl)-4-(2-(methylthio)ethyl)thiazol-2-amine

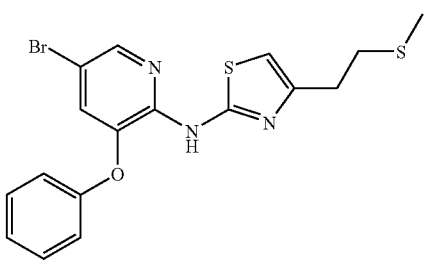

Step A: Preparation of 1-chloro-4-(methylthio)butan-2-one: LDA prepared from diisopropylamine (12.44 g, 123.0 mmol) and butyl lithium (44.71 mL, 111.8 mmol) combined in THF (100 mL) at −78° C. was added dropwise to a solution containing methyl 3-(methylthio)propanoate (3.00 g, 22.36 mmol), and chloroiodomethane (15.77 g, 89.42 mmol) in THF (100 mL) at −78° C. over 30 minutes. The reaction was stirred for an additional 10 minutes then added a solution of acetic acid 30 mL in THF (200 mL) keeping the temp below −65° C. The solution was stirred for 10 minutes and partitioned between EtOAc and brine. The organic layer was washed with saturated bicarbonate, concentrated and purified by silica gel to give the title compound (1.021 g, 29.92% yield).

Step B: Preparation of 5-bromo-N-(4-(2-(methylthio) ethyl)thiazol-2-yl)-3-phenoxypyridin-2-amine: Prepared according to the method of Example 7, Step E. $^1$H NMR (d$_6$-DMSO) δ 10.96 (bs, 1H), 8.22 (d, 1H), 7.43 (t, 2H), 7.40 (d, 1H), 7.21 (t, 1H), 7.10 (d, 2H), 6.74 (s, 1H), 2.83 (m, 2H), 2.77 (m, 2H), 2.06 (s, 3H).

Example 262

N-(1-bromo-3-phenoxypyridin-2-yl)-4-(2-(methylsulfonyl)ethyl)thiazol-2-amine

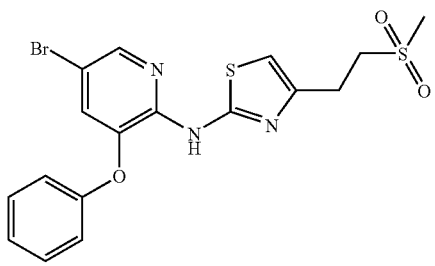

5-Bromo-N-(4-(2-(methylthio)ethyl)thiazol-2-yl)-3-phenoxypyridin-2-amine (1.132 g, 2.680 mmol) was dissolved in CH$_2$Cl$_2$ (25 mL) and cooled to 0° C. MCPBA (1.98 g, 8.04 mmol) was added and stirred at ambient temperature overnight. The reaction was quenched with sodium bisulfite and extracted with CH$_2$Cl$_2$. The organic layer was washed with saturated sodium bicarbonate, dried, filtered, and concentrated. The residue was purified by silica gel (15-40% EtOAc in hexanes) to provide the title compound (0.503 g, 41.31% yield). $^1$H NMR (d$_6$-DMSO) δ 11.05 (bs, 1H), 8.20 (d, 1H), 7.43 (t, 2H), 7.38 (m, 1H), 7.20 (t, 1H), 7.09 (d, 2H), 6.79 (s, 1H), 3.43 (m, 2H), 3.00 (m, 2H), 2.97 (s, 3H).

Example 263

4-methyl-N-(3-phenoxy-5-(1-(piperidin-4-yl)ethylthio)pyridin-2-yl)thiazol-2-amine bis(2,2,2-trifluoroacetate)

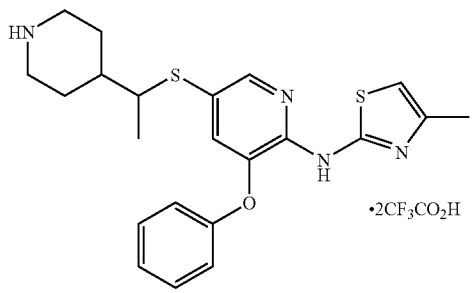

Step A: Preparation of tert-butyl 4-(1-hydroxyethyl)piperidine-1-carboxylate: Placed tert-butyl 4-formylpiperidine-1-carboxylate (2.00 g, 9.38 mmol) in THF (40 mL) and cooled to −78° C. Slowly added methylmagnesium bromide (3.44 mL, 10.3 mmol) stirred for 1 hour. Slowly added saturated ammonium chloride and extracted with CH$_2$Cl$_2$. Concentrated and redissolved in 5% MeOH in CH$_2$Cl$_2$. Added ether and filtered off solids. Concentrate filtrate to give the title compound (1.94 g, 90.2% yield)

Step B: Preparation of tert-butyl 4-(1-(methylsulfonyloxy) ethyl)piperidine-1-carboxylate: Prepared according to the method of Example 225, Step B.

Step C: Preparation of 4-methyl-N-(3-phenoxy-5-(1-(piperidin-4-yl)ethylthio)pyridin-2-yl)thiazol-2-amine bis(2,2,2-trifluoroacetate): A nitrogen purged vial was charged with methyl 3-(6-(4-methylthiazol-2-ylamino)-5-phenoxypyridin-3-ylthio)propanoate (0.150 g, 0.374 mmol) and THF (5 mL). Potassium 2-methylpropan-2-olate (0.934 mL, 0.934 mmol) was added and stirred at ambient temperature for 30 seconds. Tert-butyl 4-(1-(methylsulfonyloxy)ethyl)piperidine-1-carboxylate (0.144 g, 0.467 mmol) was added and stirred at ambient temperature under nitrogen for 20 hours. Saturated NH$_4$Cl was added and extracted with CH$_2$Cl$_2$. The organic layer was dried, filtered, and concentrated. The residue was dissolved in CH$_2$Cl$_2$ (5 mL) and TFA (2 mL) was added and stirred for 1 hour. The reaction was concentrated and purified by reverse phase chromatography (with 0.1% TFA) to provide the title compound (0.0363 g, 14.8% yield). $^1$H NMR (d$_6$-DMSO) δ 8.57 (bs, 1H), 8.23 (bs, 1H), 8.18 (d, 1H), 7.42 (t, 2H), 7.34 (d, 1H), 7.19 (t, 1H), 7.07 (d, 2H), 6.64 (s, 1H), 3.26 (d, 2H), 3.13 (m, 1H), 2.80 (m, 2H), 2.24 (s, 3H), 1.87 (m, 2H), 1.67 (m, 1H), 1.47 (m, 2H), 1.15 (d, 3H).

Example 264

N-(5-(benzyloxy)-3-(phenylthio)pyridin-2-yl)-4-methylthiazol-2-amine hydrochloride

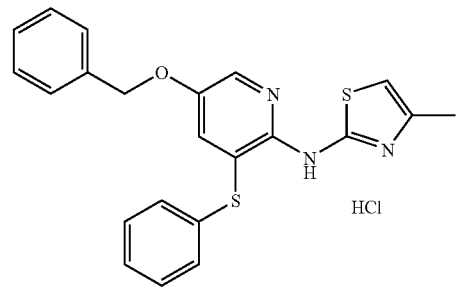

Step A: Preparation of 5-(benzyloxy)-2-chloropyridine: 6-Chloropyridin-3-ol (30.00 g, 231.6 mmol), 1-(bromomethyl)benzene (43.57 g, 254.7 mmol), and potassium carbonate (80.01 g, 579.0 mmol) were added to DMF (500 mL) and stirred at ambient temperature overnight. Water was added and extracted with ether. The organic phase was washed with 1M NaOH, dried, filtered, and concentrated to provide the title compound (50.8 g, 99.86% yield).

Step B: Preparation of 5-(benzyloxy)pyridin-2-amine hydrochloride: To a nitrogen purged solution of mL Pd$_2$(dba)$_3$ (10.19 g, 11.12 mmol), 5-(benzyloxy)-2-chloropyridine (48.87 g, 222.5 mmol), (2-diphenyl)dicyclohexyl-phosphine (7.797 g, 22.25 mmol) and THF (700 mL) was added lithium hexamethyl disilazide (267.0 mL, 267.0 mmol). The reaction was heated at 65° C. overnight and cooled to ambient temperature. 1M HCl (250 mL) was added and stirred for 30 minutes. Saturated sodium bicarbonate was added slowly. The mixture was extracted several times with CH$_2$Cl$_2$, dried, filtered, and concentrated to give the title compound (52.1 g, 98.94% yield).

Step C: Preparation of 5-(benzyloxy)-3-bromopyridin-2-amine: 5-(Benzyloxy)pyridin-2-amine hydrochloride (52.3 g, 221 mmol) and sodium acetate (45.3 g, 552 mmol) were dissolved in acetic acid (300 mL). Bromine (11.3 mL, 221 mmol) was added slowly and stirred at ambient temperature for 18 hours. After an aqueous workup, the material was purified over silica gel to give the title compound (10.5 g, 17.0% yield).

Steps D-F: Preparation of 5-(benzyloxy)-3-bromo-N-(4-methylthiazol-2-yl)pyridin-2-amine: Prepared according to the method of Example 7, Steps C-E.

Step F: Preparation of 5-(benzyloxy)-N-(4-methylthiazol-2-yl)-3-(phenylthio)pyridin-2-amine: Prepared according to the method of Example 8 to give the title compound (2.80 g, 60.5% yield). $^1$H NMR (d$_6$-DMSO) δ 8.22 (s, 1H), 7.57 (bs, 1H), 7.49-7.30 (m, 11H), 6.68 (s, 1H), 5.18 (s, 2H), 2.25 (s, 3H).

Example 265

4-methyl-N-(3-(phenylthio)-5-(2-(piperidin-4-yl)ethyl)pyridin-2-yl)thiazol-2-amine bis(2,2,2-trifluoroacetate)

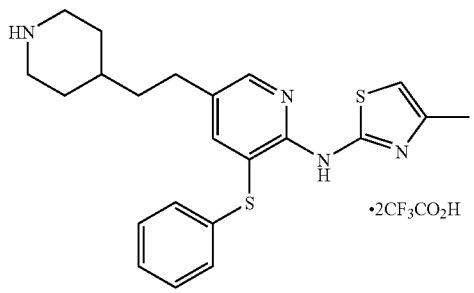

Prepared according to the method of Example 193, Steps A-C, using 5-bromo-N-(4-methylthiazol-2-yl)-3-(phenylthio)thiazole-2-amine and Tert-butyl 4-(2-oxoethyl)piperidine-1-carboxylate as the starting materials. $^1$H NMR (d$_6$-DMSO) δ 8.53 (bs, 1H), 8.27 (s, 1H), 8.22 (bs, 1H), 7.76 (bs, 1H), 7.36 (t, 2H), 7.28 (t, 1H), 7.23 (d, 2H), 6.60 (s, 1H), 3.25 (d, 2H), 2.82 (q, 2H), 2.53 (t, 2H), 2.21 (s, 3H), 1.82 (m, 2H), 1.51 (m, 3H), 1.27 (m, 2H).

Example 266

2,2-dimethyl-3-(2-(3-phenoxy-5-(thieno[3,2-b]pyridin-7-ylthio)pyridin-2-ylamino)thiazol-4-yl)propanoic acid

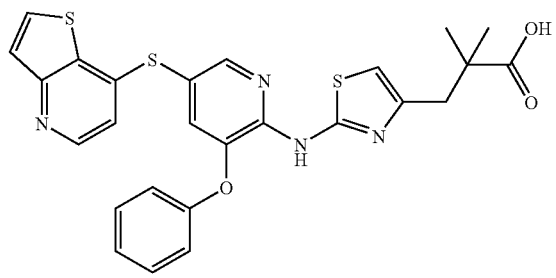

Step A: Preparation of methyl 3-(2-(5-bromo-3-phenoxypyridin-2-ylamino)thiazol-4-yl)-2,2-dimethylpropanoate: Prepared according to the method of Example 7, Step E.

Step B: Preparation of methyl 3-(2-(5-(3-methoxy-3-oxopropylthio)-3-phenoxypyridin-2-ylamino)thiazol-4-yl)-2,2-dimethylpropanoate: Prepared according to the method of Example 13.

Step C: Preparation of methyl 2,2-dimethyl-3-(2-(3-phenoxy-5-(thieno[3,2-b]pyridin-7-ylthio)pyridin-2-ylamino)thiazol-4-yl)propanoate: Prepared according to the method of Example 127.

Step D: Preparation of 2,2-dimethyl-3-(2-(3-phenoxy-5-(thieno[3,2-b]pyridin-7-ylthio)pyridin-2-ylamino)thiazol-4-yl)propanoic acid: Prepared according to the method of Example 45 to provide the title compound (0.024 g, 88% yield). $^1$H NMR (CDCl$_3$) δ 8.44 (d, 1H), 8.29 (d, 1H), 7.71 (d, 1H), 7.54 (d, 1H), 7.31-7.24 (m, 3H), 7.09 (t, 1H), 7.01 (d, 2H), 6.71 (d, 1H), 6.45 (s, 1H), 2.93 (s, 2H), 1.05 (s, 6H).

Example 267 tert-butyl 4-(5-(3-phenoxy-5-(pyridin-2-ylthio)pyridin-2-ylamino)-1,2,4-thiadiazol-3-yl)piperidine-1-carboxylate

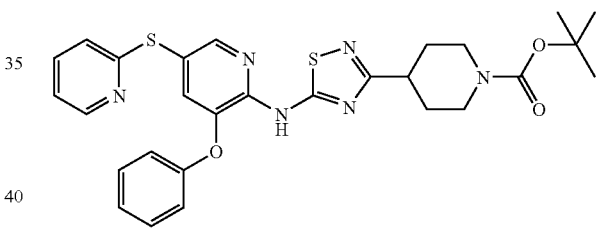

Step A: Preparation of 2-(2-(pyridin-3-yl)disulfanyl)pyridine: Prepared according to the method of Example 162, Step A from 5-bromo-3-phenoxypyridin-2-amine.

Step B: Preparation of tert-butyl 4-(5-(3-phenoxy-5-(pyridin-2-ylthio)pyridin-2-ylamino)-1,2,4-thiadiazol-3-yl)piperidine-1-carboxylate: A solution of pyridine (0.493 mL, 6.09 mmol), (Z)-tert-butyl 4-(chloro(methylsulfonyloxyimino)methyl)piperidine-1-carboxylate (0.165 g, 2.03 mmol), and CH$_3$CN (4 mL). The reaction was heated to 40° C. for 40 minutes. 3-phenoxy-5-(pyridin-2-ylthio)pyridin-2-amine (0.400 g, 1.35 mmol) was added and stirred at 50° C. over the weekend. The reaction was cooled to ambient temperature and poured into saturated aqueous NaHCO$_3$ and extracted with EtOAc. The organic layer was dried with sodium sulfate, filtered, and concentrated. The residue was purified on silica gel (20-25% EtOAc in hexanes) to provide the title compound (0.598 g, 78.5% yield). $^1$H NMR (d$_6$-DMSO) δ 12.33 (s, 1H), 8.39 (m, 1H), 8.37 (m, 1H), 7.66 (m, 1H), 7.47 (d, 1H), 7.42 (t, 2H), 7.21-7.11 (m, 5H), 3.96 (d, 2H), 2.98 (m, 3H), 1.97 (m, 2H), 1.64 (m, 2H), 1.40 (s, 9H).

Following the method of Example 267 the following compounds were made:

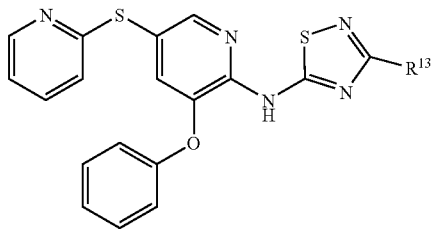

| Example | R13 | Name | NMR Data |
|---|---|---|---|
| 268 | iBu | 3-isobutyl-N-(3-phenoxy-5-(pyridin-2-ylthio)pyridin-2-yl)-1,2,4-thiadiazol-5-amine dihydrochloride | $^1$H NMR (d$_6$-DMSO) δ 8.38 (m, 2 H), 7.67 (dt, 1 H), 7.47 (d, 1 H), 7.42 (t, 2 H), 7.21-7.11 (m, 5 H), 2.63 (d, 2 H), 0.92 (d, 6 H) |
| 269 | iPr | 3-isopropyl-N-(3-phenoxy-5-(pyridin-2-ylthio)pyridin-2-yl)-1,2,4-thiadiazol-5-amine | $^1$H NMR (d$_6$-DMSO) δ 12.30 (bs, 1 H), 8.39 (m, 2 H), 7.66 (dt, 1 H), 7.48 (d, 1 H), 7.42 (t, 2 H), 7.21-7.11 (m, 5 H), 3.08 (m, 1 H), 1.29 (d, 6 H) |
| 270 | ![tetrahydrofuran] | N-(3-phenoxy-5-(pyridin-2-ylthio)pyridin-2-yl)-3-(tetrahydrofuran-2-yl)-1,2,4-thiadiazol-5-amine | $^1$H NMR (d$_6$-DMSO) δ 12.30 (s, 1 H), 8.40 (d, 1 H), 8.37 (m, 1 H), 7.66 (dt, 1 H), 7.42 (t, 2 H), 7.42 (t, 2 H), 7.21-7.11 (m, 5 H), 4.06 (t, 1 H), 3.90-3.75 (m, 3 H), 3.60 (m, 1 H), 2.27 (q, 2 H). |

Example 271

N-(3-phenoxy-5-(pyridin-2-ylthio)pyridin-2-yl)-3-(piperidin-4-yl)-1,2,4-thiadiazol-5-amine trihydrochloride

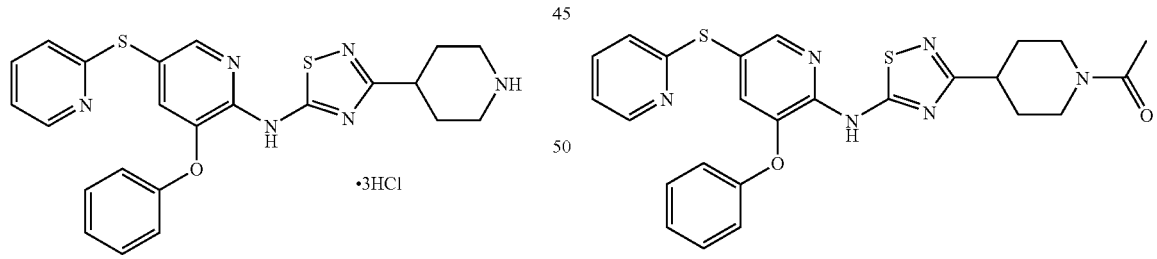

Tert-butyl 4-(5-(3-phenoxy-5-(pyridin-2-ylthio)pyridin-2-ylamino)-1,2,4-thiadiazol-3-yl)piperidine-1-carboxylate (0.587 g, 1.04 mmol) was dissolved in 1:1 CH$_2$Cl$_2$/methanol and 4N HCl in dioxane added. The reaction was stirred at ambient temperature for 1 hour. The reaction was concentrated and dried in a vacuum oven to provide the title compound (0.473 g, 98.0% yield). $^1$H NMR (d$_6$-DMSO) δ 12.39 (s, 1H), 8.95 (bs, 1H), 8.80 (bs, 1H), 8.39 (d, 1H), 8.37 (m, 1H), 7.67 (dt, 1H), 7.47 (d, 1H), 7.43 (t, 2H), 7.22-7.12 (m, 5H), 3.30 (d, 2H), 3.16-2.99 (m, 3H), 2.17 (d, 2H), 1.98 (m, 2H).

Example 272

1-(4-(5-(3-phenoxy-5-(pyridin-2-ylthio)pyridin-2-ylamino)-1,2,4-thiadiazol-3-yl)piperidin-1-yl)ethanone 3-Phenoxy-N-(3-(piperidin-4-yl)-1,2,4-thiadiazol-5-yl)-5-(pyridin-2-ylthio) pyridin-2-amine (0.075 g, 0.16 mmol), TEA (0.090 mL, 0.65 mmol), and acetic anhydride (0.017 g, 0.16 mmol) were added to THF and stirred for 3 hr. Water was added and extracted with CH$_2$Cl$_2$. The organic layer was dried, filtered, and concentrated. The residue was purified by silica gel (5% MeOH in CH$_2$Cl$_2$) to provide the title compound (0.044 g, 54% yield). $^1$H NMR (d$_6$-DMSO) δ 12.34 (s, 1H), 8.38 (m, 2H), 7.67 (dt, 1H), 7.48 (d, 1H), 7.42 (t, 2H), 7.21-7.11 (m, 5H), 4.32 (d, 1H), 3.84 (d, 1H), 3.19 (m, 1H), 3.05 (m, 1H), 2.76 (t, 1H), 2.01 (m, 5H), 1.74 (m, 1H), 1.59 (m, 1H).

The following compounds were made according to the method of Example 272.

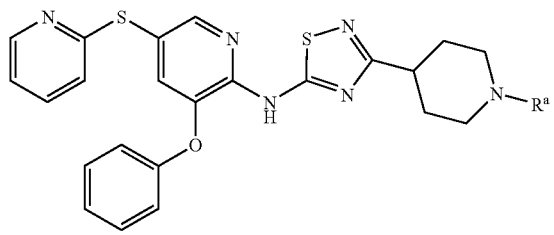

| Example | R<sup>a</sup> | Name | NMR Data |
|---|---|---|---|
| 273 | (2-methoxyacetyl group) | 2-methoxy-1-(4-(5-(3-phenoxy-5-(piperidi-2-ylthio)piperidi-2-ylamino)-1,2,4-thiadiazol-3-yl)piperidine-1-yl)ethanone dihydrochloride | $^1$H NMR (d$_6$-DMSO) δ 12.34 (s, 1 H), 8.39 (d, 1 H), 8.37 (m, 1 H), 7.67 (dt, 1 H), 7.47 (d, 1 H), 7.42 (t, 2 H), 7.21-7.11 (m, 5 H), 4.30 (d, 1 H), 4.09 (q, 2 H), 3.81 (d, 1 H), 3.28 (s, 3 H), 3.18-3.03 (m, 2 H), 2.81 (m, 1 H), 2.01 (d, 2 H), 1.73 (m, 1 H), 1.63 (m, 1 H). |
| 274 | (2-dimethylaminoacetyl group) | 2-(dimethylamino)-1-(4-(5-(3-phenoxy-5-(pyridin-2-ylthio)pyridin-2-ylamino)-1,2,4-thiadiazol-3-yl)piperidin-1-yl)ethanone dihydrochloride | $^1$H NMR (d$_6$-DMSO) δ 12.34 (s, 1 H), 9.54 (bs, 1 H), 8.39 (d, 1 H), 8.37 (m, 1 H), 7.67 (dt, 1 H), 7.48 (d, 1 H), 7.43 (t, 2 H), 7.21-7.11 (m, 5 H), 4.32 (m, 3 H), 3.65 (d, 1 H), 3.23 (m, 1 H), 3.14 (m, 1 H), 2.96 (t, 1 H), 2.81 (d, 6 H), 2.08 (d, 2 H), 1.85-1.60 (m, 2 H). |
| 275 | (N,N-dimethylcarboxamide group) | N,N-dimethyl-4-(5-(3-phenoxy-5-(pyridin-2-ylthio)pyridin-2-ylamino)-1,2,4-thiadiazol-3-yl)piperidine-1-carboxamide dihydrochloride | $^1$H NMR (d$_6$-DMSO) δ 12.34 (s, 1 H), 8.39 (d, 1 H), 8.37 (m, 1 H), 7.66 (dt, 1 H), 7.47 (d, 1 H), 7.42 (t, 2 H), 7.21-7.11 (m, 5 H), 3.58 (d, 2 H), 2.96 (m, 1 H), 2.84 (t, 2 H), 2.73 (s, 6 H), 1.96 (m, 2 H), 1.74 (m, 2 H). |
| 276 | (N,N-dimethylsulfonamide group) | N,N-dimethyl-4-(5-(3-phenoxy-5-(pyridin-2-ylthio)pyridin-2-ylamino)-1,2,4-thiadiazol-3-yl)piperidine-1-sulfonamide dihydrochloride | $^1$H NMR (d$_6$-DMSO) δ 12.36 (s, 1 H), 8.39 (d, 1 H), 8.37 (m, 1 H), 7.67 (dt, 1 H), 7.47 (d, 1 H), 7.42 (t, 2 H), 7.21-7.11 (m, 5 H), 3.60 (d, 2 H), 2.99 (m, 3 H), 2.75 (s, 6 H), 2.06 (m, 2 H), 1.77 (m, 2 H). |
| 277 | (isobutyryl group) | 2-methyl-1-(4-(5-(3-phenoxy-5-(pyridin-2-ylthio)pyridin-2-ylamino)-1,2,4-thiadiazol-3-yl)piperidin-1-yl)propan-1-one dihydrochloride | $^1$H NMR (d$_6$-DMSO) δ 12.34 (s, 1 H), 8.39 (d, 1 H), 8.37 (m, 1 H), 7.66 (dt, 1 H), 7.47 (d, 1 H), 7.42 (t, 2 H), 7.21-7.11 (m, 5 H), 4.37 (d, 1 H), 3.98 (d, 1 H), 3.20 (t, 1 H), 3.07 (m, 1 H), 2.89 (m, 1 H), 2.75 (t, 1 H), 2.02 (m, 2 H), 1.70 (m, 1 H), 1.57 (m, 1 H), 1.00 (d, 6 H). |
| 278 | (methylsulfonyl group) | 3-(1-(methylsulfonyl)piperidin-4-yl)-N-(3-phenoxy-5-(pyridin-2-ylthio)pyridin-2-yl)-1,2,4-thiadiazol-5-amine dihydrochloride | $^1$H NMR (d$_6$-DMSO) δ 12.36 (s, 1 H), 8.40 (d, 1 H), 8.37 (m, 1 H), 7.67 (dt, 1 H), 7.48 (d, 1 H), 7.43 (t, 2 H), 7.21-7.11 (m, 5 H), 3.59 (d, 2 H), 2.95-2.86 (m, 6 H), 2.14 (d, 2 H), 1.81 (m, 2 H). |
| 279 | (2-oxoethyl acetate group) | 2-oxo-2-(4-(5-(3-phenoxy-5-(pyridin-2-ylthio)pyridin-2-ylamino)-1,2,4-thiadiazol-3-yl)piperidin-1-yl)ethyl acetate dihydrochloride | $^1$H NMR (d$_6$-DMSO) δ 12.36 (s, 1 H), 8.39 (d, 1 H), 8.37 (m, 1 H), 7.66 (dt, 1 H), 7.47 (d, 1 H), 7.42 (t, 2 H), 7.21-7.11 (m, 5 H), 4.79 (m, 2 H), 4.26 (d, 1 H), 3.75 (d, 1 H), 3.22-3.04 (m, 2 H), 2.83 (t, 1 H), 2.07 (s, 3 H), 1.76 (m, 1 H), 1.61 (m, 1 H). |

Example 280

4-(5-(3-phenoxy-5-(pyridin-2-ylthio)pyridin-2-ylamino)-1,2,4-thiadiazol-3-yl)piperidine-1-carboxamide dihydrochloride

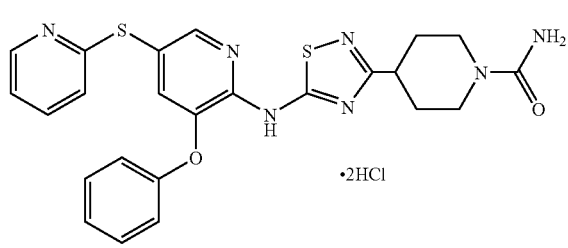

·2HCl

To a solution of 3-phenoxy-N-(3-(piperidine-4-yl)-1,2,4-thiadiazol-5-yl)-5-(piperidi-2-ylthio)piperidi-2-amine (0.055 g, 0.119 mmol) in $CH_2Cl_2$ (4 mL) was added pyridine (0.0940 g, 1.19 mmol), acetic acid (0.0714 g, 1.19 mmol), TEA (0.033 mL, 0.238 mmol), and potassium cyanate (0.0193 g, 0.238 mmol). The reaction was stirred for 18 hours. Water was added and extracted with $CH_2Cl_2$. The organic layer was dried, filtered, and concentrated. The residue was purified by silica gel (1-4% MeOH in $CH_2Cl_2$) to give the title compound (0.0333 g, 48.4% yield) after HCl salt formation. $^1H$ NMR ($d_6$-DMSO) δ 12.33 (s, 1H), 8.39 (d, 1H), 8.37 (m, 1H), 7.67 (dt, 1H), 7.47 (d, 1H), 7.42 (t, 2H), 7.21-7.11 (m, 5H), 3.94 (d, 2H), 2.97 (m, 1H), 2.83 (t, 2H), 1.19 (m, 2H), 1.64 (m, 2H).

Example 281

2-hydroxy-1-(4-(5-(3-phenoxy-5-(pyridin-2-ylthio)pyridin-2-ylamino)-1,2,4-thiadiazol-3-yl)piperidin-1-yl)ethanone

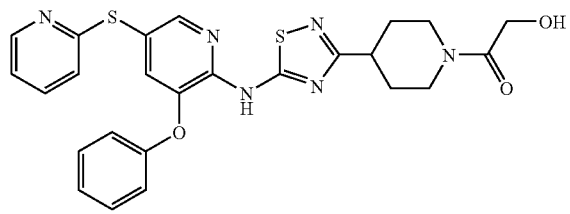

2-Oxo-2-(4-(5-(3-phenoxy-5-(piperidi-2-ylthio)piperidi-2-ylamino)-1,2,4-thiadiazol-3-yl)piperidine-1-yl)ethyl acetate (0.089 g, 0.158 mmol) and potassium carbonate (0.109 g, 0.791 mmol) were refluxed in ethanol (25 mL) for 2 hours. The reaction was cooled to ambient temperature, filtered and concentrated. The residue was purified by silica gel (1-2% MeOH in EtOAc) to give the title compound (0.030 g, 36.4% yield). $^1H$ NMR ($d_6$-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 4.49 (t, 1H), 4.31 (d, 1H), 4.10 (t, 2H), 3.71 (d, 1H), 3.10 (m, 2H), 2.86 (t, 2H), 2.02 (m, 2H), 1.79-1.60 (m, 2H).

Example 282 tert-Butyl 2-oxo-2-(4-(5-(3-phenoxy-5-(pyridin-2-ylthio)pyridin-2-ylamino)-1,2,4-thiadiazol-3-yl)piperidin-1-yl)ethylcarbamate

3-Phenoxy-N-(3-(piperidin-4-yl)-1,2,4-thiadiazol-5-yl)-5-(pyridin-2-ylthio)pyridin-2-amine (0.100 g, 0.2162 mmol), 2-(tert-butoxycarbonyl)acetic acid (0.04544 g, 0.2594 mmol), N1-((ethylimino)methylene)-N3,N3-dimethylpropane-1,3-diamine hydrochloride (0.06216 g, 0.3243 mmol), and N,N-dimethylpyridin-4-amine (0.002641 g, 0.02162 mmol) were dissolved in $CH_2Cl_2$ (5 mL). Triethylamine (0.04375 g, 0.4323 mmol) was added and the solution was stirred at ambient temperature for 3 hours. Water was added and the solution was extracted with $CH_2Cl_2$, dried, filtered, and concentrated. The residue was purified by silica gel (1-2% MeOH in $CH_2Cl_2$) to give the title compound (0.1116 g, 83.30% yield). $^1H$ NMR ($d_6$-DMSO) δ 12.35 (s, 1H), 8.39 (d, 1H), 8.37 (m, 1H), 7.66 (dt, 1H), 7.47 (d, 1H), 7.42 (t, 2H), 7.21-7.11 (m, 5H), 6.73 (t, 1H), 4.29 (t, 1H), 3.81 (m, 3H), 3.20-3.02 (m, 2H), 2.81 (t, 1H), 2.01 (m, 2H), 1.76-1.53 (m, 2H), 1.38 (s, 9H).

Example 283

(R)-2-hydroxy-1-(4-(5-(3-phenoxy-5-(pyridin-2-ylthio)pyridin-2-ylamino)-1,2,4-thiadiazol-3-yl)piperidin-1-yl)propan-1-one

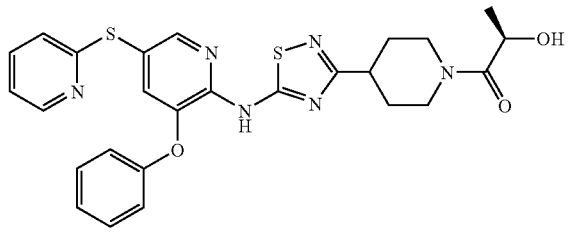

3-Phenoxy-N-(3-piperidin-4-yl)-1,2,4-thiadiazol-5-yl)-5-(pyridin-2-ylthio)pyridin-2-amine (Example 39, step C, 0.075 g, 0.16 mmol), (S)-2-hydroxypropanoic acid (0.018 g, 0.19 mmol), N1-((ethylimino)methylene)-N3,N3-dimethylpropane-1,3-diamine hydrochloride (0.047 g, 0.24 mmol), and N,N-dimethylpyridin-4-amine (0.002 g, 0.016 mmol) were dissolved in $CH_2Cl_2$ (5 mL). Triethylamine (0.033 g, 0.32 mmol) was added and the solution was stirred at room temperature for 3 hours. Water was added and extracted with $CH_2Cl_2$, dried, filtered, and concentrated. The residue was purified by silica gel (1-2% MeOH in $CH_2Cl_2$) to give (R)-2-hydroxy-1-(4-(5-(3-phenoxy-5-(pyridin-2-ylthio)pyridin-2-ylamino)-1,2,4-thiadiazol-3-yl)piperidin-1-yl)propan-1-one (0.023 g, 27% yield). $^1H$ NMR ($d_6$-DMSO) δ 12.34 (s, 1H), 8.39 (d, 1H), 8.37 (m, 1H), 7.66 (dt, 1H), 7.47 (d, 1H), 7.42 (t, 2H), 7.21-7.11 (m, 5H), 4.82 (t, 1H), 4.45 (m, 1H), 4.34 (m, 1H), 4.01 (m, 1H), 3.25-3.04 (m, 2H), 2.84 (m, 1H), 2.02 (d, 2H), 1.81-1.55 (m, 2H), 1.18 (d, 3H).

The following compound was made according to the method of Example 282:

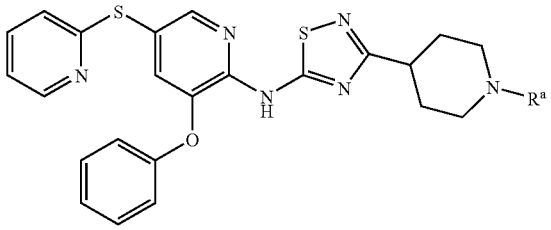

| Example | R$^a$ | Name | NMR Data |
|---|---|---|---|
| 283 | (structure) | 2-methyl-1-(4-(5-(3-phenoxy-5-(pyridin-2-ylthio)pyridin-2-ylamino)-1,2,4-thiadiazol-3-yl)piperidin-1-yl)propan-1-one | $^1$H NMR (d$_6$-DMSO) δ 12.34 (s, 1 H), 8.39 (d, 1 H), 8.37 (m, 1 H), 7.66 (dt, 1 H), 7.47 (d, 1 H), 7.42 (t, 2 H), 7.21-7.11 (m, 5 H), 4.82 (t, 1 H), 4.45 (m, 1 H), 4.34 (m, 1 H), 4.01 (m, 1 H), 3.25-3.04 (m, 2 H), 2.84 (m, 1 H), 2.02 (d, 2 H), 1.81-1.55 (m, 2 H), 1.18 (d, 3 H). |

Example 285

2-amino-1-(4-(5-(3-phenoxy-5-(pyridin-2-ylthio)pyridin-2-ylamino)-1,2,4-thiadiazol-3-yl)piperidin-1-yl)ethanone dihydrochloride

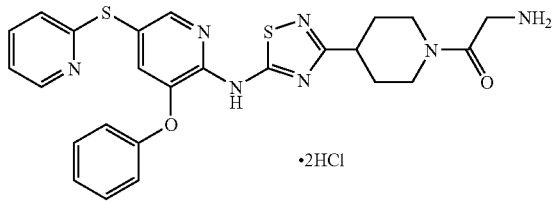

tert-Butyl 2-oxo-2-(4-(5-(3-phenoxy-5-(pyridin-2-ylthio)pyridin-2-ylamino)-1,2,4-thiadiazol-3-yl)piperidin-1-yl)ethylcarbamate (0.098 g, 0.16 mmol) was dissolved in CH$_2$Cl$_2$:MeOH (1:1, 20 mL) and added 5 mL of 4M HCl in dioxane and stirred for 2 hours. The reaction was concentrated and dried in high vacuum oven to provide 2-amino-1-(4-(5-(3-phenoxy-5-(pyridin-2-ylthio)pyridin-2-ylamino)-1,2,4-thiadiazol-3-yl)piperidin-1-yl)ethanone dihydrochloride (0.081 g, 78% yield). $^1$H NMR (d-DMSO) δ 12.34 (s, 1H), 8.39 (d, 1H), 8.37 (m, 1H), 8.13 (m, 3H), 7.67 (dt, 1H), 7.48 (d, 1H), 7.43 (t, 2H), 7.21-7.11 (m, 5H), 4.32 (d, 1H), 3.90 (m, 2H), 3.70 (m, 2H), 3.48 (m, 1H), 3.26-3.02 (m, 2H), 2.94 (t, 1H), 2.06 (d, 2H), 1.76-1.53 (m, 2H).

Example 286

2-(4-(5-(3-phenoxy-5-(pyridin-2-ylthio)pyridin-2-ylamino)-1,2,4-thiadiazol-3-ylpiperidin-1-yl)ethanol bis(2,2,2-trifluoroacetate)

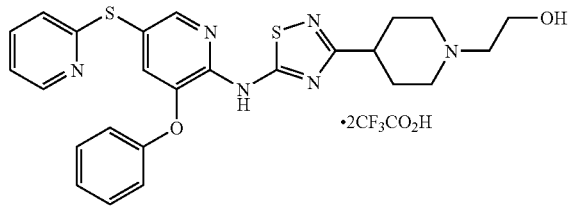

Prepared according to the method of Example 230 from 3-phenoxy-N-(3-(piperidin-4-yl)-1,2,4-thiadiazol-5-yl)-5-(pyridin-2-ylthio)pyridin-2-amine. $^1$H NMR (d$_6$-DMSO) δ 12.37 (s, 1H), 9.26 (bs, 1H), 8.39 (d, 1H), 8.37 (d, 1H), 7.67 (dt, 1H), 7.48 (d, 1H), 7.43 (t, 2H), 7.22-7.12 (m, 5H), 3.96 (s, 1H), 3.77 (t, 2H), 3.61 (d, 2H), 3.20-3.06 (m, 5H), 2.26 (d, 2H), 2.00 (m, 2H).

Example 287

4-(5-(3-Phenoxy-5-(pyridin-2-ylthio)pyridin-2-ylamino)-1,2,4-thiadiazol-3-yl)piperidine-1-sulfonamide bis(2,2,2-trifluoroacetate)

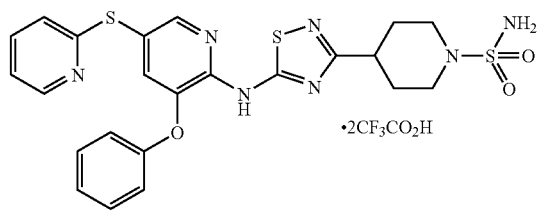

N-(3-phenoxy-5-(pyridin-2-ylthio)pyridin-2-yl)-3-(piperidin-4-yl)-1,2,4-thiadiazol-5-amine (Example 34, step C, 7.2 g, 14.01 mmol) and sulfamide (1.414 g, 14.71 mmol) were dissolved in dioxane (15 mL) and heated to reflux overnight. The reaction was cooled and water was added and extracted with DCM. The organic layer was dried over sodium sulfate, filtered and concentrated. The residue was purified by silica gel (1:1EtOAc in DCM). The purified material was dissolved in DCM and 2M HCl in ether was added. The solution was concentrated and dried in a vacuum oven to afford 4-(5-(3-phenoxy-5-(pyridin-2-ylthio)pyridin-2-ylamino)-1,2,4-thiadiazol-3-yl)piperidine-1-sulfonamide hydrochloride (3.145 g, 38.8% yield).

$^1$H NMR (d$_6$-DMSO) δ 12.35 (s, 1H), 8.39 (d, 1H), 8.37 (m, 1H), 7.67 (dt, 1H), 7.48 (d, 1H), 7.42 (t, 2H), 7.21-7.11 (m, 5H), 6.73 (bs, 2H), 3.47 (d, 2H), 2.87 (m, 1H), 2.71 (t, 2H), 2.11 (d, 2H), 1.85 (m, 2H).

Example 288

3-(1-(2-aminoethylsulfonyl)piperidin-4-yl)-N-(3-phenoxy-5-(pyridin-2-ylthio)pyridin-2-yl)-1,2,4-thiadiazol-5-amine

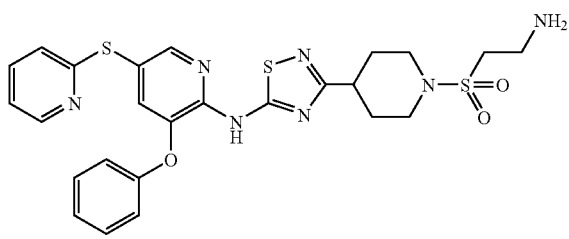

Step A: Preparation of 2-(2-(4-(5-(3-phenoxy-5-(pyridin-2-ylthio)pyridin-2-ylamino)-1,2,4-thiadiazol-3-yl)piperidin-1-ylsulfonyl)ethyl)isoindoline-1,3-dione: Prepared according to the method of Example 272 from 3-phenoxy-N-(3-(piperidin-4-yl)-1,2,4-thiadiazol-5-yl)-5-(pyridin-2-ylthio)pyridin-2-amine.

Step B: Preparation of N-(3-(1-(2-aminoethylsulfonyl)piperidin-4-yl)-1,2,4-thiadiazol-5-yl)-3-phenoxy-5-(pyridin-2-ylthio)pyridin-2-amine: 2-(2-(4-(5-(3-phenoxy-5-(pyridin-2-ylthio)pyridin-2-ylamino)-1,2,4-thiadiazol-3-yl)piperidin-1-ylsulfonyl)ethyl)isoindoline-1,3-dione (0.110 g, 0.157 mmol) and hydrazine monohydrate (0.0236 g, 0.472 mmol) were dissolved in EtOH (25 mL) and heated to reflux for 8 hours. The reaction was cooled to ambient temperature and the solids filtered and triturated with EtOH to afford the title compound (0.013 g, 14.5% yield). $^1$H NMR ($d_6$-DMSO) δ 8.38 (d, 1H), 8.36 (m, 1H), 7.66 (dt, 1H), 7.45 (d, 1H), 7.41 (t, 2H), 7.20-7.10 (m, 5H), 3.61 (d, 2H), 3.12 (t, 2H), 3.01-2.89 (m, 5H), 2.09 (d, 2H), 1.79 (m, 2H).

Example 289 tert-butyl 3-methyl-4-(2-(3-phenoxy-5-(pyridin-2-ylthio)pyridin-2-ylamino)thiazol-4-yl)piperidine-1-carboxylate

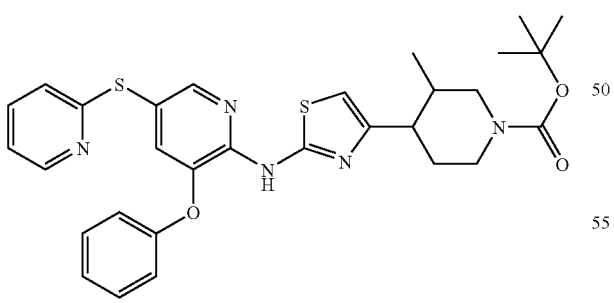

Step A: Preparation of tert-butyl 4-(methoxy(methyl)carbamoyl)-3-methylpiperidine-1-carboxylate: To a solution of 1-(tert-butoxycarbonyl)-3-methylpiperidine-4-carboxylic acid (3.00 g, 12.3 mmol) in $CH_2Cl_2$ (200 mL) was added di(1H-imidazol-1-yl)methanone (2.19 g, 13.6 mmol) portionwise. After the bubbling ceased (~60 minutes), N-methoxymethanamine hydrochloride (1.32 g, 13.6 mmol) was added in one portion. The mixture was allowed to stir overnight at ambient temperature, then was washed with water, 1N HCl, and saturated sodium bicarbonate. The organic layer was dried, filtered, and concentrated to give the desired product (2.29 g, 64.8% yield) as a colorless oil.

Step B: Preparation of tert-butyl 4-acetyl-3-methylpiperidine-1-carboxylate: 3.0 M methylmagnesium chloride in THF (4.50 mL, 13.5 mmol) was added dropwise to a solution of tert-butyl 4-(methoxy(methyl)carbamoyl)-3-methylpiperidine-1-carboxylate (3.10 g, 10.8 mmol) in THF (50 mL) at 0° C. The reaction was warmed to ambient temperature and stirred for 90 minutes. The reaction was partitioned between ether and 2N HCl, washed the organic layer twice with water, brine, dried, and concentrated to afford the title compound (2.32 g, 84.3% yield) as clear oil.

Step C: Preparation of tert-butyl 4-(2-bromoacetyl)-3-methylpiperidine-1-carboxylate: To a cooled (−78° C.) solution of LDA (5.69 mL, 11.4 mmol) in THF (100 mL) was added dropwise over 40 minutes a solution of tert-butyl 4-acetyl-3-methylpiperidine-1-carboxylate (2.29 g, 9.48 mmol) in THF (40 mL). After an additional 25 minutes, chlorotrimethylsilane (2.41 mL, 18.9 mmol) was added dropwise over 20 minutes. After stirring for 1 hour the reaction was poured into 600 mL saturated sodium bicarbonate and extracted with ether (2×400 mL). The combined ether layers were washed with brine, dried, filtered, and concentrated to afford crude TMS-enol ether, which was then redissolved in 500 mL THF and cooled to 0° C. and treated with sodium bicarbonate (1.20 g, 14.2 mmol), followed by NBS (1.69 g, 9.48 mmol). The reaction was allowed to warm to ambient temperature while stirring for 90 minutes at which point it was poured into 400 mL of saturated sodium bicarbonate solution and extracted with $Et_2O$ and the combined organic layers were washed with saturated $NaHCO_3$, brine, dried, and concentrated to give the title compound (3.35 g, 110% yield) as an orange oil.

Step D: Preparation of tert-butyl 3-methyl-4-(2-(3-phenoxy-5-(pyridin-2-ylthio)pyridin-2-ylamino)thiazol-4-yl)piperidine-1-carboxylate: Prepared according to the method of Example 7, Step E; (0.302 g, 68.6% yield). $^1$H NMR ($d_6$-DMSO) δ 11.06 (s, 1H), 8.37 (m, 1H), 8.26 (d, 1H), 7.65 (dt, 1H), 7.41 (t, 2H), 7.32 (d, 1H), 7.20-7.11 (m, 4H), 7.06 (d, 1H), 6.67 (s, 1H), 4.10 (m, 1H), 3.85 (m, 1H), 3.01-2.72 (m, 3H), 2.26 (m, 1H), 1.84-1.65 (m, 2H), 1.40 (s, 9H), 0.59 (d, 3H).

Example 290

1-(3-methyl-4-(2-(3-phenoxy-5-(pyridin-2-ylthio pyridin-2-ylamino)thiazol-4-yl)-piperidin-1-yl)ethanone dihydrochloride

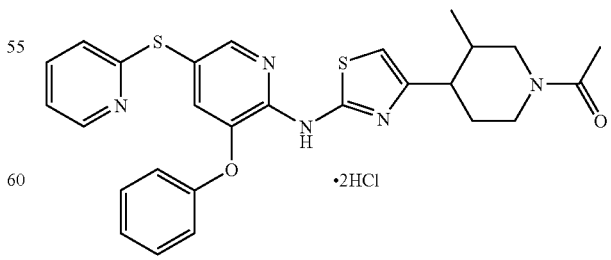

Step A: Preparation of N-(4-(3-methylpiperidin-4-yl)thiazol-2-yl)-3-phenoxy-5-(pyridin-2-ylthio)pyridin-2-amine: Prepared according to the method of Example 271 from tert-butyl 3-methyl-4-(2-(3-phenoxy-5-(pyridin-2-ylthio)pyridin-2-ylamino)thiazol-4-yl)piperidine-1-carboxylate.

Step B: Preparation of 1-(3-methyl-4-(2-(3-phenoxy-5-(pyridin-2-ylthio)pyridin-2-ylamino)thiazol-4-yl)piperidin-1-yl)ethanone dihydrochloride: Prepared according to the method of Example 272 to provide the title compound (0.0553 g, 51.4% yield) as a 1:1 mixture of diastereomers. $^1$H NMR (d$_6$-DMSO) δ 8.37 (d, 1H), 8.29 (s, 1H), 7.67 (dt, 1H), 7.43 (t, 2H), 7.37 (d, 1H), 7.17 (m, 4H), 7.10 (d, 1H), 6.73 (d, 1H), 4.50 (d, 0.5H), 4.27 (d, 0.5H), 3.94 (d, 0.5H), 3.74 (d, 0.5H), 3.33 (d, 0.5H), 3.15 (t, 0.5), 3.04 (m, 1H), 2.87 (d, 0.5), 2.67 (m, 0.5H), 2.32 (m, 1H), 2.05 (s, 1.5H), 1.98 (s, 1.5H), 1.89-1.69 (m, 2H), 0.64 (d, 1.5H), 0.56 (d, 1.5H);

Example 291

1-(4-(2-(3-phenoxy-5-(pyridin-2-ylthio)pyridin-2-ylamino)thiazol-4-yl)piperidin-1-yl)ethanone dihydrochloride

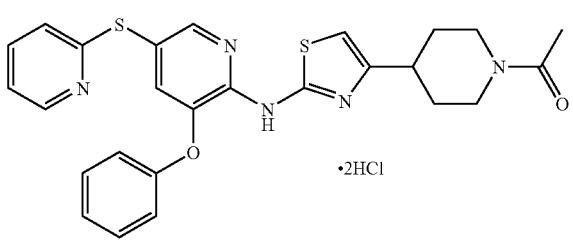

Step A: Preparation of 1-benzoyl-3-(3-phenoxy-5-(pyridin-2-ylthio)pyridin-2-yl)thiourea: Prepared according to the method of Example 7, Step C, from 3-phenoxy-5-(pyridin-2-ylthio)pyridin-2-amine.

Step B: Preparation of 1-(3-phenoxy-5-(pyridin-2-ylthio)pyridin-2-yl)thiourea: Prepared according to the method of Example 39, Step D.

Step C: Preparation of 1-(4-(2-(3-phenoxy-5-(pyridin-2-ylthio)pyridin-2-ylamino)thiazol-4-yl)piperidin-1-yl)ethanone dihydrochloride: Prepared according to the method of Example 7, Step E in 6.2% yield after HCl salt formation. $^1$H NMR (d$_6$-DMSO) δ 8.38 (m, 1H), 8.29 (d, 1H), 7.67 (dt, 1H), 7.45-7.37 (m, 3H), 7.21-7.08 (m, 5H), 6.78 (s, 1H), 4.32 (d, 1H), 3.87 (d, 1H), 3.13 (t, 1H), 2.87 (m, 1H), 2.64 (t, 1H), 2.01 (s, 3H), 1.95 (m, 2H), 1.63-1.39 (m, 2H).

Example 292

N-(5-Bromo-3-phenoxypyridin-2-yl)thiazolo[5,4-b]pyridin-2-amine

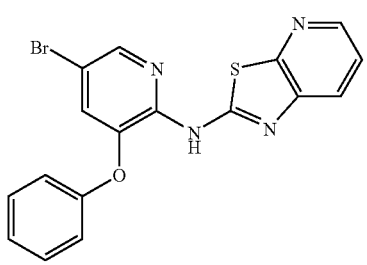

Heated a mixture of 2-chloro-3-isothiocyanatopyridine (0.257 g, 1.51 mmol) and 5-bromo-3-phenoxypyridin-2-amine (0.400 g, 1.51 mmol) in DMF (4 mL) at 80° C. for 3 hours. Heated at 120° C. overnight. Cooled, partitioned between 2N NaOH and ethyl acetate. Washed the organic layer twice with water, brine, dried, and concentrated. Subjected the residue to Biotage, eluting with 3:1 hexane:ethyl acetate to afford the title compound (0.465 g, 77.2% yield) as a white powder. $^1$H NMR (d$_6$-DMSO) δ 7.15 (d, 2H), 7.23 (t, 1H), 7.40-7.50 (m, 4H), 7.92 (s, 1H), 8.34 (s, 1H), 8.37 (d, 1H), 11.63 (bs, 1H).

Example 293

Methyl 3-(5-phenoxy-6-(thiazolo[5,4-b]pyridin-2-ylamino)pyridin-3-ylthio)propanoate

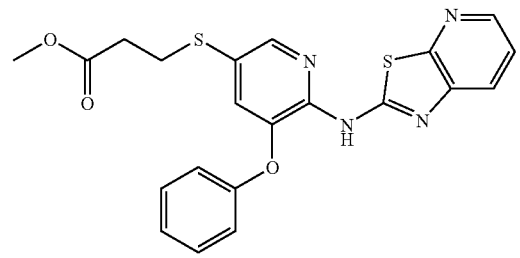

Prepared according to the method of Example 13 from N-(5-bromo-3-phenoxypyridin-2-yl)thiazolo[5,4-b]pyridin-2-amine, methyl 3-mercaptopropanoate and N-ethyl-N-isopropylpropan-2-amine in 75% yield. $^1$H NMR (d$_6$-DMSO) δ 2.59 (t, 2H), 3.09 (t, 2H), 3.56 (s, 3H), 7.12 (d, 2H), 7.20 (t, 1H), 7.38-7.46 (m, 4H), 7.91 (bs, 1H), 8.24 (s, 1H), 8.36 (d, 1H), 11.53 (bs, 1H).

Example 294

N-(3-Phenoxy-5-(pyridin-4-ylthio)pyridin-2-yl)thiazolo[5,4-b]pyridin-2-amine

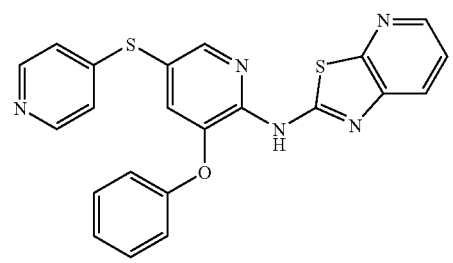

Prepared according to the method of Example 292 from 2-chloro-3-isothiocyanatopyridine (0.116 g, 0.677 mmol) and 3-phenoxy-5-(pyridin-4-ylthio)pyridin-2-amine. $^1$H NMR (d$_6$-DMSO) δ 7.10 (d, 2H), 7.17-7.23 (m, 3H), 7.40-7.47 (m, 4H), 7.97 (bs, 1H), 8.36-8.41 (m, 4H), 11.88 (bs, 1H).

Example 295

Preparation of 4-(2-(thiazolo[5,4-b]pyridin-2-ylamino)pyridin-3-ylthio)benzonitrile

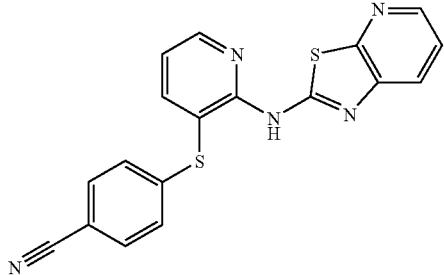

Step A: Preparation of N-(3-bromopyridin-2-yl)thiazolo[5,4-b]pyridin-2-amine: Heated a mixture of 2-chloro-3-isothiocyanatopyridine (0.986 g, 5.78 mmol) and 3-bromopyridin-2-amine (1.00 g, 5.78 mmol) in DMF (4 mL) at 80° C. for 3 hours. Heated at 120° C. overnight. Cooled, partitioned between ethyl acetate and water, washed with 2N NaOH, water, brine, dried, and concentrated. Crystallized from dichloromethane:hexanes (1:10, 110 mL) and filtered. The filtered material was further purified by dissolving in dichloromethane (10 mL), and subjecting to MPLC (Biotage) eluting with 3:2 hexane:ethyl acetate. The higher Rf component was concentrated to afford the title compound (0.654 g, 36.8% yield) as a white powder.

Step B: Preparation of methyl 3-(2-(thiazolo[5,4-b]pyridin-2-ylamino)pyridin-3-ylthio)propanoate: A mixture of N-(3-bromopyridin-2-yl)thiazolo[5,4-b]pyridin-2-amine (0.55 g, 1.79 mmol), 4,5-bis(diphenylphosphino)-9,9-dimethyl-9H-xanthene (0.052 g, 0.090 mmol), Pd$_2$dba$_3$ (0.041 g, 0.045 mmol), methyl 3-mercaptopropanoate (0.21 mL, 1.88 mmol), N-ethyl-N-isopropylpropan-2-amine (0.62 mL, 3.60 mmol), and dioxane (40 mL) was heated to 95° C. under nitrogen. Cooled to ambient temperature and filtered the solids. Concentrated and purified by MPLC (Biotage) eluting with 1:1 hexane:ethyl acetate to afford the title compound (0.541 g, 87% yield) as a dark yellow oil.

Step C: Preparation of 4-(2-(thiazolo[5,4-b]pyridin-2-ylamino)pyridin-3-ylthio)benzonitrile: Added potassium 2-methylpropan-2-olate (0.097 g, 0.87 mmol) to a solution of methyl 3-(2-(thiazolo[5,4-b]pyridin-2-ylamino)pyridin-3-ylthio)propanoate (100 mg, 0.289 mmol) in DMSO (1 mL). Stirred 15 minutes, added 4-fluorobenzonitrile (0.105 g, 0.866 mmol) and stirred overnight. Partitioned between ethyl acetate and water. Washed the organic layer with water, brine, dried, and concentrated. Purified by MPLC eluting with 3:2 hexane:ethyl acetate to afford the title compound (0.034 g, 33% yield) as a white powder: $^1$H NMR (CDCl$_3$) δ 7.10-7.15 (m, 3H), 7.32 (dd, 1H), 7.52 (d, 2H), 7.87 (d, 1H), 7.96 (d, 1H), 8.42 (d, 1H), 8.58 (d, 1H), 9.10 (bs, 1H).

Example 296

2-(2-(Thiazolo[5,4-b]pyridin-2-ylamino)pyridin-3-ylthio)benzonitrile

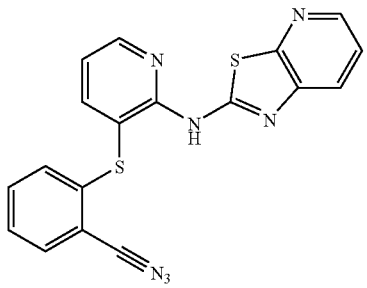

Prepared according to the method of Example 295, step C. $^1$H NMR (CDCl$_3$) δ 6.91 (d, 1H), 7.11 (dd, 1H), 7.27-7.34 (m, 2H), 7.42 (t, 1H), 7.69 (d, 1H), 7.90 (d, 1H), 7.99 (d, 1H), 8.43 (d, 1H), 8.57 (d, 1H), 9.13 (bs, 1H).

Example 297

4-(5-Phenoxy-6-(thiazolo[5,4-b]pyridin-2-ylamino)pyridin-3-ylthio)benzonitrile

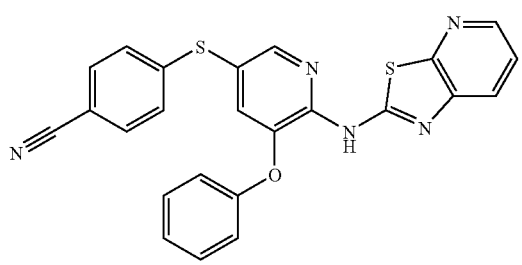

Prepared according to the method of Example 295, step C. $^1$H NMR (CDCl$_3$) δ 7.07-7.16 (m, 4H), 7.25 (m, 1H), 7.35 (dd, 1H), 7.41-7.46 (m, 2H), 7.49 (d, 2H), 7.93 (d, 1H), 8.30 (s, 1H), 8.44 (d, 1H), 9.00 (bs, 1H).

Example 298

N-(3-Phenoxy-5-(pyrimidin-2-ylthio)pyridin-2-yl)thiazolo[5,4-b]pyridin-2-amine

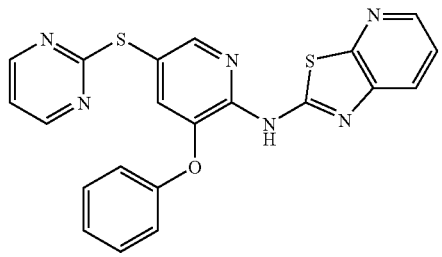

Prepared according to the method of Example 295, step C. $^1$H NMR (CDCl$_3$) δ 7.00 (t, 1H), 7.13 (d, 2H), 7.23 (t, 1H), 7.31-7.43 (m, 4H), 7.91 (d, 1H), 8.35 (s, 1H), 8.42 (d, 1H), 8.47 (d, 2H), 9.02 (bs, 1H).

Example 299

N-(3-Phenoxy-5-(thieno[3,2-b]pyridin-7-ylthio)pyridin-2-yl)thiazolo[5,4-b]pyridin-2-amine

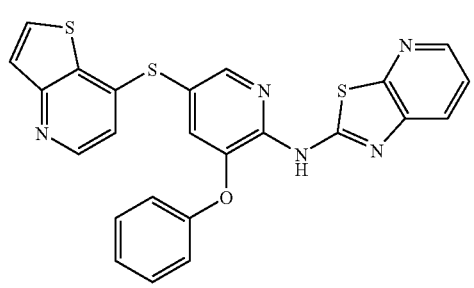

Prepared according to the method of Example 295, step C. ¹H NMR (CDCl₃) δ 6.79 (d, 1H), 7.06 (d, 2H), 7.24 (m, 2H), 7.33-7.42 (m, 3H), 7.55 (d, 1H), 7.74 (d, 1H), 7.93 (d, 1H), 8.38 (s, 1H), 8.44 (d, 1H), 8.49 (d, 1H), 9.07 (bs, 1H).

Example 300

N-(3-(Thieno[3,2-b]pyridin-7-ylthio)pyridin-2-yl)thiazolo[5,4-b]pyridin-2-amine

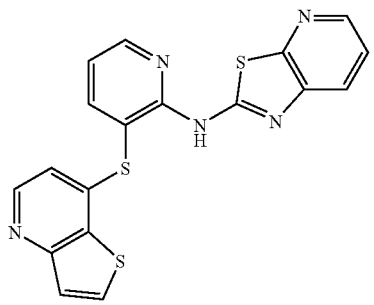

Prepared according to the method of Example 295, step C. ¹H NMR (CDCl₃) δ 6.64 (d, 1H), 7.13 (dd, 1H), 7.31 (dd, 1H), 7.59 (d, 1H), 7.80 (d, 1H), 7.85 (d, 1H), 8.01 (d, 1H), 8.42 (d, 1H), 8.47 (d, 1H), 8.61 (d, 1H), 9.16 (bs, 1H).

Example 301

Preparation of N-(5-bromo-3-phenoxypyrazin-2-yl)thiazolo[5,4-b]pyridin-2-amine

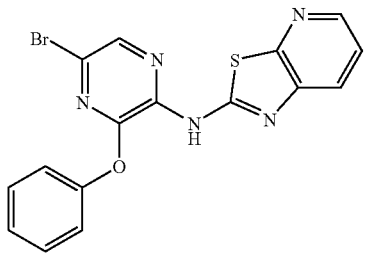

Step A: Preparation of 5-bromo-3-phenoxypyrazin-2-amine: Added sodium hydride (0.348 g, 8.70 mmol) to a solution of phenol (0.819 g, 8.70 mmol) in THF (50 mL) at 0° C. and stirred 30 minutes. Added 3,5-dibromopyrazin-2-amine (2.00 g, 7.91 mmol) in THF (10 mL). Removed the ice bath and refluxed overnight. Partitioned between ethyl acetate and water, washed with brine, dried, and concentrated. Purified by MPLC (Biotage) eluting with 5:1 hexane:ethyl acetate to afford the title compound (1.36 g, 64.6% yield) as a light yellow solid.

Step B: Preparation of N-(5-bromo-3-phenoxypyrazin-2-yl)thiazolo[5,4-b]pyridin-2-amine: 5-Bromo-3-phenoxypyrazin-2-amine (0.100 g, 0.376 mmol) and 2-chloro-3-isothiocyanatopyridine (0.0641 g, 0.376 mmol) afforded the title compound (0.078 g, 51.9% yield) as light yellow crystals: ¹H NMR (d₆-DMSO) δ 7.28-7.33 (m, 3H), 7.43-7.51 (m, 3H), 7.94 (d, 1H), 8.27 (s, 1H), 8.39 (d, 1H), 12.30 (bs, 1H).

Example 302

N-(5-Bromo-3-(4-fluorophenoxy-pyridin-2-yl)thiazolo[5,4-b]pyridin-2-amine

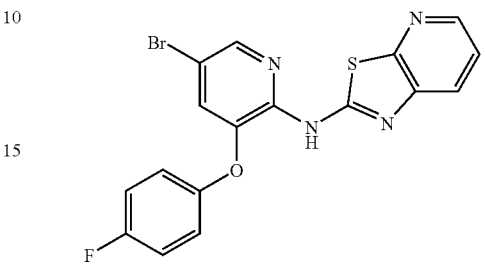

Prepared according to the method of Example 301, step B. ¹H NMR (CDCl₃) δ 7.08-7.18 (m, 5H), 7.34 (dd, 1H), 7.91 (d, 1H), 8.21 (s, 1H), 8.43 (d, 1H), 8.83 (bs, 1H).

Example 303

Preparation of 4-(5-bromo-2-(thiazolo[5,4-b]pyridin-2-ylamino)pyridin-3-yloxy)benzonitrile

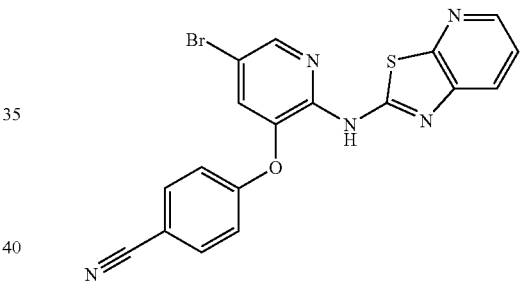

Step A: Preparation of 4-(2-aminopyridin-3-yloxy)benzonitrile: Heated a mixture of potassium carbonate (31.38 g, 227.0 mmol), 2-aminopyridin-3-ol (10.00 g, 90.82 mmol), 4-fluorobenzonitrile (11.00 g, 90.82 mmol), and DMF (80 mL) at 90° C. for 3 hours. Cooled, partitioned between ethyl acetate and water, washed the organic layer twice with water, once with 2N NaOH, brine, dried, and concentrated. Dissolved the residue in dichloromethane (20 mL), added hexanes (150 mL), concentrated to 130 mL, filtered, and dried to afford the title compound (13.95 g, 72.72% yield) as a tan powder.

Step B: Preparation of 4-(2-amino-5-bromopyridin-3-yloxy)benzonitrile: Placed 4-(2-aminopyridin-3-yloxy)benzonitrile (13.95 g, 66.05 mmol) in acetic acid (50 mL) and cooled to 0° C. Slowly added bromine (4.229 mL, 82.56 mmol) and stirred for an hour. The reaction mixture was poured onto saturated sodium bisulfite and ice. Extracted with dichloromethane three times, washed with 2N NaOH, water, brine, dried, and concentrated. Purified by MPLC eluting with 3:2 hexane:ethyl acetate to afford the title compound (12.7 g, 66.28% yield) as a light yellow solid.

Step C: Preparation of 4-(5-bromo-2-(thiazolo[5,4-b]pyridin-2-ylamino)pyridin-3-yloxy)benzonitrile: Prepared according to the method of Example 301, Step B. ¹H NMR (d₆-DMSO) δ 7.21 (d, 2H), 7.41 (dd, 1H), 7.85-7.88 (m, 3H), 7.94 (s, 1H), 8.36 (d, 1H), 8.47 (s, 1H), 11.91 (bs, 1H).

Example 304

Preparation of 4-(5-bromo-2-(4-methylthiazol-2-ylamino)pyridin-3-yloxy)benzonitrile

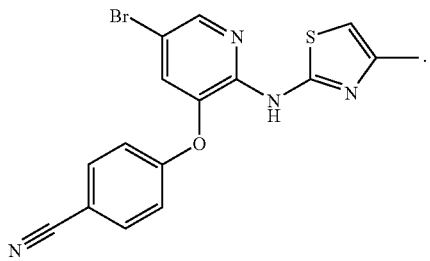

Step A: Preparation of 1-benzoyl-3-(5-bromo-3-(4-cyanophenoxy)pyridin-2-yl)thiourea: Prepared according to the method of Example 7, step C from benzoyl isothiocyanate and 4-(2-amino-5-bromopyridin-3-yloxy)benzonitrile.

Step B: Preparation of 1-(5-bromo-3-(4-cyanophenoxy)pyridin-2-yl)thiourea: Added 3 M aqueous sodium hydroxide (4.41 mL, 13.2 mmol) to a mixture of 1-benzoyl-3-(5-bromo-3-(4-cyanophenoxy)pyridin-2-yl)thiourea (3.00 g, 6.62 mmol) and MeOH (50 mL) and heated to 50° C. for 2 hours. Cooled, partitioned between ethyl acetate and water, washed twice with water, brine, dried, and concentrated. Added ethyl acetate (6 mL), heated to try to afford a solution. Added hexanes (8 mL) slowly, and cooled and triturated for 15 minutes. Filtered, to afford the title compound a (1.70 g, 73.6% yield) as a white solid.

Step C: Preparation of 4-(5-bromo-2-(4-methylthiazol-2-ylamino)pyridin-3-yloxy)benzonitrile: Prepared according to the method of Example 7, step E. $^1$H NMR (d$_6$-DMSO) δ 2.20 (s, 3H), 6.57 (s, 1H), 7.13 (d, 2H), 7.82 (s, 1H), 7.84 (d, 2H), 8.34 (s, 1H), 11.20 (bs, 1H).

Example 305

Preparation of methyl 4-(5-bromo-2-(thiazolo[5,4-b]pyridin-2-ylamino)pyridin-3-ylthio)benzoate hydrochloride

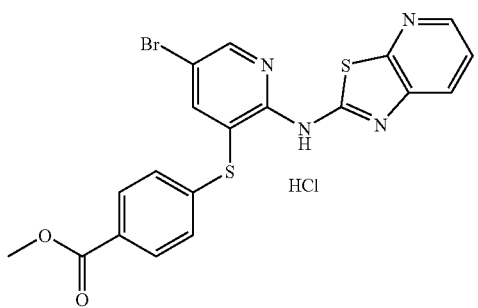

Step A: Preparation of methyl 4-(2-nitropyridin-3-ylthio)benzoate: Stirred a mixture of methyl 4-mercaptobenzoate (4.46 g, 26.5 mmol), 3-chloro-2-nitropyridine (4.00 g, 25.2 mmol) and cesium carbonate (9.04 g, 27.8 mmol) in DMSO (60 mL) at ambient temperature for 90 minutes. The solution was diluted with water, extracted with EtOAc, dried, and concentrated. The crude solid was suspended in MeOH (80 mL) and triturated for 0.5 hours. The solid was filtered and dried to provide the title compound (6.16 g, 84.1% yield).

Step B: Preparation of methyl 4-(2-aminopyridin-3-ylthio)benzoate: Added zinc powder (13.88 g, 212.2 mmol) slowly to a solution of methyl 4-(2-nitropyridin-3-ylthio)benzoate (6.16 g, 21.22 mmol) in acetic acid (75 mL) at ambient temperature in an ambient water bath. Stirred for an hour, diluted with dichloromethane, and filtered through celite. Washed the celite pad several times with dichloromethane. Concentrated the filtrate, and partitioned the residue between 2N NaOH and ethyl acetate. The organic layer was washed with water, brine, dried and concentrated to afford the title compound (5.5 g, 99.57% yield).

Step C: Preparation of methyl 4-(2-amino-5-bromopyridin-3-ylthio)benzoate: Placed methyl 4-(2-aminopyridin-3-ylthio)benzoate (5.50 g, 21.1 mmol) in acetic acid (25 mL) and cooled to 0° C. Slowly added bromine (1.35 mL, 26.4 mmol) and stirred for an hour. Poured reaction mixture onto saturated sodium bisulfite and ice. Extracted with dichloromethane three times, washed with 2N NaOH, water, brine, dried, and concentrated. Subjected to MPLC (Biotage) eluting with 3:2 hexane:ethyl acetate to afford the title compound (4.87 g, 68.0% yield).

Step D: Preparation of methyl 4-(5-bromo-2-(thiazolo[5,4-b]pyridin-2-ylamino)pyridin-3-ylthio)benzoate hydrochloride: Added methyl 4-(2-amino-5-bromopyridin-3-ylthio)benzoate (1.00 g, 2.95 mmol) to a mixture of 2-chloro-3-isothiocyanatopyridine (0.503 g, 2.95 mmol) in DMF (4 mL). Stirred at 80° C. for an hour, then at 110° C. for 2 hours. Cooled, diluted with dichloromethane (8 mL), filtered, washed with dichloromethane, and dried to afford the title compound (0.625 g, 41.6% yield). $^1$H NMR (d$_6$-DMSO) δ 3.84 (s, 3H), 7.40 (dd, 1H), 7.45 (d, 2H), 7.72 (d, 1H), 7.79 (bs, 1H), 7.96 (d, 2H), 8.34 (d, 1H), 8.56 (s, 1H).

Example 306

Preparation of 4-(5-bromo-2-(thiazolo[5,4-b]pyridin-2-ylamino)pyridin-3-yloxy)-2-(trifluoromethyl)benzonitrile

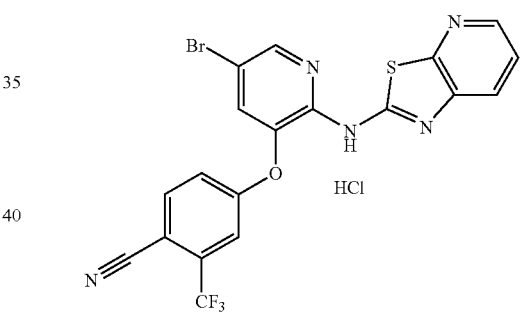

Prepared according to the method of Example 303 using 4-fluoro-2-(trifluoromethyl)benzonitrile. $^1$H NMR (d$_6$-DMSO) δ 7.39-7.45 (m, 2H), 7.74 (s, 1H), 7.89 (d, 1H), 8.11 (s, 1H), 8.14 (d, 1H), 8.38 (d, 1H), 8.52 (s, 1H).

Example 307

4-(5-Bromo-2-(thiazolo[5,4-b]pyridin-2-ylamino)pyridin-3-ylthio)benzoic acid

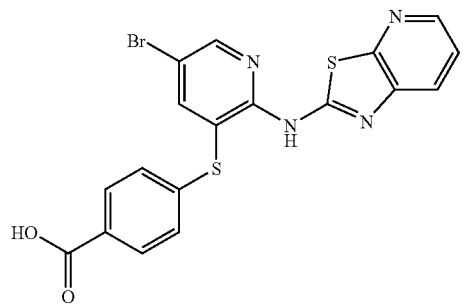

Heated a mixture of methyl 4-(5-bromo-2-(thiazolo[5,4-b]pyridin-2-ylamino)pyridin-3-ylthio)benzoate hydrochloride (0.570 g, 1.12 mmol), 1N aqueous sodium hydroxide (2.80 mL, 2.80 mmol), and methanol (6 mL) at 65° C. for an hour. Cooled, and partitioned between saturated NH₄Cl (30 mL), 1N HCl (3 mL), water (10 mL) and chloroform. The mixture was filtered, washed with water, and dried to afford the title compound (0.360 g, 70.1% yield). ¹H NMR (d-DMSO) δ 7.35 (dd, 1H), 7.43 (d, 2H), 7.50 (s, 1H), 7.67 (d, 1H), 7.94 (d, 2H), 8.44 (s, 1H).

Example 308 ethyl 2-(5-bromo-2-(thiazolo[5,4-b]pyridin-2-ylamino)pyridin-3-ylthio)-5-fluorobenzoate hydrochloride

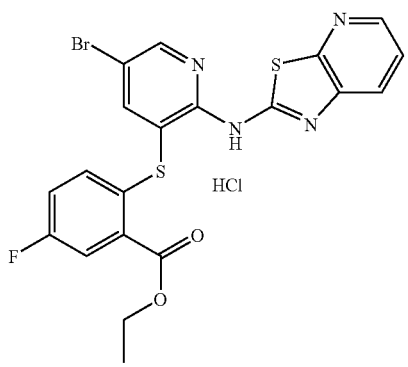

Prepared according to the method of Example 305 from ethyl 5-fluoro-2-mercaptobenzoate and 3-chloro-2-nitropyridine. ¹H NMR (CDCl₃) δ 1.48 (s, 3H), 4.50 (q, 2H), 6.66 (dd, 1H), 7.07 (m, 1H), 7.32 (dd, 1H), 7.81 (d, 1H), 7.86 (d, 1H), 8.07 (s, 1H), 8.42 (d, 1H), 8.61 (s, 1H), 9.19 (bs, 1H).

Example 309

4-(5-bromo-2-(thiazolo[5,4-b]pyridin-2-ylamino)pyridin-3-yloxy)-3-methylbenzonitrile hydrochloride

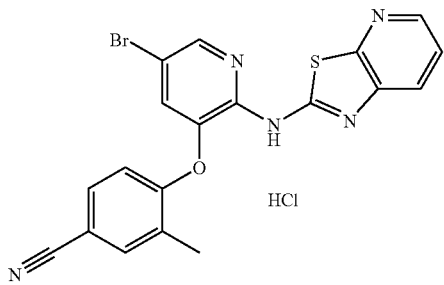

Prepared according to the method of Example 303 using 4-fluoro-3-methylbenzonitrile. ¹H NMR (d₆-DMSO) δ 2.47 (s, 3H), 7.02 (d, 1H), 7.16 (s, 1H), 7.43 (dd, 1H), 7.78 (d, 1H), 7.89 (s, 1H), 7.90 (d, 1H), 8.38 (d, 1H), 8.46 (s, 1H).

Example 310

4-(5-bromo-2-(thiazolo[5,4-b]pyridin-2-ylamino)pyridin-3-yloxy)-3-fluorobenzonitrile hydrochloride

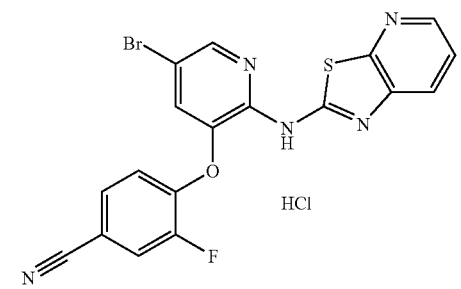

Prepared according to the method of Example 303 using 4-chloro-3-fluorobenzonitrile. ¹H NMR (d₆-DMSO) δ 7.20 (t, 1H), 7.44 (dd, 1H), 7.66 (d, 1H), 7.91 (d, 1H), 7.99 (s, 1H), 8.07 (d, 1H), 8.39 (d, 1H), 8.48 (s, 1H).

Example 311

Preparation of 4-(5-bromo-2-(thiazolo[5,4-b]pyridin-2-ylamino)pyridin-3-yloxy)-3-chlorobenzonitrile hydrochloride

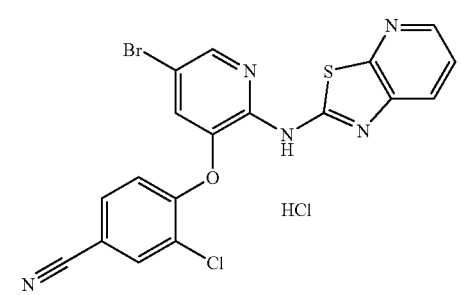

Prepared according to the method of Example 303 using 3-chloro-4-fluorobenzonitrile. ¹H NMR (d₆-DMSO) δ 7.14 (d, 1H), 7.41 (dd, 1H), 7.78 (d, 1H), 7.83 (bs, 1H), 7.93 (d, 1H), 8.23 (s, 1H), 8.36 (d, 1H), 8.48 (s, 1H), 11.97 (bs, 1H).

Example 312

Preparation of 3-(5-bromo-2-(thiazolo[5,4-b]pyridin-2-ylamino)pyridin-3-Yloxy)-4-chlorobenzonitrile hydrochloride

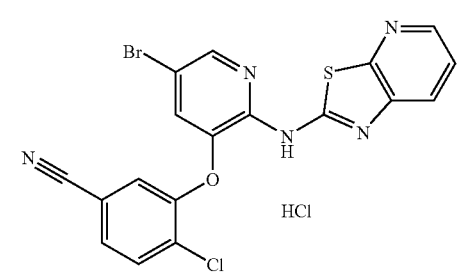

3-(2-aminopyridin-3-yloxy)-4-chlorobenzonitrile was isolated as a byproduct from step A of Example 311 and carried through the reactions in Example 303 to afford the title compound. $^1$H NMR (d$_6$-DMSO) δ 7.44 (dd, 1H), 7.71 (d, 1H), 7.74-7.77 (m, 2H), 7.84 (d, 1H), 7.92 (m, 1H), 8.39 (d, 1H), 8.43 (s, 1H).

Example 313

3-methyl-N-(5-(3-methylisoxazolo[5,4-b]pyridin-4-ylthio)-3-phenoxypyrazin-2-yl)-1,2,4-thiadiazol-5-amine

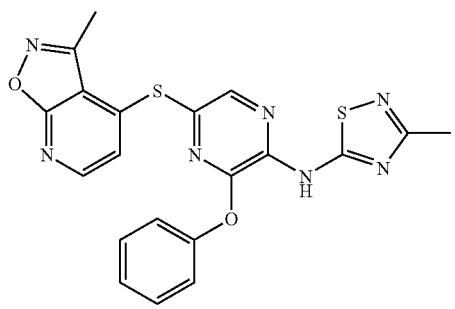

Step A: Preparation of methyl 3-(5-amino-6-phenoxypyrazin-2-ylthio)propanoate: Prepared according to the method of Example from 5-Bromo-3-phenoxypyrazin-2-amine and methyl 3-mercaptopropanoate.

Step B: Preparation of 5-(3-methylisoxazolo[5,4-b]pyridin-4-ylthio)-3-phenoxypyrazin-2-amine: Prepared according to the method of Example 127 using methyl 3-(5-amino-6-phenoxypyrazin-2-ylthio)propanoate.

Step C: Preparation of 3-methyl-N-(5-(3-methylisoxazolo[5,4-b]pyridin-4-ylthio)-3-phenoxypyrazin-2-yl)-1,2,4-thiadiazol-5-amine: Prepared according to the method of Example 183, Step D to provide the title compound (3.9 mg, 12.7% yield). $^1$H NMR (CDCl$_3$) δ 2.59 (s, 3H), 2.64 (s, 3H), 6.88 (d, J=5 Hz, 1H), 7.06, (m, 2H), 7.26 (m, 2H), 7.34 (m, 2H), 8.29 (m, 2H). Mass spectrum m/e 450.2/451.2/453.2 (M+H)$^+$.

Example 314

N-(5-bromo-3-(4-fluorophenoxy)pyrazin-2-yl)-3-methyl-1,2,4-thiadiazol-5-amine

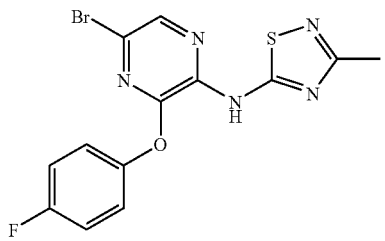

Step A: Preparation of 5-bromo-3-(4-fluorophenoxy)pyrazin-2-amine: Prepared according to the method of Example 301, Step A, from 3,5-dibromo-2-aminopyrazine.

Step B: Preparation of N-(5-bromo-3-(4-fluorophenoxy)pyrazin-2-yl)-3-methyl-1,2,4-thiadiazol-5-amine: Prepared according to the method of Example 183, Step D. $^1$H N (CDCl$_3$) δ 2.57 (s, 3H), 7.12-7.23 (m, 4H), 8.15 (s, 1H), 9.14 (br s, 1H). Mass spectrum (ESI+) m/z 382, 384 (M+H)$^+$.

Example 315

Preparation of 3-(2-(5-bromo-3-phenoxypyridin-2-ylamino)thiazol-4-yl)propanoic acid

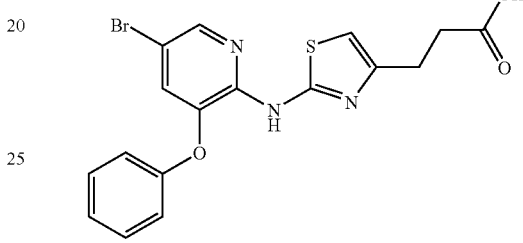

Step A: Preparation of methyl 3-(2-(5-bromo-3-phenoxypyridin-2-ylamino)thiazol-4-yl)-propanoate: A mixture of methyl 5-bromo-4-oxopentanoate (2.51 g, 12.0 mmol), 1-(5-bromo-3-phenoxypyridin-2-yl)thiourea (3.00 g, 9.25 mmol), triethylamine (2.19 mL, 15.7 mmol), and ethanol (60 mL) was refluxed for 3 hours and then stirred at ambient temperature overnight. The solvent was removed to about one third original volume and partitioned between CH$_2$Cl$_2$ and water. The organics were concentrated and purified on silica gel eluting with 40% EtOAc/Hexanes to give the title compound (3.22 g, 80.1% yield).

Step B: Preparation of 3-(2-(5-bromo-3-phenoxypyridin-2-ylamino)thiazol-4-yl)-propanoic acid: To a mixture of methyl 3-(2-(5-bromo-3-phenoxypyridin-2-ylamino)thiazol-4-yl)propanoate (0.100 g, 0.230 mmol) in 10 mL THF, and 5 mL water was added sodium hydroxide (0.0368 g, 0.921 mmol) and the reaction was stirred overnight. The mixture was concentrated to dryness. Water was added and washed with Et$_2$O and EtOAc. The aqueous was acidified with a saturated NH$_4$Cl solution, extracted with 3:1 CH$_2$Cl$_2$-THF. The organics were dried over Na$_2$SO$_4$ and concentrated to a residue. The crude solids were recrystallized from EtOAc/Hexanes to give the title compound (0.050 g, 51.7% yield). $^1$H NMR (d$_6$DMSO) δ 2.58 (t, J=7.5 Hz, 2H), 2.81 (t, J=7.5 Hz, 2H), 6.66 (s, 1H), 7.10 (d, J=7.8 Hz, 2H), 7.21 (t, J=7.4 Hz, 1H), 7.39 (d, J=2.0 Hz, 1H), 7.44 (t, J=8.0 Hz, 2H), 8.21 (d, J=2.0 Hz, 1H).

The following compounds were prepared from 1-(5-bromo-3-phenoxypyridin-2-yl)thiourea and the corresponding 1-chloroketone or 1-bromoketone, following the methods of Example 315.

| Example | Structure | Name | NMR Data |
|---|---|---|---|
| 316 | 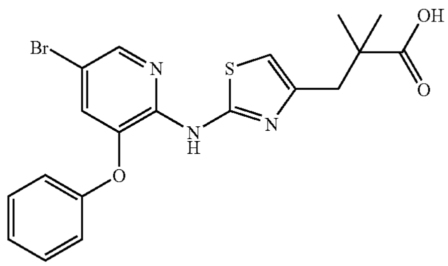 | 3-(2-(5-Bromo-3-phenoxypyridin-2-ylamino)thiazol-4-yl)-2,2-dimethylpropanoic acid | $^1$H NMR (d$_6$ DMSO) δ 1.13 (s, 6 H), 2.80 (s, 2 H), 6.63 (s, 1 H), 7.12 (d, J = 8.0 Hz, 2 H), 7.22 (t, J = 7.3 Hz, 1 H), 7.36 (d, J = 2.0 Hz, 1 H), 7.44 (t, J = 7.9 Hz, 2 H), 8.20 (d, J = 2.0 Hz, 1 H). |
| 317 | 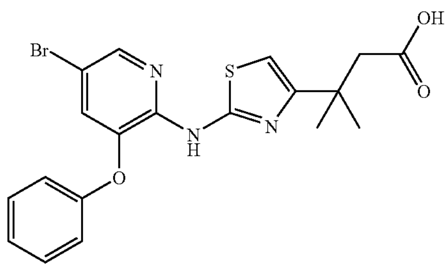 | 3-(2-(5-Bromo-3-phenoxypyridin-2-ylamino)thiazol-4-yl)-3-methylbutanoic acid | $^1$H NMR (d$_6$ DMSO) δ 1.35 (s, 6 H), 2.57 (s, 2 H), 6.65 (s, 1 H), 7.11 (d, J = 7.8 Hz, 2 H), 7.22 (t, J = 7.4 Hz, 1 H), 7.37 (d, J = 2.0 Hz, 1 H), 7.45 (t, J = 7.9 Hz, 2 H), 8.21 (d, J = 2.0 Hz, 1 H). |
| 318 | 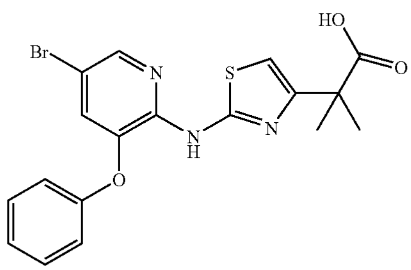 | 2-(2-(5-Bromo-3-phenoxypyridin-2-ylamino)thiazol-4-yl)-2-methylpropanoic acid | $^1$H NMR (d$_6$ DMSO) δ 1.46 (s, 6 H), 6.81 (s, 1 H), 7.10 (d, J = 7.8 Hz, 2 H), 7.21 (t, J = 7.4 Hz, 1 H), 7.39 (d, J = 2.0 Hz, 1 H), 7.44 (t, J = 7.9 Hz, 2 H), 8.22 (d, J = 2.0 Hz, 1 H), 11.03 (brs, 2 H), 12.17 (br s, 1 H). |
| 319 | 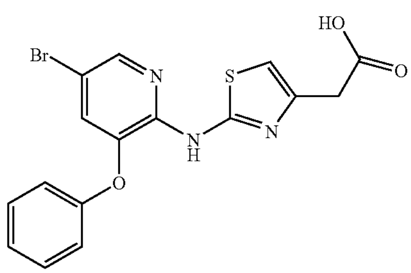 | 2-(2-(5-Bromo-3-phenoxypyridin-2-ylamino)thiazol-4-yl)acetic acid | $^1$H NMR (d$_6$ DMSO) δ 3.57 (s, 2 H), 6.84 (s, 1 H), 7.10 (d, J = 8.0 Hz, 2 H), 7.20 (t, J = 7.3 Hz, 1 H), 7.41-7.45 (m, 3 H), 8.23 (d, J = 2.0 Hz, 1 H). |

The following compounds were prepared from 1-(5-bromo-3-phenoxypyridin-2-yl)thiourea and the corresponding 1-chloroketone or 1-bromoketone, following similar methods to Example 315, Step A.

| Example | Structure | Name | NMR Data |
|---|---|---|---|
| 320 | 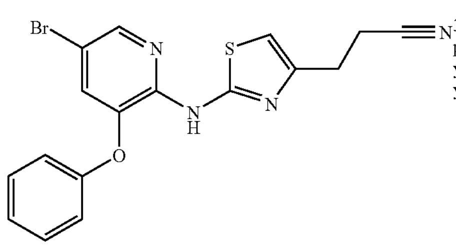 | 3-(2-(5-Bromo-3-phenoxypyridin-2-ylamino)thiazol-4-yl)propanenitrile | $^1$H NMR (d$_6$ DMSO) δ 2.82-2.89 (m, 4 H), 6.84 (s, 1 H), 7.11 (d, J = 7.8 Hz, 2 H), 7.21 (t, J = 7.4 Hz, 1 H), 7.40 (d, J = 2.0 Hz, 1 H), 7.44 (t, J = 8.0 Hz, 2 H), 8.23 (d, J = 2.0 Hz, 1 H), 11.02 (s, 1 H). |

| Example | Structure | Name | NMR Data |
|---|---|---|---|
| 321 | 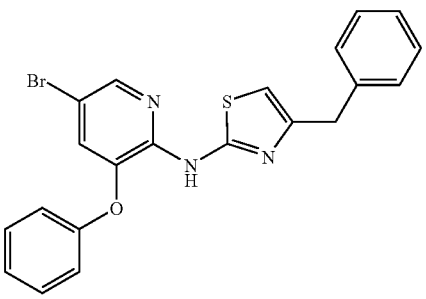 | 4-Benzyl-N-(5-bromo-3-phenoxypyridin-2-yl)thiazol-2-amine | $^1$H NMR (d$_6$ DMSO) δ 3.92 (s, 2 H), 6.66 (s, 1 H), 7.09 (d, J = 8.4 Hz, 2 H), 7.17-7.21 (m, 2 H), 7.24-7.30 (m, 4 H), 7.38 (d, J = 2.0 Hz, 1 H), 7.42 (t, J = 8.0 Hz, 2 H), 8.21 (d, J = 2.0 Hz, 1 H), 10.96 (s, 1 H). |
| 322 | 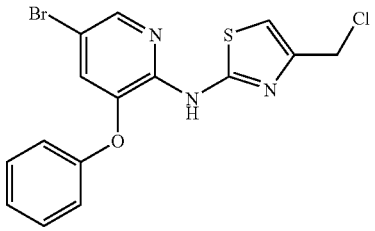 | N-(5-Bromo-3-phenoxypyridin-2-yl)-4-(chloromethyl)thiazol-2-amine | $^1$H NMR (d$_6$ DMSO) δ 4.70 (s, 2 H), 7.11 (d, J = 7.6 Hz, 2 H), 7.16 (s, 1 H), 7.21 (t, J = 7.4 Hz, 1 H), 7.42-7.46 (m, 3 H), 8.24 (d, J = 2.0 Hz, 1 H), 11.25 (s, 1 H). |

Example 323

Preparation of 3-(2-(5-bromo-3-phenoxypyridin-2-ylamino)thiazol-4-yl)-N-methylpropanamide

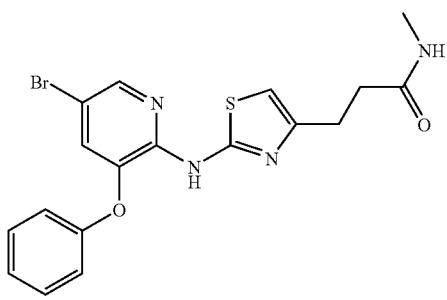

A mixture of 3-(2-(5-bromo-3-phenoxypyridin-2-ylamino)thiazol-4-yl)propanoic acid (0.100 g, 0.238 mmol) (Example 315) HOBT-H$_2$O (0.0547 g, 0.357 mmol), DIEA (d 0.742) (0.0870 mL, 0.500 mmol), EDCI (0.0684 g, 0.357 mmol), and methanamine (0.238 mL, 0.476 mmol) in 10 mL acetonitrile was stirred at ambient temperature for 5 hours and then heated at 50° C. overnight. The mixture was concentrated to a residue, dissolved in THF and precipitated with the addition of water. The solids were filtered, washed with water and dried on high vacuum overnight to give the title compound (0.072 g, 69.8% yield) as white solids. $^1$H NMR (d$_6$ DMSO) δ 2.41 (t, J=7.8 Hz, 2H), 2.56 (d, J=4.7 Hz, 3H), 2.79 (t, J=7.7 Hz, 2H), 6.62 (s, 1H), 7.10 (d, J=8.0 Hz, 2H), 7.21 (t, J=7.3 Hz, 1H), 7.40 (d, J=2.0 Hz, 1H), 7.43 (t, J=7.9 Hz, 2H), 7.77 (d, J=4.3 Hz, 1H), 8.21 (d, J=2.0 Hz, 1H), 10.94 (br s, 1H).

The following compounds were prepared from the corresponding acids (Example 322) and amines following the method of Example 323.

| Example | Structure | Name | NMR Data |
|---|---|---|---|
| 324 | 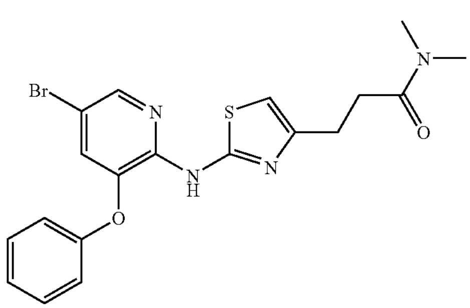 | 3-(2-(5-Bromo-3-phenoxypyridin-2-ylamino)thiazol-4-yl)-N,N-dimethylpropanamide | $^1$H NMR (d$_6$ DMSO) δ 2.64 (t, J = 7.6 Hz, 2 H), 2.76-2.81 (m, 5 H), 2.95 (s, 3 H), 6.66 (s, 1 H), 7.09 (d, J = 7.8 Hz, 2 H), 7.20 (t, J = 7.3 Hz, 1 H), 7.40 (d, J = 2.0 Hz, 1 H), 7.43 (t, J = 7.9 Hz, 2 H), 8.22 (d, J = 2.0 Hz, 1 H), 10.92 (br s, 1 H). |

| Example | Name | NMR Data |
|---|---|---|
| 325 | 3-(2-(5-Bromo-3-phenoxypyridin-2-ylamino)thiazol-4-yl)-1-(pyrrolidin-1-yl)propan-1-one | ¹H NMR (d₆ DMSO) δ 1.71-1.78 (m, 2 H), 1.81-1.88 (m, 2 H), 2.58 (t, J = 7.8 Hz, 2 H), 2.80 (t, J = 7.6 Hz, 2 H), 3.27 (t, J = 6.8 Hz, 2 H), 3.38 (t, J = 6.6 Hz, 2 H), 6.66 (s, 1 H), 1.10 (d, J = 8.0 Hz, 2 H), 7.20 (t, J = 7.4 Hz, 1 H), 7.40 (d, J = 2.0 Hz, 1 H), 7.43 (t, J = 7.9 Hz, 2 H), 8.22 (d, J = 2.0 Hz, 1 H), 10.92 (br s, 1 H). |
| 326 | 3-(2-(5-Bromo-3-phenoxypyridin-2-ylamino)thiazol-4-yl)-N-(2-methoxyethyl)-propanamide | ¹H NMR (d₆ DMSO) δ 2.43 (t, J = 7.7 Hz, 2 H), 2.79 (t, J = 7.6 Hz, 2 H), 3.18-3.27 (m, 5 H), 3.30-3.32 (m, 2 H), 6.62 (s, 1 H), 7.10 (d, J = 7.8 Hz, 2 H), 7.21 (t, J = 7.4 Hz, 1 H), 7.40 (d, J = 2.0 Hz, 1 H), 7.43 (t, J = 8.0 Hz, 2 H), 7.93 (t, J = 5.5 Hz, 1 H), 8.21 (d, J = 2.0 Hz, 1 H), 10.91 (br s, 1 H). |
| 327 | 3-(2-(5-Bromo-3-phenoxypyridin-2-ylamino)thiazol-4-yl)-N-(2-hydroxyethyl)-propanamide | ¹H NMR (d₆ DMSO) δ 2.42 (t, J = 7.7 Hz, 2 H), 2.79 (t, J = 7.5 Hz, 2 H), 3.08-3.13 (m, 2 H), 3.37-3.38 (m, 2 H), 4.64 (br s, 1 H), 6.63 (s, 1 H), 7.10 (d, J = 8.0 Hz, 2 H), 7.21 (t, J = 7.3 Hz, 1 H), 7.40 (d, J = 2.0 Hz, 1 H), 7.43 (t, J = 8.0 Hz, 2 H), 7.85 (t, J = 5.6 Hz, 1 H), 8.21 (d, J = 2.0 Hz, 1 H), 10.90 (brs, 1 H). |
| 328 | 3-(2-(5-Bromo-3-phenoxypyridin-2-ylamino)thiazol-4-yl)-N-(2-(dimethylamino)-ethyl)propanamide | ¹H NMR (d₆ DMSO) δ 2.13 (s, 6 H), 2.26 (t, J = 6.6 Hz, 2 H), 2.42 (t, J = 7.7 Hz, 2 H), 2.79 (t, J = 7.6 Hz, 2 H), 3.10-3.15 (m, 2 H), 6.63 (s, 1 H), 7.10 (d, J = 7.6 Hz, 2 H), 7.20 (t, J = 7.4 Hz, 1 H), 7.40 (d, J = 2.0 Hz, 1 H), 7.43 (t, J = 8.0 Hz, 2 H), 7.76 (t, J = 5.5 Hz, 1 H), 8.21 (d, J = 2.0 Hz, 1 H), 11.00 (br s, 1 H). |

| Example | Structure | Name | NMR Data |
|---|---|---|---|
| 329 | 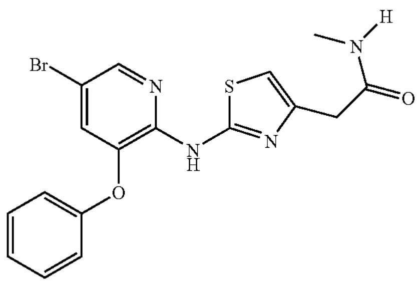 | 2-(2-(5-Bromo-3-phenoxypyridin-2-ylamino)thiazol-4-yl)-N-methylacetamide | $^1$H NMR (d$_6$ DMSO) δ 2.58 (d, J = 4.5 Hz, 3 H), 3.42 (s, 2 H), 6.78 (s, 1 H), 7.11 (d, J = 7.8 Hz, 2 H), 7.21 (t, J = 7.4 Hz, 1 H), 7.39 (d, J = 2.2 Hz, 1 H), 7.44 (t, J = 8.0 Hz, 2 H), 7.82 (d, J = 4.3 Hz, 1 H), 8.22 (d, J = 2.2 Hz, 1 H), 10.99 (s, 1 H). |
| 330 | 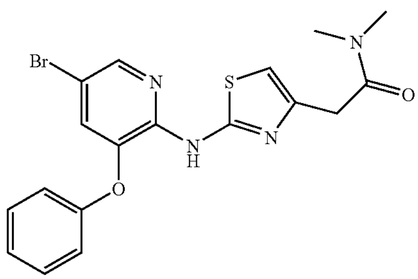 | 2-(2-(5-Bromo-3-phenoxypyridin-2-ylamino)thiazol-4-yl)-N,N-dimethylacetamide | $^1$H NMR (d$_6$ DMSO) δ 2.82 (s, 3 H), 3.03 (s, 3 H), 3.66 (s, 2 H), 6.75 (s, 1 H), 7.11 (d, J = 7.8 Hz, 2 H), 7.21 (t, J = 7.4 Hz, 1 H), 7.39 (d, J = 2.0 Hz, 1 H), 7.44 (t, J = 7.9 Hz, 2 H), 8.22 (d, J = 2.0 Hz, 1 H), 10.97 (s, 1 H). |
| 331 | 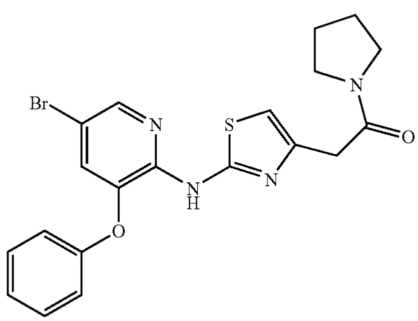 | 2-(2-(5-Bromo-3-phenoxypyridin-2-ylamino)thiazol-4-yl)-1-(pyrrolidin-1-yl)ethanone | $^1$H NMR (d$_6$ DMSO) δ 1.72-1.79 (m, 2 H), 1.83-1.89 (m, 2 H), 3.28 (t, J = 6.8 Hz, 2 H), 3.49 (t, J = 6.7 Hz, 2 H), 3.60 (s, 2 H), 6.77 (s, 1 H), 7.10 (s, 1 H), 7.12 (s, 1 H), 7.21 (t, J = 7.4 Hz, 1 H), 7.38 (d, J = 2.0 Hz, 1 H), 7.44 (t, J = 7.9 Hz, 2 H), 8.22 (d, J = 2.0 Hz, 1 H), 10.96 (s, 1 H). |
| 332 | 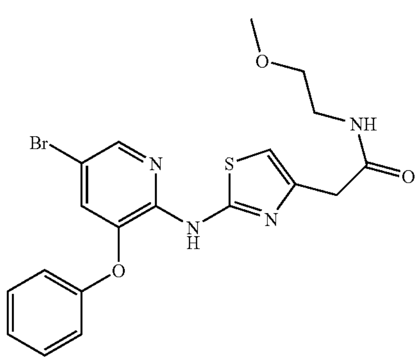 | 2-(2-(5-Bromo-3-phenoxypyridin-2-ylamino)thiazol-4-yl)-N-(2-methoxyethyl)-acetamide | $^1$H NMR (d$_6$ DMSO) δ 3.21-3.23 (m, 5 H), 3.32-3.35 (m, 2 H), 3.45 (s, 2 H), 6.77 (s, 1 H), 7.10 (s, 1 H), 7.12 (s, 1 H), 7.21 (t, J = 7.4 Hz, 1 H), 7.39 (d, J = 2.0 Hz, 1 H), 7.44 (t, J = 7.9 Hz, 2 H), 7.99 (t, J = 5.4 Hz, 1 H), 8.22 (d, J = 2.0 Hz, 1 H), 10.99 (s, 1 H). |

| Example | Structure | Name | NMR Data |
|---|---|---|---|
| 333 | 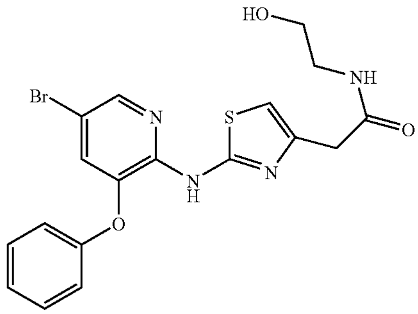 | 2-(2-(5-Bromo-3-phenoxypyridin-2-ylamino)thiazol-4-yl)-N-(2-hydroxyethyl)acetamide | $^1$H NMR (d$_6$ DMSO) δ 3.10-3.27 (m, 2 H), 3.37-3.42 (m, 2 H), 3.45 (s, 2 H), 4.65 (t, J =5.5 Hz, 1 H), 6.78 (s, 1 H), 7.10 (s, 1 H), 7.12 (s, 1 H), 7.21 (t, J = 7.3 Hz, 1 H), 7.39 (d, J = 2.0 Hz, 1 H), 7.44 (t, J = 7.9 Hz, 2 H), 7.91 (br s, 1 H), 8.22 (d, J = 2.0 Hz, 1 H), 11.00 (s, 1 H). |
| 334 | 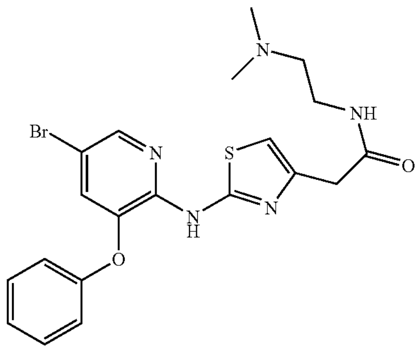 | 2-(2-(5-Bromo-3-phenoxypyridin-2-ylamino)thiazol-4-yl)-N-(2-(dimethylamino)ethyl)acetamide | $^1$H NMR (d$_6$ DMSO) δ 2.12 (s, 6 H), 2.27 (t, J = 6.7 Hz, 2 H), 3.12-3.16 (m, 2 H), 3.44 (s, 2 H), 6.78 (s, 1 H), 7.10 (s, 1 H), 7.12 (s, 1 H), 7.21 (t, J = 7.4 Hz, 1 H), 7.40 (d, J = 2.2 Hz, 1 H), 7.44 (t, J = 8.0 Hz, 2 H), 7.84 (t, J = 5.4 Hz, 1 H), 8.22 (d, J = 2.0 Hz, 1 H), 11.02 (s, 1 H). |
| 335 | 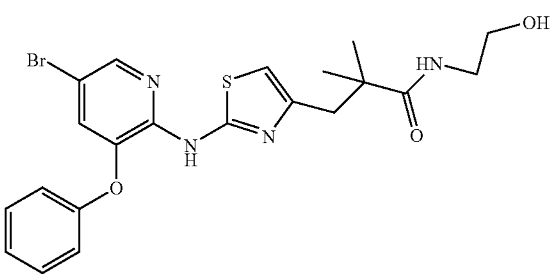 | 3-(2-(5-Bromo-3-phenoxypyridin-2-ylamino)thiazol-4-yl)-N-(2-hydroxyethyl)-2,2-dimethylpropanamide | $^1$H NMR (d$_6$ DMSO) δ 1.09 (s, 6 H), 2.78 (s, 2 H), 3.10-3.15 (m, 2 H), 3.37 (t, J = 6.1 Hz, 2 H), 4.83 (br s, 1 H), 6.61 (s, 1 H), 7.12 (d, J = 8.0 Hz, 2 H), 7.22 (t, J = 7.4 Hz, 1 H), 7.39 (d, J = 2.1 Hz, 1 H), 7.45 (t, J = 8.0 Hz, 2 H), 7.57 (t, J = 5.6 Hz, 1 H), 8.21 (d, J = 2.0 Hz, 1 H), 10.60 (br s, 1 H). |

Example 336

Preparation of N-(5-bromo-3-phenoxypyridin-2-yl)-4-(2-(5-methyl-1,3,4-oxadiazol-2-yl)ethyl)thiazol-2-amine

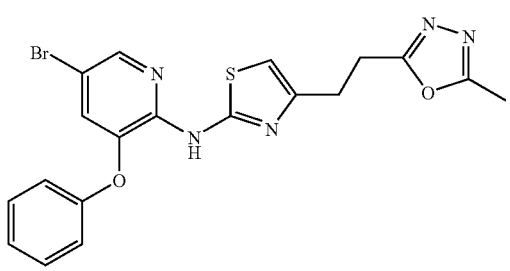

Step A: Preparation of N'-acetyl-3-(2-(5-bromo-3-phenoxypyridin-2-ylamino)thiazol-4-yl)propanehydrazide: A mixture 3-(2-(5-bromo-3-phenoxypyridin-2-ylamino)thiazol-4-yl)propanoic acid (0.300 g, 0.714 mmol), HOBT-H$_2$O (0.164 g, 1.07 mmol), DIEA (0.261 mL, 1.50 mmol), EDCI (0.205 g, 1.07 nmol), and acetohydrazide (0.106 g, 1.43 mmol) in 10 mL acetonitrile and 2 mL THF was stirred at 50° C. for 3 hours and then overnight at ambient temperature. The mixture was concentrated and diluted with CH$_2$Cl$_2$, washed with saturated aqueous NaHCO$_3$, dried over Na$_2$SO$_4$, and concentrated to provide the title compound (0.431 g, 127% yield) that was carried directly on to the next step.

Step B: Preparation of 5-bromo-N-(4-(2-(5-methyl-1,3,4-oxadiazol-2-yl)ethyl)thiazol-2-yl)-3-phenoxypyridin-2-amine: To a mixture of N'-acetyl-3-(2-(5-bromo-3-phenoxypyridin-2-ylamino)thiazol-4-yl)propanehydrazide (0.100 g, 0.210 mmol) in 5 mL acetonitrile was added POCl$_3$ (0.0769 mL, 0.840 mmol) and the reaction was heated at 50° C. for 72 hours. The mixture was concentrated to dryness, diluted with water and extracted with CH$_2$Cl$_2$. The organic layer was dried over Na$_2$SO$_4$ and purified by preparative HPLC to give the title compound (0.029 g, 30.1% yield). $^1$H NMR (d$_6$ DMSO) δ 2.50 (2, 3H), 3.00 (t, J=7.4 Hz, 2H), 3.17 (t, J=7.5 Hz, 2H), 6.76 (s, 1H), 7.11 (d, J=7.6 Hz, 2H), 7.21 (t, J=7.3 Hz, 1H), 7.40 (d, J=2.0 Hz, 1H), 7.44 (t, J=7.9 Hz, 2H), 8.22 (d, J=2.2 Hz, 1H), 10-99 (s, 1H).

The following compounds were prepared from the corresponding acid (Example 315) and corresponding acylhydrazine following the method of Example 336.

| Example | Structure | Name | NMR Data |
|---|---|---|---|
| 337 | 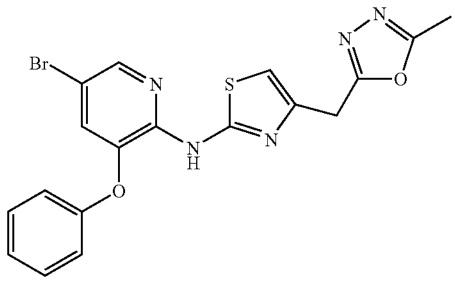 | N-(5-Bromo-3-phenoxypyridin-2-yl)-4-((5-methyl-1,3,4-oxadiazol-2-yl)methyl)thiazol-2-amine | $^1$H NMR (d$_6$ DMSO) δ 2.44 (s, 3 H), 4.21 (s, 2 H), 6.97 (s, 1 H), 7.08 (s, 1 H), 7.10 (s, 1 H), 7.20 (t, J = 7.4 Hz, 1 H), 7.40-7.45 (m, 3 H), 8.23 (d, J = 2.0 Hz, 1 H), 11.14 (s, 1 H). |
| 338 | 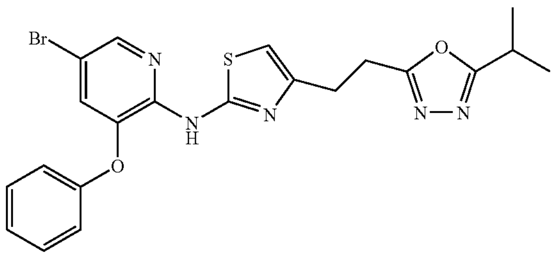 | N-(5-Bromo-3-phenoxypyridin-2-yl)-4-(2-(5-isopropyl-1,3,4-oxadiazol-2-yl)ethyl)thiazol-2-amine | $^1$H NMR (d$_6$ DMSO) δ 1.25 (d, J = 6.8 Hz, 6 H), 3.00 (t, J = 7.5 Hz, 2 H), 3.09-3.14 (m, 1 H), 3.18 (t, J = 7.5 Hz, 2 H), 6.73 (s, 1 H), 7.10 (d, J = 7.8 Hz, 2 H), 7.21 (t, J = 7.3 Hz, 1 H), 7.40 (d, J = 2.0 Hz, 1 H), 7.44 (t, J = 8.0 Hz, 2 H), 8.22 (d, J = 2.0 Hz, 1 H), 10.98 (s, 1 H). |
| 339 | 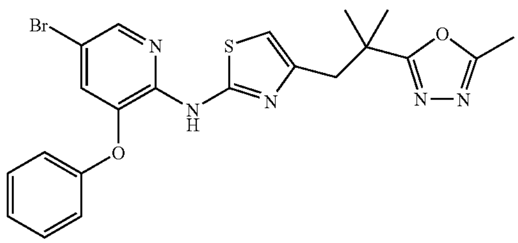 | N-(5-Bromo-3-phenoxypyridin-2-yl)-4-(2-methyl-2-(5-methyl-1,3,4-oxadiazol-2-yl)propyl)thiazol-2-amine | $^1$H NMR (d$_6$ DMSO) δ 1.36 (s, 6 H), 2.44 (s, 3 H), 2.95 (s, 2 H), 7.12 (d, J = 7.8 Hz, 2 H), 7.22 (t, J = 6.8 Hz, 1 H), 7.36 (d, J = 1.8 Hz, 1 H), 7.45 (t, J = 7.7 Hz, 2 H), 8.20 (d, J = 2.0 Hz, 1 H), 10.78 (s, 1 H). |

Example 340

Preparation of N-(5-bromo-3-phenoxypyridin-2-yl)-4-(2-(3-methyl-1,2,4-oxadiazol-5-yl)ethyl)thiazol-2-amine

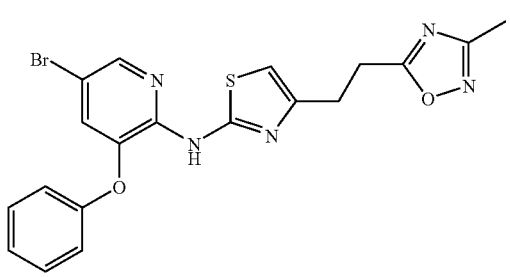

To a mixture of 3-(2-(5-bromo-3-phenoxypyridin-2-ylamino)thiazol-4-yl)propanoic acid (0.100 g, 0.238 mmol), DIEA (0.0456 mL, 0.262 mmol) in 5 mL DMF at ambient temperature was added N-((dimethylamino)fluoromethylene)-N-methylmethanaminium hexafluorophosphate (V) (0.0628 g, 0.238 mmol). The mixture was stirred for 30 minutes at ambient temperature and then N-hydroxyacetamidine (0.0194 g, 0.262 mmol) was added in one portion and the reaction was heated at 110° C. overnight. The reaction was then cooled to ambient temperature and EtOAc was added and the organic layer washed with water (2×10 mL), dried over Na$_2$SO$_4$ and concentrated to a residue that was purified on silica gel eluting with 25% EtOAc/Hexanes to give 5 the title compound (0.067 g, 61.4% yield). $^1$H NMR (d$_6$ DMSO) δ 2-29 (s, 3H), 3.04 (t, 7.6 Hz, 2H), 3.26 (t, J=7.6 Hz, 2H), 6.74 (s, 1H), 7.11 (d, J=7.8 Hz, 2H), 7.21 (t, J=7.3 Hz, 1H), 7.40 (d, J=2.0 Hz, 1H), 7.44 (t, J=8.0 Hz, 2H), 8.22 (d, J=2.0 Hz, 1H), 11.00 (s, 1H).

Example 341

N-(5-Bromo-3-phenoxypyridin-2-yl)-4-((3-methyl-1,2,4-oxadiazol-5-yl)methyl)thiazol-2-amine

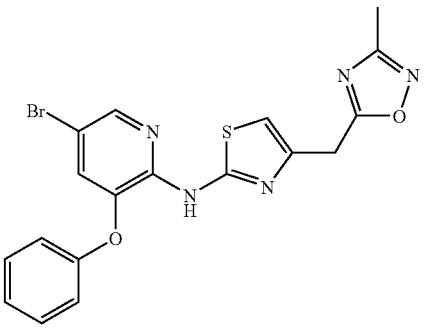

Prepared from the corresponding acid (Example 314) following the method of Example 340. $^1$H NMR (d$_6$DMSO) δ

2.29 (s, 3H), 4.29 (s, 2H), 7.00 (s, 1H), 7.08 (s, 1H), 7.10 (s, 1H), 7.20 (t, J=7.3 Hz, 1H), 7.41-7.45 (m, 3H), 8.23 (d, J=2.0 Hz, 1H), 11.13 (s, 1H).

Example 342

Preparation of N-(5-bromo-3-phenoxypyridin-2-yl)-4-(2-(5-methyloxazol-2-yl)-ethyl)thiazol-2-amine

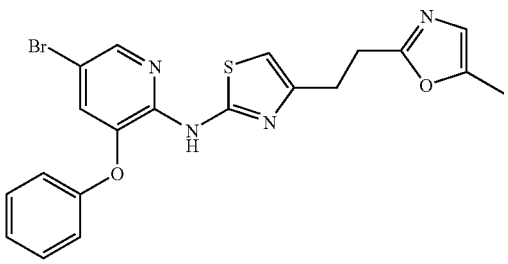

Step A: Preparation of 3-(2-(5-bromo-3-phenoxypyridin-2-ylamino)thiazol-4-yl)-N-(2-oxopropyl)propanamide: A mixture of 3-(2-(5-bromo-3-phenoxypyridin-2-ylamino)thiazol-4-yl)propanoic acid (0.800 g, 1.90 mmol), HOBT-H₂O (0.437 g, 2.86 mmol), DIEA (1.36 mL, 7.80 mmol), EDCI (0.547 g, 2.86 mmol), and 1-aminopropan-2-one hydrochloride (0.834 g, 7.61 mmol) in 50 mL THF was stirred at 50° C. for 2 days. The mixture was concentrated and diluted with CH₂Cl₂ and washed with water, dried over sodium sulfate and concentrated to a residue that was carried on to the next step without further purification.

Step B: Preparation of 5-bromo-N-(4-(2-(5-methyloxazol-2-yl)ethyl)thiazol-2-yl)-3-phenoxypyridin-2-amine hydrochloride: Prepared according to the method of Example 336, Step B (0.043 g, 12.2% yield). ¹H NMR (d₆DMSO) δ 2.25 (s, 3H), 3.00-3.08 (m, 4H), 6.72 (s, 1H), 6.81 (s, 1H), 7.14 (d, J=7.8 Hz, 2H), 7.23 (t, J=7.4 Hz, 1H), 7.43-7.47 (m, 3H), 8.25 (d, J 2.0 Hz, 1H).

Example 343

N-(5-Bromo-3-phenoxypyridin-2-yl)-4-((5-methyloxazol-2-yl)methyl)thiazol-2-amine

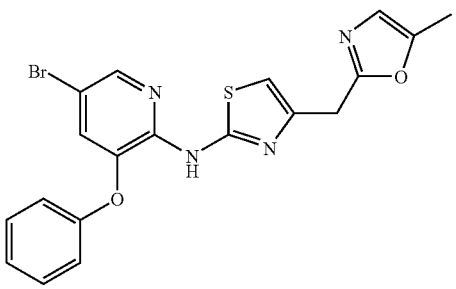

The following compound was prepared from the corresponding acid (Example 315) following the method of Example 342. ¹H NMR (d₆ DMSO) δ 2.22 (d, J=1.0 Hz, 3H), 4.05 (s, 2H), 6.71 (d, J=1.2 Hz, 1H), 6.86 (s, 1H), 7.09 (d, J=7.8 Hz, 2H), 7.20 (t, J=7.4 Hz, 1H), 7.40-7.45 (m, 3H), 8.22 (d, J=2.2 Hz, 1H), 11.09 (s, 1H).

Example 344

Preparation of 4-(2-(1H-tetrazol-5-yl)ethyl)-N-(5-bromo-3-phenoxypyridin-2-yl)thiazol-2-amine

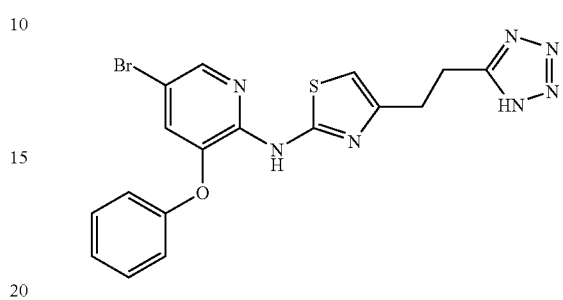

To a nitrogen purged vial was added TBAF (0.249 mL, 0.249 mmol), 3-(2-(5-bromo-3-phenoxypyridin-2-ylamino)thiazol-4-yl)propanenitrile (0.200 g, 0.498 mmol) (Example 320), and TMSN₃ (0.0992 mL, 0.748 mmol) were added, and the reaction was stirred at 120° C. for 24 Hr. The crude reaction mixture was dissolved in CH₂Cl₂ and washed with aqueous sodium bicarbonate solution. The organic layer was concentrated to a residue that was purified on silica gel by eluting with 7% MeOH/CH₂Cl₂ and further purified by triturating in refluxing EtOAc to give the title compound (0.128 g, 57.8% yield). ¹H NMR (d₆DMSO) δ 3.03 (t, J=7.5 Hz, 2H), 3.25 (t, J=7.6 Hz, 2H), 6.70 (s, 1H), 7.13 (d, J=8.0 Hz, 2H), 7.22 (t, J=7.3 Hz, 1H), 7.38 (d, J=2.0 Hz, 1H), 7.45 (t, J=7.9 Hz, 2H), 8.22 (d, J=2.2 Hz, 1H), 11.01 (s, 1H).

Example 345

Preparation of N-(5-bromo-3-phenoxypyridin-2-yl)-4-(phenoxymethyl)thiazol-2-amine

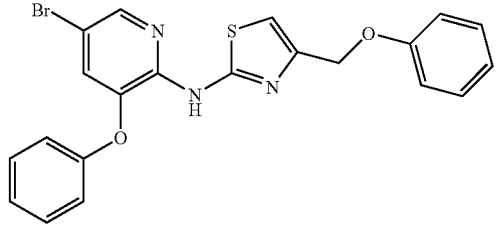

Phenol (0.0356 g, 0.378 mmol) was dissolved in 3 mL THF at ambient temperature. NaH (0.00907 g, 0.378 mmol) was added and the mixture stirred for 30 minutes at ambient temperature. Solid N-(5-Bromo-3-phenoxypyridin-2-yl)-4-(chloromethyl)thiazol-2-amine (0.030 g, 0.0756 mmol) (Example 322) was then added to the reaction and the mixture was stirred at ambient temperature overnight. The reaction was concentrated to dryness, dissolved in CH₂Cl₂, washed with water, dried over Na₂SO₄, and concentrated to dryness. The residue was purified by preparative HPLC to give the title compound (0.007 g, 20.4% yield) as the least polar of the two major products. ¹H NMR (CDCl₃) δ 5.07 (s, 2H), 6.88 (s, 1H), 6.96 (t, J=7.3 Hz, 1H), 7.01 (d, J=8.0 Hz, 2H), 7.07 (d, J=8.8 Hz, 2H), 7.14 (d, J=2.0 Hz, 1H), 7.23-7.31 (m, 3H), 7.43 (t, J=8.0 Hz, 2H), 8.14 (d, J=2.0 Hz, 1H), 8.76 (br s, 1H).

The following compounds were prepared from the corresponding phenols and thiophenols and N-(5-Bromo-3-phenoxypyridin-2-yl)-4-(chloromethyl)thiazol-2-amine (Example 322) following the method of Example 345.

| Example | Structure | Name | NMR Data |
|---|---|---|---|
| 346 | 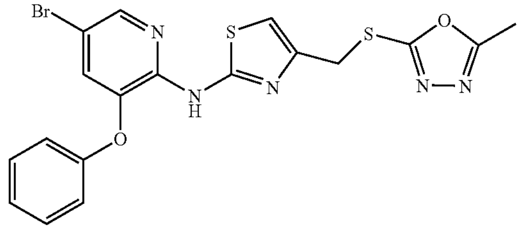 | N-(5-Bromo-3-phenoxypyridin-2-yl)-4-((5-methyl-1,3,4-oxadiazol-2-ylthio)methyl)-thiazol-2-amine | $^1$H NMR (CDCl$_3$) δ 2.37 (s, 3 H), 4.46 (s, 2 H), 7.04 (s, 1 H), 7.11 (d, J = 8.2 Hz, 2 H), 7.21 (t, J = 7.4 Hz, 1 H), 7.42-7.46 (m, 3 H), 8.23 (d, J = 1.8 Hz, 1 H). 11.19 (s, 1 H). |
| 347 | 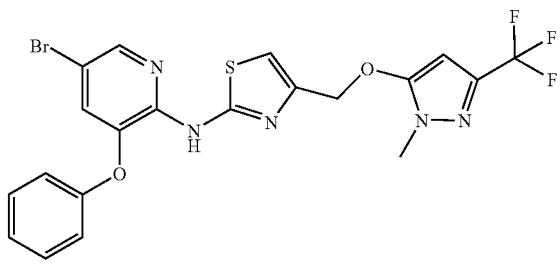 | 5-Bromo-N-(4-((1-methyl-3-(trifluoromethyl)-1H-pyrazol-5-yloxy)methyl)-thiazol-2-yl)-3-phenoxypyridin-2-amine | $^1$H NMR (d$_6$ DMSO) δ 3.62 (s, 3 H), 3.74 (s, 2 H), 6.47 (br s, 1 H), 7.15 (d, J =7.8 Hz, 2 H), 7.24 (t, J = 7.4 Hz, 1 H), 7.35 (d, J = 2.0 Hz, 1 H), 7.46 (t, J = 7.9 Hz, 2 H), 8.21 (d, J = 2.0 Hz, 1 H), 11.21 (br s, 1 H), 11.36 (br s, 1 H). |

Example 348

Preparation of N-(5-bromo-3-phenoxypyridin-2-yl)-4-(phenylamino)methylthiazol-2-amine

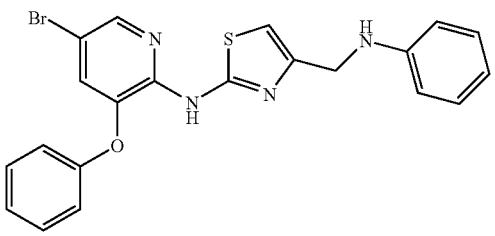

Aniline (0.0352 g, 0.378 mmol) was dissolved in 2 mL NMP at ambient temperature. Cs$_2$CO$_3$ (0.0246 g, 0.0756 mmol) and solid 5-bromo-N-(4-(chloromethyl)thiazol-2-yl)-3-phenoxypyridin-2-amine (0.030 g, 0.0756 mmol) were added to the reaction and the mixture was stirred at ambient temperature overnight. The reaction was concentrated to dryness, dissolved in CH$_2$Cl$_2$, washed with water, dried over Na$_2$SO$_4$, and concentrated to dryness. The residue was purified by preparative HPLC to give the title compound (0.010 g, 29.2% yield) as tan solids. $^1$H NMR (CDCl$_3$) δ 4.34 (br s, 3H), 6.67-6.74 (m, 4H), 7.07 (d, J=8.0 Hz, 2H), 7.13 (d, J=1.8 Hz, 1H), 7.18 (t, J=7.7 Hz, 2H), 7.24-7.27 (m, 1H), 7.43 (t, J=7.9 Hz, 2H), 8.13 (d, J=1.6 Hz, 1H), 8.74 (br s, 1H).

The following compounds were prepared from the corresponding amines and N-(5-Bromo-3-phenoxypyridin-2-yl)-4-(chloromethyl)thiazol-2-amine (Example 322) following the method of Example 348.

| Example | Structure | Name | NMR Data |
|---|---|---|---|
| 349 | 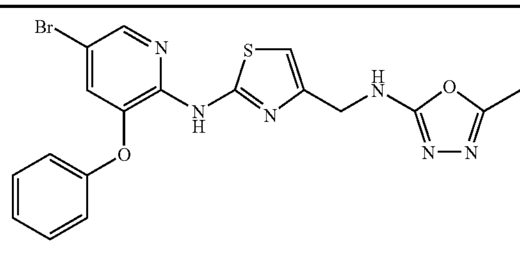 | N-((2-(5-Bromo-3-phenoxypyridin-2-ylamino)thiazol-4-yl)methyl)-5-methyl-1,3,4-oxadiazol-2-amine | $^1$H NMR (d$_6$ DMSO) δ 2.12 (s, 3H), 4.71 (s, 2H), 6.12 (s, 1H), 6.89 (s, 1H), 7.11 (d, J = 7.8 Hz, 2H), 7.21 (t, J = 7.3 Hz, 1H), 7.40-7.46 (m, 3H), 8.23 (d, J = 2.1 Hz, 1H), 11.13 (s, 1H). |
| 350 447713 | 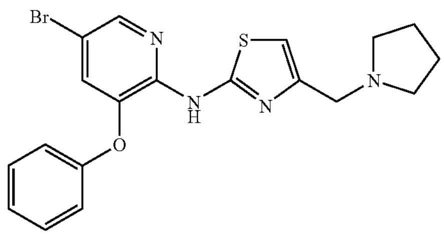 | N-(5-Bromo-3-phenoxypyridin-2-yl)-4-(pyrrolidin-1-ylmethyl)thiazol-2-amine | $^1$H NMR (d$_6$ DMSO) δ 1.72 (br s, 4H), 2.63 (br s, 4H), 3.69 (br s, 2H), 6.88 (s, 1H), 7.10 (s, 1H), 7.12 (s, 1H), 7.21 (t, J = 7.3 Hz, 1H), 7.41-7.46 (m, 3H), 8.22 (d, J = 2.0 Hz, 1H), 11.04 (br s, 1H). |

Example 351

Preparation of 5-bromo-3-phenoxy-N-(4-(phenylthiomethyl)thiazol-2-yl)pyridin-2-amine hydrochloride

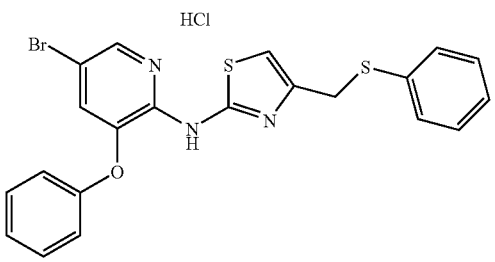

Prepared according to the method of Example 345 using 5-bromo-N-(4-(chloromethyl)thiazol-2-yl)-3-phenoxypyridin-2-amine and benzenethiol. $^1$H NMR (CDCl$_3$) δ 4.13 (s, 2H), 6.48 (s, 1H), 7.19 (d, J=8.0 Hz, 2H), 7.26-7.32 (m, 5H), 7.38 (d, J=7.0 Hz, 2H), 7.44 (t, J=7.6 Hz, 2H), 8.12 (d, J=1.6 Hz, 1H), 12.71 (s, 1H).

Example 352

Preparation of 5-(2-(2-(5-bromo-3-phenoxypyridin-2-ylamino)thiazol-4-yl)ethyl)-1,3,4-oxadiazol-2-ol

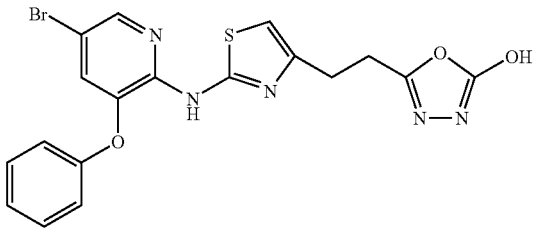

Step A: Preparation of 3-(2-(5-bromo-3-phenoxypyridin-2-ylamino)thiazol-4-yl)propanehydrazide: To a mixture of methyl 3-(2-(5-bromo-3-phenoxypyridin-2-ylamino)thiazol-4-yl)propanoate (1.00 g, 2.303 mmol) (Example 315) in 15 mL EtOH was added hydrazine monohydrate (8.835 mL, 11.51 mmol) and the mixture heated at 75° C. for 4 hours. The reaction was cooled to ambient temperature and quenched with water and the solids were filtered to give the title compound (0.831 g, 83.10% yield) as off white solids there were used without further purification.

Step B: Preparation of 5-(2-(2-(5-bromo-3-phenoxypyridin-2-ylamino)thiazol-4-yl)ethyl)-1,3,4-oxadiazol-2-ol: To a mixture of 3-(2-(5-bromo-3-phenoxypyridin-2-ylamino)thiazol-4-yl)propanehydrazide (0.150 g, 0.345 mmol) in THF (5 mL) was added TEA (0.04814 mL, 0.3454 mmol) and cooled in an ice bath. To this mixture was added CDI (0.0672 g, 0.414 mmol) in one portion. The mixture was allowed to warm to ambient temperature and was then heated at 50° C. overnight. The reaction was concentrated to dryness, dissolved in CH$_2$Cl$_2$ and washed with water, dried over Na$_2$SO$_4$, concentrated to a residue that was purified by preparative HPLC to give the title compound (0.045 g, 28.31% yield) was white solids. $^1$H NMR (d$_6$DMSO) δ 2.91 (s, 4H), 6.75 (s, 1H), 7.10 (d, J=7.8 Hz, 2H), 7.21 (t, J=7.4 Hz, 1H), 7.40 (d, J=2.1 Hz, 1H), 7.44 (t, J=7.9 Hz, 2H), 8.22 (d, J=2.1 Hz, 1H), 11.03 (br s, 1H), 12.04 (br s, 1H).

Example 353

Preparation of N-(5-bromo-3-phenoxypyridin-2-yl)-4-(2-(5-methyl-1,2,4-oxadiazol-3-yl)ethyl)thiazol-2-amine

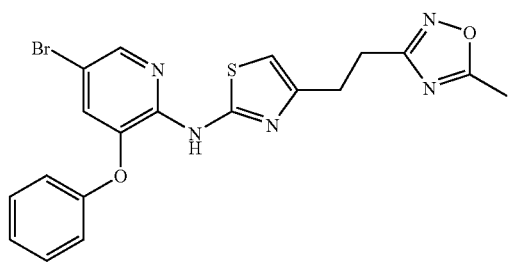

Step A: Preparation of (Z)-3-(2-(5-bromo-3-phenoxypyridin-2-ylamino)thiazol-4-yl)-N'-hydroxypropanamidine: To a mixture of 3-(2-(5-bromo-3-phenoxypyridin-2-ylamino)thiazol-4-yl)propanenitrile (1.00 g, 2.49 mmol) (Example 320) in 150 mL EtOH was added a mixture of hydroxylamine hydrochloride (0.866 g, 12.5 mmol) and NaOH (12.5 mL, 12.5 mmol) and the combined mixture was heated at reflux overnight. To the reaction was then added hydroxylamine hydrochloride (0.866 g, 12.5 mmol) and 1N NaOH (12.5 mL, 12.5 mmol) and the reaction refluxed overnight. The mixture was cooled, concentrated to a residue, diluted with CH$_2$Cl$_2$ and 1N HCl, the aqueous layer was made basic with NH$_4$OH and extracted with CH$_2$Cl$_2$. The basic organic extracts were dried on Na$_2$SO$_4$, filtered and concentrated to give the title compound (1.02 g, 94.2% yield).

Step B: Preparation of (Z)-N'-acetoxy-3-(2-(5-bromo-3-phenoxypyridin-2-ylamino)thiazol-4-yl)propanimidamide: To a suspension of (Z)-3-(2-(5-bromo-3-phenoxypyridin-2-ylamino)thiazol-4-yl)-N'-hydroxypropanamidine (0.200 g, 0.460 mmol) and K$_2$CO$_3$ (0.070 g, 0.506 mmol) in acetone (5 mL), cooled in an ice bath, was added a solution of acetyl chloride (0.032 mL, 0.460 mmol) in 3 mL acetone and the mixture was allowed to slowly warm to ambient temperature. The reaction was concentrated to dryness, dissolved in CH$_2$Cl$_2$ and washed with water, dried over Na$_2$SO$_4$, and concentrated to give the title compound (0.205 g, 93.4% yield) that was used without further purification.

Step C: Preparation of 5-bromo-N-(4-(2-(5-methyl-1,2,4-oxadiazol-3-yl)ethyl)thiazol-2-yl)-3-phenoxypyridin-2-amine: The (Z)-N'-acetoxy-3-(2-(5-bromo-3-phenoxypyridin-2-ylamino)thiazol-4-yl)propanimidamide (0.050 g, 0.10 mmol) was heated (neat) at 150° C. under high vacuum for 3 hrs. The crude reaction residue was then purified by preparative HPLC to give the title compound (0.015 g, 31% yield) as a white solid. $^1$H NMR (d$_6$ DMSO) δ 2.55 (s, 3H), 2.97-3.05 (m, 4H), 6.72 (s, 1H), 7.11 (d, J=7.8 Hz, 2H), 7.21 (t, J=7.4 Hz, 1H), 7.40 (d, J=2.0 Hz, 1H), 7.44 (t, J=7.9 Hz, 2H), 8.22 (d, J=2.0 Hz, 1H), 11.00 (s, 1H).

Example 354

Preparation of N-(5-bromo-3-(phenylthio)pyridin-2-yl)-4-(2-(5-methyl-1,3,4-oxadiazol-2-yl)ethyl)thiazol-2-amine

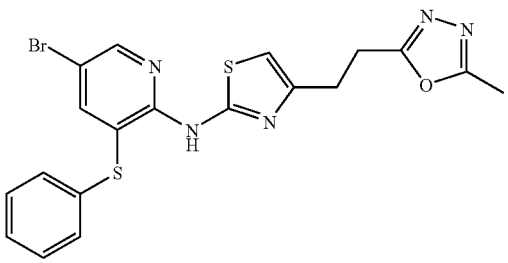

Step A: Preparation of methyl 3-(2-(5-bromo-3-(phenylthio)pyridin-2-ylamino)thiazol-4-yl)propanoate: A mixture of methyl 5-bromo-4-oxopentanoate (1.20 g, 5.73 mmol), 1-(5-bromo-3-(phenylthio)pyridin-2-yl)thiourea (1.50 g, 4.41 mmol) (Example 179), triethylamine (1.04 mL, 7.49 mmol), and MeOH (25 mL) was refluxed overnight. The reaction was concentrated to a residue and partitioned between $CH_2Cl_2$ and water. The organics were concentrated to a residue and triturated in refluxing EtOAc and the solids filtered (solids are acid). The filtrate was concentrated and purified on silica gel eluting with 30% EtOAc/Hexanes to the title compound (1.43 g, 72.0% yield).

Step B: Preparation of 3-(2-(5-bromo-3-(phenylthio)pyridin-2-ylamino)thiazol-4-yl)propanoic acid: To a mixture of methyl 3-(2-(5-bromo-3-(phenylthio)pyridin-2-ylamino)thiazol-4-yl)propanoate (1.40 g, 3.11 mmol) in 50 mL THF was added 25 mL water followed by sodium hydroxide (0.249 g, 6.22 mmol) and the mixture was stirred overnight. The mixture was concentrated to dryness, water added and acidified with $NH_4Cl$. The mixture was then extracted with THF. The organics were dried over $Na_2SO_4$ and concentrated to give the title compound (1.38 g, 102% yield) that was used as the crude material.

Step C: Preparation of N'-acetyl-3-(2-(5-bromo-3-(phenylthio)pyridin-2-ylamino)thiazol-4-yl)propanehydrazide: Prepared according to the method of Example 336, Step A.

Step D: Preparation of 5-bromo-N-(4-(2-(5-methyl-1,3,4-oxadiazol-2-yl)ethyl)thiazol-2-yl)-3-(phenylthio)pyridin-2-amine: Prepared according to the method of Example 336, Step B. $^1$H NMR ($CDCl_3$) δ 2.48 (s, 3H), 3.09-3.22 (m, 4H), 6.53 (s, 1H), 7.19-7.26 (m, 3H), 7.29-7.32 (m, 2H), 7.92 (d, J=2.1 Hz, 1H), 8.42 (d, J=2.1 Hz, 1H), 8.98 (br s, 1H).

Example 355

Preparation of N-(5-bromo-3-(4-(trifluoromethyl)phenoxy)pyridin-2-yl)-3-(tetrahydrofuran-2-yl)-1,2,4-thiadiazol-5-amine

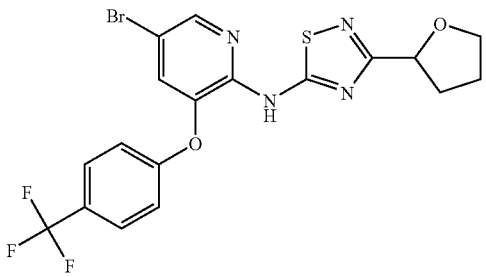

Step A: Preparation of 3-(2-bromo-4-(trifluoromethyl)phenoxy)pyridin-2-amine: A mixture of 2-aminopyridin-3-ol (1.00 g, 9.08 mmol) and DMF (20 mL) was cooled in a 0° C. bath and sodium hydride (0.240 g, 9.49 mmol) was slowly added in portions with vigorous stirring (significant gas evolution). After the addition was completed, the mixture was stirred at ambient temperature for 30 minutes to ensure all the NaH was consumed (reaction becomes very viscous). The 2-bromo-1-fluoro-4-(trifluoromethyl)benzene (1.17 mL, 8.26 mmol) was added and the mixture heated to 110° C. under nitrogen overnight. The reaction was cooled to ambient temperature and the DMF removed under reduced pressure. The resulting black sludge was quenched with 0.5 N NaOH (100 mL) and extracted with $Et_2O$). The organic layer was washed with 1N NaOH and brine, dried over sodium sulfate, filtered and concentrated to afford a brown solid. The solids were purified on silica gel eluting with 40% EtOAc/Hexanes to afford 3-(2-bromo-4-(trifluoromethyl)phenoxy)pyridin-2-amine the title compound.

Step B: Preparation of 3-(4-(trifluoromethyl)phenoxy)pyridin-2-amine: Step B: Preparation of 3-(4-(trifluoromethyl)phenoxypyridin-2-amine: A 500 mL parr shaker was charged with 3-(2-bromo-4-(trifluoromethyl)phenoxy)pyridin-2-amine (1.85 g, 5.55 mmol), NaOAc (0.911 g, 11.1 mmol) and EtOH (100 mL), purged with nitrogen and $Pd(OH)_2$/C (0.200 g, 1.42 mmol) was added and a pressure of 30 psi Hydrogen was maintained. After 2 hours, the mixture was filtered through GFF paper and the filtrate concentrated to a residue. The residue was dissolved in EtOAc, washed with a sodium bicarbonate solution, dried over $Na_2SO_4$, filtered, concentrated to a residue and purified on silica gel by eluting with 50% EtOAc/Hexanes to give the title compound (1.24 g, 87.8% yield) as a white solid.

Step C: Preparation of 5-bromo-3-(4-(trifluoromethyl)phenoxy)pyridin-2-amine: A 250 mL round-bottomed flask was charged with 3-(4-(trifluoromethyl)phenoxy)pyridin-2-amine (1.24 g, 4.88 mmol) and $CHCl_3$ (150 mL), cooled to 0° C. and bromine (0.275 mL, 5.37 mmol) was added dropwise. The reaction was stirred for 60 minutes. The reaction was quenched into a saturated aqueous $NaHCO_3$ solution and extracted with $CH_2Cl_2$ (2×150 mL). The combined organics were dried over sodium sulfate, filtered and concentrated. The residue was purified on silica gel eluting with 20% EtOAc/hexanes. The combined fractions of product were treated with charcoal, filtered through GFF paper and concentrated to afford the title compound (0.850 g, 52.3% yield) as a tan solid.

Step D: Preparation of 5-bromo-N-(3-(tetrahydrofuran-2-yl)-1,2,4-thiadiazol-5-yl)-3-(4-(trifluoromethyl)phenoxy)pyridin-2-amine: Prepared according to the method of Example 183, Step D. $^1$H NMR ($d_6$ DMSO) δ 2.21-2.27 (m, 2H), 3.54-3.61 (m, 1H), 3.74-3.86 (m, 3H), 4.03 (t, J=8.0 Hz, 1H), 7.23 (d, J=8.6 Hz, 2H), 7.76 (d, J=8.8 Hz, 2H), 7.94 (d, J=2.0 Hz, 1H), 8.48 (d, J=2.0 Hz, 1H), 12.37 (s, 1H).

Example 356

Preparation of N-(5-(pyridin-2-ylthio)-3-(4-trifluoromethyl)phenoxy)pyridin-2-yl)-3-(tetrahydrofuran-2-yl)-1,2,4-thiadiazol-5-amine

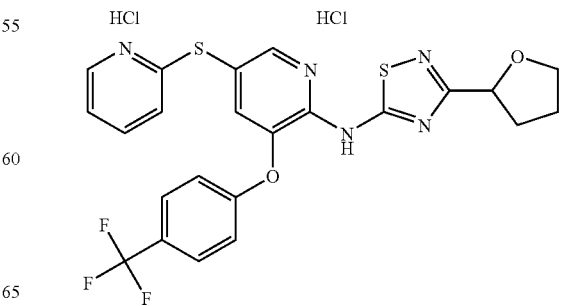

Prepared from 5-bromo-N-(3-(tetrahydrofuran-2-yl)-1,2,4-thiadiazol-5-yl)-3-(4-(trifluoromethyl)phenoxy)pyridin-2-amine according to the method of Example 162, Step A. ¹H NMR (d₆ DMSO) δ 2.23-2.28 (m, 2H), 3.56-3.63 (m, 1H), 3.75-3.80 (m, 1H), 3.82-3.88 (m, 2H), 4.04 (t, J=8.0 Hz, 1H), 7.15-7.19 (m, 2H), 7.26 (d, J=8.6 Hz, 2H), 7.66-7.70 (m, 1H), 7.76 (d, J=8.6 Hz, 2H), 7.85 (d, J=2.0 Hz, 1H), 8.40 (d, J=4.7 Hz, 1H), 8.50 (d, J=1.8 Hz, 1H), 12.50 (s, 1H).

Example 357

Preparation of N-(4-(2-(5-methyloxazol-2-yl)ethyl)thiazol-2-yl)-3-phenoxy-5-(thieno[3,2-b]pyridin-7-ylthio)pyridin-2-amine dihydrochloride

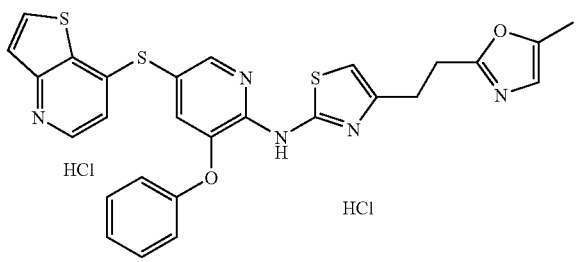

Prepared according to the method of Example 211, Steps A and B, using 5-bromo-N-(4-(2-(5-methyloxazol-2-yl)ethyl)thiazol-2-yl)-3-phenoxypyridin-2-amine as the starting material. ¹H NMR (d₆-DMSO) δ 8.63 (d, 1H), 8.44 (m, 2H), 7.75 (d, 1H), 7.52 (d, 1H), 7.40 (m, 2H), 7.17 (m, 4H), 6.83 (s, 1H), 6.72 (m, 1H), 3.11-2.99 (m, 4H), 2.25 (d, 3H). Mass spectrum (apci) m/z 543.5 (M+H-2HCl).

Example 358

Preparation of 4-(2-(5-methyloxazol-2-ylethyl)-N-(3-phenoxy-5-(piperidin-4-ylmethylthio)pyridin-2-yl)thiazol-2-amine dihydrochloride

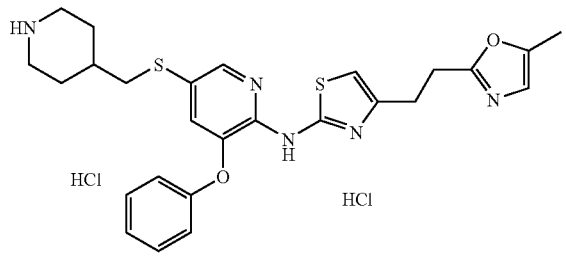

Prepared according to the method of Example 34. ¹H NMR (d₆-DMSO) δ 11.40 (bs, 1H), 8.95 (m, 1H), 8.65 (m, 1H), 8.18 (m, 1H), 7.44 (t, 2H), 7.36 (s, 1H), 7.21 (t, 1H), 7.12 (d, 2h), 6.83 (s, 1H), 6.72 (s, 1H), 3.20 (m, 2H), 3.04 (m, 4H), 2.87 (d, 2H), 2.78 (m, 2H), 2.24 (s, 3H), 1.87 (m, 2H), 1.67 (m, 1H), 1.36 (m, 2H). Mass spectrum (apci) m/z=507.5 (M+H-2HCl).

Example 359

N-(5-bromo-3-(4-fluorophenylthio)pyridin-2-yl)thiazolo[5,4-b]pyridin-2-amine hydrochloride

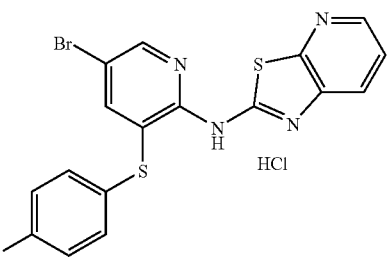

Step A: Preparation of 3-(4-fluorophenylthio)-2-nitropyridine: Prepared according to the method of Example 180, Step A using 3-chloro-2-nitropyridine and 4-fluorobenzenethiol.

Steps B and C: Preparation of N-(5-bromo-3-(4-fluorophenylthio)pyridin-2-yl)thiazolo[5,4-b]pyridin-2-amine hydrochloride: Prepared according to the method of Example 181, Steps B and C. ¹H NMR (CDCl₃) δ 7.05 (t, 2H), 7.27-7.32 (m, 2H), 7.32-7.36 (m, 1H), 7.90-7.94 (m, 2H), 8.43 (dd, 1H), 8.49 (d, 1H).

Example 360

Methyl 3-(5-bromo-2-(thiazolo[5,4-b]pyridin-2-ylamino)pyridin-3-ylthio)benzoate hydrochloride

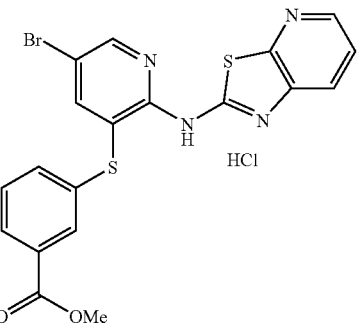

Prepared according to the method of Example 359. ¹H NMR (CDCl₃) δ 3.91 (s, 3H), 7.31-7.39 (m, 3H), 7.88-7.92 (m, 3H), 8.0 (s, 1H), 8.43 (d, 1H), 8.54 (s, 1H), 9.14 (bs, 1H).

Example 361

N-(3-(1-methyl-1H-imidazol-2-ylthio)pyridin-2-yl)thiazolo[5,4-b]pyridin-2-amine

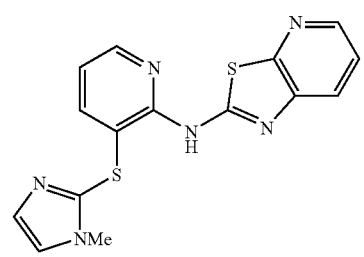

Step A: Preparation of 3-(1-methyl-1H-imidazol-2-ylthio)pyridin-2-amine: 3-(1-methyl-1H-imidazol-2-ylthio)-2-nitropyridine (prepared according to the procedure of Example 359 (2.2 g, 9.3 mmol) was dissolved in acetic acid (30 mL) and cooled in a water bath. Zn dust (<10 micron, 3.0 g, 47 mmol) was slowly added in portions and the reaction stirred at ambient temperature for 30 minutes. The solution was filtered through celite (rinsing with dichloromethane) and the filtrate was concentrated. The solution was neutralized with NH$_4$OH solution and extracted with EtOAc. The organic layer was dried and concentrated to provide the title compound (1.8 g, 94% yield) as a dark brown solid.

Step B: Preparation of N-(3-(1-methyl-1H-imidazol-2-ylthio)pyridin-2-yl)thiazolo[5,4-b]pyridin-2-amine: Prepared according to the method of Example 181 using 2-chloro-3-isothiocyanatopyridine. $^1$H NMR (CDCl$_3$) δ 3.77 (s, 3H), 6.92-6.96 (m, 1H), 7.00 (s, 1H), 7.20 (s, 1H), 7.32 (dd, 1H), 7.88 (d, 1H), 8.00 (d, 1H), 8.40 (d, 2H), 10.80 (bs, 1H).

Example 362

5-bromo-3-(4-fluorophenylthio)-N-(4-methylthiazol-2-yl)pyridin-2-amine

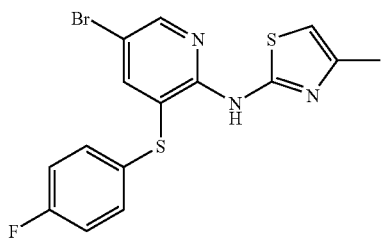

Prepared according to the method of Example 7, Steps C, D and E, from 5-bromo-3-(4-fluorophenylthio)pyridin-2-amine. $^1$H NMR (CDCl$_3$) δ 2.33 (s, 3H), 6.44 (s, 1H), 7.01 (t, 2H), 7.23 (dd, 2H), 7.87 (d, 1H), 8.40 (d, 1H).

The following compounds were also prepared following the procedure of Example 362.

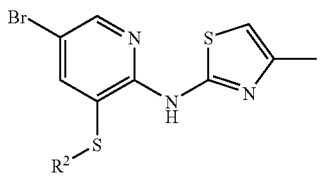

| Example | R² | Name | Data |
|---|---|---|---|
| 363 | (imidazole-NMe with CO₂Me) | Methyl 2-(5-bromo-2-(4-methylthiazol-2-ylamino)pyridin-3-ylthio)-1-methyl-1H-imidazole-5-carboxylate | $^1$H NMR (CDCl$_3$) δ 2.36 (s, 3H), 3.84 (s, 3H), 4.00 (s, 3H), 6.43 (s, 1H), 7.73 (s, 1H), 7.94 (s, 1H), 8.40 (s, 1H). |
| 364 | (pyrimidin-2-yl) | 5-bromo-N-(4-methylthiazol-1-yl)-3-(pyrimidin-2-ylthio)pyridin-2-amine | $^1$H NMR (CDCl$_3$) δ 2.31 (s, 3H), 6.44 (s, 1H), 7.04 (t, 1H), 8.00 (s, 1H), 8.47-8.49 (m, 3H), 8.85 (bs, 1H). |

Example 365

3-(5-bromo-2-(thiazolo[5,4-b]pyridin-2-ylamino)pyridin-3-ylthio)benzoic acid

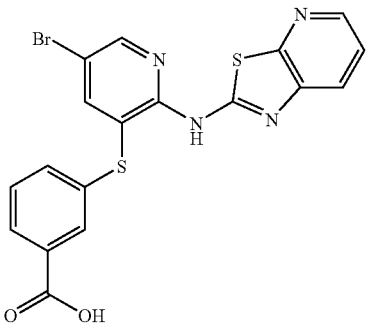

Prepared according to the method of Example 45 from methyl 3-(5-bromo-2-(thiazolo[5,4-b]pyridin-2-ylamino)pyridin-3-ylthio)benzoate. $^1$H NMR (DMSO-d$_6$) δ 7.37-7.42 (m, 1H), 7.61 (t, 1H), 7.72 (bs, 2H), 7.96 (bs, 3H), 8.32 (dd, 1H), 8.42 (bs, 1H).

Example 366

3-(5-bromo-2-(thiazolo[5,4-b]pyridin-2-ylamino)pyridin-3-ylthio)-N-(2-(dimethylamino)ethyl)benzamide

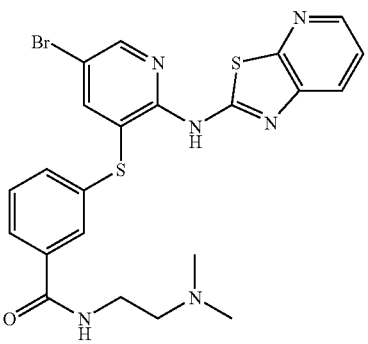

3-5-bromo-2-(thiazolo[5,4-b]pyridin-2-ylamino)pyridin-3-ylthio)benzoic acid (0.080 g, 0.17 mmol) and N1,N1-dimethylethane-1,2-diamine (0.020 g, 0.23 mmol) were dissolved in DMF. 1-(3-dimethylaminopropyl)-3- ethylcarbodiimide hydrochloride (0.037 g, 0.19 mmol) and HOBT-H$_2$O (0.029 g, 0.19 mmol) were then added. N,N-Diisopropylethylamine (0.034 mL, 0.19 mmol) was added last. The reaction was stirred at ambient temperature for 2 days. The material was diluted with water and the solid was filtered and recrystallized in EtOAc/hexanes to afford the title compound (0.030 g, 33% yield) as a white solid. $^1$H NMR (CDCl$_3$) δ 2.25 (s, 6H), 2.50 (t, 2H), 3.46-3.51 (m, 2H), 6.91 (bs, 1H), 7.28-7.37 (m, 3H), 7.62 (d, 1H), 7.68 (s, 1H), 7.86 (d, 1H), 7.97 (s, 1H), 8.41 (d, 1H), 8.48 (s, 1H).

The following compounds were also prepared following the procedure of Example 366.

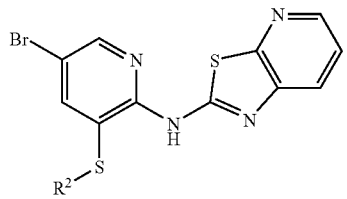

| Example | R² | Name | Data |
|---|---|---|---|
| 367 | (4-methylpiperazinyl benzoyl phenyl) | (4-(5-bromo-2-(thiazolo[5,4-b]pyridin-2-ylamino)pyridin-3-ylthio)phenyl)(4-methylpiperazin-1-yl)methanone. | $^1$H NMR (CDCl$_3$) δ 2.25 (s, 3H), 2.23-2.38 (m, 2H), 2.40-2.50 (m, 2H), 3.37-3.43 (m, 2H), 3.70-3.82 (m, 2H), 7.19 (d, 2H), 7.28-7.36 (m, 3H), 7.89 (d, 1H), 8.04 (d, 1H), 8.43 (d, 1H), 8.55 (d, 1H), 9.17 (bs, 1H). |
| 368 | (dimethylaminoethyl benzamide phenyl) | (4-(5-bromo-2-(thiazolo[5,4-b]pyridin-2-ylamino)pyridin-3-ylthio)-N-(2-(dimethylamino)ethyl)benzamide | $^1$H NMR (CDCl$_3$) δ 2.27 (s, 6H), 2.54 (bs, 2H), 3.49-3.51 (m, 2H), 6.94 (bs, 1H), 7.18 (d, 2H), 7.32 (t, 1H), 7.73 (d, 2H), 7.87 (d, 1H), 8.02 (s, 1H), 8.42 (s, 1H), 8.55 (s, 1H). |

The following compounds were also prepared following the procedure of Example 366.

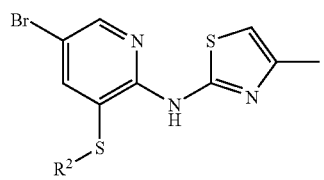

| Example | R² | Name | Data |
|---|---|---|---|
| 369 | (1-methylimidazole carboxamide with dimethylaminoethyl) | 2-(5-bromo-2-(4-methylthiazol-2-ylamino)pyridin-3-ylthio)-N-(2-(dimethylamino)ethyl)-1-methyl-1H-imidazole-5-carboxamide | $^1$H NMR (CDCl$_3$) δ 2.23 (s, 6H), 2.37 (s, 3H), 2.46 (t, 2H), 3.40-3.44 (m, 2H), 4.00 (s, 3H), 6.42 (s, 1H), 6.60 (s, 1H), 7.47 (s, 1H), 7.91 (s, 1H), 8.37 (s, 1H). |

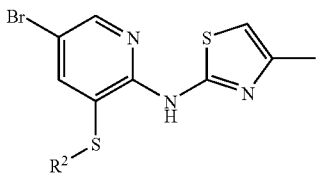

| Example | R² | Name | Data |
|---|---|---|---|
| 370 | (benzamide with N-(2-(dimethylamino)ethyl) group at meta position) | 3-(5-bromo-2-(4-methylthiazol-2-ylamino)pyridin-3-ylthio)-N-(2-(dimethylamino)ethyl)benzamide | ¹NMR (CDCl₃) δ 2.31 (s, 3H), 2.36 (s, 6H), 2.62 (bs, 2H), 3.54-3.56 (m, 2H), 6.44 (s, 1H), 7.24-7.35 (m, 3H), 7.66 (s, 2H), 7.96 (s, 1H), 8.44 (s, 1H). |

Example 371
(2-(5-bromo-2-(4-methylthiazol-2-ylamino)pyridin-3-ylthio)-1-methyl-1H-imidazol-5-yl)methanol Methyl 2-(5-bromo-2-(4-methylthiazol-2-ylamino)pyridin-3-ylthio)-1-methyl-1H-imidazole-5-carboxylate (0.076 g, 0.17 mmol) dissolved in THF (5 mL) was cooled to 0° C. DIBAL-H (1M in hexanes, 0.52 mL, 0.52 mmol) was added. After 15 minutes, DIBAL-H (0.52 mL, 0.52 mmol) was added again. The solution was diluted with a saturated solution of Rochelle's Salt (10 mL) and the solution stirred overnight. The material was extracted with dichloromethane and the organic layer was dried, and concentrated. Reverse phase HPLC purification gave the title compound (0.006 g, 9% yield) as a white solid. ¹H NMR (DMSO-d₆) δ 2.18 (s, 3H), 3.64 (s, 3H), 4.50 (d, 2H), 5.22 (t, 1H), 5.75 (s, 1H), 6.38 (bs, 1H), 7.11 (s, 1H), 8.22 (bs, 1H).

Example 372
3-(5-bromo-2-(4-methylthiazol-2-ylamino)pyridin-3-ylthio)benzoic acid Prepared from 3-(5-bromo-2-thioureidopyridin-3-ylthio)benzoic acid according to the method of Example 7, Steps C, D and E. ¹H NMR (DMSO-d₆) δ 2.17 (s, 3H), 6.44 (s, 1H), 7.40 (s, 1H), 7.56-7.66 (m, 3H), 7.90-7.95 (m, 2H), 8.32 (s, 1H), 12.40 (bs, 1H).

Example 373
3-(5-bromo-2-(4-methylthiazol-2-ylamino)pyridin-3-ylthio)benzamide 3-(5-bromo-2-(4-methylthiazol-2-ylamino)pyridin-3-ylthio)benzoic acid (0.35 g, 0.83 mmol) was dissolved in DMF (5 mL). 1-(3-dimethylaminopropyl)-3-ethylcarbodiimide hydrochloride (0.24 g, 1.2 mmol), NH₄Cl (0.133 g, 2.5 mmol) and HOBT-H₂O (0.19 g, 1.2 mmol) were added. Triethylamine (0.29 mL, 2.1 mmol) was added last. The reaction stirred at room temperature overnight. The material was diluted with water and the solid was filtered to give the title compound (0.23 g, 67% yield). ¹H NMR (DMSO-d₆) δ 2.17 (s, 3H), 6.40 (bs, 1H), 7.48 (s, 1H), 7.53-7.56 (m, 2H), 7.90-7.96 (m, 2H), 8.08 (s, 1H), 8.27 (bs, 1H).

Example 374
3-(5-Bromo-2-(4-methylthiazol-2-ylamino)pyridin-3-ylthio)benzonitrile 3-(5-Bromo-2-(4-methylthiazol-2-ylamino)pyridin-3-ylthio)benzamide (0.20 g, 0.48 mmol) was suspended in acetonitrile (4 mL). POCl$_3$ (0.11 mL, 1.2 mmol) was added and the reaction stirred in a sealed tube at 70° C. for 4 hours. The solution was cooled and neutralized with saturated NaHCO$_3$ solution. The material was extracted with EtOAc, dried, and concentrated. The crude material was triturated with ether/EtOAc and filtered. The solid was dried to give the title compound (0.065 g, 34%). $^1$H NMR (DMSO-d$_6$) δ 2.17 (s, 3H), 6.44 (bs, 1H), 7.58-7.68 (m, 3H), 7.83 (d, 1H), 7.92 (s, 1H), 8.36 (s, 1H).

Example 375

4-methyl-N-(3-(2-(trifluoromethyl)phenylthio)pyridin-2-yl)thiazol-2-amine

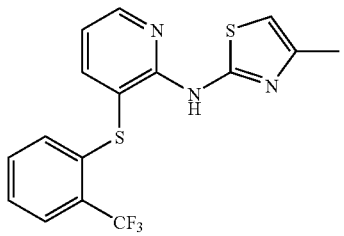

Step A: Preparation of 1,2-bis(2-(trifluoromethyl)phenyl)disulfane: A solution of 2-(trifluoromethyl)benzenethiol (0.185 mL, 1.40 mmol) in wet acetonitrile (1:5 water/acetonitrile) was added Iodine (0.178 g, 0.702 mmol) and allowed to stir over night at room temperature. The reaction was concentrated, then diluted with EtOAc and quenched with aqueous sodium thiosulfate, extracted and dried organic with brine, Na$_2$SO$_4$, filtered and concentrated to afford the title compound (219 mg, 44% yield) as a colorless oil.

Step B: Preparation of 4-methyl-N-(3-(2-(trifluoromethyl)phenylthio)pyridin-2-yl)thiazol-2-amine: A 25 mL round-bottomed flask was charged with 3-bromo-N-(4-methylthiazol-2-yl)pyridin-2-amine (0.082 g, 0.304 mmol) and THF (3 mL). The reaction was cooled to −78° C. and methyllithium (0.228 mL, 0.364 mmol) as a 1.6M solution in ether was added and stirred for 5 minutes. Butyllithium (0.146 mL, 0.364 mmol) as a 2.5M solution in hexane was added and the reaction was stirred for 5 minutes. 1,2-Bis(2-(trifluoromethyl)phenyl)disulfane (0.215 g, 0.607 mmol) was added and the reaction was warmed to room temperature and stirred for one hour. Saturated NH$_4$Cl was added, and the reaction mixture was extracted with EtOAc. The combined organic layers were dried, filtered, and concentrated. The residue was purified on silica gel (1-10% EtOAc in hexanes) to afford the title compound (59 mg, 52% yield) as a white solid. $^1$H NMR (CDCl$_3$) δ 9.04 (s, 1H), 8.47 (dd, 1H), 7.87 (dd, 1H), 7.69 (m, 2H), 7.31 (m, 1H), 6.97 (q, 1H), 6.83 (d, 1H), 6.43 (m, 1H), 2.32 (d, 3H). Mass spectrum (apci) m/z=368.2 (M+H).

The following compounds were prepared according to the method of Example 375.

| Example | Structure | Name | Data |
|---|---|---|---|
| 376 | 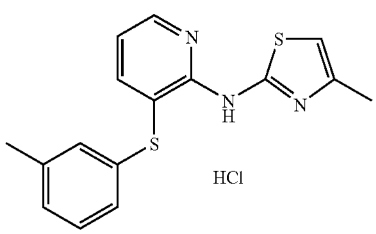 | 4-methyl-N-(3-(m-tolylthio)pyridin-2-yl)thiazol-2-amine hydrochloride | $^1$H NMR (CDCl$_3$) δ 12.0 (bs, 1H), 8.36 (m, 1H), 7.91 (d, 1H), 7.31 (m, 3H), 7.17 (t, 1H), 7.11 (m, 2H), 6.42 (s, 1H), 2.46 (m, 3H), 2.30 (s, 3H). Mass spectrum (apci) m/z = 314.2 (M + H − HCl). |
| 377 | 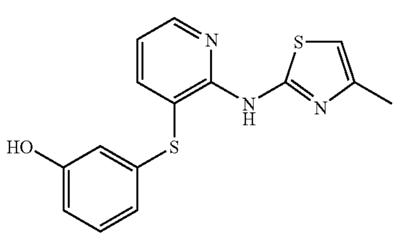 | 3-(2-(4-methylthiazol-2-ylamino)pyridin-3-ylthio)phenol | Mass spectrum (apci) m/z = 316.2 (M + H). |
| 378 | 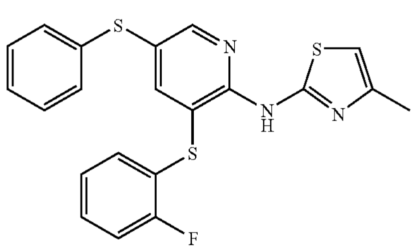 | N-(3-(2-fluorophenylthio)-5-(phenylthio)pyridin-2-yl)-4-methylthiazol-2-amine | $^1$H NMR (CDCl$_3$) δ 9.10 (bs, 1H), 8.45 (d, 1H), 7.92 (d, 1H), 7.27 (m, 6H), 7.15 (m, 3H), 6.47 (m, 1H), 2.33 (m, 3H). Mass spectrum (apci) m/z = 426.2 (M + H). |

Example 379

Preparation of N-(3-(2-bromo-5-morpholinophenoxy)pyridin-2-yl)-4-methylthiazol-2-amine

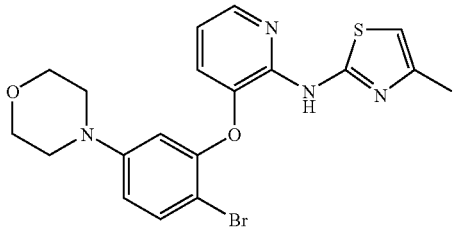

Step A: 4-(3-(2-Nitropyridin-3-yloxy)phenyl)morpholine. In a 125 mL round-bottom flask, 3-morpholinophenol (0.91 g, 5.07 mmol) was dissolved in THF (40 mL). Solution was cooled to 0° C. and NaHMDS (5.07 mL, 5.07 mmol) (1M in THF) was added slowly. The mixture was agitated for 15 minutes and solution of 3-fluoro-2-nitropyridine (0.60 g, 4.22 mmol) in THF (5 mL) was added slowly. After agitating for 2 hours the solvent was evaporated and the residue dissolved in 100 mL of $CH_2Cl_2$ and washed with diluted sodium bicarbonate solution twice, dried over magnesium sulfate, filtered and evaporated. Crude material was purified by chromatography on silica gel, eluted with 25% ethyl acetate/Hexane to give the title compound (0.93 g, 72%) was obtained as thick red oil.

Step B: 3-(3-Morpholinophenoxy)pyridin-2-amine. In a 125 mL round-bottom flask, 4-(3-(2-nitropyridin-3-yloxy)phenyl)morpholine (0.92 g, 3.05 mmol) was dissolved in 30 mL of ethanol and 200 mg of 10% Pd/C (Degussa type, 50% wet) added. The resulting mixture was agitated overnight under the atmospheric pressure of hydrogen. The mixture was filtered and the solvent was evaporated to give the title compound (0.80 g, 97%) as thick oil.

Step C: 3-(2-bromo-5-morpholinophenoxy)pyridin-2-amine. In a 250 mL round-bottom flask, 3-(3-morpholinophenoxy)pyridin-2-amine (0.720 g, 2.654 mmol) was dissolved in 25 mL of acetic acid and Bromine (2.654 mL, 2.654 mmol) (1M in AcOH) was added slowly. After agitating for 1 hour the mixture was evaporated and the residue was distributed between dichloromethane and sodium bicarbonate solution. The organic phase was separated and evaporated. The residue was purified by column chromatography on silica gel, eluted with 1-3% methanol/dichloromethane to give the title compound (0.72 g, 77%) as white solid.

Steps D, E and F: N-(3-(2-bromo-5-morpholinophenoxy)pyridin-2-yl)-4-methylthiazol-2-amine. Prepared according to the method of Example 7, Steps C, D and E; (0.48 g, 61% yield) $^1$H NMR (CDCl$_3$) δ 2.35 (s, 3H), 3.10 (t, 4H), 3.82 (t, 4H), 6.42-6.89 (m, 5H), 7.48 (d, 1H), 8.07 (d, 1H), 8.71 (d, 1H).

Example 380

Preparation of methyl 3-(2-(5-bromo-3-phenoxypyridin-2-ylamino)thiazol-4-yl)-2-methoxy-2-methylpropanoate

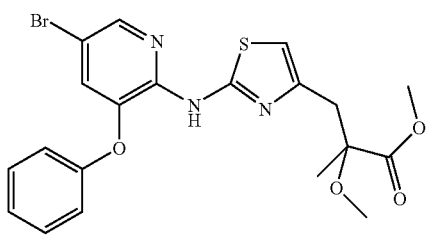

Step A: Preparation of methyl 4-bromo-2-methoxy-2-methylpent-4-enoate. A 500 mL round-bottom flask was charged with diisopropylamine (12.89 mL, 92.00 mmol) and dry THF (100 mL) and cooled to −78° C. Butyllithium (2.5 M in hexanes) (36.80 mL, 92.00 mmol) was added dropwise over 20 minutes and the mixture was agitated for additional 30 minutes. Methyl 2-methoxypropanoate (10.35 g, 87.61 mmol) was added dropwise over 20 minutes and the mixture was agitated for 30 minutes. 2,3-Dibromopropene (10.70 mL, 87.61 mmol) was added dropwise over 20 minutes, the mixture was agitated for 30 minutes and then allowed to warm up to ambient temperature and agitated for additional 2 hours. The reaction was quenched with saturated ammonium chloride solution and extracted twice with ether. Extracts were washed with sodium bicarbonate solution, brine, dried and evaporated to give the title compound (22.7 g, 98.4% yield) as pale yellow oil.

Step B: Preparation of methyl 5-bromo-2-methoxy-2-methyl-4-oxopentanoate. To a 125 mL round-bottom flask, methyl 4-bromo-2-methoxy-2-methylpent-4-enoate (0.525 g, 2.21 mmol) was added acetonitrile (8 mL), water (2 mL) and N-bromosuccinimide (0.493 g, 2.77 mmol). A catalytic amount of 1M HBr was added (0.066 mL, 0.066 mmol). The resulting solution was agitated overnight, diluted with 50 mL of dichloromethane and washed twice with saturated sodium bicarbonate, dried and evaporated. The residue was purified by chromatography on silica gel, eluting with 10% ethyl acetate/hexane to provide the title compound (0.52 g, 92.8% yield) as clear oil.

Step C: Preparation of methyl 3-(2-(5-bromo-3-phenoxypyridin-2-ylamino)thiazol-4-yl)-2-methoxy-2-methylpropanoate. In a 125 mL round-bottom flask, 1-(5-bromo-3-phenoxypyridin-2-yl)thiourea (0.50 g, 1.54 mmol) (prepared as described in Example 10, Steps A-D) and methyl 5-bromo-2-methoxy-2-methyl-4-oxopentanoate (0.586 g, 2.31 mmol) were dissolved in dry THF (25 mL), heated to 50° C. and agitated overnight. The solvent was evaporated and the residue was dissolved in chloroform and washed with diluted sodium bicarbonate solution twice, dried over magnesium sulfate, filtered and evaporated. The resulting solid was purified by chromatography on silica gel, eluted with 10-15% ethyl acetate/hexane to give the title compound (0.485 g, 65.7% yield) as yellow solid. $^1$H NMR (CDCl$_3$) δ 1.46 (s, 3H), 3.12 (s, 2H), 3.34 (s, 3H), 3.73 (s, 3H), 6.58 (s, 1H), 7.06-7.45 (m, 6H), 8.11 (s, 1H), 8.64 (bs, 1H).

Example 381

Preparation of 3-(2-(5-bromo-3-phenoxypyridin-2-ylamino)thiazol-4-yl)-2-methoxy-2-methylpropanoic acid

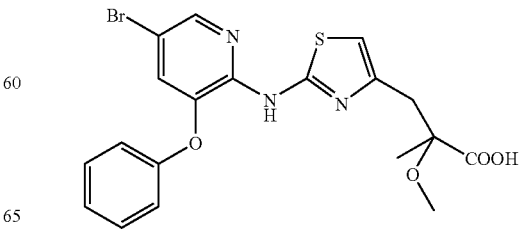

Prepared according to the method of Example 45 from methyl 3-(2-(5-bromo-3phenoxypyridin-2-ylamino)thiazol-4-yl)-2-methoxy-2-methylpropanoate. $^1$H NMR (DMSO-d$_6$ δ 1.32 (s, 3H), 3.00 (q, 2H), 3.21 (s, 3H), 6.71 (s, 1H), 7.11-7.23 (m, 3H), 7.36 (s, 1H), 7.44 (t, 2H), 8.12 (s, 1H).

Example 382

Preparation of 3-(2-(5-bromo-3-phenoxypyridin-2-ylamino)thiazol-4-yl)-2-methoxy-2-methyl-1-(pyrrolidin-1-yl)propan-1-one

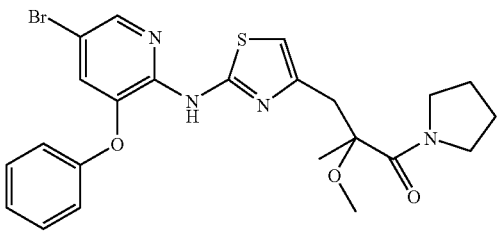

In a 20 mL scintillation vial, 3-(2-(5-bromo-3-phenoxypyridin-2-ylamino)thiazol-4-yl)-2-methoxy-2-methylpropanoic acid (0.087 g, 0.187 mmol) was dissolved in CH$_2$Cl$_2$ (5 mL) and DMF (2 mL) and N-methylmorpholine (0.031 mL, 0.281 mmol), followed by addition of 1-hydroxybenzotriazole. The mixture was cooled to 0° C. and EDCI (0.0467 g, 0.244 mmol) was added. The resulting mixture was agitated for 30 minutes and pyrrolidine (0.020 g, 0.28 mmol) was added. The mixture was then agitated overnight, diluted with 50 mL of CH$_2$Cl$_2$ and washed with citric acid solution and sodium bicarbonate solution, dried and evaporated to give crude product which was purified by chromatography on silica gel, eluting with 50-70% ethyl acetate/Hexane, to provide the title compound (0.079 g, 79% yield) as white solid. $^1$H NMR (DMSO-d$_6$ δ 1.23 (s, 3H), 1.66-1.80 (m, 4H), 3.03-3.63 (m, 9H), 7.01 (m, 1H), 7.16-7.46 (m, 7H), 8.25 (s, 1H).

Example 383

Preparation of 3-(2-(5-bromo-3-phenoxypyridin-2-ylamino)thiazol-4-yl)-N-(2-hydroxyethyl)-2-methoxy-2-methylpropanamide

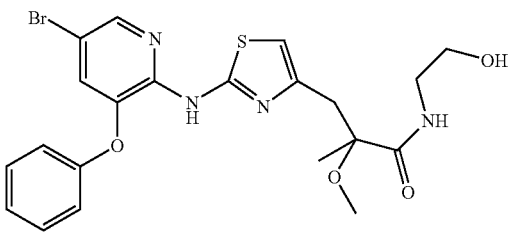

Prepared according to the method of Example 382 from 3-(2-(5-bromo-3-phenoxypyridin-2-ylamino)thiazol-4-yl)-2-methoxy-2-methylpropanoic. $^1$H NMR (DMSO-d$_6$ δ 1.40 (s, 3H), 3.14-3.48 (m, 9H), 7.03 (s, 1H), 7.21-7.53 (m, 7H), 8.23 (s, 1H).

Example 384

Preparation of N'-(3-(2-(5-bromo-3-phenoxypyridin-2-ylamino)thiazol-4-yl)-2-methoxy-2-methylpropanoyl)-N,N-dimethylformohydrazonamide

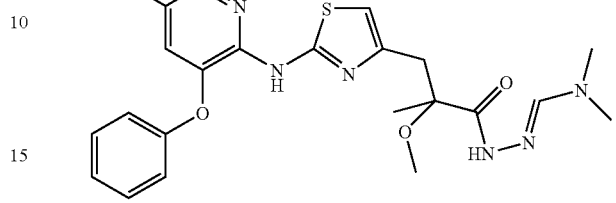

Step A: Preparation of N'-acetyl-3-(2-(5-bromo-3-phenoxypyridin-2-ylamino)thiazol-4-yl)-2-methoxy-2-methylpropanehydrazide: In a 20 mL scintillation vial, 3-(2-(5-bromo-3-phenoxypyridin-2-ylamino)thiazol-4-yl)-2-methoxy-2-methylpropanoic acid (0.087 g, 0-187 mmol) was dissolved in CH$_2$Cl$_2$ (5 mL) and DMF (2 mL) and N-methylmorpholine (0.0309 mL, 0.281 mmol), followed by addition of HOBT. The mixture was cooled to 0° C. and EDCI (0.047 g, 0.244 mmol) was added. The resulting mixture was agitated for 30 minutes and acetohydrazide (0.021 g, 0.28 mmol) was added. The mixture was then agitated overnight, diluted with 50 mL of CH$_2$Cl$_2$ and washed with citric acid solution, sodium bicarbonate solution twice, dried and evaporated to give the title compound (0.0975 g, quantitative yield). Crude product was used in the next step.

Step B: Preparation of N'-(3-(2-(5-bromo-3-phenoxypyridin-2-ylamino)thiazol-4-yl)-2-methoxy-2-methylpropanoyl)-N,N-dimethylformohydrazonamide: In a 125 mL round-bottom flask, N'-acetyl-3-(2-(5-bromo-3-phenoxypyridin-2-ylamino)thiazol-4-yl)-2-methoxy-2-methylpropanehydrazide (0.0975 g, 0.187 mmol) was dissolved in 5 mL of acetonitrile and phosphorous oxychloride (0.052 mL, 0.56 mmol) was added. The resulting mixture was heated to 50° C. and agitated for two hours. The solvent was evaporated and the residue was distributed between CH$_2$Cl$_2$ and saturated sodium bicarbonate solution. The organic layer was washed with sodium bicarbonate solution, dried and evaporated. The residue was purified by chromatography on silica gel, eluting with 20% ethyl acetate/hexane to afford the title compound (30 mg, 29%) as white solid. $^1$H NMR (CDCl$_3$) δ 1.50 (s, 3H), 2.86 (s, 6H), 3.16 (dd, 2H), 3.73 (s, 3H), 6.62 (s, 1H), 7.06-7.45 (m, 6H), 7.71 (s, 1H), 8.11 (s, 1H), 8.58 (s, 1H), 8.71 (bs, 1H).

Example 385

3-(2-(5-bromo-3-(phenylthio)pyridin-2-ylamino)thiazol-4-yl)-2-methoxy-2-methylpropanoic acid

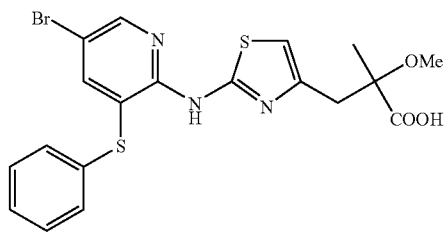

Step A: Preparation of methyl 3-(2-(5-bromo-3-(phenylthio)pyridin-2-ylamino)thiazol-4-yl)-2-methoxy-2-methylpropanoate. Prepared according to the method of Example 380, Step C from 1-(5-bromo-3-(phenylthio)pyridin-2-yl)thiourea.

Step B: Preparation of 3-(2-(5-bromo-3-(phenylthio)pyridin-2-ylamino)thiazol-4-yl)-2-methoxy-2-methylpropanoic acid. Prepared according to the method of Example 381. $^1$H NMR (DMSO-$d_6$ δ 1.32 (s, 3H), 3.00 (q, 2H), 3.21 (s, 3H), 6.71 (s, 1H), 7.11-7.23 (m, 3H), 7.36 (s, 1H), 7.44 (t, 2H), 8.12 (s, 1H). MS (APCI, pos) m/z 481 (M+1).

Example 386

Preparation of 3-(2-(5-bromo-3-(phenylthio)pyridin-2-ylamino)thiazol-4-yl)-N-(2-hydroxyethyl)-2-methoxy-2-methylpropanamide

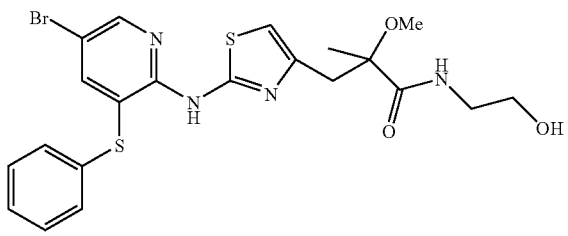

Prepared according to the method of Example 382 using 2-aminoethanol. $^1$H NMR (DMSO-$d_6$ δ 1.40 (s, 3H), 3.14-3.48 (m, 9H), 7.03 (s, 1H), 7.21-7.53 (m, 7H), 8.23 (s, 1H).

Example 387

3-(2-(5-bromo-3-(phenylthio)pyridin-2-ylamino)thiazol-4-yl)-2-methoxy-N-(2-methoxyethyl)-2-methylpropanamide

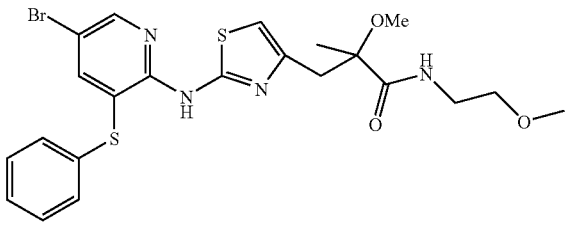

Prepared according to the method of Example 382 using 2-methoxyethanamine.
$^1$H NMR (DMSO-$d_6$ δ 1.30 (s, 3H), 3.01-3.38 (m, 12H), 7.03 (s, 1H), 7.21-7.53 (m, 7H), 8.23 (s, 1H).

Example 388

3-(2-(5-bromo-3-(phenylthio)pyridin-2-ylamino)thiazol-4-yl)-N-(2-hydroxyethyl)-2-methoxy-N,2-dimethylpropanamide

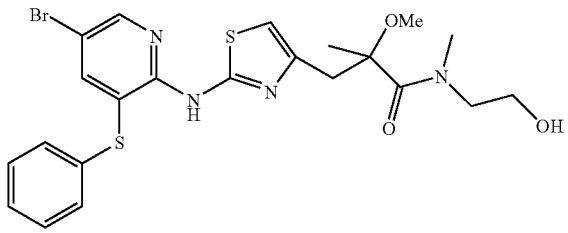

Prepared according to the method of Example 382 using 2-(methylamino)ethanol.
$^1$H NMR (DMSO-$d_6$ δ 1.41 (s, 3H), 2.58 (t, 2H), 3.13-3.28 (m, 8H), 4.20-4.35 (m, 2H), 7.03 (s, 1H), 7.21-7.53 (m, 7H), 8.23 (s, 1H).

Example 389

3-(2-(5-bromo-3-(phenylthio)pyridin-2-ylamino)thiazol-4-yl-1-((R)-3-hydroxypyrrolidin-1-yl)-2-methoxy-2-methylpropan-1-one

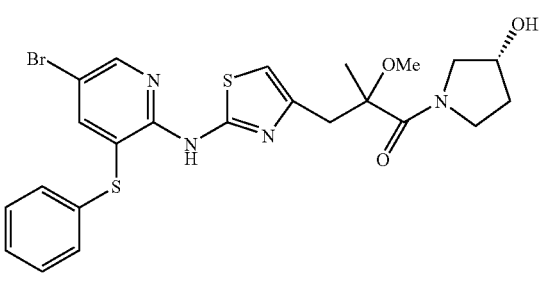

Prepared according to the method of Example 382 with (R)-pyrrolidin-3-ol. $^1$H NMR (DMSO-$d_6$ δ 1.29 (s, 3H), 1.70-1.87 (m, 2H), 3.03-3.48 (m, 7H), 4.25 (bd, 1H), 6.86 (bs, 1H), 7.36-7.50 (m, 5H), 7.79 (bs, 1H), 8.47 (s, 1H).

Example 390

1-((2-(5-bromo-3-phenoxypyridin-2-ylamino)thiazol-4-yl)methylpyrrolidin-2-one

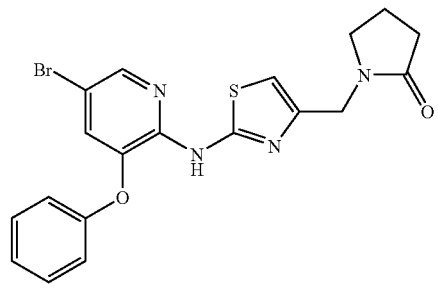

Step A: Preparation of 1-(3-chloro-2-hydroxypropyl)pyrrolidin-2-one. 2-Pyrrolidinone (4.47 g, 52.5 mmol) was mixed with THF (25 mL) and cooled to −78° C. Butyllithium (1.6 M in hexanes) (32.8 mL, 52.5 mmol) was added slowly then and the mixture was agitated for 10 minutes. Boron trifluoride ethereate (6.59 mL, 52.5 mmol) was added dropwise, followed by dropwise addition of epichlorohydrin (4.11 mL, 52.5 mmol). The resulting mixture was allowed to warm up overnight, then cooled and quenched with saturated sodium bicarbonate solution, and extracted 3 times with ethyl acetate. The extracts were washed with brine, dried and evaporated to give ~4 g of crude oil. The crude oil was purified by chromatography on silica gel, eluting with 1-2% methanol/dichloromethane, to provide the title compound (1.53 g, 16.4% yield) as clear oil.

Step B: Preparation of 1-(3-chloro-2-oxopropyl)pyrrolidin-2-one: 1-(3-Chloro-2-hydroxypropyl)pyrrolidin-2-one (0.380 g, 2.14 mmol) was dissolved in dichloromethane (10 mL) and cooled to 0° C. Dess-Martin periodinane (0.907 g, 2.14 mmol) was added and the mixture agitated at ambient temperature for 2 hours. The mixture was loaded on silica gel chromatographic column and eluted with 1% methanol/dichloromethane to provide the title compound.

Step C: Preparation of 1-((2-(5-bromo-3-phenoxypyridin-2-ylamino)thiazol-4-yl)methyl)pyrrolidin-2-one: Prepared according to the method of Example 7, Step E. $^1$H NMR (DMSO-$d_6$ δ 2.06-2.18 (m, 5H), 2.42 (t, 2H), 3.69 (t, 2H), 7.10 (d, 2H), 7.21 (t, 1H), 7.42-7.47 (m, 3H), 8.21 (s, 1H).

Example 391

3-((2-(1-bromo-3-(phenylthio)pyridin-2-ylamino)thiazol-4-yl)methyl)-1-methylpyrrolidin-2-one

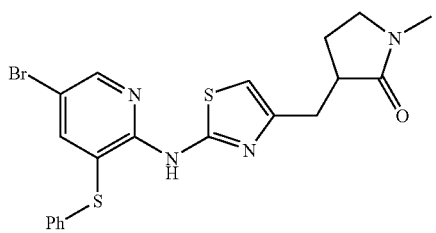

Step A: 3-(2-bromoallyl)-1-methylpyrrolidin-2-one. 1-Methyl-2-pyrrolidinone (3.87 mL, 40-3 mmol) was combined with 25 mL of THF and cooled to −78° C. Lithium diisopropylamide (26.9 mL, 40.3 mmol) (1.5M in THF) was added slowly and the mixture was agitated for 30 minutes. 2,3-Dibromopropene (4.93 mL, 40.3 mmol) was added and the mixture was agitated overnight and allowed to warm up to ambient temperature. The reaction was quenched with sodium bicarbonate solution and extracted twice with ether. The extracts were washed with brine and evaporated. The crude product was purified by chromatography on silica gel, eluting with 30-50% ethyl acetate/hexane, to provide the title compound (5.01 g, 56.9% yield) as clear oil.

Step B: 3-(3-bromo-2-oxopropyl)-1-methylpyrrolidin-2-one. 3-(2-Bromoallyl)-1-methylpyrrolidin-2-one (1.40 g, 6.42 mmol) was dissolved in acetonitrile (20 mL) and water (5 mL) and N-bromosuccinimide (1.71 g, 9.63 mmol) was added. The resulting mixture was agitated for 4 hours, diluted with 200 mL of ether, washed with sodium bicarbonate, sodium thiosulfate, brine, dried and evaporated. The residue was purified by chromatography on silica gel, eluted with 1-2% methanol/dichloromethane to provide the title compound.

Step C: 3-((2-(5-bromo-3-(phenylthio)pyridin-2-ylamino)thiazol-4-yl)methyl)-1-methylpyrrolidin-2-one. Prepared according to the method of Example 7, step E. $^1$H NMR (DMSO-$d_6$ δ 1.60-1.72 (m, 1H), 2.08-2.14 (m, 1H), 2.51-2.58 (m, 1H), 2.68-2.78 (m, 5H), 3.00 (d, 1H), 3.21-3.29 (m, 2H), 6.72 (s, 1H), 7.38-7.48 (m, 6H), 8.41 (s, 1H).

Example 392

3-((2-(5-bromo-3-phenoxypyridin-2-ylamino)thiazol-4-yl)methyl)-1-methylpyrrolidin-2-one

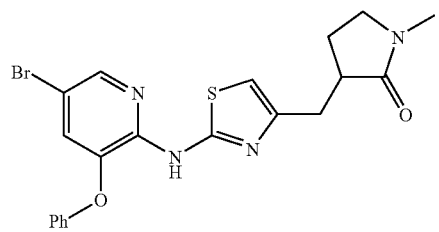

Prepared according to the method of Example 391, Step C, from 1-(5-bromo-3-(phenoxypyridin-2-yl)thiourea and 3-(3-bromo-2-oxopropyl)-1-methylpyrrolidin-2-one. $^1$H NMR (DMSO-$d_6$ δ 1.60-1.72 (m, 1H), 2.08-2.14 (m, 1H), 2.51-2.58 (m, 1H), 2.68-2.78 (m, 5H), 3.02 (d, 1H), 3.21-3.29 (m, 2H), 6.80 (s, 1H), 7.13-7.47 (m, 6H), 8.25 (s, 1H).

Example 393

3-((2-(5-bromo-3-phenoxypyridin-2-ylamino)thiazol-4-yl)methyl)pyrrolidin-2-one

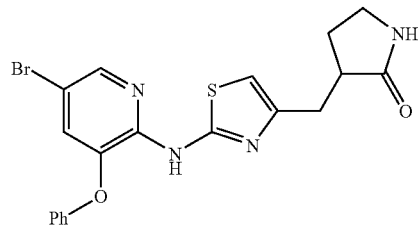

Step A: Preparation of tert-butyl 3-(2-bromoallyl)-2-oxopyrrolidine-1-carboxylate. In a 250 mL round-bottom flask, tert-butyl 2-oxopyrrolidine-1-carboxylate (4.12 g, 22.2 mmol) was combined with 25 mL of THF and cooled to −78° C. Lithium diisopropylamide (1.5M in THF) (14.8 mL, 22.2 mmol) was added slowly and the mixture was agitated for 30 minutes. 2,3-Dibromopropene (2.72 mL, 22.2 mmol) was added and the mixture was agitated overnight and allowed to warm to ambient temperature. The reaction was then quenched with sodium bicarbonate solution and extracted twice with ether. The extracts were washed with brine and evaporated. The crude product was purified by column chromatography, eluting with 20% ethyl acetate/hexane, to provide the title compound (0.560 g, 8.3% yield).

Step B: Preparation of tert-butyl 3-(3-bromo-2-oxopropyl)-2-oxopyrrolidine-1-carboxylate. In a 125 mL round-bottom flask, tert-butyl 3-(2-bromoallyl)-2-oxopyrrolidine-1-carboxylate (0.560 g, 1.84 mmol) was dissolved in mixture of acetonitrile (8 mL) and water (2 mL). N-bromosuccinimide (0.41 g, 2.30 mmol) was added and the mixture was agitated overnight. The reaction mixture was diluted with 100 mL of ether, washed with sodium bicarbonate solution, brine, dried and evaporated to provide the title compound (0.25 g, 42.4% yield).

Step C: Preparation of 3-((2-(5-bromo-3-phenoxypyridin-2-ylamino)thiazol-4-yl)methyl)-1-methylpyrrolidin-2-one. Prepared according to the method of Example 7, step E.

Step D: Preparation of 3-((2-(5-bromo-3-phenoxypyridin-2-ylamino)thiazol-4-yl)methyl)pyrrolidin-2-one. In a 20 mL scintillation vial, tert-butyl 3-((2-(5-bromo-3-phenoxypyridin-2-ylamino)thiazol-4-yl)methyl)-2-oxopyrrolidine-1-carboxylate (35 mg, 0.064 mmol) was dissolved in CH$_2$Cl$_2$ (1 mL) and HCl (4.0M solution in dioxane) (2.00 mL, 8.00 mmol) was added. The resulting mixture was agitated overnight. The solvents and excess HCl were evaporated, and product was obtained as yellow solid (25 mg, 87.5% yield). $^1$H NMR (DMSO-d$_6$ δ 1.70-1.80 (m, 1H), 2.12-2.20 (m, 1H), 2.60-2.74 (m, 1H), 3.02 (d, 1H), 3.16-3.22 (m, 2H), 3.44-3.76 (m, 5H), 6.97 (s, 1H), 7.19-7.50 (m, 6H), 7.83 (s, 1H), 8.30 (s, 1H).

Example 394

3-((2-(5-bromo-3-(phenylthio)pyridin-2-ylamino)thiazol-4-yl)methyl)pyrrolidin-2-one

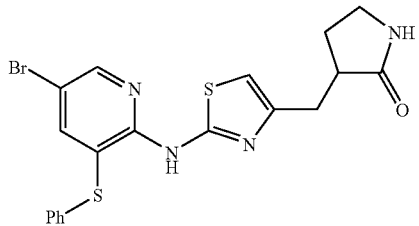

Prepared according to the method of Examples 391 and 393. $^1$H NMR ((CD$_3$)$_2$SO) δ 1.70-1.80 (m, 1H), 2.12-2.20 (m, 1H), 2.60-2.74 (m, 1H), 3.02 (d, 1H), 3.16-3.22 (m, 2H), 3.44-3.76 (m, 5H), 6.77 (s, 1H), 7.38-7.50 (m, 6H), 7.76 (s, 1H), 8.43 (s, 1H).

Example 395

2-((2-(5-bromo-3-phenoxypyridin-2-ylamino)thiazol-4-yl)methyl)-4-(tert-butoxycarbonylamino)butanoic acid

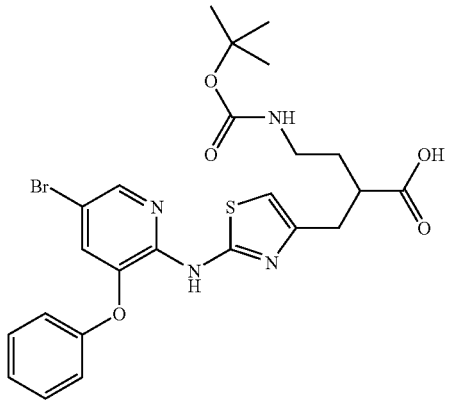

tert-Butyl 3-((2-(5-bromo-3-phenoxypyridin-2-ylamino)thiazol-4-yl)methyl)-2-oxopyrrolidine-1-carboxylate (0.070 g, 0.128 mmol) (Example 393, Steps A-C) was dissolved in 1 mL of THF and sodium hydroxide (0.963 mL, 1.93 mmol) 2M solution was added. The resulting solution was heated to 55° C. and agitated for 3 hours. Reaction was quenched with 3 mL of 2M potassium hydrosulfate solution and extracted twice with ethyl acetate. The extracts were washed with water, brine, dried and evaporated to produce the title compound. $^1$H NMR (CDCl$_3$) δ 1.40 (s, 9H), 1.60-1.74 (m, 2H), 2.64-3.08 (m, 5H), 4.65 (bs, 1H), 6.47 (s, 1H), 7.09-7.43 (m, 7H), 8.14 (s, 1H).

Example 396

2-((2-(5-bromo-3-(phenylthio)pyridin-2-ylamino)thiazol-4-ylmethyl)-4-(tert butoxycarbonylamino)butanoic acid

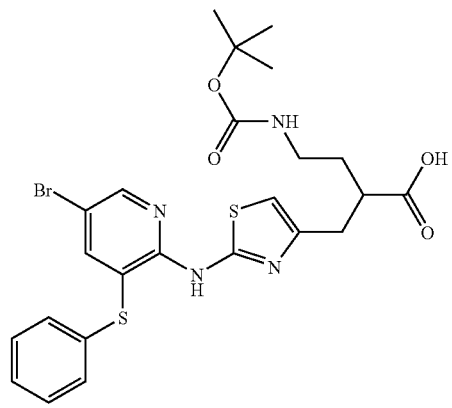

Prepared according to the method of Example 395 from tert-butyl 3-((2-(5-bromo-3-(phenylthio)pyridin-2-ylamino)thiazol-4-yl)methyl)-2-oxopyrrolidine-1-carboxylate. $^1$H NMR (CDCl$_3$) δ 1.41 (s, 9H), 1.64-1.86 (m, 2H), 2.80-3.22 (m, 5H), 4.93 (bs, 1H), 6.55 (s, 1H), 7.22-7.32 (m, 6H), 7.85 (s, 1H), 8.38 (s, 1H).

Example 397

4-amino-2-((2-(5-bromo-3-phenoxypyridin-2-ylamino)thiazol-4-ylmethyl)butanoic acid

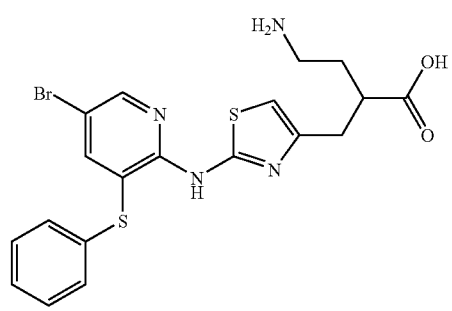

Prepared according to the method of Example 393, Step D. ¹H NMR (DMSO-d$_6$ δ 1.65-1.79 (m, 2H), 2.74-3.10 (m, 5H), 6.55 (s, 1H), 7.12-7.45 (m, 7H), 8.26 (s, 1H).

Example 398

1-(4-(2-(5-bromo-3-(phenylthio)pyridin-2-ylamino)thiazol-4-yl)piperidin-1-yl)ethanone

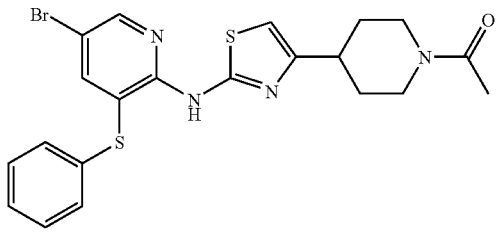

Step A: Preparation of 1-acetyl-N-methoxy-N-methylpiperidine-4-carboxamide. To a solution of 1-acetylpiperidine-4-carboxylic acid (58.50 g, 342 mmol) in dichloromethane (700 mL) was added di(1H-imidazol-1-yl)methanone (58.18 g, 359 mmol). After the addition the mixture was agitated for two hours and N-methoxymethanamine hydrochloride (35.00 g, 359 mmol) was added at once. The mixture was allowed to agitate overnight at ambient temperature and 4M HCl in dioxane (75 mL) was added slowly. The slurry was agitated for 30 minutes and then filtered. Filtrate was washed twice with sodium bicarbonate solution, dried and concentrated to give the title compound (59.10 g, 80.72% yield).

Step B: Preparation of 1,1'-(piperidine-1,4-diyl)diethanone. 1-Acetyl-N-methoxy-N-methylpiperidine-4-carboxamide (59.10 g, 276 mmol) was dissolved in THF (800 mL) and cooled to 0° C. Methylmagnesium bromide (110.3 mL, 331 mmol) (3.0M in diethyl ether) was added slowly and the resulting white slurry was agitated for 1 hour. The reaction was quenched with 300 mL of 2M HCl and the solvent was evaporated. The resulting aqueous slurry was filtered and the solids were washed with water and small amount of ether to provide the title compound (38.4 g, 82.2% yield).

Step C: Preparation of 1-(1-acetylpiperidin-4-yl)-2-bromoethanone. 1,1'-(Piperidine-1,4-diyl)diethanone (38.0 g, 225 mmol) was dissolved in methanol (700 mL) and bromine (12.1 mL, 236 mmol) was added. After agitating for 3 hours the solvent was removed. The resulting solid was washed with ethyl acetate, then distributed between ethyl acetate and sodium carbonate. The organic phase was separated, washed with brine, dried and evaporated to give the title compound.

Step D: Preparation of 1-(4-(2-(5-bromo-3-(phenylthio)pyridin-2-ylamino)thiazol-4-yl)piperidin-1-yl)ethanone. Prepared according to the method of Example 7, Step E ¹H NMR (CDCl$_3$) δ 1.58-1.64 (m, 2H), 1.99-2.11 (m, 5H), 2.64-2.86 (m, 2H), 3.16 (t, 1H), 3.88 (d, 1H), 4.68 (d, 1H), 6.44 (s, 1H), 7.18-7.32 (m, 5H), 7.92 (s, 1H), 8.23 (s, 1H), 8.50 (s, 1H).

Example 399

2-(dimethylamino)-1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone trihydrochloride

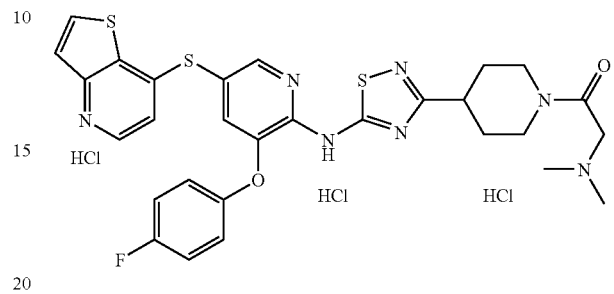

Prepared according to the method of Example 198. ¹H NMR (d$_6$-DMSO) δ 12.49 (bs, 1H), 9.62 (bs, 1H), 8.58 (d, 1H), 8.52 (d, 1H), 8.33 (d, 1H), 7.69 (d, 1H), 7.59 (d, 1H), 7.23 (m, 4H), 7.08 (d, 1H), 4.41-4.22 (m, 3H), 3.66 (d, 1H), 3.28-3.11 (m, 2H), 3.01-2.89 (m, 2H), 2.82 (d, 6H), 2.09 (m, 2H), 1.82 (m, 1H), 1.65 (m, 1H). Mass spectrum (apci) m/z=622.2 (M+H-3HCl).

Example 400

1-(4-((5-(3-(4-fluorophenoxy)-5-(thieno[3,2-b]pyridin-7-ylthio)pyridin-2-ylamino)-1,2,4-thiadiazol-3-yl)methyl)piperidin-1-yl)ethanone dihydrochloride

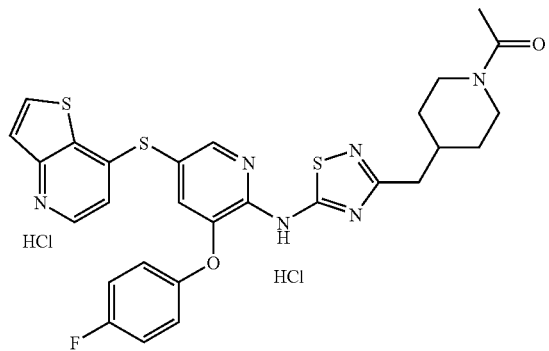

Step A: Preparation of tert-butyl 4-((5-(3-(4-fluoro-phenoxy)-5-(thieno[3,2-b]pyridin-7-ylthio)pyridin-2-ylamino)-1,2,4-thiadiazol-3-yl)methyl)-piperidine-1-carboxylate: Prepared according to the method of Example 127 from tert-butyl 4-((5-(3-(4-fluorophenoxy)-5-(3-methoxy-3-oxopropylthio)pyridin-2-ylamino)-1,2,4-thiadiazol-3-yl)methyl)piperidine-1-carboxylate (Example 96, 230 mg, 0.381 mmol).

Step B: Preparation of 3-(4-fluorophenoxy)-N-(3-(piperidin-4-ylmethyl)-1,2,4-thiadiazol-5-yl)-5-(thieno[3,2-b]pyridin-7-ylthio)pyridin-2-amine trihydrochloride: A 10 mL round-bottomed flask was charged with tert-butyl 4-((5-(3-(4-fluorophenoxy)-5-(thieno[3,2-b]pyridin-7-ylthio)pyridin-2-ylamino)-1,2,4-thiadiazol-3-yl)methyl)piperidine-1-carboxylate (52.2 mg, 0.0802 mmol) and a 1:1 mix of methanol and CH$_2$Cl$_2$ (4 mL). 4N HCl in dioxane (2 mL) was added and the reaction stirred at room temperature for 10 minutes. The solvent was removed to afford crude 3-(4-fluorophenoxy)-N-(3-(piperidin-4-ylmethyl)-1,2,4-thiadiazol-5-yl)-5-(thieno[3,2-b]pyridin-7-ylthio)pyridin-2-amine trihydrochloride (52.9 mg, 100%).

Step C: Preparation of 1-(4-((5-(3-(4-fluorophenoxy)-5-(thieno[3,2-b]pyridin-7-ylthio)pyridin-2-ylamino)-1,2,4-thiadiazol-3-yl)methyl)piperidin-1-yl)ethanone dihydrochloride: Prepared according to the method of Example 198. $^1$H NMR (d$_6$-DMSO) δ 12.46 (bs, 1H), 8.58 (d, 1H), 8.52 (d, 1H), 8.33 (d, 1H), 7.68 (d, 1H), 7.57 (d, 1H), 7.23 (m, 4H), 7.08 (d, 1H), 4.34 (d, 1H), 3.78 (d, 1H), 2.99 (t, 1H), 2.72 (d, 2H), 2.09 (m, 1H), 1.97 (s, 3H), 1.65 (m, 2H), 1.18 (m, 1H), 1.05 (m, 1H). Mass spectrum (apci) m/z=593.2 (M+H-2HCl).

Example 401

1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone hydrochloride

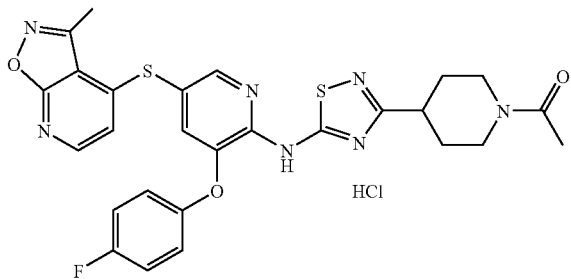

Prepared according to Example 400, using tert-butyl 4-(5-(3-(4-fluorophenoxy)-5-(3-methylisoxazolo[5,4-b]pyridin-4-ylthio)pyridin-2-ylamino)-1,2,4-thiadiazol-3-yl)piperidine 1-carboxylate in Step B. $^1$H NMR (d$_6$-DMSO) δ 12.48 (bs, 1H), 8.49 (d, 1H), 8.32 (d, 1H), 7.54 (m, 1H), 7.25 (m, 4H), 6.75 (d, 1H), 4.33 (d, 1H), 3.85 (d, 1H), 3.20 (m, 1H), 3.07 (m, 1H), 2.77 (t, 1H), 2.69 (s, 3H), 2.02 (m, 5H), 1.74 (m, 1H), 1.60 (m, 1H). Mass spectrum (apci) m/z=578.1 (M+H—HCl).

Example 402

2-(dimethylamino)-1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone dihydrochloride

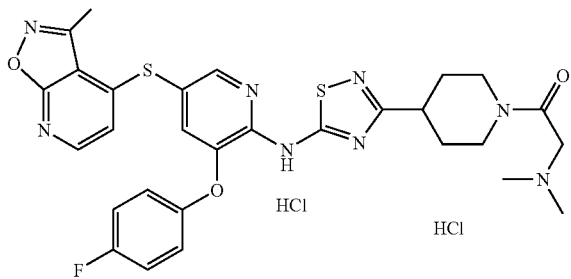

Prepared according to the method of Example 198 using 3-(4-fluorophenoxy)-5-(3-methylisoxazolo[5,4-b]pyridin-4-ylthio)-N-(3-(piperidin-4-yl)-1,2,4-thiadiazol-5-yl)pyridin-2-amine. $^1$H NMR (d$_6$-DMSO) δ 12.44 (bs, 1H), 9.55 (bs, 1H), 8.49 (d, 1H), 8.32 (d, 1H), 7.55 (d, 1H), 7.25 (m, 4H), 6.74 (d, 1H), 4.32 (m, 3H), 3.65 (d, 1H), 3.28-3.10 (m, 2H), 2.97 (t, 1H), 2.82 (d, 6H), 2.70 (s, 3H), 2.10 (d, 2H), 1.82 (m, 1H), 1.66 (m, 1H). Mass spectrum (apci) m/z 621.1 (M+H-2HCl).

Example 403

5-(3-bromophenoxy)-3-(3-methoxyphenylthio)-N-(3-(tetrahydrofuran-2-yl)-1,2,4-thiadiazol-5-yl)pyridin-2-amine hydrochloride

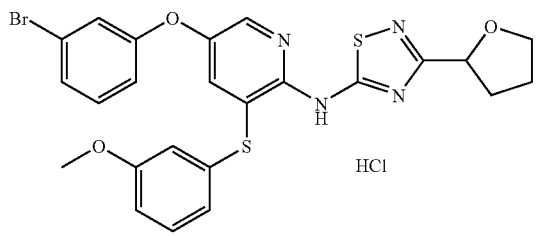

Step A: Preparation of 5-bromo-3-(3-methoxyphenylthio) picolinonitrile: A 10 mL round-bottomed flask was charged with 5-bromo-3-nitropicolinonitrile (300 mg, 1.31 mmol), 3-methoxybenzenethiol (0.150 mL, 1.31 mmol), and DMF (12 mL). NaH (37.8 mg, 1.58 mmol) was added and reaction stirred at room temperature for 10 minutes. The reaction was poured into water and extracted with EtOAc. The organic layer was dried over sodium sulfate, filtered and concentrated. The resulting residue was purified on silica gel (10% EtOAc in Hexanes) to afford the title compound (345 mg, 81%).

Step B: Preparation of 5-(3-bromophenoxy)-3-(3-methoxyphenylthio) picolinonitrile: A 10 mL round-bottomed flask was charged with 5-bromo-3-(3-methoxyphenylthio)picolinonitrile (214 mg, 0.666 mmol), 3-bromophenol (138 mg, 0.800 mmol), and DMF (6 mL). NaH (24.0 mg, 0.999 mmol) was added and reaction stirred at room temperature for 24 hours. The reaction was poured into water and extracted with EtOAc. The organic layer was dried over sodium sulfate, filtered and concentrated. The resulting residue was purified on silica gel (10% EtOAc in Hexanes) to afford the title compound (225 mg, 81.7% yield).

Step C: Preparation of 5-(3-bromophenoxy)-3-(3-methoxyphenylthio)picolinic acid: A 25 mL round-bottomed flask was charged with 5-(3-bromophenoxy)-3-(3-methoxyphenylthio)picolinonitrile (225 mg, 0.544 mmol), potassium hydroxide (2.5 M, 1.09 mL, 2.72 mmol), and EtOH (5 mL). The reaction was heated to reflux overnight. After cooling to room temperature the reaction was poured into water and pH adjusted with 1N HCl to~pH=3. The cloudy solution was extracted with CH$_2$Cl$_2$. The organic layer was dried over sodium sulfate, filtered and concentrated to afford the title compound (235 mg, 100%) which was taken forward without further purification.

Step D: Preparation of 5-(3-bromophenoxy)-3-(3-methoxyphenylthio)pyridin-2-amine: A 25 mL round-bottomed flask was charged with 2-methylpropan-2-ol (0.284 mL, 3.26 mmol), 5-(3-bromophenoxy)-3-(3-methoxyphenylthio)picolinic acid (235 mg, 0.544 mmol), triethylamine (0.0985 mL, 0.707 mmol), and Toluene (5 mL). The reaction was heated to 100° C. and DPPA (0.118 mL, 0.544 mmol) was added dropwise. The reaction was stirred at 100° C. for 30 minutes after complete addition and then cooled to room temperature and partitioned between CH$_2$Cl$_2$ and water. The organic layer was dried over sodium sulfate, filtered and concentrated. The residue was purified on silica gel (10% EtOAc in hexanes) to afford the Boc protected material. This residue was dissolved in 1:1 CH$_2$Cl$_2$:methanol (4 mL) and 4N HCl in dioxane (2 mL) was added and stirred at room temperature for 4 hours. The solvent was removed and partitioned between aqueous sodium bicarbonate and CH$_2$Cl$_2$. The organic phase was dried, filtered and concentrated to afford the title compound (128 mg, 58.4% yield).

Step E: Preparation of 5-(3-bromo-henoxy)-3-(3-methoxyphenylthio)-N-(3-(tetrahydrofuran-2-yl-1,2,4-thiadiazol-5-yl)-pyridin-2-amine: Prepared according to the method of Example 183 step D.

Step F: Preparation of 5-(3-bromophenoxy)-3-(3-methoxyphenylthio)-N-(3-(tetrahydrofuran-2-yl)-1,2,4-thiadiazol-5-yl)pyridin-2-amine hydrochloride: A 10 mL round-bottom flask was charged with 5-(3-bromophenoxy)-3-(3-methoxyphenylthio)-N-(3-(tetrahydrofuran-2-yl)-1,2,4-thiadiazol-5-yl)pyridin-2-amine (20 mg, 0.036 mmol) and dissolved in CH$_2$Cl$_2$ (1 mL). 2M HCl in ether (0.1 mL, 0.2 mmol) was added and the solvent removed to afford the title compound (21 mg, 100%). $^1$H NMR (d$_6$-DMSO) δ 11.51 (bs, 1H), 8.40 (d, 1H), 8.36 (bs, 1H), 7.68 (bs, 1H), 7.51-7.18 (m, 5H), 7.10-6.73 (m, 3H), 4.10-3.74 (m, 3H), 3.72 (s, 3H), 2.25 (m, 4H). Mass spectrum (apci) m/z=559.1 (M+H–HCl).

Example 404

3-(3-methoxyphenylthio)-5-phenoxy-N-(3-(tetrahydrofuran-2-yl)-1,2,4-thiadiazol-5-yl)pyridin-2-amine hydrochloride

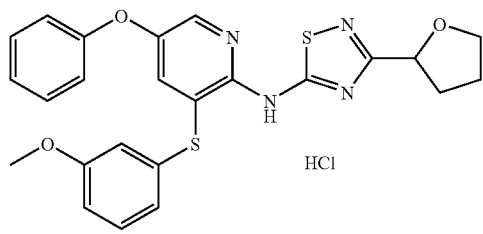

A 10 mL round-bottomed flask was charged with 5-(3-bromophenoxy)-3-(3-methoxyphenylthio)-N-(3-(tetrahydrofuran-2-yl)-1,2,4-thiadiazol-5-yl)pyridin-2-amine (41 mg, 0.074 mmol) and THF (2 mL). The reaction was cooled to –78° C. and methyllithium (0.055 mL, 0.088 mmol) was added and stirred for 5 minutes. Butyllithium (0.035 mL, 0.088 mmol) was added and stirred for 5 minutes. The reaction was then poured into saturated aqueous NH$_4$Cl and extract with EtOAc. The organic layer was dried with sodium sulfate, filtered and concentrated. The residue was purified on silica gel (35% ethyl acetate in hexanes) to afford the title compound (36 mg, 95%) after HCl salt formation. $^1$H NMR (d$_6$-DMSO) δ 11.47 (bs, 1H), 8.30 (bs, 1 h), 7.59 (bs, 1H), 7.37 (m, 2H), 7.28 (t, 1H), 7.14 (t, 1H), 7.03 (d, 2H), 6.88 (m, 3H), 4.04 (t, 1H), 3.90-3.75 (m, 3H), 3.72 (s, 3H), 3.57 (m, 1H), 2.25 (m, 2H). Mass spectrum (apci) m/z=479.2 (M+H—HCl).

Example 405

1-(3-(5-(3-methoxyphenylthio)-6-(3-(tetrahydrofuran-2-yl)-1,2,4-thiadiazol-5-ylamino)pyridin-3-yloxy)phenyl)ethanol

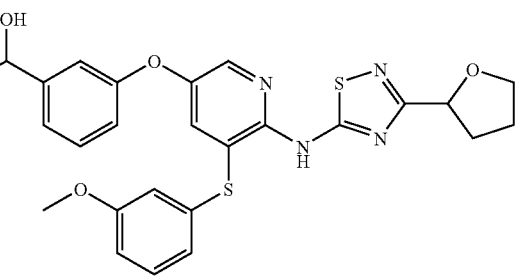

A 10 mL round-bottomed flask was charged with 5-(3-bromophenoxy)-3-(3-methoxyphenylthio)-N-(3-(tetrahydrofuran-2-yl)-1,2,4-thiadiazol-5-yl)pyridin-2-amine (43.3 mg, 0.077 mmol) and THF (2 mL). The reaction was cooled to –78° C. and methyllithium (0.058 mL, 0.093 mmol) was added and stirred for 5 min. Butyllithium (0.037 mL, 0.093 mmol) was added and the reaction was stirred for 5 min. Acetaldehyde (0.0086 mL, 0.16 mmol) was added and the reaction warmed to room temperature and poured into saturated aqueous NH$_4$Cl and extracted with EtOAc. The organic layer was dried with sodium sulfate, filtered and concentrated. The residue was purified on silica gel (35 to 100% ethyl acetate in hexanes) to afford the title compound (4.5 mg, 11.1% yield). $^1$H NMR (CDCl$_3$) δ 9.26 (bs, 1H), 8.25 (d, 1H), 7.63 (d, 1H), 7.33 (t, 1H), 7.21 (t, 1H), 7.14 (d, 1H), 7.05 (m, 1H), 6.90 (dd, 1H), 6.76 (m, 2H), 6.70 (m, 1H), 4.89 (q, 1H), 4.15 (t, 1H), 4.03 (m, 2H), 3.90 (m, 1H), 3.77 (s, 3H), 3.64 (m, 1H), 2.34 (q, 2H), 1.47 (d, 3H). Mass spectrum (apci) m/z=523.2 (M+H).

Example 406

3-(2-bromo-4-fluorophenoxy)-5-(3-methoxyphenylthio)-N-(4-(piperidin-4-yl)thiazol-2-yl)pyridin-2-amine

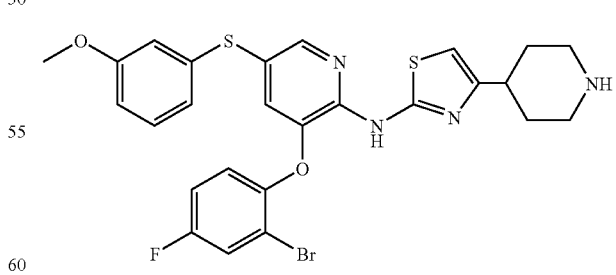

Steps A-E: Preparation of 1-benzoyl-3-(3-(2-bromo-4-fluorophenoxy)-5-(3-methoxyphenylthio)pyridin-2-yl)thiourea: Prepared according to Example 403, Steps A-D.

Step F: A 250 mL round-bottomed flask was charged with 3-(2-bromo-4-fluorophenoxy)-5-(3-methoxyphenylthio)pyridin-2-amine (7.4 g, 17.6 mmol), benzoyl isothiocyanate (3.08 mL, 22.8 mmol), and THF (125 mL). The reaction was stirred at room temperature overnight. Hexanes (700 mL) was added and stirred at room temperature for 1 hour. The solid material was decanted to afford 5.6 g of material as a yellow foam. The mother liquor was concentrated and resuspended in 9:1 hexanes:EtOAc (200 mL) to afford another 4.7 g of material. The combined crops afforded the title compound (10.3 g, 100%).

Step G: Preparation of 1-(3-(2-bromo-4-fluorophenoxy)-5-(3-methoxyphenylthio) pyridin-2-yl)thiourea: A 250 mL round-bottomed flask was charged with 1-benzoyl-3-(3-(2-bromo-4-fluorophenoxy)-5-(3-methoxyphenylthio)pyridin-2-yl)thiourea (10.3 g, 17.6 mmol) and EtOH (125 mL). 3M Sodium hydroxide (11.7 mL, 35.2 mmol) was added and heated to 50° C. overnight. The reaction was cooled to room temperature and poured into 750 mL water and stirred vigorously for 1 hour. The solids were filtered to afford the title compound (6.5 g, 76.8% yield).

Step H: Preparation of tert-butyl 4-(2-(3-(2-bromo-4-fluorophenoxy)-5-(3-methoxyphenylthio)pyridin-2-ylamino)thiazol-4-yl)piperidine-1-carboxylate: A 50 mL round-bottomed flask was charged with 1-(3-(2-bromo-4-fluorophenoxy)-5-(3-methoxyphenylthio)pyridin-2-yl)thiourea (1.5 g, 3.12 mmol), triethylamine (0.740 mL, 5.31 mmol), tert-butyl 4-(2-bromoacetyl)piperidine-1-carboxylate (1.15 g, 3.75 mmol), and EtOH (25 mL). The reaction was heated to 70° C. for 3 hours. The reaction was cooled to room temperature and partitioned between EtOAc and water. The organic layer was dried over sodium sulfate, filtered and concentrated. The residue was purified on silica gel (10% EtOAc in hexanes) to afford (1.76 g, 82.0% yield).

Step I: Preparation of 3-(2-bromo-4-fluorophenoxy)-5-(3-methoxyphenylthio)-N-(4-(piperidin-4-yl)thiazol-2-yl)pyridin-2-amine: A 20 mL vial was charged with tert-butyl 4-(2-(3-(2-bromo-4-fluorophenoxy)-5-(3-methoxyphenylthio)pyridin-2-ylamino)thiazol-4-yl)piperidine-1-carboxylate (100 mg, 0.145 mmol) and $CH_2Cl_2$ (2 mL). TFA (2 mL) was added and stirred at room temperature for 5 minutes. The reaction was poured into water and diluted with $CH_2Cl_2$. Solid $Na_2CO_3$ added slowly to neutralize the TFA. The aqueous layer was extracted and dried to afford the title compound (88 mg, 103% yield). $^1H$ NMR ($d_6$-DMSO) δ 8.16 (d, 1H), 7.74 (m, 1H), 7.30 (m, 2H), 7.21 (t, 1H), 6.92 (d, 1H), 6.78 (m, 1H), 6.70 (m, 3H), 3.69 (s, 3H), 3.17 (m, 2H), 2.77 (m, 3H), 2.01 (m, 2H), 1.62 (m, 2H). Mass spectrum (apci) m/z=587.2, 589.2 (M+H).

Example 407

4-(2-(3-(4-fluorophenoxy)-5-(3-methoxyphenylthio)pyridin-2-ylamino)thiazol-4-yl)piperidine-1-carboxylate trifluoroacetate

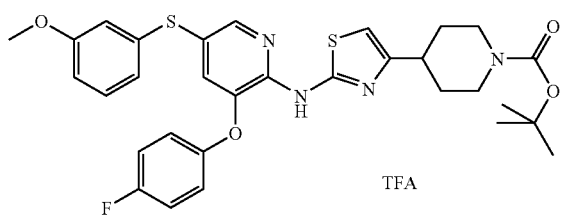

TFA

A 10 mL round-bottomed flask was charged with tert-butyl 4-(2-(3-(2-bromo-4-fluorophenoxy)-5-(3-methoxyphenylthio)pyridin-2-ylamino)thiazol-4-yl)piperidine-1-carboxylate (200 mg, 0.29 mmol) and THF (3 mL). The reaction was cooled to −78° C. and methyllithium (0.22 mL, 0.35 mmol) was added and stirred for 5 min. Butyllithium (0.140 mL, 0.35 mmol) was added and the reaction was stirred for 5 min. Iodomethane (0.0273 mL, 0.436 mmol) was added and the reaction was stirred for 5 min and then poured into saturated aqueous $NH_4Cl$ and extracted with EtOAc (1×20 mL). The organic layer was dried with sodium sulfate, filtered and concentrated to afford a mixture of products. The residue was purified on reverse phase column (35 to 100% acetonitrile in water with 0.1% TFA) to afford the title compound (68.3 mg, 33% yield). $^1H$ NMR ($CDCl_3$) δ 8.13 (d, 1H), 7.28 (d, 1H), 7.22 (m, 1H), 7.04 (m, 4H), 6.85 (m, 1H), 6.80 (m, 2H), 6.43 (s, 1H), 4.22 (m, 2H), 3.76 (s, 3h), 2.89 (m, 3H), 2.06 (m, 2H), 1.56 (m, 2H), 1.47 (s, 9H).

Example 408

1-(4-(2-(3-(4-fluoro-2-methylphenoxy)-5-(3-methoxyphenylthio)pyridin-2-ylamino)thiazol-4-yl)piperidin-1-yl)ethanone hydrochloride

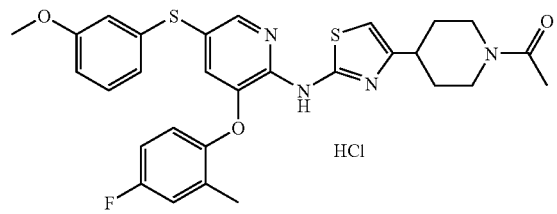

HCl

Step A: Preparation of tert-butyl 4-(2-(3-(4-fluoro-2-methylphenoxy)-5-(3-methoxyphenylthio)pyridin-2-ylamino)thiazol-4-yl)piperidine-1-carboxylate trifluoroacetate: From the reaction mixture in Example 407, the title compound was isolated from the reverse phase chromatography (70 mg, 33% yield).

Step B: Preparation of N-(3-(4-fluoro-2-methylphenoxy)-5-(3-methoxyphenylthio)pyridin-2-yl)-4-(piperidin-4-yl)thiazol-2-amine ditrifluoroacetate: A 10 mL round-bottomed flask was charged with tert-butyl 4-(2-(3-(4-fluoro-2-methylphenoxy)-5-(3-methoxyphenylthio)pyridin-2-ylamino)thiazol-4-yl)piperidine-1-carboxylate trifluoroacetate (70 mg, 0.097 mmol) and $CH_2Cl_2$ (2 mL). TFA (2 mL) was added and stirred at room temperature for 30 minutes. The solvent was removed and dried on high vacuum overnight. The crude material was taken on to the next reaction without further purification.

Step C: Preparation of 1-(4-(2-(3-(4-fluoro-2-methylphenoxy)-5-(3-methoxyphenylthio)pyridin-2-ylamino)thiazol-4-yl)piperidin-1-yl)ethanone hydrochloride: A 20 mL vial was charged with 3-(4-fluoro-2-methylphenoxy)-5-(3-methoxyphenylthio)-N-(4-(piperidin-4-yl)thiazol-2-yl)pyridin-2-amine ditrifluoroacetate (70 mg, 0.098 mmol) and $CH_2Cl_2$ (2 mL). Triethylamine (0.109 mL, 0.78 mmol) was added followed by $Ac_2O$ (0.012 mL, 0.12 mmol) and the reaction was stirred for 5 minutes. The reaction was poured into saturated aqueous $NaHCO_3$ and extracted with $CH_2Cl_2$ (1×20 mL). The organic layer was dried with sodium sulfate, filtered and concentrated. The residue was purified on silica gel (20 to 40% EtOAc in hexanes) to afford the title compound (44.8 mg, 76.3% yield) after HCl salt formation. $^1$H NMR (d$_6$-DMSO) δ 11.20 (bs, 1H), 8.14 (d, 1H), 7.22 (m, 2H), 7.04 (m, 2H), 6.88 (d, 1H), 6.77 (m, 2H), 6.71 (m, 2H), 4.43 (d, 1H), 3.88 (d, 1H), 3.69 (s, 3H), 3.14 (t, 1H), 2.87 (m, 1H), 2.65 (m, 1H), 2.19 (s, 3H), 2.01 (s, 3H), 1.95 (m, 2H), 1.58 (m, 1H), 1.45 (m, 1H). Mass spectrum (apci) m/z=565.3 (M+H—HCl).

Example 409

1-(4-(2-(3-(4-fluorophenoxy-5-(3-methoxyphenylthio)pyridin-2-ylamino)thiazol-4-yl)piperidin-1-yl)ethanone hydrochloride

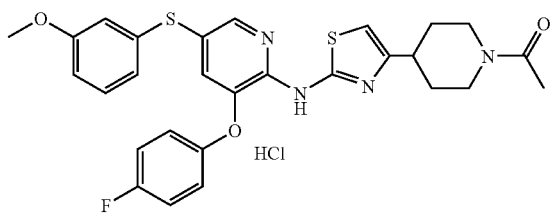

Step A: Preparation of 3-(4-fluoro-phenoxy)-5-(3-methoxyphenylthio)-N-(4-(piperidin-4-yl)thiazol-2-yl)pyridin-2-amine ditrifluoroacetate: A 10 mL round-bottomed flask was charged with tert-butyl 4-(2-(3-(4-fluorophenoxy)-5-(3-methoxyphenylthio)pyridin-2-ylamino)thiazol-4-l)piperidine-1-carboxylate (68 mg, 0.11 mmol) and CH$_2$Cl$_2$ (2 mL). TFA (2 mL) was added and stirred at room temperature for 30 minutes. The reaction was concentrated and taken on to next reaction without further purification.

Step B: Preparation of 1-(4-(2-(3-(4-fluorophenoxy)-5-(3-methoxyphenylthio)pyridin-2-ylamino)thiazol-4-yl)piperidin-1-yl)ethanone hydrochloride: Prepared according to the method of Example 198. $^1$H NMR (d$_6$-DMSO) δ 11.10 (bs, 1H), 8.19 (m, 1H), 7.22 (m, 4H), 7.15 (m, 2H), 6.79 (m, 1H), 6.74 (m, 3H), 4.42 (d, 1H), 3.87 (d, 1H), 3.70 (sp 3H), 3.13 (t, 1H), 2.85 (t, 1H), 2.63 (t, 1H), 2.01 (d, 3H), 1.94 (m, 2H), 1.57 (m, 1H), 1.44 (m, 1H). Mass spectrum (esi) m/z=551.0 (M+H—HCl).

Example 410

1-(4-(2-(3-(2-bromo-4-fluorophenoxy)-5-(3-methoxyphenylthio)pyridin-2-ylamino)thiazol-4-yl)piperidin-1-yl)ethanone hydrochloride

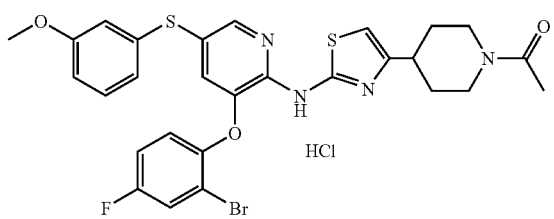

A 20 mL vial was charged with 3-(2-bromo-4-fluorophenoxy)-5-(3-methoxyphenylthio)-N-(4-(piperidin-4-yl)thiazol-2-yl)pyridin-2-amine (40 mg, 0.068 mmol), triethylamine (0.0190 mL, 0.14 mmol), and CH$_2$Cl$_2$ (2 mL). Ac$_2$O (0.008 mL, 0.082 mmol) was added and the reaction was stirred at room temperature for 10 minutes. The reaction was partitioned between CH$_2$Cl$_2$ and saturated aqueous sodium bicarbonate. The organic layer was dried with sodium sulfate, filtered and concentrated to afford the title compound (38.2 mg, 84.2% yield) as a white solid after HCl salt formation. $^1$H NMR (d$_6$-DMSO) δ 11.20 (bs, 1H), 8.17 (d, 1H), 7.74 (m, 1H), 7.31 (m, 2H), 7.21 (t, 1H), 6.93 (d, 1H), 6.78 (m, 1H), 6.74 (s, 1H), 6.71 (m, 2H), 4.43 (d, 1H), 3.87 (d, 1H), 3.69 (s, 3H), 3.14 (m, 1H), 2.86 (m, 1H), 2.64 (m, 1H), 2.01 (s, 3H), 1.95 (m, 2H), 1.58 (m, 1H), 1.45 (m, 1H). Mass spectrum (apci) m/z=631.4 (M+H—HCl).

Example 411

1-(4-(2-(3-(2-bromo-4-fluorophenoxy)-5-(3-methoxyphenylthio)pyridin-2-ylamino)thiazol-4-yl)piperidin-1-yl)-2-(dimethylamino)ethanone dihydrochloride

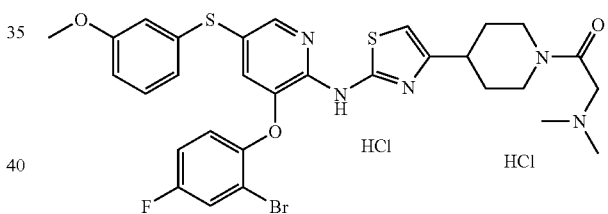

A 20 mL vial was charged with 3-(2-bromo-4-fluorophenoxy)-5-(3-methoxyphenylthio)-N-(4-(piperidin-4-yl)thiazol-2-yl)pyridin-2-amine (40 mg, 0.068 mmol), triethylamine (0.028 mL, 0.20 mmol), and CH$_2$Cl$_2$ (2 mL). 2-(Dimethylamino)acetyl chloride hydrochloride (12.9 mg, 0.0817 mmol) was added and stirred at room temperature for 10 minutes. The reaction was partitioned between CH$_2$Cl$_2$ and saturated aqueous sodium bicarbonate. The organic layer was dried with sodium sulfate, filtered and concentrated. The residue was purified on silica gel (15% MeOH in EtOAc with 0.3% ammonia) to afford 1 the title compound (35.6 mg, 70.1% yield) after HCl salt formation. $^1$H NMR (d$_6$-DMSO) δ 11.15 (bs, 1H), 9.60 (bs, 1H), 8.17 (d, 1H), 7.75 (m, 1H), 7.32 (m, 2H), 7.21 (t, 1H), 6.94 (d, 1H), 6.79 (m, 1H), 6.75 (s, 1H), 6.71 (m, 2H), 4.42 (d, 1H), 4.31 (qd, 2H), 3.69 (s, 3H), 3.19 (t, 1H), 2.93 (m, 1H), 2.82 (m, 6H), 2.04 (d, 2H), 1.64 (m, 1H), 1.52 (m, 1H). Mass spectrum (apci) m/z=674.3 (M+H-2HCl).

The following compounds were prepared by the method of Example 127.

| Example | Structure | Name | NMR Data |
|---|---|---|---|
| 412 | 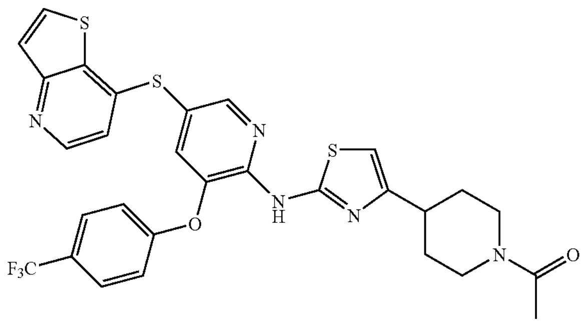 | 1-(4-(2-(5-(Thieno[3,2-b]pyridin-7-ylthio)-3-(4-(trifluoromethyl)phenoxy)pyridin-2-ylamino)thiazol-4-yl)piperidin-1-yl)ethanone | $H^1$ NMR (d$_6$ DMSO) δ 1.23-1.47 (m, 1H), 1.52-1.60 (m, 1H), 1.93 (t, J = 15.5 Hz, 2H), 2.00 (s, 3H), 2.62 (t, J = 12.4 Hz, 1H), 2.83 (br s, 1H), 3.12 (t, J = 12.1 Hz, 1H), 3.85 (d, J = 13.1 Hz, 1H), 4.42 (d, J = 13.3 Hz, 1H), 6.76 (s, 1H), 6.95 (d, J = 5.1 Hz, 1H), 7.23 (d, J = 6.4 Hz, 2H), 7.59 (d, J = 5.5 Hz, 1H), 7.72 (d, J = 8.4 Hz, 2H), 7.79 (s, 1H), 8.16 (d, J = 5.5 Hz, 1H), 8.48 (d, J = 2.0 Hz, 1H), 8.51 (d, J = 4.9 Hz, 1H), 11.44 (s, 1H). |
| 413 | 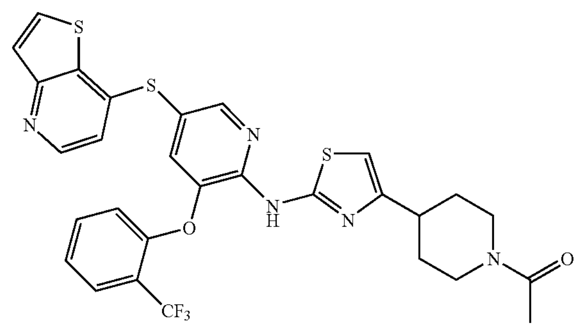 | 1-(4-(2-(5-(Thieno[3,2-b]pyridin-7-ylthio)-3-(2-(trifluoromethyl)phenoxy)pyridin-2-ylamino)thiazol-4-yl)piperidin-1-yl)ethanone | $H^1$ NMR (d$_6$ DMSO) δ 1.40-1.49 (m, 1H), 1.54-1.62 (m, 1H), 1.91-2.00 (m, 5H), 2.63 (t, J = 12.3 Hz, 1H), 2.85 (br s, 1H), 3.13 (t, J = 12.3 Hz, 1H), 3.87 (d, J = 13.8 Hz, 1H), 4.43 (d, J = 13.1 Hz, 1H), 6.76 (br s, 1H), 6.88 (d, J = 5.1 Hz, 1H), 7.21 (br s, 1H), 7.32-7.36 (m, 2H), 7.58 (d, J = 5.5 Hz, 1H), 7.65 (t, J = 7.8 Hz, 1H), 7.77 (d, J = 7.6 Hz, 1H), 8.16 (d, J = 5.5 Hz, 1H), 8.42 (d, J = 2.0 Hz, 1H), 8.48 (d, J = 5.1 Hz, 1H), 11.35 (br s, 1H). |
| 414 | 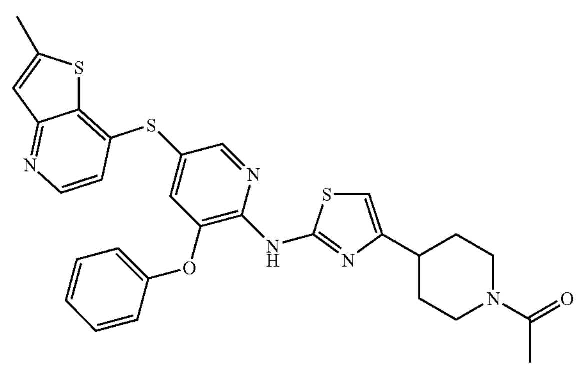 | 1-(4-(2-(5-(2-Methylthieno[3,2-b]pyridin-7-ylthio)-3-phenoxypyridin-2-ylamino)thiazol-4-yl)piperidin-1-yl)ethanone | $H^1$ NMR (CDCl$_3$) δ 1.59-1.70 (m, 2H), 2.04-2.12 (m, 5H), 2.63 (d, J = 1.2 Hz, 3H), 2.70 (t, J = 11.5 Hz, 1H), 2.84-2.90 (m, 1H), 3.19 (t, J = 11.7 Hz, 1H), 3.91 (d, J = 13.9 Hz, 1H), 4.72 (d, J = 13.3 Hz, 1H), 6.51 (s, 1H), 6.66 (d, J = 5.3 Hz, 1H), 7.04 (s, 1H), 7.06 (d, J = 1.0 Hz, 1H), 7.17-7.23 (m, 3H), 7.39 (t, J = 7.9 Hz, 2H), 8.29 (d, J = 2.0 Hz, 1H), 8.37 (d, J = 5.1 Hz, 1H), 8.84 (brs, 1H). |
| 415 | 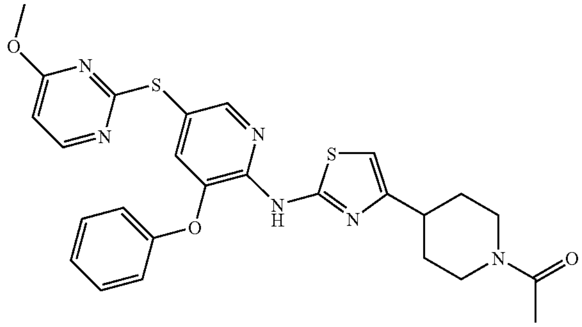 | 1-(4-(2-(5-(4-Methoxypyrimidin-2-ylthio)-3-phenoxypyridin-2-ylamino)thiazol-4-yl)piperidin-1-yl)ethanone | $H^1$ NMR (CDCl$_3$) δ 1.59-1.70 (m, 2H), 2.03-2.12 (m, 5H), 2.69 (t, J = 11.6 Hz, 1H), 2.83-2.89 (m, 1H), 3.14-3.22 (m, 1H), 3.76 (s, 3H), 3.90 (d, J = 13.5 Hz, 1H), 4.71 (d, J = 13.2 Hz, 1H), 6.39 (d, J = 5.7 Hz, 1H), 6.48 (s, 1H), 7.08 (s, 1H), 7.10 (s, 1H), 7.20 (t, J = 7.4 Hz, 1H), 7.32 (d, J = 1.88 Hz, 1H), 7.39 (t, J = 8.0 Hz, 2H), 8.15 (d, J = 5.9 Hz, 1H), 8.27 (d, J = 1.8 Hz, 1H), 8.77 (br s, 1H). |

| Example | Structure | Name | NMR Data |
|---|---|---|---|
| 416 | 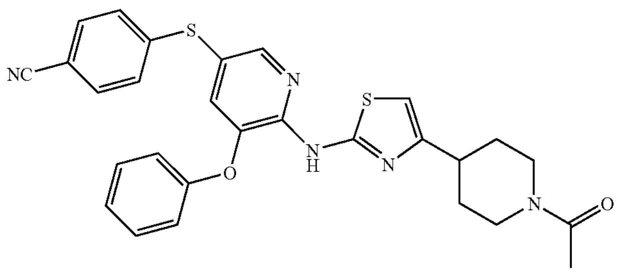 | 4-(6-(4-(1-Acetylpiperidin-4-yl)thiazol-2-ylamino)-5-phenoxypyridin-3-ylthio)benzonitrile | H$^1$ NMR (CDCl$_3$) δ 1.59-1.71 (m, 2H), 1.96-2.12 (m, 5H), 2.70 (t, J = 11.5 Hz, 1H), 2.84-2.90 (m, 1H), 3.15-3.22 (m, 1H), 3.91 (d, J = 13.5 Hz, 1H), 4.72 (d, J = 13.3 Hz, 1H), 6.51 (s, 1H), 7.05 (s, 1H), 7.07 (s, 1H), 7.09 (s, 1H), 7.11 (s, 1H), 7.12 (d, J = 2.0 Hz, 1H), 7.22-7.26 (m, 1H), 7.41 (t, J = 8.1 Hz, 2H), 7.46 (s, 1H), 7.48 (s, 1H), 8.24 (d, J = 2.0 Hz, 1H), 8.83 (br s, 1H). |
| 417 | 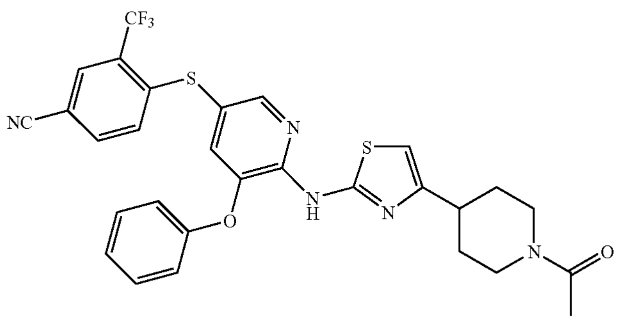 | 4-(6-(4-(1-Acetylpiperidin-4-yl)thiazol-2-ylamino)-5-phenoxypyridin-3-ylthio)-3-(trifluoromethyl)benzonitrile | H$^1$ NMR (CDCl$_3$) δ 1.64-1.70 (m, 2H), 2.04-2.12 (m, 5H), 2.70 (t, J = 12.8 Hz, 1H), 2.88 (t, J = 11.5 Hz, 1H), 3.19 (t, J = 12.9 Hz, 1H), 3.91 (d, J = 13.7 Hz, 1H), 4.72 (d, J = 13.3 Hz, 1H), 6.53 (s, 1H), 6.97 (d, J = 8.4 Hz, 1H), 7.07 (d, J = 8.0 Hz, 2H), 7.10 (s, 1H), 7.11-7.26 (m, 1H), 7.42 (t, J = 7.9 Hz, 2H), 7.54 (d, J = 8.4 Hz, 1H), 7.87 (s, 1H), 8.25 (d, J = 1.8 Hz, 1H), 8.88 (br s, 1H). |
| 418 | 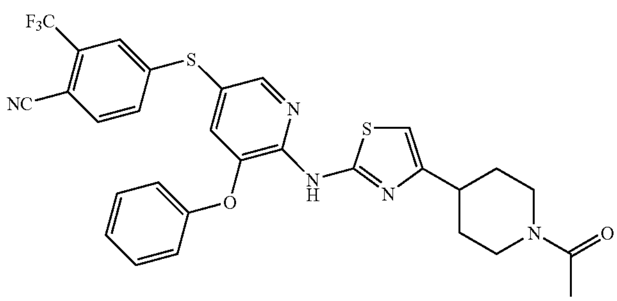 | 4-(6-(4-(1-Acetylpiperidin-4-yl)thiazol-2-ylamino)-5-phenoxypyridin-3-ylthio)-2-(trifluoromethyl)benzonitrile | H$^1$ NMR (CDCl$_3$) δ 1.59-1.71 (m, 2H), 2.04-2.12 (m, 5H), 2.70 (t, J = 11.5 Hz, 1H), 2.85-2.90 (m, 1H), 3.15-3.22 (m, 1H), 3.91 (d, J = 13.7 Hz, 1H), 4.72 (d, J = 13.3 Hz, 1H), 6.53 (s, 1H), 7.06 (s, 1H), 7.07 (s, 2H), 7.10 (d, J = 1.8 Hz, 1H), 7.22-7.25 (m, 2H), 7.39 (s, 1H), 7.42 (t, J = 8.1 Hz, 2H), 7.63 (d, J = 8.2 Hz, 1H), 8.25 (d, J = 1.94 Hz, 1H), 8.87 (br s, 1H). |
| 419 | 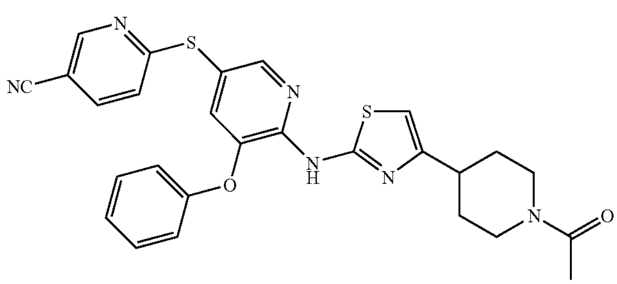 | 6-(6-(4-(1-Acetylpiperidin-4-yl)thiazol-2-ylamino)-5-phenoxypyridin-3-ylthio)nicotinonitrile | H$^1$ NMR (CDCl$_3$) δ 1.62-1.71 (m, 2H), 2.04-2.12 (m, 5H), 2.70 (t, J = 11.5 Hz, 1H), 2.84-2.90 (m, 1H), 3.15-3.22 (m, 1H), 3.91 (d, J = 13.9 Hz, 1H), 4.72 (d, J = 13.5 Hz, 1H), 6.51 (s, 1H), 7.03 (d, J = 8.4 Hz, 1H), 7.09 (s, 1H), 7.11 (s, 1H), 7.18 (d, J = 2.0 Hz, 1H), 7.22-7.26 (m, 1H), 7.42 (t, J = 8.0 Hz, 2H), 7.66-7.69 (m, 1H), 8.25 (d, J = 1.8 Hz, 1H), 8.58 (d, J = 1.6 Hz, 1H), 8.84 (br s, 1H). |
| 420 | 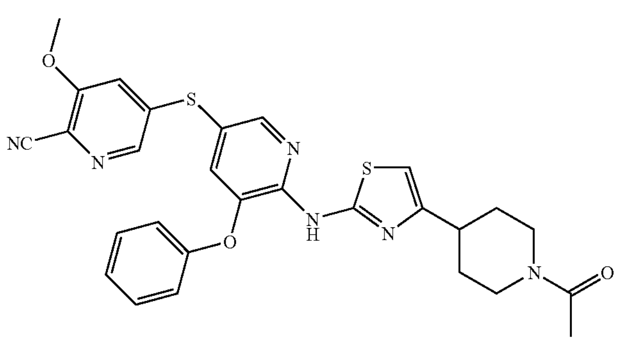 | 5-(6-(4-(1-Acetylpiperidin-4-yl)thiazol-2-ylamino)-5-phenoxypyridin-3-ylthio)-3-methoxypicolinonitrile | H$^1$ NMR (CDCl$_3$) δ 1.59-1.71 (m, 2H), 2.03-2.12 (m, 5H), 2.70 (t, J = 11.5 Hz, 1H), 2.84-2.90 (m, 1H), 3.18 (t, J = 11.7 Hz, 1H), 3.86 (s, 3H), 3.91 (d, J = 13.7 Hz, 1H), 4.72 (d, J = 13.1 Hz, 1H), 6.52 (s, 1H), 6.96 (d, J = 1.8 Hz, 1H), 7.06 (s, 1H), 7.07 (s, 1H), 7.09 (d, J = 13.3 Hz, 1H), 7.11-7.26 (m, 1H), 7.43 (t, J = 8.0 Hz, 2H), 7.87 (d, J = 1.8 Hz, 1H), 8.26 (d, J = 1.8 Hz, 1H), 8.85 (br s, 1H). |

-continued

| Example | Structure | Name | NMR Data |
|---|---|---|---|
| 421 | 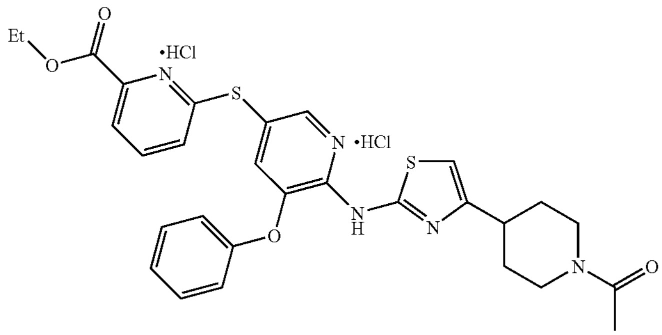 | Ethyl 6-(6-(4-(1-acetylpiperidin-4-yl)thiazol-2-ylamino)-5-phenoxypyridin-3-ylthio)picolinate dihydrochloride | H¹ NMR (d₆ DMSO) δ 1.28 (t, J = 7.0 Hz, 3H), 1.39-1.48 (m, 1H), 1.53-1.62 (m, 1H), 1.91-2.00 (m, 5H), 2.63 (t, J = 12.6 Hz, 1H), 2.84 (t, J = 11.4 Hz, 1H), 3.13 (t, J = 11.9 Hz, 1H), 3.87 (d, J = 13.7 Hz, 1H), 4.28-4.33 (m, 2H), 4.42 (d, J = 13.1 Hz, 1H), 6.73 (s, 1H), 7.10-7.21 (m, 3H), 7.29 (d, J = 7.8 Hz, 1H), 7.38 (t, J = 7.9 Hz, 2H), 7.42 (d, J = 1.8 Hz, 1H), 7.77 (d, J = 7.6 Hz, 1H), 7.83 (t, J = 7.7 Hz, 1H), 8.31 (d, J = 2.0 Hz, 1H), 11.13 (br s, 1H). |
| 422 | 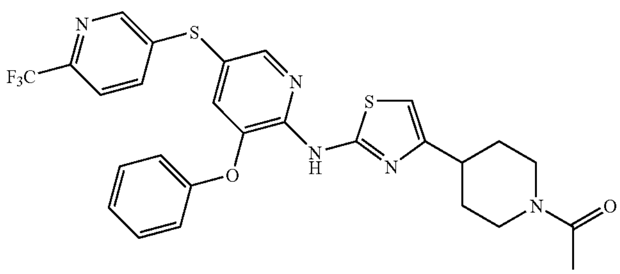 | 1-(4-(2-(3-Phenoxy-5-(6-(trifluoromethyl)pyridin-3-ylthio)pyridin-2-ylamino)thiazol-4-yl)piperidin-1-yl)ethanone | H¹ NMR (d₆ DMSO) δ 1.43-1.58 (m, 2H), 1.91-2.00 (m, 5H), 2.63 (t, J = 13.2 Hz, 1H), 2.83 (br s, 1H), 3.13 (t, J = 11.9 Hz, 1H), 3.86 (d, J = 13.5 Hz, 1H), 4.42 (d, J = 13.7 Hz, 1H), 6.74 (s, 1H), 7.12-7.16 (m, 3H), 7.38-7.41 (m, 3H), 7.75-7.79 (m, 2H), 8.33 (s, 1H), 8.57 (s, 1H), 11.14 (s, 1H). |
| 423 | 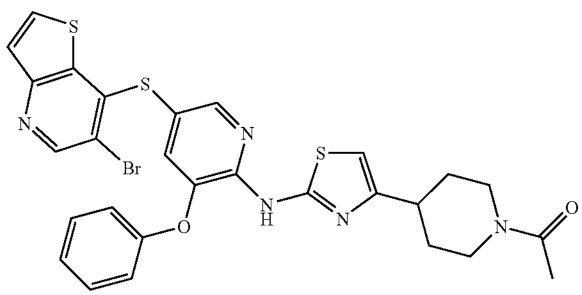 | 1-(4-(2-(5-(6-Bromothieno[3,2-b]pyridin-7-ylthio)-3-phenoxypyridin-2-ylamino)thiazol-4-yl)piperidin-1-yl)ethanone | H¹ NMR (d₆ DMSO) δ 1.42-1.46 (m, 1H), 1.55-1.58 (m, 1H), 1.93 (t, J = 16.7 Hz, 2H), 2.83 (br s, 1H), 3.12 (t, J = 12.8 Hz, 1H), 3.86 (d, J = 13.1 Hz, 1H), 4.42 (d, J = 12.3 Hz, 1H), 6.74 (s, 1H), 7.01 (d, J = 7.2 Hz, 2H), 7.12-7.14 (m, 1H), 7.34 (t, J = 7.3 Hz, 2H), 7.41 (s, 1H), 7.50 (d, J = 5.5 Hz, 1H), 8.07 (d, J = 5.5 Hz, 1H), 8.39 (s, 1H), 8.73 (s, 1H), 11.23 (s, 1H). |

Example 424

1-(4-(5-(5-(Thieno[3,2-b]pyridin-7-ylthio)-3-(2-(trifluoromethyl)phenoxy)pyridin-2-ylamino)-1,2,4-thiadiazol-3-yl)piperidin-1-yl)ethanone

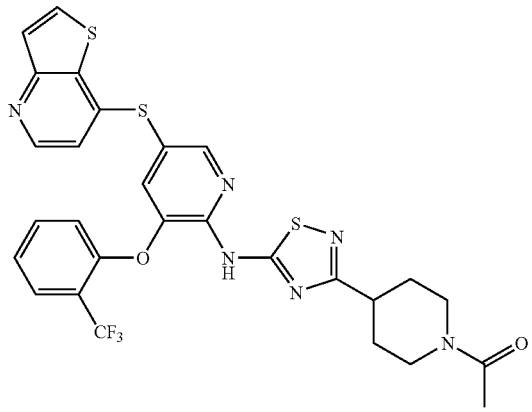

Prepared according to the method of Example 355, Example 13 and Example 127.

H¹ NMR (d₆DMSO) δ 1.55-1.65 (m, 1H), 1.69-1.79 (m, 1H), 1.97-2.05 (m, 5H), 2.77 (t, J=11.3 Hz, 1H), 3.05-3.10 (m, 1H), 3.20 (t, J=11.5 Hz, 1H), 3.85 (d, J=13.5 Hz, 1H), 4.33 (d, J=13.1 Hz, 1H), 6.91 (d, J=5.1 Hz, 1H), 7.25 (d, J=8.0 Hz, 1H), 7.36 (t, J=7.7 Hz, 1H), 7.48 (d, J=1.8 Hz, 1H), 7.58 (d, J=5.5 Hz, 1H), 7.65 (t, J=7.8 Hz, 1H), 7.78 (d, J=7.8 Hz, 1H), 8.15 (d, J=55 Hz, 1H), 8.48 (d, J=5.1 Hz, 1H), 8.54 (d, J=1.8 Hz, 1H), 12.62 (s, 1H).

Example 425 tert-butyl 4-(2-(3-(4-fluorophenoxy)-5-(thieno[3,2-b]pyridin-7-ylthio)pyridin-2-ylamino)thiazol-4-yl)piperidine-1-carboxylate

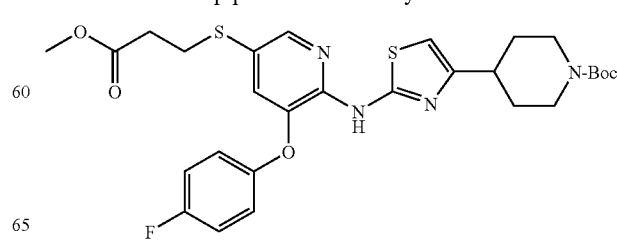

Step A: Preparation of tert-butyl 4-(2-(5-bromo-3-(4-fluorophenoxy)pyridin-2-ylamino)thiazol-4-yl)piperidine-1-carboxylate: 1-(5-bromo-3-(4-fluorophenoxy)pyridin-2-yl)thiourea (3.00 g, 8.77 mmol; prepared according to Example 179, Step D), TEA (2.08 mL, 14.9 mmol) and tert-butyl 4-(2-bromoacetyl)piperidine-1-carboxylate (3.49 g, 11.4 mmol) were refluxed in ethanol (75 mL) for 2 hours. The reaction was cooled to room temperature and filtered to afford the title compound (3.6 g, 74.7% yield).

Step B: tert-butyl 4-(2-(3-(4-fluorophenoxy)-5-(3-methoxy-3-oxopropylthio) pyridin-2-Ylamino)thiazol-4-yl)piperidine-1-carboxylate: Prepared according to the method of Example 13.

Step C: tert-butyl 4-(2-(3-(4-fluorophenoxy)-5-(thieno[3,2-b]pyridin-7-ylthio) pyridin-2-ylamino)thiazol-4-yl)piperidine-1-carboxylate: Prepared according to the method of Example 127. $^1$H NMR (d$_6$-DMSO) δ 11.21 (bs, 1H), 8.49 (d, 1H), 8.36 (d, 1H), 8.16 (d, 1H), 7.59 (d, 1H), 7.39 (d, 1H), 7.25-7.15 (m, 4H), 6.90 (d, 1H), 6.74 (s, 1H), 4.03 (m, 2H), 2.81 (m, 3H), 1.93 (m, 2H), 1.50 (m, 2H), 1.41 (s, 9H).

Example 426

N-(3-(4-fluorophenoxy)-5-(thieno[3,2-b]pyridin-7-ylthio)pyridin-2-yl)-4-(piperidin-4-yl)thiazol-2-amine dihydrochloride

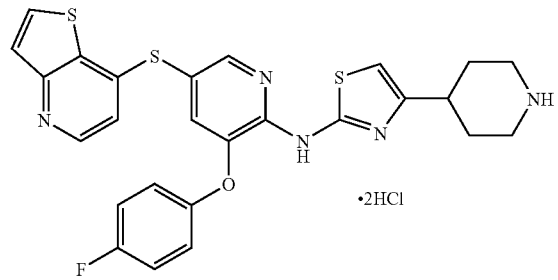

Prepared according to the method of Example 271. $^1$H NMR (d$_6$-DMSO) δ 11.26 (bs, 1H), 8.79 (m, 1H), 8.59 (m, 1H), 8.53 (d, 1H), 8.38 (d, 1H), 8.23 (d, 1H), 7.62 (d, 1H), 7.43 (d, 1H), 7.26-7.16 (m, 4H), 6.97 (d, 1H), 6.82 (s, 1H), 3.33 (d, 2H), 3.06-2.86 (m, 3H), 2.13 (d, 2H), 1.80 (m, 2H).

The following compounds also were made according to the method of Example 272.

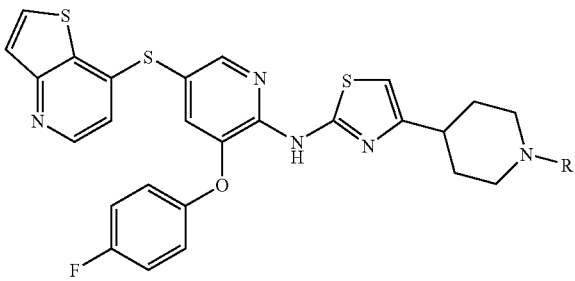

| Example | R | Name | NMR data |
|---|---|---|---|
| 427 | ![](O with methyl ketone) | 1-(4-(2-(3-(4-fluorophenoxy)-5-(thieno[3,2-b]pyridin-7-ylthio)pyridin-2-ylamino)thiazol-4-yl)piperidin-1-yl)ethanone hydrochloride | $^1$H NMR (d$_6$-DMSO) δ 11.21 (bs, 1H), 8.50 (d, 1H), 8.37 (d, 1H), 8.18 (d, 1H), 7.60 (d, 1H), 7.41 (d, 1H), 7.25-7.14 (m, 4H), 6.92 (d, 1H), 6.74 (s, 1H), 4.33 (d, 1H), 3.87 (d, 1H), 3.13 (t, 1H), 2.85 (m, 1H), 2.64 (t, 1H), 2.01 (s, 3H), 1.95 (m, 2H), 1.59 (m, 1H), 1.45 (m, 1H). |
| 428 | (acetoxy ketone) | 2-(4-(2-(3-(4-fluorophenoxy)-5-(thieno[3,2-b]pyridin-7-ylthio)pyridin-2-ylamino)thiazol-4-yl)piperidin-1-yl)-2-oxoethyl acetate | $^1$H NMR (d$_6$-DMSO) δ 11.24 (s, 1H), 8.49 (d, 1H), 8.36 (d, 1H), 8.16 (d, 1H), 7.59 (d, 1H), 7.40 (d, 1H), 7.26-7.14 (m, 4H), 6.90 (d, 1H), 6.76 (s, 1H), 4.79 (m, 2H), 4.36 (d, 1H), 3.77 (d, 1H), 3.12 (t, 1H), 2.87 (m, 1H), 2.72 (t, 1H), 2.08 (s, 3H), 1.96 (m, 2H), 1.62 (m, 1H), 1.49 (m, 1H). |
| 429 | (isopropyl carbamate) | isopropyl 4-(2-(3-(4-fluorophenoxy)-5-(thieno[3,2-b]pyridin-7-ylthio)pyridin-2-ylamino)thiazol-4-yl)piperidine-1-carboxylate hydrochloride | $^1$H NMR (d$_6$-DMSO) δ 8.61 (d, 1H), 8.41 (d, 1H), 8.39 (d, 1H), 7.71 (d, 1H), 7.48 (d, 1H), 7.26-7.17 (m, 4H), 7.11 (d, 1H), 6.79 (s, 1H), 4.77 (m, 1H), 4.04 (d, 2H), 2.85 (m, 3H), 1.94 (d, 2H), 1.51 (m, 2H), 1.19 (d, 6H). |
| 430 | (dimethylaminoketone) | 2-(dimethylamino)-1-(4-(2-(3-(4-fluorophenoxy)-5-(thieno[3,2-b]pyridin-7-ylthio)pyridin-2-ylamino)thiazol-4-yl)piperidin-1-yl)ethanone dihydrochloride | $^1$H NMR (d$_6$-DMSO) δ 9.60 (bs, 1H), 8.58 (d, 1H), 8.40 (d, 1H), 8.33 (d, 1H), 7.68 (d, 1H), 7.47 (d, 1H), 7.27-7.17 (m, 4H), 7.05 (d, 1H), 6.78 (s, 1H), 4.45-4.28 (m, 3H), 3.67 (d, 2H), 3.18 (t, 1H), 2.93 (m, 1H), 2.82 (m, 6H), 2.04 (d, 2H), 1.65 (m, 1H), 1.50 (m, 1H) |

-continued

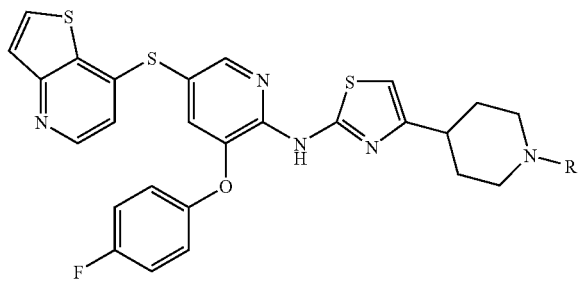

| Example | R | Name | NMR data |
|---|---|---|---|
| 431 | ![methylsulfonyl] | N-(3-(4-fluorophenoxy)-5-(thieno[3,2-b]pyridin-7-ylthio)pyridin-2-yl)-4-(1-(methylsulfonyl)piperidin-4-yl)thiazol-2-amine hydrochloride | $^1$H NMR (d$_6$-DMSO) δ 8.57 (d, 1H), 8.40 (d, 1H), 8.32 (d, 1H), 7.67 (d, 1H), 7.46 (d, 1H), 7.26-7.16 (m, 4H), 7.05 (d, 1H), 6.80 (s, 1H), 3.64 (d, 2H), 2.88 (s, 3H), 2.84 (t, 2H), 2.73 (m, 1H), 2.08 (d, 2H), 1.66 (m, 2H) |

The following compounds were also made according to the method of Example 282.

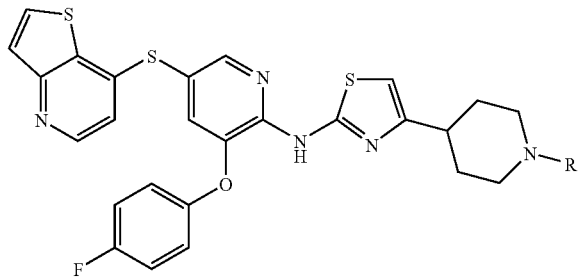

| Example | R | Name | NMR Data |
|---|---|---|---|
| 432 | ![acetamido ketone] | N-(1-(4-(2-(3-(4-fluorophenoxy)-5-(thieno[3,2-b]pyridin-7-ylthio)pyridin-2-ylamino)thiazol-4-yl)piperidin-1-yl)-1-oxopropan-2-yl)acetamide | $^1$H NMR (d$_6$-DMSO) δ 8.60 (d, 1H), 8.41 (d, 1H), 8.37 (d, 1H), 8.13 (t, 1H), 7.70 (d, 1H), 7.42 (s, 1H), 7.27-7.17 (m, 4H), 7.10 (d, 1H), 6.73 (d, 1H), 4.77 (m, 1H), 4.44 (m, 1H), 3.98 (m, 1H), 3.15 (t, 1H), 2.89 (m, 1H), 2.70 (m, 1H), 1.98 (m, 2H), 1.82 (s, 3H), 1.63-1.40 (m, 2H), 1.15 (t, 3H). |
| 433 | ![acetamido ketone] | N-(2-(4-(2-(3-(4-fluorophenoxy)-5-(thieno[3,2-b]pyridin-7-ylthio)pyridin-2-ylamino)thiazol-4-yl)piperidin-1-yl)-2-oxoethyl)acetamide hydrochloride | $^1$H NMR (d$_6$-DMSO) δ 8.58 (d, 1H), 8.40 (d, 1H), 8.33 (d, 1H), 7.96 (m, 1H), 7.68 (d, 1H), 7.46 (d, 1H), 7.26-7.16 (m, 4H), 7.06 (d, 1H), 6.77 (s, 1H), 4.41 (d, 1H), 4.01-3.84 (m, 3H), 3.12 (t, 1H), 2.88 (t, 1H), 2.71 (t, 1H), 1.97 (m, 2H), 1.87 (s, 3H), 1.60 (m, 1H), 1.47 (m, 1H). |

Example 434

4-(1-(2-aminoethylsulfonyl)piperidin-4-yl)-N-(3-(4-fluorophenoxy)-5-(thieno[3,2-b]pyridin-7-ylthio)pyridin-2-yl)thiazol-2-amine dihydrochloride

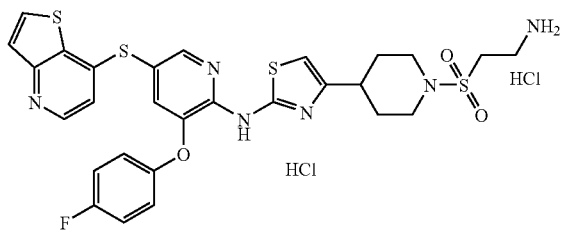

Step A: Preparation of 2-(2-(4-(2-(3-(4-fluorophenoxy)-5-(thieno[3,2-b]pyridin-7-ylthio)pyridin-2-ylamino)thiazol-4-yl)piperidin-1-ylsulfonyl)ethyl)isoindoline-1,3-dione: Prepared according to the method of Example 288, Step A.

Step B: Preparation of 4-(1-(2-aminoethylsulfonyl)piperidin-4-yl)-N-(3-(4-fluorophenoxy)-5-(thieno[3,2-b]pyridin-7-ylthio)pyridin-2-yl)thiazol-2-amine dihydrochloride: Prepared according to the method of Example 288, Step B using hydrazine monohydrate. $^1$H NMR ($d_6$-DMSO) δ 8.58 (d, 1H), 8.41 (d, 1H), 8.34 (d, 1H), 8.15 (bs, 2H), 8.07 (bs, 1H), 7.89 (m, 1H), 7.69 (d, 1H), 7.47 (d, 1H), 7.27-7.17 (m, 4H), 7.07 (d, 1H), 6.81 (s, 1H), 3.70 (d, 1H), 3.43 (t, 2H), 3.17 (m, 2H), 3.00 (t, 2H), 2.80 (m, 1H), 2.08 (d, 2H), 1.65 (m, 2H).

Example 435

4-(2-(3-(4-fluorophenoxy)-5-(thieno[3,2-b]pyridin-7-ylthio)pyridin-2-ylamino)thiazol-4-yl)piperidine-1-sulfonamide 2,2,2-trifluoroacetate

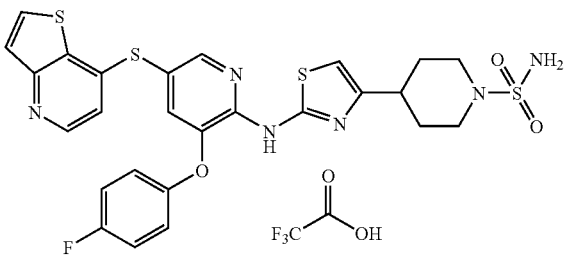

Prepared according to the method of Example 287 from 3-(4-fluorophenoxy)-N-(4-(piperidin-4-yl)thiazol-2-yl)-5-(thieno[3,2-b]pyridin-7-ylthio)pyridin-2-amine. $^1$H NMR ($d_6$-DMSO) δ 11.22 (s, 1H), 8.49 (d, 1H), 8.37 (d, 1H), 8.16 (d, 1H), 7.59 (d, 1H), 7.41 (d, 1H), 7.26-7.14 (m, 4H), 6.90 (d, 1H), 6.78 (s, 1H), 6.73 (s, 2H), 3.53 (d, 2H), 2.65 (m, 3H), 2.05 (m, 2H), 1.69 (m, 2H).

Example 436

4-(2-(3-(4-fluorophenoxy)-5-(thieno[3,2-b]pyridin-7-ylthio)pyridin-2-ylamino)thiazol-4-yl)piperidine-1-carboxamide hydrochloride

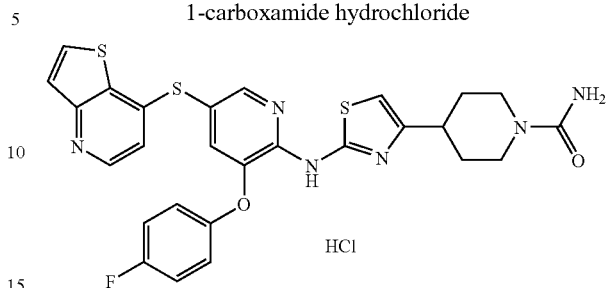

Prepared according to the method of Example 280 from 3-(4-fluorophenoxy)-N-(4-(piperidin-4-yl)thiazol-2-yl)-5-(thieno[3,2-b]pyridin-7-ylthio)pyridin-2-amine. $^1$H NMR ($d_6$-DMSO) δ 8.62 (d, 1H), 8.43 (m, 2H), 7.73 (d, 1H), 7.50 (d, 1H), 7.27-7.18 (m, 4H), 7.14 (d, 1H), 6.79 (s, 1H), 4.01 (d, 2H), 2.78 (m, 3H), 1.88 (d, 2H), 1.50 (m, 2H).

Example 437 tert-butyl 4-(2-(3-(4-fluorophenoxy)-5-(3-methylisoxazolo[5,4-b]pyridin-4-ylthio)pyridin-2-ylamino)thiazol-4-yl)piperidine-1-carboxylate

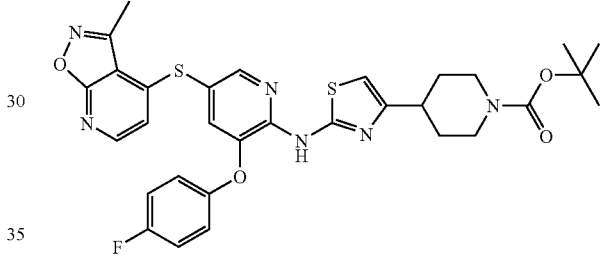

Prepared according to the method of Example 127 from tert-butyl 4-(2-(3-(4-fluorophenoxy)-5-(3-methoxy-3-oxopropylthio)pyridin-2-ylamino)thiazol-4-yl)piperidine-1-carboxylate. $^1$H NMR ($d_6$-DMSO) δ 11.25 (bs, 1H), 8.35 (d, 1H), 8.32 (d, 1H), 7.40 (d, 1H), 7.27-7.21 (m, 4H), 6.76 (s, 1H), 6.71 (d, 1H), 4.02 (m, 2H), 2.83 (m, 3H), 2.69 (s, 3H), 1.94 (d, 2H), 1.50 (m, 2H), 1.41 (s, 9H).

Example 438

N-(3-(4-fluorophenoxy)-5-(3-methylisoxazolo[5,4-b]pyridin-4-ylthio)pyridin-2-yl)-4-(piperidin-4-yl)thiazol-2-amine dihydrochloride

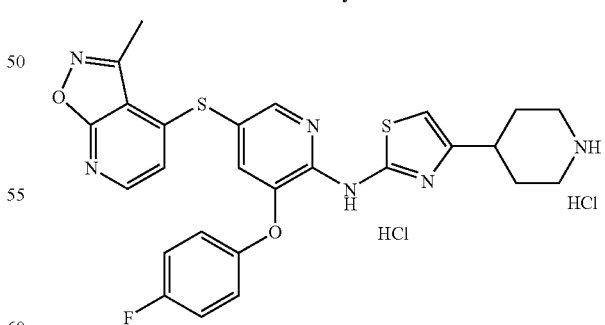

Prepared according to the method of Example 271 from tert-butyl 4-(2-(3-(4-fluorophenoxy)-5-(3-methylisoxazolo[5,4-b]pyridin-4-ylthio)pyridin-2-ylamino)thiazol-4-yl)piperidine-1-carboxylate. $^1$H NMR ($d_6$-DMSO) δ 8.88 (m, 1H), 8.70 (m, 1H), 8.36 (d, 1H), 8.32 (d, 1H), 7.42 (d, 1H), 7.29-7.10 (m, 4H), 6.83 (s, 1H), 6.72 (d, 1H), 3.33 (d, 2H), 3.06-2.85 (m, 3H), 2.69 (s, 3H), 2.14 (d, 2H), 1.81 (m, 2H).

The following compounds were also made according to the procedure of Example 272.

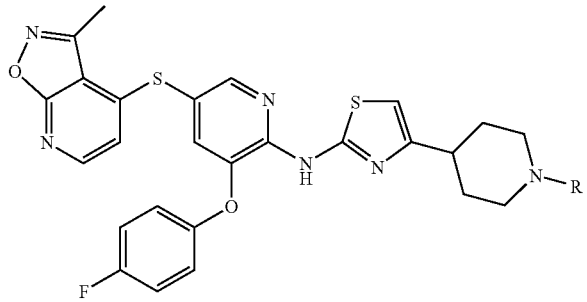

| Example | R | Name | NMR Data |
|---|---|---|---|
| 439 | (acetyl) | 1-(4-(2-(3-(4-fluorophenoxy)-5-(3-methylisoxazolo[5,4-b]pyridin-4-ylthio)pyridin-2-ylamino)thiazol-4-yl)piperidin-1-yl)ethanone hydrochloride, | $^1$H NMR (d$_6$-DMSO) δ 11.28 (bs, 1H), 8.35 (d, 1H), 8.32 (d, 1H), 7.41 (d, 1H), 7.27-7.19 (m, 4H), 6.76 (s, 1H), 6.72 (d, 1H), 4.43 (d, 1H), 3.87 (d, 1H), 3.14 (t, 1H), 2.86 (m, 1H), 2.69 (s, 3H), 2.65 (m, 1H), 2.01 (s, 3H), 1.95 (m, 2H), 1.60 (m, 1H), 1.45 (m, 1H). |
| 440 | (dimethylaminoacetyl) | 2-(dimethylamino)-1-(4-(2-(3-(4-fluorophenoxy)-5-(3-methylisoxazolo[5,4-b]pyridin-4-ylthio)pyridin-2-ylamino)thiazol-4-yl)piperidin-1-yl)ethanone dihydrochloride, | $^1$H NMR (d$_6$-DMSO) δ 11.23 (bs, 1H), 9.54 (bs, 1H), 8.36 (d, 1H), 8.32 (d, 1H), 7.42 (d, 1H), 7.28-7.19 (m, 4H), 6.78 (s, 1H), 6.71 (d, 1H), 4.42 (d, 1H), 4.30 (m, 2H), 3.66 (d, 1H), 3.19 (t, 1H), 2.91 (m, 2H), 2.81 (d, 6H), 2.69 (s, 3H), 2.04 (d, 2H), 1.65 (m, 1H), 1.51 (m, 1H) |

Example 441 methyl 4-(5-(3-phenoxy-5-(pyridin-2-ylthio)pyridin-2-ylamino)-1,2,4-thiadiazol-3-yl)piperidine-1-carboxylate hydrochloride

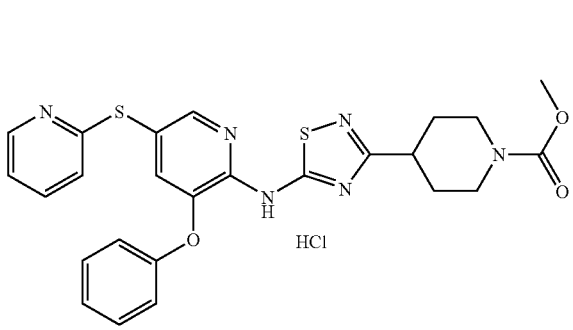

Prepared according to the method of Example 272 from 3-phenoxy-N-(3-(piperidin-4-yl)-1,2,4-thiadiazol-5-yl)-5-(pyridin-2-ylthio)pyridin-2-amine. $^1$H NMR (d$_6$-DMSO) δ 12.33 (s, 1H), 8.39 (d, 1H), 8.37 (m, 1H), 7.66 (dt, 1H), 7.47 (d, 1H), 7.42 (d, 2H), 7.21-7.11 (m, 5H), 3.98 (m, 2H), 3.60 (s, 3H), 3.01 (m, 3H), 1.99 (d, 2H), 1.65 (m, 2H).

Example 442

1-(4-(2-(5-(3-methylthieno[3,2-b]pyridin-7-ylthio)-3-phenoxypyridin-2-ylamino)thiazol-4-yl)piperidin-1-yl)ethanone

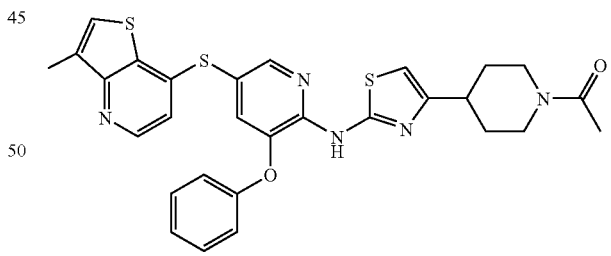

Step A: 3-amino-4-methylthiophene-2-carboxylic acid: Methyl 3-amino-4-methylthiophene-2-carboxylate (4.67 g, 27.3 mmol) and NaOH (2N in H$_2$O, 68 mL, 136 mmol) were stirred at 100° C. for 1 hour. The solution was cooled to 0° C. and acidified to pH=5 with addition of concentrated HCl solution to form a precipitant. The solution was filtered and the solid was dried under vacuum to give the title compound (2.8 g, 65%).

Step B: 4-methylthiophen-3-amine: 3-amino-4-methylthiophene-2-carboxylic acid (5.64 g, 36 mmol) in HCl (6N in H$_2$O, 30 mL, 179 mmol) was stirred at 50° C. overnight. It was cooled to room temperature and neutralized by the addition of solid NaHCO$_3$. The solution was extracted with dichloromethane (2 times), dried over Na₂SO₄, filtered and concentrated to yield the title compound (3.8 g, 94% yield).

Step C: 2,2-dimethyl-5-((4-methylthiophen-3-ylamino)methylene)-1,3-dioxane-4,6-dione: A stirred solution of 2,2-dimethyl-1,3-dioxane-4,6-dione (4.85 g, 34 mmol) in trimethoxymethane (37 mL, 337 mmol) was heated to 90° C. under nitrogen. After 2 hours, a solution was 4-methylthiophen-3-amine (3.81 g, 34 mmol) was added (as a solution in trimethoxymethane (37 mL, 337 mmol). The reaction stirred at 90° C. for 6 hours and then was allowed to cool to room temperature and concentrated. The material was placed in the refrigerator where it solidified after two days to obtain the title compound (9 g, quantitative).

Step D: 3-methylthieno[3,2-b]pyridin-7-ol: A solution of Dowtherm A (7 mL) was heated in oil bath at 235° C. under nitrogen. 2,2-dimethyl-5-((4-methylthiophen-3-ylamino)methylene)-1,3-dioxane-4,6-dione (5.0 g, 19 mmol) was added in portions over a 20 minutes period. After the last portion was added, the solution stirred at 235° C. for another 5 minutes. The solution was removed from the oil bath and allowed to cool to room temperature. Upon cooling, the product precipitated out of solution. Diethyl ether was added and the solid was filtered and dried to give the title compound (3.2 g) with residual amounts of Dowtherm A remaining.

Step E: 7-chloro-3-methylthieno[3,2-b]pyridine: Phosphorous oxychloride (2.2 mL, 24 mmol) in 1,2-dichloroethane (12 mL) was charged with 3-methylthieno[3,2-b]pyridin-7-ol (2.0 g, 12 mmol). The reaction stirred overnight at reflux under nitrogen. The mixture was the cooled and concentrated. Saturated NaHCO₃ solution was carefully added to neutralize the residue. The biphasic mixture was extracted with dichloromethane, dried, and concentrated. Flash chromatography (15% EtOAc/hexanes) gave the title compound (1.23 g, 55%).

Step F: 1-(4-(2-(5-(3-methylthieno[3,2-b]pyridin-7-ylthio)-3-phenoxypyridin-2-ylamino)thiazol-4-yl)piperidin-1-yl)ethanone: 7-chloro-3-methylthieno[3,2-b]pyridine (0.072 g, 0.39 mmol) and methyl 3-(6-(4-(1-acetylpiperidin-4-yl)thiazol-2-ylamino)-5-phenoxypyridin-3-ylthio)propanoate (0.20 g, 0.39 mmol) were dissolved in DMSO (3 mL). The solution was degassed for 15 minutes under nitrogen. KOtBu (0.13 g, 1.2 mmol) was added and the reaction stirred at room temperature for two hours. The solution was quenched with water, extracted with dichloromethane, dried, and concentrated. Flash chromatography gave the title compound (0.100 g, 44% yield). ¹H NMR (400 MHz, CDCl₃) δ 1.60-1.72 (m, 2H), 2.03-2.09 (m, 2H), 2.11 (s, 3H), 2.51 (s, 3H), 2.66-2.73 (m, 1H), 2.83-2.90 (m, 1H), 3.15-3.22 (m, 1H), 3.88-3.94 (m, 1H), 4.70-4.73 (m, 1H), 6.51 (s, 1H), 6.75 (d, 1H), 7.05 (d, 2H), 7.17-7.25 (m, 2H), 7.36-7.40 (m, 3H), 8.30 (d, 1H), 8.48 (d, 1H), 8.84 (bs, 1H).

Example 443

1-(4-(2-(5-(5-chlorothieno[3,2-b]pyridin-7-ylthio)-3-phenoxypyridin-2-ylamino)thiazol-4-yl)piperidin-1-yl)ethanone

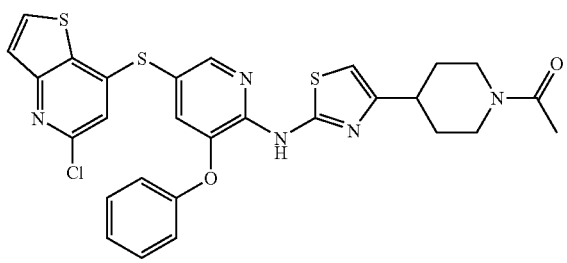

Steps A and B: Thiophen-3-amine: Prepared according to the method of Example 442, Steps A and B, using methyl 3-aminothiophene-2-carboxylate as the starting material.

Step C and D: 1-(4-(2-(5-(5-chlorothieno[3,2-b]pyridin-7-ylthio)-3-phenoxypyridin-2-ylamino)thiazol-4-yl)piperidin-1-yl)ethanone: Prepared according to the method of Example 442, Steps E and F. ¹H NMR (400 MHz, CDCl₃) δ 1.60-1.73 (m, 2H), 2.05-2.10 (m, 2H), 2.12 (s, 3H), 2.66 (t, 1H), 2.85-2.91 (m, 1H), 3.17 (t, 1H), 3.91 (d, 1H), 4.71 (d, 1H), 6.53 (s, 1H), 6.67 (s, 1H), 7.08 (d, 2H), 7.17 (s, 1H), 7.22-7.26 (m, 1H), 7.41 (t, 2H), 7.47 (d, 1H), 7.76 (d, 1H), 8.32 (s, 1H), 8.96 (s, 1H).

Example 444

Preparation of tert-butyl 4-((2-(5-bromo-3-(4-fluorophenoxy)pyridin-2-ylamino)thiazol-4-yl)methyl)-3-oxopiperazine-1-carboxylate

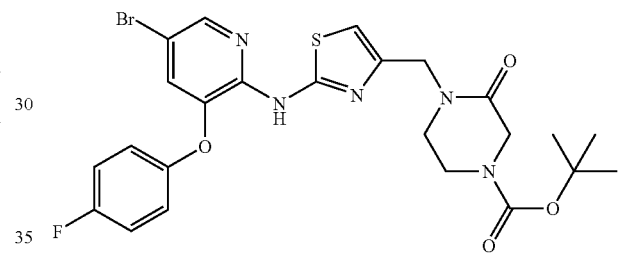

Step A: Preparation of tert-Butyl 4-(3-chloro-2-hydroxypropyl)-3-oxopiperazine-1-carboxylate. In a 50 0 ml round bottom flask with magnetic stirrer 4-Boc-piperazinone (5.08 g, 25.4 mmol) was dissolved in THF (100 mL) and cooled to −78° C. Butyllithium (1.6M in hexanes) (15.9 mL, 25.4 mmol) was added then and the mixture agitated for 30 minutes at −78° C. Boron trifluoride ethereate (3.19 mL, 25.4 mmol) was added slowly and then epichlorohydrin (1.99 mL, 25.4 mmol). The mixture was agitated for 1 hour at −78° C. and then allowed to warm up and agitated overnight. Reaction was quenched with saturated ammonium chloride, extracted three times with ethyl acetate, extracts washed with brine and evaporated. Purified by column chromatography on silica gel, eluting with 3% MeOH/CH₂Cl₂ to give the title compound (3.34 g, 45% yield).

Step B: Preparation of tert-Butyl 4-(3-chloro-2-oxopropyl)-3-oxopiperazine-1-carboxylate. In a 125 ml round-bottom flask equipped with a magnetic stirrer tert-butyl 4-(3-chloro-2-hydroxypropyl)-3-oxopiperazine-1-carboxylate (3.30 g, 11.3 mmol) was dissolved in acetonitrile (10 ml) and Dess-Martin periodinane (5.26 g, 12.4 mmol) was added. After agitating for 3 hours the mixture was diluted with ethyl acetate (100 ml) and washed with sodium bicarbonate and brine, dried and evaporated. Purified by column chromatography and eluting with 3% MeOH/CH₂Cl₂ to give the title compound (0.600 g, 18.31% yield).

Step C: Preparation of tert-Butyl 4-((2-(5-bromo-3-(4-fluorophenoxy)pyridin-2-ylamino)thiazol-4-yl)methyl)-3-oxopiperazine-1-carboxylate. In a 20 mL scintillation vial equipped with magnetic stirrer 1-(5-bromo-3-(4-fluorophenoxy)pyridin-2-yl)thiourea (0.25 g, 0.73 mmol) was suspended in ethanol (5 ml) and tert-butyl 4-(3-chloro-2-oxopropyl)-3-oxopiperazine-1-carboxylate (0.32 g, 1.10 mmol) was added followed by DIEA (0.22 mL, 1.28 mmol). Resulting mixture was heated to 60° C. and agitated for 3 hours. Mixture was then diluted with ethyl acetate and washed with sodium bicarbonate solution, brine, dried and evaporated. Purified by column chromatography on silica gel, eluting with 50-100% ethyl acetate/hexane to give the title compound (0.106 g, 25.1% yield). $^1$H NMR (CDCl$_3$) δ 1.41 (s, 9H), 2.79-3.42 (m, 6H), 6.55 (s, 2H), 7.03-7.12 (m, 4H), 8.12 (s, 1H), 8.95 (bs, 1H).

Example 445

Preparation of 1-((2-(5-bromo-3-(4-fluorophenoxy)pyridin-2-ylamino)thiazol-4-yl)methyl)piperazin-2-one

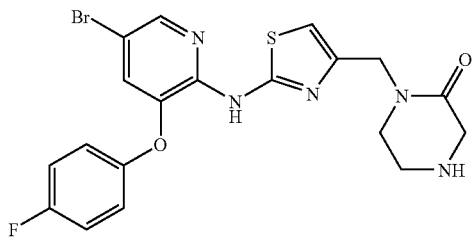

In a 20 mL scintillation vial equipped with magnetic stirrer tert-butyl 4-((2-(5-bromo-3-(4-fluorophenoxy)pyridin-2-ylamino)thiazol-4-ylmethyl)-3-oxopiperazine-1-carboxylate (0.020 g, 0.035 mmol) was dissolved in 1 ml of CH$_2$Cl$_2$ and 4M HCl in dioxane (0.50 mL, 2.0 mmol) was added. The resulting mixture was agitated for 2 hours, diluted with 5 mL of ether and the solvent was decanted off. The residue was dried to provide the title compound (0.012 g, 73% yield). $^1$H NMR (d$_6$-DMSO) δ 3.25-3.78 (m, 6H), 6.99 (s, 1H), 7.28-7.36 (m, 4H), 8.23 (s, 1H), 8.34 (s, 1H), 10.24 (s, 2H).

Example 446

1-(4-(2-(3-phenoxy-5-(thieno[2,3-d]pyrimidin-4-ylthio)pyridin-2-ylamino)thiazol-4-yl)piperidin-1-yl)ethanone

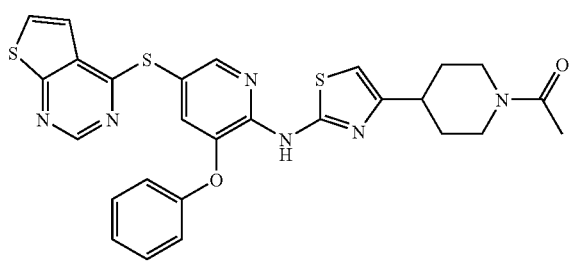

Step A: Thieno[2,3-d]pyrimidin-4(3H)-one: Methyl 2-aminothiophene-3-carboxylate (10 g, 64 mmol) was charged with formamide (50 mL). The reaction was heated at 190° C. under nitrogen for 3 hours. The solution was cooled to room temperature. The slurry was poured into 125 mL of water and extracted with chloroform:isopropyl alcohol mixture (2 times). The solution was concentrated and triturated to afford the title compound (2.25 g, 23%).

Step B: 4-Chlorothieno[2,3-d]pyrimidine: Thieno[2,3-d]pyrimidin-4(3H)-one (1.2 g, 7.9 mmol) was diluted in 1,2-dichloroethane (10 mL). Phosphorous oxychloride (1.4 mL, 15.7 mmol) was added. The reaction was stirred at 90° C. for 16 hours. An additional equivalent of phosphorous oxychloride (0.7 mL, 7.9 mmol) was added and the solution continued stirring for 4 hours. The solution was cooled, concentrated, and neutralized with saturated NaHCO$_3$ solution. The material was extracted with a chloroform:isopropyl alcohol mixture and the organic layer was separated and concentrated. Flash chromatography gave the title compound (0.39 g, 29%).

Step C: 1-(4-(2-(3-phenoxy-5-(thieno[2,3-d]pyrimidin-4-ylthio)pyridin-2-ylamino)thiazol-4-yl)piperidin-1-yl)ethanone: 4-chlorothieno[2,3-d]pyrimidine (0.050 g, 0.29 mmol) and methyl 3-(6-(4-(1-acetylpiperidin-4-yl)thiazol-2-ylamino)-5-phenoxypyridin-3-ylthio)propanoate (0.15 g, 0.29 mmol) were dissolved in DMSO (3 mL). The solution was degassed for 15 minutes. KOtBu (0.098 g, 0.88 mmol) was added and the reaction stirred at room temperature for two hours. The solution was quenched with water, extracted with dichloromethane, dried, and concentrated. Flash chromatography gave the title compound (0.075, 46%). $^1$H NMR (400 MHz, CDCl$_3$) δ 1.60-1.72 (m, 2H), 2.08-2.15 (m, 2H), 2.11 (m, 3H), 2.65-2.75 (m, 1H), 2.82-2.93 (m, 1H), 3.15-3.24 (m, 1H), 3.91 (d, 1H), 4.72 (d, 1H), 6.49 (s, 1H), 7.15 (d, 2H), 7.19 (t, 1H), 7.27-7.29 (m, 1H), 7.36-7.42 (m, 3H), 7.53 (d, 1H), 8.27 (d, 1H), 8.68 (s, 1H), 8.81 (s, 1H).

Example 447 tert-butyl 4-((2-(5-bromo-3-phenoxypyridin-2-ylamino)thiazol-4-ylmethyl)piperidine-1-carboxylate

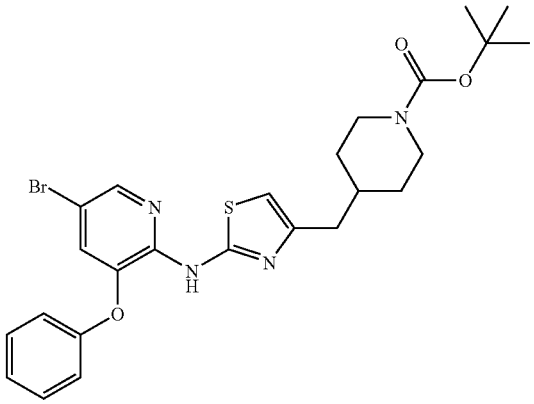

Step A: Preparation of tert-butyl 4-(2-(methoxy(methyl)amino)-2-oxoethyl)piperidine-1-carboxylate: N-methoxymethanamine hydrochloride (2.61 g, 26.7 mmol), N1-((ethylimino)methylene)-N3,N3-dimethylpropane-1,3-diamine hydrochloride (5.91 g, 30.8 mmol), 1H-benzo[d][1,2,3]triazol-1-ol hydrate (4.72 g, 30.8 mmol), and triethylamine (11.5 mL, 82.2 mmol) were added sequentially to a solution of 2-(1-(tert-butoxycarbonyl)piperidin-4-yl)acetic acid (5.00 g, 20.6 mmol) in methylene chloride (150 mL) at 0° C. Stirred at ambient temperature for 4 hours, and partitioned between ethyl acetate and 2N HCl. Washed the organic layer again with 2N HCl, twice with 2N NaOH, brine, dried, and concentrated to afford the title compound (5.93 g, 101% yield) as a clear colorless viscous oil.

Step B: Preparation of tert-butyl 4-(2-oxopropyl)piperidine-1-carboxylate: Added dropwise 3.0 M methylmagnesium chloride in THF (8.63 mL, 25.9 mmol) to a solution of tert-butyl 4-(2-(methoxy(methyl)amino)-2-oxoethyl)piperidine-1-carboxylate (5.93 g, 20.7 mmol) in THF (100 mL) at 0° C. Warmed to ambient temperature and stirred for 90 minutes. Partitioned between ether and 2N HCl, washed the organic layer twice with water, brine, dried, and concentrated to afford the title compound (4.95 g, 99.1% yield) as a clear oil.

Step C: Preparation of tert-butyl 4-(2-(trimethylsilyloxy)allyl)piperidine-1-carboxylate: To a cooled (−78° C.) solution of LDA (12.3 mL, 24.6 mmol) in THF (50 mL) was added dropwise over 40 minutes a solution of tert-butyl 4-(2-oxopropyl)piperidine-1-carboxylate (4.95 g, 20.5 mmol) in THF (20 mL). After an additional 25 minutes, chlorotrimethylsilane (5.21 mL, 41.0 mmol) was added dropwise over 20 minutes. After stirring for an hour, the reaction was poured into saturated NaHCO$_3$ and extracted with ether (2×400 mL). The combined ether layers were washed with brine, dried, filtered and concentrated to afford the title compound (6.95 g, 108% yield) which was used as is in the next step.

Step D: Preparation of tert-butyl 4-(3-bromo-2-oxopropyl)piperidine-1-carboxylate: To a solution of tert-butyl 4-(2-(trimethylsilyloxy)allyl)piperidine-1-carboxylate (6.43 g, 20.5 mmol) in THF (100 mL) at 0° C. was added sodium bicarbonate (2.58 g, 30.7 mmol) followed by 1-bromopyrrolidine-2,5-dione (3.65 g, 20.5 mmol). Warmed to ambient temperature and stirred 90 minutes. Partitioned between ether (150 mL) and saturated sodium bicarbonate. The aqueous layer was reextracted with ether (100 mL). The combined organic layers were washed with saturated bicarbonate, brine, dried, and concentrated to afford the title compound (7.2 g, 110% yield) as a yellow oil. Purity was 85% with the major impurity being succinimide. The crude material was used in the next step.

Step E: Preparation of tert-butyl 4-((2-(5-bromo-3-phenoxypyridin-2-ylamino)thiazol-4-yl)methyl)piperidine-1-carboxylate: Heated a mixture tert-butyl 4-(3-bromo-2-oxopropyl)piperidine-1-carboxylate (1.38 g, 4.32 mmol), 1-(5-bromo-3-phenoxypyridin-2-yl)thiourea (1.0 g, 3.08 mmol), triethylamine (0.731 mL, 5.24 mmol), and ethanol (50 mL) at reflux overnight. Cooled to ambient temperature and partitioned between into water and ethyl acetate. Washed the organic layer with water, brine, dried and concentrated. Purified by MPLC (Biotage) eluting with 3:1 hexane:ethyl acetate to afford the title compound (1.54 g, 92%) as a white powder: $^1$H NMR (CDCl$_3$) δ 8.66 (s, 1H), 8.13 (s, 1H), 7.43 (t, 2H), 7.25 (t, 1H), 7.12 (s, 1H), 7.06 (d, 2H), 6.45 (s, 1H), 4.08 (m, 2H), 2.67 (m, 2H), 2.56 (d, 2H), 1.85 (m, 1H), 1.66 (m, 2H), 1.44 (s, 9H), 1.15 (m, 2H).

The following compounds were prepared from the appropriate carboxylic acid according to the procedure of Example 447.

| Example | Structure | Name | $^1$H NMR |
|---|---|---|---|
| 448 | 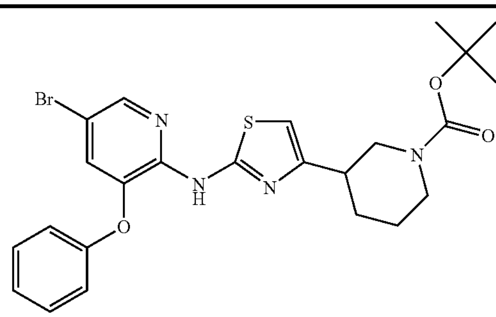 | tert-butyl 3-(2-(5-bromo-3-phenoxypyridin-2-ylamino)thiazol-4-yl)piperidine-1-carboxylate | $^1$H NMR (CDCl$_3$) δ 8.64 (s, 1H), 8.12 (s, 1H), 7.44 (t, 2H), 7.25 (t, 1H), 7.06-7.11 (m, 3H), 6.53 (s, 1H), 4.22 (m, 1H), 4.02 (m, 1H), 2.99 (m, 1H), 2.84-2.90 (m, 2H), 2.10 (m, 1H), 1.72 (m, 3H), 1.45 (s, 9H). |
| 449 | 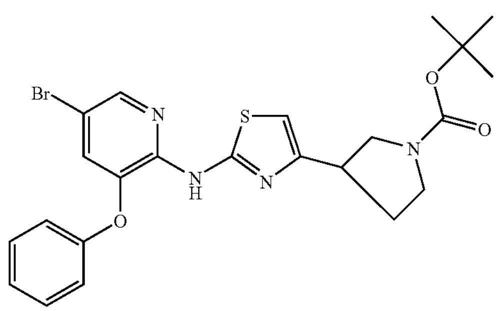 | tert-butyl 3-(2-(5-bromo-3-phenoxypyridin-2-ylamino)thiazol-4-yl)pyrrolidine-1-carboxylate | $^1$H NMR (d$_6$-DMSO) δ 10.93 (s, 1H), 8.17 (s, 1H), 7.36-7.41 (m, 3H) 7.17 (t, 1H), 7.04 (d, 2H), 6.75 (s, 1H), 3.58 (m, 1H), 3.23-3.40 (m, 4H), 2.12 (m, 1H), 1.97 (m, 1H), 1.36 (s, 9H). |
| 450 | 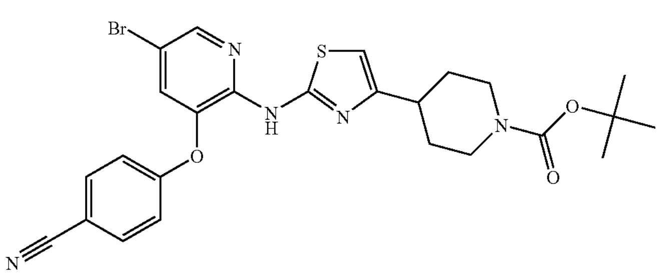 | tert-butyl 4-(2-(5-bromo-3-(4-cyanophenoxy)pyridin-2-ylamino)thiazol-4-yl)piperidine-1-carboxylate | $^1$H NMR (CDCl$_3$) δ 8.45 (s, 1H), 8.26 (s, 1H), 7.71 (d, 2H), 7.31 (s, 1H), 7.14 (d, 2H), 6.47 (s, 1H), 4.17 (m, 2H), 2.69-2.87 (m, 3H), 1.97 (m, 2H), 1.57 (m, 2H), 1.46 (s, 9H). |

Example 451 tert-butyl 3-(5-(5-bromo-3-phenoxypyridin-2-ylamino)-1,2,4-thiadiazol-3-yl)pyrrolidine-1-carboxylate

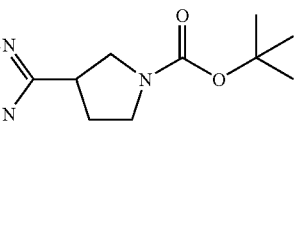

A 40 mL flask was charges with tert-butyl 3-(chloro(methylsulfonyloxyimino)methyl)pyrrolidine-1-carboxylate (1.60 g, 4.90 mmol) and acetonitrile (25 mL). Added pyridine (1.22 mL, 15.1 mmol) and isothiocyanatosodium (0.398 g, 4.90 mmol) and heated to 40° C. for 45 minutes. Added 5-bromo-3-phenoxypyridin-2-amine (1.00 g, 3.77 mmol) and heated at 60° C. overnight. The reaction was cooled to ambient temperature, poured into water and extracted with EtOAc (100 mL). The organic layer were dried with sodium sulfate, filtered and concentrated. The residue was purified by MPLC (Biotage) eluting with 3:1 hexane:ethyl acetate to afford tert-butyl 3-(5-(5-bromo-3-phenoxypyridin-2-ylamino)-1,2,4-thiadiazol-3-yl)pyrrolidine-1-carboxylate as a light yellow/off white solid: $^1$H NMR (d$_6$-DMSO) δ 12.21 (s, 1H), 8.34 (s, 1H), 7.48 (s, 1H), 7.39 (t, 2H), 7.18 (t, 1H), 7.07 (d, 2H), 3.42-3.63 (m, 3H), 3.36 (m, 1H), 2.02-2.21 (m, 3H), 1.35 (s, 9H).

Example 452 tert-butyl 4-((2-(5-(3-methoxy-3-oxopropylthio)-3-phenoxypyridin-2-ylamino)thiazol-4-yl)methyl)piperidine-1-carboxylate

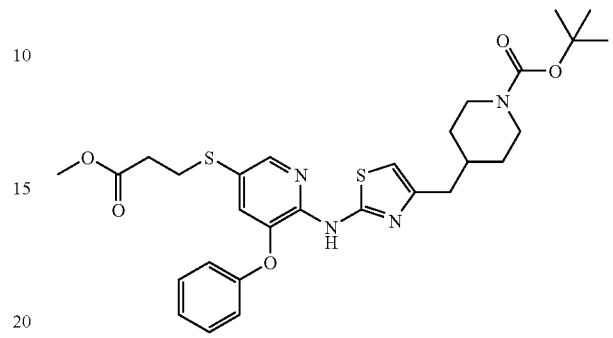

The atmosphere above a mixture of tert-butyl 4-((2-(5-bromo-3-phenoxypyridin-2-ylamino)thiazol-4-yl)methyl)piperidine-1-carboxylate (1.52 g, 2.79 mmol), N-ethyl-N-isopropylpropan-2-amine (0.971 mL, 5.57 mmol), 4,5-bis(diphenylphosphino)-9,9-dimethyl-9H-xanthene (0.161 g, 0.279 mmol), and dioxane (25 mL) was purged with nitrogen. Methyl 3-mercaptopropanoate (0.332 mL, 3.07 mmol) and Pd$_2$dba$_3$ (0.128 g, 0.139 mmol) were added, and the reaction was heated at 95° C. overnight. The reaction was cooled to ambient temperature and filtered through celite. The filtrate was concentrated and purified by MPLC (Biotage) eluting with 3:2 hexane:ethyl acetate to afford the title compound (1.54 g, 94.5% yield) as a tacky white solid: $^1$H NMR (CDCl$_3$) δ 8.70 (s, 1H), 8.16 (s, 1H), 7.40 (t, 2H), 7.24 (t, 1H), 7.14 (s, 1H), 7.06 (d, 2H), 6.46 (s, 1H), 4.08 (m, 2H), 3.65 (s, 3H), 2.99 (t, 2H), 2.67 (m, 2H), 2.56 (d, 2H), 2.55 (t, 2H), 1.85 (m, 1H), 1.66 (m, 2H), 1.45 (s, 9H), 1.16 (m, 2H).

The following compounds were prepared from the appropriate bromide according to the procedure of Example 452.

| Example | Structure | Name | $^1$H NMR |
|---|---|---|---|
| 453 | 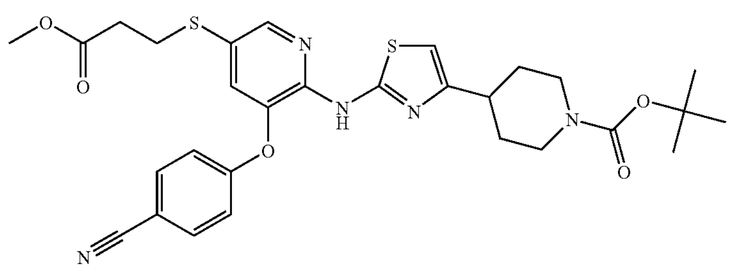 | tert-butyl 4-(2-(3-(4-cyanophenoxy)-5-(3-methoxy-3-oxopropylthio)pyridin-2-ylamino)thiazol-4-yl)piperidine-1-carboxylate | $^1$H NMR (CDCl$_3$) δ 8.46 (s, 1H), 8.27 (s, 1H), 7.70 (d, 2H), 7.31 (s, 1H), 7.13 (d, 2H), 6.47 (s, 1H), 4.19 (m, 2H), 3.66 (s, 3H), 3.04 (t, 2H), 2.71-2.85 (m, 3H), 2.59 (t, 2H), 1.97 (m, 2H), 1.59 (m, 2H), 1.46 (s, 9H). |
| 454 | 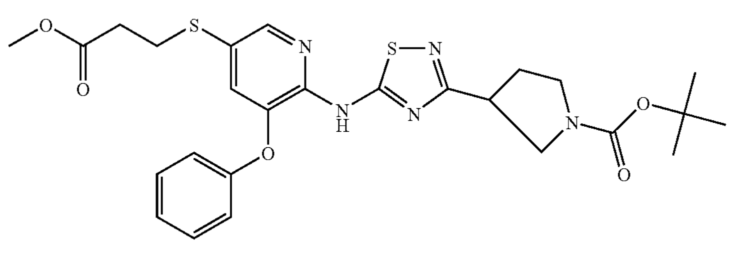 | tert-butyl 3-(5-(5-(3-methoxy-3-oxopropylthio)-3-phenoxypyridin-2-ylamino)-1,2,4-thiadiazol-3-yl)pyrrolidine-1-carboxylate | $^1$H NMR (CDCl$_3$) δ 9.02 (s, 1H), 8.0 (s, 1H), 7.44 (t, 2H), 7.28 (t, 1H), 7.18 (s, 1H), 7.09 (d, 2H), 3.82 (m, 1H), 3.67 (s, 3H), 3.54-3.67 (m, 2H), 3.43 (m, 1H), 3.04 (t, 2H), 2.57 (t, 2H), 2.22-2.35 (m, 3H), 1.46 (s, 9H). |

| Example | Structure | Name | ¹H NMR |
|---|---|---|---|
| 455 | 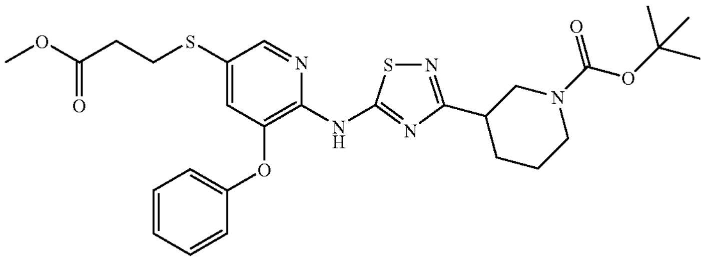 | tert-butyl 3-(2-(5-(3-methoxy-3-oxopropylthio)-3-phenoxypyridin-2-ylamino)thiazol-4-yl)piperidine-1-carboxylate | ¹H NMR (CDCl₃) δ 8.68 (s, 1H), 8.15 (s, 1H), 7.42 (t, 2H), 7.23 (t, 1H), 7.13 (s, 1H), 7.07 (d, 2H), 6.53 (s, 1H), 4.21 (m, 1H), 4.00 (m, 1H), 3.65 (s, 3H), 2.99 (t, 2H), 2.76-2.90 (m, 4H), 2.55 (t, 2H), 2.09 (m, 1H), 1.71 (m, 2H), 1.46 (s, 9H). |
| 456 | 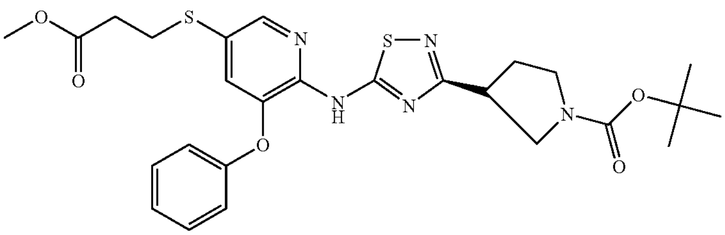 | tert-butyl 3-(2-(5-(3-methoxy-3-oxopropylthio)-3-phenoxypyridin-2-ylamino)thiazol-4-yl)pyrrolidine-1-carboxylate | ¹H NMR (CDCl₃) δ 8.69 (s, 1H), 8.16 (s, 1H), 7.42 (t, 2H), 7.24 (t, 1H), 7.13 (s, 1H), 7.08 (d, 2H), 6.54 (s, 1H), 3.76 (m, 1H), 3.65 (s, 3H), 3.64 (m, 1H), 3.50 (m, 1H), 3.41 (m, 2H), 2.99 (t, 2H), 2.56 (t, 2H), 2.24 (m, 1H), 2.11 (m, 1H), 1.46 (s, 9H). |

Example 457 tert-butyl 4-((2-(3-phenoxy-5-(thieno[3,2-b]pyridin-7-ylthio)pyridin-2-Ylamino)thiazol-4-yl)methyl)piperidine-1-carboxylate

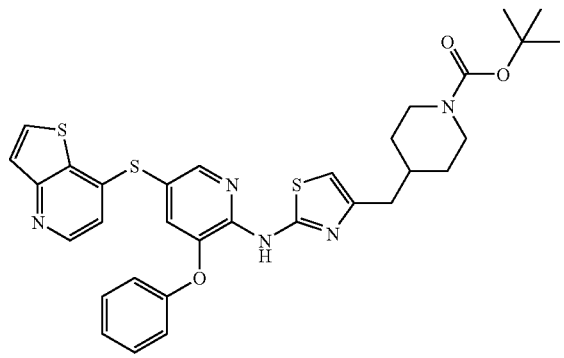

Added potassium 2-methylpropan-2-olate (0.443 g, 3.95 mmol) to a solution of 7-chlorothieno[3,2-b]pyridine (0.268 g, 1.58 mmol) and tert-butyl 4-((2-(5-(3-methoxy-3-oxopropylthio)-3-phenoxypyridin-2-ylamino)thiazol-4-yl)methyl)piperidine-1-carboxylate (0.77 g, 1.32 mmol) in DMSO (8 mL). The reaction was stirred for two hours, then set aside to react at ambient temperature for 60 hours. The reaction was partitioned between ethyl acetate and saturated ammonium chloride. Washed the organic layer twice with water and brine, dried, and concentrated. The residue was purified by MPLC (Biotage) eluting with 1:1 hexane:ethyl acetate. The major UV active component with an Rf of 0.3 was collected and concentrated to afford the title compound (0.810 g, 97.4% yield) as a white powder: ¹H NMR (CDCl₃) δ 8.88 (s, 1H), 8.46 (d, 1H), 8.32 (s, 1H), 7.72 (d, 1H), 7.54 (d, 1H), 7.38 (t, 2H), 7.20 (t, 1H), 7.18 (s, 1H), 7.04 (d, 2H), 6.73 (d, 1H), 6.51 (s, 1H), 4.09 (m, 2H), 2.68 (m, 2H), 2.59 (d, 2H), 1.87 (m, 1H), 1.66 (m, 2H), 1.45 (s, 9H), 1.16 (m, 2H).

Using the procedure in Example 457, the following compounds were prepared from the appropriate thiopropionate and electrophile.

| Example | Structure | Name | ¹H NMR |
|---|---|---|---|
| 458 | 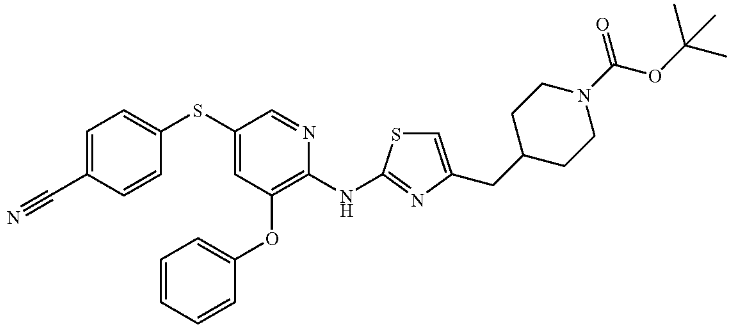 | tert-butyl 4-((2-(5-(4-cyanophenylthio)-3-phenoxypyridin-2-ylamino)thiazol-4-yl)methyl)piperidine-1-carboxylate | ¹H NMR (CDCl₃) δ 8.85 (s, 1H), 8.24 (s, 1H), 7.47 (d, 2H), 7.42 (t, 2H), 7.24 (t, 1H), 7.04-7.13 (m, 5H), 6.50 (s, 1H), 4.08 (m, 2H), 2.69 (m, 2H), 2.59 (d, 2H), 1.87 (m, 1H), 1.67 (m, 2H), 1.45 (s, 9H), 1.17 (m, 2H). |

| Example | Structure | Name | ¹H NMR |
|---|---|---|---|
| 459 | 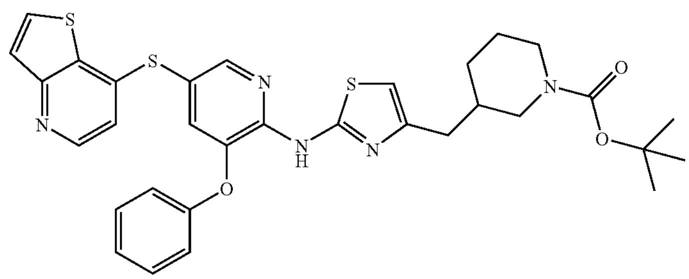 | tert-butyl 3-((2-(3-phenoxy-5-(thieno[3,2-b]pyridin-7-ylthio)pyridin-2-ylamino)thiazol-4-yl)methyl)piperidine-1-carboxylate | ¹H NMR (CDCl₃) δ 8.85 (s, 1H), 8.46 (d, 1H), 8.32 (s, 1H), 7.72 (d, 1H), 7.54 (d, 1H), 7.38 (t, 2H), 7.20 (t, 1H), 7.18 (s, 1H), 7.05 (d, 2H), 6.73 (d, 1H), 6.59 (s, 1H), 4.22 (m, 1H), 4.00 (m, 1H), 3.00 (m, 1H), 2.78-2.91 (m, 2H), 2.21 (m, 1H), 1.72 (m, 2H), 1.58 (m, 1H), 1.45 (s, 9H). |
| 460 | 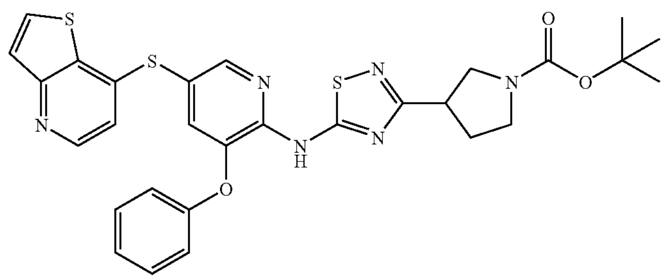 | tert-butyl 3-(5-(3-phenoxy-5-(thieno[3,2-b]pyridin-7-ylthio)pyridin-2-ylamino)-1,2,4-thiadiazol-3-yl)pyrrolidine-1-carboxylate | ¹H NMR (CDCl₃) δ 9.21 (s, 1H), 8.49 (d, 1H), 8.37 (s, 1H), 7.73 (d, 1H), 7.55 (d, 1H), 7.40 (t, 2H), 7.25 (t, 1H), 7.24 (s, 1H), 7.06 (d, 2H), 6.77 (d, 1H), 3.41-3.87 (m, 4H), 2.23-2.35 (m, 2H), 1.46 (s, 9H), 1.27 (m, 2H). |
| 461 | 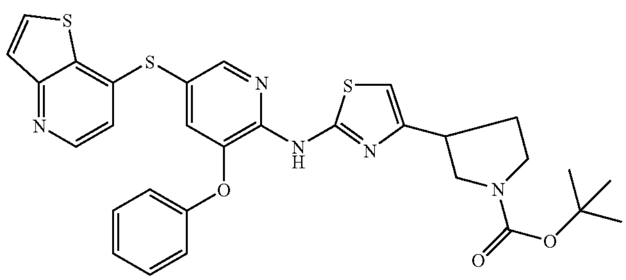 | tert-butyl 3-(2-(3-phenoxy-5-(thieno[3,2-b]pyridin-7-ylthio)pyridin-2-ylamino)thiazol-4-yl)pyrrolidine-1-carboxylate | ¹H NMR (CDCl₃) δ 8.87 (s, 1H), 8.46 (d, 1H), 8.32 (s, 1H), 7.72 (d, 1H), 7.54 (d, 1H), 7.38 (t, 2H), 7.20 (t, 1H), 7.17 (s, 1H), 7.05 (d, 2H), 6.74 (d, 1H), 6.59 (s, 1H), 3.77 (m, 1H), 3.62 (m, 1H), 3.53 (m, 1H), 3.41 (m, 2H), 2.25 (m, 1H), 2.11 (m, 1H), 1.47 (s, 7H). |
| 462 | 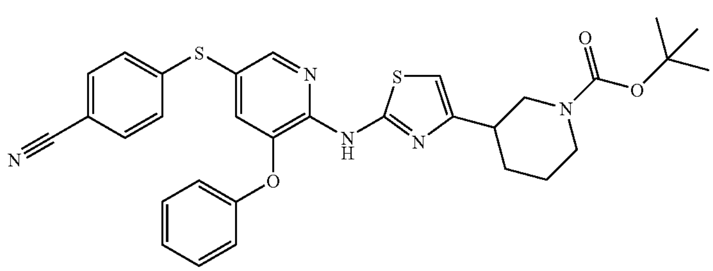 | tert-butyl 3-(2-(5-(4-cyanophenylthio)-3-phenoxypyridin-2-ylamino)thiazol-4-yl)piperidine-1-carboxylate | ¹H NMR (CDCl₃) δ 8.82 (s, 1H), 8.24 (s, 1H), 7.47 (d, 2H), 7.42 (t, 2H), 7.22 (t, 1H), 7.05-7.13 (m, 5H), 6.58 (s, 1H), 4.21 (m, 1H), 4.00 (m, 1H), 3.00 (m, 1H), 2.78-2.90 (m, 2H), 2.10 (m, 1H), 1.72 (m, 2H), 1.58 (m, 1H), 1.47 (s, 9H). |
| 463 | 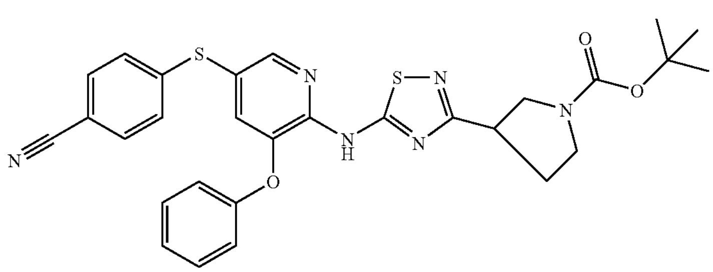 | tert-butyl 3-(5-(5-(4-cyanophenylthio)-3-phenoxypyridin-2-ylamino)-1,2,4-thiadiazol-3-yl)pyrrolidine-1-carboxylate | ¹H NMR (CDCl₃) δ 9.19 (s, 1H), 8.30 (s, 1H), 7.49 (d, 2H), 7.43 (t, 2H), 7.26 (t, 1H), 7.18 (s, 1H), 7.12 (d, 2H), 7.08 (d, 2H), 3.87 (m, 1H), 3.55-3.70 (m, 3H), 3.44 (m, 1H), 2.24-2.35 (m, 2H), 1.47 (s, 9H). |

Example 464

N-(3-phenoxy-5-(thieno[3,2-b]pyridin-7-ylthio)pyridin-2-yl)-4-(piperidin-4-ylmethyl)thiazol-2-amine dihydrochloride

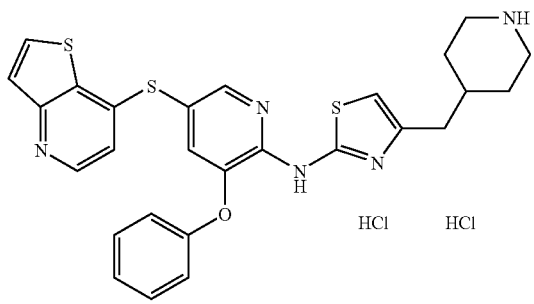

Added 4N HCl in dioxane (3.0 mL, 12.0 mmol) to a solution of tert-butyl 4-((2-(3-phenoxy-5-(thieno[3,2-b]pyridin-7-ylthio)pyridin-2-ylamino)thiazol-4-yl)methyl)piperidine-1-carboxylate (0.790 g, 1.25 mmol) in dichloromethane (4 mL) and methanol (4 mL). The reaction was stirred at ambient temperature for 3 hours. Concentrated, triturated with hexanes, filtered to afford the title compound (0.745 g, 98.5% yield) as a light yellow powder: $^1$H NMR (d-DMSO) δ 9.13 (m, 1H), 8.89 (m, 1H), 8.67 (d, 1H), 8.51 (d, 1H), 8.47 (s, 1H), 7.80 (d, 1H), 7.57 (s, 1H), 7.42 (t, 2H), 7.16-7.23 (m, 4H), 6.91 (s, 1H), 3.21 (m, 2H), 2.80 (m, 2H), 2.60 (d, 2H), 1.95 (m, 1H), 1.76 (m, 2H), 1.45 (m, 2H).

Using the procedure in Example 464, the following compounds were prepared from the appropriate Boc-protected cyclic amine.

| Example | Structure | Name | $^1$H NMR |
|---|---|---|---|
| 465 | 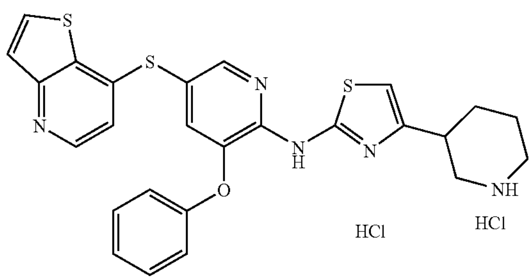 | N-(3-phenoxy-5-(thieno[3,2-b]pyridin-7-ylthio)pyridin-2-yl)-4-(piperidin-3-yl)thiazol-2-amine dihydrochloride | $^1$H NMR (d$_6$-DMSO) δ 9.48 (m, 1H), 9.31 (m, 1H), 8.67 (d, 1H), 8.51 (d, 1H), 8.46 (s, 1H), 7.81 (d, 1H), 7.54 (s, 1H), 7.42 (t, 2H), 7.16-7.25 (m, 4H), 6.95 (s, 1H), 3.48 (m, 1H), 3.27 (m, 1H), 3.19 (m, 1H), 3.07 (m, 1H), 2.84 (m, 1H), 2.08 (m, 1H), 1.82-1.90 (m, 2H), 1.67 (m, 1H). |
| 466 | 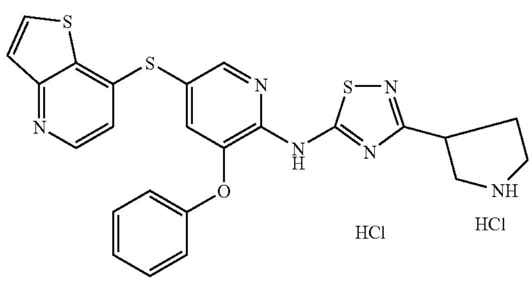 | N-(3-phenoxy-5-(thieno[3,2-b]pyridin-7-ylthio)pyridin-2-yl)-3-(pyrrolidin-3-yl)-1,2,4-thiadiazol-5-amine dihydrochloride | $^1$H NMR (d$_6$-DMSO) δ 9.48 (m, 1H), 8.63 (d, 1H), 8.56 (s, 1H), 8.43 (d, 1H), 7.78 (d, 1H), 7.63 (s, 1H), 7.42 (t, 2H), 7.16-7.20 (m, 4H), 3.73 (m, 1H), 3.60 (m, 1H), 3.48 (m, 1H), 3.28 (m, 2H), 2.38 (m, 1H), 2.21 (m, 1H). |
| 467 | 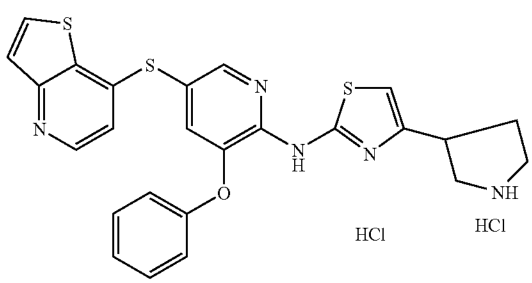 | N-(3-phenoxy-5-(thieno[3,2-b]pyridin-7-ylthio)pyridin-2-yl)-3-(pyrrolidin-3-yl)-1,2,4-thiadiazol-5-amine dihydrochloride | $^1$H NMR (d$_6$-DMSO) δ 9.61 (m, 1H), 8.67 (d, 1H), 8.51 (d, 1H), 8.46 (s, 1H), 7.80 (d, 1H), 7.54 (s, 1H), 7.41 (t, 2H), 7.23 (d, 1H), 7.16-7.20 (m, 3H), 3.19-3.60 (m, 5H), 2.30 (m, 1H), 2.06 (m, 1H). |

Example 468

4-(5-phenoxy-6-(4-(piperidin-4-ylmethyl)thiazol-2-ylamino)pyridin-3-ylthio)benzonitrile dihydrochloride

Example 471

1-(4-((2-(3-phenoxy-5-(thieno[3,2-b]pyridin-7-ylthio)pyridin-2-ylamino)thiazol-4-yl)methyl)piperidin-1-yl)ethanone

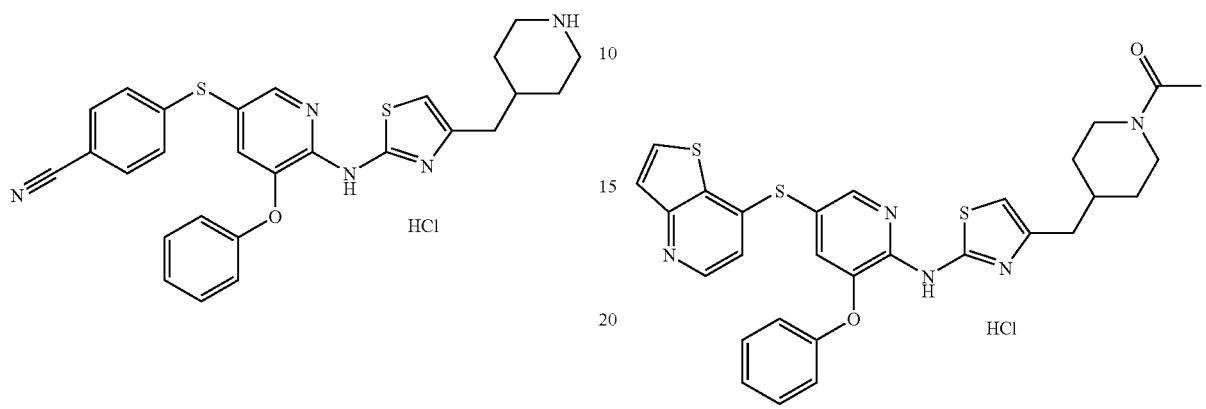

Added 2,2,2-trifluoroacetic acid (4 mL, 51.9 mmol) to a solution of tert-butyl 4-((2-(5-(4-cyanophenylthio)-3-phenoxypyridin-2-ylamino)thiazol-4-yl)methyl)piperidine-1-carboxylate (0.600 g, 1.00 mmol). Stirred at ambient temperature for 3 hours. Partitioned between ethyl acetate and 2N NaOH. Washed the organic layer with water, brine, dried and concentrated. The residue was dissolved in ether (5 mL) and 2N HCl in ether was added. Filtered, washed with hexanes, filtered to afford 4-(5-phenoxy-6-(4-(piperidin-4-ylmethyl)thiazol-2-ylamino)pyridin-3-ylthio)benzonitrile dihydrochloride (0.454 g, 79.3% yield) as a white powder: $^1$H NMR ($d_6$-DMSO) δ 8.94 (m, 1H), 8.67 (m, 1H), 8.31 (s, 1H), 7.72 (d, 2H), 7.42 (t, 2H), 7.35 (s, 1H), 7.10-7.26 (m, 5H), 7.83 (s, 1R), 3.23 (m, 2H), 2.80 (m, 2H), 2.58 (d, 2H), 1.92 (m, 1H), 1.75 (m, 2H), 1.39 (m, 2H).

Using the procedure in Example 468, the following compounds were prepared from the appropriate Boc-carbamate.

Added acetic anhydride (0.0169 g, 0.165 mmol) to a mixture of 3-phenoxy-N-(4-(piperidin-4-ylmethyl)thiazol-2-yl)-5-(thieno[3,2-b]pyridin-7-ylthio)pyridin-2-amine dihydrochloride (0.100 g, 0.165 mmol), triethylamine (0.0837 g, 0.827 mmol), and THF (5 mL) at 0° C. Warmed to ambient temperature and stirred for 4 hours. Partitioned between ethyl acetate and 2N NaOH, washed with water, brine, dried, and concentrated. The residue was dissolved in dichloromethane (2 mL) and 1N HCl in ether was added. Diluted in hexanes, and concentrated, added hexanes again and concentrated to afford the title compound ((Mixture of rotamers; 0.092 g, 91.2% yield) as a light yellow powder: $^1$H NMR ($d_6$-DMSO) δ 8.65 (d, 1H); 8.47 (d, 1H), 8.46 (s, 1H), 7.77 (d, 1H), 7.41 (s, 1H), 7.41 (d, 2H), 7.15-7.20 (m, 4H), 6.84 (s, 1H), 0.95-4.36 (m, 1H), 1.97 (s, 3H).

| Example | Structure | Name | $^1$H NMR |
|---|---|---|---|
| 469 | 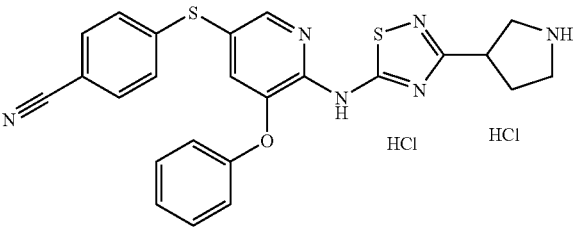 | 4-(5-phenoxy-6-(3-(pyrrolidin-3-yl)-1,2,4-thiadiazol-5-ylamino)pyridin-3-ylthio)benzonitrile dihydrochloride | $^1$H NMR ($d_6$-DMSO) δ 9.40 (m, 1H), 8.43 (s, 1H), 7.72 (d, 2H), 7.45 (s, 1H), 7.42 (t, 2H), 7.29 (d, 2H), 7.21 (t, 1H), 7.15 (d, 2H), 3.71 (m, 1H), 3.60 (m, 1H), 3.48 (m, 1H), 3.38 (m, 1H), 3.28 (m, 1H), 2.36 (m, 1H), 2.20 (m, 1H). |
| 470 | 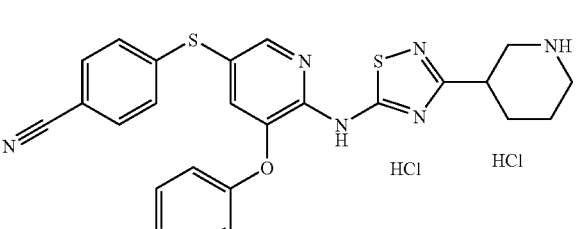 | 4-(5-phenoxy-6-(3-(piperidin-3-yl)-1,2,4-thiadiazol-5-ylamino)pyridin-3-ylthio)benzonitrile dihydrochloride | $^1$H NMR ($d_6$-DMSO) δ 9.23 (m, 1H), 9.10 (m, 1H), 8.30 (s, 1H), 7.72 (d, 2H), 7.43 (t, 2H), 7.32 (s, 1H), 7.26 (d, 2H), 7.19 (t, 1H), 7.14 (d, 2H), 3.46 (m, 1H), 3.26 (m, 1H), 3.15 (m, 1H), 2.98 (m, 1H), 2.85 (m, 1H), 2.07 (m, 1H), 1.72-1.90 (m, 2H), 1.65 (m, 1H). |

Using the procedure in Example 471, the following compounds were prepared from the appropriate amine.

| Example | Structure | Name | ¹H NMR |
|---|---|---|---|
| 472 | 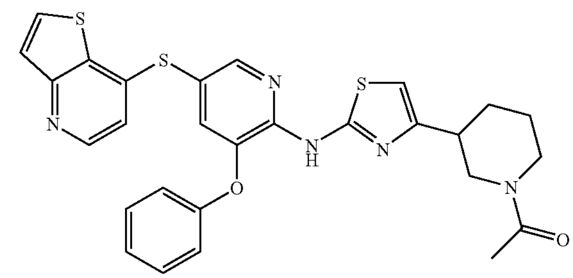 | 1-(3-(2-(3-phenoxy-5-(thieno[3,2-b]pyridin-7-ylthio)pyridin-2-ylamino)thiazol-4-yl)piperidin-1-yl)ethanone | (Mixture of rotamers) ¹H NMR (CDCl₃) δ 8.66 (d, 1H), 8.50 (d, 1H), 8.46 (s, 1H), 7.79 (d, 1H), 7.55 (s, 1H), 7.41 (t, 2H), 7.23 (d, 1H), 7.14-7.19 (m, 3H), 6.89 (d, 1H), 6.58 (bs, 1H), 1.35-4.63 (m, 9H), 2.02 (s, 3H). |
| 473 | 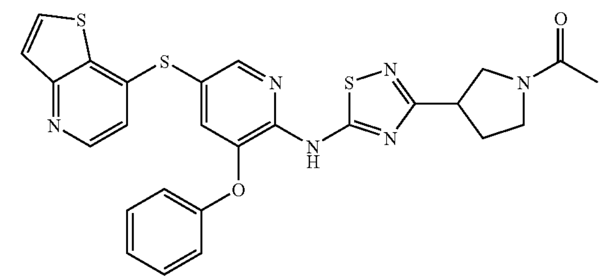 | 1-(3-(5-(3-phenoxy-5-(thieno[3,2-b]pyridin-7-ylthio)pyridin-2-ylamino)-1,2,4-thiadiazol-3-yl)pyrrolidin-1-yl)ethanone | (Mixture of rotamers) ¹H NMR (d₆-DMSO) δ 8.59 (d, 1H), 8.54 (s, 1H), 8.33 (d, 1H), 7.68 (d, 1H), 7.59 (s, 1H), 7.41 (d, 2H), 7.10-7.20 (m, 5H), 2.10-3.93 (m, 7H), 1.96 (s, 3H). |
| 474 | 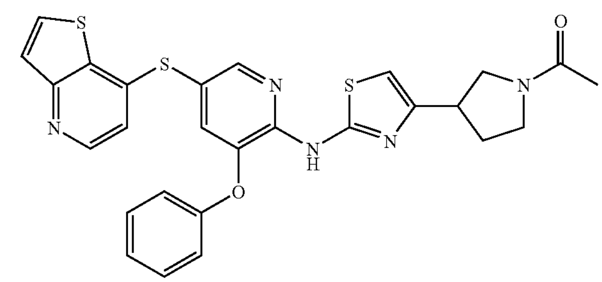 | 1-(3-(2-(3-phenoxy-5-(thieno[3,2-b]pyridin-7-ylthio)pyridin-2-ylamino)thiazol-4-yl)pyrrolidin-1-yl)ethanone | (Mixture of rotamers) ¹H NMR (d₆-DMSO) δ 8.47 (d, 1H), 8.32 (s, 1H), 7.73 (d, 1H), 7.54 (d, 1H), 7.39 (d, 2H), 7.17-7.24 (m, 3H), 7.06 (d, 2H), 6.75 (d, 1H), 6.62 (s, 1H), 6.59 (s, 1H), 2.12-3.97 (m, 7H), 1.98 (s, 3H). |
| 475 | 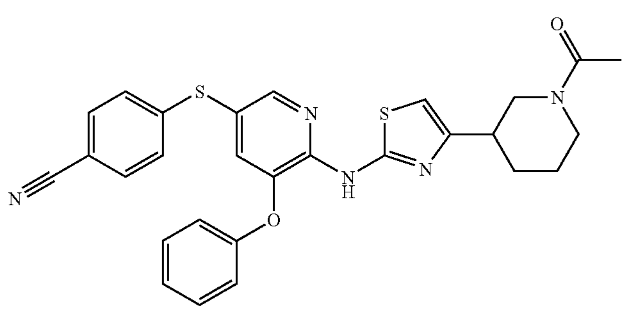 | 4-(6-(4-(1-acetylpiperidin-3-yl)thiazol-2-ylamino)-5-phenoxypyridin-3-ylthio)benzonitrile | (Mixture of rotamers) ¹H NMR (CDCl₃) δ 8.83 (m, 1H), 8.24 (s, 1H), 7.05-7.59 (m, 9H), 6.56 (s, 1H), 2.63-4.70 (m, 6H), 2.12 (s, 3H), 1.73-2.20 (m, 3H). |
| 476 | 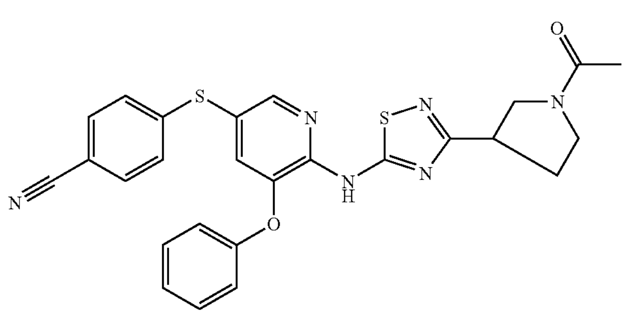 | 4-(6-(3-(1-acetylpyrrolidin-3-yl)-1,2,4-thiadiazol-5-ylamino)-5-phenoxypyridin-3-ylthio)benzonitrile | (Mixture of rotamers) ¹H NMR (CDCl₃) δ 9.16 (m, 1H), 8.30 (s, 1H), 7.06-7.53 (m, 9H), 2.29-3.99 (m, 7H), 2.08 (s, 3H). |

| Example | Structure | Name | ¹H NMR |
|---|---|---|---|
| 477 | 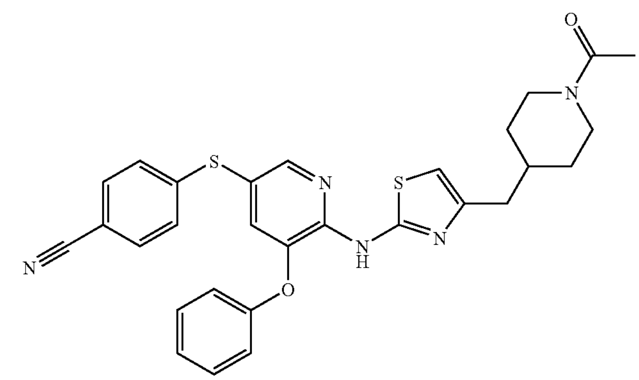 | 4-(6-(4-((1-acetylpiperidin-4-yl)methyl)thiazol-2-ylamino)-5-phenoxypyridin-3-ylthio)benzonitrile E20018-397 | ¹H NMR (d₆-DMSO) δ 11.07 (s, 1H), 8.23 (s, 1H), 7.66 (d, 2H), 7.04-7.37 (m, 8H), 6.65 (s, 1H), 4.27 (m, 1H), 3.71 (m, 1H), 2.89 (m, 1H), 2.45 (d, 2H), 2.41 (m, 1H), 1.91 (s, 3H), 1.85 (m, 1H), 1.54 (m, 2H), 0.89-1.10 (m, 2H). |

Example 478

1-(4-(2-(5-(2-chloropyridin-4-ylthio)-3-phenoxypyridin-2-ylamino)thiazol-4-yl)piperidin-1-yl)ethanone

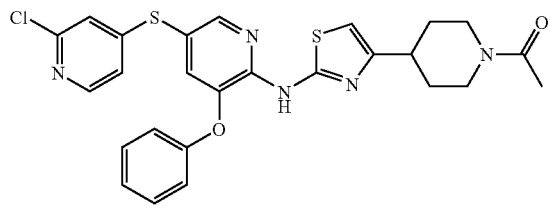

Using the procedure in Example 16, the title compound was prepared: ¹H NMR (CDCl₃) δ 8.24 (s, 1H), 8.13 (d, 1H), 7.42 (t, 1H), 7.24 (t, 1H), 7.07-7.12 (m, 2H), 6.82-6.86 (m, 2H), 6.52 (s, 1H), 4.72 (m, 1H), 3.91 (m, 1H), 3.19 (m, 1H), 2.88 (m, 1H), 2.70 (m, 1H), 2.12 (m, 1H), 2.03-2.11 (m, 2H), 1.60-1.71 (m, 2H).

Example A

In Vitro Glucokinase Assays

The in vitro efficacy of glucokinase activators of the present invention was assessed in two separate assays: an $EC_{50}$ assay to evaluate the potency of each compound at a fixed, physiologically relevant concentration of glucose, and a glucose $S_{0.5}$ assay at a fixed, near saturating (if possible) concentration of compound to evaluate its effect on the $V_m$ and $S_{0.5}$ for glucose. For each of these assays, glucokinase activity was estimated by monitoring the increase in absorbance at 340 nm in a coupled assay system containing $NAD^+$ and glucose 6-phosphate dehydrogenase. Assays were conducted at 30° C. using a thermostatically controlled absorbance plate reader (Spectramax 340PC, Molecular Devices Corp.) and clear, 96-well, flat bottom, polystyrene plates (Costar 3695, Corning). Each 50-μL assay mixture contained 10 mM $K^+$ MOPS, pH 7.2, 2 mM $MgCl_2$, 50 mM KCl, 0.01% Triton X-100, 2% DMSO, 1 mM DTT, 1 mM ATP, 1 mM $NAD^+$, 5 U/mL glucose 6-phosphate dehydrogenase, approximately 5 nM human glucokinase and (depending on the assay) varying concentrations of glucose and test compound. The absorbance at 340 nm was monitored kinetically over a period of 5 minutes (10 s/cycle), and rates were estimated from the slopes of linear fits to the raw data.

Glucokinase $EC_{50}$ Assay:

For this assay, the glucose concentration was fixed at 5 mM, while the control or test compound was varied over a 10-point, 3-fold dilution series and typically ranged from a high dose of 50 μM to a low dose of approximately 2.5 nM. A standard, four-parameter logistic model (Equation 1) was fit to the raw data (rate versus concentration of compound):

$$y = A + \frac{B-A}{1+\left[\frac{C}{x}\right]^D} \quad (1)$$

where x is the concentration of compound, y is the estimated rate, A and B are the lower and upper asymptotes, respectively, C is the $EC_{50}$ and D is the Hill slope. The $EC_{50}$ is defined as the midpoint or inflection point between the upper and lower asymptotes.

The compounds exemplified herein have been found to have an $EC_{50}$ in the range of 6 and 50,000 nM in the above described assay. Certain compounds exemplified herein have been found to have an $EC_{50}$ in the range of 3 nM and 5000 nM.

Glucose $S_{0.5}$ Assay:

For this assay, the concentration of control or test compound was fixed at or near a saturating concentration, if possible, typically 50 μM, while the glucose concentration was varied over a 10-point, 2-fold dilution series ranging from 80 to approximately 0.16 mM. The same four-parameter logistic model used for the $EC_{50}$ assay (Equation 1) was employed to estimate the relevant kinetic parameters. In this assay, the definitions for the variables and parameters are similar except that x represents the concentration of glucose, B is the rate at saturating glucose ($V_m$), C is the $S_{0.5}$ for glucose (the concentration of glucose at $V_m/2$) and D is the Hill Coefficient.

The compounds exemplified herein have been found to have an $S_{0.5}$ of between 0.3 and 5 mM in the above described assay.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may

What is claimed is:
1. A compound selected from the Formula

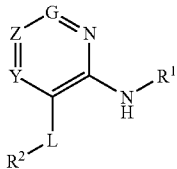

I and salts thereof, wherein:
L is O, S, C(=O) or $CHR^{14}$;
Y is $CR^4$;
Z is $CR^3$;
G is $CR^{11}$;
$R^1$ is a heteroaryl ring represented by the formula

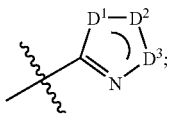

$D^1$ is S;
$D^2$ is N or $CR^{12}$;
$D^3$ is S, O or $CR^{13}$;
$R^2$ is aryl, heteroaryl, saturated or partially unsaturated cycloalkyl, or saturated or partially unsaturated heterocyclyl, wherein said aryl, heteroaryl, cycloalkyl and heterocyclyl are monocyclic or bicyclic and are optionally substituted with one or more groups independently selected from $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl, heteroaryl, F, Cl, Br, I, $CF_3$, CN, $NO_2$, $OR^6$, $C(=O)R^6$, $C(=O)OR^6$, $OC(=O)R^6$, $O(CH_2)_nC(=O)OR^6$, $O(CH_2)_nC(=O)NR^6R^7$, $C(=O)NR^6R^7$, $NR^6R^7$, $NR^6C(=O)R^7$, $SR^6$, $S(O)R^6$, and $S(O)_2R^6$, and wherein said alkyl, alkenyl, alkynyl, cycloalkyl, heterocyclyl, aryl, and heteroaryl are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ $V_n$-cycloalkyl, saturated and partially unsaturated $C_1$-$C_6$ $V_n$-heterocyclyl, $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—$C(=O)R^8$, $V_n$—$C(=O)OR^8$, $V_n$—$OC(=O)R^8$, $V_n$—$C(=O)NR^8R^9$, $V_n$—$NR^8R^9$, $V_n$—$NR^8C(=O)R^9$, $V_n$—$SR^8$, $V_n$—$S(O)R^8$, and $V_n$—$S(O)_2R^8$;
$R^3$ is $SR^6$, $S(O)R^6$, $S(O)_2R^6$ or $S(O)_2NR^6_R{}^7$;
$R^4$ is H;
$R^6$ and $R^7$ are independently H, $C_1$-$C_{12}$ alkyl, $C_2$-$C_{12}$ alkenyl, $C_2$-$C_{12}$ alkynyl, saturated or partially unsaturated $C_3$-$C_{12}$ cycloalkyl, saturated or partially unsaturated $C_1$-$C_{12}$ heterocyclyl, $V_n$-aryl, or $V_n$-heteroaryl, wherein said alkyl, alkenyl, alkynyl, cycloalkyl, heterocyclyl, aryl and heteroaryl portions are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl [optionally substituted with C(O)O(1-6C alkyl), (1-6C) alkyl or (1-6C alkyl)OH], $V_n$-aryl, $V_n$-heteroaryl, $V_n$—F, $V_n$—Cl, $V_n$—Br, $V_n$—I, $V_n$—$CF_3$, $V_n$—CN, $V_n$—$OR^8$, $V_n$—$C(=O)R^8$, $V_n$—$C(=O)OR^8$, $V_n$—$OC(=O)R^8$, $V_n$—$C(=O)NR^8R^9$, $V_n$—$NR^8R^9$, $V_n$—$NR^8C(=O)R^9$, $V_n$—$SR^8$, $V_n$—$S(O)R^8$, $V_n$—$S(O)_2R^8$, $V_n$—$S(O)_2NR^8R^9$, and $(C_1$-$C_6$ alkyl)OH;
or $R^6$ and $R^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $V_n$—F, $V_n$—Cl, V—Br, $V_n$—I, $V_n$—$OR^8$, $V_n$—$C(=O)OR^8$, $V_n$—$C(=O)NR^8R^9$, $V_n$—$NR^8R^9$, $V_n$—$NR^8C(=O)R^9$, $V_n$—$NR^8C(=O)NR^9R^{10}$, $C_1$-$C_6$ alkyl, $C_2$-$C_6$ alkenyl, and $C_2$-$C_6$ alkynyl;
$R^8$, $R^9$ and $R^{10}$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, aryl or heteroaryl, wherein said alkyl, alkenyl, alkynyl, cycloalkyl, heterocyclyl, aryl and heteroaryl are optionally substituted with one or more groups independently selected from oxo, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, $V_n$-heteroaryl, $V_n$—F, $V_n$—Cl, $V_n$—Br, $V_n$—I, $V_n$—$OR^a$, $V_n$—$NR^aR^b$, $V_n$—$C(=O)OR^a$, $V_n$—$C(=O)NR^aR^b$, and $V_n$—$NR^aC(=O)R^b$,
or $R^8$ and $R^9$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $C_1$-$C_6$ alkyl, $C_2$-$C_6$ alkenyl, $C_2$-$C_6$ alkynyl, $V_n$—F, $V_n$—Cl, $V_n$—Br, $V_n$—I, $V_n$—$OR^a$, and $V_n$—CN;
or $R^9$ and $R^{10}$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, $C_1$-$C_6$ alkyl, $C_2$-$C_6$ alkenyl, $C_2$-$C_6$ alkynyl, $V_n$—F, $V_n$—Cl, $V_n$—Br, $V_n$—I, $V_n$—$OR^a$, and $V_n$—CN;
$R^{11}$ is H;
$R^{12}$ and $R^{13}$ are independently H, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $CH_2$-heterocyclyl, aryl, heteroaryl, (1-3C alkyl)heteroaryl, $(CH_2)_n(CR^xR^y)C(O)NR^8R^9$, $(CH_2)_n(CR^xR^y)C(O)NH$—N=$CHNR^8R^9$, F, Cl, Br, I, $CF_3$, CN, $OR^6$, $C(=O)R^6$, $C(=O)OR^6$, $OC(=O)R^6$, $C(=O)NR^6R^7$, $NR^6R^7$, $NR^6C(=O)R^7$, $SR^6$, $S(O)R^6$, $S(O)_2R^6$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, C(O)(C$_1$-C$_6$ alkyl), C(O)-heterocycle [optionally substituted with O—(C$_1$-C$_6$ alkyl], SR$^a$, SO$_2$R$^f$, SO$_2$NR$^c$R$^e$, C(O)(C$_1$-C$_6$ alkyl)NR$^c$R$^d$, C(O)(C$_1$-C$_6$ alkyl)OR$^c$, C(O)CH$_2$C(O)(C$_1$-C$_6$ alkyl), C(=O)CHR$^g$NHC(=O)(C$_1$-C$_6$ alkyl), C(=O)CH$_2$OC(=O)(C$_1$-C$_6$ alkyl), C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, $V_n$-aryl, and $V_n$-heteroaryl, wherein said heterocyclyl is optionally substituted with one or more oxo, or R$^{12}$ and R$^{13}$ together with the atoms to which they are attached form a saturated, partially unsaturated or aromatic carbocyclic or heterocyclic ring, wherein said carbocyclic and heterocyclic rings are optionally substituted with one or more groups independently selected from C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, aryl, heteroaryl, oxo, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$, S(O)$_2$R$^6$ and SO$_2$NR$^6$R$^7$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, $V_n$-aryl, and $V_n$-heteroaryl;

R$^{14}$ is H, methyl, ethyl or OH;

R$^a$ and R$^b$ are independently H, C$_1$-C$_6$ alkyl, C$_2$-C$_6$ alkenyl, C$_2$-C$_6$ alkynyl, saturated and partially unsaturated $V_n$—C$_3$-C$_6$ cycloalkyl, saturated and partially unsaturated $V_n$—C$_1$-C$_6$ heterocyclyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocyclyl, $V_n$-aryl, and $V_n$-heteroaryl are optionally substituted with one or more OH;

each R$^c$, R$^e$ and R$^g$ is independently H or C$_1$-C$_6$ alkyl;

R$^d$ is H, C$_1$-C$_6$ alkyl or C(O)O(C$_1$-C$_6$ alkyl);

R$^f$ is C$_1$-C$_6$ alkyl or (C$_1$-C$_6$ alkyl)NH$_2$;

R$^x$ is H or C$_1$-C$_6$ alkyl;

R$^y$ is H, C$_1$-C$_6$ alkyl, or —O(C$_1$-C$_6$ alkyl);

V is alkylene having from 1 to 12 carbons, or alkenylene or alkynylene each having from 2 to 12 carbons, wherein said alkylene, alkenylene, or alkynylene are optionally substituted with one or more groups independently selected from C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, aryl, heteroaryl, F, Cl, Br, I, CF$_3$, cyano, OR$^8$, C(=O)OR$^8$, OC(=O)R$^8$, C(=O)NR$^8$R$^9$, NR$^8$R$^9$, (C$_1$-C$_6$ alkyl)NR$^c$R$^e$, and NR$^8$C(=O)R$^9$; and n is 0 or 1.

2. The compound of claim 1, wherein:

R$^6$ and R$^7$ are optionally substituted with one or more groups independently selected from oxo, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, $V_n$-aryl, $V_n$-heteroaryl, $V_n$—F, $V_n$—Cl, $V_n$—Br, $V_n$—I, $V_n$—CF$_3$, $V_n$—CN, $V_n$—OR$^8$, $V_n$—C(=O)R$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $V_n$—SR$^8$, $V_n$—S(O)R$^8$, $V_n$—S(O)$_2$R$^8$, and $V_n$—S(O)$_2$NR$^8$R$^9$, and R$^{12}$ and R$^{13}$ are independently H, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, aryl, heteroaryl, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$ or S(O)$_2$R$^6$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, $V_n$-aryl, and $V_n$-heteroaryl, wherein said heterocyclyl is optionally substituted with one or more oxo, or R$^{12}$ and R$^{13}$ together with the atoms to which they are attached form a saturated, partially unsaturated or aromatic carbocyclic or heterocyclic ring, wherein said carbocyclic and heterocyclic rings are optionally substituted with one or more groups independently selected from C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, aryl, heteroaryl, oxo, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$, S(O)$_2$R$^6$ and SO$_2$NR$^6$R$^7$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, $V_n$-aryl, and $V_n$-heteroaryl.

3. The compound of claim 1 wherein R$^1$ is selected from:

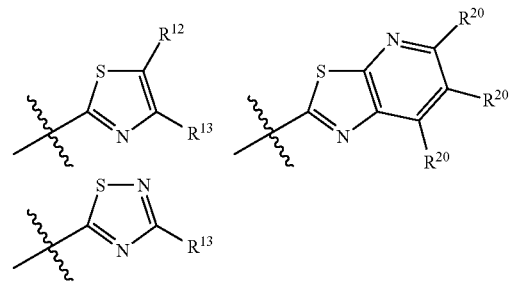

wherein R$^{20}$ is H, C$_1$-C$_6$ alkyl, C$_2$-C$_6$ alkenyl, C$_2$-C$_6$ alkynyl, saturated and partially unsaturated C$_3$-C$_6$ cycloalkyl, saturated and partially unsaturated C$_1$-C$_6$ heterocyclyl, aryl, heteroaryl, oxo, F, Cl, Br, I, CF$_3$, CN, OR$^6$, C(=O)R$^6$, C(=O)OR$^6$, OC(=O)R$^6$, C(=O)NR$^6$R$^7$, NR$^6$R$^7$, NR$^6$C(=O)R$^7$, SR$^6$, S(O)R$^6$, S(O)$_2$R$^6$ and SO$_2$NR$^6$R$^7$, wherein said alkyl, alkenyl, alkynyl, cycloalkyl, heterocyclyl, aryl and heteroaryl are optionally substituted with one or more groups independently selected from oxo, $V_n$—F, $V_n$—Cl, $V_n$—Br, $V_n$—I, $V_n$—CF$_3$, $V_n$—CN, $V_n$—OR$^8$, $V_n$—C(=O)OR$^8$, $V_n$—OC(=O)R$^8$, $V_n$—C(=O)NR$^8$R$^9$, $V_n$—NR$^8$R$^9$, $V_n$—NR$^8$C(=O)R$^9$, $C_1$-$C_6$ alkyl, $C_2$-$C_6$ alkenyl, $C_2$-$C_6$ alkynyl, saturated and partially unsaturated $C_3$-$C_6$ cycloalkyl, saturated and partially unsaturated $C_1$-$C_6$ heterocyclyl, $V_n$-aryl, and $V_n$-heteroaryl.

4. The compound of claim 3, wherein $R^{20}$ is H.

5. The compound of claim 1, having the Formula Ia

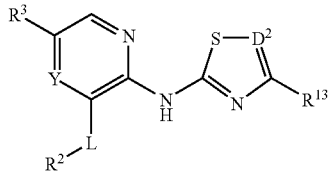

Ia wherein:
L is O, S, or CH$_2$;
Y is CH;
$D^2$ is N or CR$^{12}$;
$R^2$ is aryl, heteroaryl, saturated or partially unsaturated cycloalkyl, or saturated or partially unsaturated heterocyclyl, wherein said aryl, heteroaryl, cycloalkyl and heterocyclyl are monocyclic or bicyclic and are optionally substituted with one or more groups independently selected from $C_1$-$C_6$ alkyl, ($C_1$-$C_6$ alkyl)OH, $C_1$-$C_6$ heterocyclyl, F, Cl, Br, CF$_3$, CN, NO$_2$, OR$^6$, C(=O)R$^6$, C(=O)OR$^6$, C(=O)NR$^6$R$^7$, S(O)$_2$R$^6$, C(O)CH$_2$NH$_2$, and C(O)CH$_2$NR$^8$R$^9$,
$R^3$ is SR$^6$;
$R^6$ and $R^7$ are independently H, $C_1$-$C_{12}$ alkyl, saturated or partially unsaturated $C_3$-$C_{12}$ cycloalkyl, saturated or partially unsaturated $C_1$-$C_{12}$ heterocyclyl, $V_n$-aryl, or $V_n$-heteroaryl, wherein said alkyl, cycloalkyl, heterocyclyl, aryl and heteroaryl portions are optionally substituted with one or more groups independently selected from $C_1$-$C_6$ alkyl, saturated and partially unsaturated $C_1$-$C_6$ heterocyclyl [optionally substituted with C(O)O($C_1$-$C_6$ alkyl) or ($C_1$-$C_6$ alkyl)OH], aryl, heteroaryl, CF$_3$, F, Cl, Br, I, CN, OR$^8$, C(=O)R$^8$, C(=O)OR$^8$, C(=O)NR$^8$R$^9$, NR$^8$R$^9$, NR$^8$C(=O)R$^9$ or ($C_1$-$C_6$ alkyl)OH,
or $R^6$ and $R^7$ together with the atoms to which they are attached form a saturated or partially unsaturated heterocyclic ring, wherein said heterocyclic ring optionally comprises one or more additional ring heteroatoms independently selected from N, O or S;
$R^8$, $R^9$ and $R^{10}$ are independently H, $C_1$-$C_6$ alkyl, or saturated and partially unsaturated $C_1$-$C_6$ heterocyclyl, wherein said alkyl and heterocyclyl are optionally substituted with one or more groups independently selected from $C_1$-$C_6$ alkyl, saturated and partially unsaturated $C_1$-$C_6$ heterocyclyl, OR$^a$, NR$^a$R$^b$, C(=O)OR$^a$ and C(=O)NR$^a$R$^b$,
or $R^8$ and $R^9$ together with the atoms to which they are attached form a saturated or partially unsaturated heterocyclic ring;
or $R^9$ and $R^{10}$ together with the atoms to which they are attached form a saturated or partially unsaturated heterocyclic ring;
$R^{12}$ is H or $C_1$-$C_6$ alkyl;
$R^{13}$ is H, $C_1$-$C_6$ alkyl, $C_1$-$C_6$ alkenyl, $C_1$-$C_6$ alkynyl, saturated and partially unsaturated $C_3$-$C_6$ cycloalkyl, saturated and partially unsaturated $C_1$-$C_6$ heterocyclyl, CH$_2$-heterocyclyl, aryl, heteroaryl, (1-3C alkyl)heteroaryl, or (CH$_2$)$_n$(CR$^x$R$^y$)C(O)NR$^8$R$^9$, wherein said alkyl, alkenyl, alkynyl, cycloalkyl, CH$_2$-heterocyclyl, heterocyclyl, aryl, heteroaryl and (1-3C alkyl)heteroaryl are optionally substituted with one or more groups independently selected from oxo, F, Cl, CF$_3$, CN, OR$^8$, C(=O)OR$^8$, C(=O)NR$^8$R$^9$, NR$^8$R$^9$, C(O)($C_1$-$C_6$ alkyl), C(O)-heterocycle [optionally substituted with O—($C_1$-$C_6$ alkyl) or oxo], SR$^a$, SO$_2$R$^f$, SO$_2$NR$^c$R$^e$, C(O)($C_1$-$C_6$ alkyl)NR$^c$R$^d$, C(O)($C_1$-$C_6$ alkyl)OR$^c$, C(O)CH$_2$C(O) ($C_1$-$C_6$ alkyl), $C_1$-$C_6$ alkyl, saturated and partially unsaturated $C_1$-$C_6$ heterocycle (optionally substituted with oxo) and aryl;
or $R^{12}$ and $R^{13}$ together with the atoms to which they are attached form a heteroaryl ring;
$R^a$ and $R^b$ are independently H, $C_1$-$C_6$ alkyl, or saturated or partially unsaturated $C_1$-$C_6$ heterocyclyl;
each $R^c$, $R^e$ and $R^g$ is independently H or $C_1$-$C_6$ alkyl;
$R^d$ is H, $C_1$-$C_6$ alkyl or C(O)O($C_1$-$C_6$ alkyl);
$R^f$ is $C_1$-$C_6$ alkyl or ($C_1$-$C_6$ alkyl)NH$_2$;
V is alkylene having from 1 to 4 carbons, or alkenylene having from 2 to 4 carbons, wherein said alkylene and alkenylene are optionally substituted with $C_1$-$C_6$ alkyl, O($C_1$-$C_6$ alkyl), or ($C_1$-$C_6$ alkyl)NR$^c$R$^e$; and
n is 0 or 1.

6. The compound of claim 1, wherein $R^{12}$ is H.

7. The compound of claim 1, wherein $R^{13}$ is selected from H, $C_1$-$C_6$ alkyl, chloro($C_1$-$C_6$ alkyl), CF$_3$, (3-6C)cycloalkyl, ($C_1$-$C_6$ alkyl)CN, ($C_1$-$C_6$ alkyl)CO$_2$R$^8$, ($C_1$-$C_6$ alkyl)SR$^a$, ($C_1$-$C_6$ alkyl)SO$_2$R$^f$, ($C_1$-$C_6$ alkyl)aryl, ($C_1$-$C_6$ alkyl)OR$^8$, ($C_1$-$C_6$ alkyl)NR$^8$R$^9$, (CH$_2$)$_n$(CR$^x$R$^y$)C(O)NR$^8$R$^9$, (CH$_2$)$_n$(CR$^x$R$^y$)C(O)NH—N=CHNR$^8$R$^9$, ($C_1$-$C_6$ alkyl)C(O)-heterocyclyl, aryl, heteroaryl, ($C_1$-$C_3$ alkyl)hetAr$^1$, CH$_2$(CR$^x$R$^y$)C(O)OR$^8$, CH$_2$(CR$^x$R$^y$)C(O)heterocyclyl [optionally substituted with one or two groups selected from O—($C_1$-$C_6$ alkyl) and oxo], CH$_2$CH(CO$_2$H)—CH$_2$CH$_2$NHR$^8$, hetCyc$^1$ and CH$_2$hetCyc$^2$, wherein:
$R^x$ and $R^y$ are independently H, methyl or OMe,
n is 0 or 1,
hetCyc$^1$ is a saturated and partially unsaturated $C_1$-$C_6$ heterocyclic ring optionally substituted with one or more groups independently selected from $C_1$-$C_6$ alkyl, C(O) ($C_1$-$C_6$ alkyl), ($C_1$-$C_6$ alkyl)OH, C(O)O($C_1$-$C_6$ alkyl), C(O)($C_1$-$C_6$ alkyl)NR$^c$R$^d$, C(O)($C_1$-$C_6$ alkyl)OR$^c$, C(O) CH$_2$C(O)($C_1$-$C_6$ alkyl), C(O)NR$^8$R$^9$, SO$_2$NR$^c$R$^e$, SO$_2$R$^f$, C(=O)CHR$^g$NHC(=O)($C_1$-$C_6$ alkyl) and C(=O)CH$_2$OC(=O)($C_1$-$C_6$ alkyl),
hetCyc$^2$ is a heterocyclic ring optionally substituted with one or more groups independently selected from $C_1$-$C_6$ alkyl, C(O)($C_1$-$C_6$ alkyl), C(O)O($C_1$-$C_6$ alkyl), and oxo, and
hetAr$^1$ is a heteroaryl ring optionally substituted with $C_1$-$C_6$ alkyl, OH or CF$_3$.

8. The compound of claim 1, wherein $R^2$ is:
(i) phenyl optionally substituted with one or more groups independently selected from F, Cl, Br, CN, CF$_3$, $C_1$-$C_6$ alkyl, NO$_2$, SO$_2$($C_1$-$C_6$ alkyl), OH, O($C_1$-$C_6$ alkyl), CO$_2$H, CO$_2$($C_1$-$C_6$ alkyl), C(O) saturated and partially unsaturated $C_1$-$C_{12}$ hetercyclyl [optionally substituted with $C_1$-$C_6$ alkyl], saturated and partially unsaturated $C_1$-$C_6$ heterocyclyl and C(O)NR$^6$R$^7$;
(ii) a 5-6 membered heteroaryl ring having 1-2 nitrogen atoms;
(iii) a 9-10 membered bicyclic heteroaryl ring having a having 1 to 2 ring atoms independently selected from N and S;

(iv) a 5 membered saturated and partially unsaturated heterocyclic ring having at least one nitrogen atom, wherein the heterocyclic ring is optionally substituted with $CO_2$-($C_1$-$C_6$ alkyl), $C(O)NH(C_1$-$C_6$ alkyl), $C(O)CH_2N(C_1$-$C_6$ alkyl)$_2$, $C(O)(C_1$-$C_6$ alkyl)$CO_2H$, or $SO_2$-(heteroaryl); or (v) a 5-6 membered saturated or partially unsaturated cycloalkyl ring.

9. The compound of claim 1, wherein $R^3$ is $SR^6$.

10. The compound of claim 1, wherein $R^3$ is:

(i) S—$V_n$-aryl wherein n is 0, and aryl is phenyl optionally substituted with one or two groups independently selected from Cl, OH, CN, $CF_3$, $CO_2H$, $O(C_1$-$C_6$ alkyl), $O(C_1$-$C_6$ alkyl)$CO_2H$, $O(C_1$-$C_6$ alkyl)$NR^aR^b$, or $O(C_1$-$C_6$ alkyl)- saturated and partially unsaturated $C_1$-$C_6$ heterocycle;

(ii) S—$V_n$-aryl wherein n is 1, V is alkylene optionally substituted with $CH_2CH_2NR^cR^e$, and aryl is phenyl optionally substituted with F, Cl, or $O(C_1$-$C_6$ alkyl);

(iii) S—$V_n$-heteroaryl wherein n is 1, V is $C_1$-$C_6$ alkylene optionally substituted with $C_1$-$C_6$ alkyl, and heteroaryl is a 5-6 membered ring having 1-2 atoms independently selected from N, S and O;

(iv) S—$V_n$-heteroaryl wherein n is 1, V is $C_1$-$C_6$ alkylene, and heteroaryl is a 10-membered bicyclic heteroaryl having at least one nitrogen;

(v) $SR^6$ wherein $R^6$ is $V_n$-heteroaryl, n is 0, and the heteroaryl group is a 9-10 membered bicyclic heteroaromatic ring having 2-3 atoms independently selected from N, S and O, and optionally substituted with one or two groups independently selected from I, Br, $C_1$-$C_6$ alkyl and $CO_2H$;

(vi) S—$V_n$-heteroaryl wherein n is 0, and heteroaryl is a 5-6 membered ring having 1-4 atoms independently selected from N and S and optionally substituted with one or two groups independently selected from Cl, CN, $C_1$-$C_6$ alkyl, O—($C_1$-$C_6$ alkyl), ($C_1$-$C_6$ alkyl)$NR^8R^9$, ($C_1$-$C_6$ alkyl)CN, C(=O)O($C_1$-$C_6$ alkyl), and $CF_3$;

(vii) S—$CHR^{6a}R^{6b}$ wherein $R^{6a}$ is piperidinyl (optionally substituted with $C_1$-$C_6$ alkyl, $CO_2$—($C_1$-$C_6$ alkyl) or ($C_1$-$C_6$ alkyl)OH) or a structure having the formula

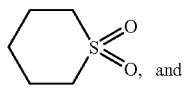

$R^{6b}$ is pyridyl, pyrimidyl, $C(O)O(C_1$-$C_6$ alkyl), ($C_1$-$C_6$ alkyl)OH, $C(O)NH(C_1$-$C_6$ alkyl), C(O)NH-heterocycle, or ($C_1$-$C_6$ alkyl);

(viii) S— saturated and partially unsaturated $C_3$-$C_{12}$ cycloalkyl, (ix) S— saturated and partially unsaturated $C_1$-$C_{12}$ heterocyclyl which is optionally substituted with oxo;

(x) S—($C_1$-$C_6$ alkyl)$C(O)OR^8$; or (xi) S—$CH_2C(O)$— saturated and partially unsaturated $C_1$-$C_6$ heterocycle, S—$CH_2C(O)$—$NR^8(C_1$-$C_6$ alkyl)$NR^aR^b$, S—$CH_2C(O)$—$NR^8(C_1$-$C_6$ alkyl)- saturated and partially unsaturated $C_1$-$C_6$ heterocycle, or S—($C_1$-$C_6$ alkyl)$NR^8R^9$.

11. A composition comprising a compound of claim 1 and a pharmaceutically acceptable diluent or carrier.

12. A method of preparing a compound of claim 1, said method comprising:
(a) reacting a compound of the formula

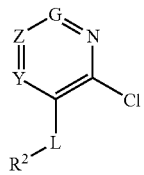

with a compound of the formula $R^1NH_2$ in the presence of a base catalyst or metal catalyst; or (b) reacting a compound of the formula

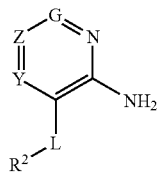

with a compound of the formula $R^1$—X, wherein X is Cl or Br, in the presence of a base catalyst or metal catalyst; or (c) for a compound of Formula I wherein $R^1$ is

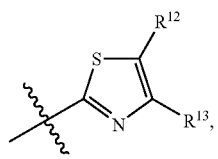

reacting a compound of the formula

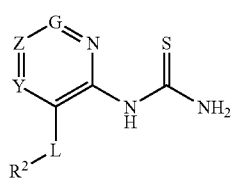

with a compound of the formula $R^{13}COCHR^{12}X$, wherein X is a leaving group, in the presence of a base; or (d) for a compound of Formula I wherein $R^1$ is

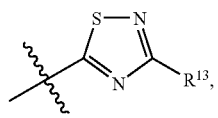

reacting a compound of the formula

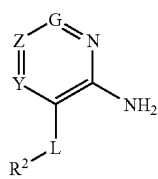

with a compound having the formula

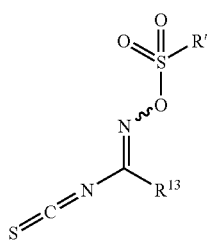

where R' is $C_1$-$C_6$ alkyl or aryl optionally substituted with $C_1$-$C_6$ alkyl, in the presence of a base; or (e) for a compound of Formula I wherein Z is $CR^3$ and $R^3$ is $SR^6$, reacting a corresponding compound having the formula

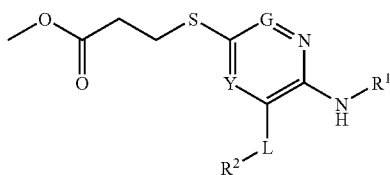

with a compound having the formula $R^6X$ wherein X is a leaving group or atom in the presence of a base; or (f) for a compound of Formula I wherein $R^1$ is

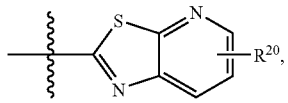

reacting a corresponding compound having the formula

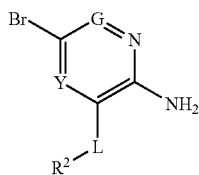

with a compound having the formula

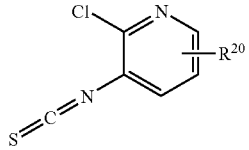

at elevated temperatures; or g) for a compound of Formula I wherein Z is $CR^3$, reacting a corresponding compound having the formula

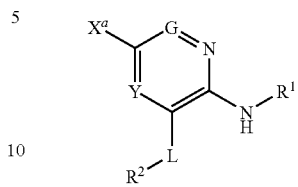

wherein $X^a$ is a leaving group or atom (e.g., a halogen such as Br, Cl or I,) with a compound having the formula $R^3$—$X^b$ wherein $X^b$ is a leaving group or atom, in the presence of a suitable base; or h) for a compound of Formula I wherein Z is C—$SR^6$ and $R^6$ is alkyl, $CH_2$-aryl, heteroaryl, or aryl and wherein said $R^6$ groups are optionally substituted, reacting a corresponding compound having the formula

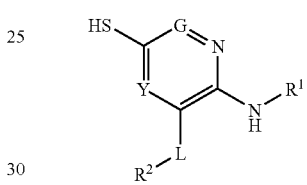

with a compound having the formula $R^6$—$X^c$ wherein $X^c$ is a leaving group or atom, in the presence of a suitable base; or i) for a compound of Formula I wherein L is O, reacting a corresponding compound having the formula

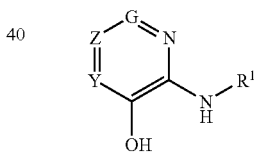

with a compound having the formula $R^2$—$X^d$, wherein $X^d$ is a leaving group or atom, in the presence of a base, or in the presence of a copper or palladium catalyst; or j) for a compound of Formula I wherein L is O or S, reacting a corresponding compound having the formula

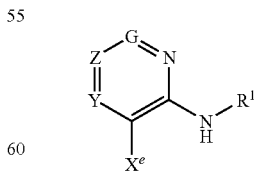

wherein $X^e$ is a leaving group or atom with a compound having the formula $R^2LH$ wherein L is O or S, respectively; in the presence of a palladium catalyst and a suitable base; or k) for a compound of Formula I wherein L is CH₂, reacting a corresponding compound having the formula

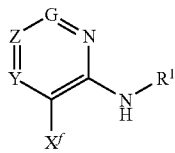

wherein X$^f$ is a leaving group or atom (e.g., Cl, Br, I, OTf or acetyloxy) in the presence of an organozinc compound having the formula R²—Zn—X$^g$ wherein X$^g$ is a halide, and a nickel or palladium catalyst; and removing any protecting group or groups and, if desired, forming a salt.

13. The compound of claim 1, wherein R² is selected from the structures:

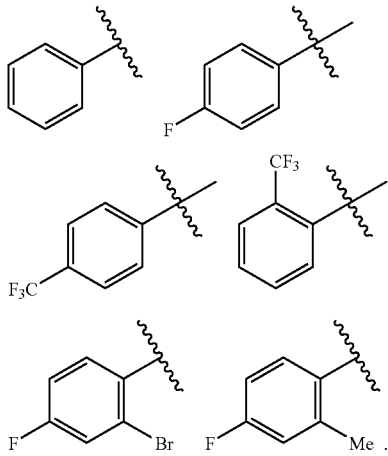

14. The compound of claim 1 wherein R⁶ is phenyl optionally substituted with one or two groups independently selected from CN, CF₃, and —O(C₁-C₆ alkyl).

15. The compound of claim 14, wherein R³ is selected from the structures:

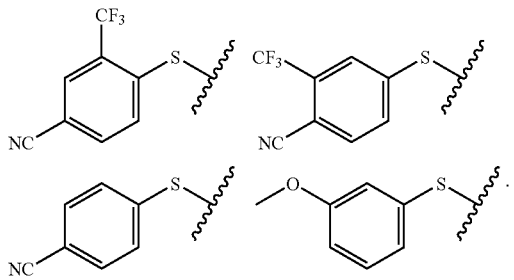

16. The compound of claim 1 wherein R⁶ is a 5-6 membered heteroaryl ring having 1-2 nitrogen atoms optionally substituted with one or two groups independently selected from Cl, CN, —O(C₁-C₆ alkyl), C(=O)O(C₁-C₆ alkyl), and CF₃.

17. The compound of claim 16, wherein R³ is selected from the structures:

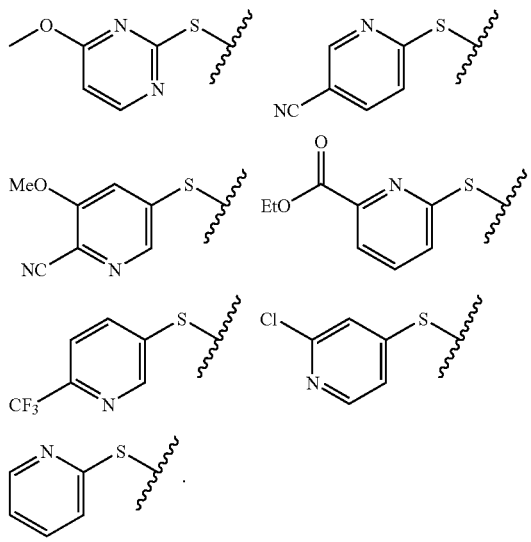

18. The compound of claim 1 wherein R⁶ is a 9-10 membered bicyclic heteroaromatic ring having 2-3 atoms independently selected from N, S and O (provided the ring does not contain an O—O bond) and is optionally substituted with one or two groups independently selected from Br, Cl, and C₁-C₆ alkyl).

19. The compound of claim 18, wherein R³ is selected from the structures:

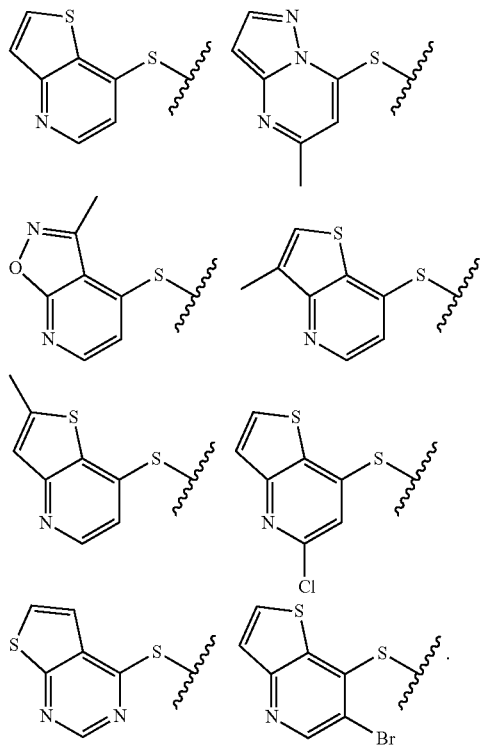

20. A compound selected from the group consisting of:

N-(4-methylthiazol-2-yl)-3-phenoxy-5-(phenylthio)pyridin-2-amine;
methyl 3-(6-(4-methylthiazol-2-ylamino)-5-phenoxypyridin-3-ylthio)propanoate ;
N-(5-(cyclohexylthio)-3-phenoxypyridin-2-yl)-4-methylthiazol-2-amine ;
N-(5-(benzylthio)-3-phenoxypyridin-2-yl)-4-methylthiazol-2-amine ;
4-methyl-N-(3-phenoxy-5-(pyridin-2-ylmethylthio)pyridin-2-yl)thiazol-2-amine ;
4-methyl-N-(3-phenoxy-5-(piperidin-4-ylmethylthio)pyridin-2-yl)thiazol-2-amine;
5-(2-methoxybenzylthio)-N-(4-methylthiazol-2-yl)-3-phenoxypyridin-2-amine;
5-(4-methoxybenzylthio)-N-(4-methylthiazol-2-yl)-3-phenoxypyridin-2-amine;
5-(2-chlorobenzylthio)-N-(4-methylthiazol-2-yl)-3-phenoxypyridin-2-amine;
N-(4-methylthiazol-2-yl)-3-phenoxy-5-(1-(pyridin-2-yl)ethylthio)pyridin-2-amine;
5-(3-methoxybenzylthio)-N-(4-methylthiazol-2-yl)-3-phenoxypyridin-2-amine;
5-(3-(dimethylamino)propylthio)-N-(4-methylthiazol-2-yl)-3-phenoxypyridin-2-amine;
N-(3-(2-chlorophenylthio)-5-(phenylthio)pyridin-2-yl)-4-methylthiazol-2-amine;
methyl 3-(5-(2-chlorophenylthio)-6-(4-methylthiazol-2-ylamino)pyridin-3-ylthio)propanoate;
N-(3-(2-chlorophenylthio)-5-(1-(pyridin-2-yl)ethylthio)pyridin-2-yl)-4-methylthiazol-2-amine;
N-(3-(2-chlorophenylthio)-5-(piperidin-4-ylmethylthio)pyridin-2-yl)-4-methylthiazol-2-amine;
N-(3-(2-chlorophenylthio)-5-(3-(dimethylamino)propylthio)pyridin-2-yl)-4-methylthiazol-2-amine;
N-(5-(2-chlorophenylthio)-3-phenoxypyridin-2-yl)-4-methylthiazol-2-amine;
N-(5-(3-chlorophenylthio)-3-phenoxypyridin-2-yl)-4-methylthiazol-2-amine;
N-(5-(2-methoxyphenylthio)-3-phenoxypyridin-2-yl)-4-methylthiazol-2-amine;
N-(5-(3-methoxyphenylthio)-3-phenoxypyridin-2-yl)-4-methylthiazol-2-amine;
3-(6-(4-methylthiazol-2-ylamino)-5-phenoxypyridin-3-ylthio)phenol;
2-(3-(6-(4-methylthiazol-2-ylamino)-5-phenoxypyridin-3-ylthio)phenoxy)acetic acid;
4-methyl-N-(3-phenoxy-5-(3-(2-(piperidin-1-yl)ethoxy)phenylthio)pyridin-2-yl)thiazol-2-amine;
N-(5-(3-(3-(dimethylamino)propoxy)phenylthio)-3-phenoxypyridin-2-yl)-4-methylthiazol-2-amine;
5-(2-fluorobenzylthio)-N-(4-methylthiazol-2-yl)-3-phenoxypyridin-2-amine;
N-(4-methylthiazol-2-yl)-3-phenoxy-5-(1-(pyridin-2-yl)propylthio)pyridin-2-amine;
2-((6-(4-methylthiazol-2-ylamino)-5-phenoxypyridin-3-ylthio)methyl)pyridin-3-ol;
3-(2-(3-phenoxy-5-(1-(pyridin-2-yl)ethylthio)pyridin-2-ylamino)thiazol-4-yl)propanoic acid;
4-chloro-3-(2-(4-methylthiazol-2-ylamino)-5-(phenylthio)pyridin-3-yloxy)benzoic acid;
4-chloro-N-(2-(dimethylamino)ethyl)-3-(2-(4-methylthiazol-2-ylamino)-5-(phenylthio)pyridin-3-yloxy)benzamide;
4-chloro-3-(2-(4-methylthiazol-2-ylamino)-5-(1-(pyridin-2-yl)ethylthio)pyridin-3-yloxy)benzoic acid;
4-chloro-N-(2-(dimethylamino)ethyl)-3-(2-(4-methylthiazol-2-ylamino)-5-(1-(pyridin-2-yl)ethylthio)pyridin-3-yloxy)benzamide;
N-(5-(2-chlorophenylthio)-3-phenoxypyridin-2-yl)-4-methylthiazol-2-amine;
N-(5-(3-chlorophenylthio)-3-phenoxypyridin-2-yl)-4-methylthiazol-2-amine;
N-(5-(2-methoxyphenylthio)-3-phenoxypyridin-2-yl)-4-methylthiazol-2-amine;
N-(5-(3-methoxyphenylthio)-3-phenoxypyridin-2-yl)-4-methylthiazol-2-amine;
methyl 3-(5-(2-chlorophenylthio)-6-(4-methylthiazol-2-ylamino)pyridin-3-ylthio)propanoate;
N-(5-(2,5-dimethoxyphenylthio)-3-phenoxypyridin-2-yl)-4-methylthiazol-2-amine;
N-(5-(2,5-dichlorophenylthio)-3-phenoxypyridin-2-yl)-4-methylthiazol-2-amine;
N-(5-(2,5-dimethylphenylthio)-3-phenoxypyridin-2-yl)-4-methylthiazol-2-amine;
N-(5-(1-(2-(dimethylamino)ethyl)-1H-tetrazol-5-ylthio)-3-phenoxypyridin-2-yl)-4-methylthiazol-2-amine;
4-methyl-N-(5-(4-methyl-4H-1,2,4-triazol-3-ylthio)-3-phenoxypyridin-2-yl)thiazol-2-amine;
3-(2-chlorophenylthio)-N-(4-methylthiazol-2-yl)-5-(phenylthio)pyridin-2-amine;
N-(5-([1,2,4]triazolo[4,3-a]pyridin-3-ylthio)-3-phenoxypyridin-2-yl)-4-methylthiazol-2-amine;
2-(4-methyl-5-(6-(4-methylthiazol-2-ylamino)-5-phenoxypyridin-3-ylthio)-4H-1,2,4-triazol-3-yl)acetonitrile;
methyl 3-(6-(4-phenethylthiazol-2-ylamino)-5-phenoxypyridin-3-ylthio)propanoate;
methyl 3-(6-(4-(1-methylpiperidin-4-yl)thiazol-2-ylamino)-5-phenoxypyridin-3-ylthio)propanoate;
methyl 3-(5-(4-fluorophenoxy)-6-(4-phenethylthiazol-2-ylamino)pyridin-3-ylthio)propanoate;
methyl 3-(5-(2-chlorophenylthio)-6-(4-methylthiazol-2-ylamino)pyridin-3-ylthio)propanoate;
methyl 3-(6-(4-methylthiazol-2-ylamino)-5-(phenylthio)pyridin-3-ylthio)propanoate;
tert-butyl 4-(5-(3-(4-fluorophenoxy)-5-(3-methoxy-3-oxopropylthio)pyridin-2-ylamino)-1,2,4-thiadiazol-3-yl)piperidine-1-carboxylate;
tert-butyl 4-((5-(3-(4-fluorophenoxy)-5-(3-methoxy-3-oxopropylthio)pyridin-2-ylamino)-1,2,4-thiadiazol-3-yl)methyl)piperidine-1-carboxylate;
N-(3-(2-chlorophenylthio)-5-(1-(pyridin-2-yl)ethylthio)pyridin-2-yl)-4-methylthiazol-2-amine;
N-(3-(2-chlorophenylthio)-5-(piperidin-4-ylmethylthio)pyridin-2-yl)-4-methylthiazol-2-amine;
N-(3-(2-chlorophenylthio)-5-(3-(dimethylamino)propylthio)pyridin-2-yl)-4-methylthiazol-2-amine;
4-phenethyl-N-(3-phenoxy-5-(piperidin-4-ylmethylthio)pyridin-2-yl)thiazol-2-amine;
3-(6-(4-methylthiazol-2-ylamino)-5-phenoxypyridin-3-ylthio)phenol;
4-methyl-N-(3-phenoxy-5-(3-(2-(piperidin-1-yl)ethoxy)phenylthio)pyridin-2-yl)thiazol-2-amine;
2-(3-(6-(4-methylthiazol-2-ylamino)-5-phenoxypyridin-3-ylthio)phenoxy)acetic acid;
N-(5-(3-(3-(dimethylamino)propoxy)phenylthio)-3-phenoxypyridin-2-yl)-4-methylthiazol-2-amine;
4-methyl-N-(3-phenoxy-5-(pyridin-2-ylthio)pyridin-2-yl)thiazol-2-amine;
4-methyl-N-(3-phenoxy-5-(pyridin-4-ylthio)pyridin-2-yl)thiazol-2-amine;

4-methyl-N-(3-phenoxy-5-(pyrimidin-2-ylthio)pyridin-2-yl)thiazol-2-amine;
4-methyl-N-(5-(6-methylpyridin-2-ylthio)-3-phenoxypyridin-2-yl)thiazol-2-amine;
4-methyl-N-(5-(4-methylthiazol-2-ylthio)-3-phenoxypyridin-2-yl)thiazol-2-amine;
N-(3-(2-chlorophenylthio)-5-(pyridin-4-ylthio)pyridin-2-yl)-4-methylthiazol-2-amine;
4-(1-methylpiperidin-4-yl)-N-(3-phenoxy-5-(phenylthio)pyridin-2-yl)thiazol-2-amine;
N-(3,5-bis(phenylthio)pyridin-2-yl)-4-methylthiazol-2-amine;
4-methyl-N-(3-(phenylthio)-5-(pyridin-2-ylthio)pyridin-2-yl)thiazol-2-amine;
3-methyl-N-(3-phenoxy-5-(pyridin-2-ylthio)pyridin-2-yl)-1,2,4-thiadiazol-5-amine;
N-(5-(4-methoxyphenylthio)-3-phenoxypyridin-2-yl)-3-methyl-1,2,4-thiadiazol-5-amine;
N-(3-(4-fluorophenoxy)-5-(pyridin-2-ylthio)pyridin-2-yl)-3-isobutyl-1,2,4-thiadiazol-5-amine;
5-(2-chloropyridin-4-ylthio)-N-(4-methylthiazol-2-yl)-3-phenoxypyridin-2-amine;
N-(5-(2-chloropyrimidin-4-ylthio)-3-phenoxypyridin-2-yl)-4-methylthiazol-2-amine;
5-(4,6-dimethylpyrimidin-2-ylthio)-N-(4-methylthiazol-2-yl)-3-phenoxypyridin-2-amine;
N-(5-(4,6-dimethoxypyrimidin-2-ylthio)-3-phenoxypyridin-2-yl)-4-methylthiazol-2-amine;
5-(4-methoxypyrimidin-2-ylthio)-N-(4-methylthiazol-2-yl)-3-phenoxypyridin-2-amine;
N-(4-methylthiazol-2-yl)-3-phenoxy-5-(thieno[3,2-b]pyridin-7-ylthio)pyridin-2-amine;
4-methyl-N-(5-(3-methylisoxazolo[5,4-b]pyridin-4-ylthio)-3-phenoxypyridin-2-yl)thiazol-2-amine;
N-(5-(2-(methoxymethyl)pyrimidin-4-ylthio)-3-phenoxypyridin-2-yl)-4-methylthiazol-2-amine;
4-phenethyl-N-(3-phenoxy-5-(thieno[3,2-b]pyridin-7-ylthio)pyridin-2-yl)thiazol-2-amine;
N-(5-(3-methylisoxazolo[5,4-b]pyridin-4-ylthio)-3-phenoxypyridin-2-yl)-4-phenethylthiazol-2-amine;
N-(5-(5-methylpyrazolo[1,5-a]pyrimidin-7-ylthio)-3-phenoxypyridin-2-yl)-4-phenethylthiazol-2-amine;
4-phenethyl-N-(3-phenoxy-5-(thieno[3,2-d]pyrimidin-4-ylthio)pyridin-2-yl)thiazol-2-amine;
4-methyl-N-(5-(5-methylpyrazolo[1,5-a]pyrimidin-7-ylthio)-3-phenoxypyridin-2-yl)thiazol-2-amine;
4-methyl-N-(3-phenoxy-5-(thieno[3,2-d]pyrimidin-4-ylthio)pyridin-2-yl)thiazol-2-amine;
4-(1-methylpiperidin-4-yl)-N-(3-phenoxy-5-(thieno[3,2-b]pyridin-7-ylthio)pyridin-2-yl)thiazol-2-amine;
N-(5-(3-methylisoxazolo[5,4-b]pyridin-4-ylthio)-3-phenoxypyridin-2-yl)-4-(1-methylpiperidin-4-yl)thiazol-2-amine;
N-(5-(2-iodothieno[3,2-b]pyridin-7-ylthio)-3-phenoxypyridin-2-yl)-4-methylthiazol-2-amine;
4-methyl-N-(5-(2-methylthieno[3,2-b]pyridin-7-ylthio)-3-phenoxypyridin-2-yl)thiazol-2-amine;
N-(5-(2-methylthieno[3,2-b]pyridin-7-ylthio)-3-phenoxypyridin-2-yl)-4-phenethylthiazol-2-amine;
N-(5-(2,5-dimethylpyrazolo[1,5-a]pyrimidin-7-ylthio)-3-phenoxypyridin-2-yl)-4-phenethylthiazol-2-amine;
N-(3-(4-fluorophenoxy)-5-(thieno[3,2-b]pyridin-7-ylthio)pyridin-2-yl)-4-phenethylthiazol-2-amine;
N-(3-(4-fluorophenoxy)-5-(3-methylisoxazolo[5,4-b]pyridin-4-ylthio)pyridin-2-yl)-4-phenethylthiazol-2-amine;
N-(3-(4-fluorophenoxy)-5-(5-methylpyrazolo[1,5-a]pyrimidin-7-ylthio)pyridin-2-yl)-4-phenethylthiazol-2-amine;
N-(5-(2,5-dimethylpyrazolo[1,5-a]pyrimidin-7-ylthio)-3-(4-fluorophenoxy)pyridin-2-yl)-4-phenethylthiazol-2-amine;
N-(3-(4-fluorophenoxy)-5-(2-methylthieno[3,2-b]pyridin-7-ylthio)pyridin-2-yl)-4-phenethylthiazol-2-amine;
4-(6-(4-methylthiazol-2-ylamino)-5-phenoxypyridin-3-ylthio)benzonitrile;
N-(3-(2-chlorophenylthio)-5-(thieno[3,2-b]pyridin-7-ylthio)pyridin-2-yl)-4-methylthiazol-2-amine;
4-(5-phenoxy-6-(4-(piperidin-4-yl)thiazol-2-ylamino)pyridin-3-ylthio)benzonitrile;
N-(5-(furo[3,2-c]pyridin-4-ylthio)-3-phenoxypyridin-2-yl)-4-methylthiazol-2-amine;
N-(5-(2-iodothieno[3,2-b]pyridin-7-ylthio)-3-phenoxypyridin-2-yl)-4-(piperidin-4-yl)thiazol-2-amine;
4-methyl-N-(3-(phenylthio)-5-(thieno[3,2-b]pyridin-7-ylthio)pyridin-2-yl)thiazol-2-amine;
4-methyl-N-(5-(3-methylisoxazolo[5,4-b]pyridin-4-ylthio)-3-(phenylthio)pyridin-2-yl)thiazol-2-amine;
4-(6-(4-methylthiazol-2-ylamino)-5-(phenylthio)pyridin-3-ylthio)benzonitrile;
4-methyl-N-(3-(phenylthio)-5-(5,6,7,8-tetrahydropyrido[4,3-d]pyrimidin-4-ylthio)pyridin-2-yl)thiazol-2-amine;
tert-butyl 4-(5-(3-(4-fluorophenoxy)-5-(thieno[3,2-b]pyridin-7-ylthio)pyridin-2-ylamino)-1,2,4-thiadiazol-3-yl)piperidine-1-carboxylate;
N-(4-cyclopropylthiazol-2-yl)-3-phenoxy-5-(pyridin-4-ylthio)pyridin-2-amine;
4-isobutyl-N-(3-phenoxy-5-(pyridin-4-ylthio)pyridin-2-yl)thiazol-2-amine;
4-cyclohexyl-N-(3-phenoxy-5-(pyridin-4-ylthio)pyridin-2-yl)thiazol-2-amine;
N-(3-phenoxy-5-(pyridin-4-ylthio)pyridin-2-yl)-4-(trifluoromethyl)thiazol-2-amine;
methyl 3-(2-(3-phenoxy-5-(pyridin-4-ylthio)pyridin-2-ylamino)thiazol-4-yl)propanoate;
N-(3-phenoxy-5-(pyridin-4-ylthio)pyridin-2-yl)-4-(pyridin-2-yl)thiazol-2-amine;
N-(3-phenoxy-5-(pyridin-4-ylthio)pyridin-2-yl)-4-phenylthiazol-2-amine;
N-(3-phenoxy-5-(pyridin-4-ylthio)pyridin-2-yl)-4-(thiophen-3-yl)thiazol-2-amine;
4-phenethyl-N-(3-phenoxy-5-(pyridin-4-ylthio)pyridin-2-yl)thiazol-2-amine;
4-ethyl-N-(3-phenoxy-5-(pyridin-4-ylthio)pyridin-2-yl)thiazol-2-amine;
N-(3-phenoxy-5-(pyridin-4-ylthio)pyridin-2-yl)thiazol-2-amine;
4-isopropyl-N-(3-phenoxy-5-(pyridin-4-ylthio)pyridin-2-yl)thiazol-2-amine;
N-(5-(2-chloro-5-methoxyphenylthio)-3-phenoxypyridin-2-yl)-4-methylthiazol-2-amine;
(R)-4-methyl-N-(5-(5-methyl-6,7-dihydro-5H-cyclopenta[d]pyrimidin-4-ylthio)-3-phenoxypyridin-2-yl)thiazol-2-amine;
3-(2-(3-phenoxy-5-(pyridin-4-ylthio)pyridin-2-ylamino)thiazol-4-yl)propanoic acid;
N-(5-(3,5-dimethylisoxazolo[4,5-b]pyridin-7-ylthio)-3-phenoxypyridin-2-yl)-4-methylthiazol-2-amine;
1-(4-(2-(3-phenoxy-5-(thieno[3,2-b]pyridin-7-ylthio)pyridin-2-ylamino)thiazol-4-yl)piperidin-1-yl)ethanone;

1-(4-(5-(3-phenoxy-5-(thieno[3,2-b]pyridin-7-ylthio)pyridin-2-ylamino)-1,2,4-thiadiazol-3-yl)piperidin-1-yl)ethanone;
1-(4-(5-(3-(phenylthio)-5-(thieno[3,2-b]pyridin-7-ylthio)pyridin-2-ylamino)-1,2,4-thiadiazol-3-yl)piperidin-1-yl)ethanone;
1-(4-(2-(3-(phenylthio)-5-(pyridin-2-ylthio)pyridin-2-ylamino)thiazol-4-yl)piperidin-1-yl)ethanone;
methyl 4-(2-(3-(phenylthio)-5-(pyridin-2-ylthio)pyridin-2-ylamino)thiazol-4-yl)piperidine-1-carboxylate;
1-(4-(2-(3-(phenylthio)-5-(thieno[3,2-b]pyridin-7-ylthio)pyridin-2-ylamino)thiazol-4-yl)piperidin-1-yl)ethanone;
4-(1-(methylsulfonyl)piperidin-4-yl)-N-(3-(phenylthio)-5-(thieno[3,2-b]pyridin-7-ylthio)pyridin-2-yl)thiazol-2-amine;
2-(dimethylamino)-1-(4-(2-(3-(phenylthio)-5-(thieno[3,2-b]pyridin-7-ylthio)pyridin-2-ylamino)thiazol-4-yl)piperidin-1-yl)ethanone;
1-(4-(5-(3-(4-fluorophenoxy)-5-(5-methylpyrazolo[1,5-a]pyrimidin-7-ylthio)pyridin-2-ylamino)-1,2,4-thiadiazol-3-yl)piperidin-1-yl)ethanone;
1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone;
N-(3-(4-fluorophenoxy)-5-(thieno[3,2-b]pyridin-7-ylthio)pyridin-2-yl)-3-(1-(methylsulfonyl)piperidin-4-yl)-1,2,4-thiadiazol-5-amine;
2-(dimethylamino)-1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone;
3-phenylthio)-N-(3-(piperidin-4-yl)-1,2,4-thiadiazol-5-yl)-5-(thieno[3,2-b]pyridin-7-ylthio)pyridin-2-amine;
N-(3-(phenylthio)-5-(pyridin-2-ylthio)pyridin-2-yl)-4-(piperidin-4-yl)thiazol-2-amine;
tert-butyl 4-(2-(3-(phenylthio)-5-(thieno[3,2-b]pyridin-7-ylthio)pyridin-2-ylamino)thiazol-4-yl)piperidine-1-carboxylate;
tert-butyl 4-(5-(3-(4-fluorophenoxy)-5-(5-methylpyrazolo[1,5-a]pyrimidin-7-ylthio)pyridin-2-ylamino)-1,2,4-thiadiazol-3-yl)piperidine-1-carboxylate;
sodium 4-(6-(4-methylthiazol-2-ylamino)-5-phenoxypyridin-3-ylthio)benzoate;
3-methyl-7-(6-(4-phenethylthiazol-2-ylamino)-5-phenoxypyridin-3-ylthio)thieno[3,2-b]pyridine-6-carboxylic acid;
3-methyl-7-(6-(4-methylthiazol-2-ylamino)-5-phenoxypyridin-3-ylthio)thieno[3,2-b]pyridine-6-carboxylic acid;
N-(5-(6,7-dihydro-5H-pyrrolo[3,4-b]pyridin-4-ylthio)-3-phenoxypyridin-2-yl)-4-methylthiazol-2-amine;
N-(4-methylthiazol-2-yl)-3-phenoxy-5-(5,6,7,8-tetrahydropyrido[4,3-d]pyrimidin-4-ylthio)pyridin-2-amine;
1-(4-((5-(3-(4-fluorophenoxy)-5-(thieno[3,2-b]pyridin-7-ylthio)pyridin-2-ylamino)-1,2,4-thiadiazol-3-yl)methyl)piperidin-1-yl)ethanone;
1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone;
2-(dimethylamino)-1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone;
tert-butyl 4-(5-(3-phenoxy-5-(thieno[3,2-b]pyridin-7-ylthio)pyridin-2-ylamino)-1,2,4-thiadiazol-3-yl)piperidine-1-carboxylate;
N-(5-((3-methoxypyridin-2-yl)methylthio)-3-phenoxypyridin-2-yl)-4-methylthiazol-2-amine;
4-methyl-N-(3-phenoxy-5-(piperidin-4-yl(pyridin-2-yl)methylthio)pyridin-2-yl)thiazol-2-amine;
4-methyl-N-(3-phenoxy-5-(piperidin-4-yl(pyrazin-2-yl)methylthio)pyridin-2-yl)thiazol-2-amine;
4-methyl-N-(3-phenoxy-5-(piperidin-4-yl(pyrimidin-2-yl)methylthio)pyridin-2-yl)thiazol-2-amine;
N-(5-((3-chloropyridin-2-yl)(piperidin-4-yl)methylthio)-3-phenoxypyridin-2-yl)-4-methylthiazol-2-amine;
N-(2-(dimethylamino)ethyl)-3-(2-(4-isobutylthiazol-2-ylamino)-5-(pyrimidin-2-ylthio)pyridin-3-yloxy)benzamide;
2-(4-((6-(4-methylthiazol-2-ylamino)-5-phenoxypyridin-3-ylthio)(pyridin-2-yl)methyl)piperidin-1-yl)ethanol;
4-methyl-N-(5-((1-methylpiperidin-4-yl)(pyridin-2-yl)methylthio)-3-phenoxypyridin-2-yl)thiazol-2-amine;
N-(5-((l-isopropyl piperidin-4-yl)(pyridine -2-yl)methylthio)-3-phenoxypyridin-2-yl)-4-methylthiazol-2-amine;
1-((6-(4-methylthiazol-2-ylamino)-5-phenoxypyridin-3-ylthio)methyl)pyrrolidin-2-one;
Ethyl 2-(1-methylpiperidin-4-yl)-2-(6-(4-methylthiazol-2-ylamino)-5-phenoxypyridin-3-ylthio)acetate;
2-(1-methylpiperidin-4-yl)-2-(6-(4-methylthiazol-2-ylamino)-5-phenoxypyridin-3-ylthio)ethanol;
N-ethyl-2-(6-(4-methylthiazol-2-ylamino)-5-phenoxypyridin-3-ylthio)-2-(piperidin-4-yl)acetamide;
2-(6-(4-methylthiazol-2-ylamino)-5-phenoxypyridin-3-ylthio)-2-(piperidin-4-yl)-1-(pyrrolidin-1-yl)ethanone;
1-(indolin-1-yl)-2-(6-(4-methylthiazol-2-ylamino)-5-phenoxypyridin-3-ylthio)-2-(piperidin-4-yl)ethanone;
1-(7-azabicyclo[2.2.1]heptan-7-yl)-2-(6-(4-methylthiazol-2-ylamino)-5-phenoxypyridin-3-ylthio)-2-(piperidin-4-yl)ethanone;
1-(2-methylpiperidin-1-yl)-2-(6-(4-methylthiazol-2-ylamino)-5-phenoxypyridin-3-ylthio)-2-(piperidine-4-yl)ethanone *mixture of diastereomers;
2-(4-((6-(4-phenethylthiazol-2-ylamino)-5-phenoxypyridin-3-ylthio)(pyridin-2-yl)methyl)piperidin-1-yl)ethanol;
4-methyl-N-(3-phenoxy-5-(1-(pyridin-2-yl)ethylthio)pyridin-2-yl)thiazol-2-amine;
N-(5-(3-(dimethylamino)-1-phenylpropylthio)-3-phenoxypyridin-2-yl)-4-methylthiazol-2-amine;
5-((5-cyclopropyl-1,3,4-thiadiazol-2-yl)methylthio)-N-(4-methylthiazol-2-yl)-3-phenoxypyridin-2-amine;
5-((1,2,4-oxadiazol-3-yl)methylthio)-N-(4-methylthiazol-2-yl)-3-phenoxypyridin-2-amine;
5-((5-methylisoxazol-3-yl)methylthio)-N-(4-methylthiazol-2-yl)-3-phenoxypyridin-2-amine;
5-((3,5-dimethylisoxazol-4-yl)methylthio)-N-(4-methylthiazol-2-yl)-3-phenoxypyridin-2-amine;
5-((5-chloro-1,2,4-thiadiazol-3-yl)methylthio)-N-(4-methylthiazol-2-yl)-3-phenoxypyridin-2-amine;
N-(5-(isoquinolin-1-ylmethylthio)-3-phenoxypyridin-2-yl)-4-methylthiazol-2-amine;
N-(4-((6-(4-methylthiazol-2-ylamino)-5-phenoxypyridin-3-ylthio)methypthiazol-2-yl)acetamide;
N-(5-((5-cyclopropyl-1,3,4-thiadiazol-2-yl)methylthio)-3-(phenylthio)pyridin-2-yl)-4-methylthiazol-2-amine;
4-methyl-N-(5-((5-methylisoxazol-3-yl)methylthio)-3-(phenylthio)pyridin-2-yl)thiazol-2-amine;
N-(5-((3,5-dimethylisoxazol-4-yl)methylthio)-3-(phenylthio)pyridin-2-yl)-4-methylthiazol-2-amine;
2-(6-(4-methylthiazol-2-ylamino)-5-phenoxypyridin-3-ylthio)-1-(pyrrolidin-1-yl)ethanone;

N-(2-(dimethylamino)ethyl)-N-methyl-2-(6-(4-methylthiazol-2-ylamino)-5-phenoxypyridin-3-ylthio)acetamide;
1-(4-methylpiperazin-1-yl)-2-(6-(4-methylthiazol-2-ylamino)-5-phenoxypyridin-3-ylthio)ethanone;
2-(6-(4-methylthiazol-2-ylamino)-5-phenoxypyridin-3-ylthio)-N-(2-(pyrrolidin-1-yl)ethyl)acetamide;
{5-[(1,1-dioxo-hexahydro-1$\lambda^6$-thiopyran-4-yl)-pyridin-2-yl-methylsulfanyl]-3-phenoxy-pyridin-2-yl}-(4-methyl-thiazol-2-yl)-amine;
4-methyl-N-(3-phenoxy-5-(1-(piperidin-4-yl)ethylthio)pyridin-2-yl)thiazol-2-amine;
2,2-dimethyl-3-(2-(3-phenoxy-5-(thieno[3,2-b]pyridin-7-ylthio)pyridin-2-ylamino)thiazol-4-yl)propanoic acid;
tert-butyl 4-(5-(3-phenoxy-5-(pyridin-2-ylthio)pyridin-2-ylamino)-1,2,4-thiadiazol-3-yl)piperidine-1-carboxylate;
3-isobutyl-N-(3-phenoxy-5-(pyridin-2-ylthio)pyridin-2-yl)-1,2,4-thiadiazol-5-amine;
3-isopropyl-N-(3-phenoxy-5-(pyridin-2-ylthio)pyridin-2-yl)-1,2,4-thiadiazol-5-amine;
N-(3-phenoxy-5-(pyridin-2-ylthio)pyridin-2-yl)-3-(tetrahydrofuran-2-yl)-1,2,4-thiadiazol-5-amine;
N-(3-phenoxy-5-(pyridin-2-ylthio)pyridin-2-yl)-3-(piperidin-4-yl)-1,2,4-thiadiazol-5-amine;
1-(4-(5-(3-phenoxy-5-(pyridin-2-ylthio)pyridin-2-ylamino)-1,2,4-thiadiazol-3-yl)piperidin-1-yl)ethanone;
2-methoxy-1-(4-(5-(3-phenoxy-5-(piperidi-2-ylthio)piperidi-2-ylamino)-1,2,4-thiadiazol-3-yl)piperidine-1-yl)ethanone;
2-(dimethylamino)-1-(4-(5-(3-phenoxy-5-(pyridin-2-ylthio)pyridin-2-ylamino)-1,2,4-thiadiazol-3-yl)piperidin-1-yl)ethanone;
N,N-dimethyl-4-(5-(3-phenoxy-5-(pyridin-2-ylthio)pyridin-2-ylamino)-1,2,4-thiadiazol-3-yl)piperidine-1-carboxamide;
N,N-dimethyl-4-(5-(3-phenoxy-5-(pyridin-2-ylthio)pyridin-2-ylamino)-1,2,4-thiadiazol-3-yl)piperidine-1-sulfonamide;
2-methyl-1-(4-(5-(3-phenoxy-5-(pyridin-2-ylthio)pyridin-2-ylamino)-1,2,4-thiadiazol-3-yl)piperidin-1-yl)propan-1-one;
3-(1-(methylsulfonyl)piperidin-4-yl)-N-(3-phenoxy-5-(pyridin-2-ylthio)pyridin-2-yl)-1,2,4-thiadiazol-5-amine;
2-oxo-2-(4-(5-(3-phenoxy-5-(pyridin-2-ylthio)pyridin-2-ylamino)-1,2,4-thiadiazol-3-yl)piperidin-1-yl)ethyl acetate;
4-(5-(3-phenoxy-5-(pyridin-2-ylthio)pyridin-2-ylamino)-1,2,4-thiadiazol-3-yl)piperidine-1-carboxamide;
2-hydroxy-1-(4-(5-(3-phenoxy-5-(pyridin-2-ylthio)pyridin-2-ylamino)-1,2,4-thiadiazol-3-yl)piperidin-1-yl)ethanone;
tert-butyl 2-oxo-2-(4-(5-(3-phenoxy-5-(pyridin-2-ylthio)pyridin-2-ylamino)-1,2,4-thiadiazol-3-yl)piperidin-1-yl)ethylcarbamate;
(R)-2-hydroxy-1-(4-(5-(3-phenoxy-5-(pyridin-2-ylthio)pyridin-2-ylamino)-1,2,4-thiadiazol-3-yl)piperidin-1-yl)propan-1-one;
2-methyl-1-(4-(5-(3-phenoxy-5-(pyridin-2-ylthio)pyridin-2-ylamino)-1,2,4-thiadiazol-3-yl)piperidin-1-yl)propan-1-one;
2-amino-1-(4-(5-(3-phenoxy-5-(pyridin-2-ylthio)pyridin-2-ylamino)-1,2,4-thiadiazol-3-yl)piperidin-1-yl)ethanone;
2-(4-(5-(3-phenoxy-5-(pyridin-2-ylthio)pyridin-2-ylamino)-1,2,4-thiadiazol-3-yl)piperidin-1-yl)ethanol;
4-(5-(3-Phenoxy-5-(pyridin-2-ylthio)pyridin-2-ylamino)-1,2,4-thiadiazol-3-yl)piperidine-1-sulfonamide;
3-(1-(2-aminoethylsulfonyl)piperidin-4-yl)-N-(3-phenoxy-5-(pyridin-2-ylthio)pyridin-2-yl)-1,2,4-thiadiazol-5-amine;
tert-butyl 3-methyl-4-(2-(3-phenoxy-5-(pyridin-2-ylthio)pyridin-2-ylamino)thiazol-4-yl)piperidine-1-carboxylate;
1-(3-methyl-4-(2-(3-phenoxy-5-(pyridin-2-ylthio)pyridin-2-ylamino)thiazol-4-yl)piperidin-1-yl)ethanone;
1-(4-(2-(3-phenoxy-5-(pyridin-2-ylthio)pyridin-2-ylamino)thiazol-4-yl)piperidin-1-yl)ethanone;
Methyl 3-(5-phenoxy-6-(thiazolo[5,4-b]pyridin-2-ylamino)pyridin-3-ylthio)propanoate;
N-(3-phenoxy-5-(pyridin-4-ylthio)pyridin-2-yl)thiazolo[5,4-b]pyridin-2-amine;
4-(5-phenoxy-6-(thiazolo[5,4-b]pyridin-2-ylamino)pyridin-3-ylthio)benzonitrile;
N-(3-phenoxy-5-(pyrimidin-2-ylthio)pyridin-2-yl)thiazolo[5,4-b]pyridin-2-amine;
N-(3-phenoxy-5-(thieno[3,2-b]pyridin-7-ylthio)pyridin-2-yl)thiazolo[5,4-b]pyridin-2-amine;
N-(5-(pyridin-2-ylthio)-3-(4-(trifluoromethyl)phenoxy)pyridin-2-yl)-3-(tetrahydrofuran-2-yl)-1,2,4-thiadiazol-5-amine;
N-(4-(2-(5-methyloxazol-2-yl)ethyl)thiazol-2-yl)-3-phenoxy-5-(thieno[3,2-b]pyridin-7-ylthio)pyridin-2-amine ;
4-(2-(5-methyloxazol-2-yl)ethyl)-N-(3-phenoxy-5-(piperidin-4-ylmethylthio)pyridin-2-yl)thiazol-2-amine;
N-(3-(2-fluorophenylthio)-5-(phenylthio)pyridin-2-yl)-4-methylthiazol-2-amine;
2-(dimethylamino)-1-(4-(5-(3-(4-fluorophenoxy)-5-(thieno[3,2-b]pyridin-7-ylthio)pyridin-2-ylamino)-1,2,4-thiadiazol-3-yl)piperidin-1-yl)ethanone;
1-(4-((5-(3-(4-fluorophenoxy)-5-(thieno[3,2-b]pyridin-7-ylthio)pyridin-2-ylamino)-1,2,4-thiadiazol-3-yl)methyl)piperidin-1-yl)ethanone;
1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone;
2-(dimethylamino)-1-(4-(5-(3-(4-fluorophenoxy)-5-(3-methylisoxazolo[5,4-b]pyridin-4-ylthio)pyridin-2-ylamino)-1,2,4-thiadiazol-3-yl)piperidin-1-yl)ethanone;
3-(2-bromo-4-fluorophenoxy)-5-(3-methoxyphenylthio)-N-(4-(piperidin-4-yl)thiazol-2-yl)pyridin-2-amine;
4-(2-(3-(4-fluorophenoxy)-5-(3-methoxyphenylthio)pyridin-2-ylamino)thiazol-4-yl)piperidine-1-carboxylate trifluoroacetate;
1-(4-(2-(3-(4-fluoro-2-methylphenoxy)-5-(3-methoxyphenylthio)pyridin-2-ylamino)thiazol-4-yl)piperidin-1-yl)ethanone;
1-(4-(2-(3-(4-fluorophenoxy)-5-(3-methoxyphenylthio)pyridin-2-ylamino)thiazol-4-yl)piperidin-1-yl)ethanone;
1-(4-(2-(3-(2-bromo-4-fluorophenoxy)-5-(3-methoxyphenylthio)pyridin-2-ylamino)thiazol-4-yl)piperidin-1-yl)ethanone;
1-(4-(2-(3-(2-bromo-4-fluorophenoxy)-5-(3-methoxyphenylthio)pyridin-2-ylamino)thiazol-4-yl)piperidin-1-yl)-2-(dimethylamino)ethanone;
1-(4-(2-(5-(thieno[3,2-b]pyridin-7-ylthio)-3-(4-(trifluoromethyl)phenoxy)pyridin-2-ylamino)thiazol-4-yl)piperidin-1-yl)ethanone;

1-(4-(2-(5-(thieno[3,2-b]pyridin-7-ylthio)-3-(2-(trifluoromethyl)phenoxy)pyridin-2-ylamino)thiazol-4-yl)piperidin-1-yl)ethanone;
1-(4-(2-(5-(2-methylthieno[3,2-b]pyridin-7-ylthio)-3-phenoxypyridin-2-ylamino)thiazol-4-yl)piperidin-1-yl)ethanone;
1-(4-(2-(5-(4-methoxypyrimidin-2-ylthio)-3-phenoxypyridin-2-ylamino)thiazol-4-yl)piperidin-1-yl)ethanone;
4-(6-(4-(1-acetylpiperidin-4-yl)thiazol-2-ylamino)-5-phenoxypyridin-3-ylthio)benzonitrile;
4-(6-(4-(1-acetylpiperidin-4-yl)thiazol-2-ylamino)-5-phenoxypyridin-3-ylthio)-3-(trifluoromethyl)benzonitrile;
4-(6-(4-(1-acetylpiperidin-4-yl)thiazol-2-ylamino)-5-phenoxypyridin-3-ylthio)-2-(trifluoromethyl)benzonitrile;
6-(6-(4-(1-acetylpiperidin-4-yl)thiazol-2-ylamino)-5-phenoxypyridin-3-ylthio)nicotinonitrile;
5-(6-(4-(1-acetylpiperidin-4-yl)thiazol-2-ylamino)-5-phenoxypyridin-3-ylthio)-3-methoxypicolinonitrile;
Ethyl 6-(6-(4-(1-acetylpiperidin-4-yl)thiazol-2-ylamino)-5-phenoxypyridin-3-ylthio)picolinate;
1-(4-(2-(3-phenoxy-5-(6-(trifluoromethyl)pyridin-3-ylthio)pyridin-2-ylamino)thiazol-4-yl)piperidin-1-yl)ethanone;
1-(4-(2-(5-(6-bromothieno[3,2-b]pyridin-7-ylthio)-3-phenoxypyridin-2-ylamino)thiazol-4-yl)piperidin-1-yl)ethanone;
1-(4-(5-(5-(thieno[3,2-b]pyridin-7-ylthio)-3-(2-(trifluoromethyl)phenoxy)pyridin-2-ylamino)-1,2,4-thiadiazol-3-yl)piperidin-1-yl)ethanone;
tert-butyl 4-(2-(3-(4-fluorophenoxy)-5-(thieno[3,2-b]pyridin-7-ylthio)pyridin-2-ylamino)thiazol-4-yl)piperidine-1-carboxylate;
N-(3-(4-fluorophenoxy)-5-(thieno[3,2-b]pyridin-7-ylthio)pyridin-2-yl)-4-(piperidin-4-yl)thiazol-2-amine;
1-(4-(2-(3-(4-fluorophenoxy)-5-(thieno[3,2-b]pyridin-7-ylthio)pyridin-2-ylamino)thiazol-4-yl)piperidin-1-yl)ethanone;
2-(4-(2-(3-(4-fluorophenoxy)-5-(thieno[3,2-b]pyridin-7-ylthio)pyridin-2-ylamino)thiazol-4-yl)piperidin-1-yl)-2-oxoethyl acetate;
Isopropyl 4-(2-(3-(4-fluorophenoxy)-5-(thieno[3,2-b]pyridin-7-ylthio)pyridin-2-ylamino)thiazol-4-yl)piperidine-1-carboxylate;
2-(dimethylamino)-1-(4-(2-(3-(4-fluorophenoxy)-5-(thieno[3,2-b]pyridin-7-ylthio)pyridin-2-ylamino)thiazol-4-yl)piperidin-1-yl)ethanone;
N-(3-(4-fluorophenoxy)-5-(thieno[3,2-b]pyridin-7-ylthio)pyridin-2-yl)-4-(1-(methylsulfonyl)piperidin-4-yl)thiazol-2-amine;
N-(1-(4-(2-(3-(4-fluorophenoxy)-5-(thieno[3,2-b]pyridin-7-ylthio)pyridin-2-ylamino)thiazol-4-yl)piperidin-1-yl)-1-oxopropan-2-yl)acetamide;
N-(2-(4-(2-(3-(4-fluorophenoxy)-5-(thieno[3,2-b]pyridin-7-ylthio)pyridin-2-ylamino)thiazol-4-yl)piperidin-1-yl)-2-oxoethyl)acetamide;
4-(1-(2-aminoethylsulfonyl)piperidin-4-yl)-N-(3-(4-fluorophenoxy)-5-(thieno[3,2-b]pyridin-7-ylthio)pyridin-2-yl)thiazol-2-amine;
4-(2-(3-(4-fluorophenoxy)-5-(thieno[3,2-b]pyridin-7-ylthio)pyridin-2-ylamino)thiazol-4-yl)piperidine-1-sulfonamide 2,2,2-trifluoroacetate;
4-(2-(3-(4-fluorophenoxy)-5-(thieno[3,2-b]pyridin-7-ylthio)pyridin-2-ylamino)thiazol-4-yl)piperidine-1-carboxamide;
tert-butyl 4-(2-(3-(4-fluorophenoxy)-5-(3-methylisoxazolo[5,4-b]pyridin-4-ylthio)pyridin-2-ylamino)thiazol-4-yl)piperidine-1-carboxylate;
N-(3-(4-fluorophenoxy)-5-(3-methylisoxazolo[5,4-b]pyridin-4-ylthio)pyridin-2-yl)-4-(piperidin-4-yl)thiazol-2-amine;
1-(4-(2-(3-(4-fluorophenoxy)-5-(3-methylisoxazolo[5,4-b]pyridin-4-ylthio)pyridin-2-ylamino)thiazol-4-yl)piperidin-1-yl)ethanone;
2-(dimethylamino)-1-(4-(2-(3-(4-fluorophenoxy)-5-(3-methylisoxazolo[5,4-b]pyridin-4-ylthio)pyridin-2-ylamino)thiazol-4-yl)piperidin-1-yl)ethanone;
Methyl 4-(5-(3-phenoxy-5-(pyridin-2-ylthio)pyridin-2-ylamino)-1,2,4-thiadiazol-3-yl)piperidine-1-carboxylate;
1-(4-(2-(5-(3-methylthieno[3,2-b]pyridin-7-ylthio)-3-phenoxypyridin-2-ylamino)thiazol-4-yl)piperidin-1-yl)ethanone;
1-(4-(2-(5-(5-chlorothieno[3,2-b]pyridin-7-ylthio)-3-phenoxypyridin-2-ylamino)thiazol-4-yl)piperidin-1-yl)ethanone;
1-(4-(2-(3-phenoxy-5-(thieno[2,3-d]pyrimidin-4-ylthio)pyridin-2-ylamino)thiazol-4-yl)piperidin-1-yl)ethanone;
tert-butyl 4-((2-(5-(3-methoxy-3-oxopropylthio)-3-phenoxypyridin-2-ylamino)thiazol-4-yl)methyl)piperidine-1-carboxylate;
tert-butyl 4-(2-(3-(4-cyanophenoxy)-5-(3-methoxy-3-oxopropylthio)pyridin-2-ylamino)thiazol-4-yl)piperidine-1-carboxylate;
tert-butyl 3-(5-(5-(3-methoxy-3-oxopropylthio)-3-phenoxypyridin-2-ylamino)-1,2,4-thiadiazol-3-yl)pyrrolidine-1-carboxylate;
tert-butyl 3-(2-(5-(3-methoxy-3-oxopropylthio)-3-phenoxypyridin-2-ylamino)thiazol-4-yl)piperidine-1-carboxylate;
tert-butyl 3-(2-(5-(3-methoxy-3-oxopropylthio)-3-phenoxypyridin-2-ylamino)thiazol-4-yl)pyrrolidine-1-carboxylate;
tert-butyl 4-((2-(3-phenoxy-5-(thieno[3,2-b]pyridin-7-ylthio)pyridin-2-ylamino)thiazol-4-yl)methyl)piperidine-1-carboxylate;
tert-butyl 4-((2-(5-(4-cyanophenylthio)-3-phenoxypyridin-2-ylamino)thiazol-4-yl)methyl)piperidine-1-carboxylate;
tert-butyl 3-((2-(3-phenoxy-5-(thieno[3,2-b]pyridin-7-ylthio)pyridin-2-ylamino)thiazol-4-yl)methyl)piperidine-1-carboxylate;
tert-butyl 3-(5-(3-phenoxy-5-(thieno[3,2-b]pyridin-7-ylthio)pyridin-2-ylamino)-1,2,4-thiadiazol-3-yl)pyrrolidine-1-carboxylate;
tert-butyl 3-(2-(3-phenoxy-5-(thieno[3,2-b]pyridin-7-ylthio)pyridin-2-ylamino)thiazol-4-yl)pyrrolidine-1-carboxylate;
tert-butyl 3-(2-(5-(4-cyanophenylthio)-3-phenoxypyridin-2-ylamino)thiazol-4-yl)piperidine-1-carboxylate;
tert-butyl 3-(5-(5-(4-cyanophenylthio)-3-phenoxypyridin-2-ylamino)-1,2,4-thiadiazol-3-yl)pyrrolidine-1-carboxylate;
N-(3-phenoxy-5-(thieno[3,2-b]pyridin-7-ylthio)pyridin-2-yl)-4-(piperidin-4-ylmethyl)thiazol-2-amine;
N-(3-phenoxy-5-(thieno[3,2-b]pyridin-7-ylthio)pyridin-2-yl)-4-(piperidin-3-yl)thiazol-2-amine;
N-(3-phenoxy-5-(thieno[3,2-b]pyridin-7-ylthio)pyridin-2-yl)-3-(pyrrolidin-3-yl)-1,2,4-thiadiazol-5-amine;
N-(3-phenoxy-5-(thieno[3,2-b]pyridin-7-ylthio)pyridin-2-yl)-4-(pyrrolidin-3-yl)thiazol-2-amine;

4-(5-phenoxy-6-(4-(piperidin-4-ylmethyl)thiazol-2-ylamino)pyridin-3-ylthio)benzonitrile;
4-(5-phenoxy-6-(3-(pyrrolidin-3-yl)-1,2,4-thiadiazol-5-ylamino)pyridin-3-ylthio)benzonitrile;
4-(5-phenoxy-6-(3-(piperidin-3-yl)-1,2,4-thiadiazol-5-ylamino)pyridin-3-ylthio)benzonitrile;
1-(4-((2-(3-phenoxy-5-(thieno[3,2-b]pyridin-7-ylthio)pyridin-2-ylamino)thiazol-4-yl)methyl)piperidin-1-yl)ethanone;
1-(3-(2-(3-phenoxy-5-(thieno[3,2-b]pyridin-7-ylthio)pyridin-2-ylamino)thiazol-4-yl)piperidin-1-yl)ethanone;
1-(3-(5-(3-phenoxy-5-(thieno[3,2-b]pyridin-7-ylthio)pyridin-2-ylamino)-1,2,4-thiadiazol-3-yl)pyrrolidin-1-yl)ethanone;
1-(3-(2-(3-phenoxy-5-(thieno[3,2-b]pyridin-7-ylthio)pyridin-2-ylamino)thiazol-4-yl)pyrrolidin-1-yl)ethanone;
4-(6-(4-(1-acetylpiperidin-3-yl)thiazol-2-ylamino)-5-phenoxypyridin-3-ylthio)benzonitrile;
4-(6-(3-(1-acetylpyrrolidin-3-yl)-1,2,4-thiadiazol-5-ylamino)-5-phenoxypyridin-3-ylthio)benzonitrile;
4-(6-(4-((1-acetylpiperidin-4-yl)methyl)thiazol-2-ylamino)-5-phenoxypyridin-3-ylthio)benzonitrile; and
1-(4-(2-(5-(2-chloropyridin-4-ylthio)-3-phenoxypyridin-2-ylamino)thiazol-4-yl)piperidin-1-yl)ethanone;
or a pharmaceutically acceptable salt thereof.

\* \* \* \* \*

UNITED STATES PATENT AND TRADEMARK OFFICE
CERTIFICATE OF CORRECTION

PATENT NO. : 8,022,223 B2
APPLICATION NO. : 12/282600
DATED : September 20, 2011
INVENTOR(S) : Thomas D. Aicher et al.

Page 1 of 2

It is certified that error appears in the above-identified patent and that said Letters Patent is hereby corrected as shown below:

In Column 12, line 9:
Please replace "$V_n$—S(O)$_2$WR$^9$" with -- $V_n$—S(O)2R$^8$R$^9$ --

In Column 17, line 7:
Please replace "Example of $^{13}$" with -- Examples of R$^{13}$ --

In Column 29, line 36:
Please replace "wherein R$^1$ is $V_n$-" with -- wherein R$^3$ is $V_n$- --

In Column 35, line 8:

Please replace " 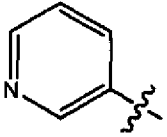 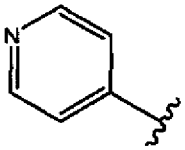 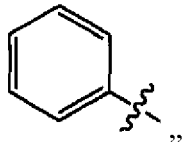 "

with --  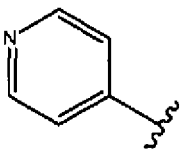 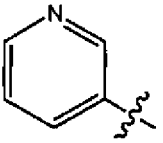 --

In Column 39, line 44:
Please replace "R$^3$ is selected from" with -- R$^6$—S is selected from --

In Column 51, line 58:
Please replace "—P(O)(O" with -- —P(O)(O) --

Signed and Sealed this
First Day of May, 2012

David J. Kappos
*Director of the United States Patent and Trademark Office*

CERTIFICATE OF CORRECTION (continued)
U.S. Pat. No. 8,022,223 B2

In Column 52, line 8:
    Please replace "$Y_2$ is 1 or methyl" with -- $Y_2$ is H or methyl --

In Column 315, Claim 1, Line 62:
    Please replace "$S(O)_2NR^6{}_R{}^7$" with -- $S(O)_2NR^6R^7$ --

In Column 319, Claim 5, Line 65:
    Please replace "$C_1$-$C_6$ alkenyl, $C_1$-$C_6$ alkynyl," with -- $C_2$-$C_6$ alkenyl, $C_2$-$C_6$ alkynyl, --

In Column 332, Claim 20, Line 59:
    Please replace "3-ylthio)methypthiazol-2-yl)acetamide;"
with -- 3-ylthio)methyl)thiazol-2-yl)acetamide; --

UNITED STATES PATENT AND TRADEMARK OFFICE
CERTIFICATE OF CORRECTION

PATENT NO. : 8,022,223 B2  Page 1 of 1
APPLICATION NO. : 12/282600
DATED : September 20, 2011
INVENTOR(S) : Thomas D. Aicher et al.

It is certified that error appears in the above-identified patent and that said Letters Patent is hereby corrected as shown below:

In Column 65, lines 45-50:

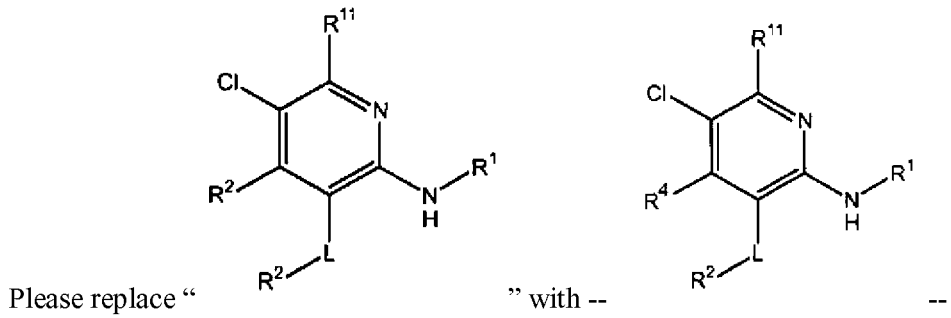

Please replace "        " with --              --

And in Column 65, lines 55-60:

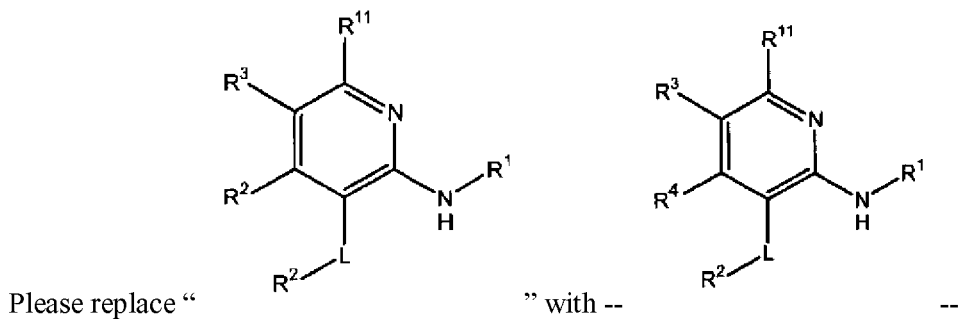

Please replace "        " with --              --

Signed and Sealed this
Twelfth Day of June, 2012

David J. Kappos
*Director of the United States Patent and Trademark Office*